US010953089B1

(12) United States Patent
Smith et al.

(10) Patent No.: US 10,953,089 B1
(45) Date of Patent: Mar. 23, 2021

(54) CORONAVIRUS VACCINE FORMULATIONS

(71) Applicant: NOVAVAX, INC., Gaithersburg, MD (US)

(72) Inventors: Gale Smith, Germantown, MD (US); Michael J. Massare, Mt. Airy, MD (US); Jing-Hui Tian, Germantown, MD (US)

(73) Assignee: NOVAVAX, INC., Gaithersburg, MD (US)

( * ) Notice: Subject to any disclaimer, the term of this patent is extended or adjusted under 35 U.S.C. 154(b) by 0 days.

(21) Appl. No.: 16/997,001

(22) Filed: Aug. 19, 2020

Related U.S. Application Data

(60) Provisional application No. 63/054,182, filed on Jul. 20, 2020, provisional application No. 63/051,706, filed on Jul. 14, 2020, provisional application No. 63/048,945, filed on Jul. 7, 2020, provisional application No. 62/983,180, filed on Feb. 28, 2020, provisional application No. 62/976,858, filed on Feb. 14, 2020, provisional application No. 62/966,271, filed on Jan. 27, 2020.

(51) Int. Cl.

| | |
|---|---|
| ***A61K 39/215*** | (2006.01) |
| ***A61P 31/14*** | (2006.01) |
| *A61K 39/00* | (2006.01) |

(52) U.S. Cl.

CPC ............ *A61K 39/215* (2013.01); *A61P 31/14* (2018.01); *A61K 2039/545* (2013.01); *A61K 2039/55577* (2013.01); *C12N 2770/20034* (2013.01)

(58) Field of Classification Search

None

See application file for complete search history.

(56) References Cited

U.S. PATENT DOCUMENTS

| | | | |
|---|---|---|---|
| 4,900,549 | A | 2/1990 | De Vries |
| 5,057,540 | A | 10/1991 | Kernsil et al. |
| 5,620,690 | A | 4/1997 | Kersten et al. |
| 6,231,859 | B1 | 5/2001 | Kensil |
| 6,352,697 | B1 | 3/2002 | Cox et al. |
| 6,428,807 | B1 | 8/2002 | Cox |

(Continued)

FOREIGN PATENT DOCUMENTS

| | | | |
|---|---|---|---|
| AU | 200324520 | B2 | 4/2009 |
| CA | 2491457 | C | 9/2012 |

(Continued)

OTHER PUBLICATIONS

Wang et al., "Subunit Vaccines Against Emerging Pathogenic Human Coronaviruses," Frontiers in Microbiology, 11:290 (Year: 2020).*

(Continued)

*Primary Examiner* — M Franco G Salvoza

(74) *Attorney, Agent, or Firm* — Cooley LLP; Fraser Brown

(57) ABSTRACT

Disclosed herein are coronavirus Spike (S) proteins and nanoparticles comprising the same, which are suitable for use in vaccines. The nanoparticles present antigens from pathogens surrounded to and associated with a detergent core resulting in enhanced stability and good immunogenicity. Dosages, formulations, and methods for preparing the vaccines and nanoparticles are also disclosed.

20 Claims, 83 Drawing Sheets
(77 of 83 Drawing Sheet(s) Filed in Color)
Specification includes a Sequence Listing.

MFVFLVLLPLVSSQCVNLTTRTQLPPAYTNSFTRGVYYPDKVFRSSVLHSTQDLFLPFFSN
VTWFHAIHVSGTNGTKRFDNPVLPFNDGVYFASTEKSNIIRGWIFGTTLDSKTQSLLIVNN
ATNVVIKVCEFQFCNDPFLGVYYHKNNKSWMESEFRVYSSANNCTFEYVSQPFLMDLEG
KQGNFKNLREFVFKNIDGYFKIYSKHTPINLVRDLPQGFSALEPLVDLPIGINITRFQTLLAL
HRSYLTPGDSSSGWTAGAAAYYVGYLQPRTFLLKYNENGTITDAVDCALDPLSETKCTLK
SFTVEKGIYQTSNFRVQPTESIVRFPNITNLCPFGEVFNATRFASVYAWNRKRISNCVADYS
VLYNSASFSTFKCYGVSPTKLNDLCFTNVYADSFVIRGDEVRQIAPGQTGKIADYNYKLP
DDFTGCVIAWNSNNLDSKVGGNYNYLYRLFRKSNLKPFERDISTEIYQAGSTPCNGVEGF
NCYFPLQSYGFQPTNGVGYQPYRVVVLSFELLHAPATVCGPKKSTNLVKNKCVNFNFNG
LTGTGVLTESNKKFLPFQQFGRDIADTTDAVRDPQTLEILDITPCSFGGVSVITPGTNTSNQ
VAVLYQDVNCTEVPVAIHADQLTPTWRVYSTGSNVFQTRAGCLIGAEHVNNSYECDIPIG
AGICASYQTQTNSPRRARSVASQSIIAYTMSLGAENSVAYSNNSIAIPTNFTISVTTEILPVS
MTKTSVDCTMYICGDSTECSNLLLQYGSFCTQLNRALTGIAVEQDKNTQEVFAQVKQIYK
TPPIKDFGGFNFSQILPDPSKPSKRSFIEDLLFNKVTLADAGFIKQYGDCLGDIAARDLICA
QKFNGLTVLPPLLTDEMIAQYTSALLAGTITSGWTFGAGAALQIPFAMQMAYRFNGIGVT
QNVLYENQKLIANQFNSAIGKIQDSLSSTASALGKLQDVVNQNAQALNTLVKQLSSNFGA
ISSVLNDILSRLDKVEAEVQIDRLITGRLQSLQTYVTQQLIRAAEIRASANLAATKMSECV
LGQSKRVDFCGKGYHLMSFPQSAPHGVVFLHVTYVPAQEKNFTTAPAICHDGKAHFPRE
GVFVSNGTHWFVTQRNFYEPQIITTDNTFVSGNCDVVIGIVNNTVYDPLQPELDSFKEEL
DKYFKNHTSPDVDLGDISGINASVVNIQKEIDRLNEVAKNLNESLIDLQELGKYEQYIKWP
WYIWLGFIAGLIAIVMVTIMLCCMTSCCSCLKGCCSCGSCCKFDEDDSEPVLKGVKLHYT

(56) References Cited

U.S. PATENT DOCUMENTS

| | | | |
|---|---|---|---|
| 6,524,584 B2 | 2/2003 | Kensil | |
| 6,558,670 B1 | 5/2003 | Friede et al. | |
| 6,846,489 B1 | 1/2005 | Garcon et al. | |
| 7,776,343 B1 | 8/2010 | Cox et al. | |
| 8,173,141 B2 | 5/2012 | Cox et al. | |
| 8,821,881 B2 | 9/2014 | Morein | |
| 10,022,437 B2 | 7/2018 | Pushko et al. | |
| 10,426,829 B2 | 10/2019 | Smith et al. | |
| 10,729,764 B2 | 8/2020 | Morein et al. | |
| 2006/0121065 A1 | 6/2006 | Morein et al. | |
| 2006/0239963 A1 | 10/2006 | Morein | |
| 2012/0107353 A1 | 5/2012 | Morein et al. | |
| 2014/0335049 A1 | 11/2014 | Morein et al. | |
| 2015/0209425 A1 | 7/2015 | Morein et al. | |
| 2016/0008451 A1* | 1/2016 | Stary ...................... | A61K 45/06 424/179.1 |
| 2016/0184427 A1 | 6/2016 | Morein et al. | |
| 2016/0206729 A1 | 7/2016 | Smith et al. | |
| 2018/0369368 A1 | 12/2018 | Morein et al. | |
| 2020/0061185 A1 | 2/2020 | Graham et al. | |
| 2020/0215189 A1 | 7/2020 | Morein et al. | |
| 2020/0407402 A1 | 12/2020 | He et al. | |

FOREIGN PATENT DOCUMENTS

| | | | |
|---|---|---|---|
| CN | 1472332 | A | 2/2004 |
| EP | 0109942 | | 5/1984 |
| EP | 0180564 | B1 | 5/1986 |
| EP | 0362279 | | 4/1990 |
| EP | 0242380 | B1 | 4/1991 |
| EP | 0436620 | B1 | 8/1994 |
| EP | 0889736 | B1 | 12/2003 |
| EP | 1539231 | B1 | 6/2009 |
| RU | 2403063 | C1 | 11/2010 |
| WO | WO 88/09336 | A1 | 12/1988 |
| WO | WO 90/03184 | A1 | 4/1990 |
| WO | WO 96/11711 | | 4/1996 |
| WO | WO 97/30728 | A1 | 8/1997 |
| WO | WO 98/36772 | | 8/1998 |
| WO | WO 2004/004762 | A1 | 1/2004 |
| WO | WO 2004/085633 | A1 | 10/2004 |
| WO | WO 2005/002620 | A1 | 1/2005 |
| WO | WO 2009/081285 | A2 | 7/2009 |
| WO | WO 2018/081318 | A1 | 5/2018 |

OTHER PUBLICATIONS

Sekimukai et al., "Gold nanoparticle-adjuvanted S protein induces a strong antigen-specific IgG response against severe acute respiratory syndrome-related coronavirus infection, but fails to induce protective antibodies and limit eosinophilic infiltration in lungs," Microbiology and Immunology,64:33-51 (Year: 2020).*

Chatterjee et al., "The 2019 novel coronavirus disease (COVID-19) pandemic: A review of the current evidence," Indian J Med Res 151(2-3):147-159 (Year: 2020).*

Gretebeck et al., "Animal models for SARS and MERS coronaviruses," Virology, 13:123-129 (Year: 2015).*

Boulter, et al., Evaluation of recombinant sporozoite antigen SPAG-1 as a vaccine candidate against Theileria annulata by the use of different delivery systems, Tropical Medicine and International Health, vol. 4, pp. A71-A77 (1999), Blackwell Science, Ltd.

EMEA (European Agency for the Evaluation of Medicinal Products), "Committee for Veterinary Medicinal Products. Quillaia Saponins. Summary Report ," EMEA/MRL/055/95-Final, pp. 1-2 (1996).

Ennis et al., "Augmentation of Human Influenza A Virus-Specific Cytotoxic T Lymphocyte Memory by Influenza Vaccine and Adjuvanted Carriers (ISCOMS)," Virology 25:256-261 (1999).

Eyles et al., "Immunodominant Francisella tularensis antigens identified using proteome microarray," Proteomics 7:2172-2183 (2007).

Genocea Biosciences, Genocea Reports Positive Initial Phase 1/2A Results for GEN-003, It's Pioneering Therapeutic Vaccine Candidate for the Treatment of Herpes Simplex Virus-2 (HSV-2), at ICAAC 2013, press release, Cambridge MA, Sep. 12, 2013, pp. 1-3.

Lavelle et al., "Cholera Toxin Promotes the Induction of Regulatory T Cells Specific for Bystander Antigens by Modulating Dendritic Cell Activation," J. Immunol. 171:2384-2392 (2003).

Lovgren-Bengtsson et al., "4.5 Preparation and Use of Adjuvants," Methods in Microbiology 32:551-588 (2002).

Pedersen, et al.; T-Helper 1 Cells Elicited by H5N1 Vaccination Predict Seroprotection, Journal of Infectious Disease, 206, pp. 158-166, Jul. 15, 2016.

Sun et al., "Advances in saponin-based adjuvants," Vaccine 27:1787-1796 (2009).

Sun et al., "ISCOMs and Isomatrix™," Vaccine 27:4388-4401 (2009).

"Committee for Veterinary Medicinal Products, Quillaia Saponins, Summary Report", the European Agency for the rgJ Evaluation of Medicinal Products, EMEA/MRL/055/95-Final, Feb. 1996, pp. 1-2.

"Safety Evaluation of Certain Food Additives and Contaminants Quillaia Extracts," WHO Food Additives Series:48, 14 pages (1996).

Adjuvanting Viral Vectored Malaria Vaccines with Matrix M, Identifier NCT01669512, ClinicaiTrials.gov, U.S. National Institutes of Health; available at http://clinicaltrials.gov/ct2/show/NCT01669512?term=MatrixM+or+Matrix+M&rank=1, Mar. 9, 2014, pp. 1-4.

Ahlberg et al., Global transcriptional response to ISCOM-Matrix adjuvant at the site of administration and in the draining lymph node early after intramuscular injection in pigs, Developmental and Comparative Immunology, vol. 38, pp. 17-26 (2012), Elsevier Ltd.

Anonymous, "Novavax to Present at the 2013 Stifel Nicolaus Healthcare Conference," Reuters, 1 page http://in.reuters.com/article/2013/09/05/idUSnGNX7PTmrq+1d8+GNW20130905 (2013).

Anonymous, "Stifel 2013 Healthcare Conference," pp. 1-35, http://www.novavax.com/download/file/2013_09_12%20Novavax_Stifel_presentation.pdf (2013).

Barr et al., "ISCOMs and other saponin based adjuvants," Advanced Drug Delivery Reviews, (1998), 32: 247-271.

Behboudi et al. "Quillaja Saponin formulations that Stimulate Proinflammatory Cytokines Elicit a Potent Acquired rgJ Cell-Mediated Immunity." Scandinavian Journal of Immunology, 50 (1999), pp. 371-377.

Bengtsson et al., "ISCOM technology-based Matrix™ adjuvant: success in future vaccines relies on formulation," Expert. Rev. Vaccines 10(4):401-403 (2011).

Bengtsson et al., Matrix-M adjuvant increases immunogenicity of seasonal influenza vaccine for the elderly, manuscrip in preparation, pp. 1-27 (2014).

Coleman et al., "Purified coronavirus spike protein nanoparticles induce coronavirus neutralizing antibodies in mice," Vaccine 32(26):3169-3174 (2014).

Copland et al., "Hydration of lipid films with an aqueous solution of Quil A: a simple method for the preparation of immune-stimulating complexes," International Journal of Pharmaceutics 196:135-139 (2000).

Coulter, et al., Studies on experimental adjuvanted influenza vaccines: comparison of immune stimulating complexes(Iscoms) and oil-in-water vaccines; Vaccine, vol. 16, No. 11/12, pp. 1243-1253 (1998), Elsevier Science Ltd., Great Britain.

Cox, et al., Development of an Influenza-ISCOM Vaccine, in Vaccine Design (eds. G. Gregoriadis et al.), Springer Science+ Business Media, New York (1997), pp. 33-49.

Cox, et al., Evaluation of a virosomal H5N1 vaccine formulated with Maxtrix M adjuvant in phase I clinical trial, Elsevier Ltd, Vaccine, 29, pp. 8049-8059, Aug. 22, 2011.

Cox, et al., Prospects for the Development of New Vaccine Adjuvants, BioDrugs, vol. 12(6), pp. 439-453 (1999), Ad is International Limited.

Database UniProt [Online], "SubName: Full=S Protein {ECO:0000313|EMBL:AGN70973.1}," EBI accesion No. UniProt:R9UQ53, Database accession No. R9UQ53 (2013).

Delmas and Laude, "Assembly of Coronavirus Spike Protein into Trimers and Its Role in Epitope Expression," Journal of Virology 64(11):5367-5375 (1990).

(56) References Cited

OTHER PUBLICATIONS

Demana et al., "Pseudo-ternary phase diagrams of aqueous mixtures of Quil A, cholesterol and phospholipid prepared by the lipid-film hydration method," International Journal of Pharmaceutics 270:229-239 (2004).
Demana et al., "A comparison of pseudo-ternary diagrams of aqueous mixtures of Quil A, cholesterol and phospholipid prepared by lipid-film hydration and dialysis," Journal of Pharmacy and Pharmacology 56:573-580 (2004).
Drane et al., "IscoMatrix Adjuvant for Prophylactic and Therapeutic Vaccines," Exp. Rev. Vaccines 6(5):761-772 (2007).
Du et al., "Identification of a Receptor-Binding Domain in the S Protein of the Novel Human Coronavirus Middle East Respiratory Syndrome Coronavirus as an Essential Target for Vaccine Development," J. Virol. 87(17):9939-9942 (2013).
Du et al., "The spike protein of SRS-CpV—a target for vaccine and therapeutic development," Nat. Rev. Microbiol. 7(3):226-236 (2009).
Ekstrom et al. "Iscom and Iscom-Matrix Enhance by Intranasal Route the IgA Responses to OVA and rCTB in rgJ ILocaland Remote Muscosal Secretions." Vaccine, 17 (1999) pp. 2690-2701.
Fossum et al., Early inflammatory response to the saponin adjuvant Matrix-M in the pig, Veterinary Immunology and Immunopathology, http://dx.doi.org/10.1 016/j.vetimm.2013.07.007 (2013), pp. 1-9, Elsevier B.V.
Gillim-Ross et al., "Emerging Respiratory Viruses: Challenges and Vaccine Strategies," Clin. Microbiol. Rev. 19(4):614-636 (2006).
Hilgenfeld et al., "From SARS to MERS: 10 years of research on highly pathogenic human coronaviruses," Antiviral Res. 100(1):286-295 (2013).
Jackson et al., "An mRNA Vaccine against SARS-CoV-2—Preliminary Report," the New England Journal of Medicine, pp. 1-12 (2020).
Jiang, et al., "A predicted receptor-binding and critical neutralizing domain in S protein of the novel human coronavirus HCoV-EMC", Journal of Infection (66):464-466 (2013).
Johansson et al., Iscoms with Different Quillaja Saponin Components Differ in Their Immunomodulating Activities, Vaccine 17:2894-2900 (1999).
Kam et al.,"Antibodies against trimeric S glycoprotein protect hamsters against SARS-CoV challenge despite their capacity to mediate FcgammaRII-dependent entry into B cells in vitro," Vaccine 25(4):729-740 (2007).
Kensil, Saponins as Vaccine Adjuvants, Critical Reviews in Therapeutic Drug Carrier Systems, vol. 13(1&2), pp. 1-55 (1996), Begell House, Inc.
Kersten et al., On the structure of immune-stimulating saponin-lipid complexes (iscoms) Biochimica et Biophysica Acta, 1062:165-171 (1991).
Kirchdoerfer et al., "Stabilized coronavirus spikes are resistant to conformational changes induced by receptor recognition or proteolysis," Scientific Reports, pp. 1-11 (2018).
Korber et al.,"Tracking Changes in SARS-CoV-2 Spike: Evidence that D614G Increases Infectivity of the COVID-19 Virus," Cell 182:1-16 (2020).
Li et al., "Immunogenicity and Protection Efficacy of Monomeric and Trimeric Recombinant SARS Coronavirus Spike Protein Subunit Vaccine Candidates," Viral Immunology 26(2):126-132 (2013).
Liu et al., "Chimeric severe acute respiratory syndrome coronavirus (SARS-CoV) S glycoprotein and influenza matrix 1 efficiently form virus-like particles (VLPs) that protect mice against challenge with SARS-CoV," Vaccine 29(38):6606-6613 (2011).
Lovgren et al., The Requirement of Lipids for the Formation of Immunostimulating Complexes (iscoms), Biotechnol. Appl. Biochem. 10:161-172 (1988).
Lovgren-Bengtsson, 6 Preparation and Use of Adjuvants; Methods in Microbiology, vol. 25, pp. 471-502 (1998), Academic Press Ltd.
Lu et al., "Immune responses against severe acute respiratory syndrome coronavirus induced by virus-like particles in mice," Immunol. 122:496-502 (2007).
Lucy et al., "Structure and Assembly of Macromolecular Lipid Complexes Composed of Globular Micelles," Journal of Molecular Biology, (1964), 8: 727-748.
Magnusson et al., Immune enhancing properties of the novel Matrix-M adjuvant leads to potentiated immune responses to an inftuenza vaccine in mice, Vaccine, http://dx.doi.org/10.1016/j.vaccine.2013.01.039 (2013), pp. 1-9, Elsevier Ltd.
Magnusson et al., Matrix-M adjuvanted envelope protein vaccine protects against lethal lineage 1 and 2 West Nile virus infection in mice, Vaccine vol. 32, pp. 800-808 (2014), Elsevier Ltd.
McKenzie et al., IscoMatrix vaccines: Safety in human clinical studies, Human Vaccines, vol. 6, No. 3, pp. 237-246 (2010), Landes BioScience.
Morein et al., "Current status and potential application of ISCOMs in veterinary medicine," Adv. Drug Deliv. Rev. 56:1367-1382 (2004).
Nord, "Novel acetylated triterpenoid saponins in a chromatographic fraction from Quilaja saponinaria Molina," Carb. Res. 329:817-829 (2000).
Ozel et al., "Quaternary Structure of the Immunostimulating Complex (Iscom)," Journal of Ultrastructure and Molecular Structure Research 102:240-248 (1989).
Ozel et al., "Quaternary Structure of the Immunostimulating Complex (Iscom)," Journal of Ultrastructure and Molecular Structure Research, (1989), 102: 240-248.
Pallesen et al., "Immunogenicity and structures of a rationally designed prefusion MERS-CoV spike antigen," PNAS E7348-E7357 (2017).
Parrish, "Novavax creates MERS-CoV vaccine candidate," http://vaccinenewsdaily.com/vaccine_development/325407-novavax-creates-mers-cov-vaccine-candidate/ (2013).
Pedersen et al., Matrix-M adjuvanted virosomal H5N1 vaccine confers protection against lethal viral challenge in a murine model, Influenza and Other Respiratory Viruses. DOI: 1 0.1111/j.1750-2659.2011.00256.x (2011 ), pp. 1-12, Blackwell Publishing Ltd.
Rimmelzwaan, et al., A randomized, double blind study in young healthy adults comparing cell mediated and humoral immune responses induced by inftuenza ISCOM vaccines and conventional vaccines, Vaccine, vol. 19, pp. 1180-1187 (2001 ), Elsevier Science Ltd.
Ronnberg et al., "Adjuvant activity of non-toxic Quillaja saponaria Molina components for use in ISCOM matrix," Vaccine, vol. 13, No. 14, pp. 1375-1382 (1995).
Safety and Immunogenicity Study of Therapeutic HSV-2 Vaccine, Identifier NCT01667341, ClinicaiTrials.gov, U.S. National Institutes of Health; available at http://clinicaltrials.gov/ct2/show/NCT01667341 ?term=matrix+m&rank=3, Mar. 9, 2014, pp. 1-4.
Sjolander, et al., ISCOMs: an adjuvant with multiple functions, Journal of Leukocyte Biology, vol. 64, pp. 713-723 (1998).
Sjolander, et al., Uptake and adjuvant activity of orally delivered saponin and ISCOM vaccines, Advanced Drug Delivery Reviews, vol. 34, pp. 321-338 (1998), Elsevier Science B.V.
Skoberne et al., An adjuvanted herpes simplex virus 2 subunit vaccine elicits a T cell response in mice and is an effective therapeutic vaccine in Guinea pigs, J. Virol. 87:3930-3942 (2013).
Song et al., "Middle East Respiratory Syndrome Coronavirus Spike Protein Delivered by Modified Vaccinia Virus Ankara Efficiently Induces Virus-Neutralizing Antibodies," J. Virol. 87(21):11950-11954 (2013).
Tian et al., "SARS-CoV-2 spike glycoprotein vaccine candidate NVX-CoV2373 elicits immunogenicity in baboons and protection in mice," Jun. 29, 2020, 50 pages.
van Boheemen et al., "Genomic Characterization of a Newly Discovered Coronavirus Associated with Acute Respiratory Distress Syndrome in Humans," mBio 3(6):e00473-12, 9 pages (2012).
van Doremalen N. et al. ChAdOx1 nCoV-19 vaccination prevents SARS-CoV-2 pneumonia in rhesus macaques. bioRxiv, 23 pages (2020).
Wald et al., Novel Therapeutic Vaccine for Genital Herpes Reduces Genital HSV-2 Shedding, in ICAAC 2013, Denver, CO, Sep. 2013, cover page and p. 279, Abstract 183(G).
Wald, "A Novel Therapeutic Vaccine (GEN003) for Genital Herpes Reduces HSV-2 Shedding: Initial Results of Clinical Trial GEN003-

(56) References Cited

OTHER PUBLICATIONS

001," Presented at Interscience Conference on Antimicrobial Agents and Chemotherapy (ICAAC 2013), Denver, CO, Sep. 12, 2013, pp. 1-21.
Wrapp et al.,Cryo EM Structure of the 2019 nCoV spike in the Prefusion Conformation Science 10.1126/science.abb2507 (2020), 9 pages.
Wrapp et al.,"Cryo EM Structure of the 2019 nCoV spike in the Prefusion Conformation," bioRxiv, posted Feb. 15, 2020 online at https://doi.org/10.1101/2020.02.11.944462, 30 pages.

* cited by examiner

Fig. 1

MFVFLVLLPLVSSQCVNLTTRTQLPPAYTNSFTRGVYYPDKVFRSSVLHSTQDLFLPFFSN
VTWFHAIHVSGTNGTKRFDNPVLPFNDGVYFASTEKSNIIRGWIFGTTLDSKTQSLLIVNN
ATNVVIKVCEFQFCNDPFLGVYYHKNNKSWMESEFRVYSSANNCTFEYVSQPFLMDLEG
KQGNFKNLREFVFKNIDGYFKIYSKHTPINLVRDLPQGFSALEPLVDLPIGINITRFQTLLAL
HRSYLTPGDSSSGWTAGAAAYYVGYLQPRTFLLKYNENGTITDAVDCALDPLSETKCTLK
SFTVEKGIYQTSNFRVQPTESIVRFPNITNLCPFGEVFNATRFASVYAWNRKRISNCVADYS
VLYNSASFSTFKCYGVSPTKLNDLCFTNVYADSFVIRGDEVRQIAPGQTGKIADYNYKLP
DDFTGCVIAWNSNNLDSKVGGNYNYLYRLFRKSNLKPFERDISTEIYQAGSTPCNGVEGF
NCYFPLQSYGFQPTNGVGYQPYRVVVLSFELLHAPATVCGPKKSTNLVKNKCVNFNFNG
LTGTGVLTESNKKFLPFQQFGRDIADTTDAVRDPQTLEILDITPCSFGGVSVITPGTNTSNQ
VAVLYQDVNCTEVPVAIHADQLTPTWRVYSTGSNVFQTRAGCLIGAEHVNNSYECDIPIG
AGICASYQTQTNSPRRARSVASQSIIAYTMSLGAENSVAYSNNSIAIPTNFTISVTTEILPVS
MTKTSVDCTMYICGDSTECSNLLLQYGSFCTQLNRALTGIAVEQDKNTQEVFAQVKQIYK
TPPIKDFGGFNFSQILPDPSKPSKRSFIEDLLFNKVTLADAGFIKQYGDCLGDIAARDLICA
QKFNGLTVLPPLLTDEMIAQYTSALLAGTITSGWTFGAGAALQIPFAMQMAYRFNGIGVT
QNVLYENQKLIANQFNSAIGKIQDSLSSTASALGKLQDVVNQNAQALNTLVKQLSSNFGA
ISSVLNDILSRLDKVEAEVQIDRLITGRLQSLQTYVTQQLIRAAEIRASANLAATKMSECV
LGQSKRVDFCGKGYHLMSFPQSAPHGVVFLHVTYVPAQEKNFTTAPAICHDGKAHFPRE
GVFVSNGTHWFVTQRNFYEPQIITTDNTFVSGNCDVVIGIVNNTVYDPLQPELDSFKEEL
DKYFKNHTSPDVDLGDISGINASVVNIQKEIDRLNEVAKNLNESLIDLQELGKYEQYIKWP
WYIWLGFIAGLIAIVMVTIMLCCMTSCCSCLKGCCSCGSCCKFDEDDSEPVLKGVKLHYT

BV2373

SS — NTD — RBD — SD1/SD2 — FP — HR1 — CH — HR2 — TM — CT 1  14      305  331      527                                                    1273

S1 | S2

S1/S2 cleavage site
682-QQAQ-685 mutation

WT: NSPRRARSVAS
3Q: NSPQQAQSVAS

S2' cleavage site 2P mutation
K986P/V987P

WT: SRLDKVEAEV
2P: SRLDPPEAEV

WT SARS-CoV-2 S

BV2365

BV2373
nm
Time (S)
300nM
150nM
75nM
37.5nM
18.8nM
9.4nM
4.7nM

WT SARS-CoV-2 S

BV2365

BV2373
A450nm
hACE2 or hDPP4 (μg mL$^{-1}$)
hACE2
hDPP4
IC50 (ng mL$^{-1}$)
hACE2: 38
hDPP4: >5000
hACE2: 36
hDPP4: >5000
hACE2: 18
hDPP4: >5000

Placebo | 10 µg BV2373 + 5 µg Matrix-M™

Bronchial

Vascular

Alveoli 7 days post infection

Fig. 30

BV2384: CoV-2019/GSAS/K986P/V987P (SEQ ID NO: 109)

Isoelectric Pt (pI) 5.89

Signal peptide

MFVFLVLLPLVSSQCVNLTTRTQLPPAYTNSFTRGVYYPDKVFRSSVLHSTQDLFLPFFSNVTWFHAIHVSGT
NGTKRFDNPVLPFNDGVYFASTEKSNIIRGWIFGTTLDSKTQSLLIVNNATNVVIKVCEFQFCNDPFLGVYYH
KNNKSWMESEFRVYSSANNCTFEYVSQPFLMDLEGKQGNFKNLREFVFKNIDGYFKIYSKHTPINLVRDLPQG
FSALEPLVDLPIGINITRFQTLLALHRSYLPGDSSSGWTAGAAAYYVGYLQPRTFLLKYNENGTITDAVDCAL
DPLSETKCTLKSFTVEKGIYQTSNFRVQPTESIVRFPNITNLCPFGEVFNATRFASVYAWNRKRISNCVADYS
VLYNSASFSTFKCYGVSPTKLNDLCFTNVYADSFVIRGDEVRQIAPGQTGKIADYNYKLPDDFTGCVIAWNSN
NLDSKVGGNYNYLYRLFRKSNLKPFERDISTEIYQAGSTPCNGVEGFNCYFPLQSYGFQPTNGVGYQPYRVVV
LSFELLHAPATVCGPKKSTNLVKNKCVNFNFNGLTGTGVLTESNKKFLPFQQFGRDIADTTDAVRDPQTLEIL
DITPCSFGGVSVITPGTNTSNQVAVLYQDVNCTEVPVAIHADQLTPTWRVYSTGSNVFQTRAGCLIGAEHVNN
SYECDIPIGAGICASYQTQTNSPGSASSVASQSIIAYTMSLGAENSVAYSNNSIAIPTNFTISVTTEILPVSM
TKTSVDCTMYICGDSTECSNLLLQYGSFCTQLNRALTGIAVEQDKNTQEVFAQVKQIYKTPPIKDFGGFNFSQ
ILPDPSKPSKRSFIEDLLFNKVTLADAGFIKQYGDCLGDIAARDLICAQKFNGLTVLPPLLTDEMIAQYTSAL
LAGTITSGWTFGAGAALQIPFAMQMAYRFNGIGVTQNVLYENQKLIANQFNSAIGKIQDSLSSTASALGKLQD
VVNQNAQALNTLVKQLSSNFGAISSVLNDILSRLDPPEAEVQIDRLITGRLQSLQTYVTQQLIRAAEIRASAN
LAATKMSECVLGQSKRVDFCGKGYHLMSFPQSAPHGVVFLHVTYVPAQEKNFTTAPAICHDGKAHFPREGVFV
SNGTHWFVTQRNFYEPQIITTDNTFVSGNCDVVIGIVNNTVYDPLQPELDSFKELDKYFKNHTSPDVDLGDIS
GINASVVNIQKEIDRLNEVAKNLNESLIDLQELGKYEQYIKWPWYIWLGFIAGLIAIVMVTIMLCCMTSCCSC
LKGCCSCGSCCKFDEDDSEPVLKGVKLHYT

Fig. 31

BV2373 (SEQ ID NO: 86)

CoV-2019/QQAQ/K986P/V987P

Inactive furin cleavage site

Signal peptide

MFVFLVLLPLVSSQCVNLTTRTQLPPAYTNSFTRGVYYPDKVFRSSVLHSTQDLFLPFFSNVTWFHAIHVSGT
NGTKRFDNPVLPFNDGVYFASTEKSNIIRGWIFGTTLDSKTQSLLIVNNATNVVIKVCEFQFCNDPFLGVYYH
KNNKSWMESEFRVYSSANNCTFEYVSQPFLMDLEGKQGNFKNLREFVFKNIDGYFKIYSKHTPINLVRDLPQG
FSALEPLVDLPIGINITRFQTLLALHRSYLTPGDSSSGWTAGAAAYYVGYLQPRTFLLKYNENGTITDAVDCA
LDPLSETKCTLKSFTVEKGIYQTSNFRVQPTESIVRFPNITNLCPFGEVFNATRFASVYAWNRKRISNCVADY
SVLYNSASFSTFKCYGVSPTKLNDLCFTNVYADSFVIRGDEVRQIAPGQTGKIADYNYKLPDDFTGCVIAWNS
NNLDSKVGGNYNYLYRLFRKSNLKPFERDISTEIYQAGSTPCNGVEGFNCYFPLQSYGFQPTNGVGYQPYRVV
VLSFELLHAPATVCGPKKSTNLVKNKCVNFNFNGLTGTGVLTESNKKFLPFQQFGRDIADTTDAVRDPQTLEI
LDITPCSFGGVSVITPGTNTSNQVAVLYQDVNCTEVPVAIHADQLTPTWRVYSTGSNVFQTRAGCLIGAEHVN
NSYECDIPIGAGICASYQTQTNSPQQAQSVASQSIIAYTMSLGAENSVAYSNNSIAIPTNFTISVTTEILPVS
MTKTSVDCTMYICGDSTECSNLLLQYGSFCTQLNRALTGIAVEQDKNTQEVFAQVKQIYKTPPIKDFGGFNFS
QILPDPSKPSKRSFIEDLLFNKVTLADAGFIKQYGDCLGDIAARDLICAQKFNGLTVLPPLLTDEMIAQYTSA
LLAGTITSGWTFGAGAALQIPFAMQMAYRFNGIGVTQNVLYENQKLIANQFNSAIGKIQDSLSSTASALGKLQ
DVVNQNAQALNTLVKQLSSNFGAISSVLNDILSRLDPPEAEVQIDRLITGRLQSLQTYVTQQLIRAAEIRASA
NLAATKMSECVLGQSKRVDFCGKGYHLMSFPQSAPHGVVFLHVTYVPAQEKNFTTAPAICHDGKAHFPREGVF
VSNGTHWFVTQRNFYEPQIITTDNTFVSGNCDVVIGIVNNTVYDPLQPELDSFKEELDKYFKNHTSPDVDLGD
ISGINASVVNIQKEIDRLNEVAKNLNESLIDLQELGKYEQYIKWPWYIWLGFIAGLIAIVMVTIMLCCMTSCC
SCLKGCCSCGSCCKFDEDDSEPVLKGVKLHYT

Densitometry

Purity: 38.5%

Protein concentration:

A280(0.9226) - A340(0.187) = 0.7356 /1.067 = 0.6894 mg/mL

Total Volume: 19.0mL X 0.6894 mg/mL = 13.098 mg

Yield: 13.098mg/4.8 liter = 2.728 mg/L

Densitometry

Purity: 94.8%

Protein concentration:
A280(0.8368) - A340(0.0248) = 0.8142 /1.067 = 0.761 mg/mL
Total Volume: 42.47mL X 0.761 mg/mL = 42.32 mg
Yield: 42.32mg/5 liter = 6.4 mg/L SARS-CoV-2 Neutralizing Titers by CPE (100% neutralization)

SARS-CoV-2 Neutralizing Titers by PRNT (EC90 titers)

Fig. 41

| Procedure | Screening | Day 0 | 7 | 21 | 28 | 35 | 49 | 105 | 189 | 386 |
|---|---|---|---|---|---|---|---|---|---|---|
| Vaccination | | X | | X | | | | | | |
| Blood sample: safety | X | | X | X | X | | | | | |
| Blood sample: immunogenicity | | X | X | X | X | X | X | X | X | |
| Nasal swab | X | | | | | X | | | | |
| Reactogenicity | | ↔ | ↔ | ↔ | ↔ | | | | | |
| Unsolicited AE | | ↔ | ↔ | ↔ | ↔ | ↔ | ↔ | | | |
| MAAE: All/Related | | ↔ | ↔ | ↔ | ↔ | ↔ | ↔ | ↔ | | |
| SAE or AESI | | ↔ | ↔ | ↔ | ↔ | ↔ | ↔ | ↔ | ↔ | ↔ |

CORONAVIRUS VACCINE FORMULATIONS

CROSS REFERENCE TO RELATED APPLICATIONS

This application claims priority to the following applications, each of which is incorporated by reference in its entirety for all purposes: U.S. Provisional Application No. 62/966,271, filed Jan. 27, 2020; U.S. Provisional Application No. 62/976,858, filed Feb. 14, 2020; U.S. Provisional Application No. 62/983,180, filed Feb. 28, 2020; U.S. Provisional Application No. 63/048,945, filed Jul. 7, 2020; U.S. Provisional Application No. 63/051,706, filed Jul. 14, 2020; and U.S. Provisional Application No. 63/054,182, filed Jul. 20, 2020.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: NOVV_088_06US_SeqList_ST25.txt, date recorded: Jul. 29, 2020; file size: 514 kilobytes).

FIELD

The present disclosure is generally related to non-naturally occurring coronavirus (CoV) Spike (S) polypeptides and nanoparticles and vaccines comprising the same, which are useful for stimulating immune responses. The nanoparticles provide antigens, for example, glycoprotein antigens, optionally associated with a detergent core and are typically produced using recombinant approaches. The nanoparticles have improved stability and enhanced epitope presentation. The disclosure also provides compositions containing the nanoparticles, methods for producing them, and methods of stimulating immune responses.

BACKGROUND OF THE INVENTION

Infectious diseases remain a problem throughout the world. While progress has been made on developing vaccines against some pathogens, many remain a threat to human health. The outbreak of sudden acute respiratory syndrome coronavirus 2 (SARS-CoV-2) (also called Wuhan coronavirus and SARS-CoV-2) has infected more than 2000 people in China and killed at least 17 people. Recently, the SARS-CoV-2 coronavirus has spread to the United States, Thailand, South Korea, Taiwan, and Japan. The SARS-CoV-2 coronavirus belongs to the same family of viruses as severe acute respiratory syndrome coronavirus (SARS-CoV) and Middle East respiratory syndrome coronavirus (MERS-CoV), which have killed hundreds of people in the past 17 years. SARS-CoV-2 causes the disease COVID-19.

The development of vaccines that prevent or reduce the severity of life-threatening infectious diseases like the SARS-CoV-2 coronavirus is desirable. However, human vaccine development remains challenging because of the highly sophisticated evasion mechanisms of pathogens and difficulties stabilizing vaccines. Optimally, a vaccine must both induce antibodies that block or neutralize infectious agents and remain stable in various environments, including environments that do not enable refrigeration.

SUMMARY OF THE INVENTION

The present disclosure provides non-naturally occurring CoV S polypeptides suitable for inducing immune responses against SARS-CoV-2 (also called Wuhan CoV and 2019-nCoV)). The disclosure also provides nanoparticles containing the glycoproteins as well as methods of stimulating immune responses.

The present disclosure also provides CoV S polypeptides suitable for inducing immune responses against multiple coronaviruses, including SARS-CoV-2, Middle East Respiratory Syndrome (MERS), and Severe Acute Respiratory Syndrome (SARS).

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 shows a schematic of the wild-type amino acid sequence of the SARS-CoV-2 Spike (S) protein (SEQ ID NO: 1). The furin cleavage site RRAR (SEQ ID NO: 6) is highlighted in bold, and the signal peptide is underlined.

Figures 11A, 11B, 11C, 11D, 11E, 11F:
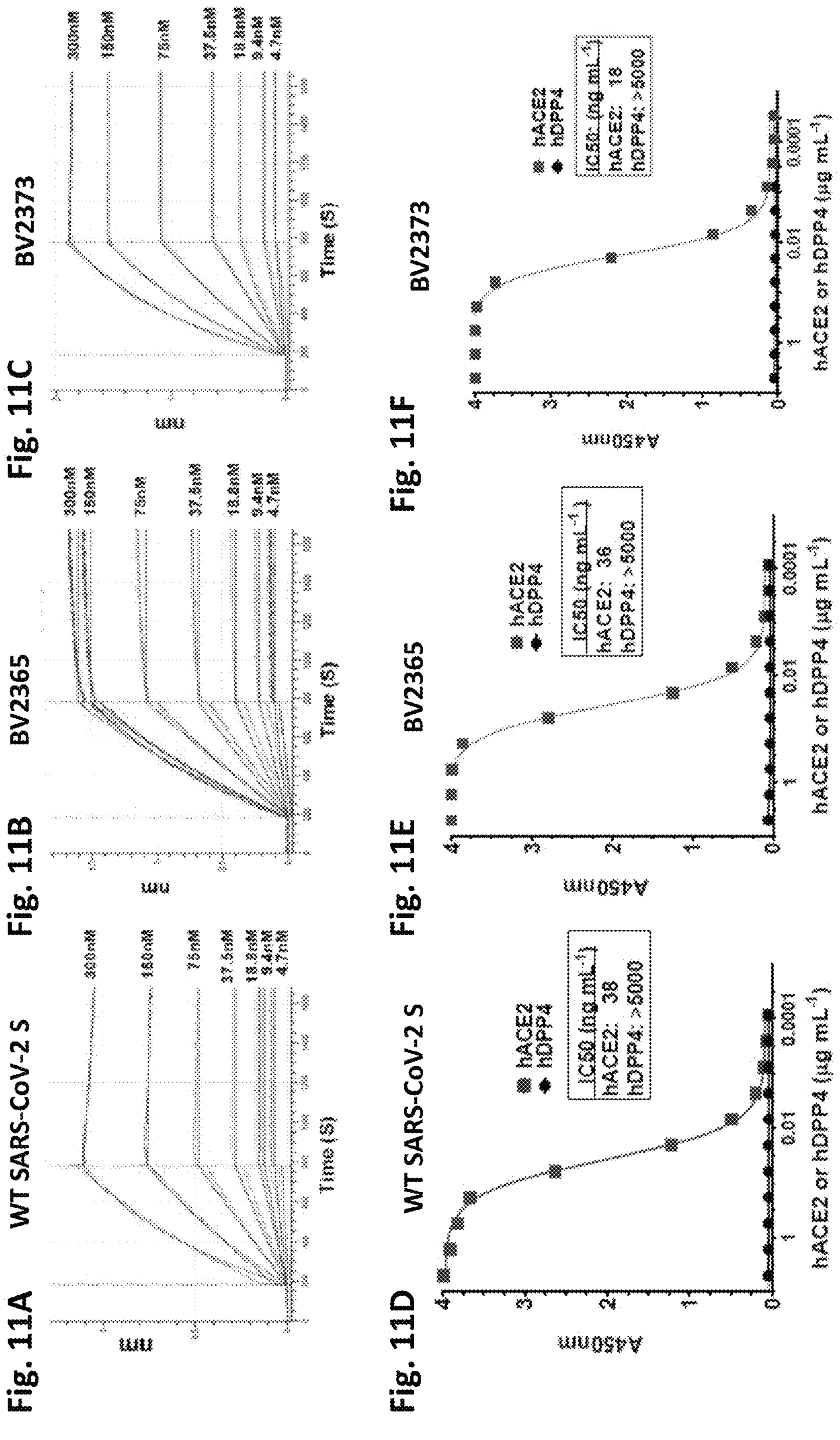
FIGS. 11A-F show that the CoV S Spike polypeptides BV2365 and BV2373 bind to hACE2. Bio-layer interferometry reveals that BV2365 (FIG. 11B) and BV2373 (FIG.

11C) bind to hACE2 with similar dissociation kinetics to the wild-type CoV S polypeptide (FIG. 11A) ELISA shows that the wild-type CoV S polypeptide (FIG. 11D) and BV2365 (FIG. 11E) bind to hACE2 with similar affinity while BV2373 binds to hACE2 at a higher affinity (FIG. 11F).

Figure 12A:
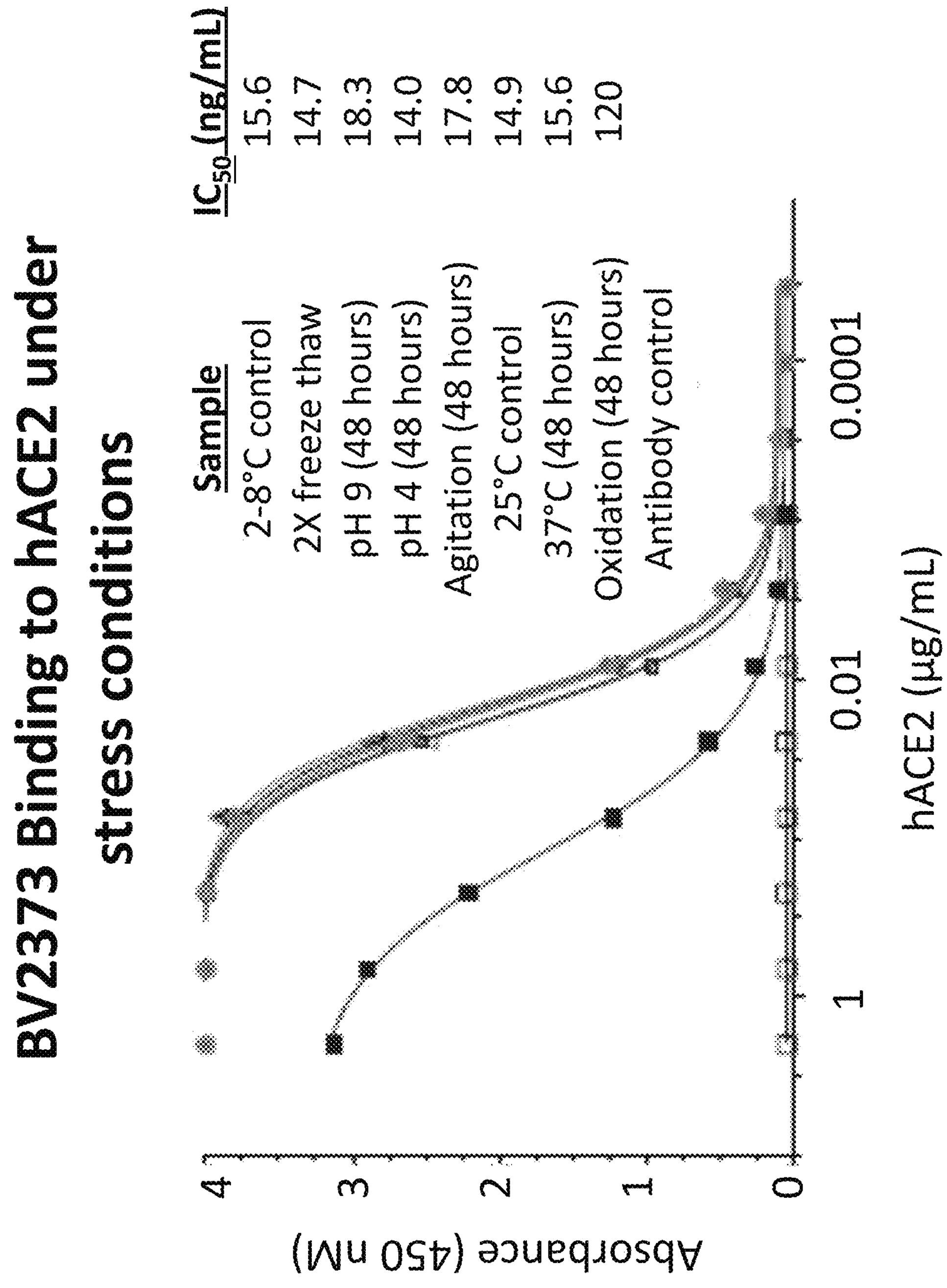
Figure 12B:
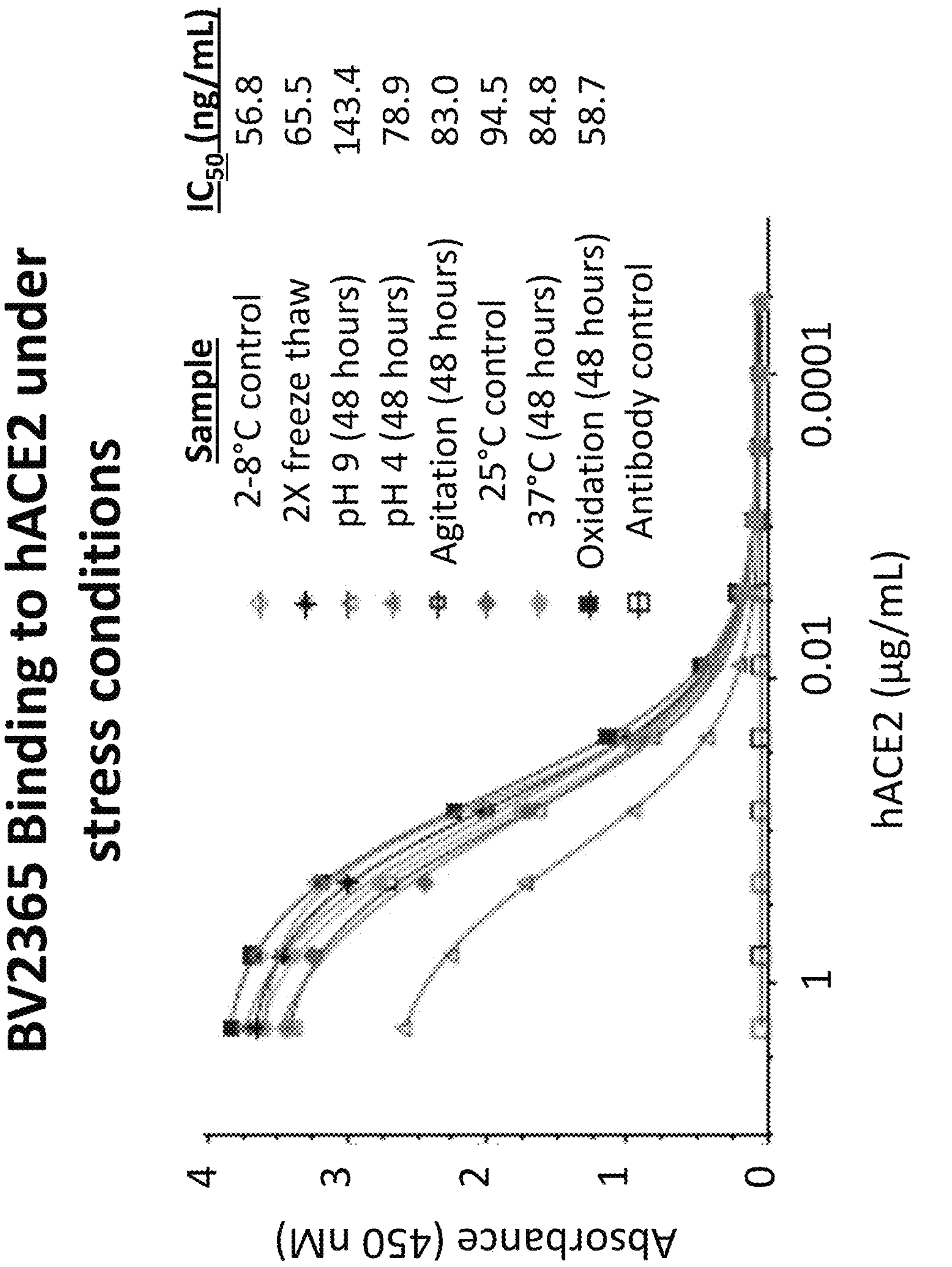

FIGS. 12A-B show the effect of stress conditions, such as temperature, two freeze/thaw cycles, oxidation, agitation, and pH extremes on binding of the CoV S polypeptides BV2373 (FIG. 12A) and BV2365 (FIG. 12B) to hACE2.

Figure 13A:
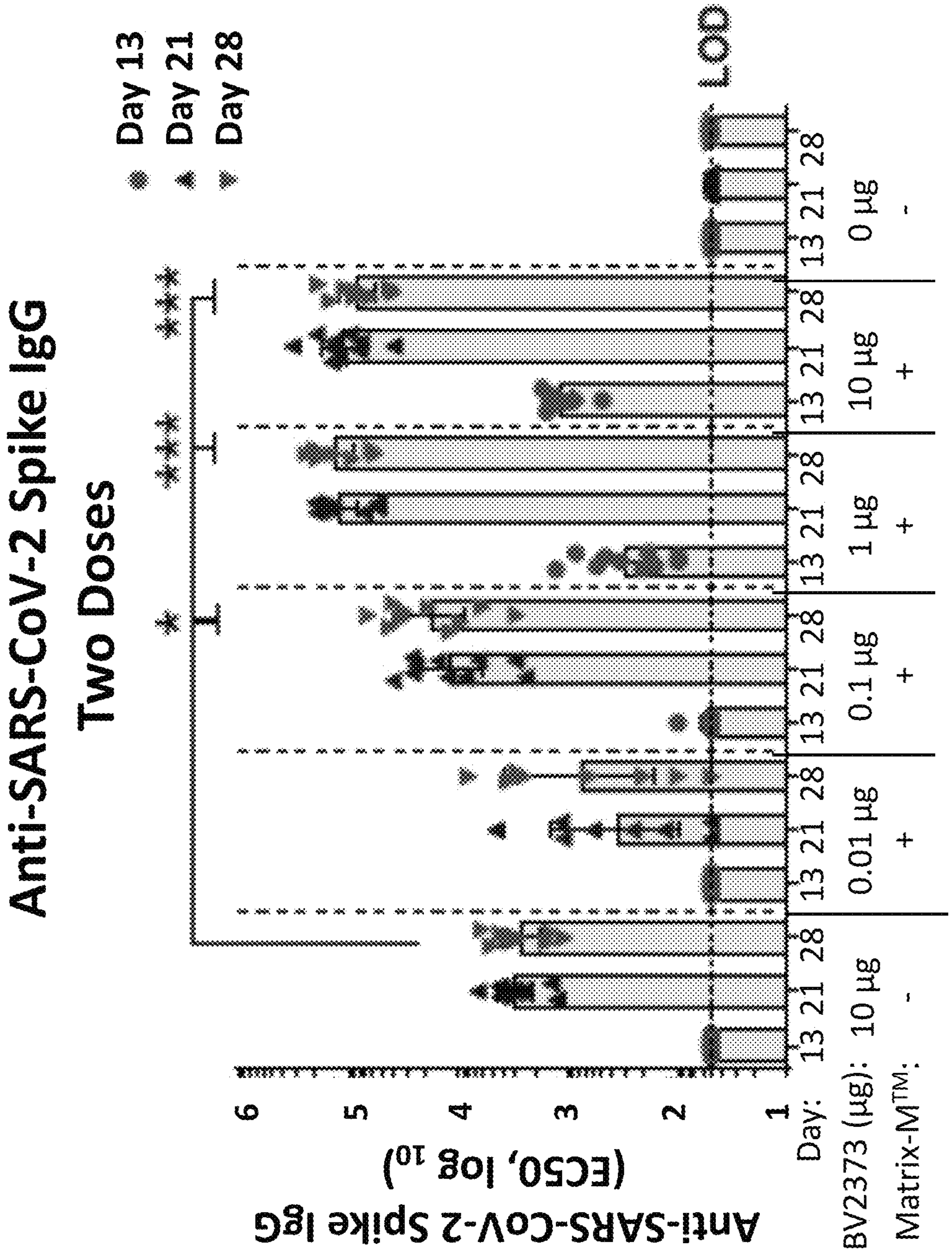
Figure 13B:
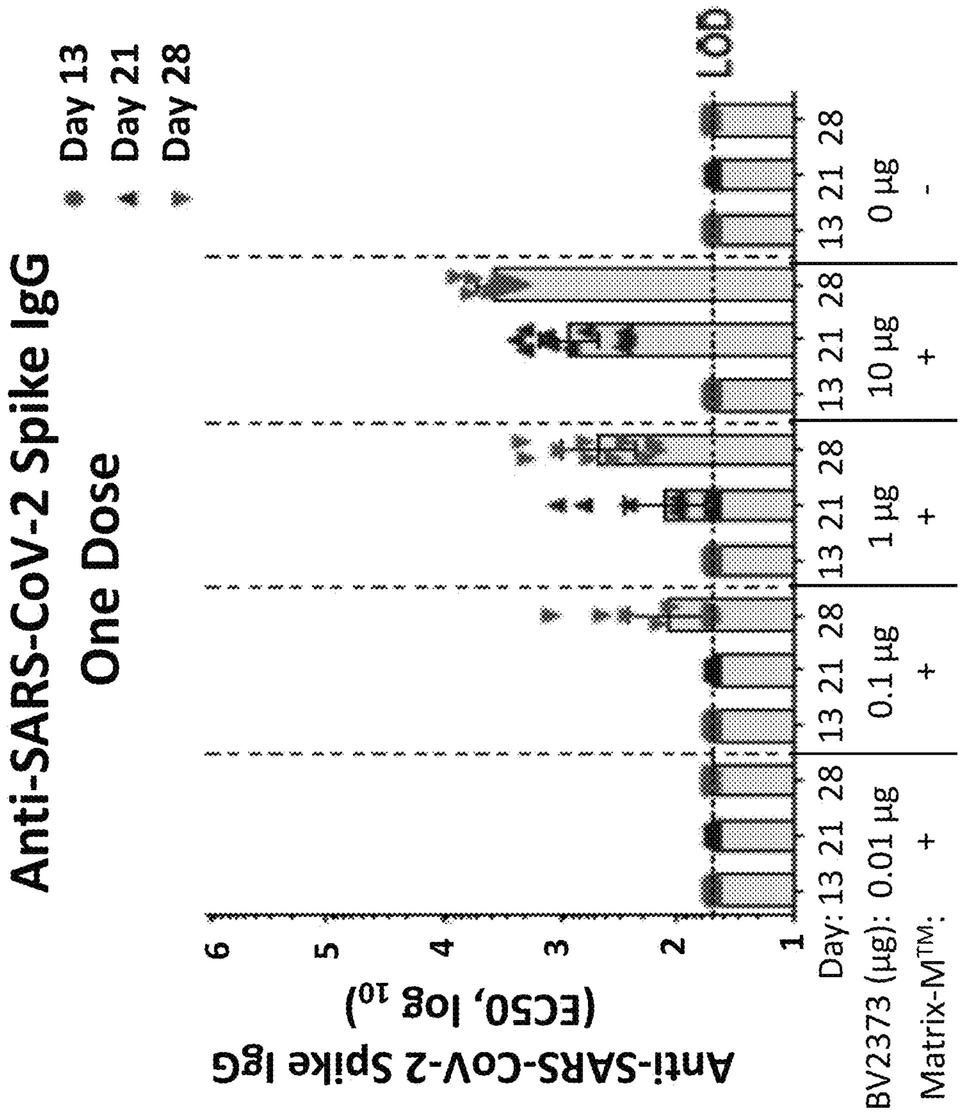

FIGS. 13A-B show anti-CoV S polypeptide IgG titers 13 days, 21 days, and 28 days after immunization of mice with two doses (FIG. 13A) and one dose of 0.1 μg to 10 μg of BV2373 with or without Fraction A and Fraction C iscom matrix (e.g., MATRIX-M™) (FIG. 13B).

Figure 14:
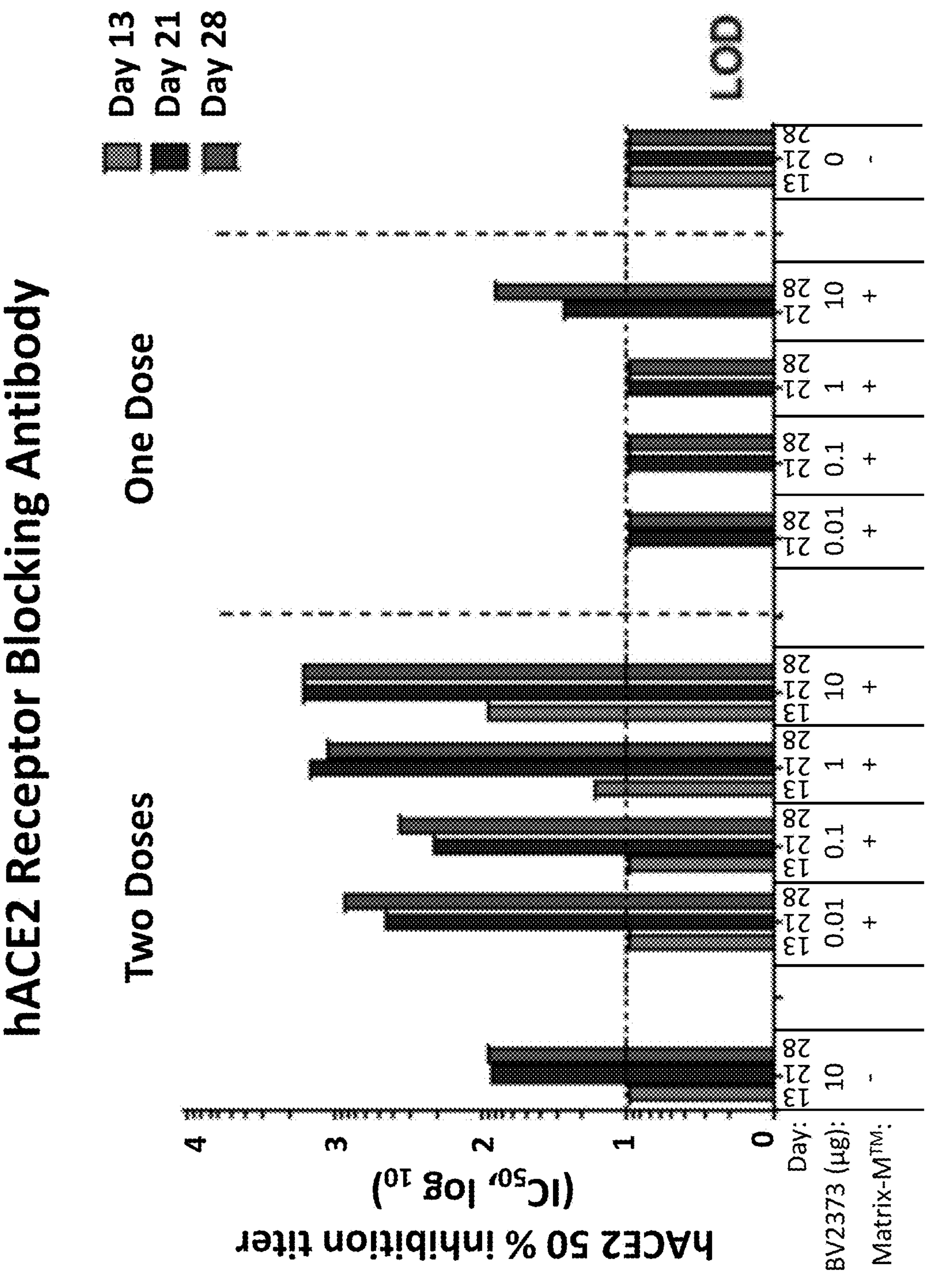

FIG. 14 shows the induction of antibodies that block interaction of hACE2 in mice immunized with one dose or two doses of 0.1 μg to 10 μg of BV2373 with or without MATRIX-M™.

Figure 15:
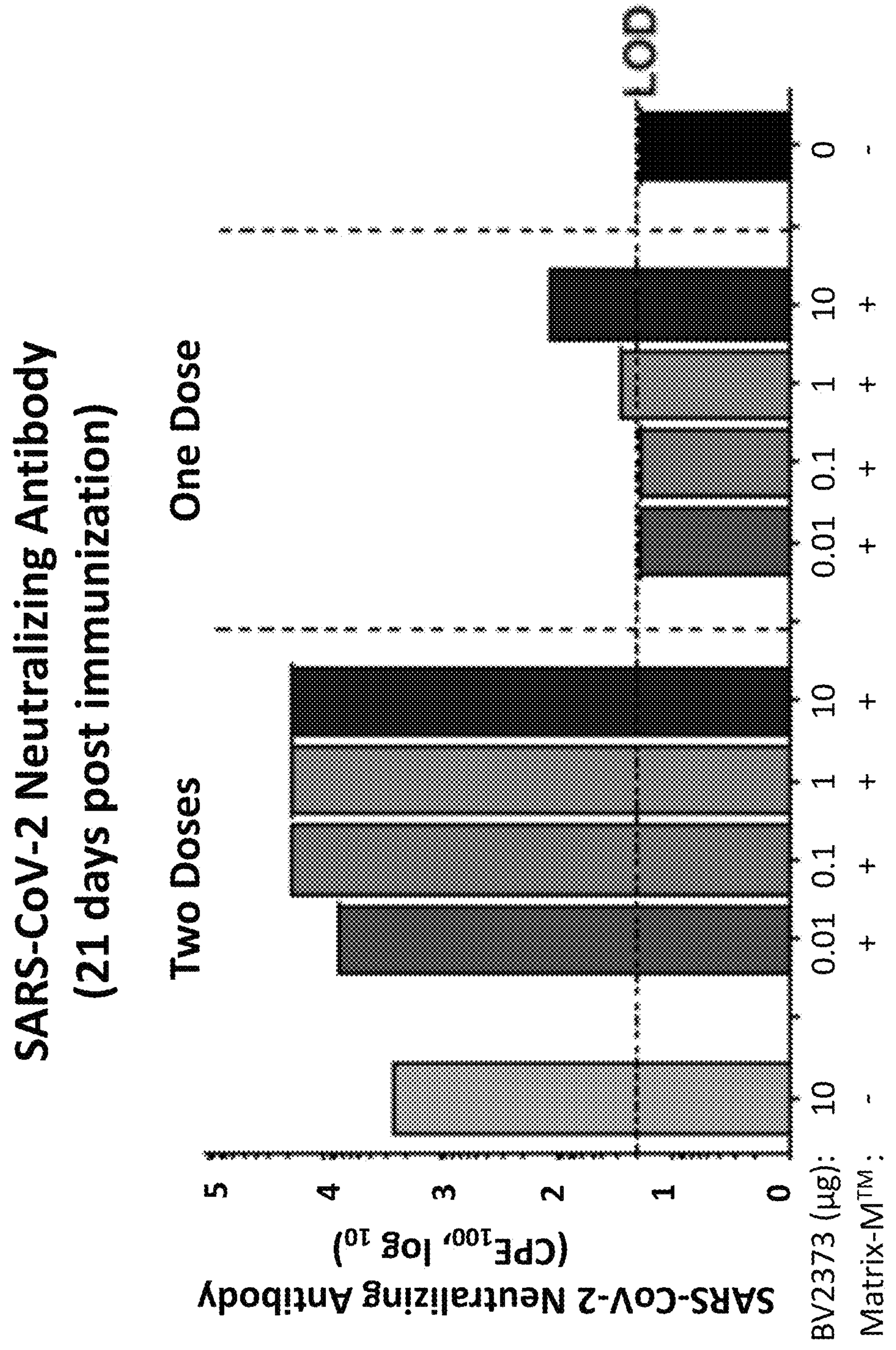

FIG. 15 shows virus neutralizing antibodies detected in mice immunized with one dose or two doses of 0.1 μg to 10 μg of BV2373 with or without MATRIX-M™.

Figure 16:
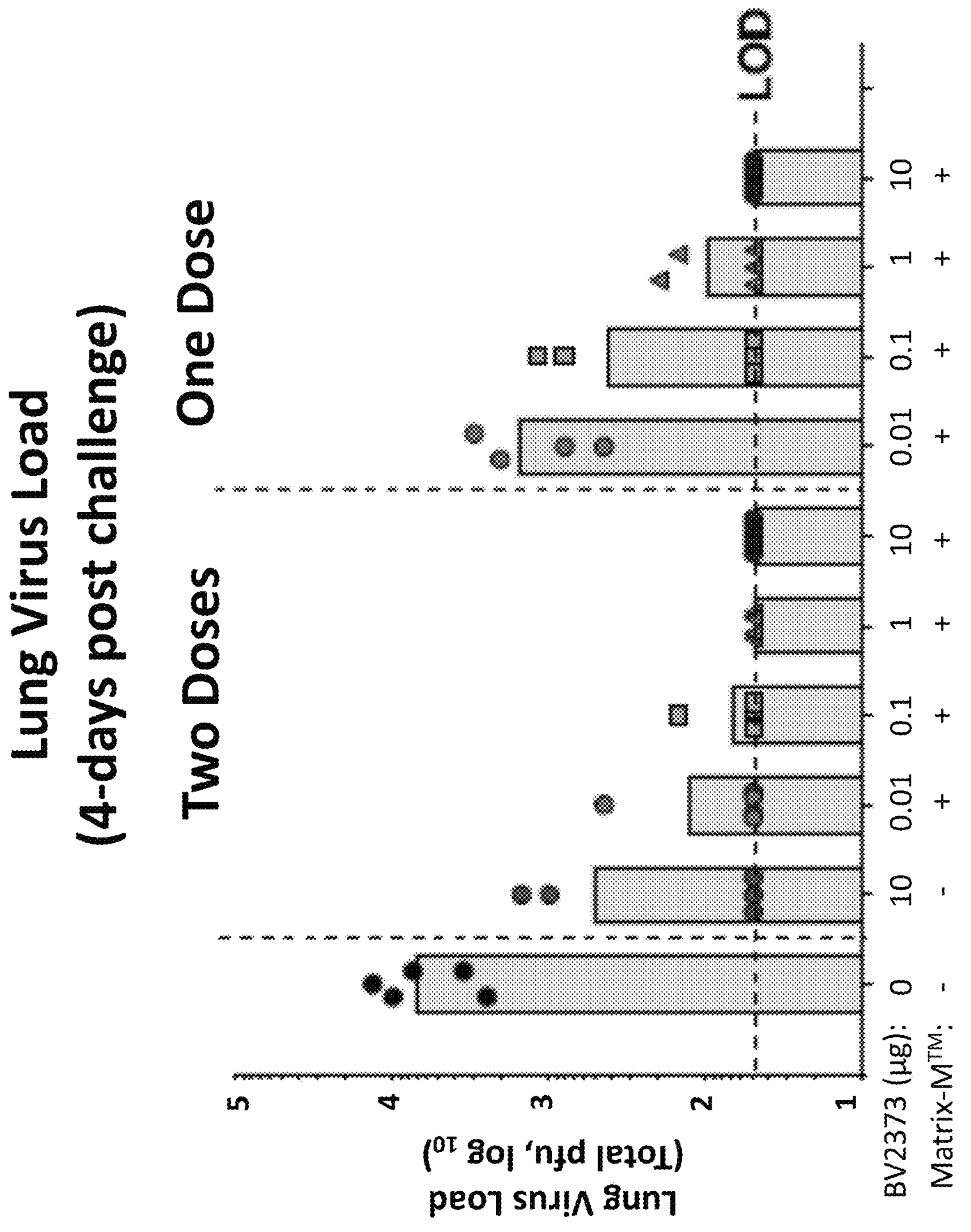

FIG. 16 shows the virus load (SARS-CoV-2) in the lungs of Ad/CMV/hACE2 mice immunized with either a single dose of BV2373 or two doses of BV2373 spaced 14 days apart with or without MATRIX-M™.

Figure 17A:
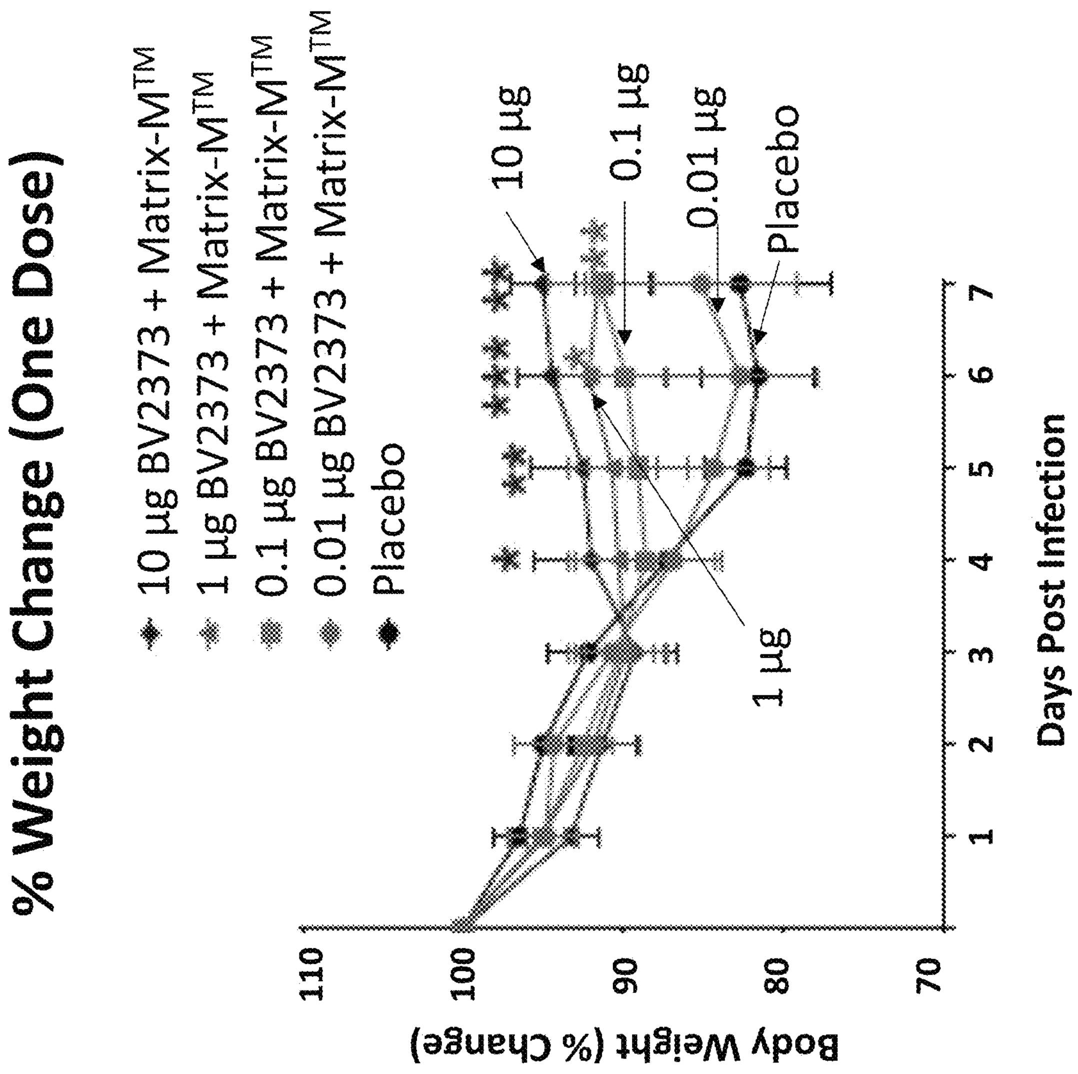
Figure 17B:
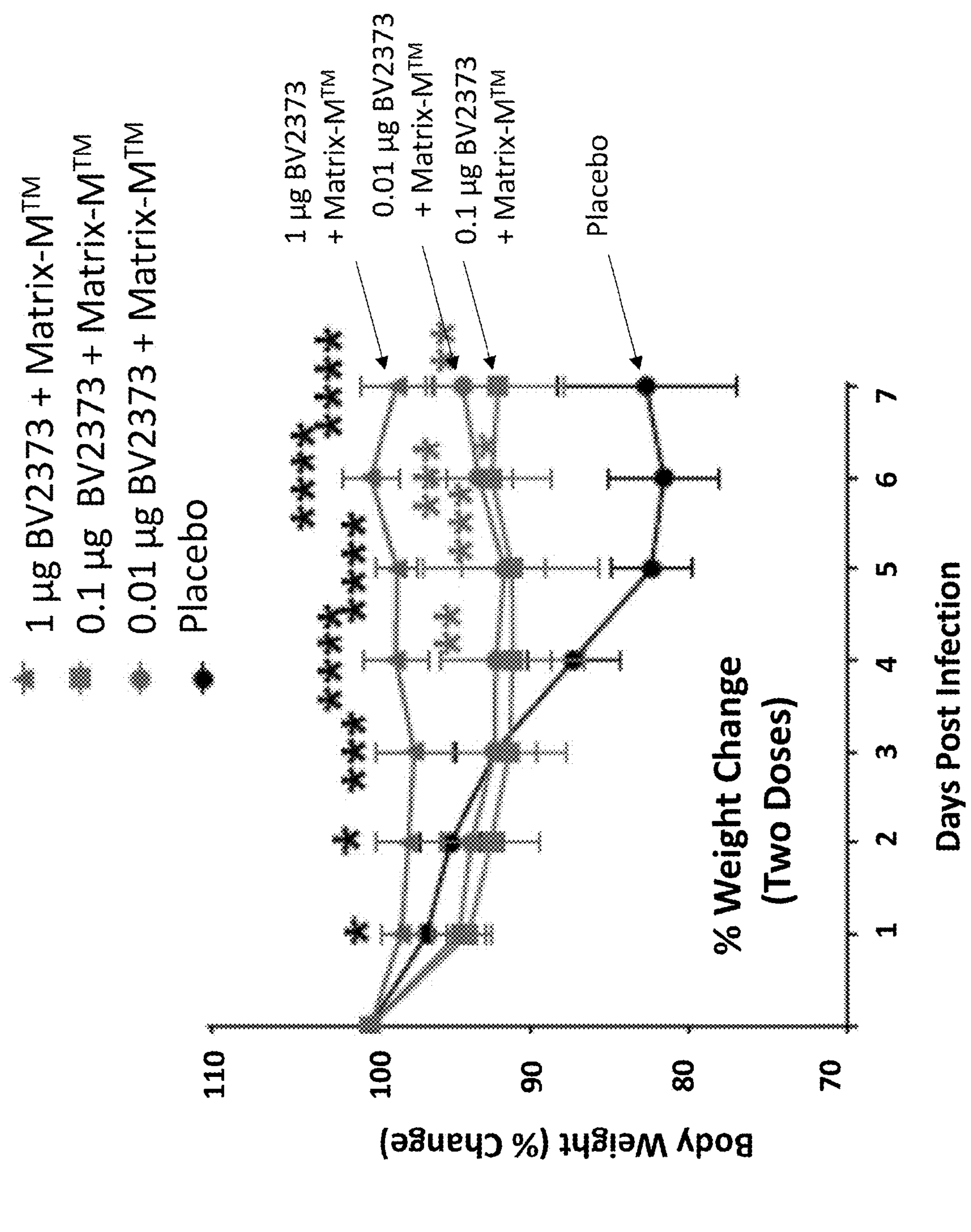
Figure 17C:
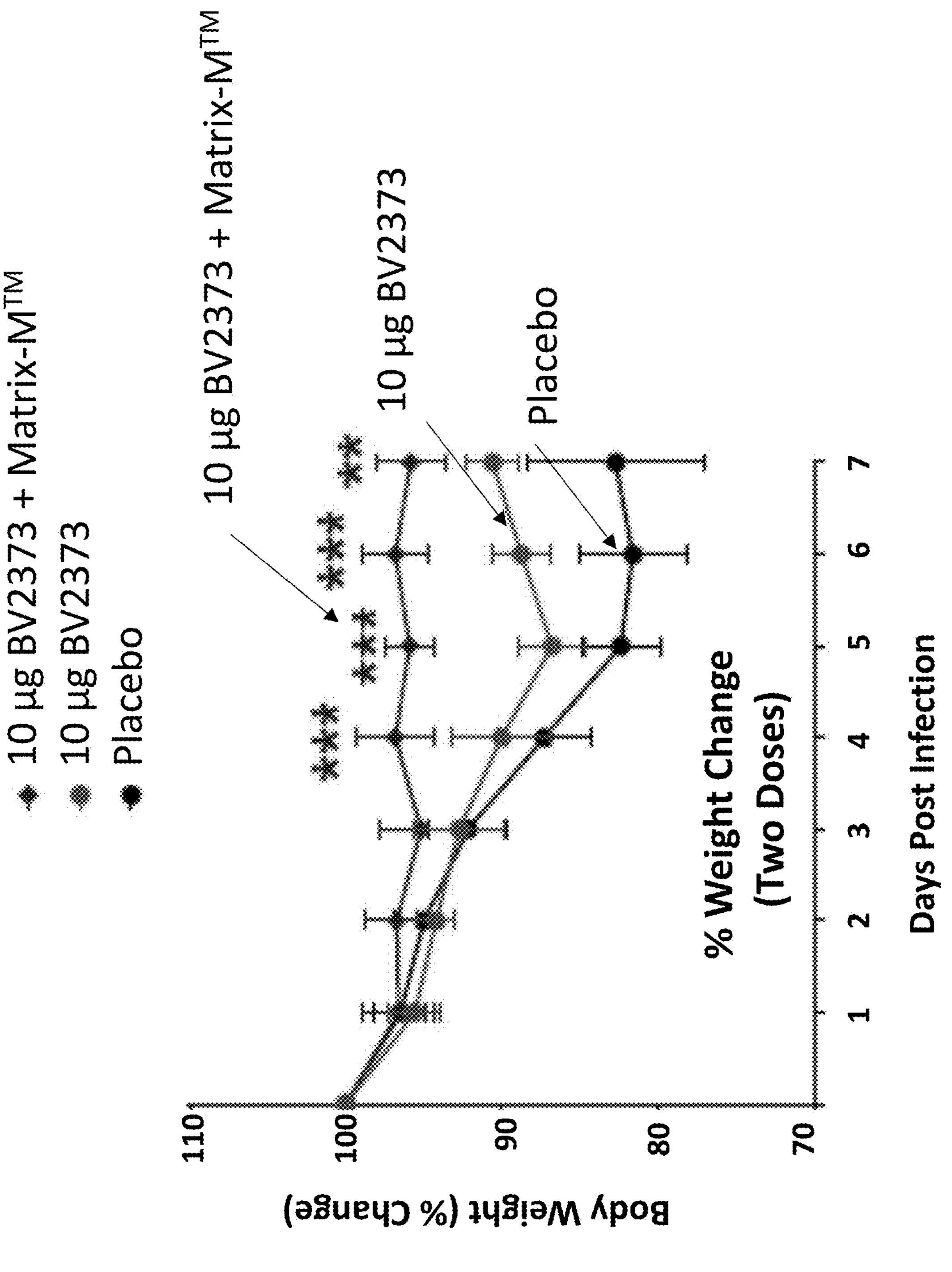

FIGS. 17A-C shows weight loss exhibited by mice after immunization with BV2373. FIG. 17A shows the effect of immunization on weight loss with a single 0.01 μg, 0.1 μg, 1 μg, or 10 μg of BV2373 plus MATRIX-M™. FIG. 17B shows the effect of immunization on weight loss with two doses of BV2373 (0.01 μg, 0.1 μg, 1 μg) plus MATRIX-M™. FIG. 17C shows the effect of immunization on weight loss with two doses of BV2373 (10 μg) in the presence or absence of MATRIX-M™.

Figure 18A:
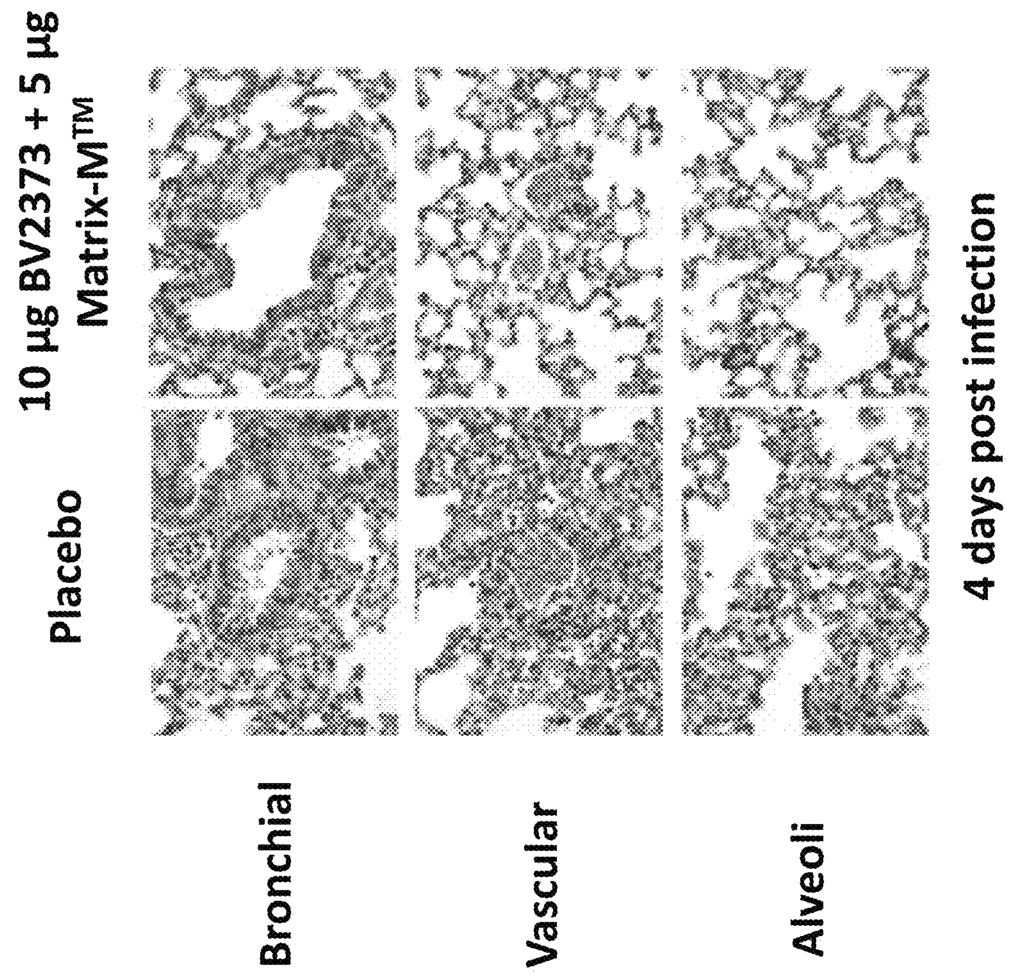
Figure 18B:
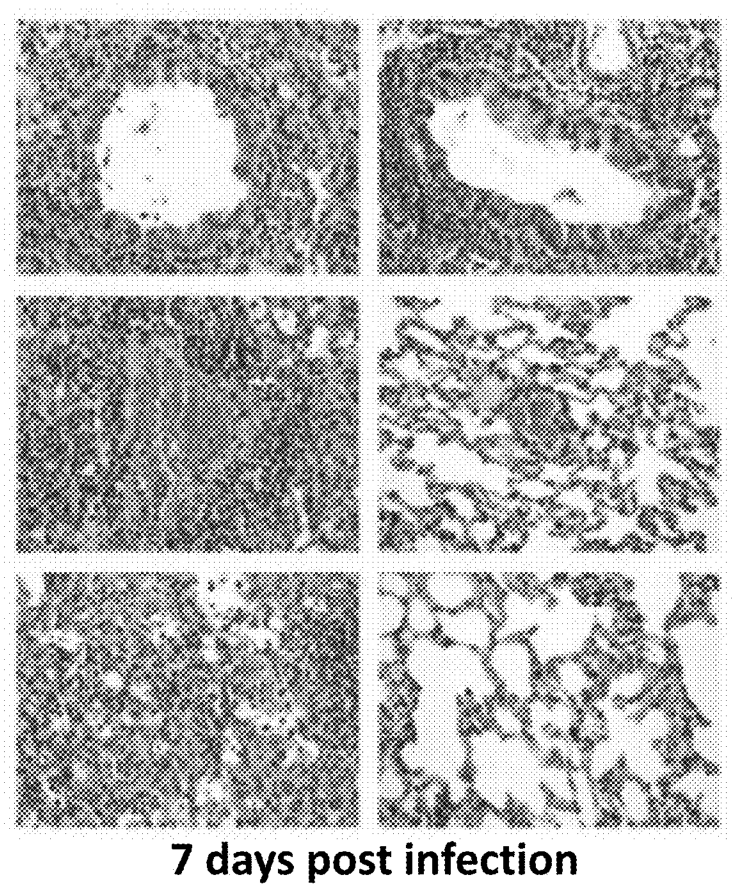

FIGS. 18A-B shows the effect of BV2373 on lung histopathology of mice four days (FIG. 18A) or seven days (FIG. 18B) after infection with SARS-CoV-2.

Figure 19:
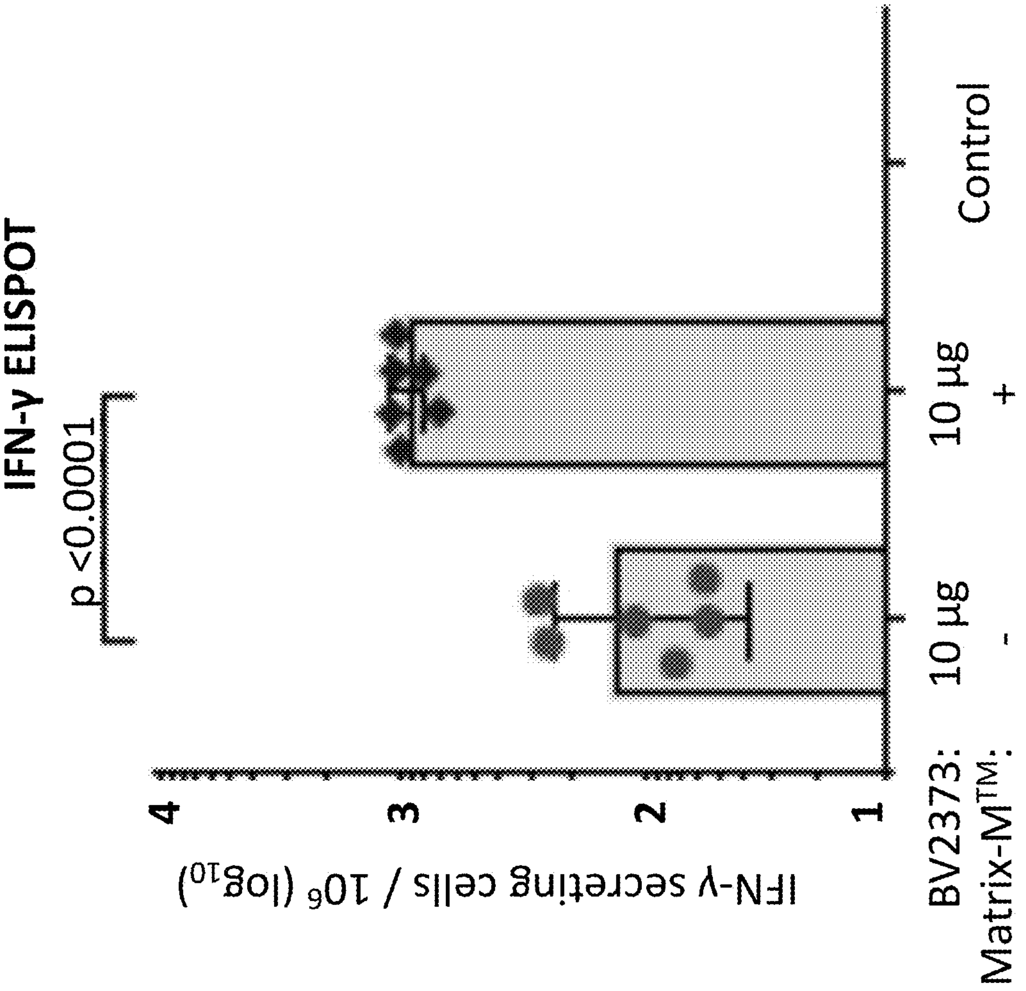

FIG. 19 shows the number of IFN-γ secreting cells after ex vivo stimulation in the spleens of mice immunized with BV2373 in the absence of adjuvant compared to mice immunized with BV2373 in the presence of MATRIX-M™.

Figure 20A:
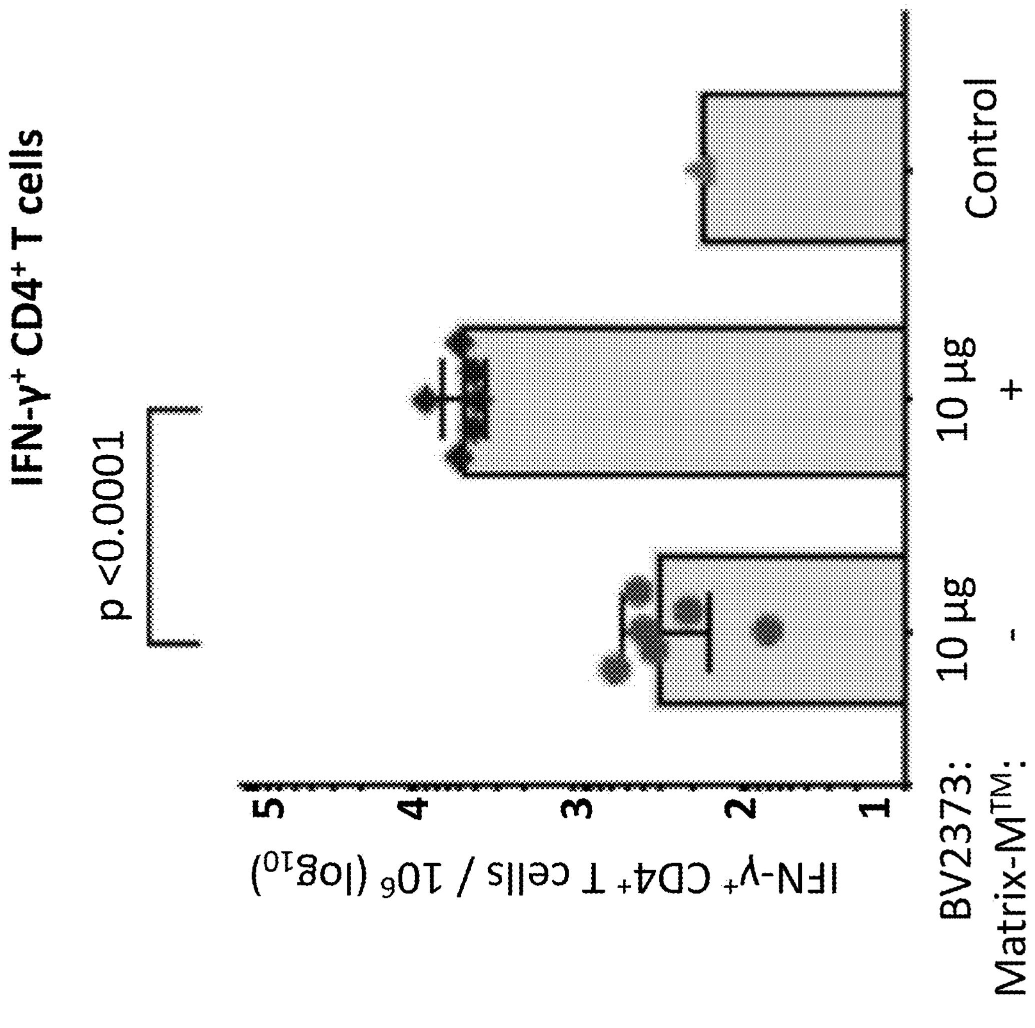
Figure 20B:
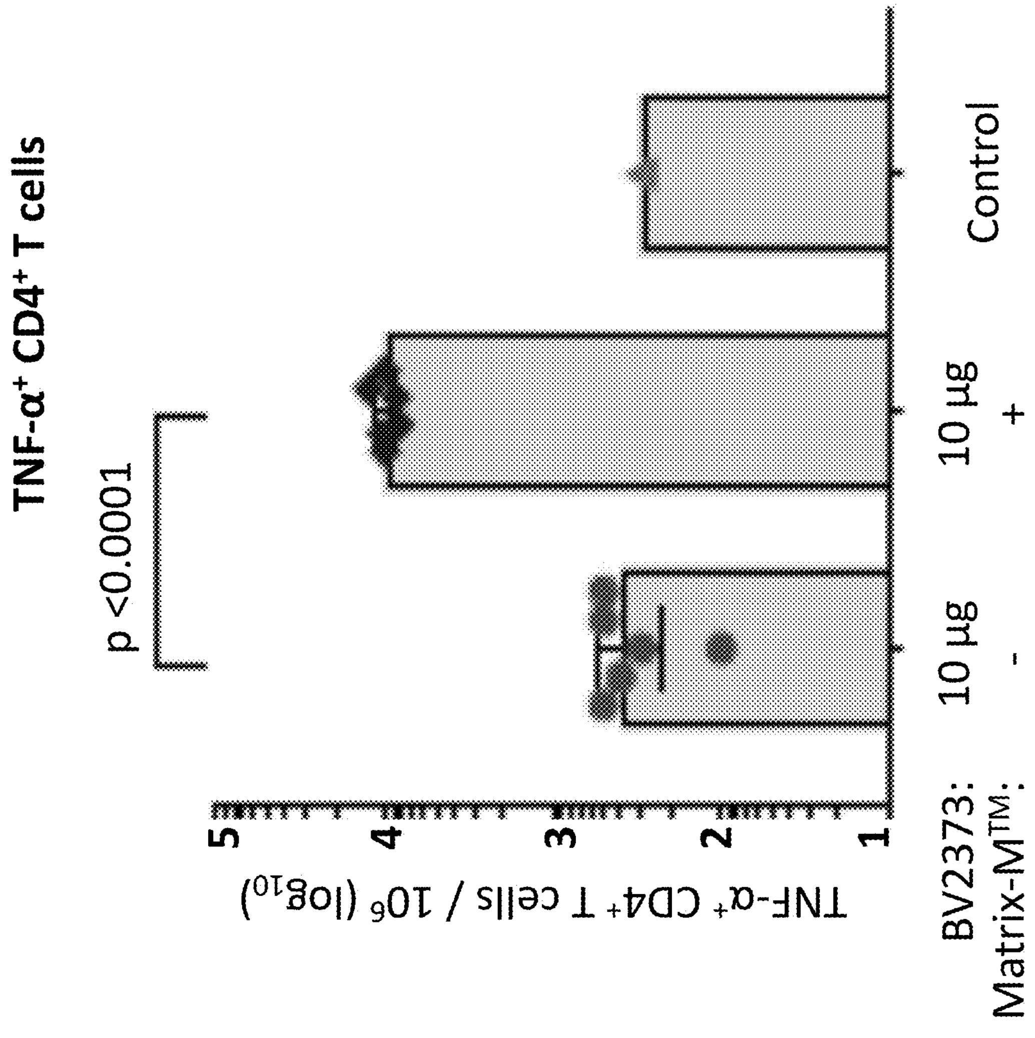
Figure 20C:
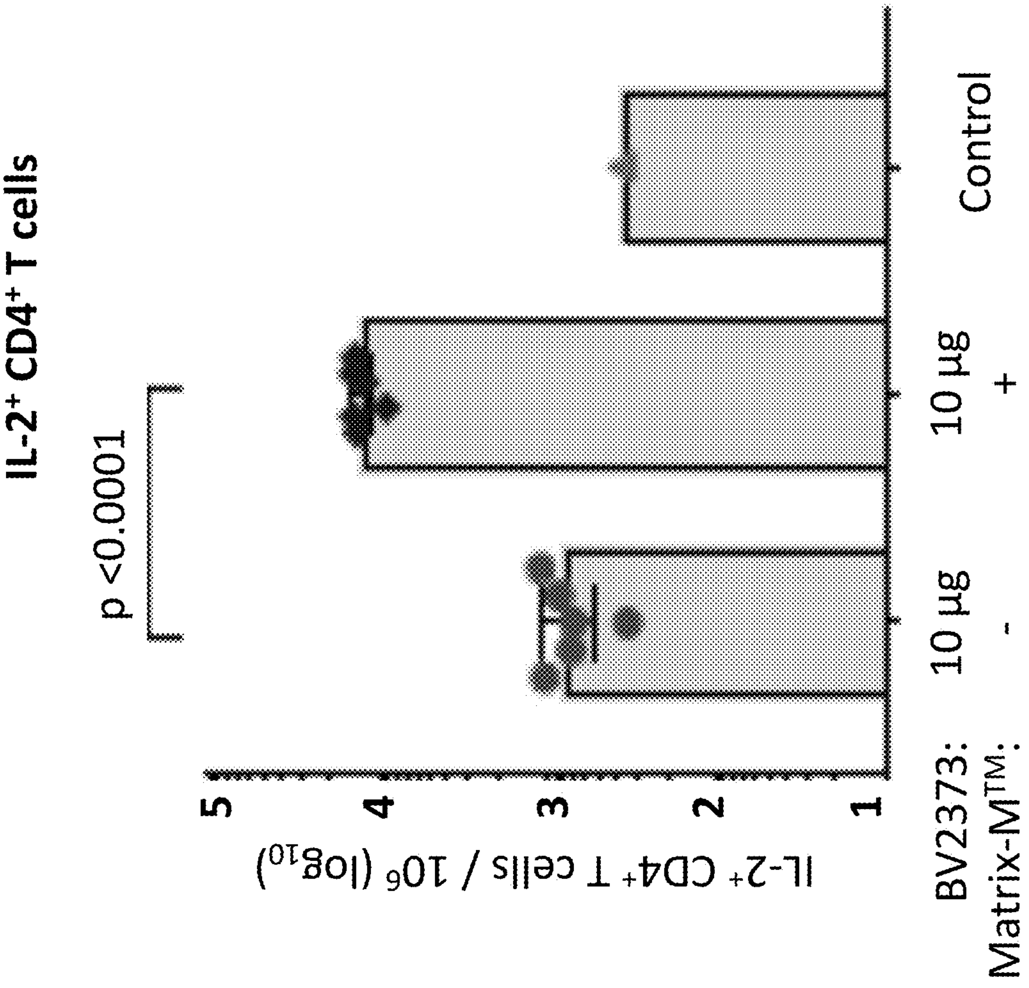
Figure 20D:
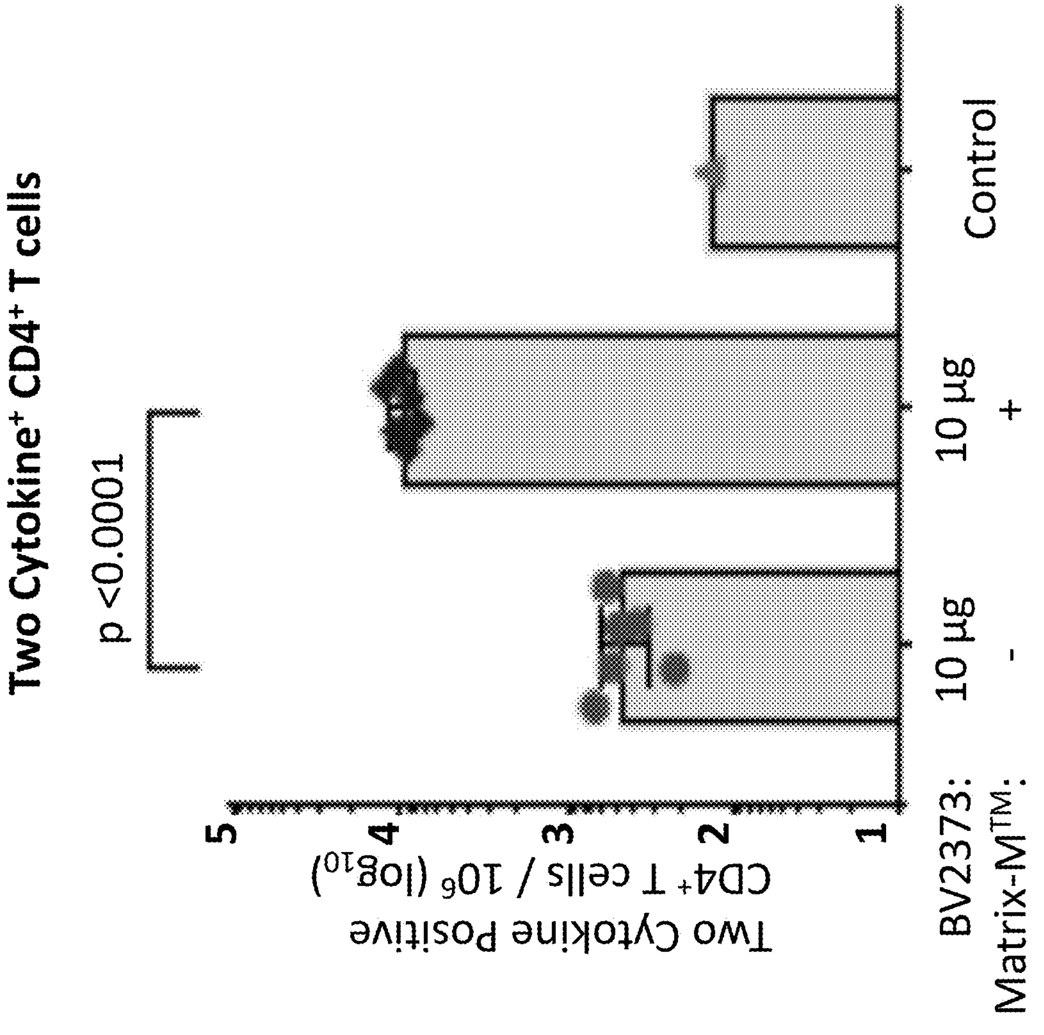
Figure 20E:
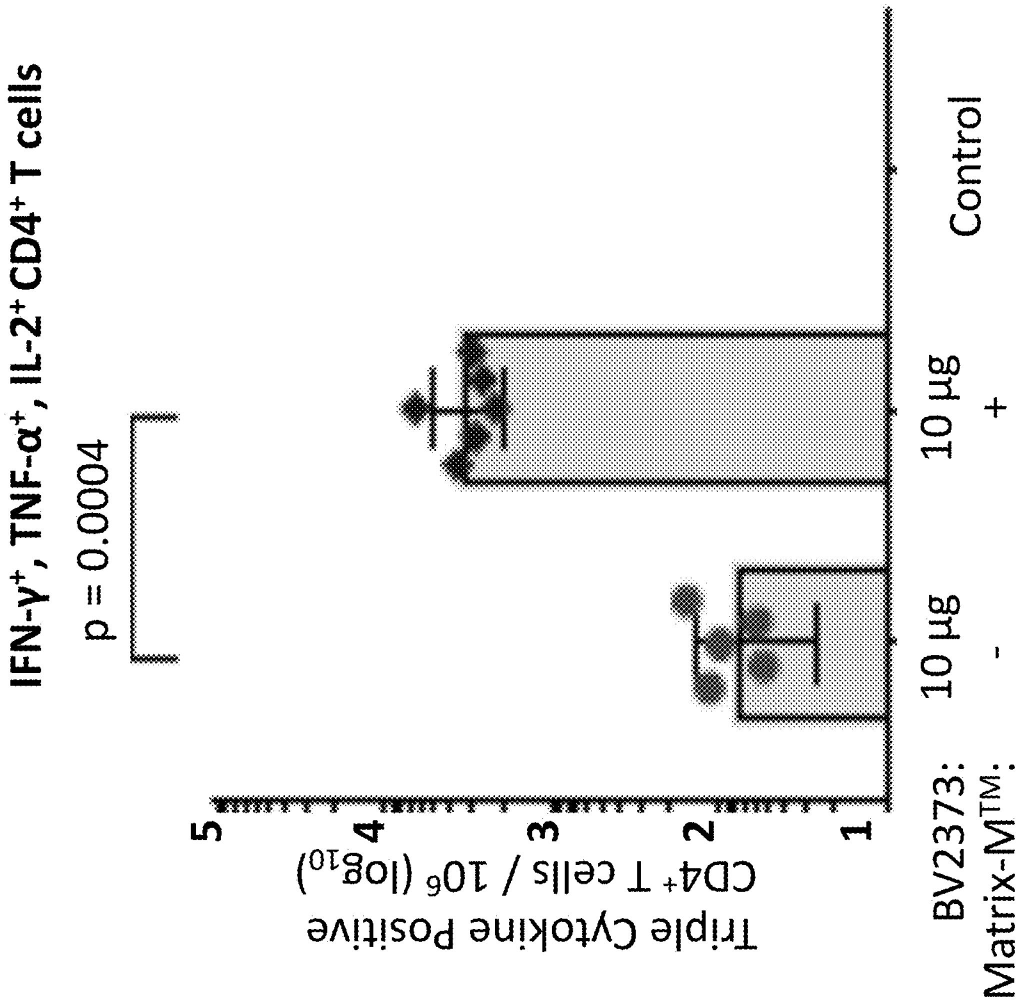

FIGS. 20A-E shows the frequency of cytokine secreting CD4+ T cells in the spleens of mice immunized with BV2373 in the presence or absence of MATRIX-M™. FIG. 20A shows the frequency of IFN-γ secreting CD4+ T cells. FIG. 20B shows the frequency of TNF-α secreting CD4+ T cells. FIG. 20C shows the frequency of IL-2 secreting CD4+ T cells. FIG. 20D shows the frequency of CD4+ T cells that secrete two cytokines selected from IFN-γ, TNF-α, and IL-2. FIG. 20E shows the frequency of CD4+ T cells that express IFN-γ, TNF-α, and IL-2.

Figure 21A:
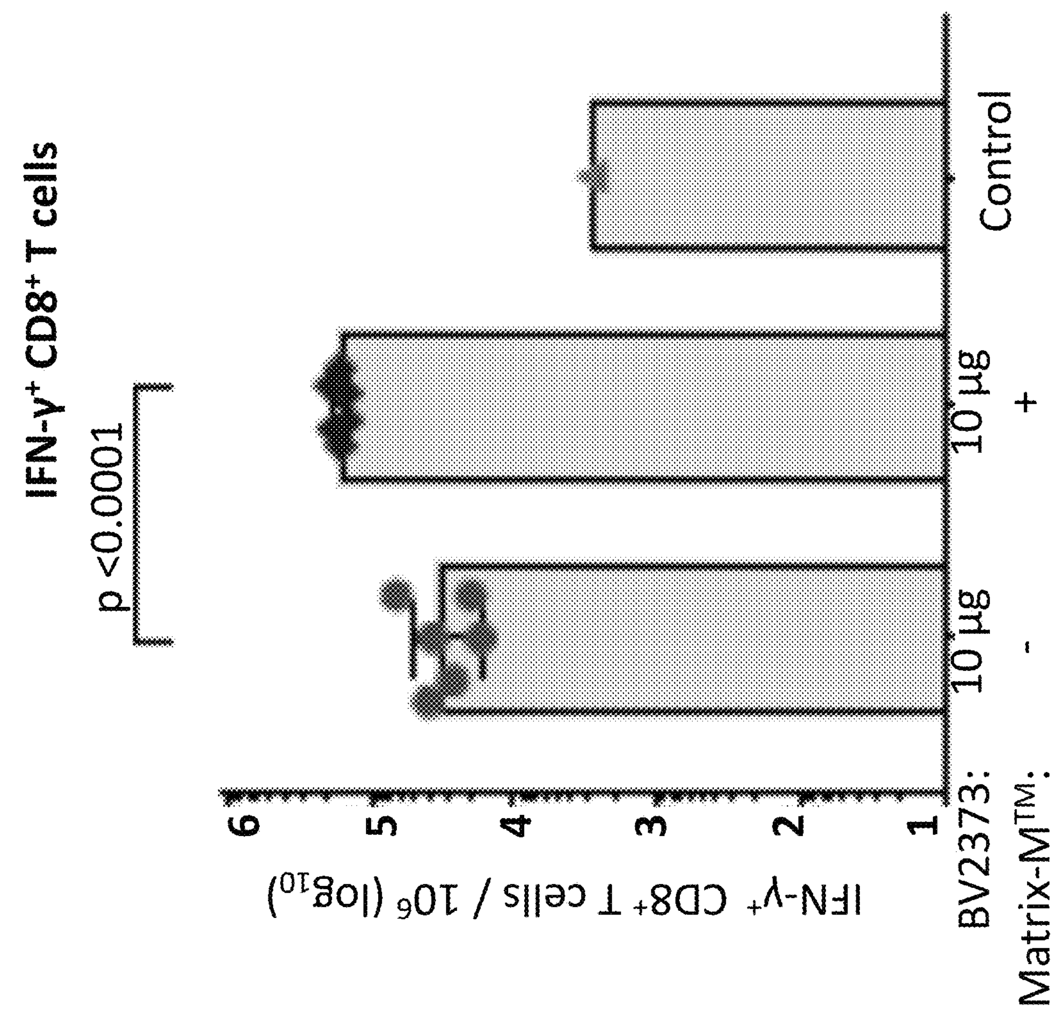
Figure 21B:
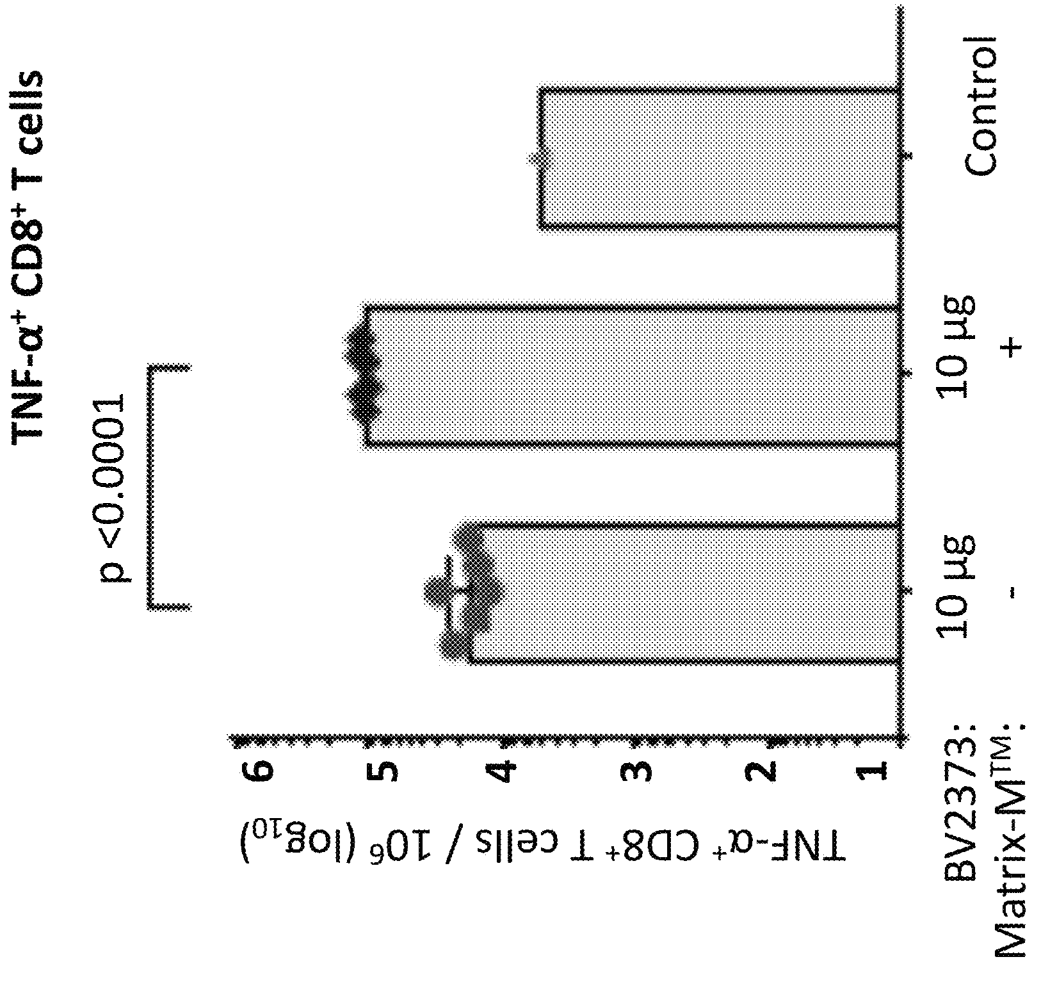
Figure 21C:
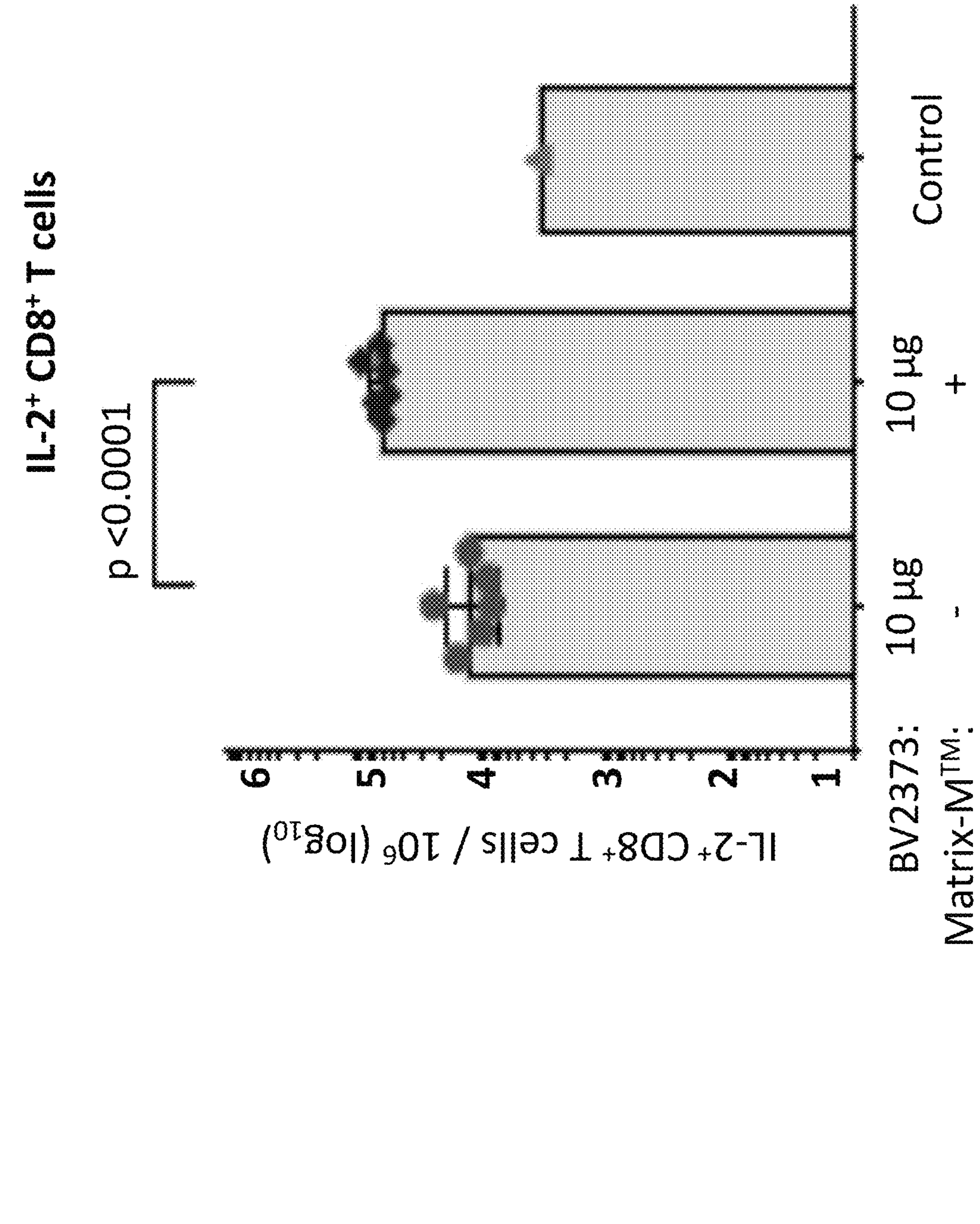
Figure 21D:
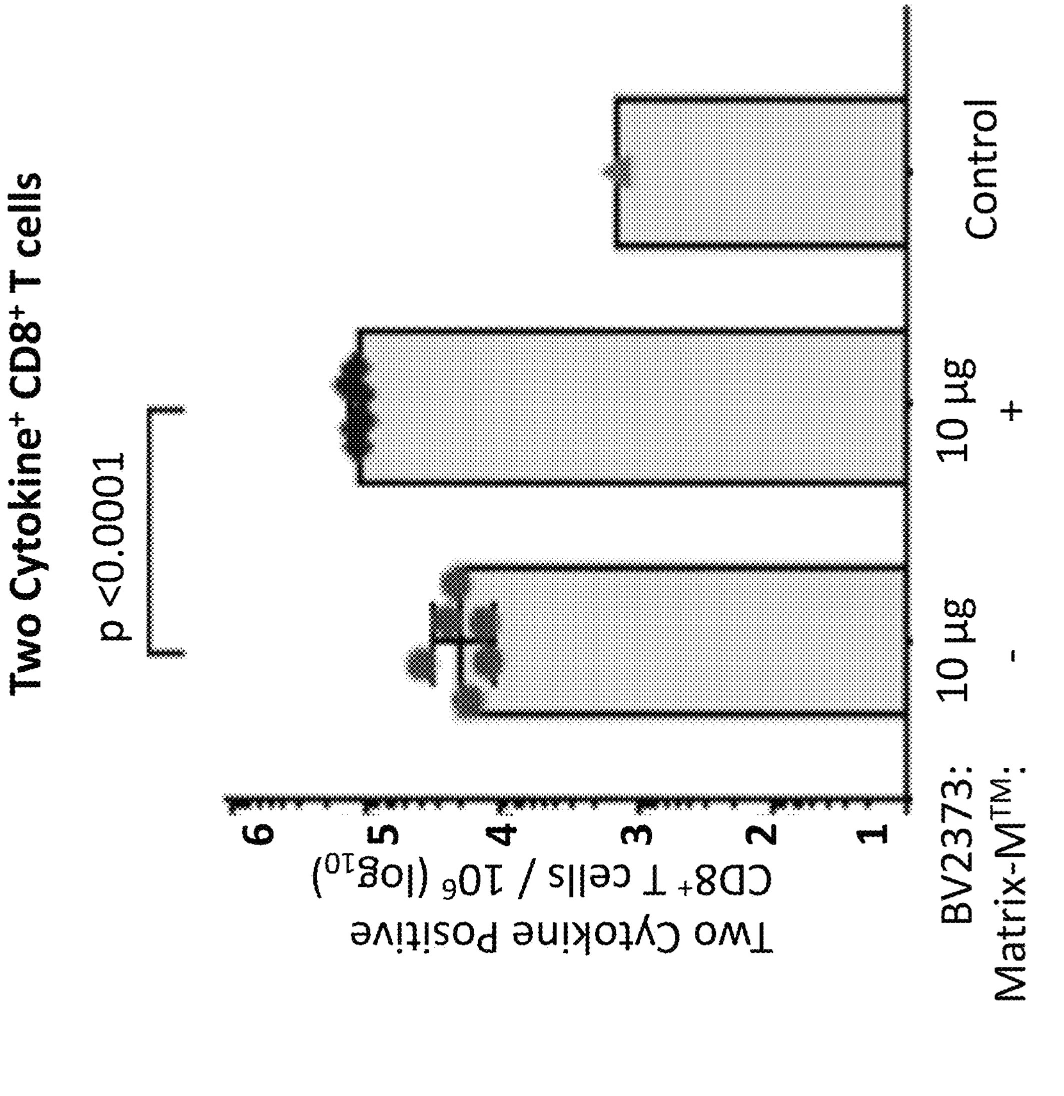
Figure 21E:
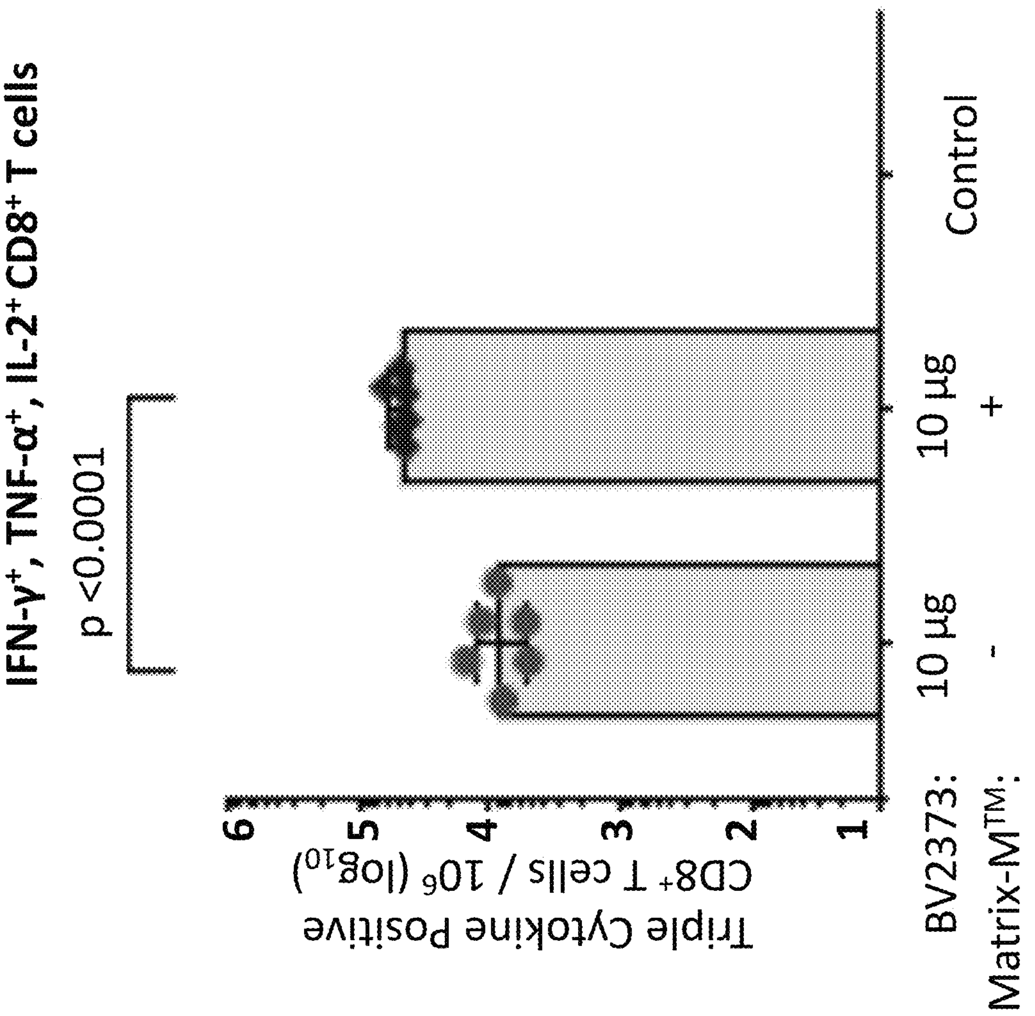

FIGS. 21A-E shows the frequency of cytokine secreting $CD8^+$ T cells in the spleens of mice immunized with BV2373 in the presence or absence of MATRIX-M™. FIG. 21A shows the frequency of IFN-γ secreting $CD8^+$ T cells. FIG. 21B shows the frequency of TNF-α secreting $CD8^+$ T cells. FIG. 21C shows the frequency of IL-2 secreting $CD8^+$ T cells. FIG. 20D shows the frequency of $CD8^+$ T cells that secrete two cytokines selected from IFN-γ, TNF-α, and IL-2. FIG. 21E shows the frequency of $CD8^+$ T cells that express IFN-γ, TNF-α, and IL-2.

Figure 22:
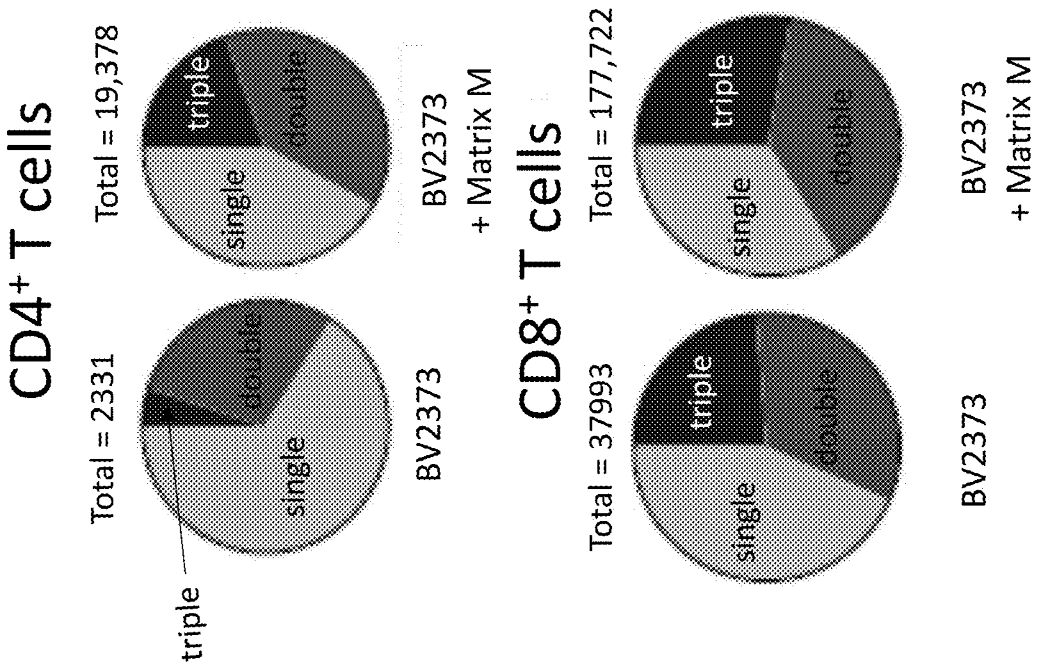

FIG. 22 illustrates the frequency of $CD4^+$ or $CD8^+$ cells that express one (single), two (double), or three (triple) cytokines selected from IFN-γ, TNF-α, and IL-2 in the spleens of mice immunized with BV2373 in the presence or absence of MATRIX-M™.

Figure 23A:
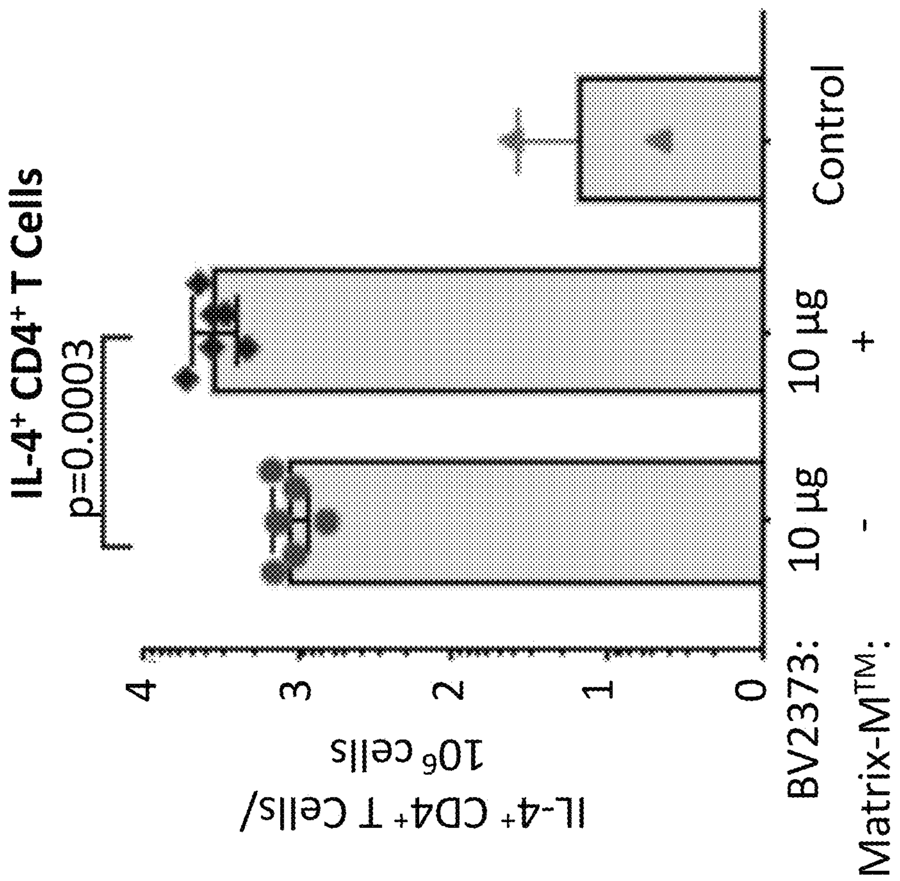
Figure 23B:
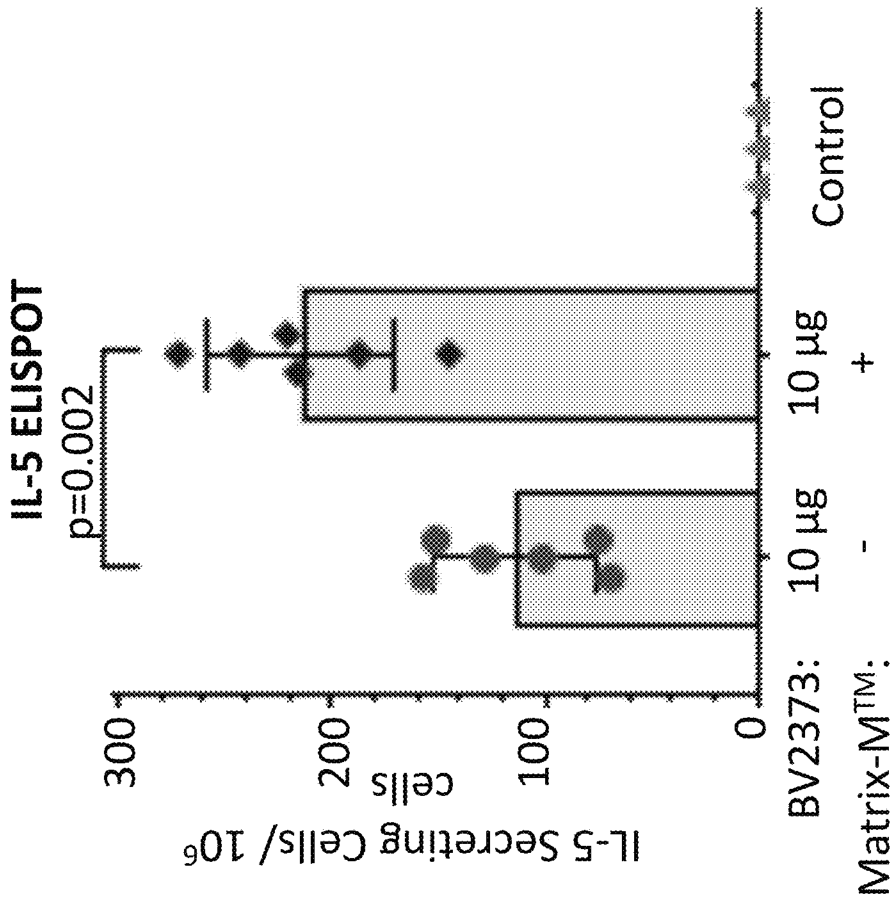
Figure 23C:
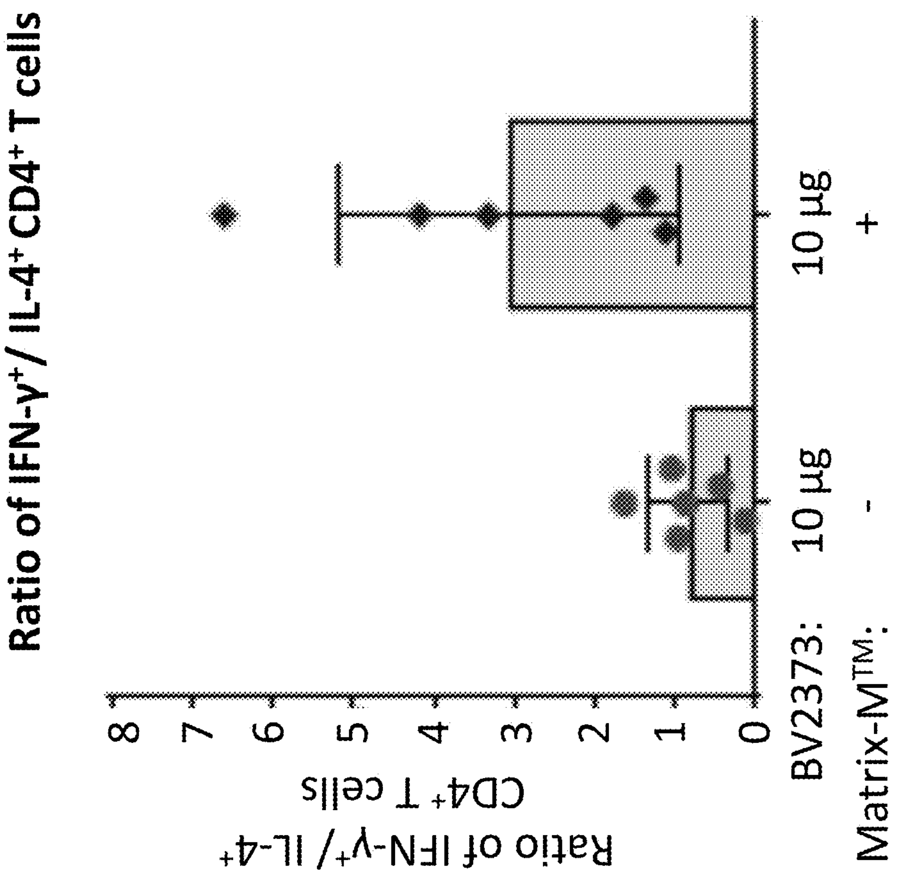

FIGS. 23A-C illustrate the effect of immunization with BV2373 in the presence or absence of MATRIX-M™ on type 2 cytokine secretion from $CD4^+$ T cells. FIG. 23A shows the frequency of IL-4 secreting cells. FIG. 23B shows the frequency of IL-5 $CD4^+$ secreting cells. FIG. 23C shows the ratio of IFN-γ secreting to IL-4 secreting $CD4^+$ T cells.

Figure 24A:
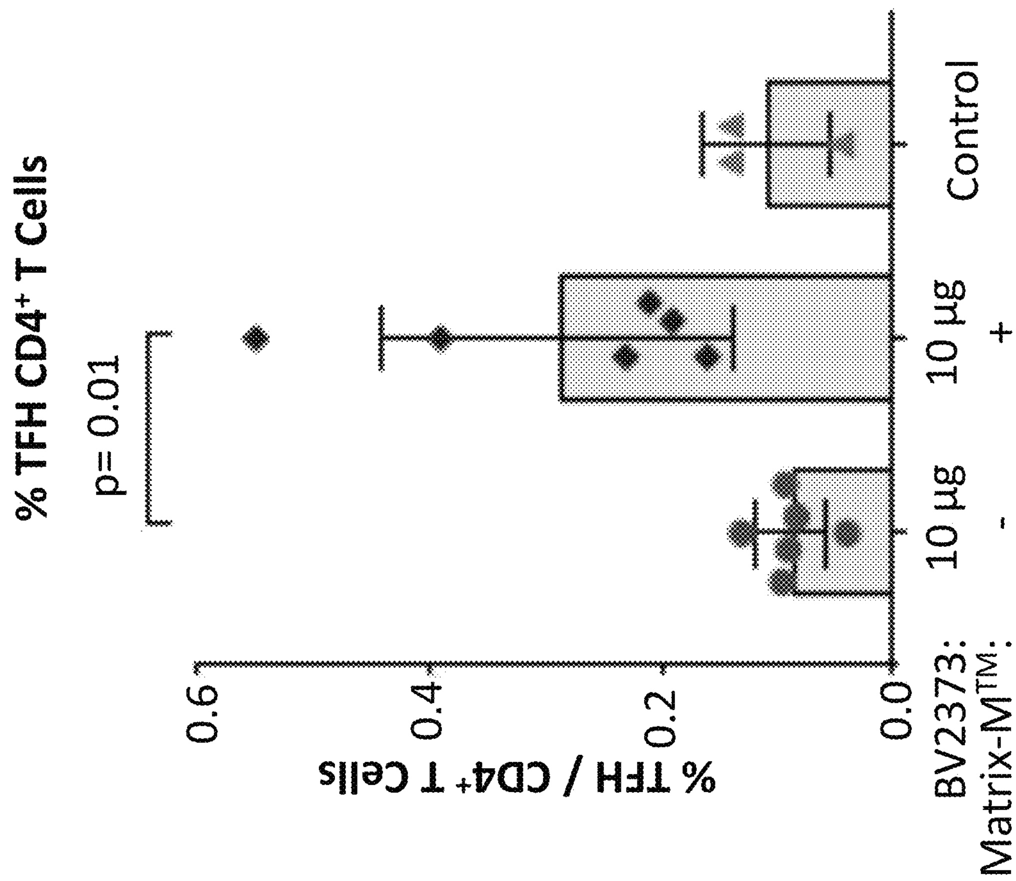
Figure 24B:
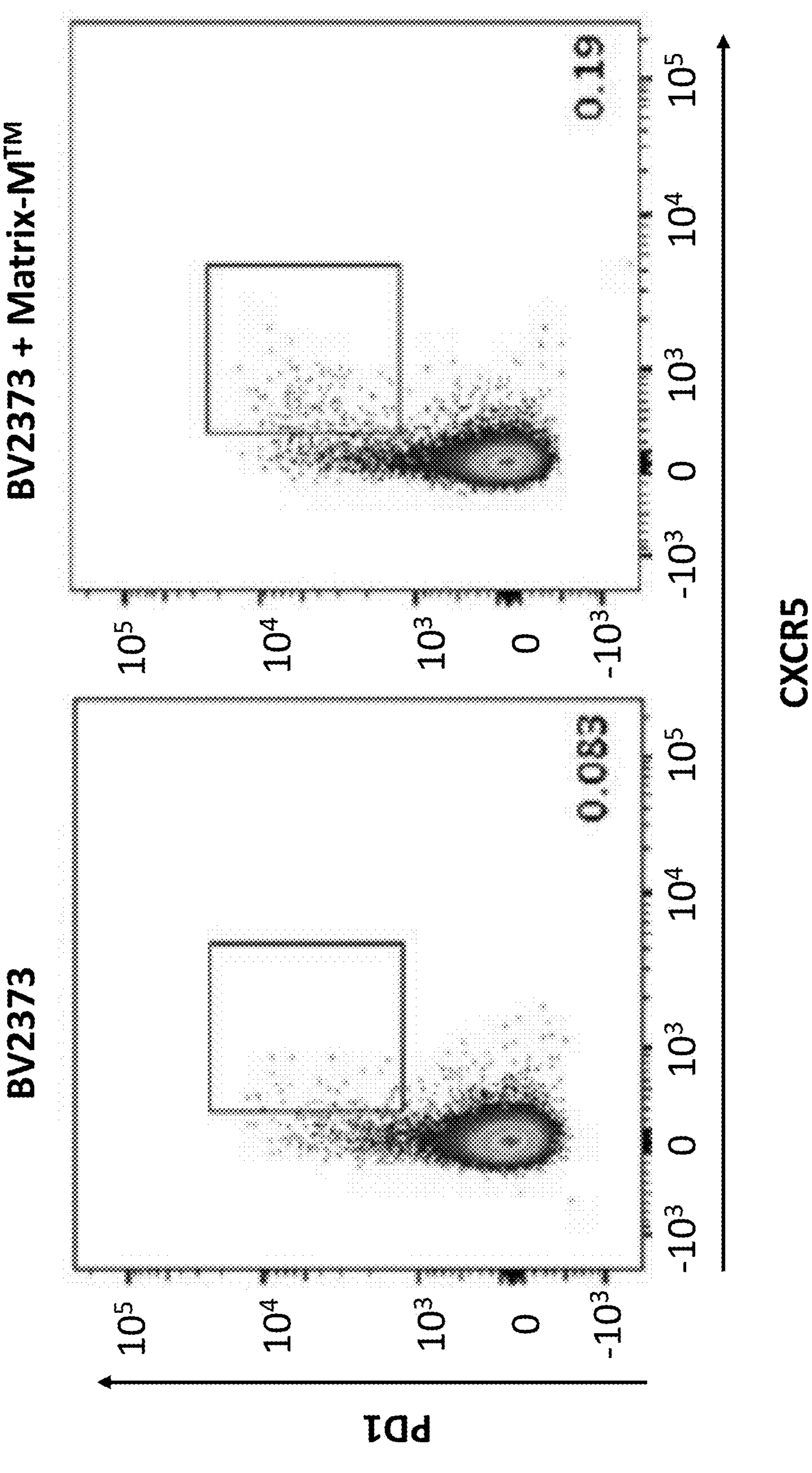

FIGS. 24A-B illustrate the effect of mouse immunization with BV2373 in the presence or absence of MATRIX-M™ on germinal center formation by assessing the presence of $CD4^+$ T follicular helper cells (TFH). FIG. 24A shows the frequency of $CD4^+$ T follicular helper cells in spleens, and FIG. 24B shows the phenotype (e.g. $CD4^+$ $CXCR5^+$ PD-$1^+$) of the $CD4^+$ T follicular helper cells.

Figure 25A:
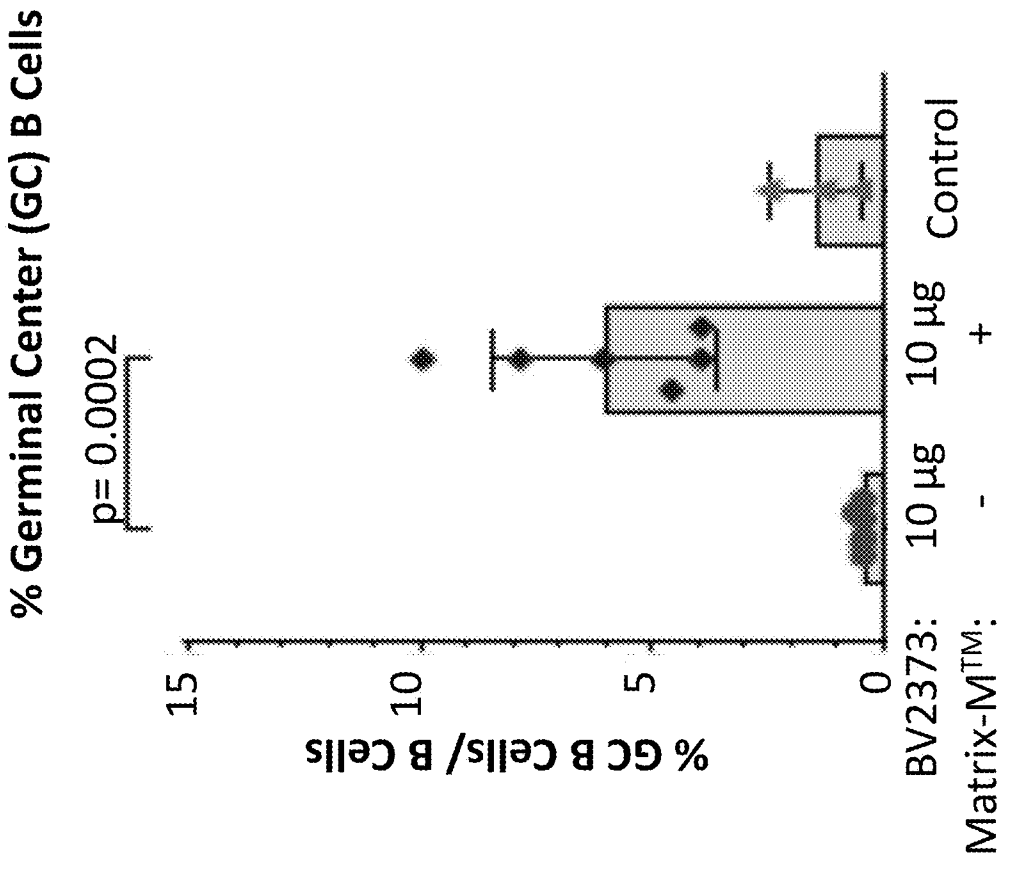
Figure 25B:
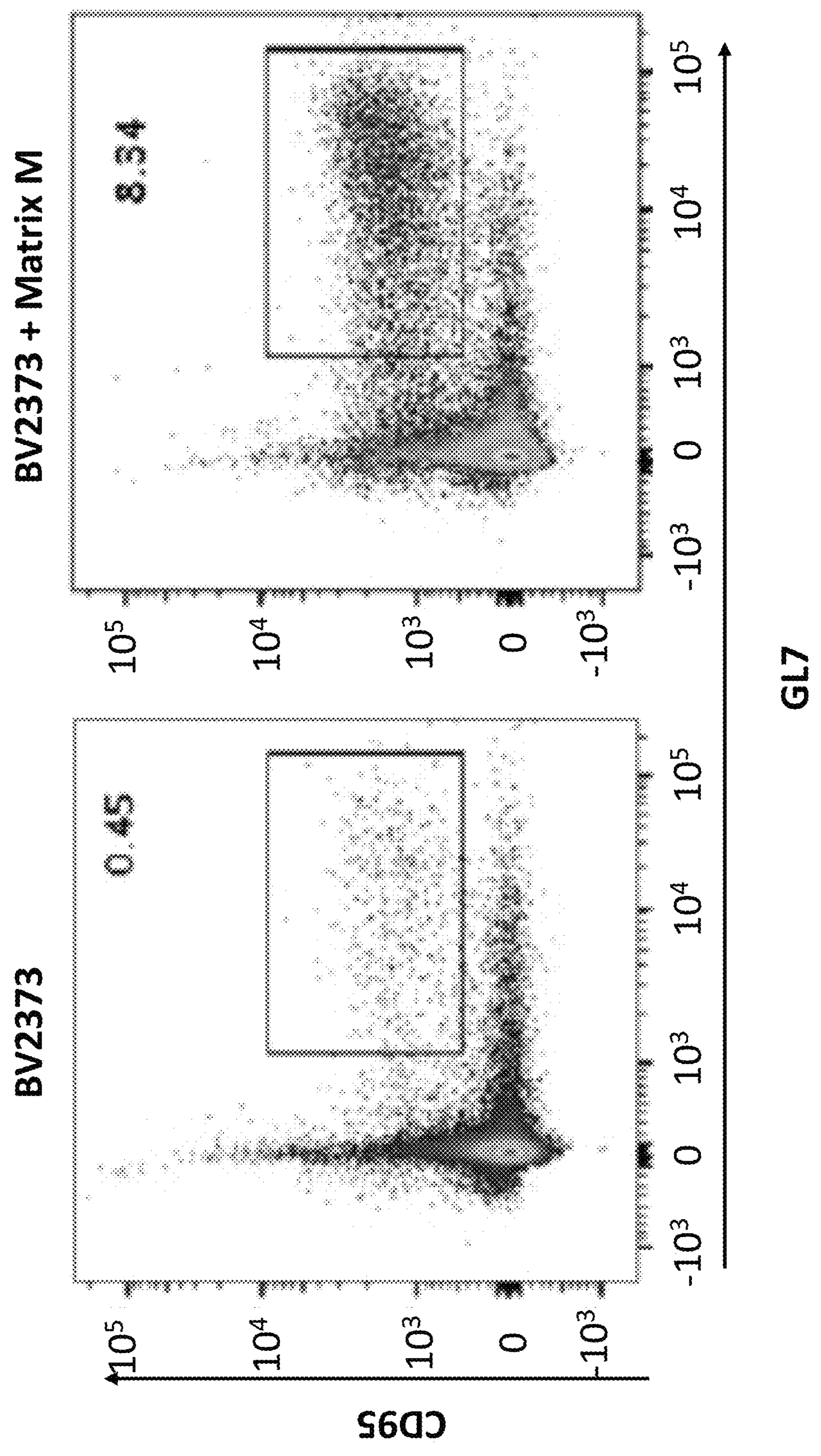

FIGS. 25A-B illustrate the effect of mouse immunization with BV2373 in the presence or absence of MATRIX-M™ on germinal center formation by assessing the presence of germinal center (GC) B cells. FIG. 25A shows the frequency of GC B cells in spleens, and FIG. 25B reveals the phenotype (e.g. $CD19^+$ $GL7^+$ CD-$95^+$) of the $CD4^+$ T follicular helper cells.

Figure 26A:
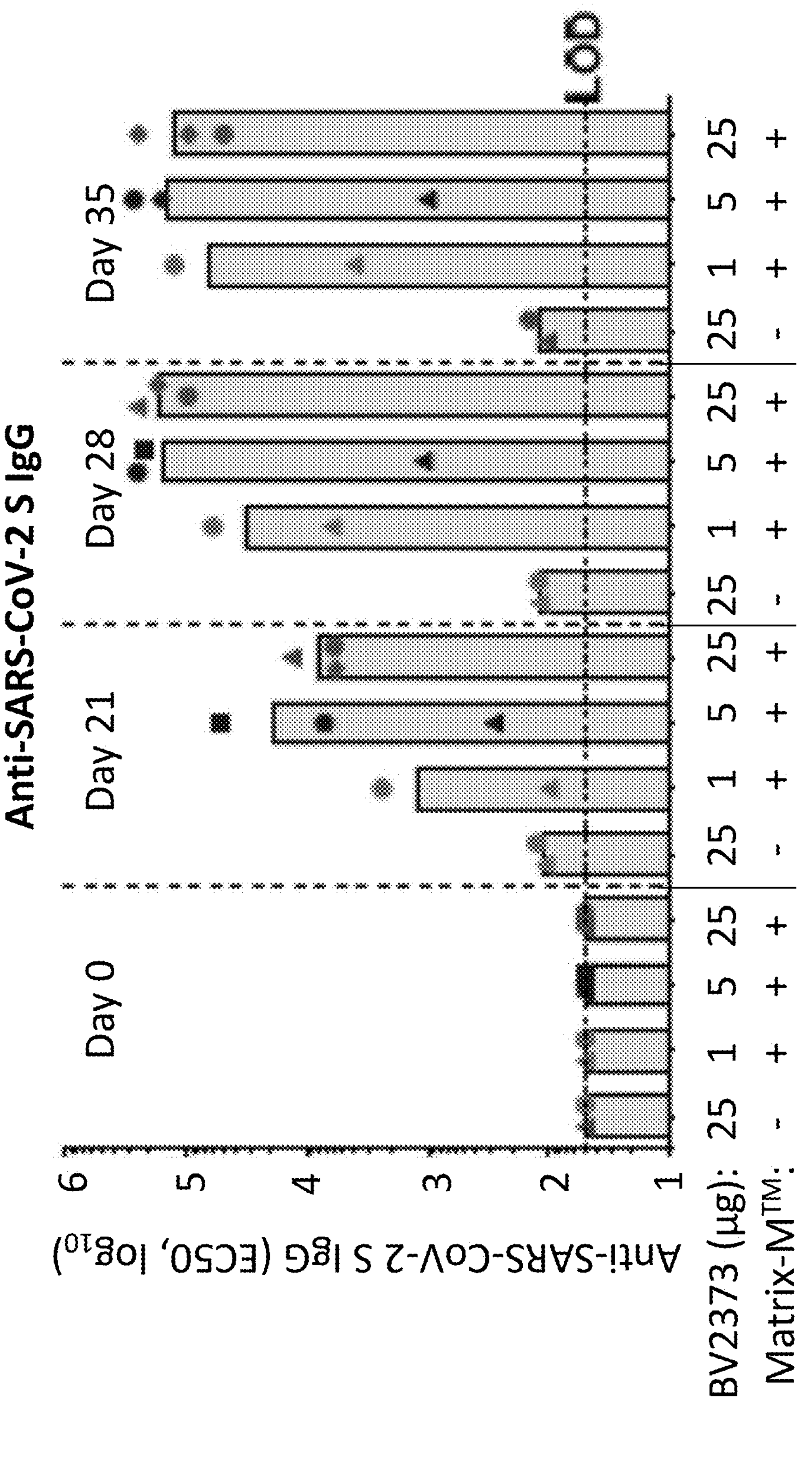
Figure 26B:
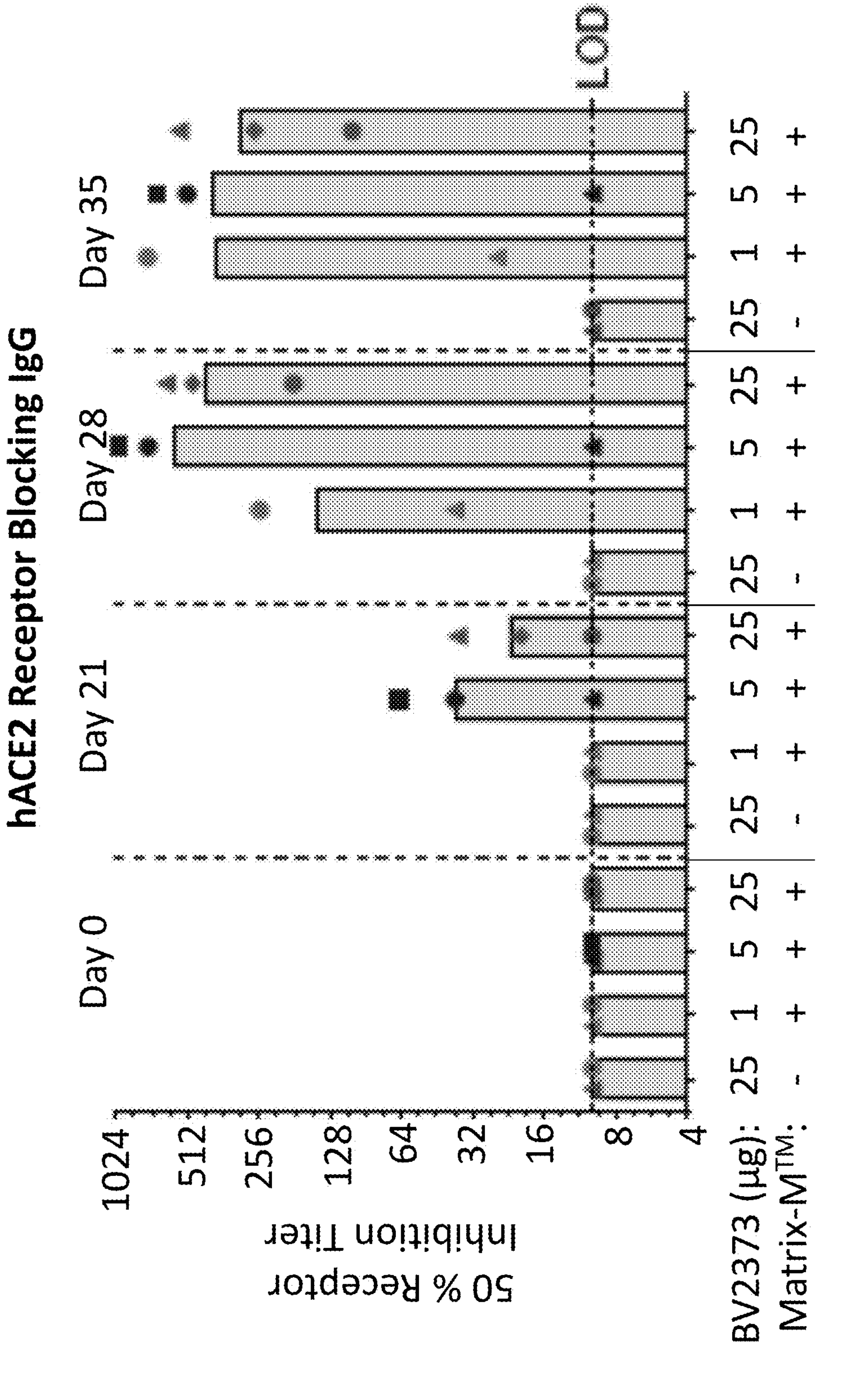
Figure 26C:
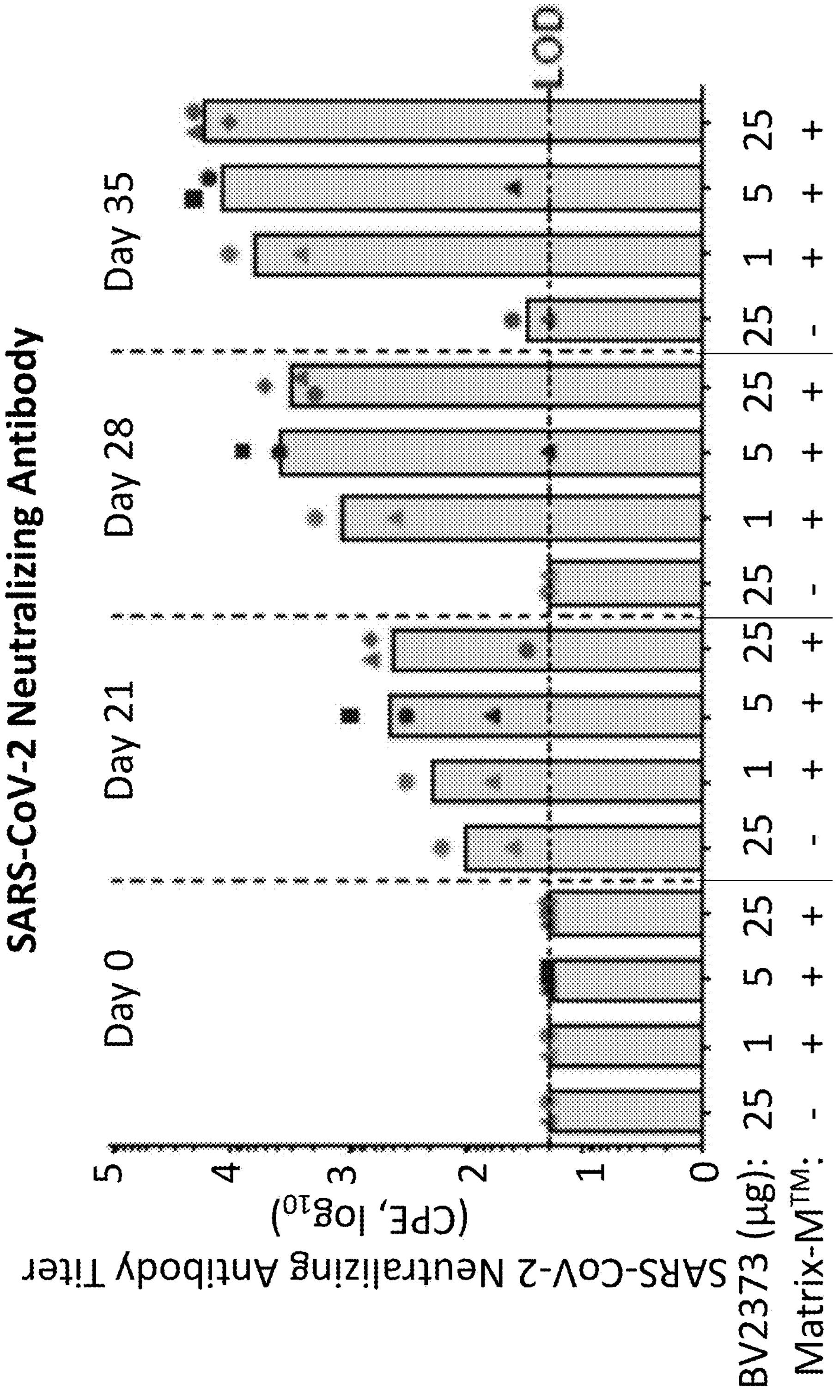

FIGS. 26A-C show the effect of immunization with BV2373 in the presence or absence of MATRIX-M™ on antibody response in olive baboons. FIG. 26A shows the anti-SARS-CoV-2 S polypeptide IgG titer in baboons after immunization with BV2373. FIG. 26B shows the presence of hACE2 receptor blocking antibodies in baboons following a single immunization with 5 μg or 25 μg of BV2373 in the presence of MATRIX-M™. FIG. 26C shows the titer of virus neutralizing antibodies following a single immunization with BV2373 and MATRIX-M™.

Figure 27:
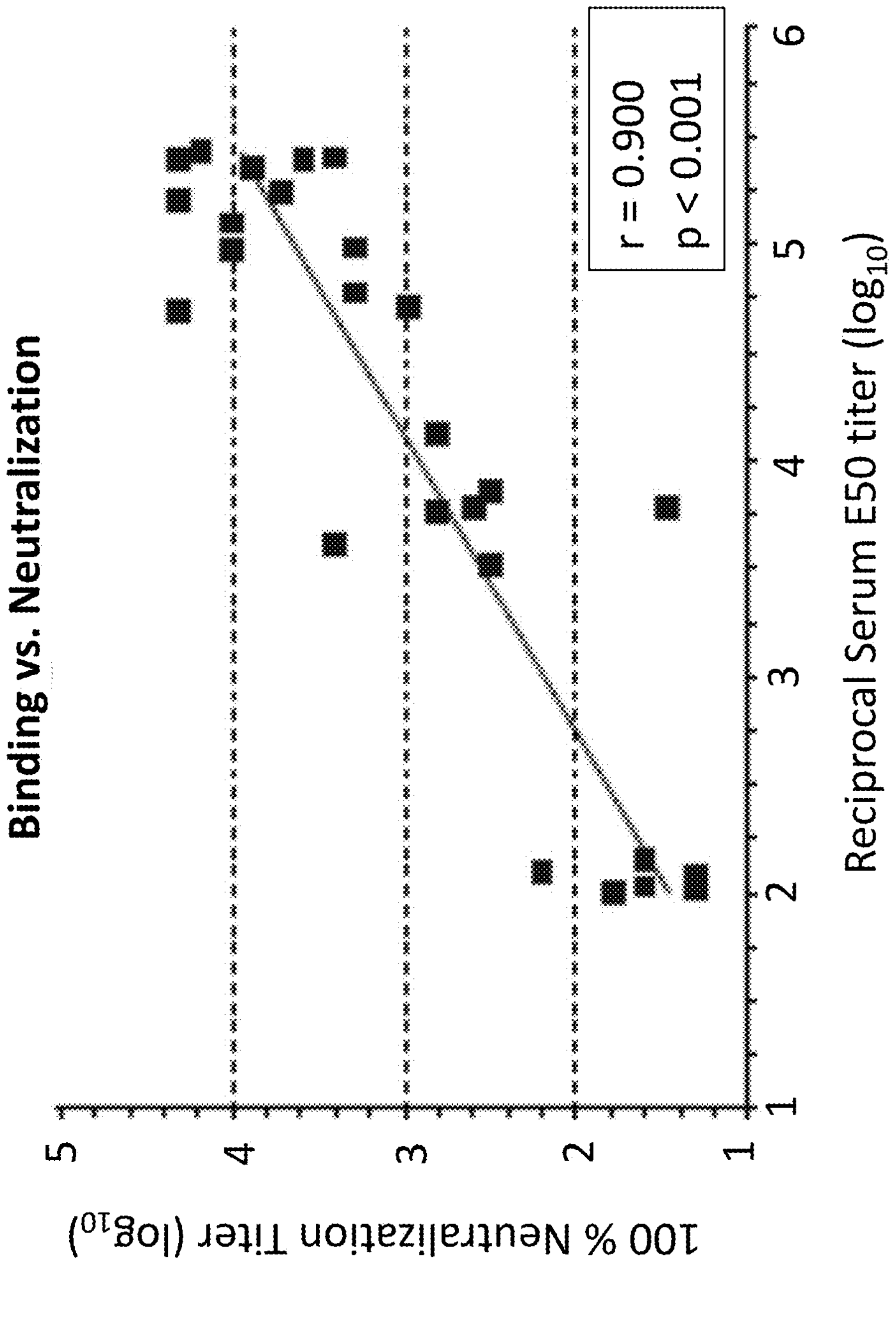

FIG. 27 shows the significant correlation between anti-SARS-CoV-2 S polypeptide IgG and neutralizing antibody titers in olive baboons after immunization with BV2373.

Figure 28:
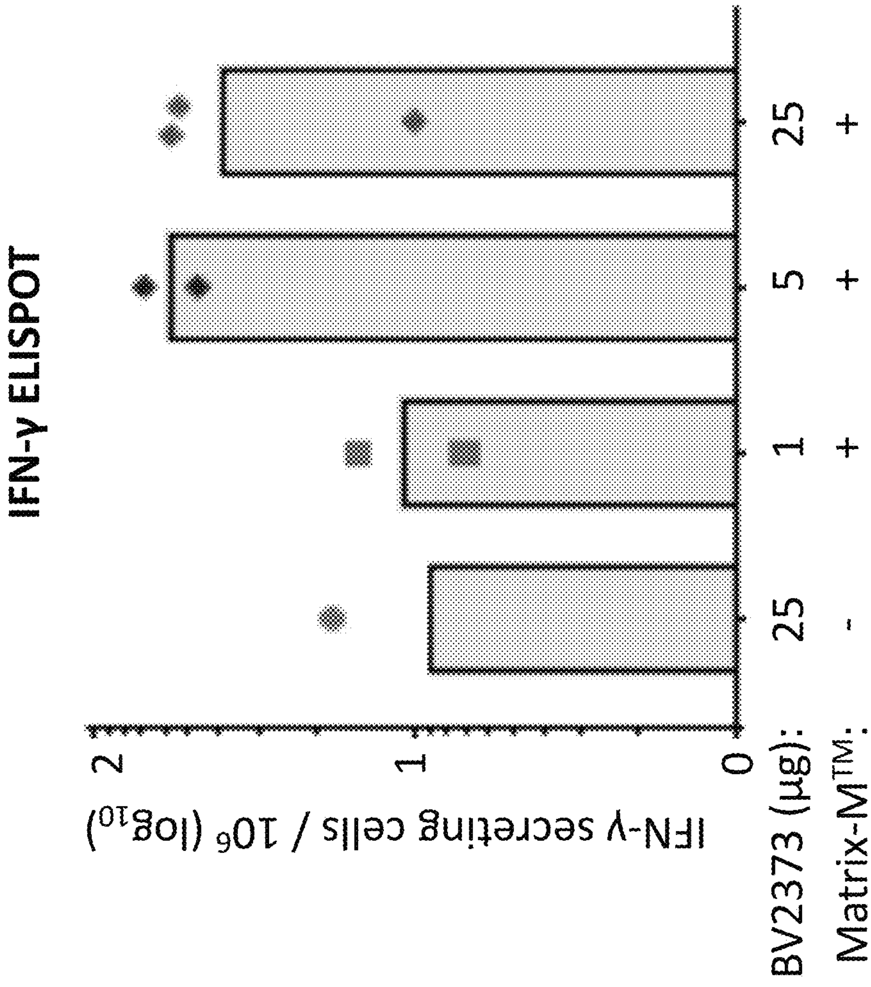

FIG. 28 shows the frequency of IFN-γ secreting cells in peripheral blood mononuclear cells (PBMC) of olive baboons immunized with BV2373 in the presence or absence of MATRIX-M™.

Figure 29A:
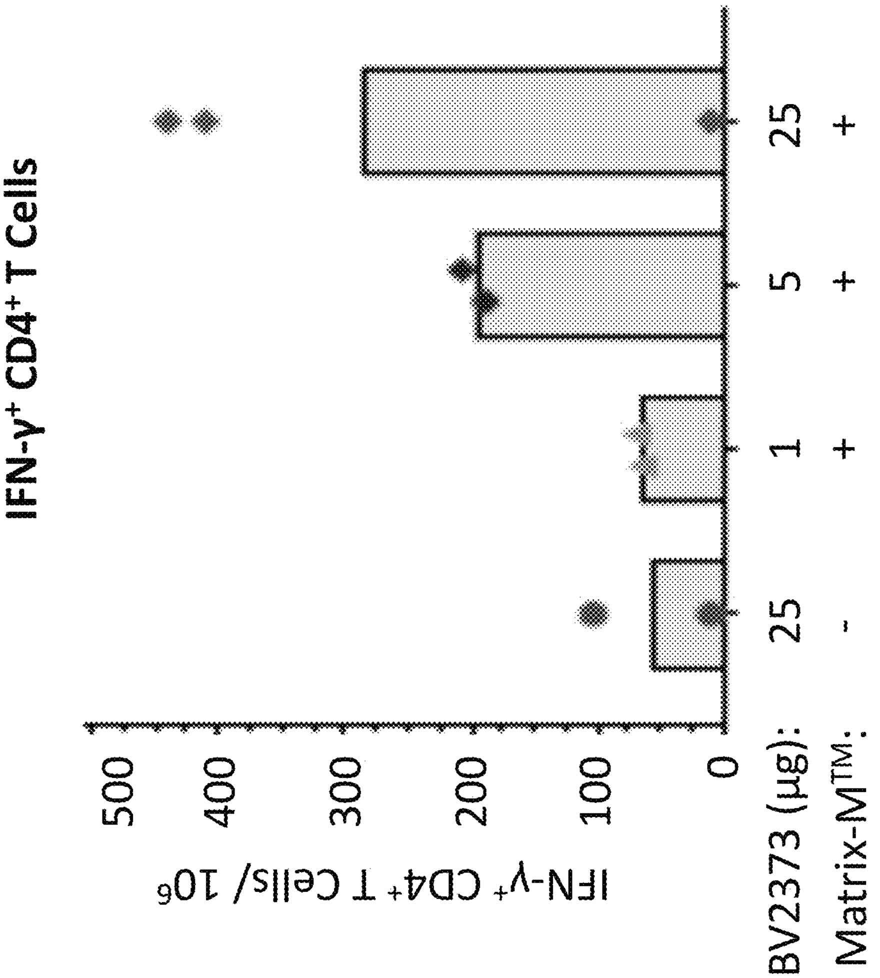
Figure 29B:
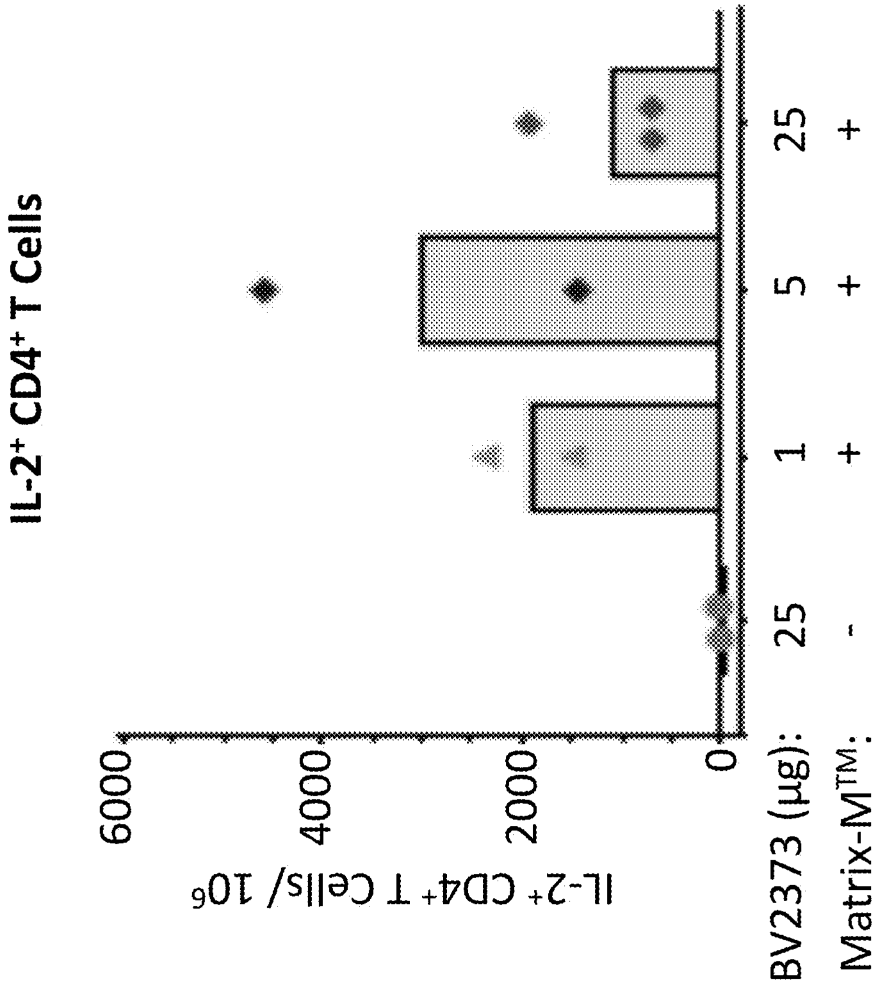
Figure 29C:
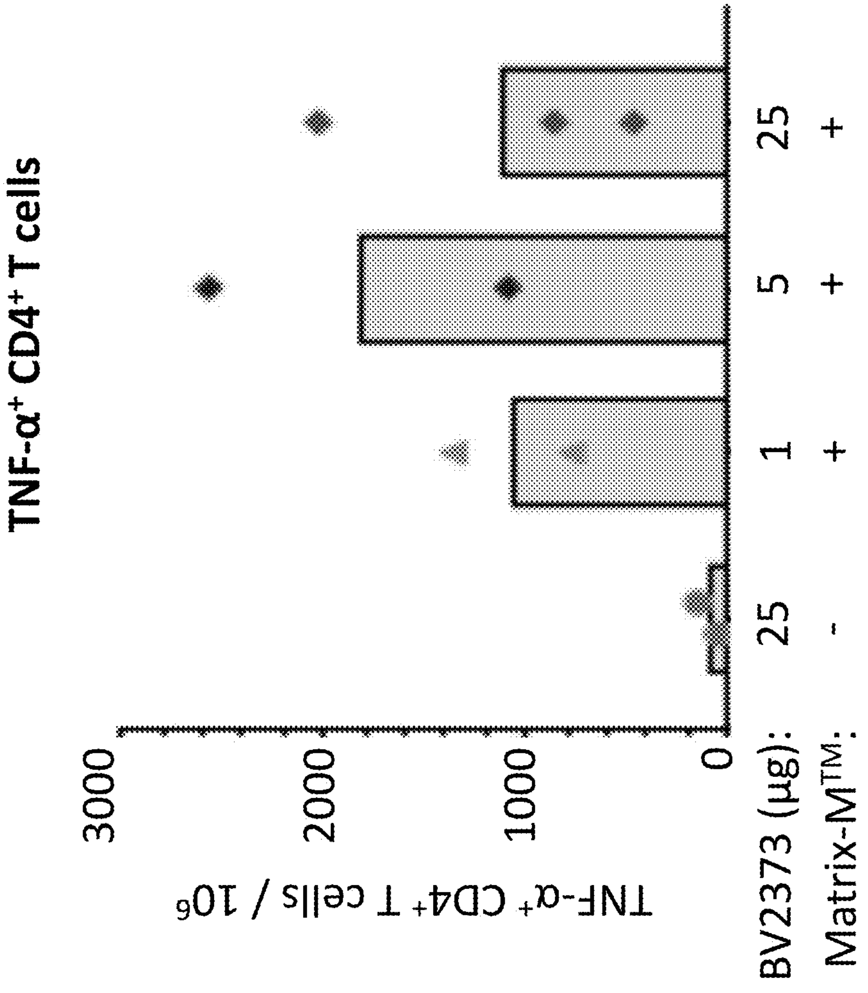
Figure 29D:
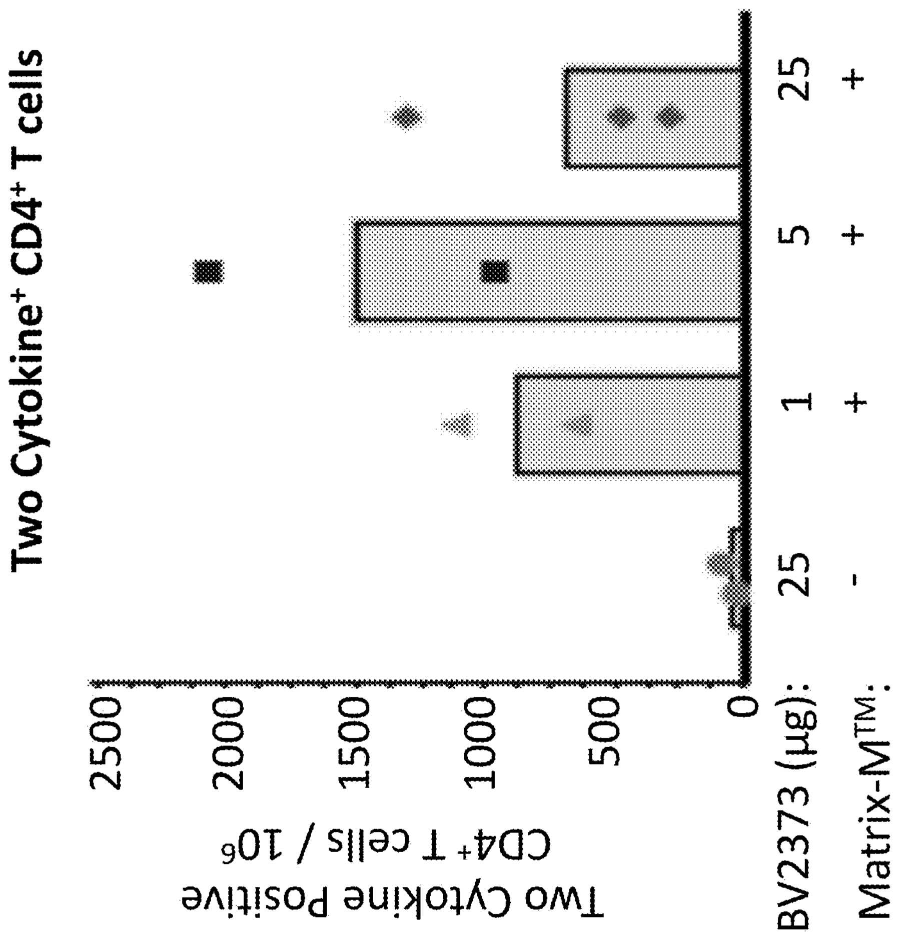
Figure 29E:
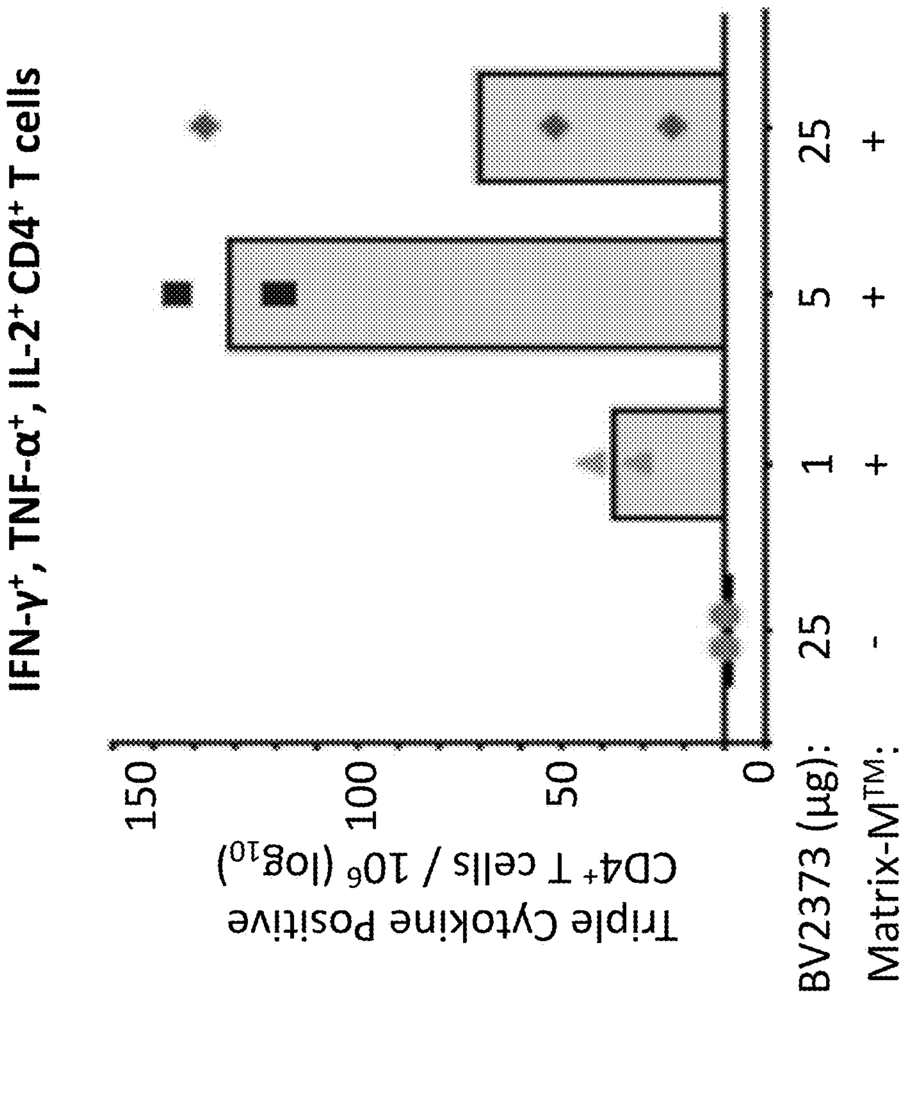

FIGS. 29A-E shows the frequency of cytokine secreting CD4+ T cells in the PBMC of olive baboons immunized with BV2373 in the presence or absence of MATRIX-M™. FIG. 29A shows the frequency of IFN-γ secreting CD4+ T cells. FIG. 29B shows the frequency of IL-2 secreting CD4+ T cells. FIG. 29C shows the frequency of TNF-α secreting CD4+ T cells. FIG. 29D shows the frequency of CD4+ T cells that secrete two cytokines selected from IFN-γ, TNF-α, and IL-2. FIG. 29E shows the frequency of CD4+ T cells that express IFN-γ, TNF-α, and IL-2.

FIG. 30 shows a schematic of the coronavirus Spike (S) protein (SEQ ID NO: 109) (BV2384). The furin cleavage site GSAS (SEQ ID NO: 97) is underlined once, and the K986P and V987P mutations are underlined twice.

FIG. 31 shows a schematic of the coronavirus Spike (S) protein (SEQ ID NO: 86) (BV2373). The furin cleavage site QQAQ (SEQ ID NO: 7) is underlined once, and the K986P and V987P mutations are underlined twice.

Figure 32:
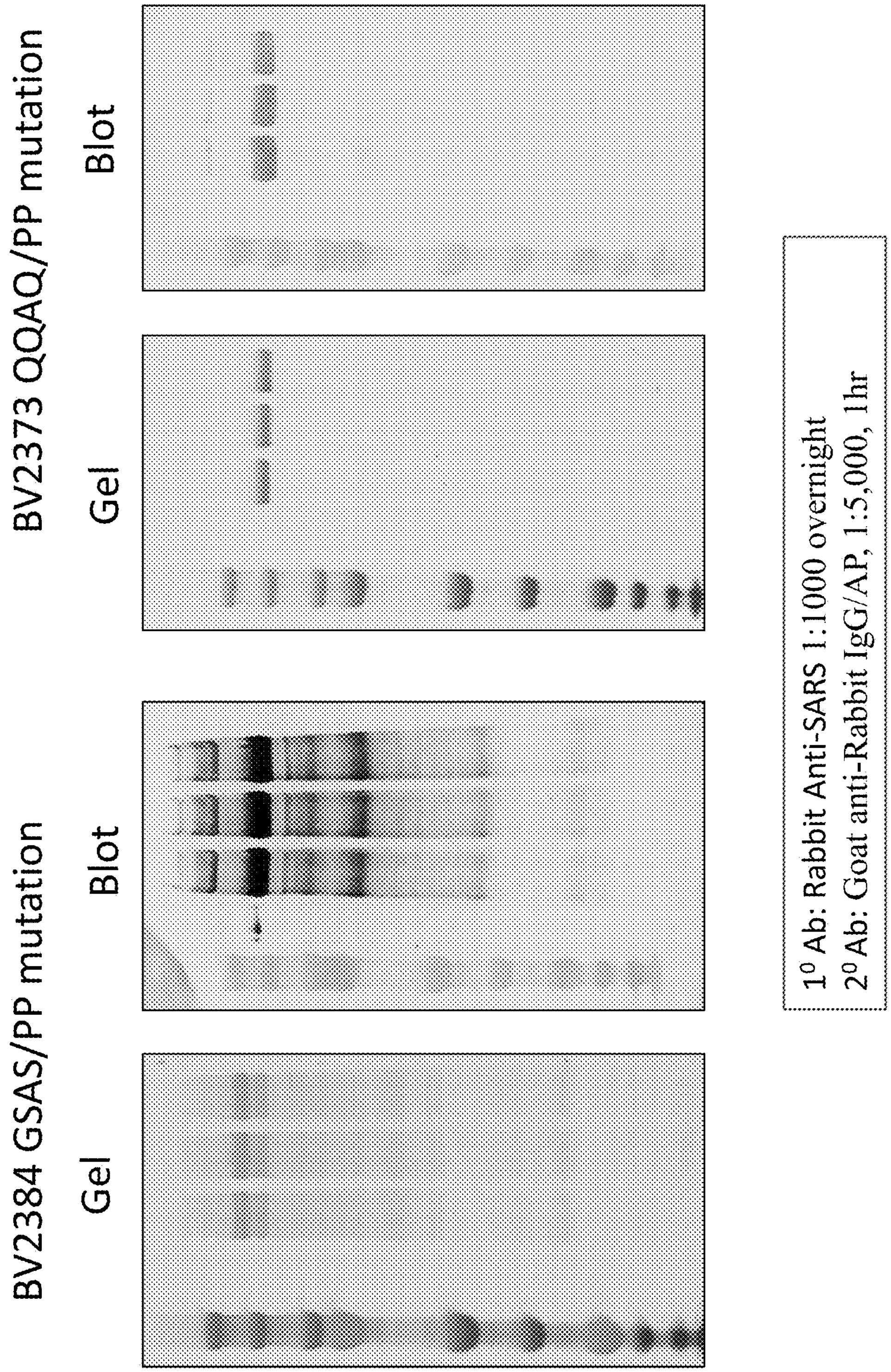

FIG. 32 shows purification of the CoV S polypeptides BV2373 (SEQ ID NO: 87) and BV2384 (SEQ ID NO: 109).

Figure 33:
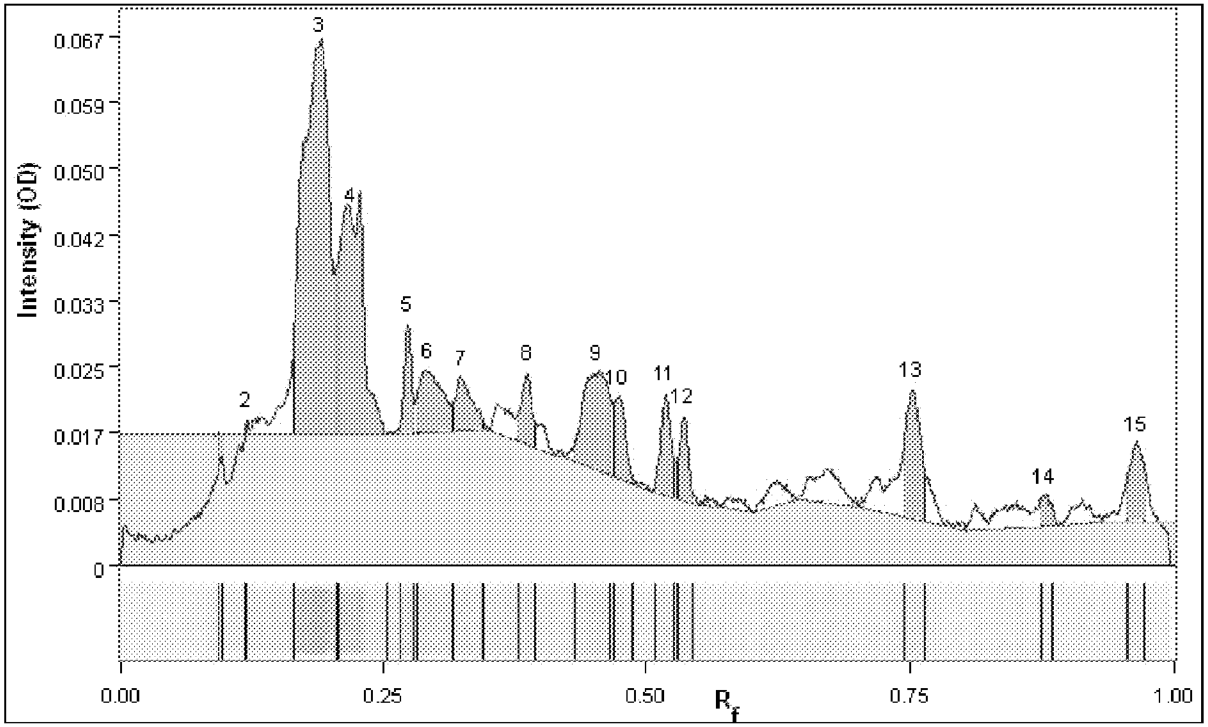

FIG. 33 shows a scanning densitometry plot of BV2384 (SEQ ID NO: 109) purity after purification.

Figure 34:
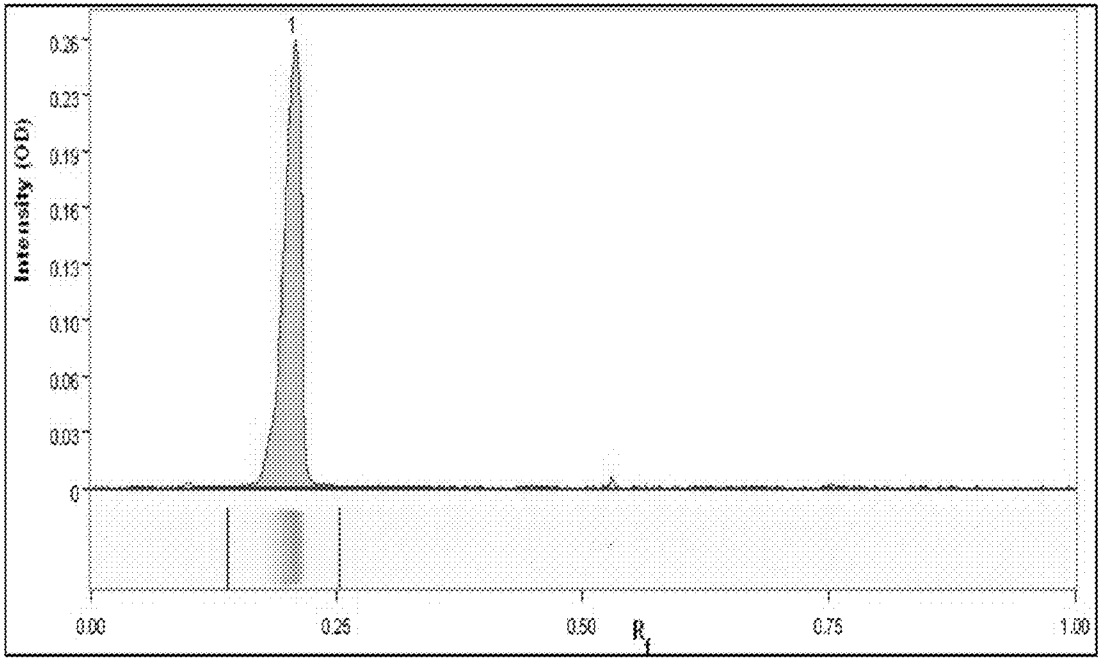
Figure 35A:
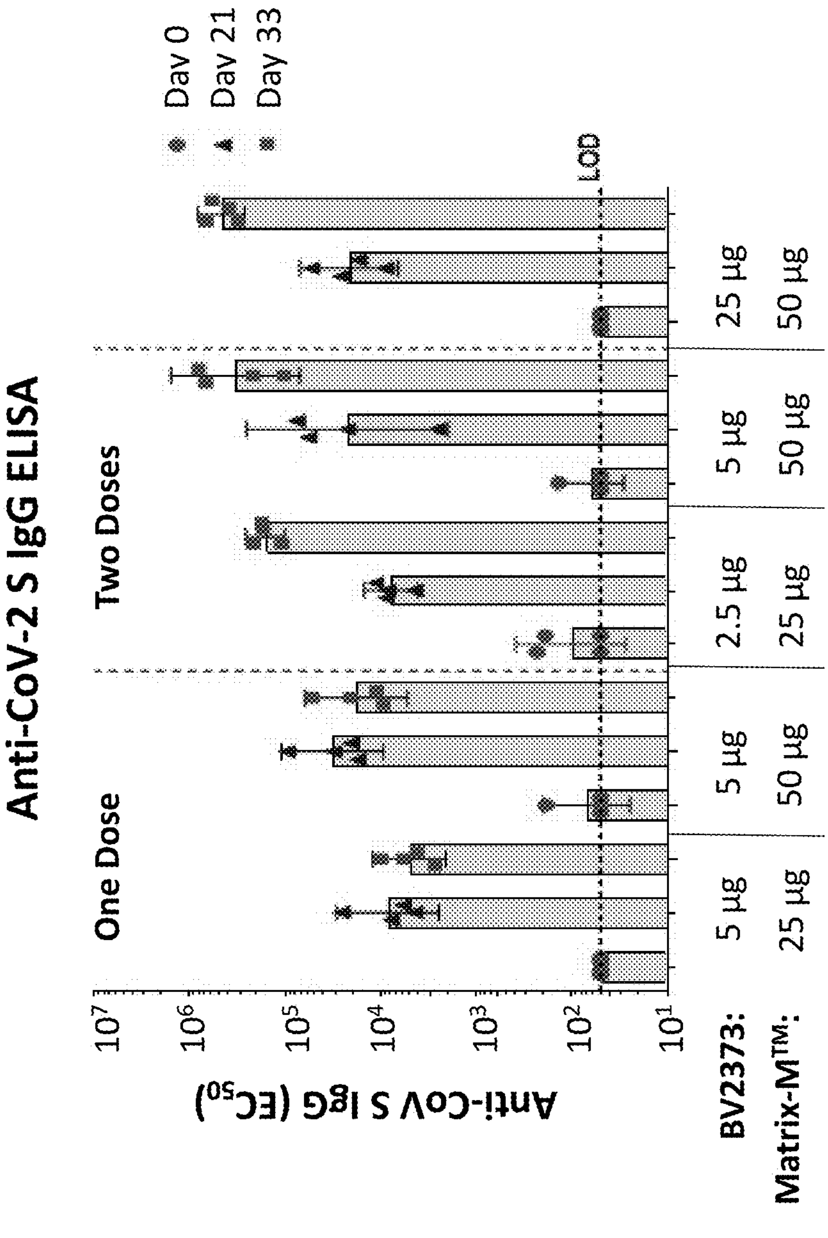
Figure 35B:
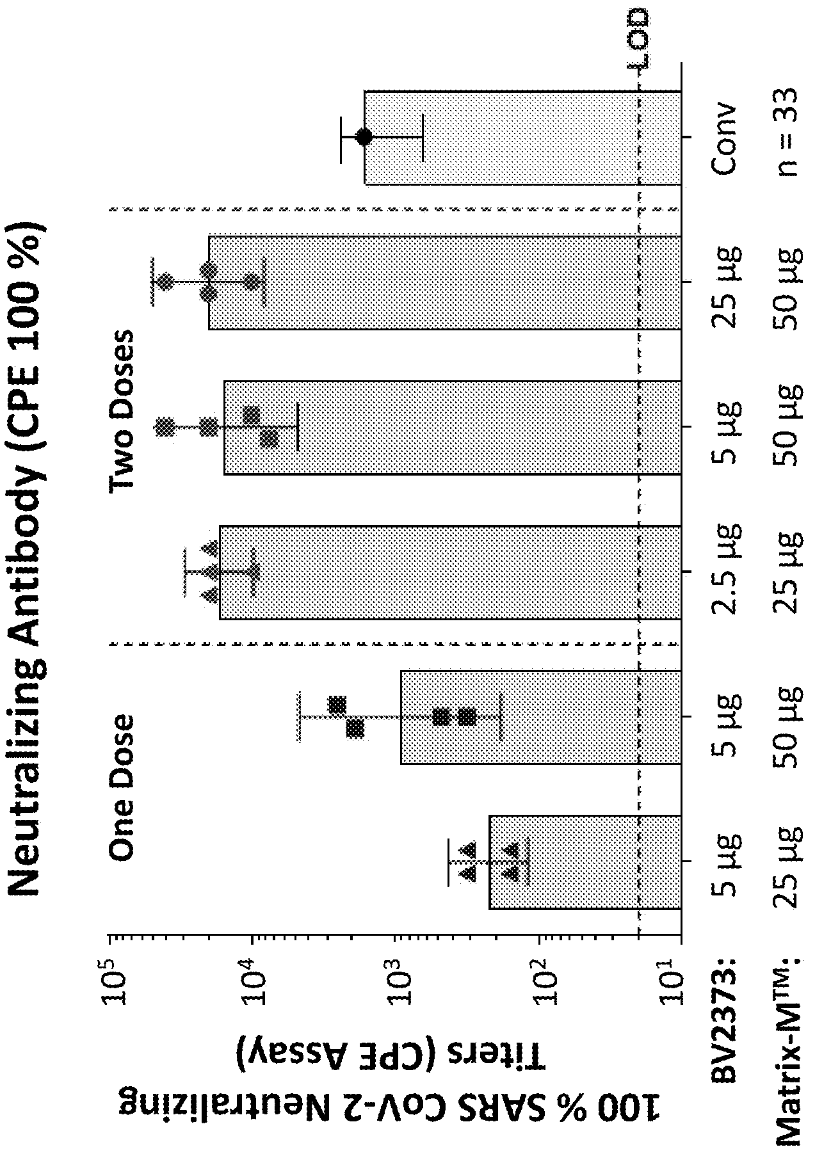

FIG. 34 shows a scanning densitometry plot of BV2373 (SEQ ID NO: 87) purity after purification FIGS. 35A-B illustrates induction of anti-S antibodies (FIG. 35A) and neutralizing antibodies (FIG. 35B) in response to administration of BV2373 and MATRIX-M™. Cynomolgus macaques were administered one or two doses (Day 0 and Day 21) of 2.5 μg, 5 μg, or 25 μg of BV2373 with 25 μg or 50 μg MATRIX-M™ adjuvant. Controls received neither BV2373 or MATRIX-M™. Antibodies were measured at Days 21 and 33.

Figure 36A:
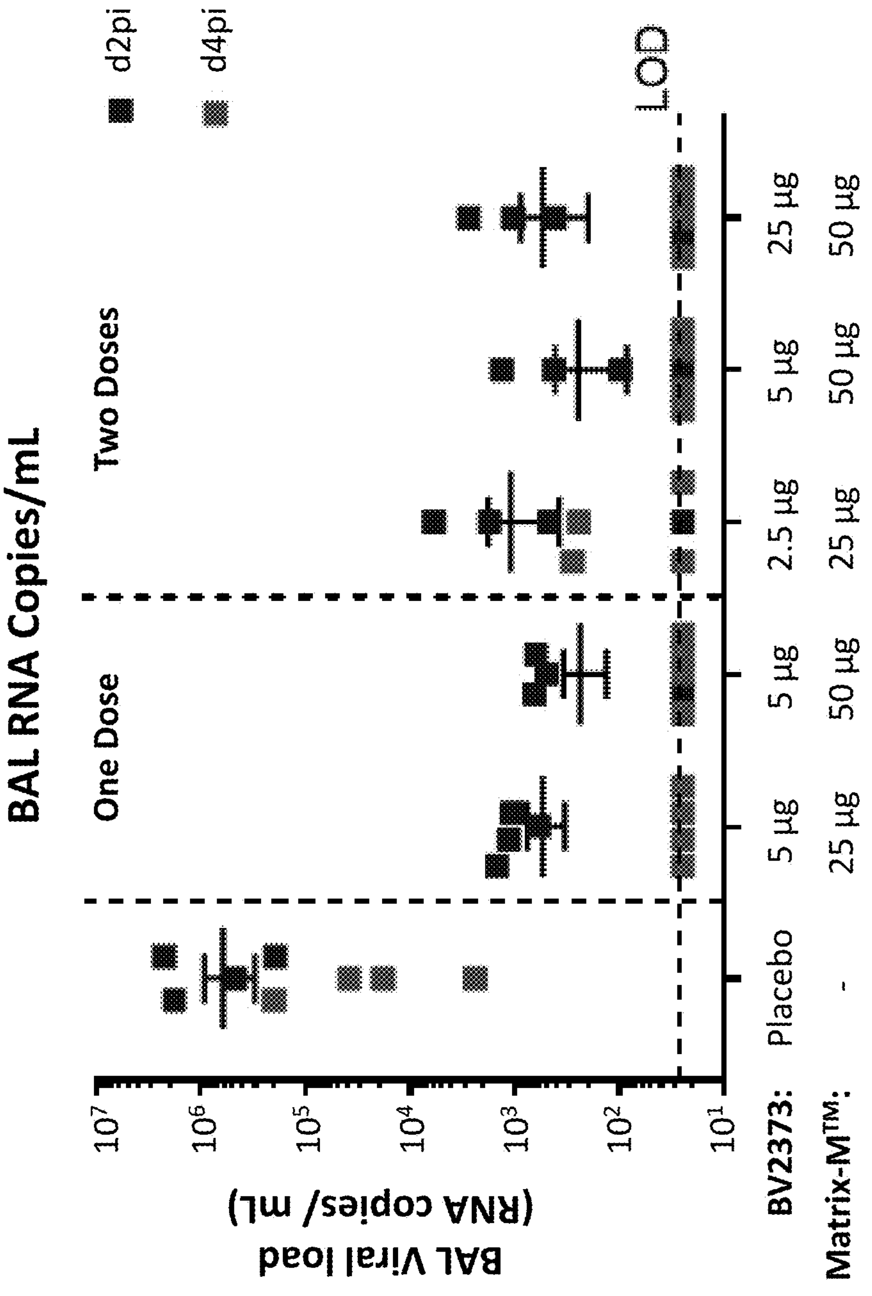
Figure 36B:
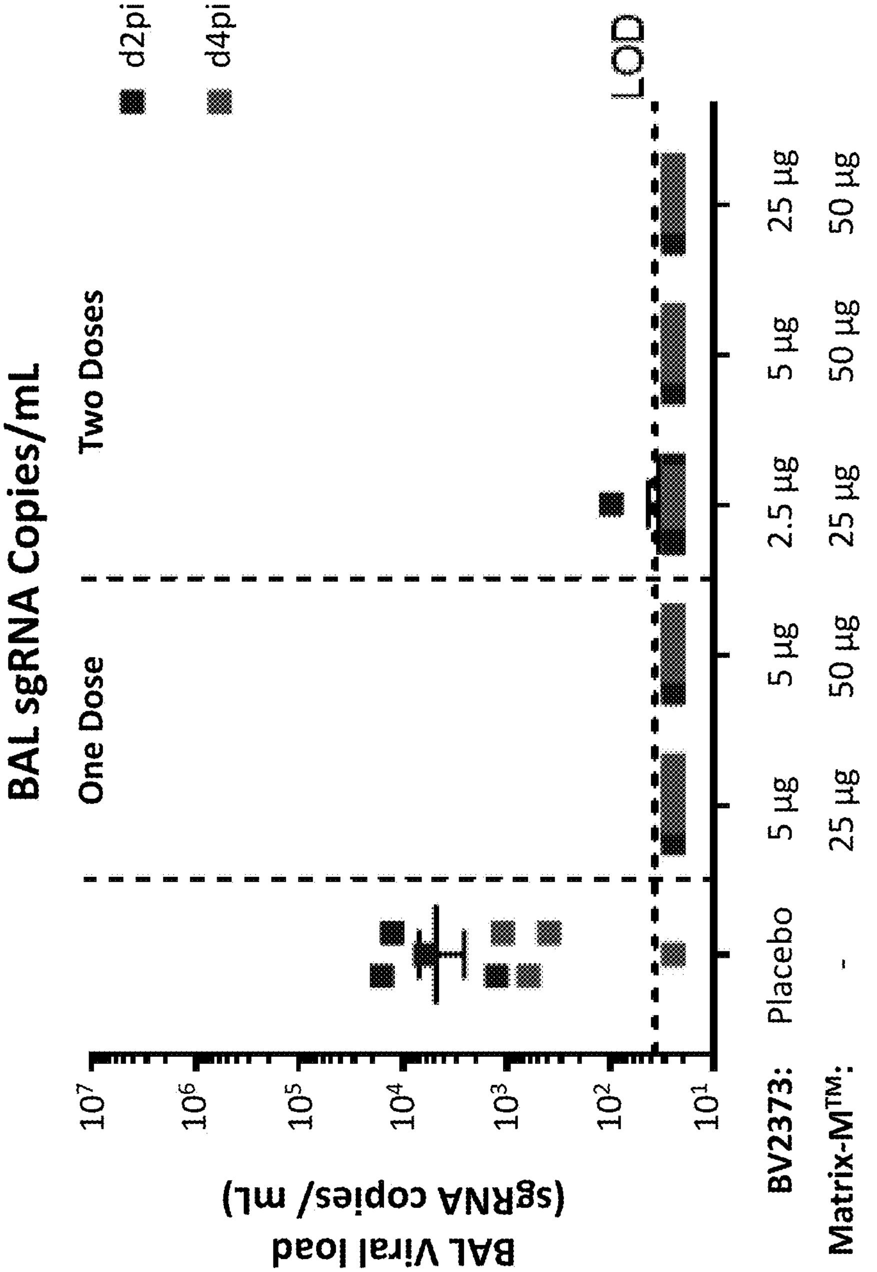

FIGS. 36A-B illustrates a decrease of SARS-CoV-2 viral replication by vaccine formulations disclosed herein as assessed in broncheoalveol lavage (BAL) in Cynomolgus macaques. Cynomolgus macaques were administered BV2373 and MATRIX-M™ as shown. Subjects were immunized Day 0 and in the groups with two doses Day 0 and Day 21. Subject animals were challenged Day 37 with $1\times10^4$ pfu SARS-CoV-2 virus. Viral RNA (FIG. 36A, corresponding to total RNA present) and viral sub-genomic RNA (FIG. 36B, corresponding to replicating virus) levels were assessed in bronchiolar lavage (BAL) at 2 days and 4 days post-challenge with infectious virus (d2pi and d4pi). Most subjects showed no viral RNA. At Day 2 small amounts of RNA were measured in some subjects. By Day 4, no RNA was measured except for two subjects at the lowest dose of 2.5 Sub-genomic RNA was not detected at either 2 Days or 4 days except for 1 subject, again at the lowest dose.

Figure 37A:
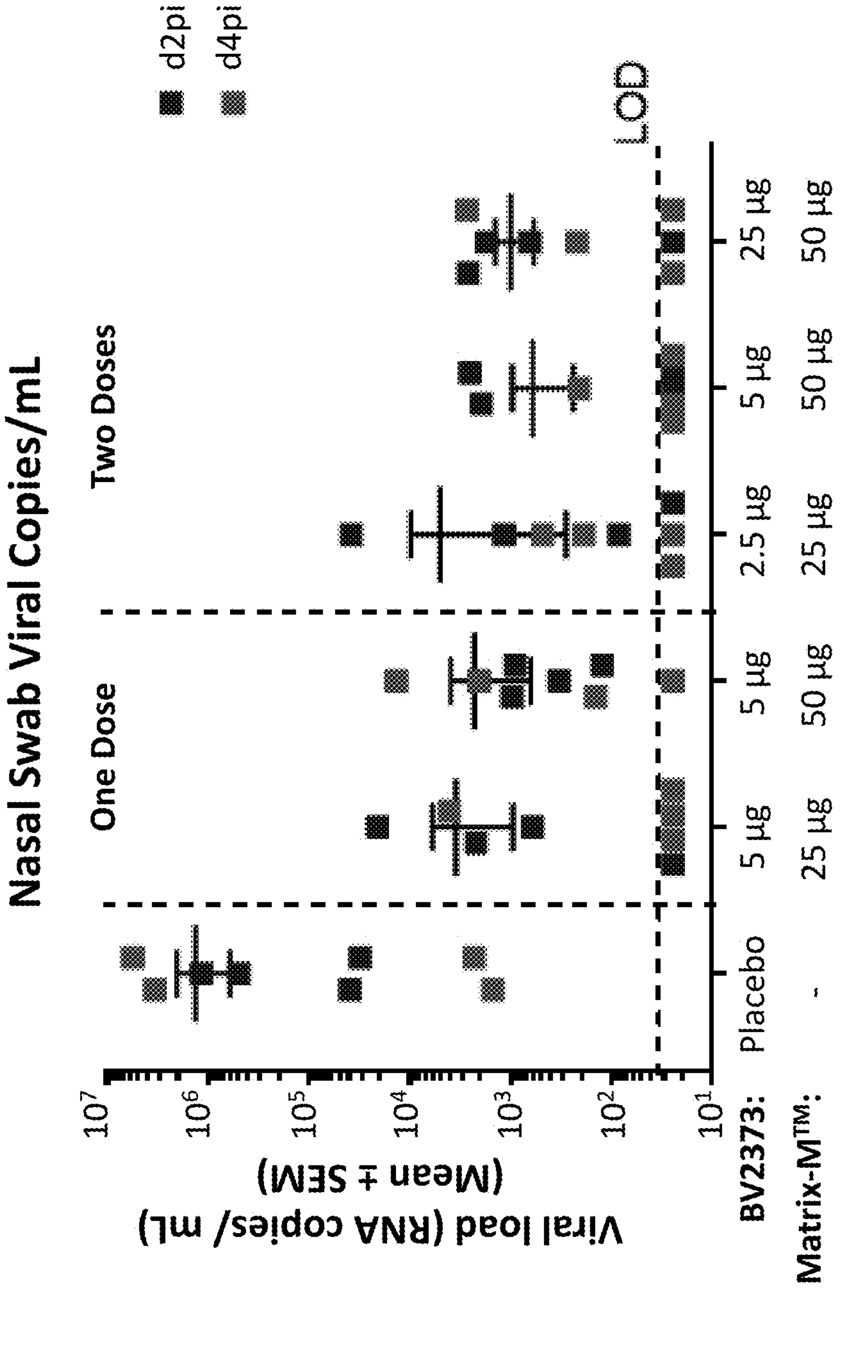
Figure 37B:
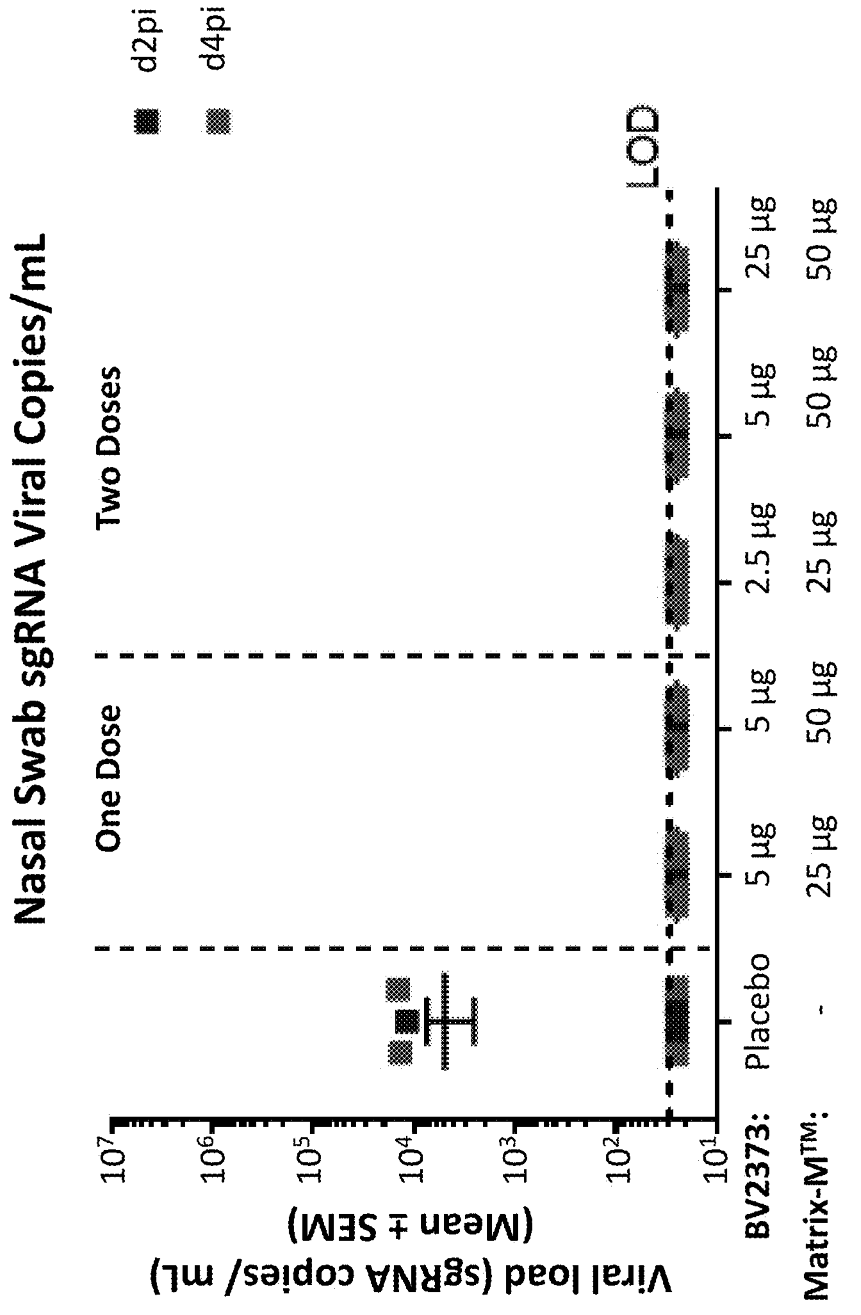

FIGS. 37A-B illustrates a decrease of SARS-CoV-2 viral replication by vaccine formulations disclosed herein as assessed in nasal swab in Cynomolgus macaques. Cynomolgus macaques were administered BV2373 with MATRIX-M™ as shown. Subjects were immunized Day 0 and in the groups with two doses Day 0 and Day 21. Subject animals were challenged Day 37 with $1\times10^4$ SARS-CoV-2 virus. Viral RNA (FIG. 37A) and viral sub-genomic (sg) RNA (FIG. 37B) were assessed by nasal swab at 2 days and 4 days post-infection (d2pi and d4pi). Most subjects showed no viral RNA. At Day 2 and Day 4 small amounts of RNA were measured in some subjects. Sub-genomic RNA was not detected at either 2 Days or 4 days. Subjects were immunized Day 0 and in the groups with two doses Day 0 and Day 21. These data show that the vaccine decreases nose total virus RNA by 100-1000 fold and sgRNA to undetectable levels, and confirm that immune response to the vaccine will block viral replication and prevent viral spread.

Figure 38A:
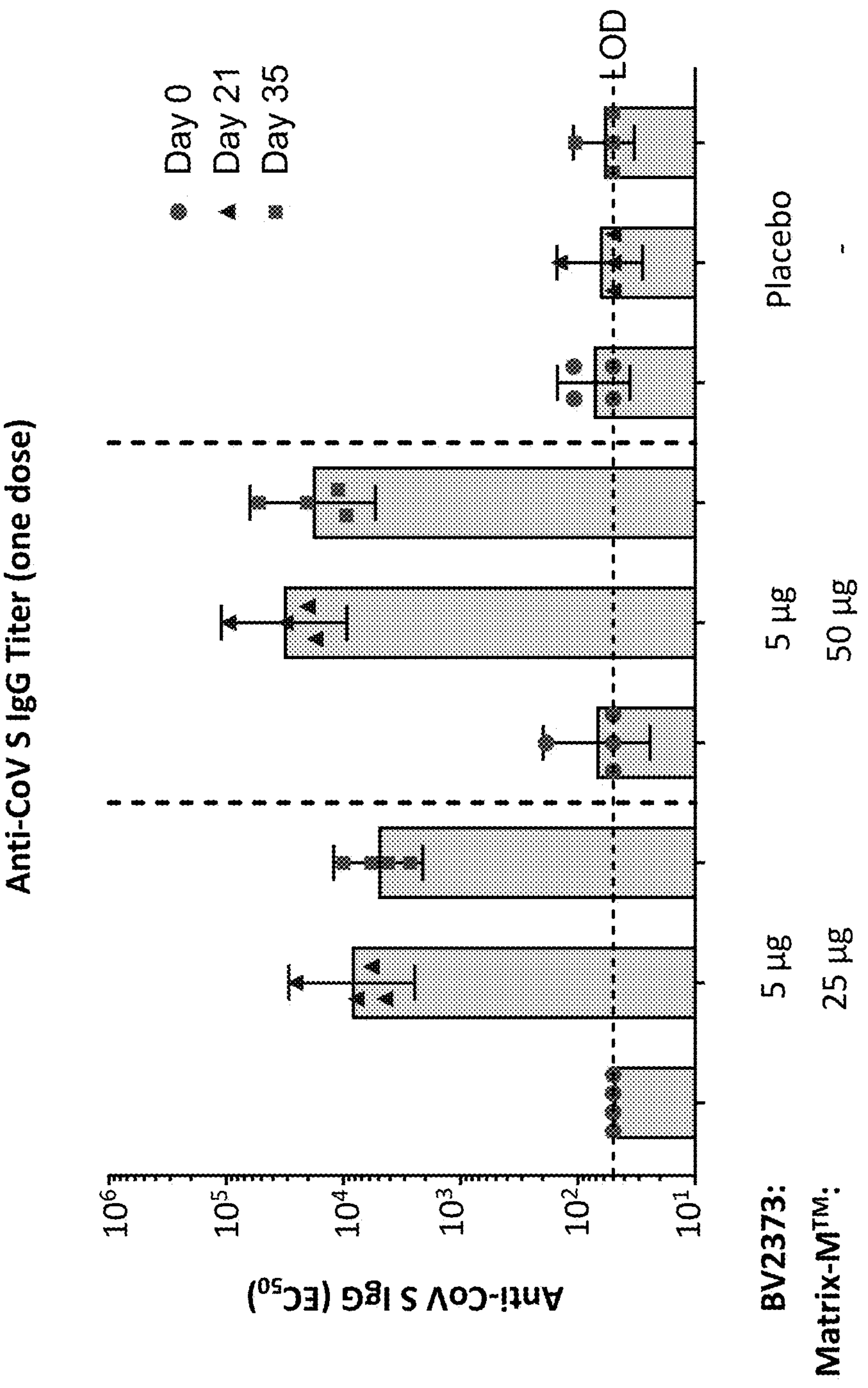
Figure 38B:
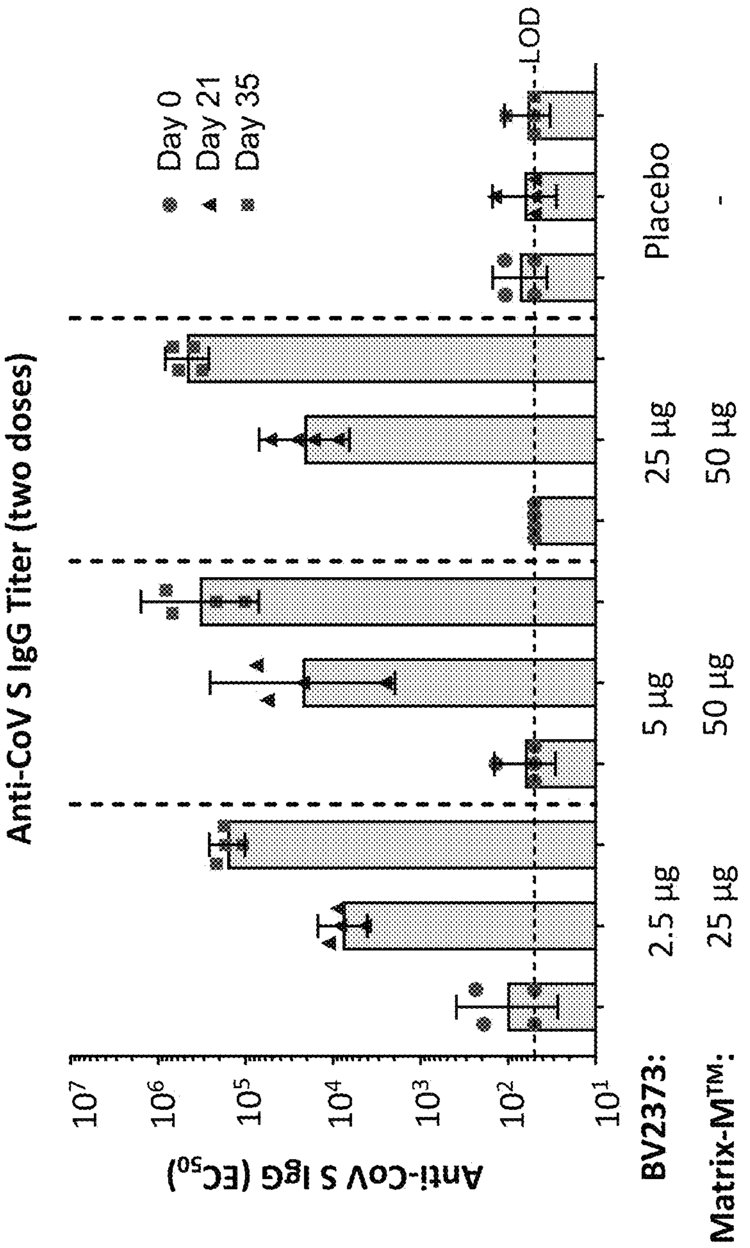

FIGS. 38A-B show anti-CoV S polypeptide IgG titers 21 days and 35 days after immunization of Cynomolgus macaques with one dose (FIG. 38A) or two doses of BV2373 and 25 μg or 50 μg of MATRIX-M™ (FIG. 38B).

Figure 38C:
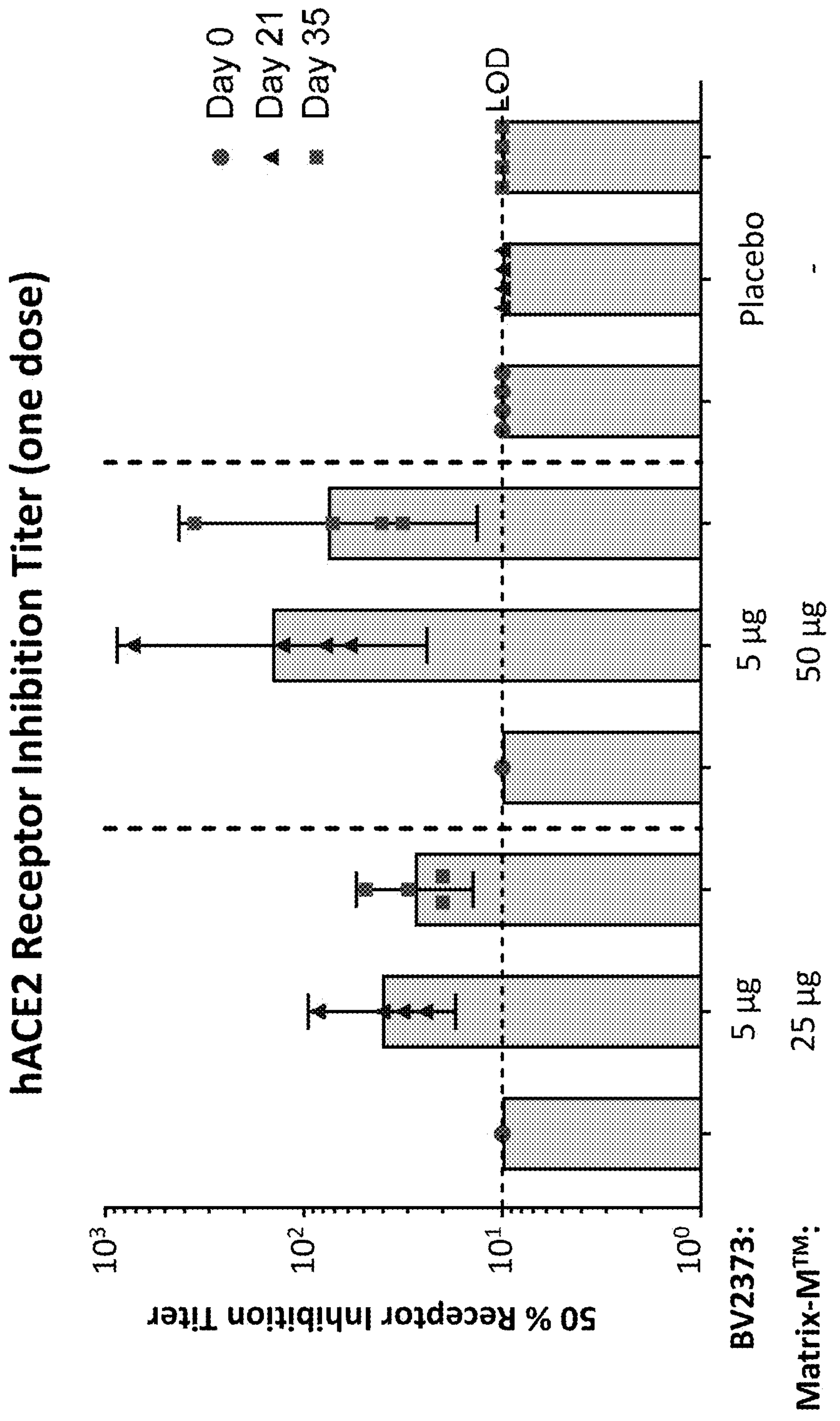
Figure 38D:
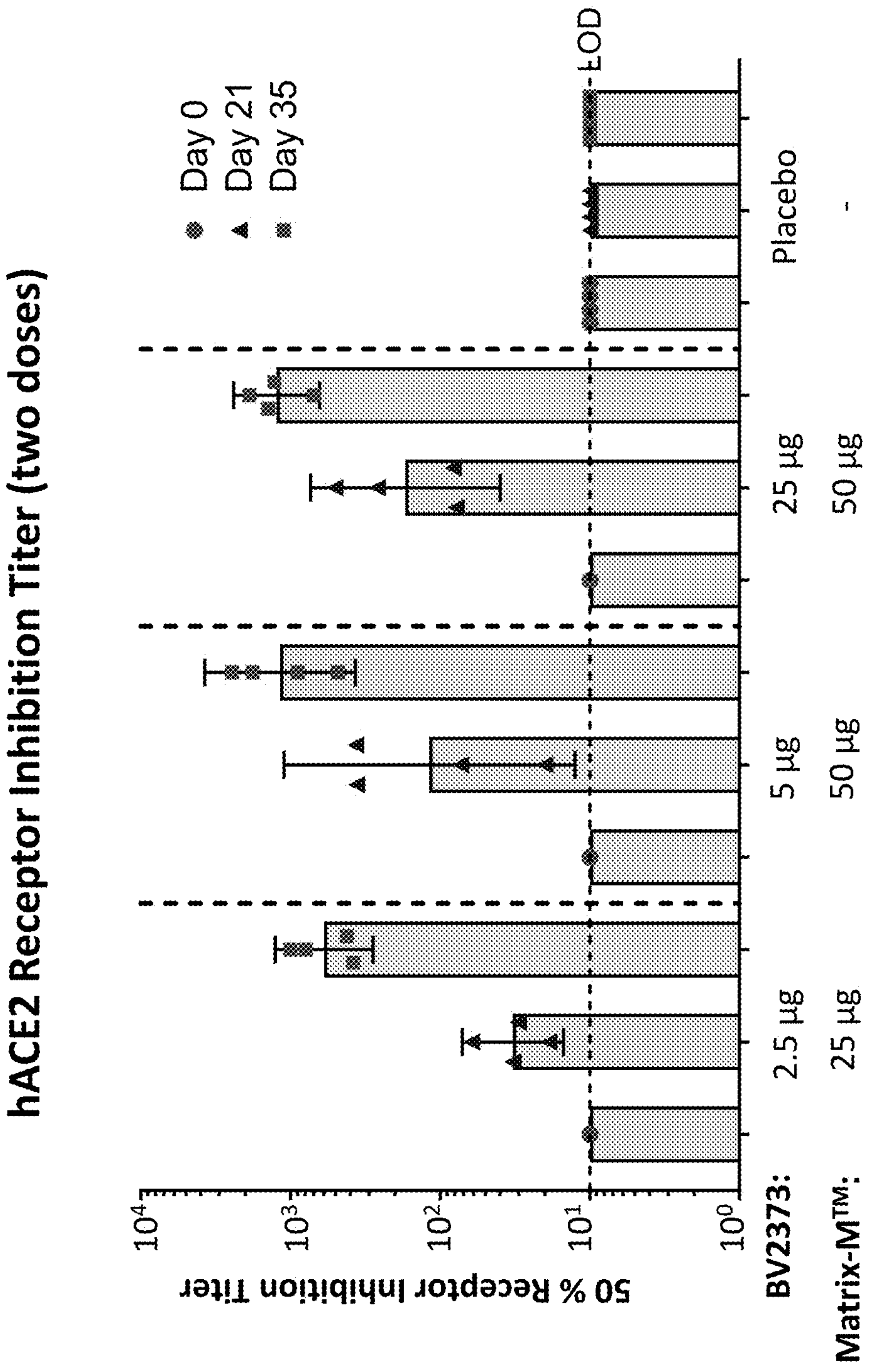

FIGS. 38C-38D shows the hACE2 inhibition titer of Cynomolgus macaques 21 days and 35 days after immunization of Cynomolgus macaques with one dose (FIG. 38C) or two doses of BV2373 (5 μg) and MATRIX-M™ (25 μg or 50 μg) (FIG. 38D).

Figure 38E:
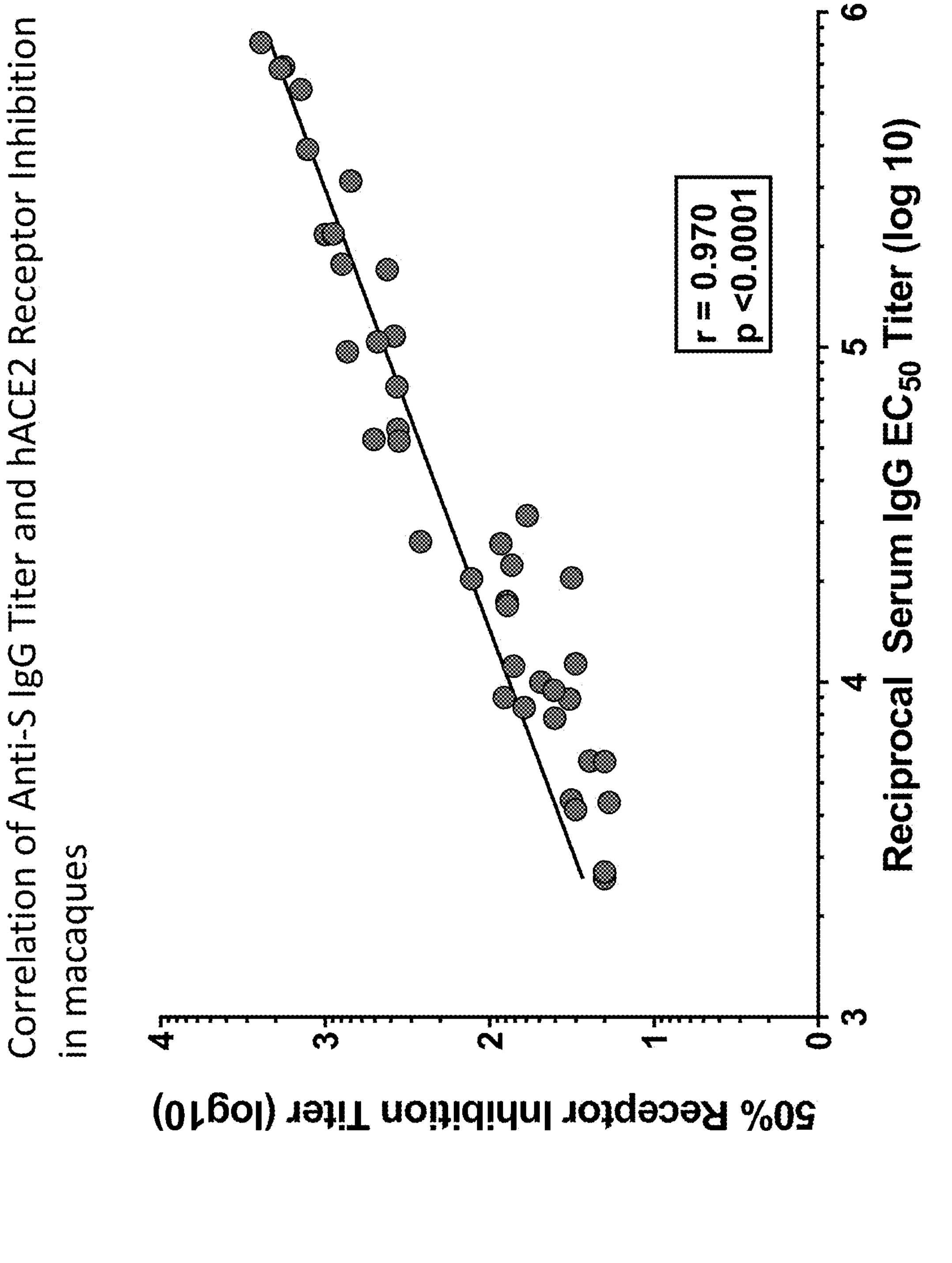

FIG. 38E shows the significant correlation between anti-CoV S polypeptide IgG titer and hACE2 inhibition titer in Cynomolgus macaques after administration of BV2373 and MATRIX-M™. Data is shown for Groups 2-6 of Table 4.

Figure 39:
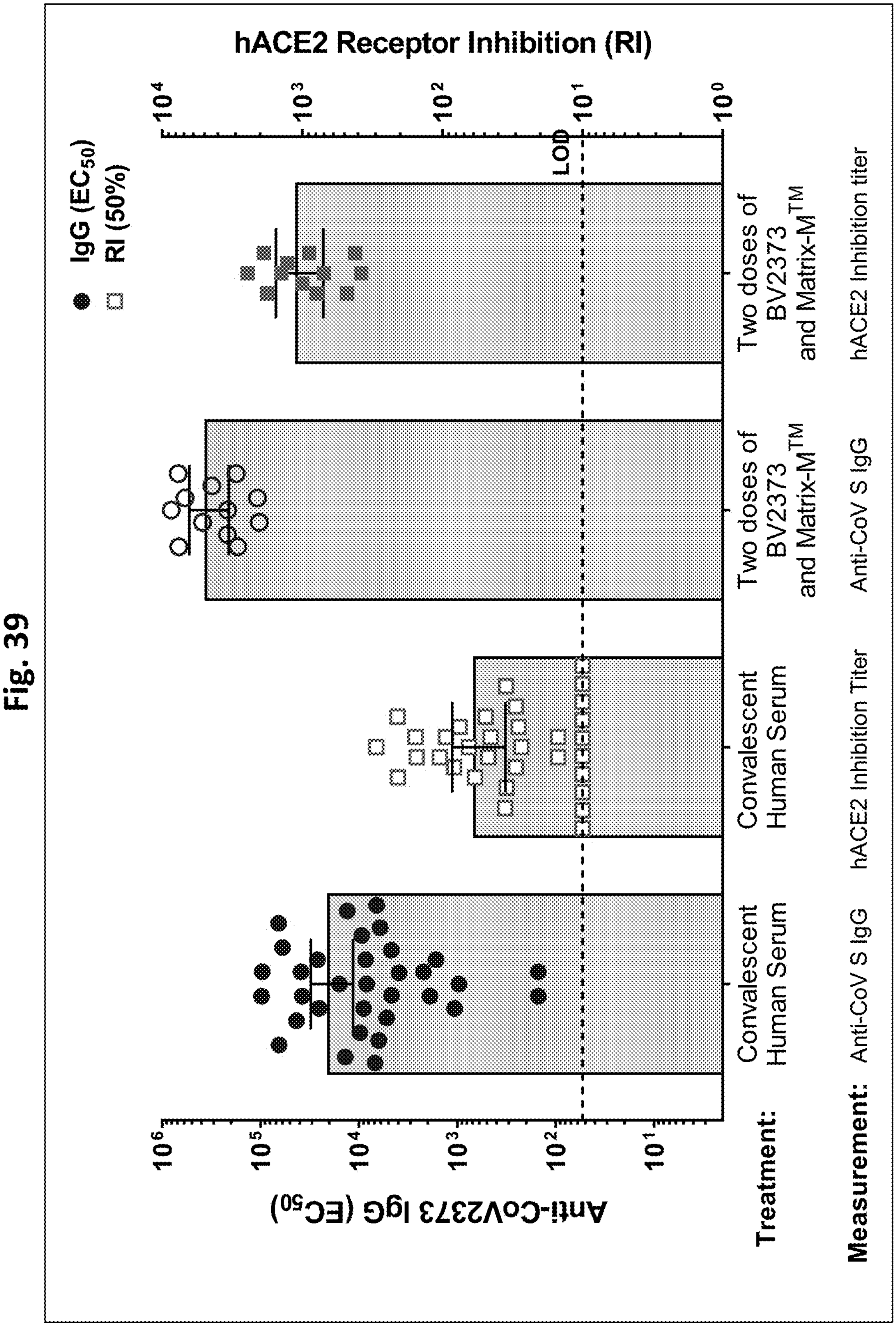

FIG. 39 shows the anti-CoV S polypeptide titers and hACE2 inhibition titer of Cynomolgus macaques 35 days after immunization with two doses of BV2373 and MATRIX-M™ or after immunization with convalescent human serum (Groups 2, 4, and 6) of Table 4. These data show that the anti-CoV S polypeptide and hACE2 inhibition titers of Cynomologus macaques immunized with BV2373 and MATRIX-M™ is superior to Cynomolgus macaques immunized with convalescent serum.

Figure 40A:
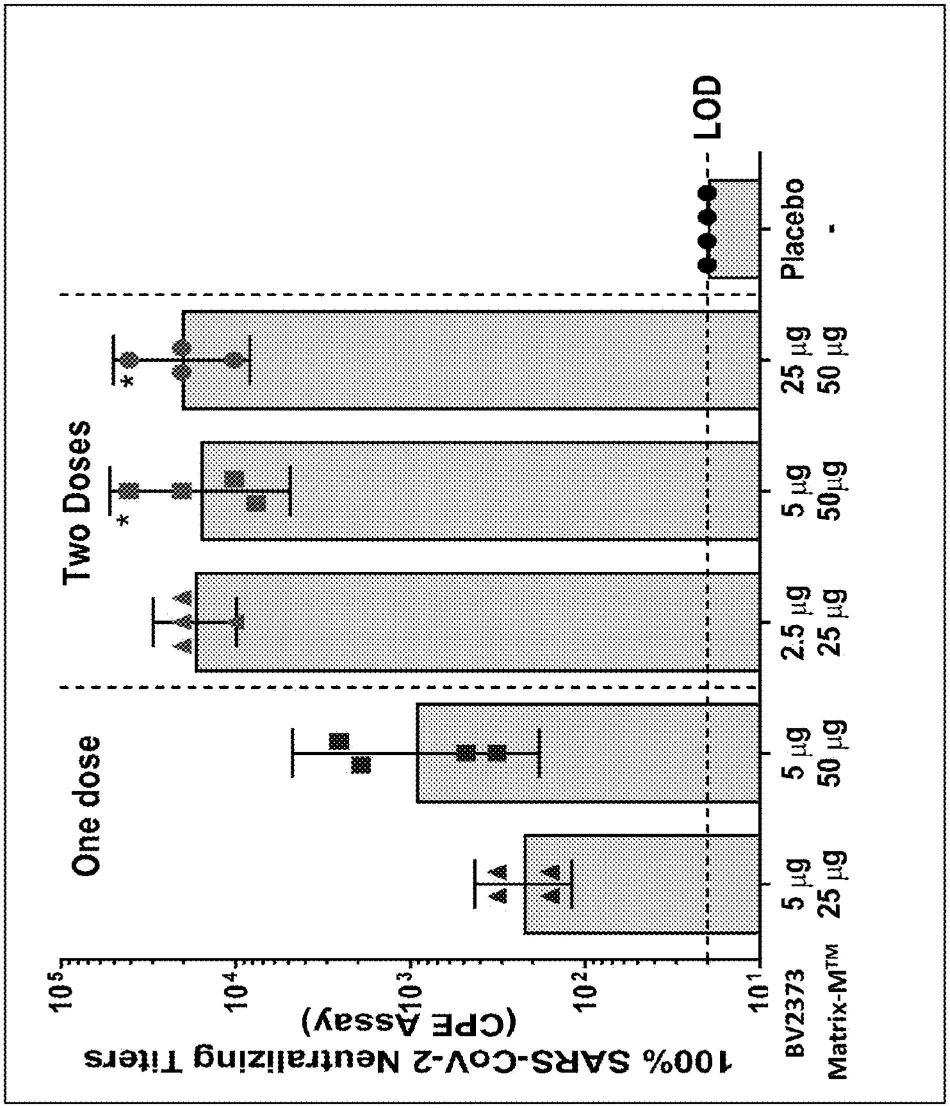
Figure 40B:
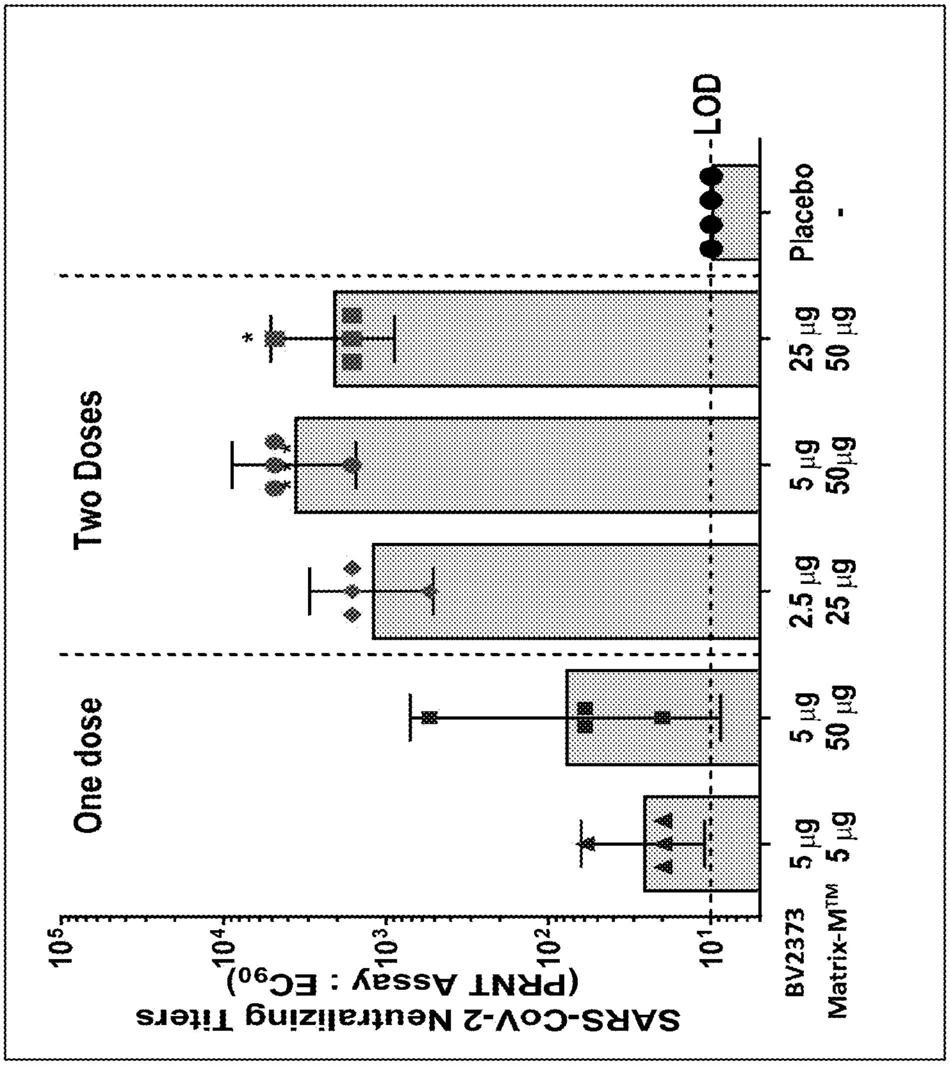

FIGS. 40A-B shows the SARS-CoV-2 neutralizing titers of Cynomolgus macaques immunized with BV2373 and MATRIX-M™ as determined by cytopathic effect (CPE) (FIG. 40A) and plaque reduction neutralization test (PRNT) (FIG. 40B).

FIG. 41 shows administration timings of a clinical trial that evaluated the safety and efficacy of a vaccine comprising BV2373 and optionally MATRIX-M™. AESI denotes an adverse event of special interest. MAEE denotes a medically attended adverse event, and SAE denotes a serious adverse event.

Figure 42A:
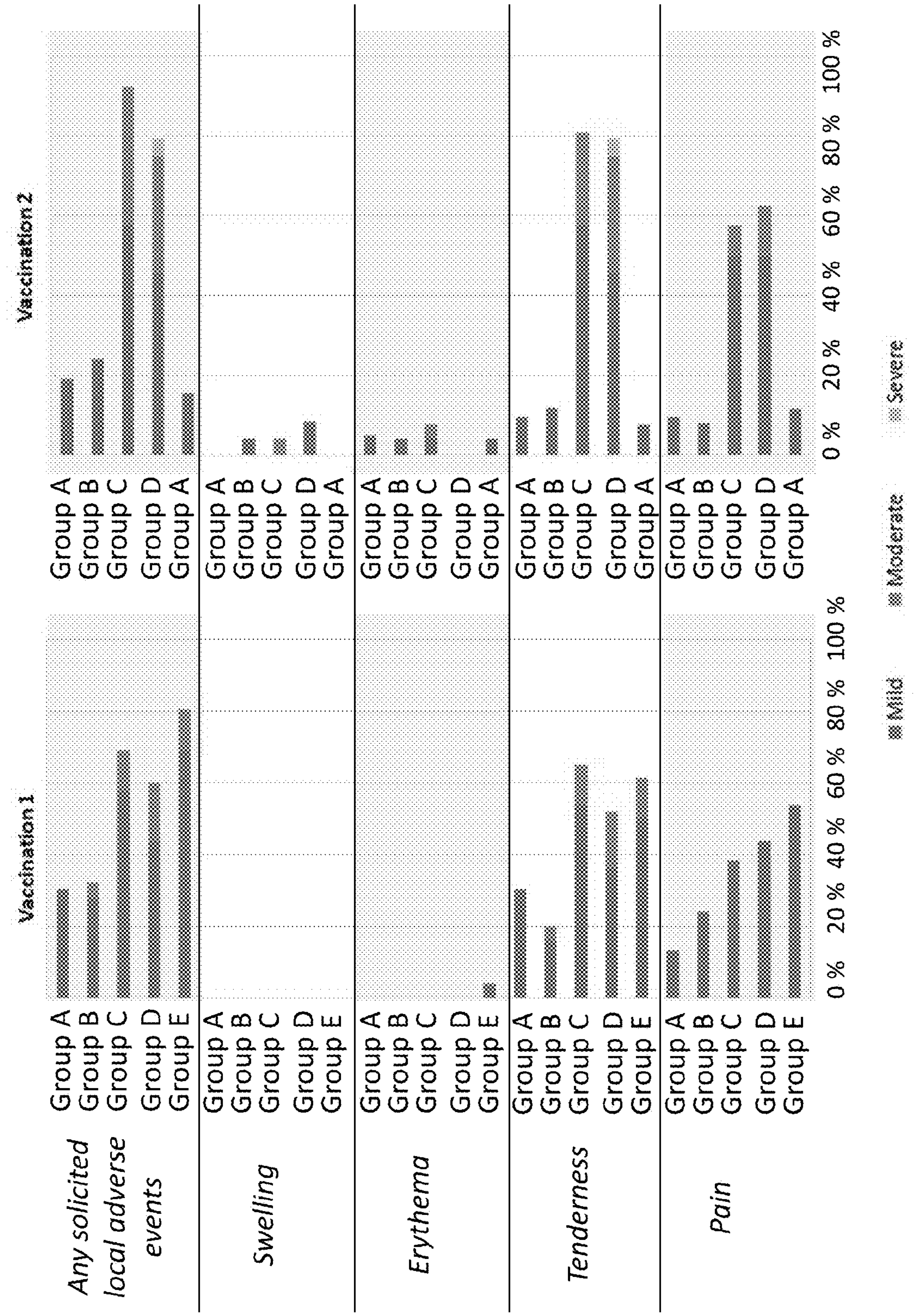
Figure 42B:
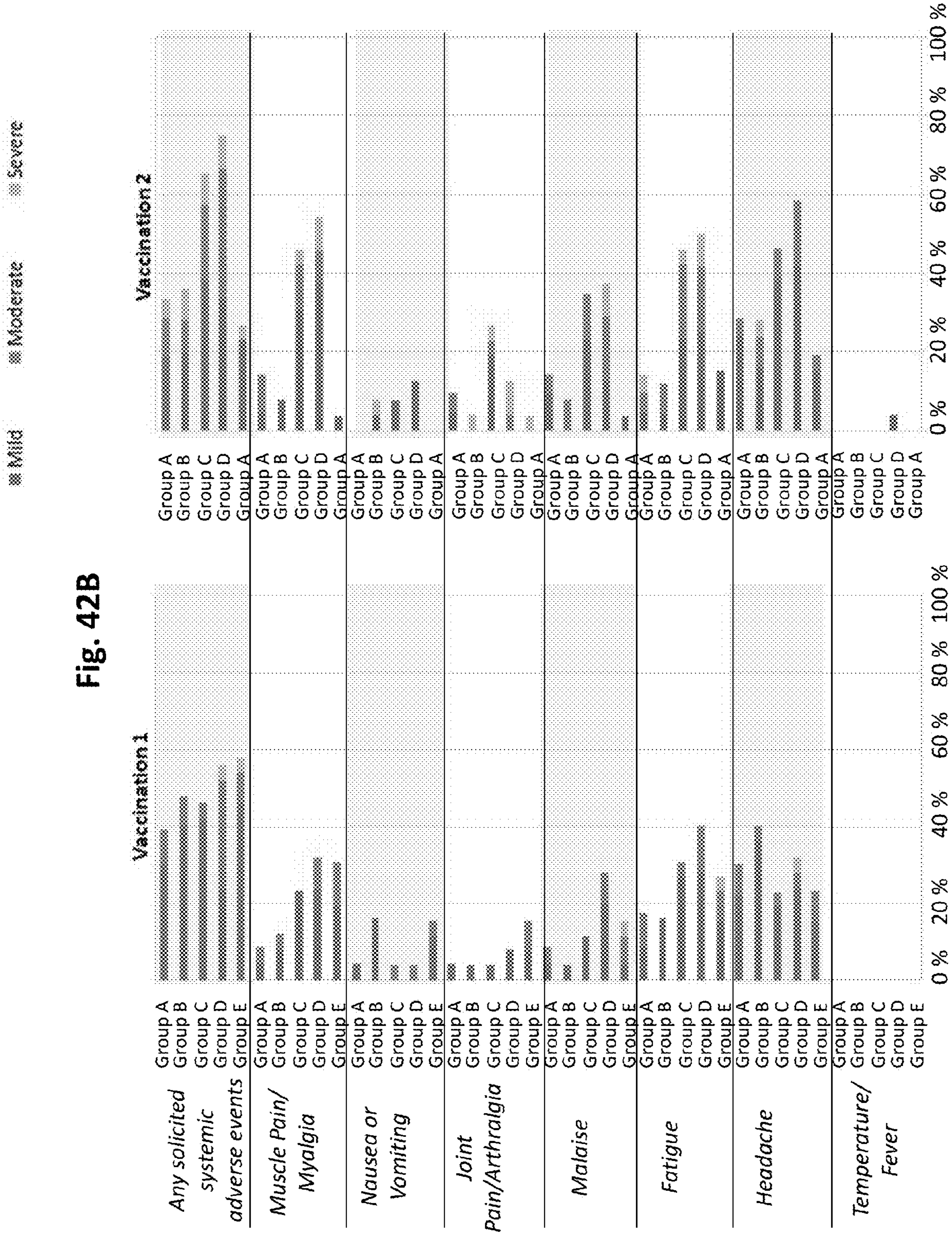

FIGS. 42A-B show the local (FIG. 42A) and systemic adverse events (FIG. 42B) experienced by patients in a clinical trial which evaluated a vaccine comprising BV2373 and MATRIX-M™. Groups A-E are identified in Table 5. The data shows that the vaccine was well tolerated and safe.

Figure 43A:
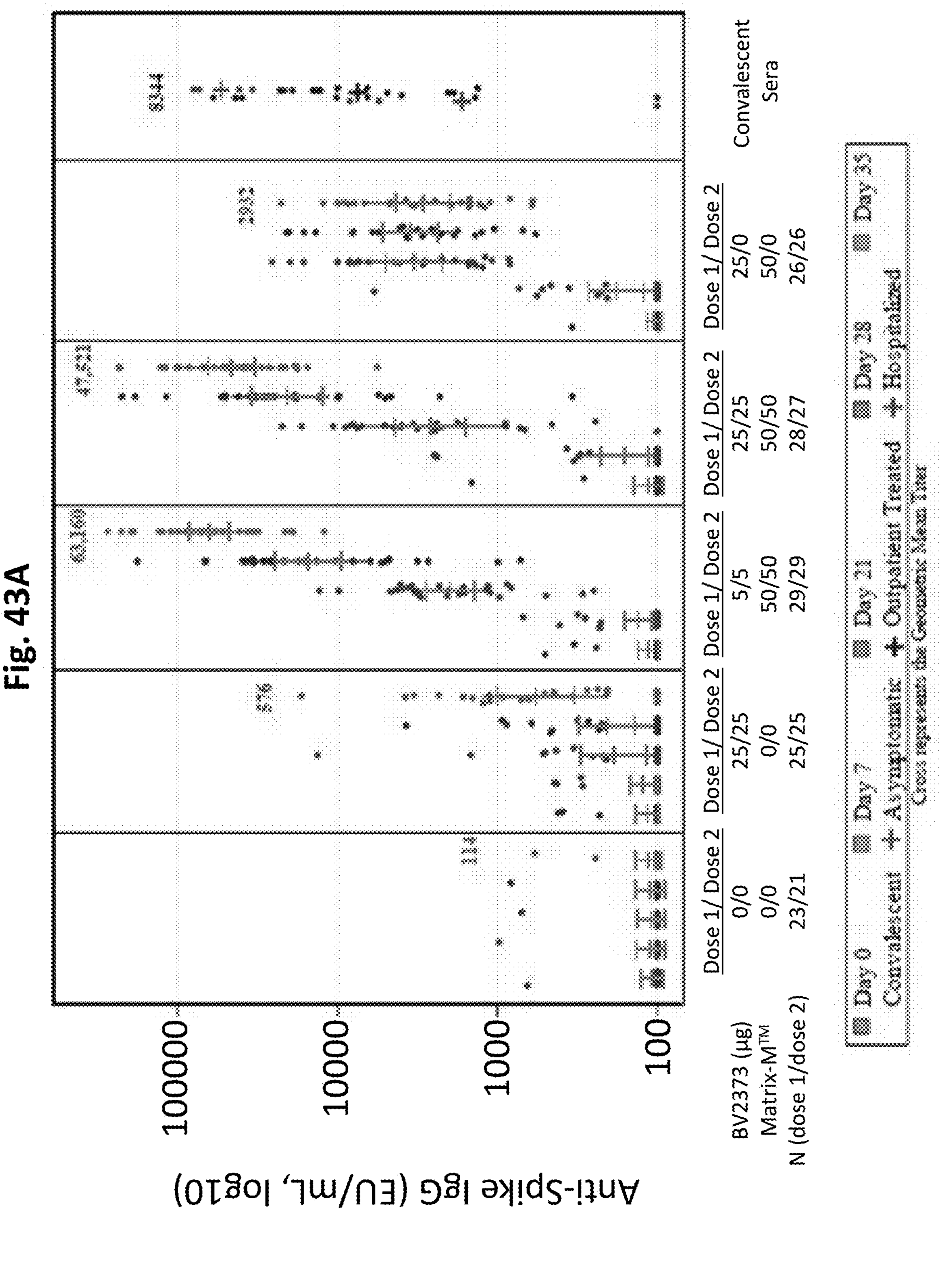
Figure 43B:
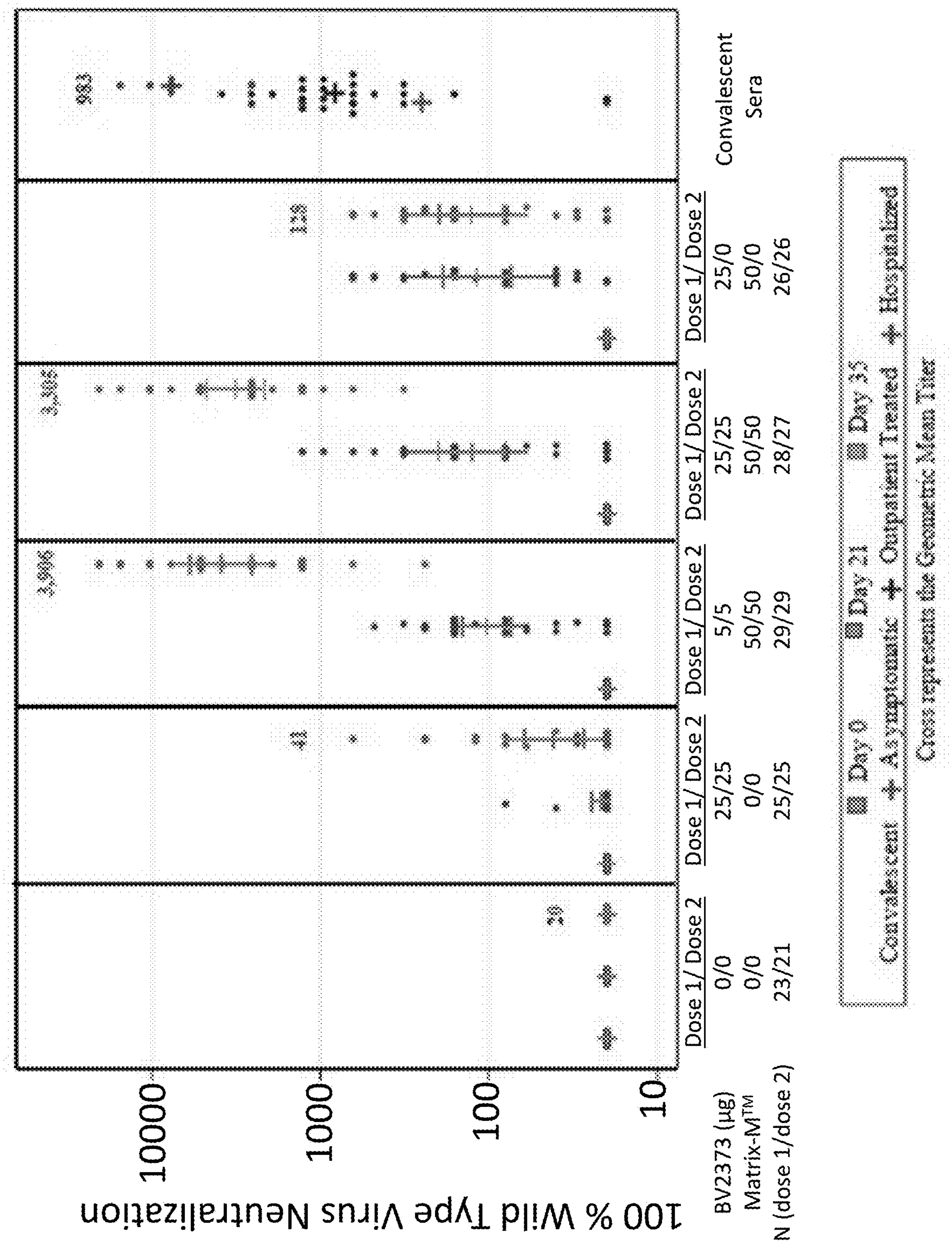

FIGS. 43A-B show the anti-CoV S polypeptide IgG (FIG. 43A) and neutralization titers (FIG. 43B) 21 days and 35 days after immunization of participants in a clinical trial which evaluated a vaccine comprising BV2373 and MATRIX-M™. Horizontal bars represent interquartile range (IRQ) and median area under the curve, respectively. Whisker endpoints are equal to the maximum and minimum values below or above the median±1.5 times the IQR. The convalescent serum panel includes specimens from PCR-confirmed COVID-19 participants from Baylor College of Medicine (29 specimens for ELISA and 32 specimens for microneutralization (MN $IC_{>99}$). Severity of COVID-19 is denoted as a red mark for hospitalized patients (including intensive care setting), a blue mark for outpatient-treated patients (sample collected in emergency department), and a green mark for asymptomatic (exposed) patients (sample collected from contact/exposure assessment).

Figure 44A:
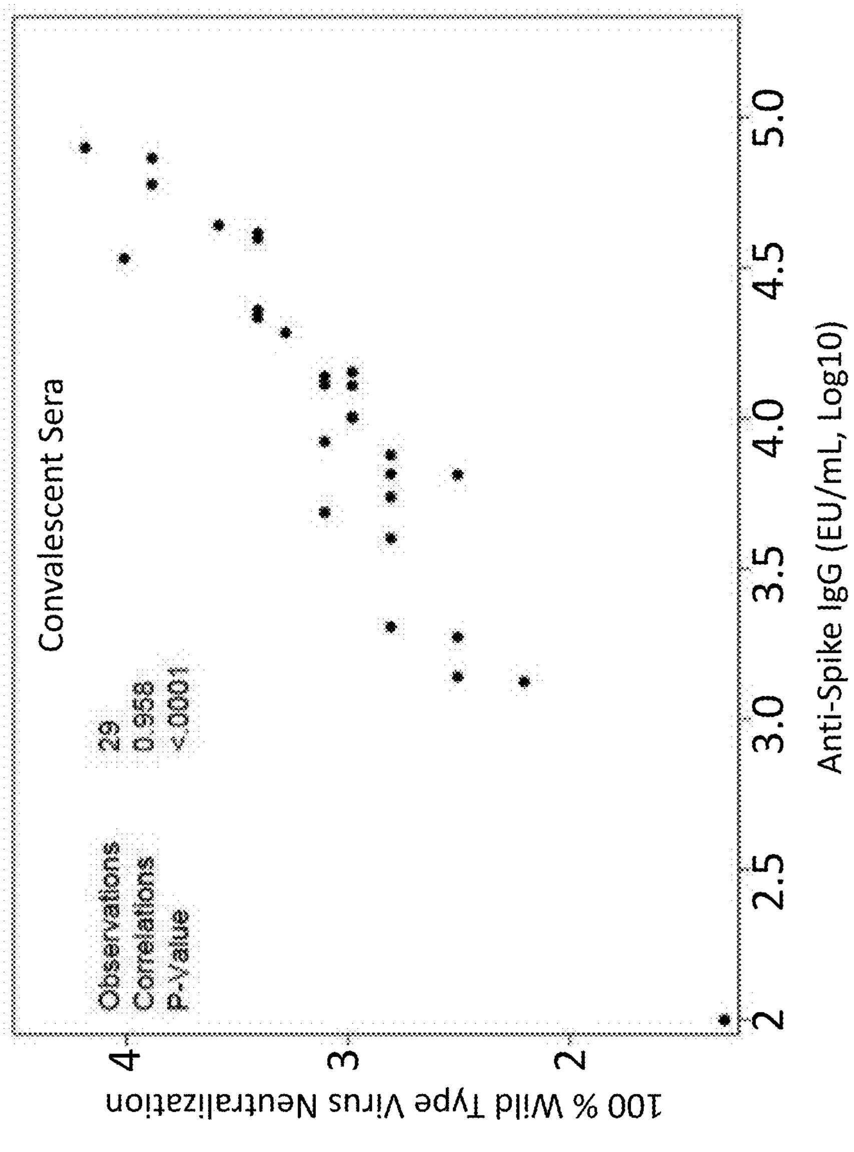
Figure 44B:
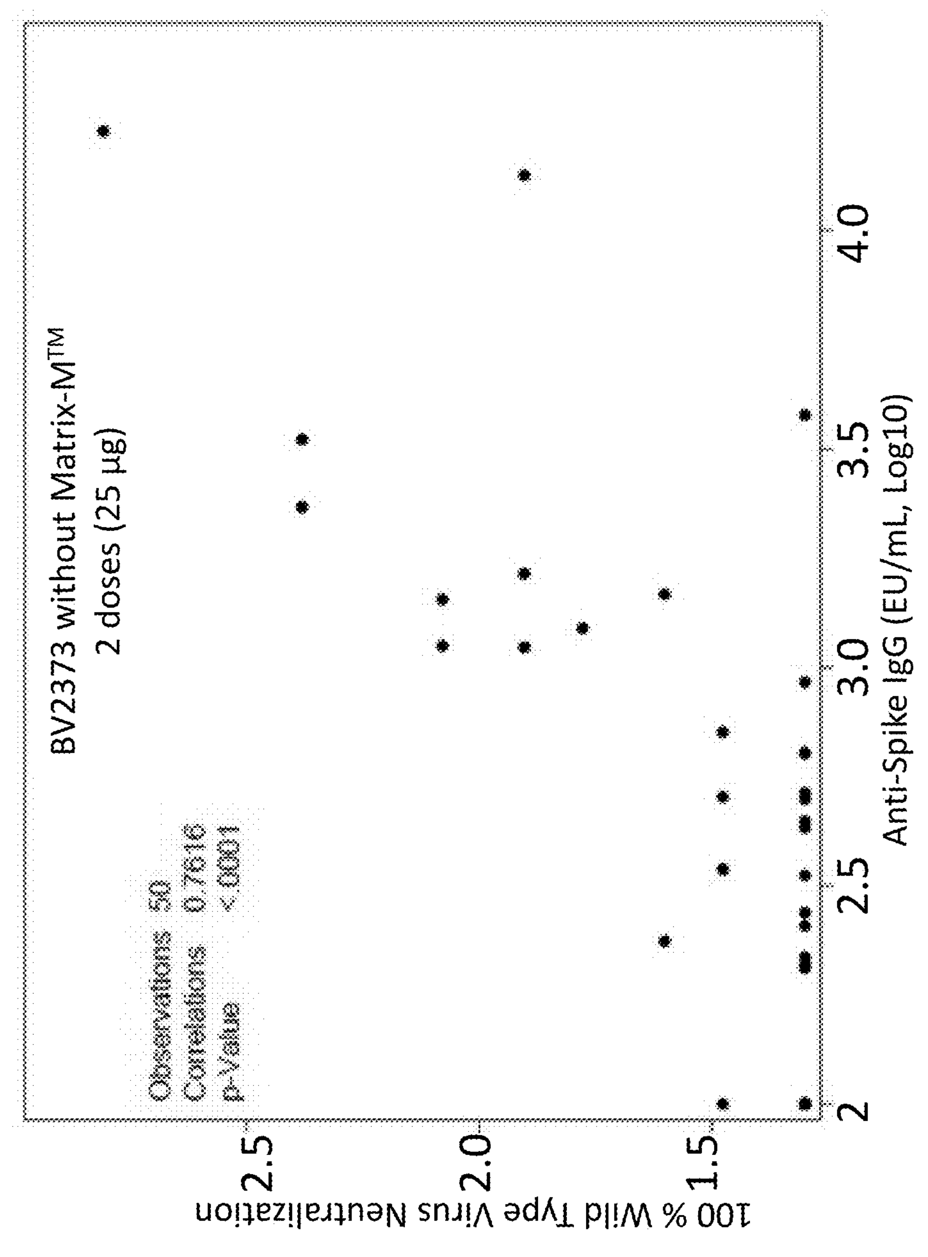
Figure 44C:
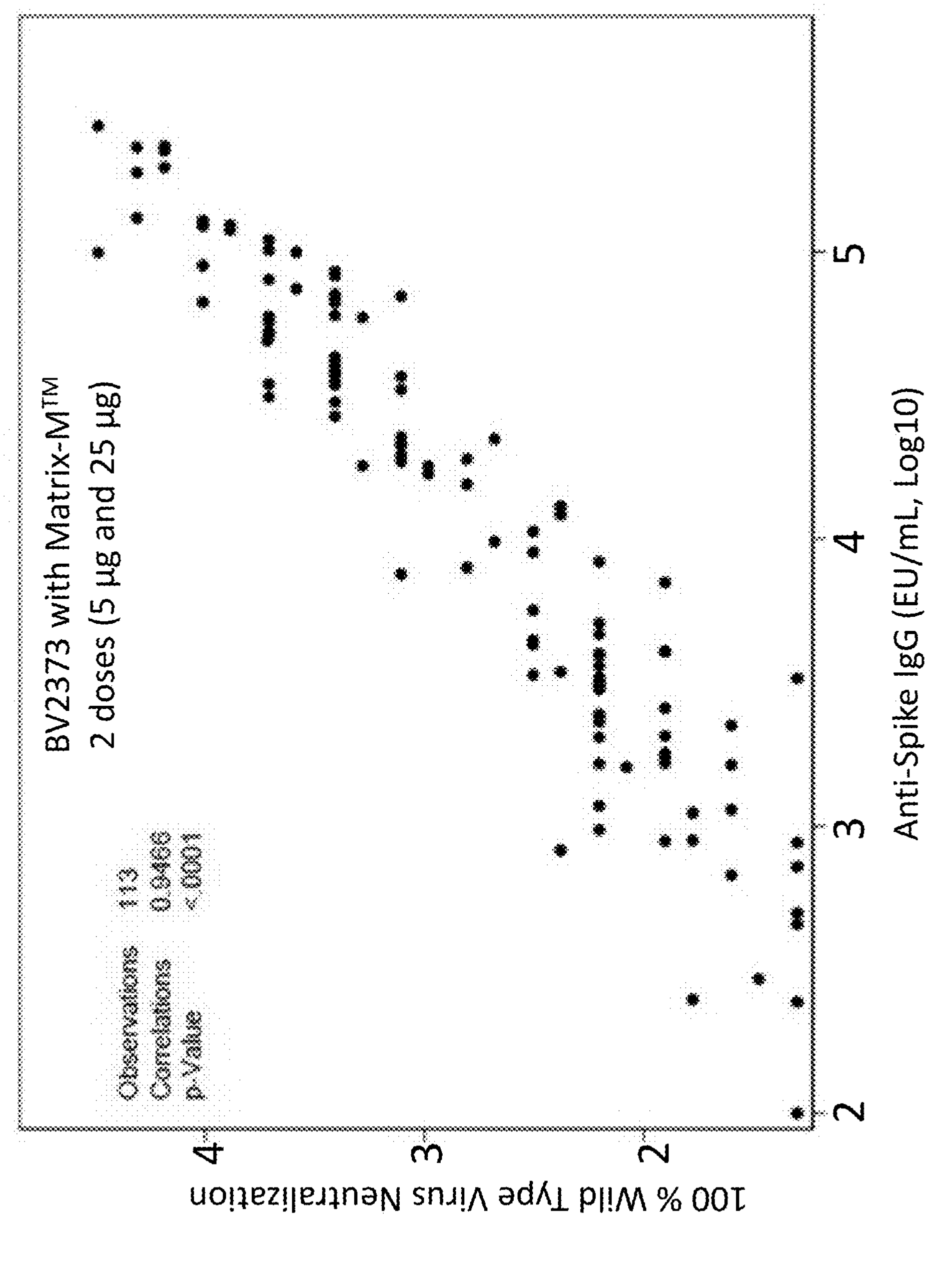
Figure 45A:
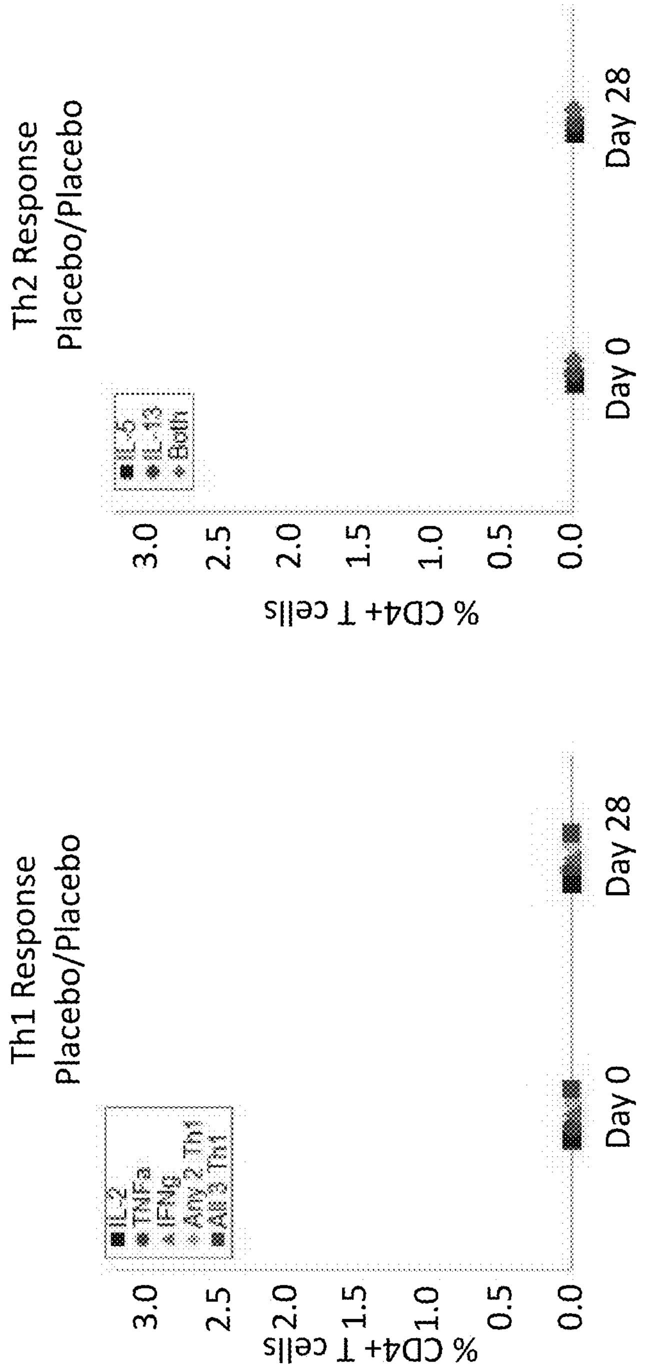
Figure 45B:
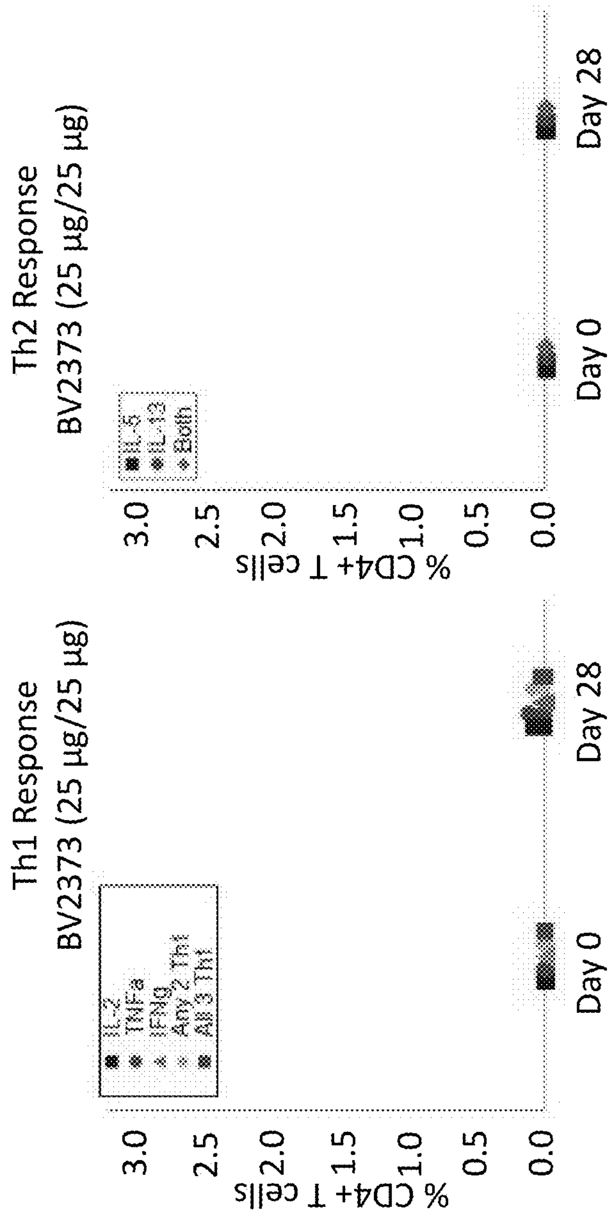
Figure 45C:
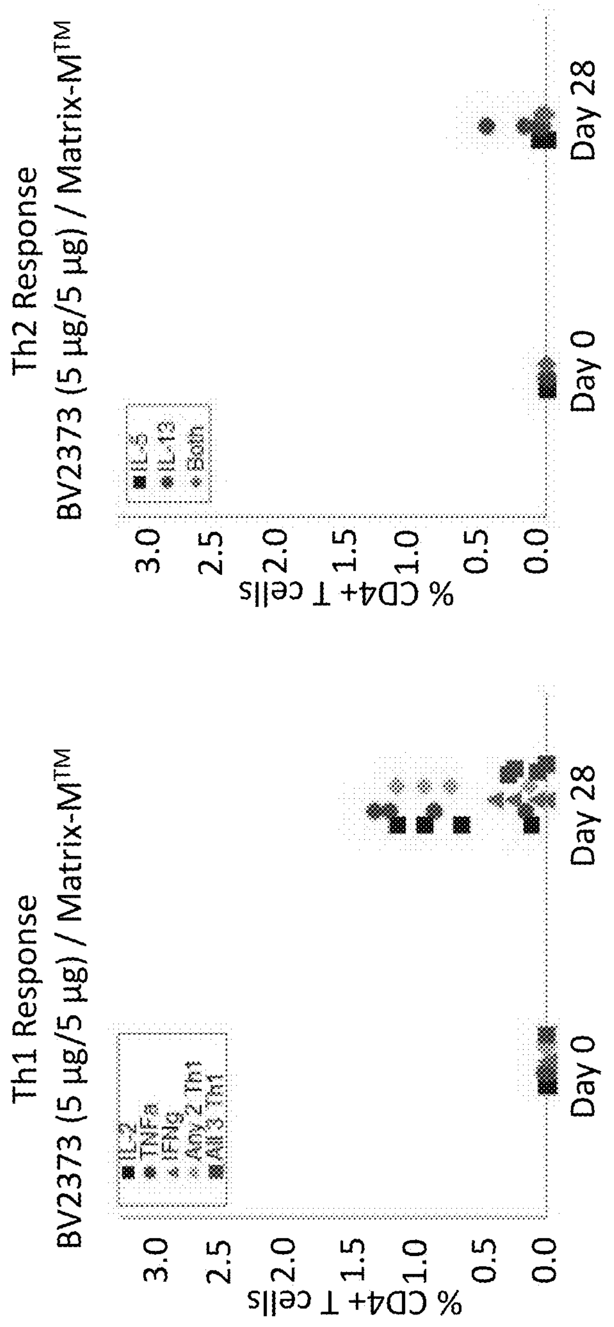
Figure 45D:
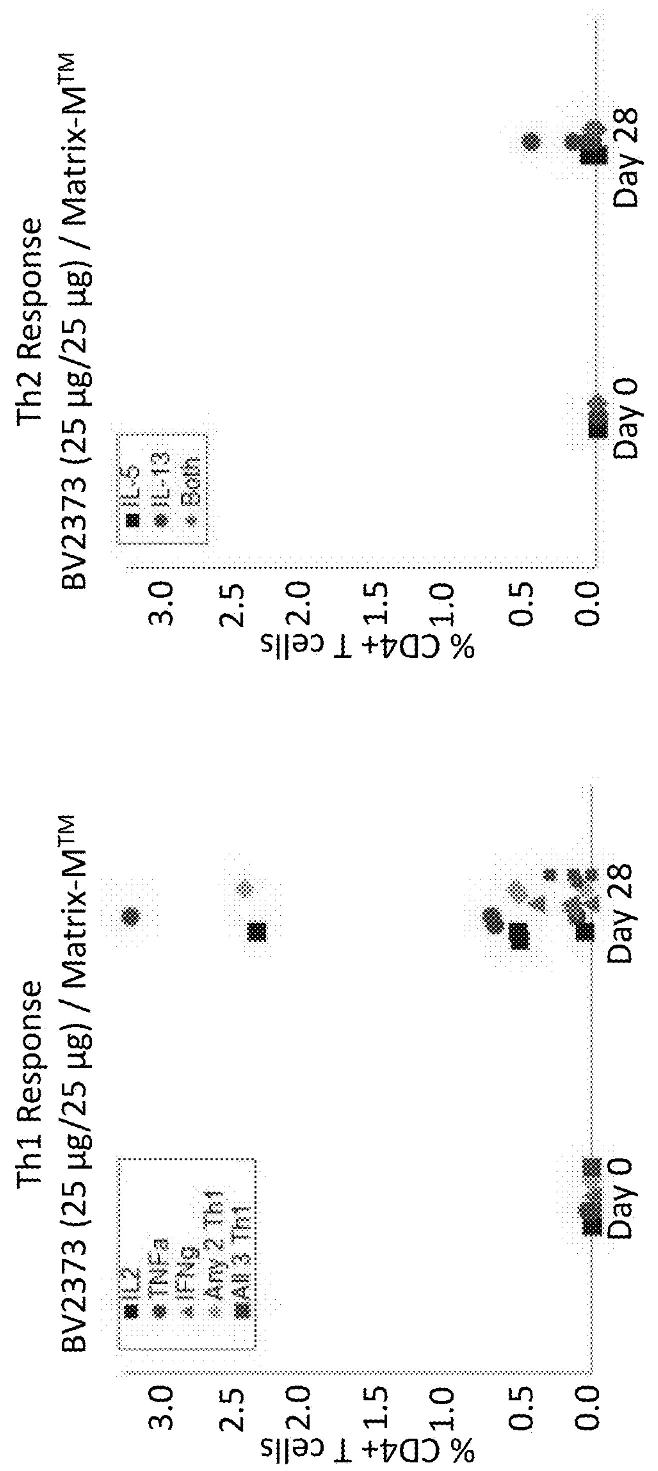

FIGS. 44A-C shows the correlation between anti-CoV S polypeptide IgG and neutralizing antibody titers in patients administered convalescent sera (FIG. 44A), two 25 μg doses of BV2373 (FIG. 44B), and two doses (5 μg and 25 μg) of BV2373 with MATRIX-M™ (FIG. 44C). A strong correlation was observed between neutralizing antibody titers and anti-CoV-S IgG titers in patients treated with convalescent sera or with adjuvanted BV2373, but not in patients treated with BV2373 in the absence of adjuvant.

FIGS. 45A-D show the frequencies of antigen-specific $CD4^+$ T cells producing T helper 1 (Th1) cytokines interferon-gamma (IFN-γ), tumor necrosis factor-alpha (TNF-α), and interleukin (IL)-2 and T helper 2 (Th2) cytokines IL-5 and IL-13 indicated cytokines from participants in Groups A (placebo, FIG. 45A), B (25 μg BV2373, FIG. 45B), C (5 μg BV2373 and 50 MATRIX-M™, FIG. 45C), and D (25 μg BV2373 and 50 μg MATRIX-M™, FIG. 45D) following stimulation with BV2373. "Any 2" in Th1 cytokine panel means $CD4^+$ T cells that can produce two types of Th1 cytokines at the same time. "All 3" indicates $CD4^+$ T cells that produce IFN-γ, TNF-α, and IL-2 simultaneously. "Both" in Th2 panel means $CD4^+$ T cells that can produce Th2 cytokines IL-5 and IL-13 at the same time.

DETAILED DESCRIPTION OF THE INVENTION

Definitions

As used herein, and in the appended claims, the singular forms "a", "an", and "the" include plural referents unless the context clearly dictates otherwise. Thus, for example, reference to "a protein" can refer to one protein or to mixtures of such protein, and reference to "the method" includes reference to equivalent steps and/or methods known to those skilled in the art, and so forth.

As used herein, the term "adjuvant" refers to a compound that, when used in combination with an immunogen, augments or otherwise alters or modifies the immune response induced against the immunogen. Modification of the immune response may include intensification or broadening the specificity of either or both antibody and cellular immune responses.

As used herein, the term "about" or "approximately" when preceding a numerical value indicates the value plus or minus a range of 10%. For example, "about 100" encompasses 90 and 110.

As used herein, the terms "immunogen," "antigen," and "epitope" refer to substances such as proteins, including glycoproteins, and peptides that are capable of eliciting an immune response.

As used herein, an "immunogenic composition" is a composition that comprises an antigen where administration of the composition to a subject results in the development in the subject of a humoral and/or a cellular immune response to the antigen.

As used herein, a "subunit" composition, for example a vaccine, that includes one or more selected antigens but not all antigens from a pathogen. Such a composition is substantially free of intact virus or the lysate of such cells or particles and is typically prepared from at least partially purified, often substantially purified immunogenic polypeptides from the pathogen. The antigens in the subunit composition disclosed herein are typically prepared recombinantly, often using a baculovirus system.

As used herein, "substantially" refers to isolation of a substance (e.g. a compound, polynucleotide, or polypeptide) such that the substance forms the majority percent of the sample in which it is contained. For example, in a sample, a substantially purified component comprises 85%, preferably 85%-90%, more preferably at least 95%-99.5%, and most preferably at least 99% of the sample. If a component is substantially replaced the amount remaining in a sample is less than or equal to about 0.5% to about 10%, preferably less than about 0.5% to about 1.0%.

The terms "treat," "treatment," and "treating," as used herein, refer to an approach for obtaining beneficial or desired results, for example, clinical results. For the purposes of this disclosure, beneficial or desired results may include inhibiting or suppressing the initiation or progression of an infection or a disease; ameliorating, or reducing the development of, symptoms of an infection or disease; or a combination thereof.

"Prevention," as used herein, is used interchangeably with "prophylaxis" and can mean complete prevention of an infection or disease, or prevention of the development of symptoms of that infection or disease; a delay in the onset of an infection or disease or its symptoms; or a decrease in the severity of a subsequently developed infection or disease or its symptoms.

As used herein an "effective dose" or "effective amount" refers to an amount of an immunogen sufficient to induce an immune response that reduces at least one symptom of pathogen infection. An effective dose or effective amount may be determined e.g., by measuring amounts of neutralizing secretory and/or serum antibodies, e.g., by plaque neutralization, complement fixation, enzyme-linked immunosorbent (ELISA), or microneutralization assay.

As used herein, the term "vaccine" refers to an immunogenic composition, such as an immunogen derived from a pathogen, which is used to induce an immune response against the pathogen that provides protective immunity (e.g., immunity that protects a subject against infection with the pathogen and/or reduces the severity of the disease or condition caused by infection with the pathogen). The protective immune response may include formation of antibodies and/or a cell-mediated response. Depending on context, the term "vaccine" may also refer to a suspension or solution of an immunogen that is administered to a subject to produce protective immunity.

As used herein, the term "subject" includes humans and other animals. Typically, the subject is a human. For example, the subject may be an adult, a teenager, a child (2 years to 14 years of age), an infant (birth to 2 year), or a neonate (up to 2 months). In particular aspects, the subject is up to 4 months old, or up to 6 months old. In some aspects, the adults are seniors about 65 years or older, or about 60 years or older. In some aspects, the subject is a pregnant woman or a woman intending to become pregnant. In other aspects, subject is not a human; for example a non-human primate; for example, a baboon, a chimpanzee, a gorilla, or a macaque. In certain aspects, the subject may be a pet, such as a dog or cat.

As used herein, the term "pharmaceutically acceptable" means being approved by a regulatory agency of a U.S. Federal or a state government or listed in the U.S. Pharmacopeia, European Pharmacopeia or other generally recognized pharmacopeia for use in mammals, and more particularly in humans. These compositions can be useful as a vaccine and/or antigenic compositions for inducing a protective immune response in a vertebrate.

As used herein, the term "about" means plus or minus 10% of the indicated numerical value.

As used herein, the term "NVX-CoV2373" refers to a vaccine composition comprising the BV2373 Spike glycoprotein (SEQ ID NO: 87) and Fraction A and Fraction C iscom matrix (e.g., MATRIX-M™).

Vaccine Compositions Containing Coronavirus (CoV) Spike (S) Proteins

The disclosure provides non-naturally occurring coronavirus (CoV) Spike (S) polypeptides, nanoparticles containing CoV S polypeptides, and immunogenic compositions and vaccine compositions containing either non-naturally occurring CoV S polypeptides or nanoparticles containing CoV S polypeptides. In embodiments, provided herein are methods of using CoV S polypeptides, nanoparticles, immunogenic compositions, and vaccine compositions to stimulate an immune response.

Also provided herein are methods of manufacturing the nanoparticles and vaccine compositions. Advantageously, the methods provide nanoparticles that are substantially free from contamination by other proteins, such as proteins associated with recombinant expression of proteins in insect cells. In embodiments, expression occurs in baculovirus/Sf9 systems.

CoV S Polypeptide Antigens

The vaccine compositions of the disclosure contain non-naturally occurring CoV S polypeptides. CoV S polypeptides may be derived from coronaviruses, including but not limited to SARS-CoV-2, for example from SARS-CoV-2, from MERS CoV, and from SARS CoV. In contrast to the SARS-CoV S protein, the SARS-CoV-2 S protein has a four amino acid insertion in the S1/S2 cleavage site resulting in a polybasic RRAR furin-like cleavage motif. The SARS-CoV-2 S protein is synthesized as an inactive precursor (S0) that is proteolytically cleaved at the furin cleavage site into 51 and S2 subunits which remain non-covalently linked to form prefusion trimers. The S2 domain of the SARS-CoV-2 S protein comprises a fusion peptide (FP), two heptad repeats (HR1 and HR2), a transmembrane (TM) domain, and a cytoplasmic tail. The 51 domain of the SARS-CoV-2 S protein folds into four distinct domains: the N-terminal domain (NTD) and the C-terminal domain, which contains the receptor binding domain (RBD) and two subdomains SD1 and SD2. The prefusion SARS-CoV-2 S protein trimers undergo a structural rearrangement from a prefusion to a postfusion conformation upon S-protein receptor binding and cleavage.

Figure 2:
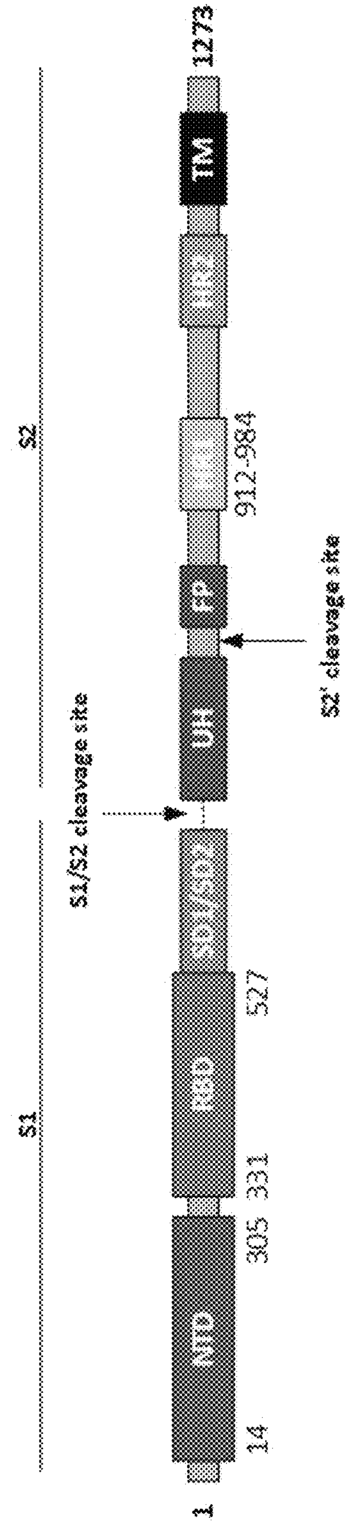
FIG. 2 shows the primary structure of the wild-type CoV S polypeptide, which has an inactive furin cleavage site, a fusion peptide deletion, and K986P and V987P mutations. The domain positions are numbered with respect to the amino acid sequence of the wild-type CoV S polypeptide from SARS-CoV-2 containing a signal peptide (SEQ ID NO: 1).
Figure 3:
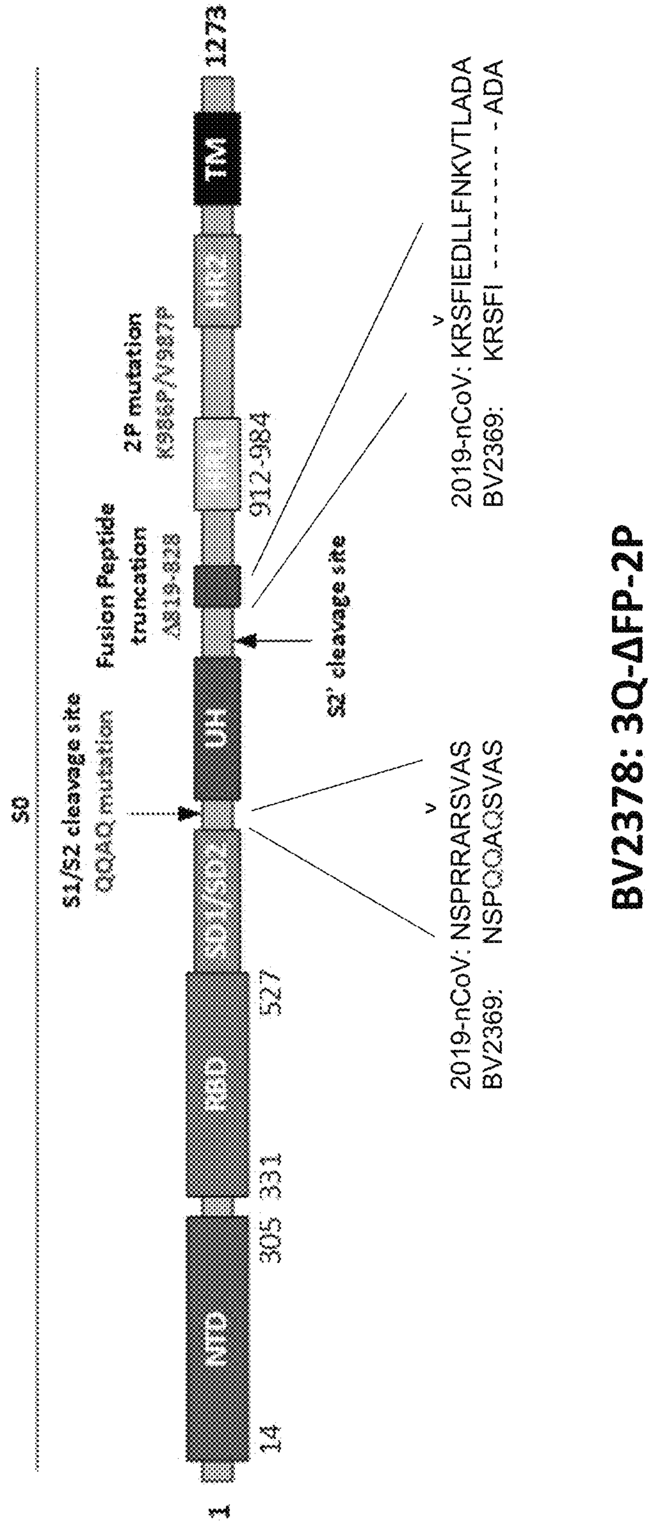
FIG. 3 shows the primary structure of the BV2378 CoV S polypeptide, which has an inactive furin cleavage site, a fusion peptide deletion, and K986P and V987P mutations. The domain positions are numbered with respect to the amino acid sequence of the wild-type CoV S polypeptide from SARS-CoV-2 containing a signal peptide (SEQ ID NO: 1).

In embodiments, the CoV S polypeptides are glycoproteins, due to post-translational glycosylation. The glycoproteins comprise one or more of an NTD, an RBD, an SD1/SD2 portion a UH domain, an intact or modified fusion protein region, an HR1 domain an HR2 domain, and a TM domain. In embodiments, the amino acids for each domain are given in FIG. 2 and FIG. 3 (shown corresponding to SEQ ID NO: 1). In embodiments, each domain may have at least 95%, at least 97% or at least 99% identity to the sequences for each domain as in SEQ ID NO: 1. Each domain may have a deletion or an insertion of about 10, about 20, or about 30 amino acids compared to those shown in SEQ ID NO: 1. Note that FIGS. 2 and 3 illustrate the 13-amino acid N-terminal signal peptide that is absent from the mature peptide. The CoV S polypeptides may be used to stimulate immune responses against the native CoV Spike (S) polypeptide.

In embodiments, the native CoV Spike (S) polypeptide (SEQ ID NO: 2) is modified resulting in non-naturally occurring CoV Spike (S) polypeptides (FIG. 1). In embodiments, the CoV Spike (S) glycoproteins comprise one or more modifications selected from the group consisting of:

(a) an inactivated mutated furin cleavage site amino acids 669-672;

(b) a deletion of one or more amino acids from amino acids 676-685;

(c) a deletion of one or more amino acids from amino acids 702-711;

(d) a deletion of one or more amino acids of the fusion peptide (amino acids 806-815);

(e) mutation of amino acid 601;

(f) mutation of amino acid 973;

(g) mutation of amino acid 974;

(h) a deletion of one or more amino acids from the N-terminal domain (NTD) (amino acids 1-318); and (i) a deletion of one or more amino acids from the transmembrane and cytoplasmic domain (TMCT) (amino acids 1201-1260), wherein the amino acids of the CoV S glycoprotein are numbered with respect to SEQ ID NO: 2. FIG. 3 shows a CoV S polypeptide called BV2378, which has an inactive furin cleavage site, deleted fusion peptide, a K986P, and a V987 mutation.

In embodiments, the CoV S polypeptides described herein exist in a prefusion conformation. In embodiments, the CoV S polypeptides described herein comprise a flexible HR2 domain. Unless otherwise mentioned, the flexibility of a domain is determined by transition electron microscopy (TEM) and 2D class averaging. A reduction in electron density corresponds to a flexible domain.

In embodiments, the CoV S polypeptides contain a furin site (RRAR), amino acids 669 to 672 of the native CoV Spike (S) polypeptide (SEQ ID NO: 2), that is inactivated by one or more mutations. Inactivation of the furin cleavage site prevents furin from cleaving the CoV S polypeptide. In embodiments, the CoV S polypeptides described herein which contain an inactivated furin cleavage site are expressed as a single chain.

In embodiments, one or more of the amino acids comprising the native furin cleavage site is mutated to any natural amino acid. In embodiments, the amino acids are L-amino acids. Non-limiting examples of amino acids include alanine, arginine, glycine, asparagine, aspartic acid, cysteine, glutamine, glutamic acid, serine, threonine, histidine, lysine, methionine, proline, valine, isoleucine, leucine, tyrosine, tryptophan, and phenylalanine.

In embodiments, one or more of the amino acids comprising the native furin cleavage site is mutated to glutamine. In embodiments, 1, 2, 3, or 4 amino acids may be mutated to glutamine. In embodiments, one of the arginines comprising the native furin cleavage site is mutated to glutamine. In embodiments, two of the arginines comprising the native furin cleavage site are mutated to glutamine. In embodiments, three of the arginines comprising the native furin cleavage site are mutated to glutamine.

In embodiments, one or more of the amino acids comprising the native furin cleavage site, is mutated to alanine. In embodiments, 1, 2, 3, or 4 amino acids may be mutated to alanine. embodiments, one of the arginines comprising the native furin cleavage site is mutated to alanine. In embodiments, two of the arginines comprising the native furin cleavage site are mutated to alanine. In embodiments, three of the arginines comprising the native furin cleavage site are mutated to alanine.

In embodiments, one or more of the amino acids comprising the native furin cleavage site is mutated to glycine. In embodiments, 1, 2, 3, or 4 amino acids may be mutated to glycine. In embodiments, one of the arginines of the native furin cleavage site is mutated to glycine. In embodiments, two of the arginines comprising the native furin cleavage site are mutated to glycine. In embodiments, three of the arginines comprising the native furin cleavage site are mutated to glycine.

In embodiments, one or more of the amino acids comprising the native furin cleavage site, is mutated to asparagine. For example 1, 2, 3, or 4 amino acids may be mutated to asparagine. In embodiments, one of the arginines comprising the native furin cleavage site is mutated to asparagine. In embodiments, two of the arginines comprising the native furin cleavage site are mutated to asparagine. In embodiments, three of the arginines comprising the native furin cleavage site are mutated to asparagine.

Non-limiting examples of the amino acid sequences of the inactivated furin sites contained within the CoV S polypeptides are found in Table 1.

TABLE 1

Inactivated Furin Cleavage Sites

| Amino Acid Sequence of Furin Cleavage Site | Active or Inactive Furin Cleavage Site |
|---|---|
| RRAR (SEQ ID NO: 6) | Active |
| QQAQ (SEQ ID NO: 7) | Inactive |
| QRAR (SEQ ID NO: 8) | Inactive |
| RQAR (SEQ ID NO: 9) | Inactive |
| RRAQ (SEQ ID NO: 10) | Inactive |
| QQAR (SEQ ID NO: 11) | Inactive |
| RQAQ (SEQ ID NO: 12) | Inactive |
| QRAQ (SEQ ID NO: 13) | Inactive |
| NNAN (SEQ ID NO: 14) | Inactive |
| NRAR (SEQ ID NO: 15) | Inactive |
| RNAR (SEQ ID NO: 16) | Inactive |
| RRAN (SEQ ID NO: 17) | Inactive |
| NNAR (SEQ ID NO: 18) | Inactive |
| RNAN (SEQ ID NO: 19) | Inactive |
| NRAN (SEQ ID NO: 20) | Inactive |
| AAAA (SEQ ID NO: 21) | Inactive |
| ARAR (SEQ ID NO: 22) | Inactive |
| RAAR (SEQ ID NO: 23) | Inactive |
| RRAA (SEQ ID NO: 24) | Inactive |

TABLE 1-continued

| Inactivated Furin Cleavage Sites | |
|---|---|
| Amino Acid Sequence of Furin Cleavage Site | Active or Inactive Furin Cleavage Site |
| AAAR (SEQ ID NO: 25) | Inactive |
| RAAA (SEQ ID NO: 26) | Inactive |
| ARAA (SEQ ID NO: 27) | Inactive |
| GGAG (SEQ ID NO: 28) | Inactive |
| GRAR (SEQ ID NO: 29) | Inactive |
| RGAR (SEQ ID NO: 30) | Inactive |
| RRAG (SEQ ID NO: 31) | Inactive |
| GGAR (SEQ ID NO: 32) | Inactive |
| RGAG (SEQ ID NO: 33) | Inactive |
| GRAG (SEQ ID NO: 34) | Inactive |
| GSAS (SEQ ID NO: 97) | Inactive |
| GSGA (SEQ ID NO: 113) | Inactive |

In embodiments, in lieu of an active furin cleavage site (SEQ ID NO: 6) the CoV S polypeptides described herein contain an inactivated furin cleavage site. In embodiments, the amino acid sequence of the inactivated furin cleavage site is represented by any one of SEQ ID NO: 7-34 or SEQ ID NO: 97. In embodiments, the amino acid sequence of the inactivated furin cleavage site is QQAQ (SEQ ID NO: 7). In embodiments, the amino acid sequence of the inactivated furin cleavage site is GSAS (SEQ ID NO: 97). In embodiments, the amino acid sequence of the inactivated furin cleavage site is GSGA (SEQ ID NO: 113).

In embodiments, the CoV S polypeptides contain a deletion, corresponding to one or more deletions within amino acids 676-685 of the native CoV Spike (S) polypeptide (SEQ ID NO: 2). In embodiments, 1, 2, 3, 4, 5, 6, 7, 8, 9, or 10 amino acids of amino acids 676-685 of the native CoV Spike (S) polypeptide (SEQ ID NO:2) are deleted. In embodiments, the deletions of amino acids within amino acids 676-685 are consecutive e.g. amino acids 676 and 677 are deleted or amino acids 680 and 681 are deleted. In embodiments, the deletions of amino acids within amino acids 676-685 are non-consecutive e.g. amino acids 676 and 680 are deleted or amino acids 677 and 682 are deleted. In embodiments, CoV S polypeptides containing a deletion, corresponding to one or more deletions within amino acids 676-685, have an amino acid sequence selected from the group consisting of SEQ ID NO: 62 and SEQ ID NO: 63.

In embodiments, the CoV S polypeptides contain a deletion, corresponding to one or more deletions within amino acids 702-711 of the native CoV Spike (S) polypeptide (SEQ ID NO: 2). In embodiments, 1, 2, 3, 4, 5, 6, 7, 8, 9, or 10 amino acids of amino acids 702-711 of the native SARS-CoV-2 Spike (S) polypeptide (SEQ ID NO:2) are deleted. In embodiments, the one or more deletions of amino acids within amino acids 702-711 are consecutive e.g. amino acids 702 and 703 are deleted or amino acids 708 and 709 are deleted. In embodiments, the deletions of amino acids within amino acids 702-711 are non-consecutive e.g. amino acids 702 and 704 are deleted or amino acids 707 and 710 are deleted. In embodiments, the CoV S polypeptides containing a deletion, corresponding to one or more deletions within amino acids 702-711, have an amino acid sequence selected from the group consisting of SEQ ID NO: 64 and SEQ ID NO: 65.

In embodiments, the CoV S polypeptides contain a deletion of the fusion peptide (SEQ ID NO: 104), which corresponds to amino acids 806-815 of SEQ ID NO: 2. In embodiments, 1, 2, 3, 4, 5, 6, 7, 8, 9, or 10 amino acids of the fusion peptide of the CoV Spike (S) polypeptide (SEQ ID NO:2) are deleted. In embodiments, the deletions of amino acids within the fusion peptide are consecutive e.g. amino acids 806 and 807 are deleted or amino acids 809 and 810 are deleted. In embodiments, the deletions of amino acids within the fusion peptide are non-consecutive e.g. amino acids 806 and 808 are deleted or amino acids 810 and 813 are deleted. In embodiments, the CoV S polypeptides containing a deletion, corresponding to one or more amino acids of the fusion peptide, have an amino acid sequence selected from SEQ ID NOS: 66, 77, and 105-108.

In embodiments, the CoV S polypeptides contain a deletion of one or more amino acids from the N-terminal domain (NTD) (corresponding to amino acids 1-318 of SEQ ID NO: 2. The amino acid sequence of the NTD is represented by SEQ ID NO: 45. In embodiments, the CoV S polypeptides contain a deletion of amino acids 1-318 of the N-terminal domain (NTD) of SEQ ID NO: 2. In embodiments, deletion of the NTD enhances protein expression of the CoV Spike (S) polypeptide. In embodiments, the CoV S polypeptides which have an NTD deletion have amino acid sequences represented by SEQ ID NOS: 46, 48, 49, 51, 52, and 54. In embodiments, the CoV S polypeptides which have an NTD deletion are encoded by an isolated nucleic acid sequence selected from the group consisting of SEQ ID NO: 47, SEQ ID NO: 50, and SEQ ID NO: 53.

In embodiments, the CoV Spike (S) polypeptides contain a deletion of one or more amino acids from the transmembrane and cytoplasmic domain (TMCT) (corresponding to amino acids 1201-1260). The amino acid sequence of the TMCT is represented by SEQ ID NO: 39. In embodiments, the CoV S polypeptides which have a deletion of one or more residues of the TMCT have enhanced protein expression. In embodiments, the CoV Spike (S) polypeptides which have one or more deletions from the TMCT have an amino acid sequence selected from the group consisting of SEQ ID NO: 40, 41, 42, 52, 54, 59, 61, 88, and 89. In embodiments, the CoV S polypeptides which have one or more deletions from the TMCT are encoded by an isolated nucleic acid sequence selected from the group consisting of SEQ ID NO: 39, 43, 53, and 60.

In embodiments, the CoV S polypeptides contain a mutation at Asp-601 of the native CoV Spike (S) polypeptide (SEQ ID NO: 2). In embodiments, Asp-601 is mutated to any natural amino acid. In embodiments, Asp-601 is mutated to glycine.

In embodiments, the CoV S polypeptides contain mutations that stabilize the prefusion conformation of the CoV S polypeptide. In embodiments, the CoV S polypeptides contain proline substitutions which stabilize the prefusion conformation. This strategy has been utilized for to develop a prefusion stabilized MERS-CoV S protein as described in the following documents which are each incorporated by reference herein in their entirety: Proc Natl Acad Sci USA. 2017 Aug. 29; 114 (35):E7348-E7357; Sci Rep. 2018 Oct. 24; 8(1):15701; U.S. Publication No. 2020/0061185; and PCT Application No. PCT/US2017/058370.

In embodiments, the CoV S polypeptides contain a mutation at Lys-973 of the native CoV Spike (S) polypeptide (SEQ ID NO: 2). In embodiments, Lys-973 is mutated to any natural amino acid. In embodiments, Lys-973 is mutated to proline. In embodiments, the CoV S polypeptides containing a mutation at amino acid 973 are selected from the group consisting of SEQ ID NO: 84-89, 105-106, and 109-110.

In embodiments, the CoV S polypeptides contain a mutation at Val-974 of the native CoV Spike (S) polypeptide (SEQ ID NO: 2). In embodiments, Val-974 is mutated to any natural amino acid. In embodiments, Val-974 is mutated to proline. In embodiments, the CoV S polypeptides containing a mutation at amino acid 974 are selected from the group consisting of SEQ ID NO: 84-89, 105-106, and 109-110.

In embodiments, the CoV S polypeptides contain a mutation at Lys-973 and Val-974 of the native CoV Spike (S) polypeptide (SEQ ID NO: 2). In embodiments, Lys-973 and Val-974 are mutated to any natural amino acid. In embodiments, Lys-973 and Val-974 are mutated to proline. In embodiments, the CoV S polypeptides containing a mutation at amino acids 973 and 974 are selected from SEQ ID NOS: 84-89, 105-106, and 109-110.

Figure 8:
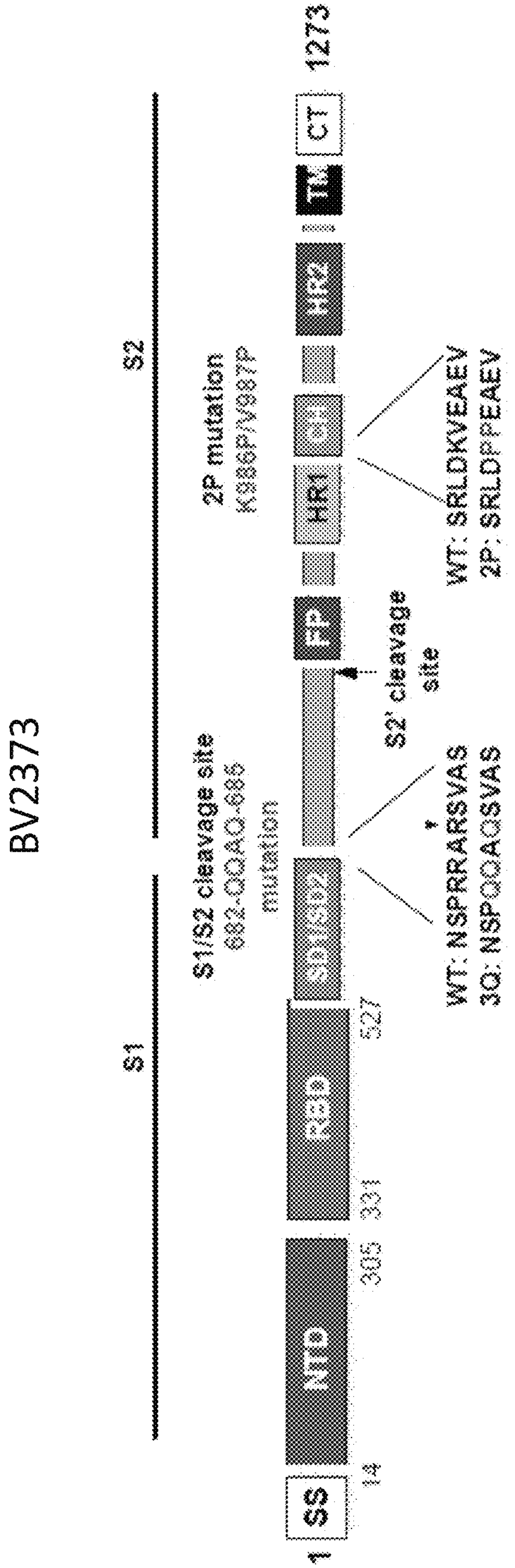
FIG. 8 shows the primary structure of the BV2373 CoV S polypeptide and modifications to the furin cleavage site, K986P, and V987P.

In embodiments, the CoV S polypeptides contain a mutation at Lys-973 and Val-974 and an inactivated furin cleavage site. In embodiments, the CoV S polypeptides contain mutations of Lys-973 and Val-974 to proline and an inactivated furin cleavage site, having the amino acid sequence of QQAQ (SEQ ID NO: 7) or GSAS (SEQ ID NO: 96). An exemplary CoV S polypeptide containing a mutation at Lys-973 and Val-974 and an inactivated furin cleavage site is depicted in FIG. 8. In embodiments, the CoV S polypeptides containing mutations of Lys-973 and Val-974 to proline and an inactivated furin cleavage site have an amino acid sequences of SEQ ID NOS: 86 or 87 and a nucleic acid sequence of SEQ ID NO: 96.

In embodiments, the CoV S polypeptides contain a mutation at Lys-973 and Val-974, an inactivated furin cleavage site, and a deletion of one or more amino acids of the fusion peptide. In embodiments, the CoV S polypeptides contain mutations of Lys-973 and Val-974 to proline, an inactivated furin cleavage site having the amino acid sequence of QQAQ (SEQ ID NO: 7) or GSAS (SEQ ID NO: 96), and deletion of one or more amino acids of the fusion peptide. In embodiments, the CoV S polypeptides containing mutations of Lys-973 and Val-974 to proline, an inactivated furin cleavage site, and deletion of one or more amino acids of the fusion peptide has an amino acid sequence of SEQ ID NO: 105 or 106.

In embodiments, the CoV Spike (S) polypeptides comprise a polypeptide linker. In embodiments, the polypeptide linker contains glycine and serine. In embodiments, the linker has about 50%, about 55%, about 60%, about 65%, about 70%, about 75%, about 80%, about 85%, about 90%, about 95%, or about 100% glycine.

In embodiments, the polypeptide linker has a repeat of $(SGGG)_n$ (SEQ ID NO: 91), wherein n is an integer from 1 to 50 (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50). In embodiments, the polypeptide linker has an amino acid sequence corresponding to SEQ ID NO: 90.

In embodiments, the polypeptide linker has a repeat of $(GGGGS)_n$ (SEQ ID NO: 93), wherein n is an integer from 1 to 50 (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50).

In embodiments, the polypeptide linker has a repeat of $(GGGS)_n$ (SEQ ID NO: 92), wherein n is an integer from 1 to 50 (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50).

In some aspects, the polypeptide linker is a poly-$(Gly)_n$ linker, wherein n is 1, 2, 3, 4, 5, 6, 7, 8, 9, 10, 15, 16, 17, 18, 19, or 20. In other embodiments, the linker is selected from the group consisting of: dipeptides, tripeptides, and quadripeptides. In embodiments, the linker is a dipeptide selected from the group consisting of alanine-serine (AS), leucine-glutamic acid (LE), and serine-arginine (SR).

In embodiments, the polypeptide linker comprises between 1 to 100 contiguous amino acids of a naturally occurring CoV S polypeptide or of a CoV S polypeptide disclosed herein. In embodiments, the polypeptide linker has an amino acid sequence corresponding to SEQ ID NO: 94.

In embodiments, the CoV Spike (S) polypeptides comprise a foldon. In embodiments, the TMCT is replaced with a foldon. In embodiments, a foldon causes trimerization of the CoV Spike (S) polypeptide. In embodiments, the foldon is an amino acid sequence known in the art. In embodiments, the foldon has an amino acid sequence of SEQ ID NO: 68. In embodiments, the foldon is a T4 fibritin trimerization motif. In embodiments, the T4 fibritin trimerization domain has an amino acid sequence of SEQ ID NO: 103. In embodiments, the foldon is separated in amino acid sequence from the CoV Spike (S) polypeptide by a polypeptide linker. Non-limiting examples of polypeptide linkers are found throughout this disclosure.

In embodiments, the disclosure provides CoV S polypeptides comprising a fragment of a coronavirus S protein and nanoparticles and vaccines comprising the same. In embodiments, the fragment of the coronavirus S protein is between 10 and 1500 amino acids in length (e.g. about 10, about 20, about 30, about 40, about 50, about 60, about 70, about 80, about 90, about 100, about 150, about 200, about 250, about 300, about 350, about 400, about 450, about 500, about 550, about 600, about 650, about 700, about 750, about 800, about 850, about 900, about 950, about 1000, about 1050, about 1100, about 1150, about 1200, about 1250, about 1300, about 1350, about 1400, about 1450, or about 1500 amino acids in length). In embodiments, the fragment of the coronavirus S protein is selected from the group consisting of the receptor binding domain (RBD), subdomain 1, subdomain 2, upper helix, fusion peptide, connecting region, heptad repeat 1, central helix, heptad repeat 2, NTD, and TMCT.

In embodiments, the CoV S polypeptide comprises an RBD and a subdomain 1. In embodiments, the CoV S polypeptide comprising an RBD and a subdomain 1 is amino acids 319 to 591 of SEQ ID NO: 1.

In embodiments, the CoV S polypeptide contains a fragment of a coronavirus S protein, wherein the fragment of the coronavirus S protein is the RBD. Non-limiting examples of RBDs include the RBD of SARS-CoV-2 (amino acid sequence=SEQ ID NO: 69), the RBD of SARS (amino acid sequence=SEQ ID NO: 70), and the RBD of MERS, (amino acid sequence=SEQ ID NO: 71).

In embodiments, the CoV S polypeptide contains two or more RBDs, which are connected by a polypeptide linker. In embodiments, the polypeptide linker has an amino acid sequence of SEQ ID NO: 90 or SEQ ID NO: 94.

In embodiments, the CoV S polypeptide contains 1, 2, 3, 4, 5, 6, 7, 8, 9, 10, 11, 12, 13, 14, 15, 16, 17, 18, 19, or 20 RBDs.

In some embodiments, the CoV S polypeptide contains two or more SARS-CoV-2 RBDs, which are connected by a polypeptide linker. In embodiments, the antigen containing two or more SARS-CoV-2 RBDs has an amino acid sequence corresponding to one of SEQ ID NOS: 72-75.

In embodiments, the CoV S polypeptide contains a SARS-CoV-2 RBD and a SARS RBD. In embodiments, the CoV S polypeptide comprises a SARS-CoV-2 RBD and a SARS RBD, wherein each RBD is separated by a polypeptide linker. In embodiments, the CoV S polypeptide comprising a SARS-CoV-2 RBD and a SARS RBD has an amino acid sequence selected from the group consisting of SEQ ID NOS: 76-79.

In embodiments, the CoV S polypeptide contains a SARS-CoV-2 RBD and a MERS RBD. In embodiments, the CoV S polypeptide comprises a SARS-CoV-2 RBD and a MERS RBD, wherein each RBD is separated by a polypeptide linker.

In embodiments, the CoV S polypeptide comprises a SARS RBD and a MERS RBD. In embodiments, the CoV S polypeptide comprises a SARS RBD and a MERS RBD, wherein each RBD is separated by a polypeptide linker.

In embodiments, the CoV S polypeptide contains a SARS-CoV-2 RBD, a SARS RBD, and a MERS RBD. In embodiments, the CoV S polypeptide contains a SARS-CoV-2 RBD, a SARS RBD, and a MERS RBD, wherein each RBD is separated by a polypeptide linker. In embodiments, the CoV S polypeptide comprising a SARS-CoV-2 RBD, a SARS RBD, and a MERS RBD has an amino acid sequence selected from the group consisting of SEQ ID NOS: 80-83.

In embodiments, the CoV S polypeptides described herein are expressed with an N-terminal signal peptide. In embodiments, the N-terminal signal peptide consists of an amino acid sequence of SEQ ID NO: 5 (MFVFLVLLPLVSS). In embodiments, the signal peptide may be replaced with any signal peptide that enables expression of the CoV S protein. In embodiments, one or more of the CoV S protein signal peptide amino acids may be deleted or mutated. An initiating methionine residue is maintained to initiate expression. In embodiments, the CoV S polypeptides are encoded by a nucleic acid sequence selected from the group consisting of SEQ ID NO: 35, SEQ ID NO: 37, SEQ ID NO: 95, SEQ ID NO: 43, SEQ ID NO: 47, SEQ ID NO: 50, SEQ ID NO: 53, SEQ ID NO: 55, SEQ ID NO: 57, SEQ ID NO: 96, and SEQ ID NO: 60.

Following expression of the CoV S protein in a host cell, the N-terminal signal peptide is cleaved to provide the mature CoV protein sequence (SEQ ID NOS: 2, 4, 38, 41, 44, 48, 51, 54, 58, 61, 63, 65, 67, 73, 75, 78, 79, 82, 83, 85, 87, 89, 106, and 110). In embodiments, the signal peptide is cleaved by host cell proteases. In aspects, the full-length protein may be isolated from the host cell and the signal peptide cleaved subsequently.

Following cleavage of the signal peptide from the CoV Spike (S) polypeptide with an amino acid sequence corresponding to SEQ ID NOS: 1, 3, 36, 40, 42, 46, 49, 52, 56, 59, 62, 64, 66, 72, 74, 76, 77, 80, 81, 84, 86, 87, 105, 107, 88, and 109 during expression and purification, a mature polypeptide having an amino acid sequence selected from the group consisting of SEQ ID NOS: 2, 4, 38, 41, 44, 48, 51, 54, 58, 61, 63, 65, 67, 73, 75, 78, 79, 82, 83, 85, 106, 108, 89, and 110 is obtained and used to produce a CoV S nanoparticle vaccine or CoV S nanoparticles.

Advantageously, the disclosed CoV S polypeptides may have enhanced protein expression and stability relative to the native CoV Spike (S) protein.

In embodiments, the CoV S polypeptides described herein contain further modifications from the native coronavirus S protein (SEQ ID NO: 2). In embodiments, the coronavirus S proteins described herein exhibit at least 80%, or at least 90%, or at least 95%, or at least 97%, or at least 99% identity to the native coronavirus S protein. A person of skill in the art would use known techniques to calculate the percent identity of the recombinant coronavirus S protein to the native protein. For example, percentage identity can be calculated using the tools CLUSTALW2 or Basic Local Alignment Search Tool (BLAST), which are available online. The following default parameters may be used for CLUSTALW2 Pairwise alignment: Protein Weight Matrix=Gonnet; Gap Open=10; Gap Extension=0.1.

In embodiments, the CoV S polypeptides described herein comprise about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, or about 25 substitutions compared to the coronavirus S protein (SEQ ID NO: 87).

In embodiments, the coronavirus S polypeptide is extended at the N-terminus, the C-terminus, or both the N-terminus and the C-terminus. In some aspects, the extension is a tag useful for a function, such as purification or detection. In some aspects the tag contains an epitope. For example, the tag may be a polyglutamate tag, a FLAG-tag, a HA-tag, a polyHis-tag (having about 5-10 histidines) (SEQ ID NO: 101), a hexahistidine tag (SEQ ID NO: 100), an 8×-His-tag (having eight histidines) (SEQ ID NO: 102), a Myc-tag, a Glutathione-S-transferase-tag, a Green fluorescent protein-tag, Maltose binding protein-tag, a Thioredoxin-tag, or an Fc-tag. In other aspects, the extension may be an N-terminal signal peptide fused to the protein to enhance expression. While such signal peptides are often cleaved during expression in the cell, some nanoparticles may contain the antigen with an intact signal peptide. Thus, when a nanoparticle comprises an antigen, the antigen may contain an extension and thus may be a fusion protein when incorporated into nanoparticles. For the purposes of calculating identity to the sequence, extensions are not included. In embodiments, the tag is a protease cleavage site. Non-limiting examples of protease cleavage sites include the HRV3C protease cleavage site, chymotrypsin, trypsin, elastase, endopeptidase, caspase-1, caspase-2, caspase-3, caspase-4, caspase-5, caspase-6, caspase-7, caspase-8, caspase-9, caspase-10, enterokinase, factor Xa, Granzyme B, TEV protease, and thrombin. In embodiments, the protease cleavage site is an HRV3C protease cleavage site. In embodiments, the protease cleavage site comprises an amino acid sequence of SEQ ID NO: 98.

In embodiments, the CoV S glycoprotein comprises a fusion protein. In embodiments, the CoV S glycoprotein comprises an N-terminal fusion protein. In embodiments, the Cov S glycoprotein comprises a C-terminal fusion protein. In embodiments, the fusion protein encompasses a tag useful for protein expression, purification, or detection. In embodiments, the tag is a polyHis-tag (having about 5-10 histidines), a Myc-tag, a Glutathione-S-transferase-tag, a Green fluorescent protein-tag, Maltose binding protein-tag, a Thioredoxin-tag, a Strep-tag, a Twin-Strep-tag, or an Fc-tag. In embodiments, the tag is an Fc-tag. In embodiments, the Fc-tag is monomeric, dimeric, or trimeric. In embodiments, the tag is a hexahistidine tag, e.g. a polyHis-tag which contains six histidines (SEQ ID NO: 100). In embodiments, the tag is a Twin-Strep-tag with an amino acid sequence of SEQ ID NO: 99.

In embodiments, the CoV S polypeptide is a fusion protein comprising another coronavirus protein. In embodiments, the other coronavirus protein is from the same coronavirus. In embodiments, the other coronavirus protein is from a different coronavirus.

In some aspects, the CoV S protein may be truncated. For example, the N-terminus may be truncated by about 10 amino acids, about 30 amino acids, about 50 amino acids, about 75 amino acids, about 100 amino acids, or about 200 amino acids. The C-terminus may be truncated instead of or in addition to the N-terminus. For example, the C-terminus may be truncated by about 10 amino acids, about 30 amino acids, about 50 amino acids, about 75 amino acids, about 100 amino acids, or about 200 amino acids. For purposes of calculating identity to the protein having truncations, identity is measured over the remaining portion of the protein.

Nanoparticles Containing CoV Spike (S) Polypeptides

Figure 10:
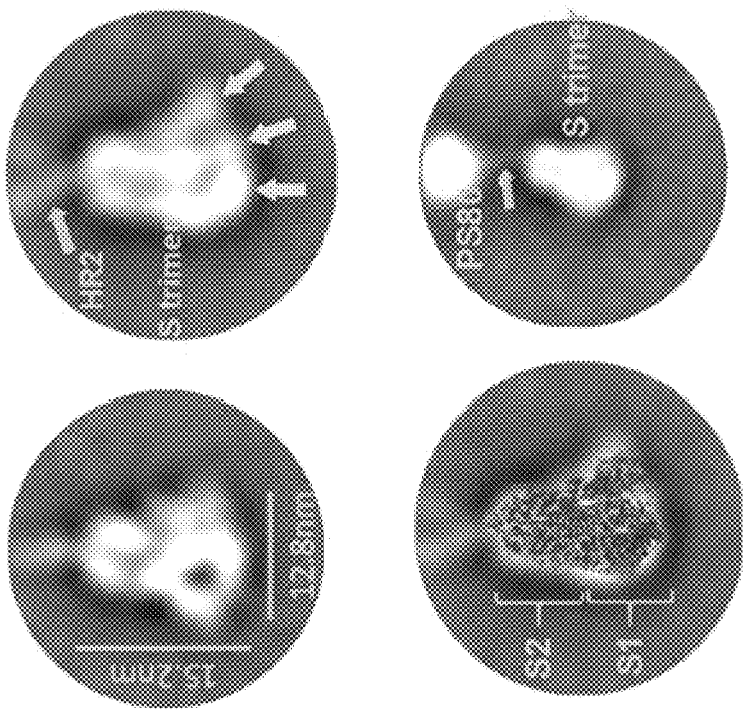
FIG. 10 shows a cryo-electron microscopy (cryoEM) structure of the BV2373 CoV S polypeptide overlaid on the cryoEM structure of the SARS-CoV-2 spike protein (EMB ID: 21374).

In embodiments, the mature CoV S polypeptide antigens are used to produce a vaccine comprising coronavirus S nanoparticles. In embodiments, nanoparticles of the present disclosure comprise the CoV S polypeptides described herein. In embodiments, the nanoparticles of the present disclosure comprise CoV S polypeptides associated with a detergent core. The presence of the detergent facilitates formation of the nanoparticles by forming a core that organizes and presents the antigens. In embodiments, the nanoparticles may contain the CoV S polypeptides assembled into multi-oligomeric glycoprotein-detergent (e.g. PS80) nanoparticles with the head regions projecting outward and hydrophobic regions and PS80 detergent forming a central core surrounded by the glycoprotein. In embodiments, the CoV S polypeptide inherently contains or is adapted to contain a transmembrane domain to promote association of the protein into a detergent core. In embodiments, the CoV S polypeptide contains a head domain. FIG. 10 shows an exemplary structure of a CoV S polypeptide of the disclosure. Primarily the transmembrane domains of a CoV S polypeptide trimer associate with detergent; however, other portions of the polypeptide may also interact. Advantageously, the nanoparticles have improved resistance to environmental stresses such that they provide enhanced stability and/or improved presentation to the immune system due to organization of multiple copies of the protein around the detergent.

In embodiments, the detergent core is a non-ionic detergent core. In embodiments, the CoV S polypeptide is associated with the non-ionic detergent core. In embodiments, the detergent is selected from the group consisting of polysorbate-20 (PS20), polysorbate-40 (PS40), polysorbate-60 (PS60), polysorbate-65 (PS65) and polysorbate-80 (PS80).

In embodiments, the detergent is PS80.

In embodiments, the CoV S polypeptide forms a trimer. In embodiments, the CoV S polypeptide nanoparticles are composed of multiple polypeptide trimers surrounding a non-ionic detergent core. In embodiments, the nanoparticles contain at least about 1 trimer or more. In embodiments, the nanoparticles contain at least about 5 trimers to about 30 trimers of the Spike protein. In embodiments, each nanoparticle may contain 1, 2, 3, 4, 5, 6, 7, 8, 9, 10, 11, 12, or 15, 20, 25, or 30 trimers, including all values and ranges in between. Compositions disclosed herein may contain nanoparticles having different numbers of trimers. For example, a composition may contain nanoparticles where the number of trimers ranges from 2-9; in embodiments, the nanoparticles in a composition may contain from 2-6 trimers. In embodiments, the compositions contain a heterogeneous population of nanoparticles having 2 to 6 trimers per nanoparticle, or 2 to 9 trimers per nanoparticle. In embodiments, the compositions may contain a substantially homogenous population of nanoparticles. For example, the population may contain about 95% nanoparticles having 5 trimers.

The nanoparticles disclosed herein range in particle size. In embodiments, the nanoparticles disclosed herein range in particle size from a Z-ave size from about 20 nm to about 60 nm, about 20 nm to about 50 nm, about 20 nm to about 45 nm, about 20 nm to about 35 nm, about 20 nm to about 30 nm, about 25 nm to about 35 nm, or about 25 nm to about 45 nm. Particle size (Z-ave) is measured by dynamic light scattering (DLS) using a Zetasizer NanoZS (Malvern, UK), unless otherwise specified.

In embodiments, the nanoparticles comprising the CoV S polypeptides disclosed herein have a reduced particle size compared to nanoparticles comprising a wild-type CoV S polypeptide. In embodiments, the CoV S polypeptides are at least about 40% smaller in particle size, for example, at least about 40%, at least about 45%, at least about 50%, at least about 55%, at least about 60%, at least about 65%, at least about 70%, at least about 75%, at least about 80%, or at least about 85% smaller in particle size.

The nanoparticles comprising CoV S polypeptides disclosed herein are more homogenous in size, shape, and mass than nanoparticles comprising a wild-type CoV S polypeptide. The polydispersity index (PDI), which is a measure of heterogeneity, is measured by dynamic light scattering using a Malvern Setasizer unless otherwise specified. In embodiments, the particles measured herein have a PDI from about 0.2 to about 0.45, for example, about 0.2, about 0.25, about 0.29, about 0.3, about 0.35, about 0.40, or about 0.45. In embodiments, the nanoparticles measured herein have a PDI that is at least about 25% smaller than the PDI of nanoparticles comprising the wild-type CoV S polypeptide, for example, at least about 25%, at least about 30%, at least about 35%, at least about 40%, at least about 45%, at least about 50%, at least about 55%, or at least about 60%, smaller.

The CoV S polypeptides and nanoparticles comprising the same have improved thermal stability as compared to the wild-type CoV S polypeptide or a nanoparticle thereof. The thermal stability of the CoV S polypeptides is measured using differential scanning calorimetry (DSC) unless otherwise specified. The enthalpy of transition (ΔHcal) is the energy required to unfold a CoV S polypeptide. In embodiments, the CoV S polypeptides have an increased ΔHcal as compared to the wild-type CoV S polypeptide. In embodiments, the ΔHcal of a CoV S polypeptide is about 2-fold, about 3-fold, about 4-fold, about 5-fold, about 6-fold, about 7-fold, about 8-fold, about 9-fold, or about 10-fold greater than the ΔHcal of a wild-type CoV S polypeptide.

Several nanoparticle types may be included in vaccine compositions disclosed herein. In some aspects, the nanoparticle type is in the form of an anisotropic rod, which may be a dimer or a monomer. In other aspects, the nanoparticle type is a spherical oligomer. In yet other aspects, the nanoparticle may be described as an intermediate nanoparticle, having sedimentation properties intermediate between the first two types. Formation of nanoparticle types may be regulated by controlling detergent and protein concentration during the production process. Nanoparticle type may be determined by measuring sedimentation co-efficient.

Production of Nanoparticles Containing CoV S Polypeptide Antigens

The nanoparticles of the present disclosure are non-naturally occurring products, the components of which do not occur together in nature. Generally, the methods disclosed herein use a detergent exchange approach wherein a first detergent is used to isolate a protein and then that first detergent is exchanged for a second detergent to form the nanoparticles.

The antigens contained in the nanoparticles are typically produced by recombinant expression in host cells. Standard recombinant techniques may be used. In embodiments, the CoV S polypeptides are expressed in insect host cells using a baculovirus system. In embodiments, the baculovirus is a cathepsin-L knock-out baculovirus, a chitinase knock-out baculovirus. Optionally, the baculovirus is a double knockout for both cathepsin-L and chitinase. High level expression may be obtained in insect cell expression systems. Non limiting examples of insect cells are, *Spodoptera frugiperda* (Sf) cells, e.g. Sf9, Sf21, Trichoplusiani cells, e.g. High Five cells, and *Drosophila* S2 cells. In embodiments, the CoV S polypeptide described herein are produced in any suitable host cell. In embodiments, the host cell is an insect cell. In embodiments, the insect cell is an Sf9 cell.

Typical transfection and cell growth methods can be used to culture the cells. Vectors, e.g., vectors comprising polynucleotides that encode fusion proteins, can be transfected into host cells according to methods well known in the art. For example, introducing nucleic acids into eukaryotic cells can be achieved by calcium phosphate co-precipitation, electroporation, microinjection, lipofection, and transfection employing polyamine transfection reagents. In one embodiment, the vector is a recombinant baculovirus.

Methods to grow host cells include, but are not limited to, batch, batch-fed, continuous and perfusion cell culture techniques. Cell culture means the growth and propagation of cells in a bioreactor (a fermentation chamber) where cells propagate and express protein (e.g. recombinant proteins) for purification and isolation. Typically, cell culture is performed under sterile, controlled temperature and atmospheric conditions in a bioreactor. A bioreactor is a chamber used to culture cells in which environmental conditions such as temperature, atmosphere, agitation and/or pH can be monitored. In one embodiment, the bioreactor is a stainless steel chamber. In another embodiment, the bioreactor is a pre-sterilized plastic bag (e.g. Cellbag®, Wave Biotech, Bridgewater, N.J.). In other embodiment, the pre-sterilized plastic bags are about 50 L to 3500 L bags.

Extraction and Purification of Nanoparticles Containing CoV Spike (S) Protein Antigens After growth of the host cells, the protein may be harvested from the host cells using detergents and purification protocols. Once the host cells have grown for 48 to 96 hours, the cells are isolated from the media and a detergent-containing solution is added to solubilize the cell membrane, releasing the protein in a detergent extract. Triton X-100 and TERGITOL® nonylphenol ethoxylate, also known as NP-9, are each preferred detergents for extraction. The detergent may be added to a final concentration of about 0.1% to about 1.0%. For example, the concentration may be about 0.1%, about 0.2%, about 0.3%, about 0.5%, about 0.7%, about 0.8%, or about 1.0%. The range may be about 0.1% to about 0.3%. In aspects, the concentration is about 0.5%.

In other aspects, different first detergents may be used to isolate the protein from the host cell. For example, the first detergent may be Bis(polyethylene glycol bis[imidazoylcarbonyl]), nonoxynol-9, Bis(polyethylene glycol bis[imidazoyl carbonyl]), BRIJ® Polyethylene glycol dodecyl ether 35, BRIJ® Polyethylene glycol (3) cetyl ether 56, BRIJ® alcohol ethoxylate 72, BRIJ® Polyoxyl 2 stearyl ether 76, BRIJ® polyethylene glycol monoolelyl ether 92V, BRIJ® Polyoxyethylene (10) oleyl ether 97, BRIJ® Polyethylene glycol hexadecyl ether 58P, CREMOPHOR® EL Macrogolglycerol ricinoleate, Decaethyleneglycol monododecyl ether, N-Decanoyl-N-methylglucamine, n-Decyl alpha-Dglucopyranoside, Decyl beta-D-maltopyranoside, n-Dodecanoyl-N-methylglucamide, nDodecyl alpha-D-maltoside, n-Dodecyl beta-D-maltoside, n-Dodecyl beta-D-maltoside, Heptaethylene glycol monodecyl ether, Heptaethylene glycol monododecyl ether, Heptaethylene glycol monotetradecyl ether, n-Hexadecyl beta-D-maltoside, Hexaethylene glycol monododecyl ether, Hexaethylene glycol monohexadecyl ether, Hexaethylene glycol monooctadecyl ether, Hexaethylene glycol monotetradecyl ether, Igepal CA-630, Igepal CA-630, Methyl-6-0-(N-heptylcarbamoyl)-alpha-D-glucopyranoside, Nonaethylene glycol monododecyl ether, N-Nonanoyl-N-methylglucamine, N-NonanoylN-methylglucamine, Octaethylene glycol monodecyl ether, Octaethylene glycolmonododecyl ether, Octaethylene glycol monohexadecyl ether, Octaethylene glycol monooctadecyl ether, Octaethylene glycol monotetradecyl ether, Octyl-beta-D glucopyranoside, Pentaethylene glycol monodecyl ether, Pentaethylene glycol monododecyl ether, Pentaethylene glycol monohexadecyl ether, Pentaethylene glycol monohexyl ether, Pentaethylene glycol monooctadecyl ether, Pentaethylene glycol monooctyl ether, Polyethylene glycol diglycidyl ether, Polyethylene glycol ether W-1, Polyoxyethylene 10 tridecyl ether, Polyoxyethylene 100 stearate, Polyoxyethylene 20 isohexadecyl ether, Polyoxyethylene 20 oleyl ether, Polyoxyethylene 40 stearate, Polyoxyethylene stearate, Polyoxyethylene 8 stearate, Polyoxyethylene bis(imidazolyl carbonyl), Polyoxyethylene 25 propylene glycol stearate, Saponin from *Quillaja* bark, SPAN® 20 sorbitan laurate, SPAN® 40 sorbitan monopalmitate, SPAN® 60 sorbitan stearate, SPAN® 65 sorbitan tristearate, SPAN® 80 sorbitane monooleate, SPAN® 85 sorbitane trioleate, TERGITOL® secondary alcohol ethoxylate Type 15-S-12, TERGITOL® secondary alcohol ethoxylate Type 15-S-30, TERGITOL® secondary alcohol ethoxylate Type 15-S-5, TERGITOL® secondary alcohol ethoxylate Type 15-S-7, TERGITOL® secondary alcohol ethoxylate Type 15-S-9, TERGITOL® nonylphenol ethoxylate Type NP-10, TERGITOL® nonylphenol ethoxylate Type NP-4, TERGITOL® nonylphenol ethoxylate Type NP-40, TERGITOL® nonylphenol ethoxylate Type NP-7, TERGITOL® nonylphenol ethoxylate Type NP-9, TERGITOL® branched secondary alcohol ethoxylate Type TMN-10, TERGITOL® branched secondary alcohol ethoxylate Type TMN-6, TRITON™ X-100 Polyethylene glycol tert-octylphenyl ether or combinations thereof.

The nanoparticles may then be isolated from cellular debris using centrifugation. In embodiments, gradient centrifugation, such as using cesium chloride, sucrose and iodixanol, may be used. Other techniques may be used as alternatives or in addition, such as standard purification techniques including, e.g., ion exchange, affinity, and gel filtration chromatography.

For example, the first column may be an ion exchange chromatography resin, such as FRACTOGEL® EMD methacrylate based polymeric beads TMAE (EMD Millipore), the second column may be a lentil (*Lens culinaris*) lectin affinity resin, and the third column may be a cation exchange column such as a FRACTOGEL® EMD methacrylate based polymeric beads S03 (EMD Millipore) resin. In other aspects, the cation exchange column may be an MMC column or a Nuvia C Prime column (Bio-Rad Laboratories, Inc). Preferably, the methods disclosed herein do not use a detergent extraction column; for example a hydrophobic interaction column. Such a column is often used to remove detergents during purification but may negatively impact the methods disclosed here.

Detergent Exchange of Nanoparticles Containing CoV S Polypeptide Antigens

To form nanoparticles, the first detergent, used to extract the protein from the host cell is substantially replaced with a second detergent to arrive at the nanoparticle structure. NP-9 is a preferred extraction detergent. Typically, the nanoparticles do not contain detectable NP-9 when measured by HPLC. The second detergent is typically selected from the group consisting of PS20, PS40, PS60, PS65, and PS80. Preferably, the second detergent is PS80.

In particular aspects, detergent exchange is performed using affinity chromatography to bind glycoproteins via their carbohydrate moiety. For example, the affinity chromatography may use a legume lectin column. Legume lectins are proteins originally identified in plants and found to interact specifically and reversibly with carbohydrate residues. See, for example, Sharon and Lis, "Legume lectins—a large family of homologous proteins," FASEB J. 1990 November; 4(14):3198-208; Liener, "The Lectins: Properties, Functions, and Applications in Biology and Medicine," Elsevier, 2012. Suitable lectins include concanavalin A (con A), pea lectin, sainfoin lect, and lentil lectin. Lentil lectin is a preferred column for detergent exchange due to its binding properties. Lectin columns are commercially available; for example, Capto Lentil Lectin, is available from GE Healthcare. In certain aspects, the lentil lectin column may use a recombinant lectin. At the molecular level, it is thought that the carbohydrate moieties bind to the lentil lectin, freeing the amino acids of the protein to coalesce around the detergent resulting in the formation of a detergent core providing nanoparticles having multiple copies of the antigen, e.g., glycoprotein oligomers which can be dimers, trimers, or tetramers anchored in the detergent. In embodiments, the CoV S polypeptides form trimers. In embodiments, the CoV S polypeptide trimers are anchored in detergent. In embodiments, each CoV S polypeptide nanoparticle contains at least one trimer associated with a non-ionic core.

The detergent, when incubated with the protein to form the nanoparticles during detergent exchange, may be present at up to about 0.1% (w/v) during early purifications steps and this amount is lowered to achieve the final nanoparticles having optimum stability. For example, the non-ionic detergent (e.g., PS80) may be about 0.005% (v/v) to about 0.1% (v/v), for example, about 0.005% (v/v), about 0.006% (v/v), about 0.007% (v/v), about 0.008% (v/v), about 0.009% (v/v), about 0.01% (v/v), about 0.015% (v/v), about 0.02% (v/v), about 0.025% (v/v), about 0.03% (v/v), about 0.035% (v/v), about 0.04% (v/v), about 0.045% (v/v), about 0.05% (v/v), about 0.055% (v/v), about 0.06% (v/v), about 0.065% (v/v), about 0.07% (v/v), about 0.075% (v/v), about 0.08% (v/v), about 0.085% (v/v), about 0.09% (v/v), about 0.095% (v/v), or about 0.1% (v/v) PS80. In embodiments, the nanoparticle contains about 0.03% to about 0.05% PS80. In embodiments, the nanoparticle contains about 0.01% (v/v) PS80.

In embodiments, purified CoV S polypeptides are dialyzed. In embodiments, dialysis occurs after purification. In embodiments, the CoV S polypeptides are dialyzed in a solution comprising sodium phosphate, NaCl, and PS80. In embodiments, the dialysis solution comprising sodium phosphate contains between about 5 mM and about 100 mM of sodium phosphate, for example, about 5 mM, about 10 mM, about 15 mM, about 20 mM, about 25 mM, about 30 mM, about 35 mM, about 40 mM, about 45 mM, about 50 mM, about 55 mM, about 60 mM, about 65 mM, about 70 mM, about 75 mM, about 80 mM, about 85 mM, about 90 mM, about 95 mM, or about 100 mM sodium phosphate. In embodiments, the pH of the solution comprising sodium phosphate is about 6.5, about 6.6, about 6.7, about 6.8, about 6.9, about 7.0, about 7.1, about 7.2, about 7.3, about 7.4, or about 7.5. In embodiments, the dialysis solution comprising sodium chloride comprises about 50 mM NaCl to about 500 mM NaCl, for example, about 50 mM, about 60 mM, about 70 mM, about 80 mM, about 90 mM, about 100 mM, about 110 mM, about 120 mM, about 130 mM, about 140 mM, about 150 mM, about 160 mM, about 170 mM, about 180 mM, about 190 mM, about 200 mM, about 210 mM, about 220 mM, about 230 mM, about 240 mM, about 250 mM, about 260 mM, about 270 mM, about 280 mM, about 290 mM, about 300 mM, about 310 mM, about 320 mM, about 330 mM, about 340 mM, about 350 mM, about 360 mM, about 370 mM, about 380 mM, about 390 mM, about 400 mM, about 410 mM, about 420 mM, about 430 mM, about 440 mM, about 450 mM, about 460 mM, about 470 mM, about 480 mM, about 490 mM, or about 500 mM NaCl. In embodiments, the dialysis solution comprising PS80 comprises about 0.005% (v/v), about 0.006% (v/v), about 0.007% (v/v), about 0.008% (v/v), about 0.009% (v/v), about 0.01% (v/v), about 0.015% (v/v), about 0.02% (v/v), about 0.025% (v/v), about 0.03% (v/v), about 0.035% (v/v), about 0.04% (v/v), about 0.045% (v/v), about 0.05% (v/v), about 0.055% (v/v), about 0.06% (v/v), about 0.065% (v/v), about 0.07% (v/v), about 0.075% (v/v), about 0.08% (v/v), about 0.085% (v/v), about 0.09% (v/v), about 0.095% (v/v), or about 0.1% (v/v) PS80. In embodiments, the dialysis solution comprises about 25 mM sodium phosphate (pH 7.2), about 300 mM NaCl, and about 0.01% (v/v) PS80.

Detergent exchange may be performed with proteins purified as discussed above and purified, frozen for storage, and then thawed for detergent exchange.

Stability of compositions disclosed herein may be measured in a variety of ways. In one approach, a peptide map may be prepared to determine the integrity of the antigen protein after various treatments designed to stress the nanoparticles by mimicking harsh storage conditions. Thus, a measure of stability is the relative abundance of antigen peptides in a stressed sample compared to a control sample. For example, the stability of nanoparticles containing the CoV S polypeptides may be evaluated by exposing the nanoparticles to various pHs, proteases, salt, oxidizing agents, including but not limited to hydrogen peroxide, various temperatures, freeze/thaw cycles, and agitation. FIGS. 12A-B show that BV2373 (SEQ ID NO: 87) and BV2365 (SEQ ID NO: 4) retain binding to hACE2 under a variety of stress conditions. It is thought that the position of the glycoprotein anchored into the detergent core provides enhanced stability by reducing undesirable interactions. For example, the improved protection against protease-based degradation may be achieved through a shielding effect whereby anchoring the glycoproteins into the core at the molar ratios disclosed herein results in steric hindrance blocking protease access. Stability may also be measured by monitoring intact proteins. FIG. 33 and FIG. 34 compare nanoparticles containing CoV polypeptides having amino acid sequences of SEQ ID NOS: 109 and 87, respectively. FIG. 34 indicates that CoV polypeptides having an amino acid sequence of SEQ ID NO: 87 show particularly good stability during purification. The polypeptide of FIG. 34 comprises a furin cleavage site having an amino acid sequence of QQAQ (SEQ ID NO: 7).

Vaccine Compositions Containing CoV S Polypeptide Antigens

The disclosure provides vaccine compositions comprising CoV S polypeptides, for example, in a nanoparticle. In some aspects, the vaccine composition may contain nanoparticles with antigens from more than one viral strain from the same species of virus. In another embodiment, the disclosures provide for a pharmaceutical pack or kit comprising one or more containers filled with one or more of the components of the vaccine compositions.

Compositions disclosed herein may be used either prophylactically or therapeutically, but will typically be prophylactic. Accordingly, the disclosure includes methods for treating or preventing infection. The methods involve administering to the subject a therapeutic or prophylactic amount of the immunogenic compositions of the disclosure. Preferably, the pharmaceutical composition is a vaccine composition that provides a protective effect. In other aspects, the protective effect may include amelioration of a symptom associated with infection in a percentage of the exposed population. For example, the composition may prevent or reduce one or more virus disease symptoms selected from: fever fatigue, muscle pain, headache, sore throat, vomiting, diarrhea, rash, symptoms of impaired kidney and liver function, internal bleeding and external bleeding, compared to an untreated subject.

The nanoparticles may be formulated for administration as vaccines in the presence of various excipients, buffers, and the like. For example, the vaccine compositions may contain sodium phosphate, sodium chloride, and/or histidine. Sodium phosphate may be present at about 10 mM to about 50 mM, about 15 mM to about 25 mM, or about 25 mM; in particular cases, about 22 mM sodium phosphate is present. Histidine may be present about 0.1% (w/v), about 0.5% (w/v), about 0.7% (w/v), about 1% (w/v), about 1.5% (w/v), about 2% (w/v), or about 2.5% (w/v). Sodium chloride, when present, may be about 150 mM. In certain compositions, the sodium chloride may be present in higher concentrations, for example from about 200 mM to about 500 mM. In embodiments, the sodium chloride is present in a high concentration, including but not limited to about 200 mM, about 250 mM, about 300 mM, about 350 mM, about 400 mM, about 450 mM, or about 500 mM.

In embodiments, the nanoparticles described herein have improved stability at certain pH levels. In embodiments, the nanoparticles are stable at slightly acidic pH levels. For example, the nanoparticles that are stable at a slightly acidic pH, for example from pH 5.8 to pH 7.0. In embodiments, the nanoparticles and compositions containing nanoparticles may be stable at pHs ranging from about pH 5.8 to about pH 7.0, including about pH 5.9 to about pH 6.8, about pH 6.0 to about pH 6.5, about pH 6.1 to about pH 6.4, about pH 6.1 to about pH 6.3, or about pH 6.2. In embodiments, the nanoparticles and compositions described herein are stabile at neutral pHs, including from about pH 7.0 to about pH 7.4. In embodiments, the nanoparticles and compositions described herein are stable at slightly alkaline pHs, for example from about pH 7.0 to about pH 8.5, from about pH 7.0 to about pH 8.0, or from about pH 7.0 to about pH 7.5, including all values and ranges in between.

Adjuvants

In certain embodiments, the compositions disclosed herein may be combined with one or more adjuvants to enhance an immune response. In other embodiments, the compositions are prepared without adjuvants, and are thus available to be administered as adjuvant-free compositions. Advantageously, adjuvant-free compositions disclosed herein may provide protective immune responses when administered as a single dose. Alum-free compositions that induce robust immune responses are especially useful in adults about 60 and older.

Aluminum-Based Adjuvants

In embodiments, the adjuvant may be alum (e.g. $AlPO_4$ or $Al(OH)_3$). Typically, the nanoparticle is substantially bound to the alum. For example, the nanoparticle may be at least 80% bound, at least 85% bound, at least 90% bound or at least 95% bound to the alum. Often, the nanoparticle is 92% to 97% bound to the alum in a composition. The amount of alum is present per dose is typically in a range between about 400 μg to about 1250 μg. For example, the alum may be present in a per dose amount of about 300 μg to about 900 μg, about 400 μg to about 800 μg, about 500 μg to about 700 μg, about 400 μg to about 600 μg, or about 400 μg to about 500 μg. Typically, the alum is present at about 400 μg for a dose of 120 μg of the protein nanoparticle.

Saponin Adjuvants

Adjuvants containing saponin may also be combined with the immunogens disclosed herein. Saponins are glycosides derived from the bark of the *Quillaja saponaria* Molina tree. Typically, saponin is prepared using a multi-step purification process resulting in multiple fractions. As used, herein, the term "a saponin fraction from *Quillaja saponaria* Molina" is used generically to describe a semi-purified or defined saponin fraction of *Quillaja saponaria* or a substantially pure fraction thereof.

Saponin Fractions

Several approaches for producing saponin fractions are suitable. Fractions A, B, and C are described in U.S. Pat. No. 6,352,697 and may be prepared as follows. A lipophilic fraction from Quil A, a crude aqueous *Quillaja saponaria* Molina extract, is separated by chromatography and eluted with 70% acetonitrile in water to recover the lipophilic fraction. This lipophilic fraction is then separated by semi-preparative HPLC with elution using a gradient of from 25% to 60% acetonitrile in acidic water. The fraction referred to herein as "Fraction A" or "QH-A" is, or corresponds to, the fraction, which is eluted at approximately 39% acetonitrile. The fraction referred to herein as "Fraction B" or "QH-B" is, or corresponds to, the fraction, which is eluted at approximately 47% acetonitrile. The fraction referred to herein as "Fraction C" or "QH-C" is, or corresponds to, the fraction, which is eluted at approximately 49% acetonitrile. Additional information regarding purification of Fractions is found in U.S. Pat. No. 5,057,540. When prepared as described herein, Fractions A, B and C of *Quillaja saponaria* Molina each represent groups or families of chemically closely related molecules with definable properties. The chromatographic conditions under which they are obtained are such that the batch-to-batch reproducibility in terms of elution profile and biological activity is highly consistent.

Other saponin fractions have been described. Fractions B3, B4 and B4b are described in EP 0436620. Fractions QA1-QA22 are described EP03632279 B2, Q-VAC (Nor-Feed, AS Denmark), *Quillaja saponaria* Molina Spikoside (Isconova AB, Ultunaallén 2B, 756 51 Uppsala, Sweden). Fractions QA-1, QA-2, QA-3, QA-4, QA-5, QA-6, QA-7, QA-8, QA-9, QA-10, QA-11, QA-12, QA-13, QA-14, QA-15, QA-16, QA-17, QA-18, QA-19, QA-20, QA-21, and QA-22 of EP 0 3632 279 B2, especially QA-7, QA-17, QA-18, and QA-21 may be used. They are obtained as described in EP 0 3632 279 B2, especially at page 6 and in Example 1 on page 8 and 9.

The saponin fractions described herein and used for forming adjuvants are often substantially pure fractions; that is, the fractions are substantially free of the presence of contamination from other materials. In particular aspects, a substantially pure saponin fraction may contain up to 40% by weight, up to 30% by weight, up to 25% by weight, up to 20% by weight, up to 15% by weight, up to 10% by weight, up to 7% by weight, up to 5% by weight, up to 2% by weight, up to 1% by weight, up to 0.5% by weight, or up to 0.1% by weight of other compounds such as other saponins or other adjuvant materials.

ISCOM Structures

Saponin fractions may be administered in the form of a cage-like particle referred to as an ISCOM (Immune Stimulating COMplex). ISCOMs may be prepared as described in EP0109942B1, EP0242380B1 and EP0180546 B1. In particular embodiments a transport and/or a passenger antigen may be used, as described in EP 9600647-3 (PCT/SE97/00289).

Matrix Adjuvants

In embodiments, the ISCOM is an ISCOM matrix complex. An ISCOM matrix complex comprises at least one saponin fraction and a lipid. The lipid is at least a sterol, such as cholesterol. In particular aspects, the ISCOM matrix complex also contains a phospholipid. The ISCOM matrix complexes may also contain one or more other immunomodulatory (adjuvant-active) substances, not necessarily a glycoside, and may be produced as described in EP0436620B1, which is incorporated by reference in its entirety herein.

In other aspects, the ISCOM is an ISCOM complex. An ISCOM complex contains at least one saponin, at least one lipid, and at least one kind of antigen or epitope. The ISCOM complex contains antigen associated by detergent treatment such that that a portion of the antigen integrates into the particle. In contrast, ISCOM matrix is formulated as an admixture with antigen and the association between ISCOM matrix particles and antigen is mediated by electrostatic and/or hydrophobic interactions.

According to one embodiment, the saponin fraction integrated into an ISCOM matrix complex or an ISCOM complex, or at least one additional adjuvant, which also is integrated into the ISCOM or ISCOM matrix complex or mixed therewith, is selected from fraction A, fraction B, or fraction C of *Quillaja saponaria*, a semipurified preparation of *Quillaja saponaria*, a purified preparation of *Quillaja saponaria*, or any purified sub-fraction e.g., QA 1-21.

In particular aspects, each ISCOM particle may contain at least two saponin fractions. Any combinations of weight % of different saponin fractions may be used. Any combination of weight % of any two fractions may be used. For example, the particle may contain any weight % of fraction A and any weight % of another saponin fraction, such as a crude saponin fraction or fraction C, respectively. Accordingly, in particular aspects, each ISCOM matrix particle or each ISCOM complex particle may contain from 0.1 to 99.9 by weight, 5 to 95% by weight, 10 to 90% by weight 15 to 85% by weight, 20 to 80% by weight, 25 to 75% by weight, 30 to 70% by weight, 35 to 65% by weight, 40 to 60% by weight, 45 to 55% by weight, 40 to 60% by weight, or 50% by weight of one saponin fraction, e.g. fraction A and the rest up to 100% in each case of another saponin e.g. any crude fraction or any other faction e.g. fraction C. The weight is calculated as the total weight of the saponin fractions. Examples of ISCOM matrix complex and ISCOM complex adjuvants are disclosed in U.S Published Application No. 2013/0129770, which is incorporated by reference in its entirety herein.

In particular embodiments, the ISCOM matrix or ISCOM complex comprises from 5-99% by weight of one fraction, e.g. fraction A and the rest up to 100% of weight of another fraction e.g. a crude saponin fraction or fraction C. The weight is calculated as the total weight of the saponin fractions.

In another embodiment, the ISCOM matrix or ISCOM complex comprises from 40% to 99% by weight of one fraction, e.g. fraction A and from 1% to 60% by weight of another fraction, e.g. a crude saponin fraction or fraction C. The weight is calculated as the total weight of the saponin fractions.

In yet another embodiment, the ISCOM matrix or ISCOM complex comprises from 70% to 95% by weight of one fraction e.g., fraction A, and from 30% to 5% by weight of another fraction, e.g., a crude saponin fraction, or fraction C. The weight is calculated as the total weight of the saponin fractions. In other embodiments, the saponin fraction from *Quillaja saponaria* Molina is selected from any one of QA 1-21.

In addition to particles containing mixtures of saponin fractions, ISCOM matrix particles and ISCOM complex particles may each be formed using only one saponin fraction. Compositions disclosed herein may contain multiple particles wherein each particle contains only one saponin fraction. That is, certain compositions may contain one or more different types of ISCOM-matrix complexes particles and/or one or more different types of ISCOM complexes particles, where each individual particle contains one saponin fraction from *Quillaja saponaria* Molina, wherein the saponin fraction in one complex is different from the saponin fraction in the other complex particles.

In particular aspects, one type of saponin fraction or a crude saponin fraction may be integrated into one ISCOM matrix complex or particle and another type of substantially pure saponin fraction, or a crude saponin fraction, may be integrated into another ISCOM matrix complex or particle. A composition or vaccine may comprise at least two types of complexes or particles each type having one type of saponins integrated into physically different particles.

In the compositions, mixtures of ISCOM matrix complex particles and/or ISCOM complex particles may be used in which one saponin fraction *Quillaja saponaria* Molina and another saponin fraction *Quillaja saponaria* Molina are separately incorporated into different ISCOM matrix complex particles and/or ISCOM complex particles.

The ISCOM matrix or ISCOM complex particles, which each have one saponin fraction, may be present in composition at any combination of weight %. In particular aspects, a composition may contain 0.1% to 99.9% by weight, 5% to 95% by weight, 10% to 90% by weight, 15% to 85% by weight, 20% to 80% by weight, 25% to 75% by weight, 30% to 70% by weight, 35% to 65% by weight, 40% to 60% by weight, 45% to 55% by weight, 40 to 60% by weight, or 50% by weight, of an ISCOM matrix or complex containing a first saponin fraction with the remaining portion made up by an ISCOM matrix or complex containing a different saponin fraction. In some aspects, the remaining portion is one or more ISCOM matrix or complexes where each matrix or complex particle contains only one saponin fraction. In other aspects, the ISCOM matrix or complex particles may contain more than one saponin fraction.

In particular compositions, the only saponin fraction in a first ISCOM matrix or ISCOM complex particle is Fraction A and the only saponin fraction in a second ISCOM matrix or ISCOM complex particle is Fraction C.

Preferred compositions comprise a first ISCOM matrix containing Fraction A and a second ISCOM matrix containing Fraction C, wherein the Fraction A ISCOM matrix constitutes about 70% per weight of the total saponin adjuvant, and the Fraction C ISCOM matrix constitutes about 30% per weight of the total saponin adjuvant. In another preferred composition, the Fraction A ISCOM matrix constitutes about 85% per weight of the total saponin adjuvant, and the Fraction C ISCOM matrix constitutes about 15% per weight of the total saponin adjuvant. Thus, in certain compositions, the Fraction A ISCOM matrix is present in a range of about 70% to about 85%, and Fraction C ISCOM matrix is present in a range of about 15% to about 30%, of the total weight amount of saponin adjuvant in the composition. In embodiments, the Fraction A ISCOM matrix accounts for 50-96% by weight and Fraction C ISCOM matrix accounts for the remainder, respectively, of the sums of the weights of Fraction A ISCOM matrix and Fraction C ISCOM in the adjuvant. In a particularly preferred composition, referred to herein as MATRIX-M™, the Fraction A ISCOM matrix is present at about 85% and Fraction C ISCOM matrix is present at about 15% of the total weight amount of saponin adjuvant in the composition. MATRIX-M™ may be referred to interchangeably as Matrix-M1.

Exemplary QS-7 and QS-21 fractions, their production and their use is described in U.S. Pat. Nos. 5,057,540; 6,231,859; 6,352,697; 6,524,584; 6,846,489; 7,776,343, and 8,173,141, which are incorporated by reference herein.

In some, compositions other adjuvants may be used in addition or as an alternative. The inclusion of any adjuvant described in Vogel et al., "A Compendium of Vaccine Adjuvants and Excipients (2nd Edition)," herein incorporated by reference in its entirety for all purposes, is envisioned within the scope of this disclosure. Other adjuvants include complete Freund's adjuvant (a non-specific stimulator of the immune response containing killed *Mycobacterium tuberculosis*), incomplete Freund's adjuvants and aluminum hydroxide adjuvant. Other adjuvants comprise GMCSP, BCG, MDP compounds, such as thur-MDP and nor-MDP, CGP (MTP-PE), lipid A, and monophosphoryl lipid A (MPL), MF-59, RIBI, which contains three components extracted from bacteria, MPL, trehalose dimycolate (TDM) and cell wall skeleton (CWS) in a 2% squalene/TWEEN® polysorbate 80 emulsion. In embodiments, the adjuvant may be a paucilamellar lipid vesicle; for example, NOVASOMES®. NOVASOMES® are paucilamellar non-phospholipid vesicles ranging from about 100 nm to about 500 nm. They comprise BRIJ® alcohol ethoxylate 72, cholesterol, oleic acid and squalene. NOVASOMES® have been shown to be an effective adjuvant (see, U.S. Pat. Nos. 5,629,021, 6,387,373, and 4,911,928.

Administration and Dosage

In embodiments, the disclosure provides a method for eliciting an immune response against one or more coronaviruses. In embodiments, the response is against one or more of the SARS-CoV-2 virus, MERS, and SARS. The method involves administering an immunologically effective amount of a composition containing a nanoparticle or containing a recombinant CoV Spike (S) polypeptide to a subject. Advantageously, the proteins disclosed herein induce one or more of particularly useful anti-coronavirus responses.

In embodiments, the nanoparticles or CoV S polypeptides are administered with an adjuvant. In other aspects, the nanoparticles or CoV S polypeptides are administered without an adjuvant. In some aspects, the adjuvant may be bound to the nanoparticle, such as by a non-covalent interaction. In other aspects, the adjuvant is co-administered with the nanoparticle but the adjuvant and nanoparticle do not interact substantially.

In embodiments, the nanoparticles may be used for the prevention and/or treatment of one or more of a SARS-CoV-2 infection, a SARS infection, or a MERS infection. Thus, the disclosure provides a method for eliciting an immune response against one or more of the SARS-CoV-2 virus, MERS, and SARS. The method involves administering an immunologically effective amount of a composition containing a nanoparticle or a CoV S polypeptide to a subject. Advantageously, the proteins disclosed herein induce particularly useful anti-coronavirus responses.

Compositions disclosed herein may be administered via a systemic route or a mucosal route or a transdermal route or directly into a specific tissue. As used herein, the term "systemic administration" includes parenteral routes of administration. In particular, parenteral administration includes subcutaneous, intraperitoneal, intravenous, intraarterial, intramuscular, or intrasternal injection, intravenous, or kidney dialytic infusion techniques. Typically, the systemic, parenteral administration is intramuscular injection. As used herein, the term "mucosal administration" includes oral, intranasal, intravaginal, intra-rectal, intra-tracheal, intestinal and ophthalmic administration. Preferably, administration is intramuscular.

Compositions may be administered on a single dose schedule or a multiple dose schedule. Multiple doses may be used in a primary immunization schedule or in a booster immunization schedule. In a multiple dose schedule the various doses may be given by the same or different routes e.g., a parenteral prime and mucosal boost, a mucosal prime and parenteral boost, etc. In some aspects, a follow-on boost dose is administered about 2 weeks, about 3 weeks, about 4 weeks, about 5 weeks, or about 6 weeks after the prior dose. In embodiments, the follow-on boost dose is administered 3 weeks after administration of the prior dose. In embodiments, the first dose is administered at day 0, and the boost dose is administered at day 21. In embodiments, the first dose is administered at day 0, and the boost dose is administered at day 28.

In embodiments, the dose, as measured in μg, may be the total weight of the dose including the solute, or the weight of the CoV S polypeptide nanoparticles, or the weight of the CoV S polypeptide. Dose is measured using protein concentration assay either A280 or ELISA.

The dose of antigen, including for pediatric administration, may be in the range of about 5 μg to about 25 μg, about 1 μg to about 300 μg, about 90 μg to about 270 μg, about 100 μg to about 160 μg, about 110 μg to about 150 μg, about 120 μg to about 140 μg, or about 140 μg to about 160 μg. In embodiments, the dose is about 120 μg, administered with alum. In some aspects, a pediatric dose may be in the range of about 1 μg to about 90 μg. In embodiments, the dose of CoV Spike (S) polypeptide is about 1 μg, about 2 μg, about 3 μg, about 4 μg, about 5 μg, about 6 μg, about 7 μg, about 8 μg, about 9 μg, about 10 μg, about 11 μg, about 12 μg, about 13 μg, about 14 μg, about 15 μg, about 16 μg, about 17 μg, about 18 μg, about 19 μg, about 20 μg, about 21, about 22, about 23, about 24, about 25 μg, about 26 μg, about 27 μg, about 28 μg, about 29 μg, about 30 μg, about 40 μg, about 50, about 60, about 70, about 80, about 90 about 100 μg, about 110 μg, about 120 μg, about 130 μg, about 140 μg, about 150 μg, about 160 μg, about 170 μg, about 180 μg, about 190 μg, about 200 μg, about 210 μg, about 220 μg, about 230 μg, about 240 μg, about 250 μg, about 260 μg, about 270 μg, about 280 μg, about 290 μg, or about 300 μg, including all values and ranges in between. In embodiments, the dose of CoV S polypeptide is 5 μg. In embodiments, the dose of CoV S polypeptide is 25 μg.

Certain populations may be administered with or without adjuvants. In certain aspects, compositions may be free of added adjuvant. In such circumstances, the dose may be increased by about 10%.

In embodiments, the dose of the adjuvant administered with a non-naturally occurring CoV S polypeptide is from about 1 μg to about 100 μg, for example, about 1 μg, about 2 μg, about 3 μg, about 4 μg, about 5 μg, about 6 μg, about 7 μg, about 8 μg, about 9 μg, about 10 μg, about 11 μg, about 12 μg, about 13 μg, about 14 μg, about 15 μg, about 16 μg, about 17 μg, about 18 μg, about 19 μg, about 20 μg, about 21, about 22, about 23, about 24, about 25 μg, about 26 μg, about 27 μg, about 28 μg, about 29 μg, about 30 μg, about 31 μg, about 32 μg, about 33 μg, about 34 μg, about 35 μg, about 36 μg, about 37 μg, about 38 μg, about 39 μg, about 40 μg, about 41 μg, about 42 μg, about 43 μg, about 44 μg, about 45 μg, about 46 μg, about 47 μg, about 48 μg, about 49 μg, about 50 μg, about 51 μg, about 52 μg, about 53 μg, about 54 μg, about 55 μg, about 56 μg, about 57 μg, about 58 μg, about 59 μg, about 60 μg, about 61 μg, about 62 μg, about 63 μg, about 64 μg, about 65 μg, about 66 μg, about 67 μg, about 68 μg, about 69 μg, about 70 μg, about 71 μg, about 72 μg, about 73 μg, about 74 μg, about 75 μg, about 76 μg, about 77 μg, about 78 μg, about 79 μg, about 80 μg, about 81 μg, about 82 μg, about 83 μg, about 84 μg, about 85 μg, about 86 μg, about 87 μg, about 88 μg, about 89 μg, about 90 μg, about 91 μg, about 92 μg, about 93 μg, about 94 μg, about 95 μg, about 96 μg, about 97 μg, about 98 μg, about 99 μg, or about 100 μg of adjuvant. In embodiments, the dose of adjuvant is about 50 μg. In embodiments, the adjuvant is a saponin adjuvant, e.g., MATRIX-M™.

In embodiments, the dose is administered in a volume of about 0.1 mL to about 1.5 mL, for example, about 0.1 mL, about 0.2 mL, about 0.25 mL, about 0.3 mL, about 0.4 mL, about 0.5 mL, about 0.6 mL, about 0.7 mL, about 0.8 mL, about 0.9 mL, about 1.0 mL, about 1.1 mL, about 1.2 mL, about 1.3 mL, about 1.4 mL, or about 1.5 mL. In embodiments, the dose is administered in a volume of 0.25 mL. In embodiments, the dose is administered in a volume of 0.5 mL. In embodiments, the dose is administered in a volume of 0.6 mL.

In particular embodiments for a vaccine against MERS, SARS, or the SARS-CoV-2 coronavirus, the dose may comprise a CoV S polypeptide concentration of about 1 μg/mL to about 50 μg/mL, 10 μg/mL to about 100 μg/mL, about 10 μg/mL to about 50 μg/mL, about 175 μg/mL to about 325 μg/mL, about 200 μg/mL to about 300 μg/mL, about 220 μg/mL to about 280 μg/mL, or about 240 μg/mL to about 260 μg/mL.

In another embodiment, the disclosure provides a method of formulating a vaccine composition that induces immunity to an infection or at least one disease symptom thereof to a mammal, comprising adding to the composition an effective dose of a nanoparticle or a CoV S polypeptide. The disclosed CoV S polypeptides and nanoparticles are useful for preparing compositions that stimulate an immune response that confers immunity or substantial immunity to infectious agents. Thus, in one embodiment, the disclosure provides a method of inducing immunity to infections or at least one disease symptom thereof in a subject, comprising administering at least one effective dose of a nanoparticle and/or a CoV S polypeptide.

In embodiments, the CoV S polypeptides or nanoparticles comprising the same are administered in combination with an additional immunogenic composition. In embodiments, the additional immunogenic composition induces an immune response against SARS-CoV-2. In embodiments, the additional immunogenic composition is administered within about 1 minute, about 5 minutes, about 10 minutes, about 20 minutes, about 30 minutes, about 40 minutes, about 50 minutes, about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, about 28 days, about 29 days, about 30 days, or about 31 days of the disclosed CoV S polypeptides or nanoparticles comprising the same. In embodiments, the additional composition is administered with a first dose of a composition comprising a CoV S polypeptide or nanoparticle comprising the same. In embodiments, the additional composition is administered with a boost dose of a composition comprising a CoV S polypeptide or nanoparticle comprising the same.

In embodiments, the additional immunogenic composition comprises an mRNA encoding a SARS-Cov-2 Spike glycoprotein, a plasmid DNA encoding a SARS-Cov-2 Spike glycoprotein, an viral vector encoding a SARS-Cov-2 Spike glycoprotein, or an inactivated SARS-CoV-2 virus.

In embodiments, the additional immunogenic composition comprises mRNA that encodes for a CoV S polypeptide. In embodiments, the mRNA encodes for a CoV S polypeptide comprising proline substitutions at positions 986 and 987 of SEQ ID NO: 1. In embodiments, the mRNA encodes for a CoV S polypeptide comprising an intact furin cleavage site. In embodiments, the mRNA encodes for a CoV S polypeptide comprising proline substitutions at positions 986 and 987 of SEQ ID NO: 1 and an intact furin cleavage site. In embodiments, the mRNA encodes for a CoV S polypeptide comprising proline substitutions at positions 986 and 987 of SEQ ID NO: 1 and an inactive furin cleavage site. In embodiments, the mRNA encodes for a CoV S polypeptide having an amino acid sequence of SEQ ID NO: 87. In embodiments, the mRNA encoding for a CoV S polypeptide is encapsulated in a lipid nanoparticle. An exemplary immunogenic composition comprising mRNA that encodes for a CoV S polypeptide is described in Jackson et al. N. Eng. J. Med. 2020. An mRNA Vaccine against SARS-CoV-2-preliminary report, which is incorporated by reference in its entirety herein. In embodiments, the composition comprising mRNA that encodes for a CoV S polypeptide is administered at a dose of 25 μg, 100 μg, or 250 μg.

In embodiments, the additional immunogenic composition comprises an adenovirus vector encoding for a CoV S polypeptide. In embodiments, the AAV vector encodes for a wild-type CoV S polypeptide. In embodiments, the AAV vector encodes for a CoV S polypeptide comprising proline substitutions at positions 986 and 987 of SEQ ID NO: 1 and an intact furin cleavage site. In embodiments, the AAV vector encodes for a CoV S polypeptide comprising proline substitutions at positions 986 and 987 of SEQ ID NO: 1 and an inactive furin cleavage site. In embodiments, the AAV vector encodes for a CoV S polypeptide having an amino acid sequence of SEQ ID NO: 87. The following publications describe immunogenic compositions comprising an adenovirus vector encoding for a CoV S polypeptide, each of which is incorporated by reference in its entirety herein: van Doremalen N. et al. A single dose of ChAdOx1 MERS provides protective immunity in rhesus macaques. Science Advances, 2020; van Doremalen N. et al. ChAdOx1 nCoV-19 vaccination prevents SARS-CoV-2 pneumonia in rhesus macaques. bioRxiv, (2020).

In embodiments, the additional immunogenic composition comprises deoxyribonucleic acid (DNA). In embodiments, the additional immunogenic composition comprises plasmid DNA. In embodiments, the plasmid DNA encodes for a CoV S polypeptide. In embodiments, the DNA encodes for a CoV S polypeptide comprising proline substitutions at positions 986 and 987 of SEQ ID NO: 1 and an intact furin cleavage site. In embodiments, the DNA encodes for a CoV S polypeptide comprising proline substitutions at positions 986 and 987 of SEQ ID NO: 1 and an inactive furin cleavage site. In embodiments, the DNA encodes for a CoV S polypeptide having an amino acid sequence of SEQ ID NO: 87.

In embodiments, the additional immunogenic composition comprises an inactivated virus vaccine.

In embodiments, the CoV S proteins or nanoparticles comprising CoV S proteins are useful for preparing immunogenic compositions to stimulate an immune response that confers immunity or substantial immunity to one or more of MERS, SARS, and SARS-CoV-2. Both mucosal and cellular immunity may contribute to immunity to infection and disease. Antibodies secreted locally in the upper respiratory tract are a major factor in resistance to natural infection. Secretory immunoglobulin A (sIgA) is involved in protection of the upper respiratory tract and serum IgG in protection of the lower respiratory tract. The immune response induced by an infection protects against reinfection with the same virus or an antigenically similar viral strain. The antibodies produced in a host after immunization with the nanoparticles disclosed herein can also be administered to others, thereby providing passive administration in the subject.

In embodiments, the present disclosure provides a method of producing one or more of high affinity anti-MERS-CoV, anti-SARS-CoV, and anti-SARS-CoV-2 virus antibodies. The high affinity antibodies produced by immunization with the nanoparticles disclosed herein are produced by administering an immunogenic composition comprising an S CoV polypeptide or a nanoparticle comprising an S CoV polypeptide to an animal, collecting the serum and/or plasma from the animal, and purifying the antibody from the serum/ and or plasma. In one embodiment, the animal is a human. In embodiments, the animal is a chicken, mouse, guinea pig, rat, rabbit, goat, human, horse, sheep, or cow. In one embodiment, the animal is bovine or equine. In another embodiment, the bovine or equine animal is transgenic. In yet a further embodiment, the transgenic bovine or equine animal produces human antibodies. In embodiments, the animal produces monoclonal antibodies. In embodiments, the animal produces polyclonal antibodies. In one embodiment, the method further comprises administration of an adjuvant or immune stimulating compound. In a further embodiment, the purified high affinity antibody is administered to a human subject. In one embodiment, the human subject is at risk for infection with one or more of MERS, SARS, and SARS-CoV-2.

All patents, patent applications, references, and journal articles cited in this disclosure are expressly incorporated herein by reference in their entireties for all purposes.

EXAMPLES

Example 1

Figure 4:
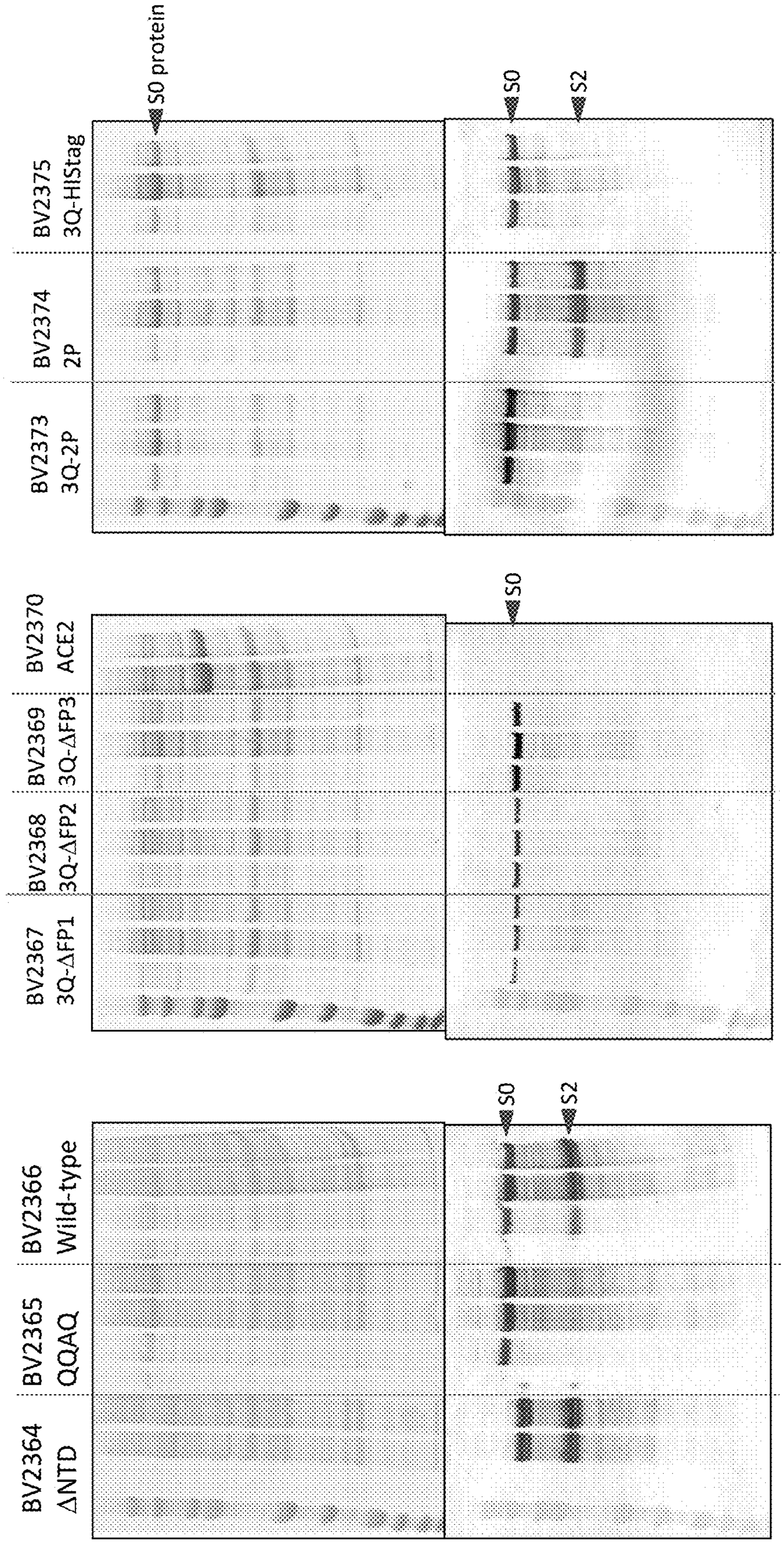
FIG. 4 shows purification of the CoV S polypeptides BV2364, BV2365, BV2366, BV2367, BV2368, BV2369, BV2373, BV2374, and BV2375. The data reveal that BV2365 (SEQ ID NO: 4) and BV2373 (SEQ ID NO: 87) which has an inactive furin cleavage site having an amino acid sequence of QQAQ (SEQ ID NO: 7) is expressed as a single chain (S0). In contrast, CoV S polypeptides containing an intact furin cleavage site (e.g. BV2364, BV2366, and BV2374) are cleaved, as evident by the presence of the cleavage product S2.
Figure 5:
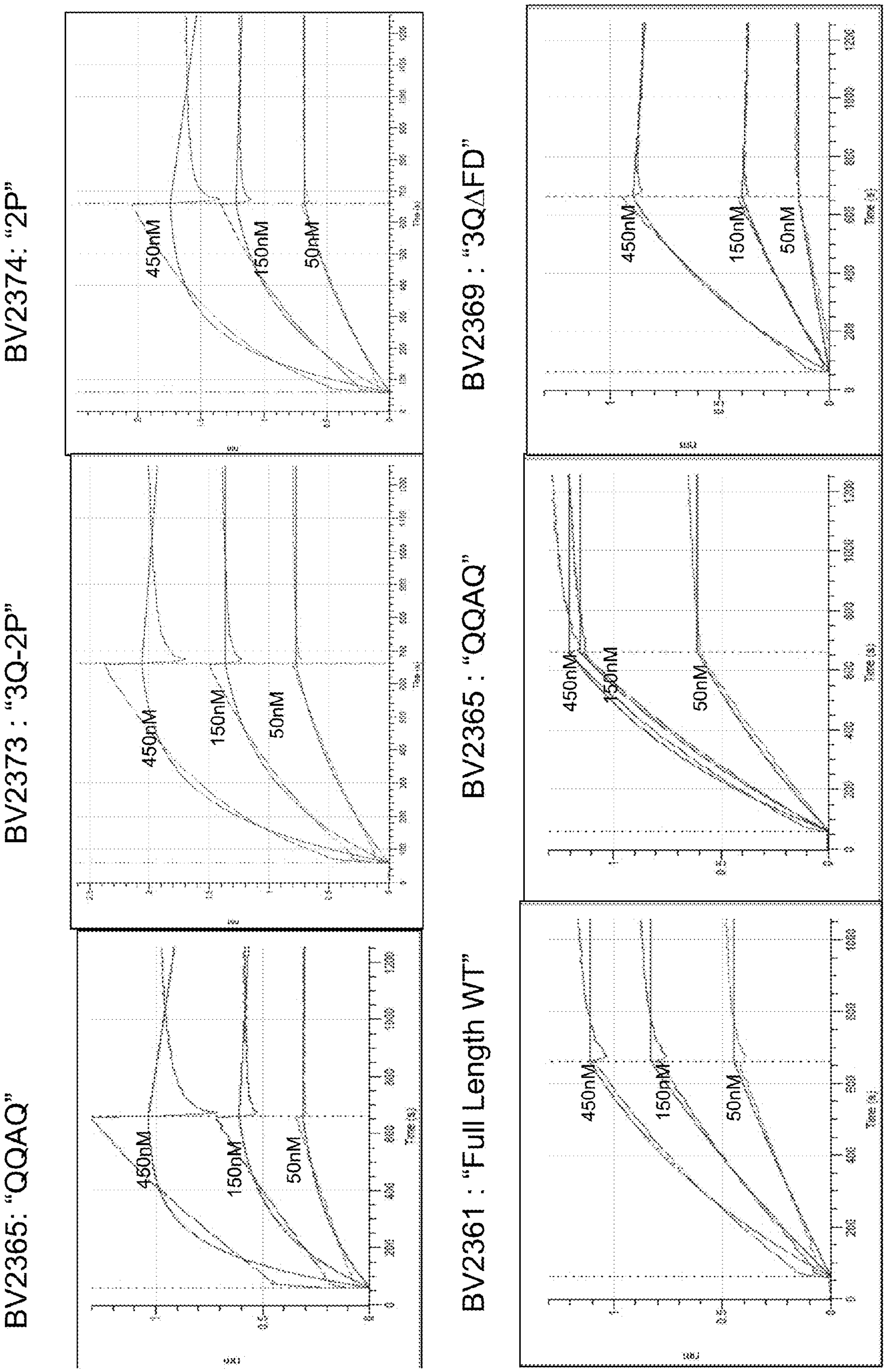
FIG. 5 shows that the CoV S polypeptides BV2361, BV2365, BV2369, BV2365, BV2373, and BV2374 bind to human angiotensin-converting enzyme 2 precursor (hACE2) by bio-layer interferometry.
Figure 6:
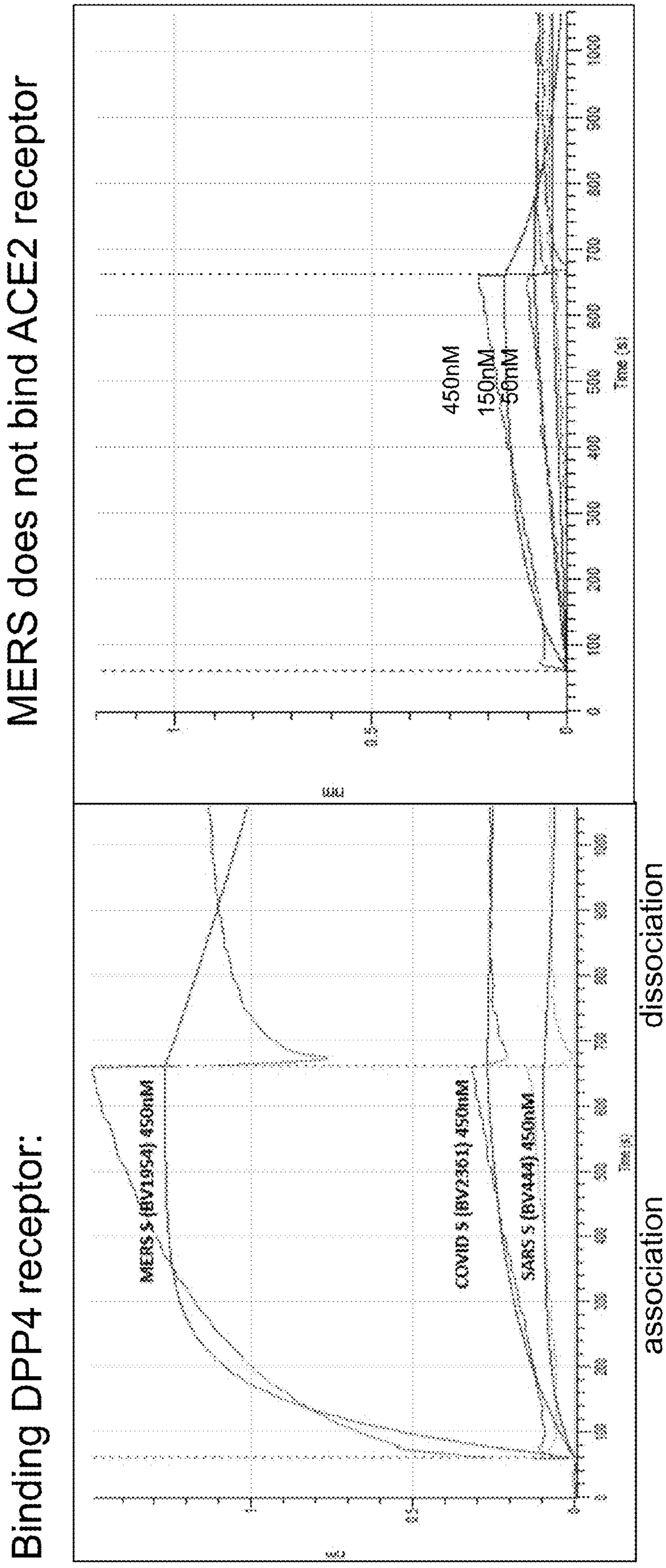
FIG. 6 shows that BV2361 from SARS-CoV-2 does not bind the MERS-CoV receptor, dipeptidyl peptidase IV (DPP4) and the MERS S protein does not bind to human angiotensin-converting enzyme 2 precursor (hACE2) by bio-layer interferometry.
Figure 7:
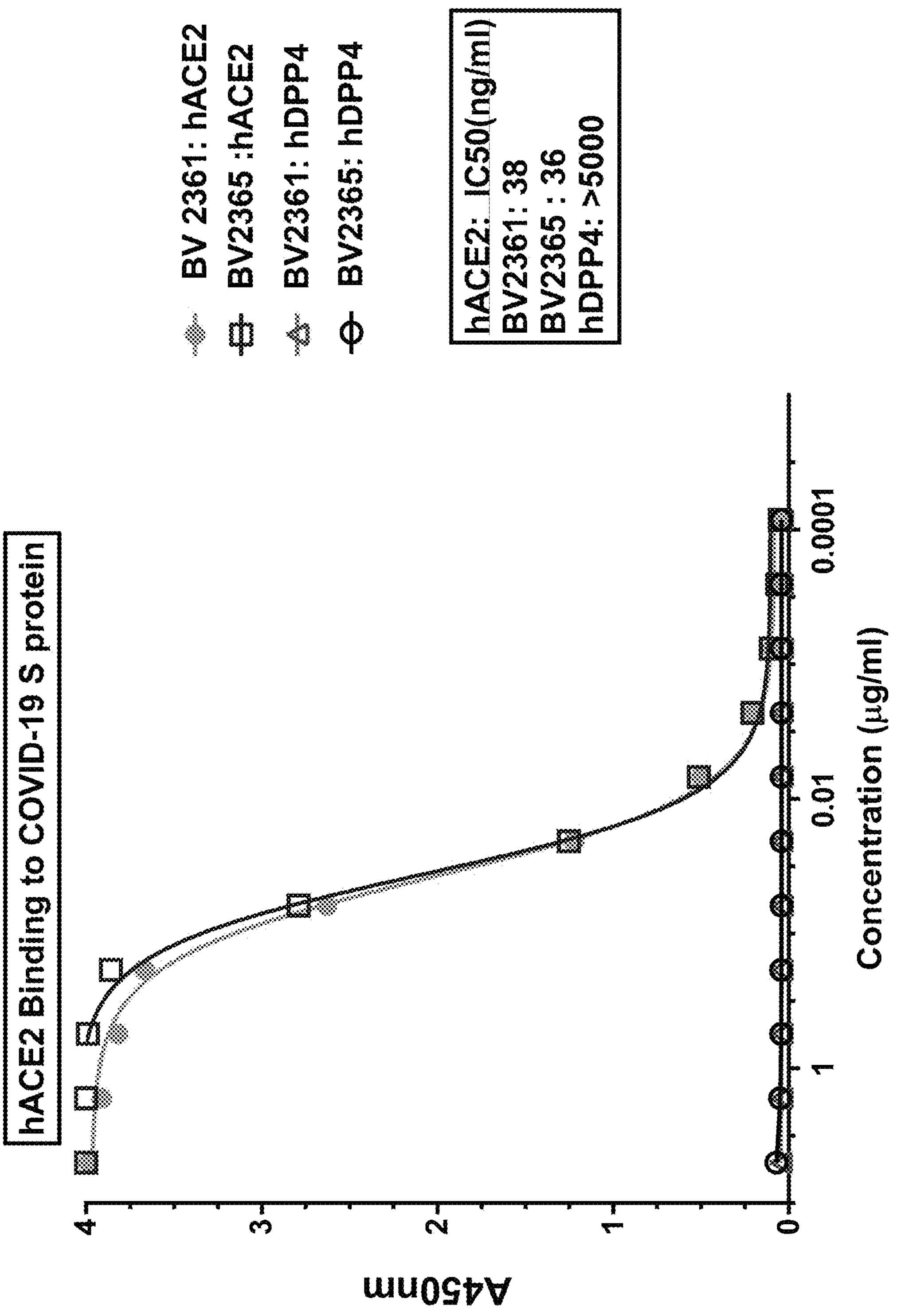
FIG. 7 shows that BV2361 binds to hACE2 by enzyme-linked immunosorbent assay (ELISA).
Figure 9:
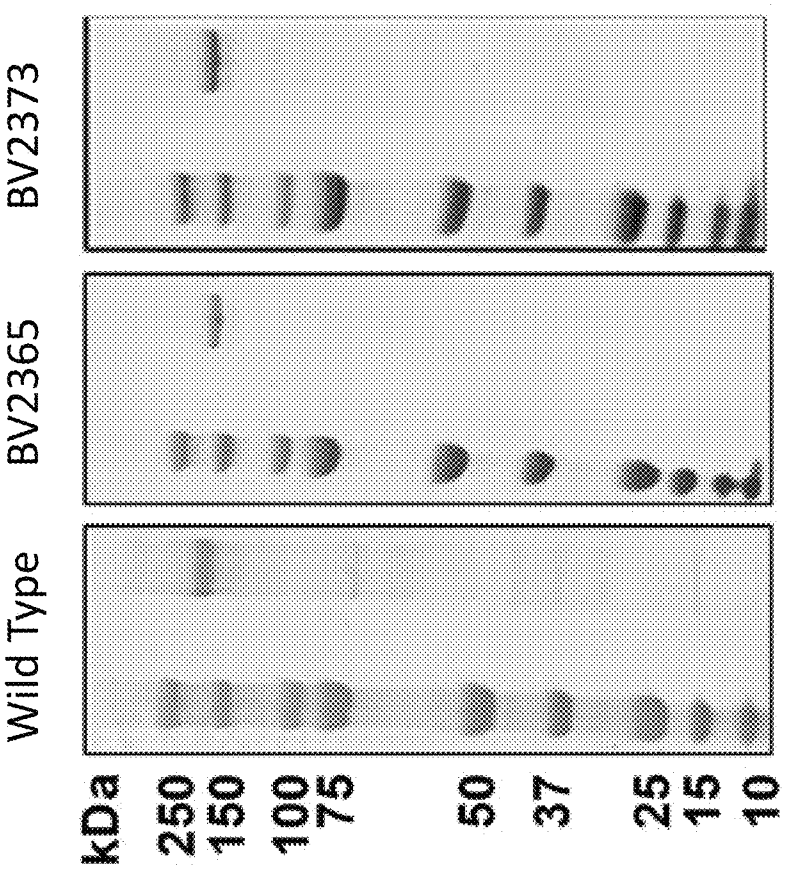
FIG. 9 shows purification of the wild type CoV S polypeptide and the CoV S polypeptides BV2365 and BV2373.

Expression and Purification of Coronavirus Spike (S) Polypeptide Nanoparticles The native coronavirus Spike (S) polypeptide (SEQ ID NO: 1 and SEQ ID NO:2) and CoV Spike polypeptides which have amino acid sequences corresponding to SEQ ID NOS: 3, 4, 38, 41, 44, 48, 51, 54, 58, 61, 63, 65, 67, 73, 75, 78, 79, 82, 83, 85, 87, 106, 108, and 89 have been expressed in a baculovirus expression system and recombinant plaques expressing the coronavirus Spike (S) polypeptides were picked and confirmed. In each case the signal peptide is SEQ ID NO: 5. FIG. 4 and FIG. 9 show successful purification of the CoV Spike polypeptides BV2364, BV2365, BV2366, BV2367, BV2368, BV2369, BV2373, BV2374, and BV2375. Table 2 shows the sequence characteristics of the aforementioned CoV Spike polypeptides.

TABLE 2

Selected CoV Spike Polypeptides

| CoV S polypeptide | Modification | SEQ ID NO. |
|---|---|---|
| BV2364 | Deleted N-Terminal Domain | 48 |
| BV2365 | Inactive furin cleavage site | 4 |
| BV2361/BV2366 | Wild-type | 2 |
| BV2367 | Deletion of amino acids 676-685, inactive furin cleavage site | 63 |
| BV2368 | Deletion of amino acids 702-711, inactive furin cleavage site | 65 |
| BV2369 | Deletion of amino acids 806-815, inactive furin cleavage site | 67 |
| BV2373, formulated into a composition referred to herein as "NVX-CoV2373" | Inactive furin cleavage site, K973P mutation, V974P mutation | 87 |
| BV2374 | K973P mutation, V974P mutation | 85 |
| BV2374 | Inactive furin cleavage site and His-tag | 58 |
| BV2384 | Inactive furin cleavage site (GSAS), K973P, V974P mutation | 110 |

The wild-type BV2361 protein (SEQ ID NO: 2) binds to human angiotensin-converting enzyme 2 precursor (hACE2). Bio-layer interferometry and ELISA were performed to assess binding of the CoV S polypeptides.

Bio-Layer Interferometry (BLI):

The BLI experiments were performed using an Octet QK384 system (Pall Forte Bio, Fremont, Calif.). His-tagged human ACE2 (2 μg mL-1) was immobilized on nickel-charged Ni-NTA biosensor tips. After baseline, SARS-CoV-2 S protein containing samples were 2-fold serially diluted and were allowed to associate for 600 seconds followed by dissociation for an additional 900 sec. Data was analyzed with Octet software HT 101:1 global curve fit.

The CoV S polypeptides BV2361, BV2365, BV2369, BV2365, BV2373, BV2374 retain the ability to bind to hACE2 (FIG. 5, FIGS. 11A-C). Dissociation kinetics showed that the S-proteins remained tightly bound as evident by minimal or no dissociation over 900 seconds of observation in the absence of fluid phase S protein (FIGS. 11A-C).

Furthermore, binding is specific. The wild-type CoV S protein, BV2361 and the CoV S polypeptides BV2365 and BV2373 do not bind the MERS-CoV receptor, dipeptidyl peptidase IV (DPP4). Additionally, the MERS S protein does not bind to human angiotensin-converting enzyme 2 precursor (hACE2) (FIG. 6 and FIGS. 11D-F).

ELISA

The specificity of the CoV S polypeptides for hACE2 was confirmed by ELISA. Ninety-six well plates were coated with 100 μL SARS-CoV-2 spike protein (2 μg/mL) overnight at 4° C. Plates were washed with phosphate buffered saline with 0.05% Tween (PBS-T) buffer and blocked with TBS Startblock blocking buffer (ThermoFisher, Scientific). His-tagged hACE2 and hDPP4 receptors were 3-fold serially diluted (5-0.0001 μg mL-1) and added to coated wells for 2 hours at room temperature. The plates were washed with PBS-T. Optimally diluted horseradish peroxidase (HRP) conjugated anti-histidine was added and color developed by addition of and 3,3',5,5'-tetramethylbenzidine peroxidase substrate (TMB, T0440-IL, Sigma, St. Louis, Mo., USA). Plates were read at an OD of 450 nm with a SpectraMax Plus plate reader (Molecular Devices, Sunnyvale, Calif., USA) and data analyzed with SoftMax software. EC50 values were calculated by 4-parameter fitting using GraphPad Prism 7.05 software.

The ELISA results showed that the wild-type CoV S polypeptide (BV2361), BV2365, and BV2373 proteins specifically bound hACE2 but failed to bind the hDPP-4 receptor used by MERS-CoV ($IC_{50}$>5000 ng mL-1). The wild-type CoV S polypeptide and BV2365 bound to hACE2 with similar affinity ($IC_{50}$=36-38 ng/mL), while BV2373 attained 50% saturation of hACE2 binding at 2-fold lower concentration ($IC_{50}$=18 ng/mL) (FIG. 7, FIGS. 11D-F).

Protein and Nanoparticle Production

The recombinant virus is amplified by infection of Sf9 insect cells. A culture of insect cells is infected at ~3 MOI (Multiplicity of infection=virus ffu or pfu/cell) with baculovirus. The culture and supernatant is harvested 48-72 hrs post-infection. The crude cell harvest, approximately 30 mL, is clarified by centrifugation for 15 minutes at approximately 800×g. The resulting crude cell harvests containing the coronavirus Spike (S) protein are purified as nanoparticles as described below.

To produce nanoparticles, non-ionic surfactant TERGITOL® nonylphenol ethoxylate NP-9 is used in the membrane protein extraction protocol. Crude extraction is further purified by passing through anion exchange chromatography, lentil lectin affinity/HIC and cation exchange chromatography. The washed cells are lysed by detergent treatment and then subjected to low pH treatment which leads to precipitation of BV and Sf9 host cell DNA and protein. The neutralized low pH treatment lysate is clarified and further purified on anion exchange and affinity chromatography before a second low pH treatment is performed.

Affinity chromatography is used to remove 519/BV proteins, DNA and NP-9, as well as to concentrate the coronavirus Spike (S) protein. Briefly, lentil lectin is a metalloprotein containing calcium and manganese, which reversibly binds polysaccharides and glycosylated proteins containing glucose or mannose. The coronavirus Spike (S) protein-containing anion exchange flow through fraction is loaded onto the lentil lectin affinity chromatography resin (Capto Lentil Lectin, GE Healthcare). The glycosylated coronavirus Spike (S) protein is selectively bound to the resin while non-glycosylated proteins and DNA are removed in the column flow through. Weakly bound glycoproteins are removed by buffers containing high salt and low molar concentration of methyl alpha-D-mannopyranoside (MMP).

The column washes are also used to detergent exchange the NP-9 detergent with the surfactant polysorbate 80 (PS80). The coronavirus Spike (S) polypeptides are eluted in nanoparticle structure from the lentil lectin column with a high concentration of MMP. After elution, the coronavirus Spike (S) protein trimers are assembled into nanoparticles composed of coronavirus Spike (S) protein trimers and PS80 contained in a detergent core.

Example 2

Immunogenicity of Coronavirus Spike (S) Polypeptide Nanoparticle Vaccines in Mice The coronavirus Spike (S) protein composition comprising a CoV S polypeptide of SEQ ID NO: 87 (also called "BV2373") as described in Example 1 was evaluated for immunogenicity and toxicity in a murine model, using female BALB/c mice (7-9 weeks old; Harlan Laboratories Inc., Frederick, Md.). The compositions were evaluated in the presence and in the absence of a saponin adjuvant, e.g., MATRIX-M™. Compositions containing MATRIX-M™ contained 5 μg of MATRIX-M™. Vaccines containing coronavirus Spike (S) polypeptide at various doses, including 0.01 μg, 0.1 μg, 1 μg, and 10 μg, were administered intramuscularly as a single dose (also referred to as a single priming dose) (study day 14) or as two doses (also referred to as a prime/boost regimen) spaced 14-days apart (study day 0 and 14). A placebo group served as a non-immunized control. Serum was collected for analysis on study days −1, 13, 21, and 28. Vaccinated and control animals were intranasally challenged with SARS-CoV-2 42 days following one (a single dose) or two (two doses) immunizations.

Vaccine Immunogenicity

Animals immunized with a single priming dose of 0.1-10 μg BV2373 and MATRIX-M™ had elevated anti-S IgG titers that were detected 21-28 days after a single immunization (FIG. 13B). Mice immunized with a 10 μg dose of BV2373 and MATRIX-M™ produced antibodies that blocked hACE2 receptor binding to the CoV S protein and virus neutralizing antibodies that were detected 21-28 days after a single priming dose (FIG. 14 and FIG. 15). Animals immunized with the prime/boost regimen (two doses) had significantly elevated anti-S IgG titers that were detected 7-16 days following the booster immunization across all dose levels (FIG. 13A). Animals immunized with BV2373 (1 μg and 10 μg) and MATRIX-M™ had similar high anti-S IgG titers following immunization (GMT=139,000 and 84,000, respectively). Mice immunized with BV2373 (0.1 μg, 1 μg, or 10 μg) and MATRIX-M™ had significantly ($p \leq 0.05$ and $p \leq 0.0001$) higher anti-S IgG titers compared to mice immunized with 10 μg BV2373 without adjuvant (FIG. 13A). These results indicate the potential for 10- to 100-fold dose sparing provided by the MATRIX-M™ adjuvant. Furthermore, immunization with two doses of BV2373 and MATRIX-M™ elicited high titer antibodies that blocked hACE2 receptor binding to S-protein (IC50=218-1642) and neutralized the cytopathic effect (CPE) of SARS-CoV-2 on Vero E6 cells (100% blocking of CPE=7680-20,000) across all dose levels (FIG. 14 and FIG. 15).

SARS CoV-2 Challenge

To evaluate the induction of protective immunity, immunized mice were challenged with SARS-CoV-2. Since mice do not support replication of the wild-type SARS-CoV-2 virus, on day 52 post initial vaccination, mice were intranasally infected with an adenovirus expressing hACE2 (Ad/hACE2) to render them permissive. Mice were intranasally inoculated with $1.5 \times 10^5$ pfu of SARS-CoV-2 in 50

μL divided between nares. Challenged mice were weighed on the day of infection and daily for up to 7 days post infection. At 4- and 7-days post infection, 5 mice were sacrificed from each vaccination and control group, and lungs were harvested and prepared for pulmonary histology.

The viral titer was quantified by a plaque assay. Briefly, the harvested lungs were homogenized in PBS using 1.0 mm glass beads (Sigma Aldrich) and a Beadruptor (Omini International Inc.). Homogenates were added to Vero E6 near confluent cultures and SARS-CoV-2 virus titers determined by counting plaque forming units (pfu) using a 6-point dilution curve At 4 days post infection, placebo-treated mice had $10^4$ SARS-CoV-2 pfu/lung, while the mice immunized with BV2363 without MATRIX-M™ had $10^3$ pfu/lung (FIG. 16). The BV2373 with MATRIX-M™ prime-only groups of mice exhibited a dose dependent reduction in virus titer, with recipients of the 10 μg BV2373 dose having no detectable virus at day 4 post infection. Mice receiving 1 μg, 0.1 μg and 0.01 μg BV2373 doses all showed a marked reduction in titer compared to placebo-vaccinated mice. In the prime/boost groups, mice immunized with 10 μg, 1 μg and 0.1 μg doses had almost undetectable lung virus loads, while the 0.01 μg group displayed a reduction of 1 log reduction relative to placebo animals.

Weight loss paralleled the viral load findings. Animals receiving a single dose of BV2373 (0.1 μg, 1 μg, and 10 μg) and MATRIX-M™ showed marked protection from weight loss compared to the unvaccinated placebo animals (FIG. 17A). The mice receiving a prime and boost dose with adjuvant also demonstrated significant protection against weight loss at all dose levels (FIGS. 17B-C). The effect of the presence of adjuvant on protection against weight loss was evaluated. Mice receiving the prime/boost (two doses) plus adjuvant were significantly protected from weight loss relative to placebo, while the group immunized without adjuvant was not (FIG. 17C). These results showed that BV2373 confers protection against SARS-CoV-2 and that low doses of the vaccine associated with lower serologic responses do not exacerbate weight loss or demonstrate exaggerated illness.

Lung histopathology was evaluated on days 4 and day 7 post infection (FIG. 18A and FIG. 18B). At day 4 post infection, placebo-immunized mice showed denudation of epithelial cells in the large airways with thickening of the alveolar septa surrounded by a mixed inflammatory cell population. Periarteriolar cuffing was observed throughout the lungs with inflammatory cells consisting primarily of neutrophils and macrophages. By day 7 post infection, the placebo-treated mice displayed peribronchiolar inflammation with increased periarteriolar cuffing. The thickened alveolar septa remained with increased diffuse interstitial inflammation throughout the alveolar septa (FIG. 18B).

The BV2373 immunized mice showed significant reduction in lung pathology at both day 4 and day 7 post infection in a dose-dependent manner. The prime only group displays reduced inflammation at the 10 μg and 1 μg dose with a reduction in inflammation surrounding the bronchi and arterioles compared to placebo mice. In the lower doses of the prime-only groups, lung inflammation resembles that of the placebo groups, correlating with weight loss and lung virus titer. The prime/boost immunized groups displayed a significant reduction in lung inflammation for all doses tested, which again correlated with lung viral titer and weight loss data. The epithelial cells in the large and small bronchi at day 4 and 7 were substantially preserved with minimal bronchiolar sloughing and signs of viral infection. The arterioles of animals immunized with 10 μg, 1 μg and 0.1 μg doses have minimal inflammation with only moderate cuffing seen with the 0.01 μg dose, similar to placebo. Alveolar inflammation was reduced in animals that received the higher doses with only the lower 0.01 μg dose associated with inflammation (FIGS. 18A-18B). These data demonstrate that BV2373 reduces lung inflammation after challenge and that even doses and regimens of BV2373 that elicit minimal or no detectable neutralizing activity are not associated with exacerbation of the inflammatory response to the virus. Furthermore, the vaccine does not cause vaccine associated enhanced respiratory disease (VAERD) in challenged mice.

T Cell Response

The effect of the vaccine composition comprising a CoV S polypeptide of SEQ ID NO: 87 on the T cell response was evaluated. BALB/c mice (N=6 per group) were immunized intramuscularly with 10 μg BV2373 with or without 5 μg MATRIX-M™ in 2 doses spaced 21-days apart. Spleens were collected 7-days after the second immunization (study day 28). A non-vaccinated group (N=3) served as a control.

Antigen-specific T cell responses were measured by ELISPOT™ enzyme linked immunosorbent assay and intracellular cytokine staining (ICCS) from spleens collected 7-days after the second immunization (study day 28). The number of IFN-γ secreting cells after ex vivo stimulation increased 20-fold (p=0.002) in spleens of mice immunized with BV2373 and MATRIX-M™ compared to BV2373 alone as measured by the ELISPOT™ assay (FIG. 19). In order to examine CD4+ and CD8+ T cell responses separately, ICCS assays were performed in combination with surface marker staining. Data shown are gated on CD44hi CD62L-effector memory T cell population. The frequency of IFN-γ+, TNF-α+, and IL-2+ cytokine-secreting CD4+ and CD8+ T cells was significantly higher (p<0.0001) in spleens from mice immunized with BV2373 as compared to mice immunized without adjuvant (FIG. 20A-C and FIG. 21A-C). Further, the frequency of multifunctional CD4+ and CD8+ T cells, which simultaneously produce at least two or three cytokines was also significantly increased (p<0.0001) in spleens from the BV2373/MATRIX-M™ immunized mice as compared to mice immunized in the absence of adjuvant (FIGS. 20D-E and FIGS. 21D-E). Immunization with BV2373/MATRIX-M™ resulted in higher proportions of multifunctional phenotypes (e.g., T cells that secrete more than one of IFN-γ, TNF-α, and IL-2) within both CD4+ and CD8+ T cell populations. The proportions of multifunctional phenotypes detected in memory CD4+ T cells were higher than those in CD8+ T cells (FIG. 22).

Type 2 cytokine IL-4 and IL-5 secretion from CD4+ T cells was also determined by ICCS and ELISPOT™ respectively. Immunization with BV2373/MATRIX-M™ also increased type 2 cytokine IL-4 and IL-5 secretion (2-fold) compared to immunization with BV2373 alone, but to a lesser degree than enhancement of type 1 cytokine production (e.g. IFN-γ increased 20-fold) (FIGS. 23A-C). These results indicate that administration of the MATRIX-M™ adjuvant skewed the CD4+ T cell development toward Th1 responses.

The effect of immunization on germinal center formation was assessed by measuring the frequency of CD4+T follicular helper (TFH) cells and germinal center (GC) B cells in spleens. MATRIX-M™ administration significantly increased the frequency of TFH cells (CD4+ CXCR5+PD-1+) was significantly increased (p=0.01), as well as the frequency of GC B cells (CD19+GL7+CD95+) (p=0.0002) in spleens (FIGS. 24A-B and FIGS. 25A-B).

Example 3

Immunogenicity of Coronavirus Spike (S) Polypeptide Nanoparticle Vaccines in Olive Baboons The immunogenicity of a vaccine composition comprising BV2373 in baboons was assessed. Adult olive baboons were immunized with a dose range (1 μg, 5 μg and 25 μg) of BV2373 and 50 μg MATRIX-M™ adjuvant administered by intramuscular (IM) injection in two doses spaced 21-days apart. To assess the adjuvanting activity of MATRIX-M™ in non-human primates, another group of animals was immunized with 25 μg of BV2373 without MATRIX-M™. Anti-S protein IgG titers were detected within 21-days of a single priming immunization in animals immunized with BV2373/MATRIX-M™ across all the dose levels (GMT=1249-19,000). Anti-S protein IgG titers increased over a log (GMT=33,000-174,000) within 1 to 2 weeks following a booster immunization (days 28 and 35) across all of the dose levels. (FIG. 26A).

Low levels of hACE2 receptor blocking antibodies were detected in animals following a single immunization with BV2373 (5 μg or 25 μg) and MATRIX-M™ (GMT=22-37). Receptor blocking antibody titers were significantly increased within one to two weeks of the booster immunization across all groups immunized with BV2373/MATRIX-M™ (GMT=150-600) (FIG. 26B). Virus neutralizing antibodies were elevated (GMT=190-446) across all dose groups after a single immunization with BV2373/MATRIX-M™. Animals immunized with 25 μg BV2373 alone had no detectable antibodies that block S-protein binding to hACE2 (FIG. 26C). Neutralizing titers were increased 6- to 8-fold one week following the booster immunization (GMT=1160-3846). Neutralizing titers increased an additional 25- to 38-fold following the second immunization (GMT=6400-17,000) (FIG. 26C). There was a significant correlation ($p<0.0001$) between anti-S IgG levels and neutralizing antibody titers (FIG. 27). The immunogenicity of the adjuvanted vaccine in nonhuman primates is consistent with the results of Example 2 and further supports the role of MATRIX-M™ in promoting the generation of neutralizing antibodies and dose sparing.

PBMCs were collected 7 days after the second immunization (day 28), and the T cell response was measured by ELISPOT assay. PBMCs from animals immunized with BV2373 (5 μg or 25 μg) and MATRIX-M™ had the highest number of IFN-γ secreting cells, which was 5-fold greater compared to animals immunized with 25 μg BV2373 alone or BV2373 (1 μg) and MATRIX-M™ (FIG. 28). By ICCS analysis, immunization with BV2373 (5 μg) and MATRIX-M™ showed the highest frequency of IFN-γ+, IL-2+, and TNF-α+CD4+ T cells (FIGS. 29A-C). This trend was also true for multifunctional CD4+ T cells, in which at least two or three type 1 cytokines were produced simultaneously (FIGS. 29D-E).

Example 4

Structural Characterization of Coronavirus Spike (S) Polypeptide Nanoparticle Vaccines Transmission electron microscopy (TEM) and two dimensional (2D) class averaging were used to determine the ultrastructure of BV2373. High magnification (67,000× and 100,000×) TEM images of negatively stained BV2373 showed particles corresponding to S-protein homotrimers.

An automated picking protocol was used to construct 2D class average images (Lander G. C. et al. *J Struct Biol.* 166, 95-102 (2009); Sorzano C. O. et al., *J Struct Biol.* 148, 194-204 (2004).). Two rounds of 2D class averaging of homotrimeric structures revealed a triangular particle appearance with a 15 nm length and 13 nm width (FIG. 10, top left). Overlaying the recently solved cryoEM structure of the SARS-CoV-2 spike protein (EMD ID: 21374) over the 2D BV2373 image showed a good fit with the crown-shaped 51 (NTD and RBD) and the S2 stem (FIG. 10, bottom left). Also apparent in the 2D images was a faint projection that protruded from the tip of the trimeric structure opposite of the NTD/RBD crown (FIG. 10, top right). 2D class averaging using a larger box size showed these faint projections form a connection between the S-trimer and an amorphous structure. (FIG. 10, bottom right).

Dynamic light scattering (DLS) show that the wild-type CoV S protein had a Z-avg particle diameter of 69.53 nm compared to a 2-fold smaller particle size of BV2365 (33.4 nm) and BV2373 (27.2 nm). The polydispersity index (PDI) indicated that BV2365 and BV2373 particles were generally uniform in size, shape, and mass (PDI=0.25-0.29) compared to the wild-type spike-protein (PDI=0.46) (Table 3).

TABLE 3

Particle Size and Thermostability of SARS-CoV-2 Trimeric Spike Proteins

| | Differential Scanning Calorimetry (DSC) | | Dynamic Light Scattering (DLS) | |
|---|---|---|---|---|
| SARS-CoV-2 S protein | $T_{max}$ (° C.) | ΔHcal (kJ/mol) | Z- avg diameter[2] (nm) | PDI[3] |
| Wild-type | 58.6 | 153 | 69.53 | 0.46 |
| BV2365 | 61.3 | 466 | 33.40 | 0.25 |
| BV2373 | 60.4 | 732 | 27.21 | 0.29 |

[1]$T_{max}$: melting temperature
[2]Z-avg: Z-average particle size
[3]PDI: polydispersity index The thermal stability of the S-trimers was determined by differential scanning calorimetry (DSC). The thermal transition temperature of the wild-type CoV S-protein ($T_{max}$=58.6° C.) was similar to BV2365 and BV2373 with a $T_{max}$=61.3° C. and 60.4° C., respectively (Table 3). Of greater significance, was the 3-5 fold increased enthalpy of transition required to unfold the BV2365 and BV2373 variants (ΔHcal=466 and 732 kJ/mol, respectively) compared to the lower enthalpy required to unfold the WT spike protein (ΔHcal=153 kJ/mol). These results are consistent with improved thermal stability of the BV2365 and BV2373 compared to that of WT spike protein (Table 3).

The stability of the CoV Spike (S) polypeptide nanoparticle vaccines was evaluated by dynamic light scattering. Various pHs, temperatures, salt concentrations, and proteases were used to compare the stability of the CoV Spike (S) polypeptide nanoparticle vaccines to nanoparticle vaccines containing the native CoV Spike (S) polypeptide.

Example 5

Stability of Coronavirus Spike (S) Polypeptide Nanoparticle Vaccines

The stability of the CoV Spike (S) polypeptide nanoparticle vaccines was evaluated by dynamic light scattering. Various pHs, temperatures, salt concentrations, and proteases were used to compare the stability of the CoV Spike (S) polypeptide nanoparticle vaccines to nanoparticle vaccines containing the native CoV Spike (S) polypeptide. The stability of BV2365 without the 2-proline substitutions and BV2373 with two prolines substitution was assessed under different environmental stress conditions using the hACE2 capture ELISA. Incubation of BV2373 at pH extremes (48 hours at pH 4 and pH 9), with prolonged agitation (48 hours), and through freeze/thaw (2 cycles), and elevated temperature (48 hours at 25° C. and 37° C.) had no effect on hACE2 receptor binding (IC50=14.0-18.3 ng mL-1).

Oxidizing conditions with hydrogen peroxide reduced binding of hACE2 binding to BV2373 8-fold (IC50=120 ng mL-1) (FIG. 12A). BV2365 without the 2-proline substitutions was less stable as determined by a significant loss of hACE2 binding under multiple conditions (FIG. 12B).

The stability of BV2384 (SEQ ID NO: 110) and BV2373 (SEQ ID NO: 87) were compared. BV2384 has a furin cleavage site sequence of GSAS (SEQ ID NO: 97), whereas BV2373 has a furin cleavage site of QQAQ (SEQ ID NO: 7). As demonstrated by SDS-PAGE and Western Blot, BV2384 showed extensive degradation in comparison to BV2373 (FIG. 32). Furthermore, scanning densitometry and recovery data demonstrate the unexpected loss of full length CoV S protein BV2384, lower purity, and recovery (FIG. 33) in comparison to BV2373 (FIG. 34).

Example 6

Immune Response in Cynomolgus Macaques

We assessed the immune response induced by BV2373 in a Cynomolgus macaque model of SARS-CoV-2 infection. Groups 1-6 were treated as shown in Table 4.

TABLE 4

Groups 1-6 of Cynomolgus macaque study

| Group (N = 4) | BV2373 Dose | MATRIX-M ™ Dose | Immunization (Days) | Blood Draw (days) | Challenge (Day) |
|---|---|---|---|---|---|
| 1 | Placebo | — | 0, 21 | 0, 21, 33 | 35 |
| 2 | 2.5 μg | 25 μg | 0, 21 | 0, 21, 33 | 35 |
| 3 | 5 μg | 25 μg | 0 | 0, 21, 33 | 35 |
| 4 | 5 μg | 50 μg | 0, 21 | 0, 21, 33 | 35 |
| 5 | 5 μg | 50 μg | 0 | 0, 21, 33 | 35 |
| 6 | 25 μg | 50 μg | 0, 21 | 0, 21, 33 | 35 |

Administration of a vaccine comprising BV2373 resulted in the induction of anti-CoV-S antibodies (FIG. 35A) including neutralizing antibodies (FIG. 35B). Anti-CoV-S antibodies were induced after administration of one (FIG. 38A) or two doses (FIG. 38B) of BV2373. Administration of the vaccine comprising BV2373 also resulted in the production of antibodies that blocked binding of the CoV S protein to hACE2 (FIG. 38C and FIG. 38D). There was a significant correlation between anti-CoV S polypeptide IgG titer and hACE2 inhibition titer in Cynomolgus macaques after administration of BV2373 (FIG. 38E). The ability of BV2373 to induce the production of neutralizing antibodies was evaluated by cytopathic effect (CPE) (FIG. 40A) and plaque reduction neutralization test (PRNT) (FIG. 40B). The data revealed that vaccine formulations of Table 4 produced SARS-CoV-2 neutralizing titers, in contrast to the control.

The vaccine comprising BV2373's ability to induce anti-CoV-S antibodies and antibodies that block binding of hACE2 to the CoV S protein in Cynomolgus macaques was compared to human convalescent serum. The data revealed that the BV2373 vaccine formulation induced superior anti-CoV S polypeptide and hACE2 inhibition titers as compared to human convalescent serum (FIG. 39).

The BV2373 vaccine formulation also caused a decrease of SARS-CoV-2 viral replication (FIGS. 36A-B). Viral RNA (FIG. 36A, corresponding to total RNA present) and viral sub-genomic RNA (sgRNA) (FIG. 36B, corresponding to replicating virus) levels were assessed in bronchiolar lavage (BAL) at 2 days and 4 days post-challenge with infectious virus (d2pi and d4pi). Most subjects showed no viral RNA. At Day 2 small amounts of RNA were measured in some subjects. By Day 4, no RNA was measured except for two subjects at the lowest dose of 2.5 μg. Sub-genomic RNA was not detected at either 2 days or 4 days except for 1 subject, again at the lowest dose. Viral RNA (FIG. 37A) and viral sub-genomic (sg) RNA (FIG. 37B) were assessed by nasal swab at 2 days and 4 days post-infection (d2pi and d4pi). Most subjects showed no viral RNA. At Day 2 and Day 4 small amounts of RNA were measured in some subjects. Sub-genomic RNA was not detected at either 2 Days or 4 days. Subjects were immunized Day 0 and in the groups with two doses Day 0 and Day 21. These data show that the vaccine decreases nose total virus RNA by 100-1000 fold and sgRNA to undetectable levels, and confirm that immune response to the vaccine will block viral replication and prevent viral spread.

Example 7

Evaluation of CoV S Polypeptide Nanoparticle Vaccines in Humans

We assessed the safety and efficacy of a vaccine comprising BV2373 in a randomized, observer-blinded, placebo-controlled Phase 1 clinical trial in 131 healthy participants 18-59 years of age. Participants were immunized with two intramuscular injections, 21 days apart. Participants received BV2373 with or without MATRIX-M™ (n=106) or placebo (n=25). Groups A-E were treated as shown in Table 5. FIG. 41 shows a timeline of the evaluation of clinical endpoints.

TABLE 5

Groups A-E of Phase 1 Human Study

| | Participants | | Day 0 | | Day 21 (+5 days) | |
|---|---|---|---|---|---|---|
| Group (N = 25) | Randomized | Sentinel | BV2373 Dose | MATRIX-M ™ Dose | BV2373 Dose | MATRIX-M ™ Dose |
| A | 25 | — | 0 μg | 0 μg | 0 μg | 0 μg |
| B | 25 | — | 25 μg | 0 μg | 25 μg | 0 μg |
| C | 25 | 3 | 5 μg | 50 μg | 5 μg | 50 μg |
| D | 25 | 3 | 25 μg | 50 μg | 25 μg | 50 μg |
| E | 25 | — | 25 μg | 50 μg | 0 μg | 0 μg |

Overall reactogenicity was mild, and the vaccinations were well tolerated. Local reactogenicity was more frequent in patients treated with BV2373 and MATRIX-M™ (FIGS. 42A-B).

The immunogenicity of BV2373 with and without MATRIX-M™ was evaluated. 21 days after vaccination, anti-CoV-S antibodies were detected for all vaccine regimens (FIG. 43A). Geometric mean fold rises (GMFR) in vaccine regimens comprising MATRIX-M™ exceeded those induced by unadjuvanted BV2373. 7 days after a second vaccination (day 28), the anti-CoV-S titer increased an additional eight-fold over responses seen with first vaccination and within 14 days (Day 35) responses had more than doubled yet again, achieving GMFRs approximately 100-fold over those observed with BV2373 alone. A single vaccination with BV2373/MATRIX-M™ achieved similar anti-CoV-S titer levels to those in asymptomatic (exposed) COVID-19 patients. A second vaccination achieved GMEU levels that exceeded convalescent serum from outpatient-treated COVID-19 patients by six-fold, achieved levels similar to convalescent serum from patients hospitalized with COVID-19, and exceeded overall convalescent serum anti-CoV-S antibodies by nearly six-fold. The responses in the two-dose 5-μg and 25-μg BV2373/MATRIX-M™ regimens were similar. This highlights the ability of the adjuvant (MATRIX-M™) to enable dose sparing.

Neutralizing antibodies were induced in all groups treated with BV2373 (FIG. 43B). Groups treated with BV2373 and MATRIX-M™ regimens exhibited an approximately five-fold GMFR than groups treated with BV2373 alone (FIG. 43B). Second vaccinations with adjuvant had a profound effect on neutralizing antibody titers—inducing >100 fold rise over single vaccinations without adjuvant. When compared to convalescent serum, second vaccinations with BV2373/MATRIX-M™ achieved GMT levels four-fold greater than outpatient-treated COVID-19 patients, levels spanning those of patients hospitalized with COVID-19, and exceeded overall convalescent serum GMT by four fold.

Convalescent serum, obtained from COVID-19 patients with clinical symptoms requiring medical care, demonstrated proportional anti-CoV-S IgG and neutralization titers that increased with illness severity (FIGS. 43A-B).

A strong correlation was observed between neutralizing antibody titers and anti-CoV-S IgG in patients treated with BV2373 and MATRIX-M™ (r=0.9466, FIG. 44C) similar to that observed in patients treated with convalescent sera (r=0.958) (FIG. 44A). This correlation was not observed in subjected administered unadjuvanted BV2373 (r=0.7616) (FIG. 44B). Both 5 μg and 25 μg BV2373/MATRIX-M™ groups (groups C-E of Table 5) demonstrated similar magnitudes of two-dose responses and every participant seroconverted using either assay measurement when a two-dose regimen was utilized.

T-cell responses in 16 participants (four participants from each of Groups A through D) showed that BV2373/MATRIX-M™ regimens induced antigen-specific polyfunctional CD4+ T-cell responses in terms of IFN-γ, IL-2, and TNF-α production upon stimulation with BV2373. There was a strong bias toward production of Th1 cytokines (FIGS. 45A-D).

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as, an acknowledgment or any form of suggestion that they constitute valid prior art or form part of the common general knowledge in any country in the world.

What is claimed is:

1. An immunogenic composition comprising:
(i) a nanoparticle comprising a coronavirus S (CoV S) glycoprotein having the amino acid sequence of SEQ ID NO: 87, and a non-ionic detergent core;
(ii) a pharmaceutically acceptable buffer, and
(iii) a saponin adjuvant.

2. The immunogenic composition of claim 1, comprising between about 5 μg and about 25 μg of CoV S glycoprotein.

3. The immunogenic composition of claim 2, comprising about 5 μg of CoV S glycoprotein.

4. The immunogenic composition of claim 1, wherein the saponin adjuvant comprises at least two iscom particles, wherein:
the first iscom particle comprises fraction A of *Quillaja saponaria* Molina and not fraction C of *Quillaja saponaria* Molina; and
the second iscom particle comprises fraction C of *Quillaja saponaria* Molina and not fraction A of *Quillaja saponaria* Molina.

5. The immunogenic composition of claim 4, wherein fraction A of *Quillaja saponaria* Molina accounts for 50-96% by weight and fraction C of *Quillaja saponaria* Molina accounts for the remainder, respectively, of the sum of the weights of fraction A of *Quillaja saponaria* Molina and fraction C of *Quillaja saponaria* Molina in the adjuvant.

6. The immunogenic composition of claim 4, wherein fraction A of *Quillaja saponaria* Molina and fraction C of *Quillaja saponaria* Molina account for about 85% by weight and about 15% by weight, respectively, of the sum of the weights of fraction A of *Quillaja saponaria* Molina and fraction C of *Quillaja saponaria* Molina in the adjuvant.

7. The immunogenic composition of claim 1, comprising about 50 μg of saponin adjuvant.

8. The immunogenic composition of claim 1, wherein the non-ionic detergent core is selected from the group consisting of polysorbate-20 (PS20), polysorbate-40 (PS40), polysorbate-60 (PS60), polysorbate-65 (PS65), and polysorbate-80 (PS80).

9. A method of stimulating an immune response against SARS-CoV-2 in a subject comprising administering the immunogenic composition of claim 1.

10. The method of claim 9, comprising between about 5 μg and about 25 μg of CoV S glycoprotein.

11. The method of claim 10, comprising 5 μg of CoV S glycoprotein.

12. The method of claim 9, wherein the saponin adjuvant comprises at least two iscom particles, wherein:
the first iscom particle comprises fraction A of *Quillaja saponaria* Molina and not fraction C of *Quillaja saponaria* Molina; and
the second iscom particle comprises fraction C of *Quillaja saponaria* Molina and not fraction A of *Quillaja saponaria* Molina.

13. The method of claim 12, wherein fraction A of *Quillaja saponaria* Molina accounts for 50-96% by weight and fraction C of *Quillaja saponaria* Molina accounts for the remainder, respectively, of the sum of the weights of fraction A of *Quillaja saponaria* Molina and fraction C of *Quillaja saponaria* Molina in the adjuvant.

14. The method of claim 12, wherein fraction A of *Quillaja saponaria* Molina and fraction C of *Quillaja saponaria* Molina account for about 85% by weight and about 15% by weight, respectively, of the sum of the weights of fraction A of *Quillaja saponaria* Molina and fraction C of *Quillaja saponaria* Molina in the adjuvant.

15. The method of claim 9, comprising about 50 μg of saponin adjuvant.

16. The method of claim 9, wherein the non-ionic detergent core is selected from the group consisting of polysorbate-20 (PS20), polysorbate-40 (PS40), polysorbate-60 (PS60), polysorbate-65 (PS65), and polysorbate-80 (PS80).

17. The method of claim 9, wherein the subject is administered a first dose at day 0 and a boost dose at day 21.

18. The method of claim 9, wherein a single dose of the immunogenic composition is administered.

19. The method of claim 9, comprising administering a second immunogenic composition different from the first immunogenic composition.

20. The method of claim 19 wherein the second immunogenic composition comprises an mRNA encoding a SARS-Cov-2 Spike glycoprotein, a plasmid DNA encoding a SARS-Cov-2 Spike glycoprotein, an viral vector encoding a SARS-Cov-2 Spike glycoprotein, or an inactivated SARS-CoV-2 virus.

* * * * *

UNITED STATES PATENT AND TRADEMARK OFFICE

CERTIFICATE OF CORRECTION

PATENT NO. : 10,953,089 B1
APPLICATION NO. : 16/997001
DATED : March 23, 2021
INVENTOR(S) : Gale Smith et al.

It is certified that error appears in the above-identified patent and that said Letters Patent is hereby corrected as shown below:

In the Claims

At Claim 8, Column 365, Line 48, replace:
"The immunogenic composition of claim 1, wherein the non-ionic detergent core is selected from the group consisting of polysorbate-20 (PS20), polysorbate-40 (PS40), polysorbate-60 (PS60), polysorbate-65 (PS65), and polysorbate-80 (PS80)"
With:
--The immunogenic composition of claim 1, wherein the non-ionic detergent is selected from the group consisting of polysorbate-20 (PS20), polysorbate-40 (PS40), polysorbate-60 (PS60), polysorbate-65 (PS65), and polysorbate-80 (PS80)--

At Claim 10, Column 365, Line 56, replace:
"The method of claim 9, comprising between about 5 μg and about 25 ug of CoV S glycoprotein"
With:
--The method of claim 9, wherein the immunogenic composition comprises between about 5 μg and about 25 μg of CoV S glycoprotein--

At Claim 11, Column 366, Line 14, replace:
"The method of claim 10, comprising 5 μg of CoV S glycoprotein."
With:
--The method of claim 10, wherein the immunogenic composition comprises 5 μg of CoV S glycoprotein.--

At Claim 15, Column 366, Line 37, replace:
"The method of claim 9, comprising about 50 μg of saponin adjuvant."
With:
--The method of claim 9, wherein the immunogenic composition comprises about 50 μg of saponin adjuvant.--

Signed and Sealed this
Fifteenth Day of February, 2022

Drew Hirshfeld
*Performing the Functions and Duties of the*
*Under Secretary of Commerce for Intellectual Property and*
*Director of the United States Patent and Trademark Office*

At Claim 16, Column 366, Line 39, replace:
"The method of claim 9, wherein the non-ionic detergent core is selected from the group consisting of polysorbate-20 (PS20), polysorbate-40 (PS40), polysorbate-60 (PS60), polysorbate-65 (PS65), and polysorbate-80 (PS80)."
With:
--The method of claim 9, wherein the non-ionic detergent is selected from the group consisting of polysorbate-20 (PS20), polysorbate-40 (PS40), polysorbate-60 (PS60), polysorbate-65 (PS65), and polysorbate-80 (PS80).--

SEQUENCE LISTING

```
<160> NUMBER OF SEQ ID NOS: 111

<210> SEQ ID NO 1
<211> LENGTH: 1273
<212> TYPE: PRT
<213> ORGANISM: Betacoronavirus severe acute respiratory syndrome
      coronavirus 2

<400> SEQUENCE: 1

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175
```

-continued

```
Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590
```

-continued

```
Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
            980                 985                 990

Ile Asp Arg Leu Ile Thr Gly Arg  Leu Gln Ser Leu Gln  Thr Tyr Val
        995                 1000                1005

Thr Gln  Gln Leu Ile Arg Ala  Ala Glu Ile Arg Ala  Ser Ala Asn
```

```
    1010                1015                1020

Leu Ala  Ala Thr Lys Met Ser  Glu Cys Val Leu Gly  Gln Ser Lys
    1025                1030                1035

Arg Val  Asp Phe Cys Gly Lys  Gly Tyr His Leu Met  Ser Phe Pro
    1040                1045                1050

Gln Ser  Ala Pro His Gly Val  Val Phe Leu His Val  Thr Tyr Val
    1055                1060                1065

Pro Ala  Gln Glu Lys Asn Phe  Thr Thr Ala Pro Ala  Ile Cys His
    1070                1075                1080

Asp Gly  Lys Ala His Phe Pro  Arg Glu Gly Val Phe  Val Ser Asn
    1085                1090                1095

Gly Thr  His Trp Phe Val Thr  Gln Arg Asn Phe Tyr  Glu Pro Gln
    1100                1105                1110

Ile Ile  Thr Thr Asp Asn Thr  Phe Val Ser Gly Asn  Cys Asp Val
    1115                1120                1125

Val Ile  Gly Ile Val Asn Asn  Thr Val Tyr Asp Pro  Leu Gln Pro
    1130                1135                1140

Glu Leu  Asp Ser Phe Lys Glu  Glu Leu Asp Lys Tyr  Phe Lys Asn
    1145                1150                1155

His Thr  Ser Pro Asp Val Asp  Leu Gly Asp Ile Ser  Gly Ile Asn
    1160                1165                1170

Ala Ser  Val Val Asn Ile Gln  Lys Glu Ile Asp Arg  Leu Asn Glu
    1175                1180                1185

Val Ala  Lys Asn Leu Asn Glu  Ser Leu Ile Asp Leu  Gln Glu Leu
    1190                1195                1200

Gly Lys  Tyr Glu Gln Tyr Ile  Lys Trp Pro Trp Tyr  Ile Trp Leu
    1205                1210                1215

Gly Phe  Ile Ala Gly Leu Ile  Ala Ile Val Met Val  Thr Ile Met
    1220                1225                1230

Leu Cys  Cys Met Thr Ser Cys  Cys Ser Cys Leu Lys  Gly Cys Cys
    1235                1240                1245

Ser Cys  Gly Ser Cys Cys Lys  Phe Asp Glu Asp Asp  Ser Glu Pro
    1250                1255                1260

Val Leu  Lys Gly Val Lys Leu  His Tyr Thr
    1265                1270


<210> SEQ ID NO 2
<211> LENGTH: 1260
<212> TYPE: PRT
<213> ORGANISM: Betacoronavirus severe acute respiratory syndrome
      coronavirus 2

<400> SEQUENCE: 2

Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
            20                  25                  30

Ser Val Leu His Ser Thr Gln Asp Leu Phe Leu Pro Phe Phe Ser Asn
        35                  40                  45

Val Thr Trp Phe His Ala Ile His Val Ser Gly Thr Asn Gly Thr Lys
    50                  55                  60

Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                85                  90                  95
```

-continued

```
Leu Asp Ser Lys Thr Gln Ser Leu Leu Ile Val Asn Asn Ala Thr Asn
            100                 105                 110

Val Val Ile Lys Val Cys Glu Phe Gln Phe Cys Asn Asp Pro Phe Leu
        115                 120                 125

Gly Val Tyr Tyr His Lys Asn Asn Lys Ser Trp Met Glu Ser Glu Phe
    130                 135                 140

Arg Val Tyr Ser Ser Ala Asn Asn Cys Thr Phe Glu Tyr Val Ser Gln
145                 150                 155                 160

Pro Phe Leu Met Asp Leu Glu Gly Lys Gln Gly Asn Phe Lys Asn Leu
                165                 170                 175

Arg Glu Phe Val Phe Lys Asn Ile Asp Gly Tyr Phe Lys Ile Tyr Ser
            180                 185                 190

Lys His Thr Pro Ile Asn Leu Val Arg Asp Leu Pro Gln Gly Phe Ser
        195                 200                 205

Ala Leu Glu Pro Leu Val Asp Leu Pro Ile Gly Ile Asn Ile Thr Arg
    210                 215                 220

Phe Gln Thr Leu Leu Ala Leu His Arg Ser Tyr Leu Thr Pro Gly Asp
225                 230                 235                 240

Ser Ser Ser Gly Trp Thr Ala Gly Ala Ala Ala Tyr Tyr Val Gly Tyr
                245                 250                 255

Leu Gln Pro Arg Thr Phe Leu Leu Lys Tyr Asn Glu Asn Gly Thr Ile
            260                 265                 270

Thr Asp Ala Val Asp Cys Ala Leu Asp Pro Leu Ser Glu Thr Lys Cys
        275                 280                 285

Thr Leu Lys Ser Phe Thr Val Glu Lys Gly Ile Tyr Gln Thr Ser Asn
    290                 295                 300

Phe Arg Val Gln Pro Thr Glu Ser Ile Val Arg Phe Pro Asn Ile Thr
305                 310                 315                 320

Asn Leu Cys Pro Phe Gly Glu Val Phe Asn Ala Thr Arg Phe Ala Ser
                325                 330                 335

Val Tyr Ala Trp Asn Arg Lys Arg Ile Ser Asn Cys Val Ala Asp Tyr
            340                 345                 350

Ser Val Leu Tyr Asn Ser Ala Ser Phe Ser Thr Phe Lys Cys Tyr Gly
        355                 360                 365

Val Ser Pro Thr Lys Leu Asn Asp Leu Cys Phe Thr Asn Val Tyr Ala
    370                 375                 380

Asp Ser Phe Val Ile Arg Gly Asp Glu Val Arg Gln Ile Ala Pro Gly
385                 390                 395                 400

Gln Thr Gly Lys Ile Ala Asp Tyr Asn Tyr Lys Leu Pro Asp Asp Phe
                405                 410                 415

Thr Gly Cys Val Ile Ala Trp Asn Ser Asn Asn Leu Asp Ser Lys Val
            420                 425                 430

Gly Gly Asn Tyr Asn Tyr Leu Tyr Arg Leu Phe Arg Lys Ser Asn Leu
        435                 440                 445

Lys Pro Phe Glu Arg Asp Ile Ser Thr Glu Ile Tyr Gln Ala Gly Ser
    450                 455                 460

Thr Pro Cys Asn Gly Val Glu Gly Phe Asn Cys Tyr Phe Pro Leu Gln
465                 470                 475                 480

Ser Tyr Gly Phe Gln Pro Thr Asn Gly Val Gly Tyr Gln Pro Tyr Arg
                485                 490                 495

Val Val Val Leu Ser Phe Glu Leu Leu His Ala Pro Ala Thr Val Cys
            500                 505                 510
```

-continued

```
Gly Pro Lys Lys Ser Thr Asn Leu Val Lys Asn Lys Cys Val Asn Phe
        515                 520                 525

Asn Phe Asn Gly Leu Thr Gly Thr Gly Val Leu Thr Glu Ser Asn Lys
    530                 535                 540

Lys Phe Leu Pro Phe Gln Gln Phe Gly Arg Asp Ile Ala Asp Thr Thr
545                 550                 555                 560

Asp Ala Val Arg Asp Pro Gln Thr Leu Glu Ile Leu Asp Ile Thr Pro
                565                 570                 575

Cys Ser Phe Gly Gly Val Ser Val Ile Thr Pro Gly Thr Asn Thr Ser
            580                 585                 590

Asn Gln Val Ala Val Leu Tyr Gln Asp Val Asn Cys Thr Glu Val Pro
        595                 600                 605

Val Ala Ile His Ala Asp Gln Leu Thr Pro Thr Trp Arg Val Tyr Ser
    610                 615                 620

Thr Gly Ser Asn Val Phe Gln Thr Arg Ala Gly Cys Leu Ile Gly Ala
625                 630                 635                 640

Glu His Val Asn Asn Ser Tyr Glu Cys Asp Ile Pro Ile Gly Ala Gly
                645                 650                 655

Ile Cys Ala Ser Tyr Gln Thr Gln Thr Asn Ser Pro Arg Arg Ala Arg
            660                 665                 670

Ser Val Ala Ser Gln Ser Ile Ile Ala Tyr Thr Met Ser Leu Gly Ala
        675                 680                 685

Glu Asn Ser Val Ala Tyr Ser Asn Asn Ser Ile Ala Ile Pro Thr Asn
    690                 695                 700

Phe Thr Ile Ser Val Thr Thr Glu Ile Leu Pro Val Ser Met Thr Lys
705                 710                 715                 720

Thr Ser Val Asp Cys Thr Met Tyr Ile Cys Gly Asp Ser Thr Glu Cys
                725                 730                 735

Ser Asn Leu Leu Leu Gln Tyr Gly Ser Phe Cys Thr Gln Leu Asn Arg
            740                 745                 750

Ala Leu Thr Gly Ile Ala Val Glu Gln Asp Lys Asn Thr Gln Glu Val
        755                 760                 765

Phe Ala Gln Val Lys Gln Ile Tyr Lys Thr Pro Pro Ile Lys Asp Phe
    770                 775                 780

Gly Gly Phe Asn Phe Ser Gln Ile Leu Pro Asp Pro Ser Lys Pro Ser
785                 790                 795                 800

Lys Arg Ser Phe Ile Glu Asp Leu Leu Phe Asn Lys Val Thr Leu Ala
                805                 810                 815

Asp Ala Gly Phe Ile Lys Gln Tyr Gly Asp Cys Leu Gly Asp Ile Ala
            820                 825                 830

Ala Arg Asp Leu Ile Cys Ala Gln Lys Phe Asn Gly Leu Thr Val Leu
        835                 840                 845

Pro Pro Leu Leu Thr Asp Glu Met Ile Ala Gln Tyr Thr Ser Ala Leu
    850                 855                 860

Leu Ala Gly Thr Ile Thr Ser Gly Trp Thr Phe Gly Ala Gly Ala Ala
865                 870                 875                 880

Leu Gln Ile Pro Phe Ala Met Gln Met Ala Tyr Arg Phe Asn Gly Ile
                885                 890                 895

Gly Val Thr Gln Asn Val Leu Tyr Glu Asn Gln Lys Leu Ile Ala Asn
            900                 905                 910

Gln Phe Asn Ser Ala Ile Gly Lys Ile Gln Asp Ser Leu Ser Ser Thr
        915                 920                 925

Ala Ser Ala Leu Gly Lys Leu Gln Asp Val Val Asn Gln Asn Ala Gln
```

-continued

```
    930                 935                 940

Ala Leu Asn Thr Leu Val Lys Gln Leu Ser Ser Asn Phe Gly Ala Ile
945                 950                 955                 960

Ser Ser Val Leu Asn Asp Ile Leu Ser Arg Leu Asp Lys Val Glu Ala
                965                 970                 975

Glu Val Gln Ile Asp Arg Leu Ile Thr Gly Arg Leu Gln Ser Leu Gln
            980                 985                 990

Thr Tyr Val Thr Gln Gln Leu Ile  Arg Ala Ala Glu Ile  Arg Ala Ser
        995                 1000                1005

Ala Asn  Leu Ala Ala Thr Lys  Met Ser Glu Cys Val  Leu Gly Gln
    1010                1015                1020

Ser Lys  Arg Val Asp Phe Cys  Gly Lys Gly Tyr His  Leu Met Ser
    1025                1030                1035

Phe Pro  Gln Ser Ala Pro His  Gly Val Val Phe Leu  His Val Thr
    1040                1045                1050

Tyr Val  Pro Ala Gln Glu Lys  Asn Phe Thr Thr Ala  Pro Ala Ile
    1055                1060                1065

Cys His  Asp Gly Lys Ala His  Phe Pro Arg Glu Gly  Val Phe Val
    1070                1075                1080

Ser Asn  Gly Thr His Trp Phe  Val Thr Gln Arg Asn  Phe Tyr Glu
    1085                1090                1095

Pro Gln  Ile Ile Thr Thr Asp  Asn Thr Phe Val Ser  Gly Asn Cys
    1100                1105                1110

Asp Val  Val Ile Gly Ile Val  Asn Asn Thr Val Tyr  Asp Pro Leu
    1115                1120                1125

Gln Pro  Glu Leu Asp Ser Phe  Lys Glu Glu Leu Asp  Lys Tyr Phe
    1130                1135                1140

Lys Asn  His Thr Ser Pro Asp  Val Asp Leu Gly Asp  Ile Ser Gly
    1145                1150                1155

Ile Asn  Ala Ser Val Val Asn  Ile Gln Lys Glu Ile  Asp Arg Leu
    1160                1165                1170

Asn Glu  Val Ala Lys Asn Leu  Asn Glu Ser Leu Ile  Asp Leu Gln
    1175                1180                1185

Glu Leu  Gly Lys Tyr Glu Gln  Tyr Ile Lys Trp Pro  Trp Tyr Ile
    1190                1195                1200

Trp Leu  Gly Phe Ile Ala Gly  Leu Ile Ala Ile Val  Met Val Thr
    1205                1210                1215

Ile Met  Leu Cys Cys Met Thr  Ser Cys Cys Ser Cys  Leu Lys Gly
    1220                1225                1230

Cys Cys  Ser Cys Gly Ser Cys  Cys Lys Phe Asp Glu  Asp Asp Ser
    1235                1240                1245

Glu Pro  Val Leu Lys Gly Val  Lys Leu His Tyr Thr
    1250                1255                1260


<210> SEQ ID NO 3
<211> LENGTH: 1273
<212> TYPE: PRT
<213> ORGANISM: Artificial Sequence
<220> FEATURE:
<223> OTHER INFORMATION: RECOMBINANT S PROTEIN

<400> SEQUENCE: 3

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
```

-continued

```
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445
```

-continued

```
Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Gln Gln Ala Gln Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860
```

```
Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
            980                 985                 990

Ile Asp Arg Leu Ile Thr Gly Arg  Leu Gln Ser Leu Gln  Thr Tyr Val
        995                 1000                1005

Thr Gln  Gln Leu Ile Arg Ala  Ala Glu Ile Arg Ala  Ser Ala Asn
    1010                1015                1020

Leu Ala  Ala Thr Lys Met Ser  Glu Cys Val Leu Gly  Gln Ser Lys
    1025                1030                1035

Arg Val  Asp Phe Cys Gly Lys  Gly Tyr His Leu Met  Ser Phe Pro
    1040                1045                1050

Gln Ser  Ala Pro His Gly Val  Val Phe Leu His Val  Thr Tyr Val
    1055                1060                1065

Pro Ala  Gln Glu Lys Asn Phe  Thr Thr Ala Pro Ala  Ile Cys His
    1070                1075                1080

Asp Gly  Lys Ala His Phe Pro  Arg Glu Gly Val Phe  Val Ser Asn
    1085                1090                1095

Gly Thr  His Trp Phe Val Thr  Gln Arg Asn Phe Tyr  Glu Pro Gln
    1100                1105                1110

Ile Ile  Thr Thr Asp Asn Thr  Phe Val Ser Gly Asn  Cys Asp Val
    1115                1120                1125

Val Ile  Gly Ile Val Asn Asn  Thr Val Tyr Asp Pro  Leu Gln Pro
    1130                1135                1140

Glu Leu  Asp Ser Phe Lys Glu  Glu Leu Asp Lys Tyr  Phe Lys Asn
    1145                1150                1155

His Thr  Ser Pro Asp Val Asp  Leu Gly Asp Ile Ser  Gly Ile Asn
    1160                1165                1170

Ala Ser  Val Val Asn Ile Gln  Lys Glu Ile Asp Arg  Leu Asn Glu
    1175                1180                1185

Val Ala  Lys Asn Leu Asn Glu  Ser Leu Ile Asp Leu  Gln Glu Leu
    1190                1195                1200

Gly Lys  Tyr Glu Gln Tyr Ile  Lys Trp Pro Trp Tyr  Ile Trp Leu
    1205                1210                1215

Gly Phe  Ile Ala Gly Leu Ile  Ala Ile Val Met Val  Thr Ile Met
    1220                1225                1230

Leu Cys  Cys Met Thr Ser Cys  Cys Ser Cys Leu Lys  Gly Cys Cys
    1235                1240                1245

Ser Cys  Gly Ser Cys Cys Lys  Phe Asp Glu Asp Asp  Ser Glu Pro
    1250                1255                1260

Val Leu  Lys Gly Val Lys Leu  His Tyr Thr
```

1265 1270

<210> SEQ ID NO 4
<211> LENGTH: 1260
<212> TYPE: PRT
<213> ORGANISM: Artificial Sequence
<220> FEATURE:
<223> OTHER INFORMATION: RECOMBINANT S PROTEIN

<400> SEQUENCE: 4

Gln Cys Val Asn Leu Thr Thr Arg Thr Gln Leu Pro Pro Ala Tyr Thr
1 5 10 15

Asn Ser Phe Thr Arg Gly Val Tyr Tyr Pro Asp Lys Val Phe Arg Ser
20 25 30

Ser Val Leu His Ser Thr Gln Asp Leu Phe Leu Pro Phe Phe Ser Asn
35 40 45

Val Thr Trp Phe His Ala Ile His Val Ser Gly Thr Asn Gly Thr Lys
50 55 60

Arg Phe Asp Asn Pro Val Leu Pro Phe Asn Asp Gly Val Tyr Phe Ala
65 70 75 80

Ser Thr Glu Lys Ser Asn Ile Ile Arg Gly Trp Ile Phe Gly Thr Thr
85 90 95

Leu Asp Ser Lys Thr Gln Ser Leu Leu Ile Val Asn Asn Ala Thr Asn
100 105 110

Val Val Ile Lys Val Cys Glu Phe Gln Phe Cys Asn Asp Pro Phe Leu
115 120 125

Gly Val Tyr Tyr His Lys Asn Asn Lys Ser Trp Met Glu Ser Glu Phe
130 135 140

Arg Val Tyr Ser Ser Ala Asn Asn Cys Thr Phe Glu Tyr Val Ser Gln
145 150 155 160

Pro Phe Leu Met Asp Leu Glu Gly Lys Gln Gly Asn Phe Lys Asn Leu
165 170 175

Arg Glu Phe Val Phe Lys Asn Ile Asp Gly Tyr Phe Lys Ile Tyr Ser
180 185 190

Lys His Thr Pro Ile Asn Leu Val Arg Asp Leu Pro Gln Gly Phe Ser
195 200 205

Ala Leu Glu Pro Leu Val Asp Leu Pro Ile Gly Ile Asn Ile Thr Arg
210 215 220

Phe Gln Thr Leu Leu Ala Leu His Arg Ser Tyr Leu Thr Pro Gly Asp
225 230 235 240

Ser Ser Ser Gly Trp Thr Ala Gly Ala Ala Ala Tyr Tyr Val Gly Tyr
245 250 255

Leu Gln Pro Arg Thr Phe Leu Leu Lys Tyr Asn Glu Asn Gly Thr Ile
260 265 270

Thr Asp Ala Val Asp Cys Ala Leu Asp Pro Leu Ser Glu Thr Lys Cys
275 280 285

Thr Leu Lys Ser Phe Thr Val Glu Lys Gly Ile Tyr Gln Thr Ser Asn
290 295 300

Phe Arg Val Gln Pro Thr Glu Ser Ile Val Arg Phe Pro Asn Ile Thr
305 310 315 320

Asn Leu Cys Pro Phe Gly Glu Val Phe Asn Ala Thr Arg Phe Ala Ser
325 330 335

Val Tyr Ala Trp Asn Arg Lys Arg Ile Ser Asn Cys Val Ala Asp Tyr
340 345 350

Ser Val Leu Tyr Asn Ser Ala Ser Phe Ser Thr Phe Lys Cys Tyr Gly

-continued

```
        355                 360                 365

Val Ser Pro Thr Lys Leu Asn Asp Leu Cys Phe Thr Asn Val Tyr Ala
    370                 375                 380

Asp Ser Phe Val Ile Arg Gly Asp Glu Val Arg Gln Ile Ala Pro Gly
385                 390                 395                 400

Gln Thr Gly Lys Ile Ala Asp Tyr Asn Tyr Lys Leu Pro Asp Asp Phe
                405                 410                 415

Thr Gly Cys Val Ile Ala Trp Asn Ser Asn Asn Leu Asp Ser Lys Val
            420                 425                 430

Gly Gly Asn Tyr Asn Tyr Leu Tyr Arg Leu Phe Arg Lys Ser Asn Leu
        435                 440                 445

Lys Pro Phe Glu Arg Asp Ile Ser Thr Glu Ile Tyr Gln Ala Gly Ser
    450                 455                 460

Thr Pro Cys Asn Gly Val Glu Gly Phe Asn Cys Tyr Phe Pro Leu Gln
465                 470                 475                 480

Ser Tyr Gly Phe Gln Pro Thr Asn Gly Val Gly Tyr Gln Pro Tyr Arg
                485                 490                 495

Val Val Val Leu Ser Phe Glu Leu Leu His Ala Pro Ala Thr Val Cys
            500                 505                 510

Gly Pro Lys Lys Ser Thr Asn Leu Val Lys Asn Lys Cys Val Asn Phe
        515                 520                 525

Asn Phe Asn Gly Leu Thr Gly Thr Gly Val Leu Thr Glu Ser Asn Lys
    530                 535                 540

Lys Phe Leu Pro Phe Gln Gln Phe Gly Arg Asp Ile Ala Asp Thr Thr
545                 550                 555                 560

Asp Ala Val Arg Asp Pro Gln Thr Leu Glu Ile Leu Asp Ile Thr Pro
                565                 570                 575

Cys Ser Phe Gly Gly Val Ser Val Ile Thr Pro Gly Thr Asn Thr Ser
            580                 585                 590

Asn Gln Val Ala Val Leu Tyr Gln Asp Val Asn Cys Thr Glu Val Pro
        595                 600                 605

Val Ala Ile His Ala Asp Gln Leu Thr Pro Thr Trp Arg Val Tyr Ser
    610                 615                 620

Thr Gly Ser Asn Val Phe Gln Thr Arg Ala Gly Cys Leu Ile Gly Ala
625                 630                 635                 640

Glu His Val Asn Asn Ser Tyr Glu Cys Asp Ile Pro Ile Gly Ala Gly
                645                 650                 655

Ile Cys Ala Ser Tyr Gln Thr Gln Thr Asn Ser Pro Gln Gln Ala Gln
            660                 665                 670

Ser Val Ala Ser Gln Ser Ile Ile Ala Tyr Thr Met Ser Leu Gly Ala
        675                 680                 685

Glu Asn Ser Val Ala Tyr Ser Asn Asn Ser Ile Ala Ile Pro Thr Asn
    690                 695                 700

Phe Thr Ile Ser Val Thr Thr Glu Ile Leu Pro Val Ser Met Thr Lys
705                 710                 715                 720

Thr Ser Val Asp Cys Thr Met Tyr Ile Cys Gly Asp Ser Thr Glu Cys
                725                 730                 735

Ser Asn Leu Leu Leu Gln Tyr Gly Ser Phe Cys Thr Gln Leu Asn Arg
            740                 745                 750

Ala Leu Thr Gly Ile Ala Val Glu Gln Asp Lys Asn Thr Gln Glu Val
        755                 760                 765

Phe Ala Gln Val Lys Gln Ile Tyr Lys Thr Pro Pro Ile Lys Asp Phe
    770                 775                 780
```

-continued

```
Gly Gly Phe Asn Phe Ser Gln Ile Leu Pro Asp Pro Ser Lys Pro Ser
785                 790                 795                 800

Lys Arg Ser Phe Ile Glu Asp Leu Leu Phe Asn Lys Val Thr Leu Ala
                805                 810                 815

Asp Ala Gly Phe Ile Lys Gln Tyr Gly Asp Cys Leu Gly Asp Ile Ala
            820                 825                 830

Ala Arg Asp Leu Ile Cys Ala Gln Lys Phe Asn Gly Leu Thr Val Leu
        835                 840                 845

Pro Pro Leu Leu Thr Asp Glu Met Ile Ala Gln Tyr Thr Ser Ala Leu
    850                 855                 860

Leu Ala Gly Thr Ile Thr Ser Gly Trp Thr Phe Gly Ala Gly Ala Ala
865                 870                 875                 880

Leu Gln Ile Pro Phe Ala Met Gln Met Ala Tyr Arg Phe Asn Gly Ile
                885                 890                 895

Gly Val Thr Gln Asn Val Leu Tyr Glu Asn Gln Lys Leu Ile Ala Asn
            900                 905                 910

Gln Phe Asn Ser Ala Ile Gly Lys Ile Gln Asp Ser Leu Ser Ser Thr
        915                 920                 925

Ala Ser Ala Leu Gly Lys Leu Gln Asp Val Val Asn Gln Asn Ala Gln
    930                 935                 940

Ala Leu Asn Thr Leu Val Lys Gln Leu Ser Ser Asn Phe Gly Ala Ile
945                 950                 955                 960

Ser Ser Val Leu Asn Asp Ile Leu Ser Arg Leu Asp Lys Val Glu Ala
                965                 970                 975

Glu Val Gln Ile Asp Arg Leu Ile Thr Gly Arg Leu Gln Ser Leu Gln
            980                 985                 990

Thr Tyr Val Thr Gln Gln Leu Ile  Arg Ala Ala Glu Ile  Arg Ala Ser
        995                 1000                1005

Ala Asn  Leu Ala Ala Thr Lys  Met Ser Glu Cys Val  Leu Gly Gln
    1010                 1015                 1020

Ser Lys  Arg Val Asp Phe Cys  Gly Lys Gly Tyr His  Leu Met Ser
    1025                 1030                 1035

Phe Pro  Gln Ser Ala Pro His  Gly Val Val Phe Leu  His Val Thr
    1040                 1045                 1050

Tyr Val  Pro Ala Gln Glu Lys  Asn Phe Thr Thr Ala  Pro Ala Ile
    1055                 1060                 1065

Cys His  Asp Gly Lys Ala His  Phe Pro Arg Glu Gly  Val Phe Val
    1070                 1075                 1080

Ser Asn  Gly Thr His Trp Phe  Val Thr Gln Arg Asn  Phe Tyr Glu
    1085                 1090                 1095

Pro Gln  Ile Ile Thr Thr Asp  Asn Thr Phe Val Ser  Gly Asn Cys
    1100                 1105                 1110

Asp Val  Val Ile Gly Ile Val  Asn Asn Thr Val Tyr  Asp Pro Leu
    1115                 1120                 1125

Gln Pro  Glu Leu Asp Ser Phe  Lys Glu Glu Leu Asp  Lys Tyr Phe
    1130                 1135                 1140

Lys Asn  His Thr Ser Pro Asp  Val Asp Leu Gly Asp  Ile Ser Gly
    1145                 1150                 1155

Ile Asn  Ala Ser Val Val Asn  Ile Gln Lys Glu Ile  Asp Arg Leu
    1160                 1165                 1170

Asn Glu  Val Ala Lys Asn Leu  Asn Glu Ser Leu Ile  Asp Leu Gln
    1175                 1180                 1185
```

-continued

```
Glu Leu  Gly Lys Tyr Glu Gln  Tyr Ile Lys Trp Pro  Trp Tyr Ile
    1190                 1195                 1200

Trp Leu  Gly Phe Ile Ala Gly  Leu Ile Ala Ile Val  Met Val Thr
    1205                 1210                 1215

Ile Met  Leu Cys Cys Met Thr  Ser Cys Cys Ser Cys  Leu Lys Gly
    1220                 1225                 1230

Cys Cys  Ser Cys Gly Ser Cys  Cys Lys Phe Asp Glu  Asp Asp Ser
    1235                 1240                 1245

Glu Pro  Val Leu Lys Gly Val  Lys Leu His Tyr Thr
    1250                 1255                 1260


<210> SEQ ID NO 5
<211> LENGTH: 13
<212> TYPE: PRT
<213> ORGANISM: Artificial Sequence
<220> FEATURE:
<223> OTHER INFORMATION: SIGNAL PEPTIDE

<400> SEQUENCE: 5

Met Phe Val Phe Leu Val Leu Leu Pro Leu Val Ser Ser
1               5                   10


<210> SEQ ID NO 6
<211> LENGTH: 4
<212> TYPE: PRT
<213> ORGANISM: Artificial Sequence
<220> FEATURE:
<223> OTHER INFORMATION: RECOMBINANT FURIN CLEAVAGE SITE

<400> SEQUENCE: 6

Arg Arg Ala Arg
1


<210> SEQ ID NO 7
<211> LENGTH: 4
<212> TYPE: PRT
<213> ORGANISM: Artificial Sequence
<220> FEATURE:
<223> OTHER INFORMATION: RECOMBINANT FURIN CLEAVAGE SITE

<400> SEQUENCE: 7

Gln Gln Ala Gln
1


<210> SEQ ID NO 8
<211> LENGTH: 4
<212> TYPE: PRT
<213> ORGANISM: Artificial Sequence
<220> FEATURE:
<223> OTHER INFORMATION: RECOMBINANT FURIN CLEAVAGE SITE

<400> SEQUENCE: 8

Gln Arg Ala Arg
1


<210> SEQ ID NO 9
<211> LENGTH: 4
<212> TYPE: PRT
<213> ORGANISM: Artificial Sequence
<220> FEATURE:
<223> OTHER INFORMATION: RECOMBINANT FURIN CLEAVAGE SITE

<400> SEQUENCE: 9

Arg Gln Ala Arg
1
```

-continued

<210> SEQ ID NO 10
<211> LENGTH: 4
<212> TYPE: PRT
<213> ORGANISM: Artificial Sequence
<220> FEATURE:
<223> OTHER INFORMATION: RECOMBINANT FURIN CLEAVAGE SITE

<400> SEQUENCE: 10

Arg Arg Ala Gln
1

<210> SEQ ID NO 11
<211> LENGTH: 4
<212> TYPE: PRT
<213> ORGANISM: Artificial Sequence
<220> FEATURE:
<223> OTHER INFORMATION: RECOMBINANT FURIN CLEAVAGE SITE

<400> SEQUENCE: 11

Gln Gln Ala Arg
1

<210> SEQ ID NO 12
<211> LENGTH: 4
<212> TYPE: PRT
<213> ORGANISM: Artificial Sequence
<220> FEATURE:
<223> OTHER INFORMATION: RECOMBINANT FURIN CLEAVAGE SITE

<400> SEQUENCE: 12

Arg Gln Ala Gln
1

<210> SEQ ID NO 13
<211> LENGTH: 4
<212> TYPE: PRT
<213> ORGANISM: Artificial Sequence
<220> FEATURE:
<223> OTHER INFORMATION: RECOMBINANT FURIN CLEAVAGE SITE

<400> SEQUENCE: 13

Gln Arg Ala Gln
1

<210> SEQ ID NO 14
<211> LENGTH: 4
<212> TYPE: PRT
<213> ORGANISM: Artificial Sequence
<220> FEATURE:
<223> OTHER INFORMATION: RECOMBINANT FURIN CLEAVAGE SITE

<400> SEQUENCE: 14

Asn Asn Ala Asn
1

<210> SEQ ID NO 15
<211> LENGTH: 4
<212> TYPE: PRT
<213> ORGANISM: Artificial Sequence
<220> FEATURE:
<223> OTHER INFORMATION: RECOMBINANT FURIN CLEAVAGE SITE

<400> SEQUENCE: 15

Asn Arg Ala Arg
1

-continued

<210> SEQ ID NO 16
<211> LENGTH: 4
<212> TYPE: PRT
<213> ORGANISM: Artificial Sequence
<220> FEATURE:
<223> OTHER INFORMATION: RECOMBINANT FURIN CLEAVAGE SITE

<400> SEQUENCE: 16

Arg Asn Ala Arg
1

<210> SEQ ID NO 17
<211> LENGTH: 4
<212> TYPE: PRT
<213> ORGANISM: Artificial Sequence
<220> FEATURE:
<223> OTHER INFORMATION: RECOMBINANT FURIN CLEAVAGE SITE

<400> SEQUENCE: 17

Arg Arg Ala Asn
1

<210> SEQ ID NO 18
<211> LENGTH: 4
<212> TYPE: PRT
<213> ORGANISM: Artificial Sequence
<220> FEATURE:
<223> OTHER INFORMATION: RECOMBINANT FURIN CLEAVAGE SITE

<400> SEQUENCE: 18

Asn Asn Ala Arg
1

<210> SEQ ID NO 19
<211> LENGTH: 4
<212> TYPE: PRT
<213> ORGANISM: Artificial Sequence
<220> FEATURE:
<223> OTHER INFORMATION: RECOMBINANT FURIN CLEAVAGE SITE

<400> SEQUENCE: 19

Arg Asn Ala Asn
1

<210> SEQ ID NO 20
<211> LENGTH: 4
<212> TYPE: PRT
<213> ORGANISM: Artificial Sequence
<220> FEATURE:
<223> OTHER INFORMATION: RECOMBINANT FURIN CLEAVAGE SITE

<400> SEQUENCE: 20

Asn Arg Ala Asn
1

<210> SEQ ID NO 21
<211> LENGTH: 4
<212> TYPE: PRT
<213> ORGANISM: Artificial Sequence
<220> FEATURE:
<223> OTHER INFORMATION: RECOMBINANT FURIN CLEAVAGE SITE

<400> SEQUENCE: 21

Ala Ala Ala Ala
1

<210> SEQ ID NO 22
<211> LENGTH: 4
<212> TYPE: PRT
<213> ORGANISM: Artificial Sequence
<220> FEATURE:
<223> OTHER INFORMATION: RECOMBINANT FURIN CLEAVAGE SITE

<400> SEQUENCE: 22

Ala Arg Ala Arg
1

<210> SEQ ID NO 23
<211> LENGTH: 4
<212> TYPE: PRT
<213> ORGANISM: Artificial Sequence
<220> FEATURE:
<223> OTHER INFORMATION: RECOMBINANT FURIN CLEAVAGE SITE

<400> SEQUENCE: 23

Arg Ala Ala Arg
1

<210> SEQ ID NO 24
<211> LENGTH: 4
<212> TYPE: PRT
<213> ORGANISM: Artificial Sequence
<220> FEATURE:
<223> OTHER INFORMATION: RECOMBINANT FURIN CLEAVAGE SITE

<400> SEQUENCE: 24

Arg Arg Ala Ala
1

<210> SEQ ID NO 25
<211> LENGTH: 4
<212> TYPE: PRT
<213> ORGANISM: Artificial Sequence
<220> FEATURE:
<223> OTHER INFORMATION: RECOMBINANT FURIN CLEAVAGE SITE

<400> SEQUENCE: 25

Ala Ala Ala Arg
1

<210> SEQ ID NO 26
<211> LENGTH: 4
<212> TYPE: PRT
<213> ORGANISM: Artificial Sequence
<220> FEATURE:
<223> OTHER INFORMATION: RECOMBINANT FURIN CLEAVAGE SITE

<400> SEQUENCE: 26

Arg Ala Ala Ala
1

<210> SEQ ID NO 27
<211> LENGTH: 4
<212> TYPE: PRT
<213> ORGANISM: Artificial Sequence
<220> FEATURE:
<223> OTHER INFORMATION: RECOMBINANT FURIN CLEAVAGE SITE

<400> SEQUENCE: 27

Ala Arg Ala Ala
1

<210> SEQ ID NO 28

<211> LENGTH: 4
<212> TYPE: PRT
<213> ORGANISM: Artificial Sequence
<220> FEATURE:
<223> OTHER INFORMATION: RECOMBINANT FURIN CLEAVAGE SITE

<400> SEQUENCE: 28

Gly Gly Ala Gly
1

<210> SEQ ID NO 29
<211> LENGTH: 4
<212> TYPE: PRT
<213> ORGANISM: Artificial Sequence
<220> FEATURE:
<223> OTHER INFORMATION: RECOMBINANT FURIN CLEAVAGE SITE

<400> SEQUENCE: 29

Gly Arg Ala Arg
1

<210> SEQ ID NO 30
<211> LENGTH: 4
<212> TYPE: PRT
<213> ORGANISM: Artificial Sequence
<220> FEATURE:
<223> OTHER INFORMATION: RECOMBINANT FURIN CLEAVAGE SITE

<400> SEQUENCE: 30

Arg Gly Ala Arg
1

<210> SEQ ID NO 31
<211> LENGTH: 4
<212> TYPE: PRT
<213> ORGANISM: Artificial Sequence
<220> FEATURE:
<223> OTHER INFORMATION: RECOMBINANT FURIN CLEAVAGE SITE

<400> SEQUENCE: 31

Arg Arg Ala Gly
1

<210> SEQ ID NO 32
<211> LENGTH: 4
<212> TYPE: PRT
<213> ORGANISM: Artificial Sequence
<220> FEATURE:
<223> OTHER INFORMATION: RECOMBINANT FURIN CLEAVAGE SITE

<400> SEQUENCE: 32

Gly Gly Ala Arg
1

<210> SEQ ID NO 33
<211> LENGTH: 4
<212> TYPE: PRT
<213> ORGANISM: Artificial Sequence
<220> FEATURE:
<223> OTHER INFORMATION: RECOMBINANT FURIN CLEAVAGE SITE

<400> SEQUENCE: 33

Arg Gly Ala Gly
1

<210> SEQ ID NO 34
<211> LENGTH: 4

-continued

<212> TYPE: PRT
<213> ORGANISM: Artificial Sequence
<220> FEATURE:
<223> OTHER INFORMATION: RECOMBINANT FURIN CLEAVAGE SITE

<400> SEQUENCE: 34

Gly Arg Ala Gly
1

<210> SEQ ID NO 35
<211> LENGTH: 3819
<212> TYPE: DNA
<213> ORGANISM: Artificial Sequence
<220> FEATURE:
<223> OTHER INFORMATION: RECOMBINANT SPIKE PROTEIN

<400> SEQUENCE: 35
atgttcgtct tcctggtgct gctgcccctg gtgtccagcc agtgcgtgaa cctgaccact 60
aggactcagc tgcctcccgc ttacaccaac tcattcactc gcggtgtgta ctaccctgac 120
aaggtcttcc gttcttcagt gctgcactca actcaggacc tgttcctgcc cttcttctcc 180
aacgtcacct ggttccacgc catccacgtg tccggcacca acggcactaa gcgcttcgac 240
aacccagtgc tgcctttcaa cgacggtgtc tacttcgctt caaccgagaa gtccaacatc 300
atccgtggat ggatcttcgg caccactctg gacagcaaga ctcagtctct gctgatcgtc 360
aacaacgcca ccaacgtggt catcaaggtc tgcgaattcc agttctgcaa cgacccattc 420
ctgggcgtct actaccacaa gaacaacaag tcatggatgg agtccgaatt ccgcgtctac 480
tccagcgcta acaactgcac tttcgagtac gtgtcccagc ctttcctgat ggacctggaa 540
ggaaagcagg gtaacttcaa gaacctgagg gagttcgtgt tcaagaacat cgacggatac 600
ttcaagattt acagcaagca caccccaatc aacctggtgc gcgacctgcc tcagggtttc 660
tctgctctgg agccactggt ggacctgcct atcggcatca acatcacccg cttccagact 720
ctgctggctc tgcaccgttc ctacctgact ccaggcgact catcttctgg atggactgct 780
ggagctgctg cttactacgt gggctacctg cagcctcgca ccttcctgct gaagtacaac 840
gaaaacggaa ccatcactga cgccgtcgac tgcgctctgg accctctgtc agaaaccaag 900
tgcactctga agtccttcac cgtggagaag ggcatctacc agacttcaaa cttcagggtg 960
cagcccaccg aatccatcgt cagattccct aacatcacta acctgtgccc cttcggagag 1020
gtcttcaacg ccacccgctt cgcttccgtg tacgcctgga acaggaagag aatctcaaac 1080
tgcgtcgctg actactccgt gctgtacaac tcagcctcct tcagcacctt caagtgctac 1140
ggcgtgtcac caactaagct gaacgacctg tgcttcacca acgtctacgc cgactccttc 1200
gtgatcaggg gagacgaggt cagacagatc gctcctggcc agactggaaa gatcgccgac 1260
tacaactaca agctgcccga cgacttcacc ggttgcgtca tcgcttggaa cagcaacaac 1320
ctggactcta aagtgggtgg caactacaac tacctgtacc gcctgttccg taagtcaaac 1380
ctgaagccat tcgagaggga catcagcact gaaatctacc aggccggatc taccccttgc 1440
aacggtgtcg agggcttcaa ctgctacttc cccctgcagt cctacggttt ccagccaact 1500
aacggtgtgg gctaccagcc ttacagagtg gtcgtgctga gcttcgaact gctccacgct 1560
cctgctactg tgtgcggtcc aaagaagtct accaacctgg tcaagaacaa gtgcgtgaac 1620
ttcaacttca acggcctgac cggaactggt gtcctgaccg agagcaacaa gaagttcctg 1680
cccttccagc agttcggaag ggacatcgct gacaccactg acgctgtgcg cgaccctcag 1740
accctggaaa tcctggacat cactccatgc tcattcggag gtgtctccgt gatcacccct 1800

```
ggcaccaaca cttctaacca ggtcgctgtg ctgtaccagg acgtcaactg caccgaggtc   1860
cctgtggcca tccacgctga ccagctgacc cccacttggc gcgtgtactc caccggcagc   1920
aacgtgttcc agactcgtgc tggttgcctg atcggcgccg agcacgtgaa caacagctac   1980
gaatgcgaca tccccatcgg cgctggaatc tgcgcctctt accagaccca gactaacagc   2040
ccacgcaggg ctcgctctgt ggcctctcag tcaatcatcg cttacaccat gtcactgggc   2100
gctgaaaact ccgtggccta ctctaacaac tcaatcgcca tccccaccaa cttcactatc   2160
agcgtgacca ctgagatcct gccagtcagc atgaccaaga cttctgtgga ctgcactatg   2220
tacatctgcg gagacagcac cgaatgctct aacctgctgc tgcagtacgg ctctttctgc   2280
acccagctga accgtgctct gactggaatc gccgtggagc aggacaagaa cactcaggaa   2340
gtcttcgctc aggtgaagca aatctacaag accccaccta tcaaggactt cggcggattc   2400
aacttctccc agatcctgcc tgacccctcc aagccaagca agcgctcttt catcgaggac   2460
ctgctgttca acaaggtcac tctggccgac gctggattca tcaagcagta cggagactgc   2520
ctgggtgaca tcgccgctcg tgacctgatc tgcgctcaga agttcaacgg tctgaccgtg   2580
ctgcccccac tgctgactga cgaaatgatc gcccagtaca ctagcgccct gctggctgga   2640
accatcactt ctggttggac cttcggtgct ggcgccgctc tgcagatccc tttcgctatg   2700
cagatggcct accgtttcaa cggaatcggt gtcacccaga acgtgctgta cgagaaccag   2760
aagctgatcg ctaaccagtt caactcagcc atcggaaaga tccaggacag cctgagctct   2820
actgcctctg ctctgggcaa gctgcaggac gtcgtgaacc agaacgccca ggctctgaac   2880
accctggtca agcagctgtc atccaacttc ggtgctatca gctctgtgct gaacgacatc   2940
ctgtcccgcc tggacaaggt cgaggccgaa gtgcagatcg accgcctgat cactggccgt   3000
ctgcagtcac tgcagaccta cgtgactcag cagctgatca gggccgctga aatcagagcc   3060
tccgctaacc tggccgctac caagatgagc gagtgcgtcc tgggtcaatc taagcgtgtg   3120
gacttctgcg gcaagggata ccacctgatg tcattccctc agtctgctcc ccacggtgtg   3180
gtgttcctgc acgtcaccta cgtgccagcc caggagaaga acttcaccac tgcccctgct   3240
atctgccacg acggcaaggc tcacttcccc agggaaggtg tcttcgtgag caacggcacc   3300
cactggttcg tcactcagag aaacttctac gagccacaga tcatcaccac tgacaacact   3360
ttcgtgtctg gaaactgcga cgtggtcatc ggtatcgtca acaacaccgt gtacgacccc   3420
ctgcagccag agctggactc attcaaggag gaactggaca agtacttcaa gaaccacacc   3480
tcccctgacg tcgacctggg cgacatctca ggaatcaacg cttccgtcgt gaacatccag   3540
aaggagatcg accgcctgaa cgaagtggcc aagaacctga acgaaagcct gatcgacctg   3600
caggagctgg gcaagtacga acagtacatc aagtggcctt ggtacatctg gctgggtttc   3660
atcgctggcc tcatcgctat cgtgatggtg accatcatgc tgtgctgcat gacttcatgc   3720
tgctcctgcc tgaagggctg ctgcagctgc ggatcttgct gcaagttcga cgaggacgac   3780
tctgaacccg tcctgaaggg cgtgaagctg cactacacc                          3819
```

<210> SEQ ID NO 36
<211> LENGTH: 1279
<212> TYPE: PRT
<213> ORGANISM: Artificial Sequence
<220> FEATURE:
<223> OTHER INFORMATION: RECOMBINANT SPIKE PROTEIN

<400> SEQUENCE: 36

-continued

```
Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
```

-continued

```
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845
```

-continued

```
Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
            980                 985                 990

Ile Asp Arg Leu Ile Thr Gly Arg  Leu Gln Ser Leu Gln  Thr Tyr Val
        995                 1000                1005

Thr Gln  Gln Leu Ile Arg Ala  Ala Glu Ile Arg Ala  Ser Ala Asn
    1010                 1015                1020

Leu Ala  Ala Thr Lys Met Ser  Glu Cys Val Leu Gly  Gln Ser Lys
    1025                 1030                1035

Arg Val  Asp Phe Cys Gly Lys  Gly Tyr His Leu Met  Ser Phe Pro
    1040                 1045                1050

Gln Ser  Ala Pro His Gly Val  Val Phe Leu His Val  Thr Tyr Val
    1055                 1060                1065

Pro Ala  Gln Glu Lys Asn Phe  Thr Thr Ala Pro Ala  Ile Cys His
    1070                 1075                1080

Asp Gly  Lys Ala His Phe Pro  Arg Glu Gly Val Phe  Val Ser Asn
    1085                 1090                1095

Gly Thr  His Trp Phe Val Thr  Gln Arg Asn Phe Tyr  Glu Pro Gln
    1100                 1105                1110

Ile Ile  Thr Thr Asp Asn Thr  Phe Val Ser Gly Asn  Cys Asp Val
    1115                 1120                1125

Val Ile  Gly Ile Val Asn Asn  Thr Val Tyr Asp Pro  Leu Gln Pro
    1130                 1135                1140

Glu Leu  Asp Ser Phe Lys Glu  Glu Leu Asp Lys Tyr  Phe Lys Asn
    1145                 1150                1155

His Thr  Ser Pro Asp Val Asp  Leu Gly Asp Ile Ser  Gly Ile Asn
    1160                 1165                1170

Ala Ser  Val Val Asn Ile Gln  Lys Glu Ile Asp Arg  Leu Asn Glu
    1175                 1180                1185

Val Ala  Lys Asn Leu Asn Glu  Ser Leu Ile Asp Leu  Gln Glu Leu
    1190                 1195                1200

Gly Lys  Tyr Glu Gln Tyr Ile  Lys Trp Pro Trp Tyr  Ile Trp Leu
    1205                 1210                1215

Gly Phe  Ile Ala Gly Leu Ile  Ala Ile Val Met Val  Thr Ile Met
    1220                 1225                1230

Leu Cys  Cys Met Thr Ser Cys  Cys Ser Cys Leu Lys  Gly Cys Cys
    1235                 1240                1245
```

-continued

```
Ser Cys  Gly Ser Cys Cys Lys  Phe Asp Glu Asp Asp  Ser Glu Pro
    1250                 1255                 1260

Val Leu  Lys Gly Val Lys Leu  His Tyr Thr His His  His His His
    1265                 1270                 1275

His
```

<210> SEQ ID NO 37
<211> LENGTH: 3837
<212> TYPE: DNA
<213> ORGANISM: Artificial Sequence
<220> FEATURE:
<223> OTHER INFORMATION: RECOMBINANT SPIKE PROTEIN

<400> SEQUENCE: 37

```
atgttcgtct tcctggtgct gctgcccctg gtgtccagcc agtgcgtgaa cctgaccact     60

aggactcagc tgcctcccgc ttacaccaac tcattcactc gcggtgtgta ctaccctgac    120

aaggtcttcc gttcttcagt gctgcactca actcaggacc tgttcctgcc cttcttctcc    180

aacgtcacct ggttccacgc catccacgtg tccggcacca acggcactaa gcgcttcgac    240

aacccagtgc tgcctttcaa cgacggtgtc tacttcgctt caaccgagaa gtccaacatc    300

atccgtggat ggatcttcgg caccactctg gacagcaaga ctcagtctct gctgatcgtc    360

aacaacgcca ccaacgtggt catcaaggtc tgcgaattcc agttctgcaa cgacccattc    420

ctgggcgtct actaccacaa gaacaacaag tcatggatgg agtccgaatt ccgcgtctac    480

tccagcgcta acaactgcac tttcgagtac gtgtcccagc ctttcctgat ggacctggaa    540

ggaaagcagg gtaacttcaa gaacctgagg gagttcgtgt tcaagaacat cgacggatac    600

ttcaagattt acagcaagca caccccaatc aacctggtgc gcgacctgcc tcagggtttc    660

tctgctctgg agccactggt ggacctgcct atcggcatca acatcacccg cttccagact    720

ctgctggctc tgcaccgttc ctacctgact ccaggcgact catcttctgg atggactgct    780

ggagctgctg cttactacgt gggctacctg cagcctcgca ccttcctgct gaagtacaac    840

gaaaacggaa ccatcactga cgccgtcgac tgcgctctgg accctctgtc agaaaccaag    900

tgcactctga agtccttcac cgtggagaag ggcatctacc agacttcaaa cttcagggtg    960

cagcccaccg aatccatcgt cagattccct aacatcacta acctgtgccc cttcggagag   1020

gtcttcaacg ccacccgctt cgcttccgtg tacgcctgga acaggaagag aatctcaaac   1080

tgcgtcgctg actactccgt gctgtacaac tcagcctcct tcagcacctt caagtgctac   1140

ggcgtgtcac caactaagct gaacgacctg tgcttcacca acgtctacgc cgactccttc   1200

gtgatcaggg gagacgaggt cagacagatc gctcctggcc agactggaaa gatcgccgac   1260

tacaactaca agctgcccga cgacttcacc ggttgcgtca tcgcttggaa cagcaacaac   1320

ctggactcta aagtgggtgg caactacaac tacctgtacc gcctgttccg taagtcaaac   1380

ctgaagccat tcgagaggga catcagcact gaaatctacc aggccggatc taccccttgc   1440

aacggtgtcg agggcttcaa ctgctacttc cccctgcagt cctacggttt ccagccaact   1500

aacggtgtgg gctaccagcc ttacagagtg gtcgtgctga gcttcgaact gctccacgct   1560

cctgctactg tgtgcggtcc aaagaagtct accaacctgg tcaagaacaa gtgcgtgaac   1620

ttcaacttca acggcctgac cggaactggt gtcctgaccg agagcaacaa gaagttcctg   1680

cccttccagc agttcggaag ggacatcgct gacaccactg acgctgtgcg cgaccctcag   1740

accctggaaa tcctggacat cactccatgc tcattcggag gtgtctccgt gatcacccct   1800

ggcaccaaca cttctaacca ggtcgctgtg ctgtaccagg acgtcaactg caccgaggtc   1860
```

```
cctgtggcca tccacgctga ccagctgacc cccacttggc gcgtgtactc caccggcagc   1920
aacgtgttcc agactcgtgc tggttgcctg atcggcgccg agcacgtgaa caacagctac   1980
gaatgcgaca tccccatcgg cgctggaatc tgcgcctctt accagaccca gactaacagc   2040
ccacgcaggg ctcgctctgt ggcctctcag tcaatcatcg cttacaccat gtcactgggc   2100
gctgaaaact ccgtggccta ctctaacaac tcaatcgcca tccccaccaa cttcactatc   2160
agcgtgacca ctgagatcct gccagtcagc atgaccaaga cttctgtgga ctgcactatg   2220
tacatctgcg gagacagcac cgaatgctct aacctgctgc tgcagtacgg ctctttctgc   2280
acccagctga accgtgctct gactggaatc gccgtggagc aggacaagaa cactcaggaa   2340
gtcttcgctc aggtgaagca aatctacaag accccaccta tcaaggactt cggcggattc   2400
aacttctccc agatcctgcc tgacccctcc aagccaagca agcgctcttt catcgaggac   2460
ctgctgttca acaaggtcac tctggccgac gctggattca tcaagcagta cggagactgc   2520
ctgggtgaca tcgccgctcg tgacctgatc tgcgctcaga agttcaacgg tctgaccgtg   2580
ctgcccccac tgctgactga cgaaatgatc gcccagtaca ctagcgccct gctggctgga   2640
accatcactt ctggttggac cttcggtgct ggcgccgctc tgcagatccc tttcgctatg   2700
cagatggcct accgtttcaa cggaatcggt gtcacccaga acgtgctgta cgagaaccag   2760
aagctgatcg ctaaccagtt caactcagcc atcggaaaga tccaggacag cctgagctct   2820
actgcctctg ctctgggcaa gctgcaggac gtcgtgaacc agaacgccca ggctctgaac   2880
accctggtca agcagctgtc atccaacttc ggtgctatca gctctgtgct gaacgacatc   2940
ctgtcccgcc tggacaaggt cgaggccgaa gtgcagatcg accgcctgat cactggccgt   3000
ctgcagtcac tgcagaccta cgtgactcag cagctgatca gggccgctga aatcagagcc   3060
tccgctaacc tggccgctac caagatgagc gagtgcgtcc tgggtcaatc taagcgtgtg   3120
gacttctgcg gcaagggata ccacctgatg tcattccctc agtctgctcc ccacggtgtg   3180
gtgttcctgc acgtcaccta cgtgccagcc caggagaaga acttcaccac tgcccctgct   3240
atctgccacg acggcaaggc tcacttcccc agggaaggtg tcttcgtgag caacggcacc   3300
cactggttcg tcactcagag aaacttctac gagccacaga tcatcaccac tgacaacact   3360
ttcgtgtctg gaaactgcga cgtggtcatc ggtatcgtca acaacaccgt gtacgacccc   3420
ctgcagccag agctggactc attcaaggag gaactggaca agtacttcaa gaaccacacc   3480
tcccctgacg tcgacctggg cgacatctca ggaatcaacg cttccgtcgt gaacatccag   3540
aaggagatcg accgcctgaa cgaagtggcc aagaacctga acgaaagcct gatcgacctg   3600
caggagctgg gcaagtacga acagtacatc aagtggcctt ggtacatctg gctgggtttc   3660
atcgctggcc tcatcgctat cgtgatggtg accatcatgc tgtgctgcat gacttcatgc   3720
tgctcctgcc tgaagggctg ctgcagctgc ggatcttgct gcaagttcga cgaggacgac   3780
tctgaacccg tcctgaaggg cgtgaagctg cactacaccc accaccacca ccaccac      3837
```

<210> SEQ ID NO 38
<211> LENGTH: 1266
<212> TYPE: PRT
<213> ORGANISM: Artificial Sequence
<220> FEATURE:
<223> OTHER INFORMATION: RECOMBINANT SPIKE PROTEIN

<400> SEQUENCE: 38

```
Gln Cys Val Asn Leu Thr Thr Arg Thr Gln Leu Pro Pro Ala Tyr Thr
1               5                   10                  15
```

-continued

```
Asn Ser Phe Thr Arg Gly Val Tyr Tyr Pro Asp Lys Val Phe Arg Ser
            20                  25                  30

Ser Val Leu His Ser Thr Gln Asp Leu Phe Leu Pro Phe Phe Ser Asn
        35                  40                  45

Val Thr Trp Phe His Ala Ile His Val Ser Gly Thr Asn Gly Thr Lys
    50                  55                  60

Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                85                  90                  95

Leu Asp Ser Lys Thr Gln Ser Leu Leu Ile Val Asn Asn Ala Thr Asn
            100                 105                 110

Val Val Ile Lys Val Cys Glu Phe Gln Phe Cys Asn Asp Pro Phe Leu
        115                 120                 125

Gly Val Tyr Tyr His Lys Asn Asn Lys Ser Trp Met Glu Ser Glu Phe
    130                 135                 140

Arg Val Tyr Ser Ser Ala Asn Asn Cys Thr Phe Glu Tyr Val Ser Gln
145                 150                 155                 160

Pro Phe Leu Met Asp Leu Glu Gly Lys Gln Gly Asn Phe Lys Asn Leu
                165                 170                 175

Arg Glu Phe Val Phe Lys Asn Ile Asp Gly Tyr Phe Lys Ile Tyr Ser
            180                 185                 190

Lys His Thr Pro Ile Asn Leu Val Arg Asp Leu Pro Gln Gly Phe Ser
        195                 200                 205

Ala Leu Glu Pro Leu Val Asp Leu Pro Ile Gly Ile Asn Ile Thr Arg
    210                 215                 220

Phe Gln Thr Leu Leu Ala Leu His Arg Ser Tyr Leu Thr Pro Gly Asp
225                 230                 235                 240

Ser Ser Ser Gly Trp Thr Ala Gly Ala Ala Ala Tyr Tyr Val Gly Tyr
                245                 250                 255

Leu Gln Pro Arg Thr Phe Leu Leu Lys Tyr Asn Glu Asn Gly Thr Ile
            260                 265                 270

Thr Asp Ala Val Asp Cys Ala Leu Asp Pro Leu Ser Glu Thr Lys Cys
        275                 280                 285

Thr Leu Lys Ser Phe Thr Val Glu Lys Gly Ile Tyr Gln Thr Ser Asn
    290                 295                 300

Phe Arg Val Gln Pro Thr Glu Ser Ile Val Arg Phe Pro Asn Ile Thr
305                 310                 315                 320

Asn Leu Cys Pro Phe Gly Glu Val Phe Asn Ala Thr Arg Phe Ala Ser
                325                 330                 335

Val Tyr Ala Trp Asn Arg Lys Arg Ile Ser Asn Cys Val Ala Asp Tyr
            340                 345                 350

Ser Val Leu Tyr Asn Ser Ala Ser Phe Ser Thr Phe Lys Cys Tyr Gly
        355                 360                 365

Val Ser Pro Thr Lys Leu Asn Asp Leu Cys Phe Thr Asn Val Tyr Ala
    370                 375                 380

Asp Ser Phe Val Ile Arg Gly Asp Glu Val Arg Gln Ile Ala Pro Gly
385                 390                 395                 400

Gln Thr Gly Lys Ile Ala Asp Tyr Asn Tyr Lys Leu Pro Asp Asp Phe
                405                 410                 415

Thr Gly Cys Val Ile Ala Trp Asn Ser Asn Asn Leu Asp Ser Lys Val
            420                 425                 430
```

-continued

```
Gly Gly Asn Tyr Asn Tyr Leu Tyr Arg Leu Phe Arg Lys Ser Asn Leu
        435                 440                 445

Lys Pro Phe Glu Arg Asp Ile Ser Thr Glu Ile Tyr Gln Ala Gly Ser
    450                 455                 460

Thr Pro Cys Asn Gly Val Glu Gly Phe Asn Cys Tyr Phe Pro Leu Gln
465                 470                 475                 480

Ser Tyr Gly Phe Gln Pro Thr Asn Gly Val Gly Tyr Gln Pro Tyr Arg
                485                 490                 495

Val Val Val Leu Ser Phe Glu Leu Leu His Ala Pro Ala Thr Val Cys
            500                 505                 510

Gly Pro Lys Lys Ser Thr Asn Leu Val Lys Asn Lys Cys Val Asn Phe
        515                 520                 525

Asn Phe Asn Gly Leu Thr Gly Thr Gly Val Leu Thr Glu Ser Asn Lys
    530                 535                 540

Lys Phe Leu Pro Phe Gln Gln Phe Gly Arg Asp Ile Ala Asp Thr Thr
545                 550                 555                 560

Asp Ala Val Arg Asp Pro Gln Thr Leu Glu Ile Leu Asp Ile Thr Pro
                565                 570                 575

Cys Ser Phe Gly Gly Val Ser Val Ile Thr Pro Gly Thr Asn Thr Ser
            580                 585                 590

Asn Gln Val Ala Val Leu Tyr Gln Asp Val Asn Cys Thr Glu Val Pro
        595                 600                 605

Val Ala Ile His Ala Asp Gln Leu Thr Pro Thr Trp Arg Val Tyr Ser
    610                 615                 620

Thr Gly Ser Asn Val Phe Gln Thr Arg Ala Gly Cys Leu Ile Gly Ala
625                 630                 635                 640

Glu His Val Asn Asn Ser Tyr Glu Cys Asp Ile Pro Ile Gly Ala Gly
                645                 650                 655

Ile Cys Ala Ser Tyr Gln Thr Gln Thr Asn Ser Pro Arg Arg Ala Arg
            660                 665                 670

Ser Val Ala Ser Gln Ser Ile Ile Ala Tyr Thr Met Ser Leu Gly Ala
        675                 680                 685

Glu Asn Ser Val Ala Tyr Ser Asn Asn Ser Ile Ala Ile Pro Thr Asn
    690                 695                 700

Phe Thr Ile Ser Val Thr Thr Glu Ile Leu Pro Val Ser Met Thr Lys
705                 710                 715                 720

Thr Ser Val Asp Cys Thr Met Tyr Ile Cys Gly Asp Ser Thr Glu Cys
                725                 730                 735

Ser Asn Leu Leu Leu Gln Tyr Gly Ser Phe Cys Thr Gln Leu Asn Arg
            740                 745                 750

Ala Leu Thr Gly Ile Ala Val Glu Gln Asp Lys Asn Thr Gln Glu Val
        755                 760                 765

Phe Ala Gln Val Lys Gln Ile Tyr Lys Thr Pro Pro Ile Lys Asp Phe
    770                 775                 780

Gly Gly Phe Asn Phe Ser Gln Ile Leu Pro Asp Pro Ser Lys Pro Ser
785                 790                 795                 800

Lys Arg Ser Phe Ile Glu Asp Leu Leu Phe Asn Lys Val Thr Leu Ala
                805                 810                 815

Asp Ala Gly Phe Ile Lys Gln Tyr Gly Asp Cys Leu Gly Asp Ile Ala
            820                 825                 830

Ala Arg Asp Leu Ile Cys Ala Gln Lys Phe Asn Gly Leu Thr Val Leu
        835                 840                 845

Pro Pro Leu Leu Thr Asp Glu Met Ile Ala Gln Tyr Thr Ser Ala Leu
```

-continued

```
    850                 855                 860

Leu Ala Gly Thr Ile Thr Ser Gly Trp Thr Phe Gly Ala Gly Ala Ala
865                 870                 875                 880

Leu Gln Ile Pro Phe Ala Met Gln Met Ala Tyr Arg Phe Asn Gly Ile
                885                 890                 895

Gly Val Thr Gln Asn Val Leu Tyr Glu Asn Gln Lys Leu Ile Ala Asn
            900                 905                 910

Gln Phe Asn Ser Ala Ile Gly Lys Ile Gln Asp Ser Leu Ser Ser Thr
        915                 920                 925

Ala Ser Ala Leu Gly Lys Leu Gln Asp Val Val Asn Gln Asn Ala Gln
    930                 935                 940

Ala Leu Asn Thr Leu Val Lys Gln Leu Ser Ser Asn Phe Gly Ala Ile
945                 950                 955                 960

Ser Ser Val Leu Asn Asp Ile Leu Ser Arg Leu Asp Lys Val Glu Ala
                965                 970                 975

Glu Val Gln Ile Asp Arg Leu Ile Thr Gly Arg Leu Gln Ser Leu Gln
            980                 985                 990

Thr Tyr Val Thr Gln Gln Leu Ile  Arg Ala Ala Glu Ile  Arg Ala Ser
        995                 1000                1005

Ala Asn  Leu Ala Ala Thr Lys  Met Ser Glu Cys Val  Leu Gly Gln
    1010                 1015                1020

Ser Lys  Arg Val Asp Phe Cys  Gly Lys Gly Tyr His  Leu Met Ser
    1025                 1030                1035

Phe Pro  Gln Ser Ala Pro His  Gly Val Val Phe Leu  His Val Thr
    1040                 1045                1050

Tyr Val  Pro Ala Gln Glu Lys  Asn Phe Thr Thr Ala  Pro Ala Ile
    1055                 1060                1065

Cys His  Asp Gly Lys Ala His  Phe Pro Arg Glu Gly  Val Phe Val
    1070                 1075                1080

Ser Asn  Gly Thr His Trp Phe  Val Thr Gln Arg Asn  Phe Tyr Glu
    1085                 1090                1095

Pro Gln  Ile Ile Thr Thr Asp  Asn Thr Phe Val Ser  Gly Asn Cys
    1100                 1105                1110

Asp Val  Val Ile Gly Ile Val  Asn Asn Thr Val Tyr  Asp Pro Leu
    1115                 1120                1125

Gln Pro  Glu Leu Asp Ser Phe  Lys Glu Glu Leu Asp  Lys Tyr Phe
    1130                 1135                1140

Lys Asn  His Thr Ser Pro Asp  Val Asp Leu Gly Asp  Ile Ser Gly
    1145                 1150                1155

Ile Asn  Ala Ser Val Val Asn  Ile Gln Lys Glu Ile  Asp Arg Leu
    1160                 1165                1170

Asn Glu  Val Ala Lys Asn Leu  Asn Glu Ser Leu Ile  Asp Leu Gln
    1175                 1180                1185

Glu Leu  Gly Lys Tyr Glu Gln  Tyr Ile Lys Trp Pro  Trp Tyr Ile
    1190                 1195                1200

Trp Leu  Gly Phe Ile Ala Gly  Leu Ile Ala Ile Val  Met Val Thr
    1205                 1210                1215

Ile Met  Leu Cys Cys Met Thr  Ser Cys Cys Ser Cys  Leu Lys Gly
    1220                 1225                1230

Cys Cys  Ser Cys Gly Ser Cys  Cys Lys Phe Asp Glu  Asp Asp Ser
    1235                 1240                1245

Glu Pro  Val Leu Lys Gly Val  Lys Leu His Tyr Thr  His His His
    1250                 1255                1260
```

```
His His  His
    1265


<210> SEQ ID NO 39
<211> LENGTH: 60
<212> TYPE: PRT
<213> ORGANISM: Artificial Sequence
<220> FEATURE:
<223> OTHER INFORMATION: RECOMBINANT SPIKE PROTEIN

<400> SEQUENCE: 39

Trp Tyr Ile Trp Leu Gly Phe Ile Ala Gly Leu Ile Ala Ile Val Met
1               5                   10                  15

Val Thr Ile Met Leu Cys Cys Met Thr Ser Cys Cys Ser Cys Leu Lys
            20                  25                  30

Gly Cys Cys Ser Cys Gly Ser Cys Cys Lys Phe Asp Glu Asp Asp Ser
        35                  40                  45

Glu Pro Val Leu Lys Gly Val Lys Leu His Tyr Thr
    50                  55                  60


<210> SEQ ID NO 40
<211> LENGTH: 1213
<212> TYPE: PRT
<213> ORGANISM: Artificial Sequence
<220> FEATURE:
<223> OTHER INFORMATION: RECOMBINANT SPIKE PROTEIN

<400> SEQUENCE: 40

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
```

```
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655
```

```
Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
            980                 985                 990

Ile Asp Arg Leu Ile Thr Gly Arg  Leu Gln Ser Leu Gln  Thr Tyr Val
        995                 1000                1005

Thr Gln  Gln Leu Ile Arg Ala  Ala Glu Ile Arg Ala  Ser Ala Asn
    1010                 1015                1020

Leu Ala  Ala Thr Lys Met Ser  Glu Cys Val Leu Gly  Gln Ser Lys
    1025                 1030                1035

Arg Val  Asp Phe Cys Gly Lys  Gly Tyr His Leu Met  Ser Phe Pro
    1040                 1045                1050

Gln Ser  Ala Pro His Gly Val  Val Phe Leu His Val  Thr Tyr Val
    1055                 1060                1065
```

-continued

```
Pro Ala  Gln Glu Lys Asn Phe  Thr Thr Ala Pro Ala  Ile Cys His
    1070                 1075                 1080

Asp Gly  Lys Ala His Phe Pro  Arg Glu Gly Val Phe  Val Ser Asn
    1085                 1090                 1095

Gly Thr  His Trp Phe Val Thr  Gln Arg Asn Phe Tyr  Glu Pro Gln
    1100                 1105                 1110

Ile Ile  Thr Thr Asp Asn Thr  Phe Val Ser Gly Asn  Cys Asp Val
    1115                 1120                 1125

Val Ile  Gly Ile Val Asn Asn  Thr Val Tyr Asp Pro  Leu Gln Pro
    1130                 1135                 1140

Glu Leu  Asp Ser Phe Lys Glu  Glu Leu Asp Lys Tyr  Phe Lys Asn
    1145                 1150                 1155

His Thr  Ser Pro Asp Val Asp  Leu Gly Asp Ile Ser  Gly Ile Asn
    1160                 1165                 1170

Ala Ser  Val Val Asn Ile Gln  Lys Glu Ile Asp Arg  Leu Asn Glu
    1175                 1180                 1185

Val Ala  Lys Asn Leu Asn Glu  Ser Leu Ile Asp Leu  Gln Glu Leu
    1190                 1195                 1200

Gly Lys  Tyr Glu Gln Tyr Ile  Lys Trp Pro
    1205                 1210


<210> SEQ ID NO 41
<211> LENGTH: 1200
<212> TYPE: PRT
<213> ORGANISM: Artificial Sequence
<220> FEATURE:
<223> OTHER INFORMATION: RECOMBINANT SPIKE PROTEIN

<400> SEQUENCE: 41

Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
            20                  25                  30

Ser Val Leu His Ser Thr Gln Asp Leu Phe Leu Pro Phe Phe Ser Asn
        35                  40                  45

Val Thr Trp Phe His Ala Ile His Val Ser Gly Thr Asn Gly Thr Lys
    50                  55                  60

Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                85                  90                  95

Leu Asp Ser Lys Thr Gln Ser Leu Leu Ile Val Asn Asn Ala Thr Asn
            100                 105                 110

Val Val Ile Lys Val Cys Glu Phe Gln Phe Cys Asn Asp Pro Phe Leu
        115                 120                 125

Gly Val Tyr Tyr His Lys Asn Asn Lys Ser Trp Met Glu Ser Glu Phe
    130                 135                 140

Arg Val Tyr Ser Ser Ala Asn Asn Cys Thr Phe Glu Tyr Val Ser Gln
145                 150                 155                 160

Pro Phe Leu Met Asp Leu Glu Gly Lys Gln Gly Asn Phe Lys Asn Leu
                165                 170                 175

Arg Glu Phe Val Phe Lys Asn Ile Asp Gly Tyr Phe Lys Ile Tyr Ser
            180                 185                 190

Lys His Thr Pro Ile Asn Leu Val Arg Asp Leu Pro Gln Gly Phe Ser
        195                 200                 205
```

```
Ala Leu Glu Pro Leu Val Asp Leu Pro Ile Gly Ile Asn Ile Thr Arg
    210                 215                 220

Phe Gln Thr Leu Leu Ala Leu His Arg Ser Tyr Leu Thr Pro Gly Asp
225                 230                 235                 240

Ser Ser Ser Gly Trp Thr Ala Gly Ala Ala Ala Tyr Tyr Val Gly Tyr
                245                 250                 255

Leu Gln Pro Arg Thr Phe Leu Leu Lys Tyr Asn Glu Asn Gly Thr Ile
            260                 265                 270

Thr Asp Ala Val Asp Cys Ala Leu Asp Pro Leu Ser Glu Thr Lys Cys
        275                 280                 285

Thr Leu Lys Ser Phe Thr Val Glu Lys Gly Ile Tyr Gln Thr Ser Asn
    290                 295                 300

Phe Arg Val Gln Pro Thr Glu Ser Ile Val Arg Phe Pro Asn Ile Thr
305                 310                 315                 320

Asn Leu Cys Pro Phe Gly Glu Val Phe Asn Ala Thr Arg Phe Ala Ser
                325                 330                 335

Val Tyr Ala Trp Asn Arg Lys Arg Ile Ser Asn Cys Val Ala Asp Tyr
            340                 345                 350

Ser Val Leu Tyr Asn Ser Ala Ser Phe Ser Thr Phe Lys Cys Tyr Gly
        355                 360                 365

Val Ser Pro Thr Lys Leu Asn Asp Leu Cys Phe Thr Asn Val Tyr Ala
    370                 375                 380

Asp Ser Phe Val Ile Arg Gly Asp Glu Val Arg Gln Ile Ala Pro Gly
385                 390                 395                 400

Gln Thr Gly Lys Ile Ala Asp Tyr Asn Tyr Lys Leu Pro Asp Asp Phe
                405                 410                 415

Thr Gly Cys Val Ile Ala Trp Asn Ser Asn Asn Leu Asp Ser Lys Val
            420                 425                 430

Gly Gly Asn Tyr Asn Tyr Leu Tyr Arg Leu Phe Arg Lys Ser Asn Leu
        435                 440                 445

Lys Pro Phe Glu Arg Asp Ile Ser Thr Glu Ile Tyr Gln Ala Gly Ser
    450                 455                 460

Thr Pro Cys Asn Gly Val Glu Gly Phe Asn Cys Tyr Phe Pro Leu Gln
465                 470                 475                 480

Ser Tyr Gly Phe Gln Pro Thr Asn Gly Val Gly Tyr Gln Pro Tyr Arg
                485                 490                 495

Val Val Val Leu Ser Phe Glu Leu Leu His Ala Pro Ala Thr Val Cys
            500                 505                 510

Gly Pro Lys Lys Ser Thr Asn Leu Val Lys Asn Lys Cys Val Asn Phe
        515                 520                 525

Asn Phe Asn Gly Leu Thr Gly Thr Gly Val Leu Thr Glu Ser Asn Lys
    530                 535                 540

Lys Phe Leu Pro Phe Gln Gln Phe Gly Arg Asp Ile Ala Asp Thr Thr
545                 550                 555                 560

Asp Ala Val Arg Asp Pro Gln Thr Leu Glu Ile Leu Asp Ile Thr Pro
                565                 570                 575

Cys Ser Phe Gly Gly Val Ser Val Ile Thr Pro Gly Thr Asn Thr Ser
            580                 585                 590

Asn Gln Val Ala Val Leu Tyr Gln Asp Val Asn Cys Thr Glu Val Pro
        595                 600                 605

Val Ala Ile His Ala Asp Gln Leu Thr Pro Thr Trp Arg Val Tyr Ser
    610                 615                 620

Thr Gly Ser Asn Val Phe Gln Thr Arg Ala Gly Cys Leu Ile Gly Ala
```

-continued

```
625                 630                 635                 640

Glu His Val Asn Asn Ser Tyr Glu Cys Asp Ile Pro Ile Gly Ala Gly
                645                 650                 655

Ile Cys Ala Ser Tyr Gln Thr Gln Thr Asn Ser Pro Arg Arg Ala Arg
            660                 665                 670

Ser Val Ala Ser Gln Ser Ile Ile Ala Tyr Thr Met Ser Leu Gly Ala
        675                 680                 685

Glu Asn Ser Val Ala Tyr Ser Asn Asn Ser Ile Ala Ile Pro Thr Asn
    690                 695                 700

Phe Thr Ile Ser Val Thr Thr Glu Ile Leu Pro Val Ser Met Thr Lys
705                 710                 715                 720

Thr Ser Val Asp Cys Thr Met Tyr Ile Cys Gly Asp Ser Thr Glu Cys
                725                 730                 735

Ser Asn Leu Leu Leu Gln Tyr Gly Ser Phe Cys Thr Gln Leu Asn Arg
            740                 745                 750

Ala Leu Thr Gly Ile Ala Val Glu Gln Asp Lys Asn Thr Gln Glu Val
        755                 760                 765

Phe Ala Gln Val Lys Gln Ile Tyr Lys Thr Pro Pro Ile Lys Asp Phe
    770                 775                 780

Gly Gly Phe Asn Phe Ser Gln Ile Leu Pro Asp Pro Ser Lys Pro Ser
785                 790                 795                 800

Lys Arg Ser Phe Ile Glu Asp Leu Leu Phe Asn Lys Val Thr Leu Ala
                805                 810                 815

Asp Ala Gly Phe Ile Lys Gln Tyr Gly Asp Cys Leu Gly Asp Ile Ala
            820                 825                 830

Ala Arg Asp Leu Ile Cys Ala Gln Lys Phe Asn Gly Leu Thr Val Leu
        835                 840                 845

Pro Pro Leu Leu Thr Asp Glu Met Ile Ala Gln Tyr Thr Ser Ala Leu
    850                 855                 860

Leu Ala Gly Thr Ile Thr Ser Gly Trp Thr Phe Gly Ala Gly Ala Ala
865                 870                 875                 880

Leu Gln Ile Pro Phe Ala Met Gln Met Ala Tyr Arg Phe Asn Gly Ile
                885                 890                 895

Gly Val Thr Gln Asn Val Leu Tyr Glu Asn Gln Lys Leu Ile Ala Asn
            900                 905                 910

Gln Phe Asn Ser Ala Ile Gly Lys Ile Gln Asp Ser Leu Ser Ser Thr
        915                 920                 925

Ala Ser Ala Leu Gly Lys Leu Gln Asp Val Val Asn Gln Asn Ala Gln
    930                 935                 940

Ala Leu Asn Thr Leu Val Lys Gln Leu Ser Ser Asn Phe Gly Ala Ile
945                 950                 955                 960

Ser Ser Val Leu Asn Asp Ile Leu Ser Arg Leu Asp Lys Val Glu Ala
                965                 970                 975

Glu Val Gln Ile Asp Arg Leu Ile Thr Gly Arg Leu Gln Ser Leu Gln
            980                 985                 990

Thr Tyr Val Thr Gln Gln Leu Ile  Arg Ala Ala Glu Ile  Arg Ala Ser
        995                 1000                1005

Ala Asn  Leu Ala Ala Thr Lys  Met Ser Glu Cys Val  Leu Gly Gln
    1010                1015                1020

Ser Lys  Arg Val Asp Phe Cys  Gly Lys Gly Tyr His  Leu Met Ser
    1025                1030                1035

Phe Pro  Gln Ser Ala Pro His  Gly Val Val Phe Leu  His Val Thr
    1040                1045                1050
```

```
Tyr Val  Pro Ala Gln Glu Lys  Asn Phe Thr Thr Ala  Pro Ala Ile
    1055                 1060                 1065

Cys His  Asp Gly Lys Ala His  Phe Pro Arg Glu Gly  Val Phe Val
    1070                 1075                 1080

Ser Asn  Gly Thr His Trp Phe  Val Thr Gln Arg Asn  Phe Tyr Glu
    1085                 1090                 1095

Pro Gln  Ile Ile Thr Thr Asp  Asn Thr Phe Val Ser  Gly Asn Cys
    1100                 1105                 1110

Asp Val  Val Ile Gly Ile Val  Asn Asn Thr Val Tyr  Asp Pro Leu
    1115                 1120                 1125

Gln Pro  Glu Leu Asp Ser Phe  Lys Glu Glu Leu Asp  Lys Tyr Phe
    1130                 1135                 1140

Lys Asn  His Thr Ser Pro Asp  Val Asp Leu Gly Asp  Ile Ser Gly
    1145                 1150                 1155

Ile Asn  Ala Ser Val Val Asn  Ile Gln Lys Glu Ile  Asp Arg Leu
    1160                 1165                 1170

Asn Glu  Val Ala Lys Asn Leu  Asn Glu Ser Leu Ile  Asp Leu Gln
    1175                 1180                 1185

Glu Leu  Gly Lys Tyr Glu Gln  Tyr Ile Lys Trp Pro
    1190                 1195                 1200
```

<210> SEQ ID NO 42
<211> LENGTH: 1219
<212> TYPE: PRT
<213> ORGANISM: Artificial Sequence
<220> FEATURE:
<223> OTHER INFORMATION: RECOMBINANT SPIKE PROTEIN

<400> SEQUENCE: 42

```
Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205
```

```
Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620
```

-continued

```
His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
            980                 985                 990

Ile Asp Arg Leu Ile Thr Gly Arg  Leu Gln Ser Leu Gln  Thr Tyr Val
        995                 1000                 1005

Thr Gln  Gln Leu Ile Arg Ala  Ala Glu Ile Arg Ala  Ser Ala Asn
    1010                 1015                 1020

Leu Ala  Ala Thr Lys Met Ser  Glu Cys Val Leu Gly  Gln Ser Lys
    1025                 1030                 1035

Arg Val  Asp Phe Cys Gly Lys  Gly Tyr His Leu Met  Ser Phe Pro
```

```
    1040                1045                1050

Gln Ser  Ala Pro His Gly Val  Val Phe Leu His Val  Thr Tyr Val
    1055                1060                1065

Pro Ala  Gln Glu Lys Asn Phe  Thr Thr Ala Pro Ala  Ile Cys His
    1070                1075                1080

Asp Gly  Lys Ala His Phe Pro  Arg Glu Gly Val Phe  Val Ser Asn
    1085                1090                1095

Gly Thr  His Trp Phe Val Thr  Gln Arg Asn Phe Tyr  Glu Pro Gln
    1100                1105                1110

Ile Ile  Thr Thr Asp Asn Thr  Phe Val Ser Gly Asn  Cys Asp Val
    1115                1120                1125

Val Ile  Gly Ile Val Asn Asn  Thr Val Tyr Asp Pro  Leu Gln Pro
    1130                1135                1140

Glu Leu  Asp Ser Phe Lys Glu  Glu Leu Asp Lys Tyr  Phe Lys Asn
    1145                1150                1155

His Thr  Ser Pro Asp Val Asp  Leu Gly Asp Ile Ser  Gly Ile Asn
    1160                1165                1170

Ala Ser  Val Val Asn Ile Gln  Lys Glu Ile Asp Arg  Leu Asn Glu
    1175                1180                1185

Val Ala  Lys Asn Leu Asn Glu  Ser Leu Ile Asp Leu  Gln Glu Leu
    1190                1195                1200

Gly Lys  Tyr Glu Gln Tyr Ile  Lys Trp Pro His His  His His His
    1205                1210                1215

His


<210> SEQ ID NO 43
<211> LENGTH: 3657
<212> TYPE: DNA
<213> ORGANISM: Artificial Sequence
<220> FEATURE:
<223> OTHER INFORMATION: RECOMBINANT SPIKE PROTEIN

<400> SEQUENCE: 43

atgttcgtct tcctggtgct gctgcccctg gtgtccagcc agtgcgtgaa cctgaccact      60

aggactcagc tgcctcccgc ttacaccaac tcattcactc gcggtgtgta ctaccctgac     120

aaggtcttcc gttcttcagt gctgcactca actcaggacc tgttcctgcc cttcttctcc     180

aacgtcacct ggttccacgc catccacgtg tccggcacca acggcactaa gcgcttcgac     240

aacccagtgc tgcctttcaa cgacggtgtc tacttcgctt caaccgagaa gtccaacatc     300

atccgtggat ggatcttcgg caccactctg gacagcaaga ctcagtctct gctgatcgtc     360

aacaacgcca ccaacgtggt catcaaggtc tgcgaattcc agttctgcaa cgacccattc     420

ctgggcgtct actaccacaa gaacaacaag tcatggatgg agtccgaatt ccgcgtctac     480

tccagcgcta acaactgcac tttcgagtac gtgtcccagc ctttcctgat ggacctggaa     540

ggaaagcagg gtaacttcaa gaacctgagg gagttcgtgt tcaagaacat cgacggatac     600

ttcaagattt acagcaagca caccccaatc aacctggtgc gcgacctgcc tcagggtttc     660

tctgctctgg agccactggt ggacctgcct atcggcatca acatcacccg cttccagact     720

ctgctggctc tgcaccgttc ctacctgact ccaggcgact catcttctgg atggactgct     780

ggagctgctg cttactacgt gggctacctg cagcctcgca ccttcctgct gaagtacaac     840

gaaaacggaa ccatcactga cgccgtcgac tgcgctctgg accctctgtc agaaaccaag     900

tgcactctga agtccttcac cgtggagaag ggcatctacc agacttcaaa cttcagggtg     960
```

cagcccaccg aatccatcgt cagattccct aacatcacta acctgtgccc cttcggagag 1020
gtcttcaacg ccacccgctt cgcttccgtg tacgcctgga acaggaagag aatctcaaac 1080
tgcgtcgctg actactccgt gctgtacaac tcagcctcct tcagcacctt caagtgctac 1140
ggcgtgtcac caactaagct gaacgacctg tgcttcacca acgtctacgc cgactccttc 1200
gtgatcaggg gagacgaggt cagacagatc gctcctggcc agactggaaa gatcgccgac 1260
tacaactaca agctgcccga cgacttcacc ggttgcgtca tcgcttggaa cagcaacaac 1320
ctggactcta aagtgggtgg caactacaac tacctgtacc gcctgttccg taagtcaaac 1380
ctgaagccat tcgagaggga catcagcact gaaatctacc aggccggatc taccccttgc 1440
aacggtgtcg agggcttcaa ctgctacttc cccctgcagt cctacggttt ccagccaact 1500
aacggtgtgg gctaccagcc ttacagagtg gtcgtgctga gcttcgaact gctccacgct 1560
cctgctactg tgtgcggtcc aaagaagtct accaacctgg tcaagaacaa gtgcgtgaac 1620
ttcaacttca acggcctgac cggaactggt gtcctgaccg agagcaacaa gaagttcctg 1680
cccttccagc agttcggaag ggacatcgct gacaccactg acgctgtgcg cgaccctcag 1740
accctggaaa tcctggacat cactccatgc tcattcggag gtgtctccgt gatcacccct 1800
ggcaccaaca cttctaacca ggtcgctgtg ctgtaccagg acgtcaactg caccgaggtc 1860
cctgtggcca tccacgctga ccagctgacc cccacttggc gcgtgtactc caccggcagc 1920
aacgtgttcc agactcgtgc tggttgcctg atcggcgccg agcacgtgaa caacagctac 1980
gaatgcgaca tccccatcgg cgctggaatc tgcgcctctt accagaccca gactaacagc 2040
ccacgcaggg ctcgctctgt ggcctctcag tcaatcatcg cttacaccat gtcactgggc 2100
gctgaaaact ccgtggccta ctctaacaac tcaatcgcca tccccaccaa cttcactatc 2160
agcgtgacca ctgagatcct gccagtcagc atgaccaaga cttctgtgga ctgcactatg 2220
tacatctgcg gagacagcac cgaatgctct aacctgctgc tgcagtacgg ctctttctgc 2280
acccagctga accgtgctct gactggaatc gccgtggagc aggacaagaa cactcaggaa 2340
gtcttcgctc aggtgaagca aatctacaag accccaccta tcaaggactt cggcggattc 2400
aacttctccc agatcctgcc tgacccctcc aagccaagca agcgctcttt catcgaggac 2460
ctgctgttca acaaggtcac tctggccgac gctggattca tcaagcagta cggagactgc 2520
ctgggtgaca tcgccgctcg tgacctgatc tgcgctcaga agttcaacgg tctgaccgtg 2580
ctgcccccac tgctgactga cgaaatgatc gcccagtaca ctagcgccct gctggctgga 2640
accatcactt ctggttggac cttcggtgct ggcgccgctc tgcagatccc tttcgctatg 2700
cagatggcct accgtttcaa cggaatcggt gtcacccaga acgtgctgta cgagaaccag 2760
aagctgatcg ctaaccagtt caactcagcc atcggaaaga tccaggacag cctgagctct 2820
actgcctctg ctctgggcaa gctgcaggac gtcgtgaacc agaacgccca ggctctgaac 2880
accctggtca agcagctgtc atccaacttc ggtgctatca gctctgtgct gaacgacatc 2940
ctgtcccgcc tggacaaggt cgaggccgaa gtgcagatcg accgcctgat cactggccgt 3000
ctgcagtcac tgcagaccta cgtgactcag cagctgatca gggccgctga aatcagagcc 3060
tccgctaacc tggccgctac caagatgagc gagtgcgtcc tgggtcaatc taagcgtgtg 3120
gacttctgcg gcaagggata ccacctgatg tcattccctc agtctgctcc ccacggtgtg 3180
gtgttcctgc acgtcaccta cgtgccagcc caggagaaga acttcaccac tgcccctgct 3240
atctgccacg acggcaaggc tcacttcccc agggaaggtg tcttcgtgag caacggcacc 3300
cactggttcg tcactcagag aaacttctac gagccacaga tcatcaccac tgacaacact 3360

```
ttcgtgtctg gaaactgcga cgtggtcatc ggtatcgtca acaacaccgt gtacgacccc   3420

ctgcagccag agctggactc attcaaggag gaactggaca agtacttcaa gaaccacacc   3480

tcccctgacg tcgacctggg cgacatctca ggaatcaacg cttccgtcgt gaacatccag   3540

aaggagatcg accgcctgaa cgaagtggcc aagaacctga acgaaagcct gatcgacctg   3600

caggagctgg gcaagtacga acagtacatc aagtggcctc accaccacca ccaccac      3657


<210> SEQ ID NO 44
<211> LENGTH: 1219
<212> TYPE: PRT
<213> ORGANISM: Artificial Sequence
<220> FEATURE:
<223> OTHER INFORMATION: RECOMBINANT SPIKE PROTEIN

<400> SEQUENCE: 44

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
```

-continued

```
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735
```

```
Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
            980                 985                 990

Ile Asp Arg Leu Ile Thr Gly Arg  Leu Gln Ser Leu Gln  Thr Tyr Val
        995                 1000                1005

Thr Gln  Gln Leu Ile Arg Ala  Ala Glu Ile Arg Ala  Ser Ala Asn
    1010                1015                1020

Leu Ala  Ala Thr Lys Met Ser  Glu Cys Val Leu Gly  Gln Ser Lys
    1025                1030                1035

Arg Val  Asp Phe Cys Gly Lys  Gly Tyr His Leu Met  Ser Phe Pro
    1040                1045                1050

Gln Ser  Ala Pro His Gly Val  Val Phe Leu His Val  Thr Tyr Val
    1055                1060                1065

Pro Ala  Gln Glu Lys Asn Phe  Thr Thr Ala Pro Ala  Ile Cys His
    1070                1075                1080

Asp Gly  Lys Ala His Phe Pro  Arg Glu Gly Val Phe  Val Ser Asn
    1085                1090                1095

Gly Thr  His Trp Phe Val Thr  Gln Arg Asn Phe Tyr  Glu Pro Gln
    1100                1105                1110

Ile Ile  Thr Thr Asp Asn Thr  Phe Val Ser Gly Asn  Cys Asp Val
    1115                1120                1125

Val Ile  Gly Ile Val Asn Asn  Thr Val Tyr Asp Pro  Leu Gln Pro
    1130                1135                1140
```

-continued

```
Glu Leu  Asp Ser Phe Lys Glu  Glu Leu Asp Lys Tyr  Phe Lys Asn
    1145                 1150                 1155

His Thr  Ser Pro Asp Val Asp  Leu Gly Asp Ile Ser  Gly Ile Asn
    1160                 1165                 1170

Ala Ser  Val Val Asn Ile Gln  Lys Glu Ile Asp Arg  Leu Asn Glu
    1175                 1180                 1185

Val Ala  Lys Asn Leu Asn Glu  Ser Leu Ile Asp Leu  Gln Glu Leu
    1190                 1195                 1200

Gly Lys  Tyr Glu Gln Tyr Ile  Lys Trp Pro His His  His His His
    1205                 1210                 1215

His
```

```
<210> SEQ ID NO 45
<211> LENGTH: 318
<212> TYPE: PRT
<213> ORGANISM: Artificial Sequence
<220> FEATURE:
<223> OTHER INFORMATION: RECOMBINANT SPIKE PROTEIN

<400> SEQUENCE: 45

Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
            20                  25                  30

Ser Val Leu His Ser Thr Gln Asp Leu Phe Leu Pro Phe Phe Ser Asn
        35                  40                  45

Val Thr Trp Phe His Ala Ile His Val Ser Gly Thr Asn Gly Thr Lys
    50                  55                  60

Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                85                  90                  95

Leu Asp Ser Lys Thr Gln Ser Leu Leu Ile Val Asn Asn Ala Thr Asn
            100                 105                 110

Val Val Ile Lys Val Cys Glu Phe Gln Phe Cys Asn Asp Pro Phe Leu
        115                 120                 125

Gly Val Tyr Tyr His Lys Asn Asn Lys Ser Trp Met Glu Ser Glu Phe
    130                 135                 140

Arg Val Tyr Ser Ser Ala Asn Asn Cys Thr Phe Glu Tyr Val Ser Gln
145                 150                 155                 160

Pro Phe Leu Met Asp Leu Glu Gly Lys Gln Gly Asn Phe Lys Asn Leu
                165                 170                 175

Arg Glu Phe Val Phe Lys Asn Ile Asp Gly Tyr Phe Lys Ile Tyr Ser
            180                 185                 190

Lys His Thr Pro Ile Asn Leu Val Arg Asp Leu Pro Gln Gly Phe Ser
        195                 200                 205

Ala Leu Glu Pro Leu Val Asp Leu Pro Ile Gly Ile Asn Ile Thr Arg
    210                 215                 220

Phe Gln Thr Leu Leu Ala Leu His Arg Ser Tyr Leu Thr Pro Gly Asp
225                 230                 235                 240

Ser Ser Ser Gly Trp Thr Ala Gly Ala Ala Ala Tyr Tyr Val Gly Tyr
                245                 250                 255

Leu Gln Pro Arg Thr Phe Leu Leu Lys Tyr Asn Glu Asn Gly Thr Ile
            260                 265                 270

Thr Asp Ala Val Asp Cys Ala Leu Asp Pro Leu Ser Glu Thr Lys Cys
```

275 280 285

Thr Leu Lys Ser Phe Thr Val Glu Lys Gly Ile Tyr Gln Thr Ser Asn
290 295 300

Phe Arg Val Gln Pro Thr Glu Ser Ile Val Arg Phe Pro Asn
305 310 315

<210> SEQ ID NO 46
<211> LENGTH: 955
<212> TYPE: PRT
<213> ORGANISM: Artificial Sequence
<220> FEATURE:
<223> OTHER INFORMATION: RECOMBINANT SPIKE PROTEIN

<400> SEQUENCE: 46

Met Phe Val Phe Leu Val Leu Leu Pro Leu Val Ser Ser Ile Thr Asn
1 5 10 15

Leu Cys Pro Phe Gly Glu Val Phe Asn Ala Thr Arg Phe Ala Ser Val
20 25 30

Tyr Ala Trp Asn Arg Lys Arg Ile Ser Asn Cys Val Ala Asp Tyr Ser
35 40 45

Val Leu Tyr Asn Ser Ala Ser Phe Ser Thr Phe Lys Cys Tyr Gly Val
50 55 60

Ser Pro Thr Lys Leu Asn Asp Leu Cys Phe Thr Asn Val Tyr Ala Asp
65 70 75 80

Ser Phe Val Ile Arg Gly Asp Glu Val Arg Gln Ile Ala Pro Gly Gln
85 90 95

Thr Gly Lys Ile Ala Asp Tyr Asn Tyr Lys Leu Pro Asp Asp Phe Thr
100 105 110

Gly Cys Val Ile Ala Trp Asn Ser Asn Asn Leu Asp Ser Lys Val Gly
115 120 125

Gly Asn Tyr Asn Tyr Leu Tyr Arg Leu Phe Arg Lys Ser Asn Leu Lys
130 135 140

Pro Phe Glu Arg Asp Ile Ser Thr Glu Ile Tyr Gln Ala Gly Ser Thr
145 150 155 160

Pro Cys Asn Gly Val Glu Gly Phe Asn Cys Tyr Phe Pro Leu Gln Ser
165 170 175

Tyr Gly Phe Gln Pro Thr Asn Gly Val Gly Tyr Gln Pro Tyr Arg Val
180 185 190

Val Val Leu Ser Phe Glu Leu Leu His Ala Pro Ala Thr Val Cys Gly
195 200 205

Pro Lys Lys Ser Thr Asn Leu Val Lys Asn Lys Cys Val Asn Phe Asn
210 215 220

Phe Asn Gly Leu Thr Gly Thr Gly Val Leu Thr Glu Ser Asn Lys Lys
225 230 235 240

Phe Leu Pro Phe Gln Gln Phe Gly Arg Asp Ile Ala Asp Thr Thr Asp
245 250 255

Ala Val Arg Asp Pro Gln Thr Leu Glu Ile Leu Asp Ile Thr Pro Cys
260 265 270

Ser Phe Gly Gly Val Ser Val Ile Thr Pro Gly Thr Asn Thr Ser Asn
275 280 285

Gln Val Ala Val Leu Tyr Gln Asp Val Asn Cys Thr Glu Val Pro Val
290 295 300

Ala Ile His Ala Asp Gln Leu Thr Pro Thr Trp Arg Val Tyr Ser Thr
305 310 315 320

Gly Ser Asn Val Phe Gln Thr Arg Ala Gly Cys Leu Ile Gly Ala Glu

```
                325                 330                 335

His Val Asn Asn Ser Tyr Glu Cys Asp Ile Pro Ile Gly Ala Gly Ile
            340                 345                 350

Cys Ala Ser Tyr Gln Thr Gln Thr Asn Ser Pro Arg Arg Ala Arg Ser
        355                 360                 365

Val Ala Ser Gln Ser Ile Ile Ala Tyr Thr Met Ser Leu Gly Ala Glu
    370                 375                 380

Asn Ser Val Ala Tyr Ser Asn Asn Ser Ile Ala Ile Pro Thr Asn Phe
385                 390                 395                 400

Thr Ile Ser Val Thr Thr Glu Ile Leu Pro Val Ser Met Thr Lys Thr
                405                 410                 415

Ser Val Asp Cys Thr Met Tyr Ile Cys Gly Asp Ser Thr Glu Cys Ser
            420                 425                 430

Asn Leu Leu Leu Gln Tyr Gly Ser Phe Cys Thr Gln Leu Asn Arg Ala
        435                 440                 445

Leu Thr Gly Ile Ala Val Glu Gln Asp Lys Asn Thr Gln Glu Val Phe
    450                 455                 460

Ala Gln Val Lys Gln Ile Tyr Lys Thr Pro Pro Ile Lys Asp Phe Gly
465                 470                 475                 480

Gly Phe Asn Phe Ser Gln Ile Leu Pro Asp Pro Ser Lys Pro Ser Lys
                485                 490                 495

Arg Ser Phe Ile Glu Asp Leu Leu Phe Asn Lys Val Thr Leu Ala Asp
            500                 505                 510

Ala Gly Phe Ile Lys Gln Tyr Gly Asp Cys Leu Gly Asp Ile Ala Ala
        515                 520                 525

Arg Asp Leu Ile Cys Ala Gln Lys Phe Asn Gly Leu Thr Val Leu Pro
    530                 535                 540

Pro Leu Leu Thr Asp Glu Met Ile Ala Gln Tyr Thr Ser Ala Leu Leu
545                 550                 555                 560

Ala Gly Thr Ile Thr Ser Gly Trp Thr Phe Gly Ala Gly Ala Ala Leu
                565                 570                 575

Gln Ile Pro Phe Ala Met Gln Met Ala Tyr Arg Phe Asn Gly Ile Gly
            580                 585                 590

Val Thr Gln Asn Val Leu Tyr Glu Asn Gln Lys Leu Ile Ala Asn Gln
        595                 600                 605

Phe Asn Ser Ala Ile Gly Lys Ile Gln Asp Ser Leu Ser Ser Thr Ala
    610                 615                 620

Ser Ala Leu Gly Lys Leu Gln Asp Val Val Asn Gln Asn Ala Gln Ala
625                 630                 635                 640

Leu Asn Thr Leu Val Lys Gln Leu Ser Ser Asn Phe Gly Ala Ile Ser
                645                 650                 655

Ser Val Leu Asn Asp Ile Leu Ser Arg Leu Asp Lys Val Glu Ala Glu
            660                 665                 670

Val Gln Ile Asp Arg Leu Ile Thr Gly Arg Leu Gln Ser Leu Gln Thr
        675                 680                 685

Tyr Val Thr Gln Gln Leu Ile Arg Ala Ala Glu Ile Arg Ala Ser Ala
    690                 695                 700

Asn Leu Ala Ala Thr Lys Met Ser Glu Cys Val Leu Gly Gln Ser Lys
705                 710                 715                 720

Arg Val Asp Phe Cys Gly Lys Gly Tyr His Leu Met Ser Phe Pro Gln
                725                 730                 735

Ser Ala Pro His Gly Val Val Phe Leu His Val Thr Tyr Val Pro Ala
            740                 745                 750
```

-continued

```
Gln Glu Lys Asn Phe Thr Thr Ala Pro Ala Ile Cys His Asp Gly Lys
        755                 760                 765

Ala His Phe Pro Arg Glu Gly Val Phe Val Ser Asn Gly Thr His Trp
    770                 775                 780

Phe Val Thr Gln Arg Asn Phe Tyr Glu Pro Gln Ile Ile Thr Thr Asp
785                 790                 795                 800

Asn Thr Phe Val Ser Gly Asn Cys Asp Val Val Ile Gly Ile Val Asn
                805                 810                 815

Asn Thr Val Tyr Asp Pro Leu Gln Pro Glu Leu Asp Ser Phe Lys Glu
            820                 825                 830

Glu Leu Asp Lys Tyr Phe Lys Asn His Thr Ser Pro Asp Val Asp Leu
        835                 840                 845

Gly Asp Ile Ser Gly Ile Asn Ala Ser Val Val Asn Ile Gln Lys Glu
    850                 855                 860

Ile Asp Arg Leu Asn Glu Val Ala Lys Asn Leu Asn Glu Ser Leu Ile
865                 870                 875                 880

Asp Leu Gln Glu Leu Gly Lys Tyr Glu Gln Tyr Ile Lys Trp Pro Trp
                885                 890                 895

Tyr Ile Trp Leu Gly Phe Ile Ala Gly Leu Ile Ala Ile Val Met Val
            900                 905                 910

Thr Ile Met Leu Cys Cys Met Thr Ser Cys Cys Ser Cys Leu Lys Gly
        915                 920                 925

Cys Cys Ser Cys Gly Ser Cys Cys Lys Phe Asp Glu Asp Asp Ser Glu
    930                 935                 940

Pro Val Leu Lys Gly Val Lys Leu His Tyr Thr
945                 950                 955
```

<210> SEQ ID NO 47
<211> LENGTH: 2868
<212> TYPE: DNA
<213> ORGANISM: Artificial Sequence
<220> FEATURE:
<223> OTHER INFORMATION: RECOMBINANT SPIKE PROTEIN

<400> SEQUENCE: 47

```
atgttcgtct tcctggtgct gctgcccctg gtgtccagca tcactaacct gtgccccttc     60

ggagaggtct tcaacgccac ccgcttcgct tccgtgtacg cctggaacag gaagagaatc    120

tcaaactgcg tcgctgacta ctccgtgctg tacaactcag cctccttcag caccttcaag    180

tgctacggcg tgtcaccaac taagctgaac gacctgtgct tcaccaacgt ctacgccgac    240

tccttcgtga tcaggggaga cgaggtcaga cagatcgctc ctggccagac tggaaagatc    300

gccgactaca actacaagct gcccgacgac ttcaccggtt gcgtcatcgc ttggaacagc    360

aacaacctgg actctaaagt gggtggcaac tacaactacc tgtaccgcct gttccgtaag    420

tcaaacctga agccattcga gagggacatc agcactgaaa tctaccaggc cggatctacc    480

ccttgcaacg gtgtcgaggg cttcaactgc tacttccccc tgcagtccta cggtttccag    540

ccaactaacg gtgtgggcta ccagccttac agagtggtcg tgctgagctt cgaactgctc    600

cacgctcctg ctactgtgtg cggtccaaag aagtctacca acctggtcaa gaacaagtgc    660

gtgaacttca acttcaacgg cctgaccgga actggtgtcc tgaccgagag caacaagaag    720

ttcctgccct tccagcagtt cggaagggac atcgctgaca ccactgacgc tgtgcgcgac    780

cctcagaccc tggaaatcct ggacatcact ccatgctcat tcggaggtgt ctccgtgatc    840

acccctggca ccaacacttc taaccaggtc gctgtgctgt accaggacgt caactgcacc    900
```

-continued gaggtccctg tggccatcca cgctgaccag ctgaccccca cttggcgcgt gtactccacc 960
ggcagcaacg tgttccagac tcgtgctggt tgcctgatcg gcgccgagca cgtgaacaac 1020
agctacgaat gcgacatccc catcggcgct ggaatctgcg cctcttacca gacccagact 1080
aacagcccac gcagggctcg ctctgtggcc tctcagtcaa tcatcgctta caccatgtca 1140
ctgggcgctg aaaactccgt ggcctactct aacaactcaa tcgccatccc caccaacttc 1200
actatcagcg tgaccactga gatcctgcca gtcagcatga ccaagacttc tgtggactgc 1260
actatgtaca tctgcggaga cagcaccgaa tgctctaacc tgctgctgca gtacggctct 1320
ttctgcaccc agctgaaccg tgctctgact ggaatcgccg tggagcagga caagaacact 1380
caggaagtct tcgctcaggt gaagcaaatc tacaagaccc cacctatcaa ggacttcggc 1440
ggattcaact tctcccagat cctgcctgac ccctccaagc caagcaagcg ctctttcatc 1500
gaggacctgc tgttcaacaa ggtcactctg gccgacgctg gattcatcaa gcagtacgga 1560
gactgcctgg gtgacatcgc cgctcgtgac ctgatctgcg ctcagaagtt caacggtctg 1620
accgtgctgc ccccactgct gactgacgaa atgatcgccc agtacactag cgccctgctg 1680
gctggaacca tcacttctgg ttggaccttc ggtgctggcg ccgctctgca gatccctttc 1740
gctatgcaga tggcctaccg tttcaacgga atcggtgtca cccagaacgt gctgtacgag 1800
aaccagaagc tgatcgctaa ccagttcaac tcagccatcg gaaagatcca ggacagcctg 1860
agctctactg cctctgctct gggcaagctg caggacgtcg tgaaccagaa cgcccaggct 1920
ctgaacaccc tggtcaagca gctgtcatcc aacttcggtg ctatcagctc tgtgctgaac 1980
gacatcctgt cccgcctgga caaggtcgag gccgaagtgc agatcgaccg cctgatcact 2040
ggccgtctgc agtcactgca gacctacgtg actcagcagc tgatcagggc cgctgaaatc 2100
agagcctccg ctaacctggc cgctaccaag atgagcgagt gcgtcctggg tcaatctaag 2160
cgtgtggact tctgcggcaa gggataccac ctgatgtcat tccctcagtc tgctccccac 2220
ggtgtggtgt tcctgcacgt cacctacgtg ccagcccagg agaagaactt caccactgcc 2280
cctgctatct gccacgacgg caaggctcac ttccccaggg aaggtgtctt cgtgagcaac 2340
ggcacccact ggttcgtcac tcagagaaac ttctacgagc cacagatcat caccactgac 2400
aacactttcg tgtctggaaa ctgcgacgtg gtcatcggta tcgtcaacaa caccgtgtac 2460
gaccccctgc agccagagct ggactcattc aaggaggaac tggacaagta cttcaagaac 2520
cacacctccc ctgacgtcga cctgggcgac atctcaggaa tcaacgcttc cgtcgtgaac 2580
atccagaagg agatcgaccg cctgaacgaa gtggccaaga acctgaacga aagcctgatc 2640
gacctgcagg agctgggcaa gtacgaacag tacatcaagt ggccttggta catctggctg 2700
ggtttcatcg ctggcctcat cgctatcgtg atggtgacca tcatgctgtg ctgcatgact 2760
tcatgctgct cctgcctgaa gggctgctgc agctgcggat cttgctgcaa gttcgacgag 2820
gacgactctg aacccgtcct gaagggcgtg aagctgcact acacctaa 2868

<210> SEQ ID NO 48
<211> LENGTH: 942
<212> TYPE: PRT
<213> ORGANISM: Artificial Sequence
<220> FEATURE:
<223> OTHER INFORMATION: RECOMBINANT SPIKE PROTEIN

<400> SEQUENCE: 48

Ile Thr Asn Leu Cys Pro Phe Gly Glu Val Phe Asn Ala Thr Arg Phe
1               5                   10                  15

```
Ala Ser Val Tyr Ala Trp Asn Arg Lys Arg Ile Ser Asn Cys Val Ala
            20                  25                  30

Asp Tyr Ser Val Leu Tyr Asn Ser Ala Ser Phe Ser Thr Phe Lys Cys
        35                  40                  45

Tyr Gly Val Ser Pro Thr Lys Leu Asn Asp Leu Cys Phe Thr Asn Val
    50                  55                  60

Tyr Ala Asp Ser Phe Val Ile Arg Gly Asp Glu Val Arg Gln Ile Ala
65                  70                  75                  80

Pro Gly Gln Thr Gly Lys Ile Ala Asp Tyr Asn Tyr Lys Leu Pro Asp
                85                  90                  95

Asp Phe Thr Gly Cys Val Ile Ala Trp Asn Ser Asn Asn Leu Asp Ser
            100                 105                 110

Lys Val Gly Gly Asn Tyr Asn Tyr Leu Tyr Arg Leu Phe Arg Lys Ser
        115                 120                 125

Asn Leu Lys Pro Phe Glu Arg Asp Ile Ser Thr Glu Ile Tyr Gln Ala
    130                 135                 140

Gly Ser Thr Pro Cys Asn Gly Val Glu Gly Phe Asn Cys Tyr Phe Pro
145                 150                 155                 160

Leu Gln Ser Tyr Gly Phe Gln Pro Thr Asn Gly Val Gly Tyr Gln Pro
                165                 170                 175

Tyr Arg Val Val Val Leu Ser Phe Glu Leu Leu His Ala Pro Ala Thr
            180                 185                 190

Val Cys Gly Pro Lys Lys Ser Thr Asn Leu Val Lys Asn Lys Cys Val
        195                 200                 205

Asn Phe Asn Phe Asn Gly Leu Thr Gly Thr Gly Val Leu Thr Glu Ser
    210                 215                 220

Asn Lys Lys Phe Leu Pro Phe Gln Gln Phe Gly Arg Asp Ile Ala Asp
225                 230                 235                 240

Thr Thr Asp Ala Val Arg Asp Pro Gln Thr Leu Glu Ile Leu Asp Ile
                245                 250                 255

Thr Pro Cys Ser Phe Gly Gly Val Ser Val Ile Thr Pro Gly Thr Asn
            260                 265                 270

Thr Ser Asn Gln Val Ala Val Leu Tyr Gln Asp Val Asn Cys Thr Glu
        275                 280                 285

Val Pro Val Ala Ile His Ala Asp Gln Leu Thr Pro Thr Trp Arg Val
    290                 295                 300

Tyr Ser Thr Gly Ser Asn Val Phe Gln Thr Arg Ala Gly Cys Leu Ile
305                 310                 315                 320

Gly Ala Glu His Val Asn Asn Ser Tyr Glu Cys Asp Ile Pro Ile Gly
                325                 330                 335

Ala Gly Ile Cys Ala Ser Tyr Gln Thr Gln Thr Asn Ser Pro Arg Arg
            340                 345                 350

Ala Arg Ser Val Ala Ser Gln Ser Ile Ile Ala Tyr Thr Met Ser Leu
        355                 360                 365

Gly Ala Glu Asn Ser Val Ala Tyr Ser Asn Asn Ser Ile Ala Ile Pro
    370                 375                 380

Thr Asn Phe Thr Ile Ser Val Thr Thr Glu Ile Leu Pro Val Ser Met
385                 390                 395                 400

Thr Lys Thr Ser Val Asp Cys Thr Met Tyr Ile Cys Gly Asp Ser Thr
                405                 410                 415

Glu Cys Ser Asn Leu Leu Leu Gln Tyr Gly Ser Phe Cys Thr Gln Leu
            420                 425                 430
```

-continued

```
Asn Arg Ala Leu Thr Gly Ile Ala Val Glu Gln Asp Lys Asn Thr Gln
        435                 440                 445

Glu Val Phe Ala Gln Val Lys Gln Ile Tyr Lys Thr Pro Pro Ile Lys
    450                 455                 460

Asp Phe Gly Gly Phe Asn Phe Ser Gln Ile Leu Pro Asp Pro Ser Lys
465                 470                 475                 480

Pro Ser Lys Arg Ser Phe Ile Glu Asp Leu Leu Phe Asn Lys Val Thr
                485                 490                 495

Leu Ala Asp Ala Gly Phe Ile Lys Gln Tyr Gly Asp Cys Leu Gly Asp
            500                 505                 510

Ile Ala Ala Arg Asp Leu Ile Cys Ala Gln Lys Phe Asn Gly Leu Thr
        515                 520                 525

Val Leu Pro Pro Leu Leu Thr Asp Glu Met Ile Ala Gln Tyr Thr Ser
    530                 535                 540

Ala Leu Leu Ala Gly Thr Ile Thr Ser Gly Trp Thr Phe Gly Ala Gly
545                 550                 555                 560

Ala Ala Leu Gln Ile Pro Phe Ala Met Gln Met Ala Tyr Arg Phe Asn
                565                 570                 575

Gly Ile Gly Val Thr Gln Asn Val Leu Tyr Glu Asn Gln Lys Leu Ile
            580                 585                 590

Ala Asn Gln Phe Asn Ser Ala Ile Gly Lys Ile Gln Asp Ser Leu Ser
        595                 600                 605

Ser Thr Ala Ser Ala Leu Gly Lys Leu Gln Asp Val Val Asn Gln Asn
    610                 615                 620

Ala Gln Ala Leu Asn Thr Leu Val Lys Gln Leu Ser Ser Asn Phe Gly
625                 630                 635                 640

Ala Ile Ser Ser Val Leu Asn Asp Ile Leu Ser Arg Leu Asp Lys Val
                645                 650                 655

Glu Ala Glu Val Gln Ile Asp Arg Leu Ile Thr Gly Arg Leu Gln Ser
            660                 665                 670

Leu Gln Thr Tyr Val Thr Gln Gln Leu Ile Arg Ala Ala Glu Ile Arg
        675                 680                 685

Ala Ser Ala Asn Leu Ala Ala Thr Lys Met Ser Glu Cys Val Leu Gly
    690                 695                 700

Gln Ser Lys Arg Val Asp Phe Cys Gly Lys Gly Tyr His Leu Met Ser
705                 710                 715                 720

Phe Pro Gln Ser Ala Pro His Gly Val Val Phe Leu His Val Thr Tyr
                725                 730                 735

Val Pro Ala Gln Glu Lys Asn Phe Thr Thr Ala Pro Ala Ile Cys His
            740                 745                 750

Asp Gly Lys Ala His Phe Pro Arg Glu Gly Val Phe Val Ser Asn Gly
        755                 760                 765

Thr His Trp Phe Val Thr Gln Arg Asn Phe Tyr Glu Pro Gln Ile Ile
    770                 775                 780

Thr Thr Asp Asn Thr Phe Val Ser Gly Asn Cys Asp Val Val Ile Gly
785                 790                 795                 800

Ile Val Asn Asn Thr Val Tyr Asp Pro Leu Gln Pro Glu Leu Asp Ser
                805                 810                 815

Phe Lys Glu Glu Leu Asp Lys Tyr Phe Lys Asn His Thr Ser Pro Asp
            820                 825                 830

Val Asp Leu Gly Asp Ile Ser Gly Ile Asn Ala Ser Val Val Asn Ile
        835                 840                 845

Gln Lys Glu Ile Asp Arg Leu Asn Glu Val Ala Lys Asn Leu Asn Glu
```

```
    850                 855                 860

Ser Leu Ile Asp Leu Gln Glu Leu Gly Lys Tyr Glu Gln Tyr Ile Lys
865                 870                 875                 880

Trp Pro Trp Tyr Ile Trp Leu Gly Phe Ile Ala Gly Leu Ile Ala Ile
                885                 890                 895

Val Met Val Thr Ile Met Leu Cys Cys Met Thr Ser Cys Cys Ser Cys
            900                 905                 910

Leu Lys Gly Cys Cys Ser Cys Gly Ser Cys Cys Lys Phe Asp Glu Asp
        915                 920                 925

Asp Ser Glu Pro Val Leu Lys Gly Val Lys Leu His Tyr Thr
    930                 935                 940


<210> SEQ ID NO 49
<211> LENGTH: 960
<212> TYPE: PRT
<213> ORGANISM: Artificial Sequence
<220> FEATURE:
<223> OTHER INFORMATION: RECOMBINANT SPIKE PROTEIN

<400> SEQUENCE: 49

Met Phe Val Phe Leu Val Leu Leu Pro Leu Val Ser Ser Ile Thr Asn
1               5                   10                  15

Leu Cys Pro Phe Gly Glu Val Phe Asn Ala Thr Arg Phe Ala Ser Val
            20                  25                  30

Tyr Ala Trp Asn Arg Lys Arg Ile Ser Asn Cys Val Ala Asp Tyr Ser
        35                  40                  45

Val Leu Tyr Asn Ser Ala Ser Phe Ser Thr Phe Lys Cys Tyr Gly Val
    50                  55                  60

Ser Pro Thr Lys Leu Asn Asp Leu Cys Phe Thr Asn Val Tyr Ala Asp
65                  70                  75                  80

Ser Phe Val Ile Arg Gly Asp Glu Val Arg Gln Ile Ala Pro Gly Gln
                85                  90                  95

Thr Gly Lys Ile Ala Asp Tyr Asn Tyr Lys Leu Pro Asp Asp Phe Thr
            100                 105                 110

Gly Cys Val Ile Ala Trp Asn Ser Asn Asn Leu Asp Ser Lys Val Gly
        115                 120                 125

Gly Asn Tyr Asn Tyr Leu Tyr Arg Leu Phe Arg Lys Ser Asn Leu Lys
    130                 135                 140

Pro Phe Glu Arg Asp Ile Ser Thr Glu Ile Tyr Gln Ala Gly Ser Thr
145                 150                 155                 160

Pro Cys Asn Gly Val Glu Gly Phe Asn Cys Tyr Phe Pro Leu Gln Ser
                165                 170                 175

Tyr Gly Phe Gln Pro Thr Asn Gly Val Gly Tyr Gln Pro Tyr Arg Val
            180                 185                 190

Val Val Leu Ser Phe Glu Leu Leu His Ala Pro Ala Thr Val Cys Gly
        195                 200                 205

Pro Lys Lys Ser Thr Asn Leu Val Lys Asn Lys Cys Val Asn Phe Asn
    210                 215                 220

Phe Asn Gly Leu Thr Gly Thr Gly Val Leu Thr Glu Ser Asn Lys Lys
225                 230                 235                 240

Phe Leu Pro Phe Gln Gln Phe Gly Arg Asp Ile Ala Asp Thr Thr Asp
                245                 250                 255

Ala Val Arg Asp Pro Gln Thr Leu Glu Ile Leu Asp Ile Thr Pro Cys
            260                 265                 270

Ser Phe Gly Gly Val Ser Val Ile Thr Pro Gly Thr Asn Thr Ser Asn
```

```
        275                 280                 285

Gln Val Ala Val Leu Tyr Gln Asp Val Asn Cys Thr Glu Val Pro Val
    290                 295                 300

Ala Ile His Ala Asp Gln Leu Thr Pro Thr Trp Arg Val Tyr Ser Thr
305                 310                 315                 320

Gly Ser Asn Val Phe Gln Thr Arg Ala Gly Cys Leu Ile Gly Ala Glu
                325                 330                 335

His Val Asn Asn Ser Tyr Glu Cys Asp Ile Pro Ile Gly Ala Gly Ile
            340                 345                 350

Cys Ala Ser Tyr Gln Thr Gln Thr Asn Ser Pro Arg Arg Ala Arg Ser
        355                 360                 365

Val Ala Ser Gln Ser Ile Ile Ala Tyr Thr Met Ser Leu Gly Ala Glu
    370                 375                 380

Asn Ser Val Ala Tyr Ser Asn Asn Ser Ile Ala Ile Pro Thr Asn Phe
385                 390                 395                 400

Thr Ile Ser Val Thr Thr Glu Ile Leu Pro Val Ser Met Thr Lys Thr
                405                 410                 415

Ser Val Asp Cys Thr Met Tyr Ile Cys Gly Asp Ser Thr Glu Cys Ser
            420                 425                 430

Asn Leu Leu Leu Gln Tyr Gly Ser Phe Cys Thr Gln Leu Asn Arg Ala
        435                 440                 445

Leu Thr Gly Ile Ala Val Glu Gln Asp Lys Asn Thr Gln Glu Val Phe
    450                 455                 460

Ala Gln Val Lys Gln Ile Tyr Lys Thr Pro Pro Ile Lys Asp Phe Gly
465                 470                 475                 480

Gly Phe Asn Phe Ser Gln Ile Leu Pro Asp Pro Ser Lys Pro Ser Lys
                485                 490                 495

Arg Ser Phe Ile Glu Asp Leu Leu Phe Asn Lys Val Thr Leu Ala Asp
            500                 505                 510

Ala Gly Phe Ile Lys Gln Tyr Gly Asp Cys Leu Gly Asp Ile Ala Ala
        515                 520                 525

Arg Asp Leu Ile Cys Ala Gln Lys Phe Asn Gly Leu Thr Val Leu Pro
    530                 535                 540

Pro Leu Leu Thr Asp Glu Met Ile Ala Gln Tyr Thr Ser Ala Leu Leu
545                 550                 555                 560

Ala Gly Thr Ile Thr Ser Gly Trp Thr Phe Gly Ala Gly Ala Ala Leu
                565                 570                 575

Gln Ile Pro Phe Ala Met Gln Met Ala Tyr Arg Phe Asn Gly Ile Gly
            580                 585                 590

Val Thr Gln Asn Val Leu Tyr Glu Asn Gln Lys Leu Ile Ala Asn Gln
        595                 600                 605

Phe Asn Ser Ala Ile Gly Lys Ile Gln Asp Ser Leu Ser Ser Thr Ala
    610                 615                 620

Ser Ala Leu Gly Lys Leu Gln Asp Val Val Asn Gln Asn Ala Gln Ala
625                 630                 635                 640

Leu Asn Thr Leu Val Lys Gln Leu Ser Ser Asn Phe Gly Ala Ile Ser
                645                 650                 655

Ser Val Leu Asn Asp Ile Leu Ser Arg Leu Asp Lys Val Glu Ala Glu
            660                 665                 670

Val Gln Ile Asp Arg Leu Ile Thr Gly Arg Leu Gln Ser Leu Gln Thr
        675                 680                 685

Tyr Val Thr Gln Gln Leu Ile Arg Ala Ala Glu Ile Arg Ala Ser Ala
    690                 695                 700
```

```
Asn Leu Ala Ala Thr Lys Met Ser Glu Cys Val Leu Gly Gln Ser Lys
705                 710                 715                 720

Arg Val Asp Phe Cys Gly Lys Gly Tyr His Leu Met Ser Phe Pro Gln
                725                 730                 735

Ser Ala Pro His Gly Val Val Phe Leu His Val Thr Tyr Val Pro Ala
            740                 745                 750

Gln Glu Lys Asn Phe Thr Thr Ala Pro Ala Ile Cys His Asp Gly Lys
        755                 760                 765

Ala His Phe Pro Arg Glu Gly Val Phe Val Ser Asn Gly Thr His Trp
    770                 775                 780

Phe Val Thr Gln Arg Asn Phe Tyr Glu Pro Gln Ile Ile Thr Thr Asp
785                 790                 795                 800

Asn Thr Phe Val Ser Gly Asn Cys Asp Val Val Ile Gly Ile Val Asn
                805                 810                 815

Asn Thr Val Tyr Asp Pro Leu Gln Pro Glu Leu Asp Ser Phe Lys Glu
            820                 825                 830

Glu Leu Asp Lys Tyr Phe Lys Asn His Thr Ser Pro Asp Val Asp Leu
        835                 840                 845

Gly Asp Ile Ser Gly Ile Asn Ala Ser Val Val Asn Ile Gln Lys Glu
    850                 855                 860

Ile Asp Arg Leu Asn Glu Val Ala Lys Asn Leu Asn Glu Ser Leu Ile
865                 870                 875                 880

Asp Leu Gln Glu Leu Gly Lys Tyr Glu Gln Tyr Ile Lys Trp Pro Trp
                885                 890                 895

Tyr Ile Trp Leu Gly Phe Ile Ala Gly Leu Ile Ala Ile Val Met Val
            900                 905                 910

Thr Ile Met Leu Cys Cys Met Thr Ser Cys Cys Ser Cys Leu Lys Gly
        915                 920                 925

Cys Cys Ser Cys Gly Ser Cys Cys Lys Phe Asp Glu Asp Asp Ser Glu
    930                 935                 940

Pro Val Leu Lys Gly Val Lys Leu His Tyr Thr His His His His His
945                 950                 955                 960
```

<210> SEQ ID NO 50
<211> LENGTH: 2883
<212> TYPE: DNA
<213> ORGANISM: Artificial Sequence
<220> FEATURE:
<223> OTHER INFORMATION: RECOMBINANT SPIKE PROTEIN

<400> SEQUENCE: 50

```
atgttcgtct tcctggtgct gctgcccctg gtgtccagca tcactaacct gtgccccttc      60

ggagaggtct tcaacgccac ccgcttcgct tccgtgtacg cctggaacag gaagagaatc     120

tcaaactgcg tcgctgacta ctccgtgctg tacaactcag cctccttcag caccttcaag     180

tgctacggcg tgtcaccaac taagctgaac gacctgtgct tcaccaacgt ctacgccgac     240

tccttcgtga tcaggggaga cgaggtcaga cagatcgctc ctggccagac tggaaagatc     300

gccgactaca actacaagct gcccgacgac ttcaccggtt gcgtcatcgc ttggaacagc     360

aacaacctgg actctaaagt gggtggcaac tacaactacc tgtaccgcct gttccgtaag     420

tcaaacctga agccattcga gagggacatc agcactgaaa tctaccaggc cggatctacc     480

ccttgcaacg gtgtcgaggg cttcaactgc tacttccccc tgcagtccta cggtttccag     540

ccaactaacg gtgtgggcta ccagccttac agagtggtcg tgctgagctt cgaactgctc     600
```

-continued

```
cacgctcctg ctactgtgtg cggtccaaag aagtctacca acctggtcaa gaacaagtgc    660
gtgaacttca acttcaacgg cctgaccgga actggtgtcc tgaccgagag caacaagaag    720
ttcctgccct tccagcagtt cggaagggac atcgctgaca ccactgacgc tgtgcgcgac    780
cctcagaccc tggaaatcct ggacatcact ccatgctcat tcggaggtgt ctccgtgatc    840
acccctggca ccaacacttc taaccaggtc gctgtgctgt accaggacgt caactgcacc    900
gaggtccctg tggccatcca cgctgaccag ctgaccccca cttggcgcgt gtactccacc    960
ggcagcaacg tgttccagac tcgtgctggt tgcctgatcg gcgccgagca cgtgaacaac   1020
agctacgaat gcgacatccc catcggcgct ggaatctgcg cctcttacca gacccagact   1080
aacagcccac gcagggctcg ctctgtggcc tctcagtcaa tcatcgctta caccatgtca   1140
ctgggcgctg aaaactccgt ggcctactct aacaactcaa tcgccatccc caccaacttc   1200
actatcagcg tgaccactga gatcctgcca gtcagcatga ccaagacttc tgtggactgc   1260
actatgtaca tctgcggaga cagcaccgaa tgctctaacc tgctgctgca gtacggctct   1320
ttctgcaccc agctgaaccg tgctctgact ggaatcgccg tggagcagga caagaacact   1380
caggaagtct tcgctcaggt gaagcaaatc tacaagaccc cacctatcaa ggacttcggc   1440
ggattcaact tctcccagat cctgcctgac ccctccaagc caagcaagcg ctctttcatc   1500
gaggacctgc tgttcaacaa ggtcactctg gccgacgctg gattcatcaa gcagtacgga   1560
gactgcctgg gtgacatcgc cgctcgtgac ctgatctgcg ctcagaagtt caacggtctg   1620
accgtgctgc cccactgct  gactgacgaa atgatcgccc agtacactag cgccctgctg   1680
gctggaacca tcacttctgg ttggaccttc ggtgctggcg ccgctctgca gatccctttc   1740
gctatgcaga tggcctaccg tttcaacgga atcggtgtca cccagaacgt gctgtacgag   1800
aaccagaagc tgatcgctaa ccagttcaac tcagccatcg gaaagatcca ggacagcctg   1860
agctctactg cctctgctct gggcaagctg caggacgtcg tgaaccagaa cgcccaggct   1920
ctgaacaccc tggtcaagca gctgtcatcc aacttcggtg ctatcagctc tgtgctgaac   1980
gacatcctgt cccgcctgga caaggtcgag gccgaagtgc agatcgaccg cctgatcact   2040
ggccgtctgc agtcactgca gacctacgtg actcagcagc tgatcagggc cgctgaaatc   2100
agagcctccg ctaacctggc cgctaccaag atgagcgagt gcgtcctggg tcaatctaag   2160
cgtgtggact tctgcggcaa gggataccac ctgatgtcat tccctcagtc tgctccccac   2220
ggtgtggtgt tcctgcacgt cacctacgtg ccagcccagg agaagaactt caccactgcc   2280
cctgctatct gccacgacgg caaggctcac ttccccaggg aaggtgtctt cgtgagcaac   2340
ggcacccact ggttcgtcac tcagagaaac ttctacgagc cacagatcat caccactgac   2400
aacactttcg tgtctggaaa ctgcgacgtg gtcatcggta tcgtcaacaa caccgtgtac   2460
gaccccctgc agccagagct ggactcattc aaggaggaac tggacaagta cttcaagaac   2520
cacacctccc ctgacgtcga cctgggcgac atctcaggaa tcaacgcttc cgtcgtgaac   2580
atccagaagg agatcgaccg cctgaacgaa gtggccaaga acctgaacga aagcctgatc   2640
gacctgcagg agctgggcaa gtacgaacag tacatcaagt ggccttggta catctggctg   2700
ggtttcatcg ctggcctcat cgctatcgtg atggtgacca tcatgctgtg ctgcatgact   2760
tcatgctgct cctgcctgaa gggctgctgc agctgcggat cttgctgcaa gttcgacgag   2820
gacgactctg aacccgtcct gaagggcgtg aagctgcact acacccacca ccaccaccac   2880
cac                                                                 2883
```

```
<210> SEQ ID NO 51
<211> LENGTH: 947
<212> TYPE: PRT
<213> ORGANISM: Artificial Sequence
<220> FEATURE:
<223> OTHER INFORMATION: RECOMBINANT SPIKE PROTEIN

<400> SEQUENCE: 51

Ile Thr Asn Leu Cys Pro Phe Gly Glu Val Phe Asn Ala Thr Arg Phe
1               5                   10                  15

Ala Ser Val Tyr Ala Trp Asn Arg Lys Arg Ile Ser Asn Cys Val Ala
            20                  25                  30

Asp Tyr Ser Val Leu Tyr Asn Ser Ala Ser Phe Ser Thr Phe Lys Cys
        35                  40                  45

Tyr Gly Val Ser Pro Thr Lys Leu Asn Asp Leu Cys Phe Thr Asn Val
    50                  55                  60

Tyr Ala Asp Ser Phe Val Ile Arg Gly Asp Glu Val Arg Gln Ile Ala
65                  70                  75                  80

Pro Gly Gln Thr Gly Lys Ile Ala Asp Tyr Asn Tyr Lys Leu Pro Asp
                85                  90                  95

Asp Phe Thr Gly Cys Val Ile Ala Trp Asn Ser Asn Asn Leu Asp Ser
            100                 105                 110

Lys Val Gly Gly Asn Tyr Asn Tyr Leu Tyr Arg Leu Phe Arg Lys Ser
        115                 120                 125

Asn Leu Lys Pro Phe Glu Arg Asp Ile Ser Thr Glu Ile Tyr Gln Ala
    130                 135                 140

Gly Ser Thr Pro Cys Asn Gly Val Glu Gly Phe Asn Cys Tyr Phe Pro
145                 150                 155                 160

Leu Gln Ser Tyr Gly Phe Gln Pro Thr Asn Gly Val Gly Tyr Gln Pro
                165                 170                 175

Tyr Arg Val Val Val Leu Ser Phe Glu Leu Leu His Ala Pro Ala Thr
            180                 185                 190

Val Cys Gly Pro Lys Lys Ser Thr Asn Leu Val Lys Asn Lys Cys Val
        195                 200                 205

Asn Phe Asn Phe Asn Gly Leu Thr Gly Thr Gly Val Leu Thr Glu Ser
    210                 215                 220

Asn Lys Lys Phe Leu Pro Phe Gln Gln Phe Gly Arg Asp Ile Ala Asp
225                 230                 235                 240

Thr Thr Asp Ala Val Arg Asp Pro Gln Thr Leu Glu Ile Leu Asp Ile
                245                 250                 255

Thr Pro Cys Ser Phe Gly Gly Val Ser Val Ile Thr Pro Gly Thr Asn
            260                 265                 270

Thr Ser Asn Gln Val Ala Val Leu Tyr Gln Asp Val Asn Cys Thr Glu
        275                 280                 285

Val Pro Val Ala Ile His Ala Asp Gln Leu Thr Pro Thr Trp Arg Val
    290                 295                 300

Tyr Ser Thr Gly Ser Asn Val Phe Gln Thr Arg Ala Gly Cys Leu Ile
305                 310                 315                 320

Gly Ala Glu His Val Asn Asn Ser Tyr Glu Cys Asp Ile Pro Ile Gly
                325                 330                 335

Ala Gly Ile Cys Ala Ser Tyr Gln Thr Gln Thr Asn Ser Pro Arg Arg
            340                 345                 350

Ala Arg Ser Val Ala Ser Gln Ser Ile Ile Ala Tyr Thr Met Ser Leu
        355                 360                 365

Gly Ala Glu Asn Ser Val Ala Tyr Ser Asn Asn Ser Ile Ala Ile Pro
```

```
    370                 375                 380

Thr Asn Phe Thr Ile Ser Val Thr Thr Glu Ile Leu Pro Val Ser Met
385                 390                 395                 400

Thr Lys Thr Ser Val Asp Cys Thr Met Tyr Ile Cys Gly Asp Ser Thr
                405                 410                 415

Glu Cys Ser Asn Leu Leu Leu Gln Tyr Gly Ser Phe Cys Thr Gln Leu
            420                 425                 430

Asn Arg Ala Leu Thr Gly Ile Ala Val Glu Gln Asp Lys Asn Thr Gln
        435                 440                 445

Glu Val Phe Ala Gln Val Lys Gln Ile Tyr Lys Thr Pro Pro Ile Lys
    450                 455                 460

Asp Phe Gly Gly Phe Asn Phe Ser Gln Ile Leu Pro Asp Pro Ser Lys
465                 470                 475                 480

Pro Ser Lys Arg Ser Phe Ile Glu Asp Leu Leu Phe Asn Lys Val Thr
                485                 490                 495

Leu Ala Asp Ala Gly Phe Ile Lys Gln Tyr Gly Asp Cys Leu Gly Asp
            500                 505                 510

Ile Ala Ala Arg Asp Leu Ile Cys Ala Gln Lys Phe Asn Gly Leu Thr
        515                 520                 525

Val Leu Pro Pro Leu Leu Thr Asp Glu Met Ile Ala Gln Tyr Thr Ser
    530                 535                 540

Ala Leu Leu Ala Gly Thr Ile Thr Ser Gly Trp Thr Phe Gly Ala Gly
545                 550                 555                 560

Ala Ala Leu Gln Ile Pro Phe Ala Met Gln Met Ala Tyr Arg Phe Asn
                565                 570                 575

Gly Ile Gly Val Thr Gln Asn Val Leu Tyr Glu Asn Gln Lys Leu Ile
            580                 585                 590

Ala Asn Gln Phe Asn Ser Ala Ile Gly Lys Ile Gln Asp Ser Leu Ser
        595                 600                 605

Ser Thr Ala Ser Ala Leu Gly Lys Leu Gln Asp Val Val Asn Gln Asn
    610                 615                 620

Ala Gln Ala Leu Asn Thr Leu Val Lys Gln Leu Ser Ser Asn Phe Gly
625                 630                 635                 640

Ala Ile Ser Ser Val Leu Asn Asp Ile Leu Ser Arg Leu Asp Lys Val
                645                 650                 655

Glu Ala Glu Val Gln Ile Asp Arg Leu Ile Thr Gly Arg Leu Gln Ser
            660                 665                 670

Leu Gln Thr Tyr Val Thr Gln Gln Leu Ile Arg Ala Ala Glu Ile Arg
        675                 680                 685

Ala Ser Ala Asn Leu Ala Ala Thr Lys Met Ser Glu Cys Val Leu Gly
    690                 695                 700

Gln Ser Lys Arg Val Asp Phe Cys Gly Lys Gly Tyr His Leu Met Ser
705                 710                 715                 720

Phe Pro Gln Ser Ala Pro His Gly Val Val Phe Leu His Val Thr Tyr
                725                 730                 735

Val Pro Ala Gln Glu Lys Asn Phe Thr Thr Ala Pro Ala Ile Cys His
            740                 745                 750

Asp Gly Lys Ala His Phe Pro Arg Glu Gly Val Phe Val Ser Asn Gly
        755                 760                 765

Thr His Trp Phe Val Thr Gln Arg Asn Phe Tyr Glu Pro Gln Ile Ile
    770                 775                 780

Thr Thr Asp Asn Thr Phe Val Ser Gly Asn Cys Asp Val Val Ile Gly
785                 790                 795                 800
```

```
Ile Val Asn Asn Thr Val Tyr Asp Pro Leu Gln Pro Glu Leu Asp Ser
                805                 810                 815

Phe Lys Glu Glu Leu Asp Lys Tyr Phe Lys Asn His Thr Ser Pro Asp
            820                 825                 830

Val Asp Leu Gly Asp Ile Ser Gly Ile Asn Ala Ser Val Val Asn Ile
        835                 840                 845

Gln Lys Glu Ile Asp Arg Leu Asn Glu Val Ala Lys Asn Leu Asn Glu
    850                 855                 860

Ser Leu Ile Asp Leu Gln Glu Leu Gly Lys Tyr Glu Gln Tyr Ile Lys
865                 870                 875                 880

Trp Pro Trp Tyr Ile Trp Leu Gly Phe Ile Ala Gly Leu Ile Ala Ile
                885                 890                 895

Val Met Val Thr Ile Met Leu Cys Cys Met Thr Ser Cys Cys Ser Cys
            900                 905                 910

Leu Lys Gly Cys Cys Ser Cys Gly Ser Cys Cys Lys Phe Asp Glu Asp
        915                 920                 925

Asp Ser Glu Pro Val Leu Lys Gly Val Lys Leu His Tyr Thr His His
    930                 935                 940

His His His
945


<210> SEQ ID NO 52
<211> LENGTH: 901
<212> TYPE: PRT
<213> ORGANISM: Artificial Sequence
<220> FEATURE:
<223> OTHER INFORMATION: RECOMBINANT SPIKE PROTEIN

<400> SEQUENCE: 52

Met Phe Val Phe Leu Val Leu Leu Pro Leu Val Ser Ser Ile Thr Asn
1               5                   10                  15

Leu Cys Pro Phe Gly Glu Val Phe Asn Ala Thr Arg Phe Ala Ser Val
            20                  25                  30

Tyr Ala Trp Asn Arg Lys Arg Ile Ser Asn Cys Val Ala Asp Tyr Ser
        35                  40                  45

Val Leu Tyr Asn Ser Ala Ser Phe Ser Thr Phe Lys Cys Tyr Gly Val
    50                  55                  60

Ser Pro Thr Lys Leu Asn Asp Leu Cys Phe Thr Asn Val Tyr Ala Asp
65                  70                  75                  80

Ser Phe Val Ile Arg Gly Asp Glu Val Arg Gln Ile Ala Pro Gly Gln
                85                  90                  95

Thr Gly Lys Ile Ala Asp Tyr Asn Tyr Lys Leu Pro Asp Asp Phe Thr
            100                 105                 110

Gly Cys Val Ile Ala Trp Asn Ser Asn Asn Leu Asp Ser Lys Val Gly
        115                 120                 125

Gly Asn Tyr Asn Tyr Leu Tyr Arg Leu Phe Arg Lys Ser Asn Leu Lys
    130                 135                 140

Pro Phe Glu Arg Asp Ile Ser Thr Glu Ile Tyr Gln Ala Gly Ser Thr
145                 150                 155                 160

Pro Cys Asn Gly Val Glu Gly Phe Asn Cys Tyr Phe Pro Leu Gln Ser
                165                 170                 175

Tyr Gly Phe Gln Pro Thr Asn Gly Val Gly Tyr Gln Pro Tyr Arg Val
            180                 185                 190

Val Val Leu Ser Phe Glu Leu Leu His Ala Pro Ala Thr Val Cys Gly
        195                 200                 205
```

-continued

```
Pro Lys Lys Ser Thr Asn Leu Val Lys Asn Lys Cys Val Asn Phe Asn
    210                 215                 220

Phe Asn Gly Leu Thr Gly Thr Gly Val Leu Thr Glu Ser Asn Lys Lys
225                 230                 235                 240

Phe Leu Pro Phe Gln Gln Phe Gly Arg Asp Ile Ala Asp Thr Thr Asp
                245                 250                 255

Ala Val Arg Asp Pro Gln Thr Leu Glu Ile Leu Asp Ile Thr Pro Cys
            260                 265                 270

Ser Phe Gly Gly Val Ser Val Ile Thr Pro Gly Thr Asn Thr Ser Asn
        275                 280                 285

Gln Val Ala Val Leu Tyr Gln Asp Val Asn Cys Thr Glu Val Pro Val
    290                 295                 300

Ala Ile His Ala Asp Gln Leu Thr Pro Thr Trp Arg Val Tyr Ser Thr
305                 310                 315                 320

Gly Ser Asn Val Phe Gln Thr Arg Ala Gly Cys Leu Ile Gly Ala Glu
                325                 330                 335

His Val Asn Asn Ser Tyr Glu Cys Asp Ile Pro Ile Gly Ala Gly Ile
            340                 345                 350

Cys Ala Ser Tyr Gln Thr Gln Thr Asn Ser Pro Arg Arg Ala Arg Ser
        355                 360                 365

Val Ala Ser Gln Ser Ile Ile Ala Tyr Thr Met Ser Leu Gly Ala Glu
    370                 375                 380

Asn Ser Val Ala Tyr Ser Asn Asn Ser Ile Ala Ile Pro Thr Asn Phe
385                 390                 395                 400

Thr Ile Ser Val Thr Thr Glu Ile Leu Pro Val Ser Met Thr Lys Thr
                405                 410                 415

Ser Val Asp Cys Thr Met Tyr Ile Cys Gly Asp Ser Thr Glu Cys Ser
            420                 425                 430

Asn Leu Leu Leu Gln Tyr Gly Ser Phe Cys Thr Gln Leu Asn Arg Ala
        435                 440                 445

Leu Thr Gly Ile Ala Val Glu Gln Asp Lys Asn Thr Gln Glu Val Phe
    450                 455                 460

Ala Gln Val Lys Gln Ile Tyr Lys Thr Pro Pro Ile Lys Asp Phe Gly
465                 470                 475                 480

Gly Phe Asn Phe Ser Gln Ile Leu Pro Asp Pro Ser Lys Pro Ser Lys
                485                 490                 495

Arg Ser Phe Ile Glu Asp Leu Leu Phe Asn Lys Val Thr Leu Ala Asp
            500                 505                 510

Ala Gly Phe Ile Lys Gln Tyr Gly Asp Cys Leu Gly Asp Ile Ala Ala
        515                 520                 525

Arg Asp Leu Ile Cys Ala Gln Lys Phe Asn Gly Leu Thr Val Leu Pro
    530                 535                 540

Pro Leu Leu Thr Asp Glu Met Ile Ala Gln Tyr Thr Ser Ala Leu Leu
545                 550                 555                 560

Ala Gly Thr Ile Thr Ser Gly Trp Thr Phe Gly Ala Gly Ala Ala Leu
                565                 570                 575

Gln Ile Pro Phe Ala Met Gln Met Ala Tyr Arg Phe Asn Gly Ile Gly
            580                 585                 590

Val Thr Gln Asn Val Leu Tyr Glu Asn Gln Lys Leu Ile Ala Asn Gln
        595                 600                 605

Phe Asn Ser Ala Ile Gly Lys Ile Gln Asp Ser Leu Ser Ser Thr Ala
    610                 615                 620
```

```
Ser Ala Leu Gly Lys Leu Gln Asp Val Val Asn Gln Asn Ala Gln Ala
625                 630                 635                 640

Leu Asn Thr Leu Val Lys Gln Leu Ser Ser Asn Phe Gly Ala Ile Ser
                645                 650                 655

Ser Val Leu Asn Asp Ile Leu Ser Arg Leu Asp Lys Val Glu Ala Glu
            660                 665                 670

Val Gln Ile Asp Arg Leu Ile Thr Gly Arg Leu Gln Ser Leu Gln Thr
        675                 680                 685

Tyr Val Thr Gln Gln Leu Ile Arg Ala Ala Glu Ile Arg Ala Ser Ala
    690                 695                 700

Asn Leu Ala Ala Thr Lys Met Ser Glu Cys Val Leu Gly Gln Ser Lys
705                 710                 715                 720

Arg Val Asp Phe Cys Gly Lys Gly Tyr His Leu Met Ser Phe Pro Gln
                725                 730                 735

Ser Ala Pro His Gly Val Val Phe Leu His Val Thr Tyr Val Pro Ala
            740                 745                 750

Gln Glu Lys Asn Phe Thr Thr Ala Pro Ala Ile Cys His Asp Gly Lys
        755                 760                 765

Ala His Phe Pro Arg Glu Gly Val Phe Val Ser Asn Gly Thr His Trp
    770                 775                 780

Phe Val Thr Gln Arg Asn Phe Tyr Glu Pro Gln Ile Ile Thr Thr Asp
785                 790                 795                 800

Asn Thr Phe Val Ser Gly Asn Cys Asp Val Val Ile Gly Ile Val Asn
                805                 810                 815

Asn Thr Val Tyr Asp Pro Leu Gln Pro Glu Leu Asp Ser Phe Lys Glu
            820                 825                 830

Glu Leu Asp Lys Tyr Phe Lys Asn His Thr Ser Pro Asp Val Asp Leu
        835                 840                 845

Gly Asp Ile Ser Gly Ile Asn Ala Ser Val Val Asn Ile Gln Lys Glu
    850                 855                 860

Ile Asp Arg Leu Asn Glu Val Ala Lys Asn Leu Asn Glu Ser Leu Ile
865                 870                 875                 880

Asp Leu Gln Glu Leu Gly Lys Tyr Glu Gln Tyr Ile Lys Trp Pro His
                885                 890                 895

His His His His His
            900


<210> SEQ ID NO 53
<211> LENGTH: 2706
<212> TYPE: DNA
<213> ORGANISM: Artificial Sequence
<220> FEATURE:
<223> OTHER INFORMATION: RECOMBINANT SPIKE PROTEIN

<400> SEQUENCE: 53

atgttcgtct tcctggtgct gctgcccctg gtgtccagca tcactaacct gtgccccttc      60

ggagaggtct tcaacgccac ccgcttcgct tccgtgtacg cctggaacag gaagagaatc     120

tcaaactgcg tcgctgacta ctccgtgctg tacaactcag cctccttcag caccttcaag     180

tgctacggcg tgtcaccaac taagctgaac gacctgtgct tcaccaacgt ctacgccgac     240

tccttcgtga tcaggggaga cgaggtcaga cagatcgctc ctggccagac tggaaagatc     300

gccgactaca actacaagct gcccgacgac ttcaccggtt gcgtcatcgc ttggaacagc     360

aacaacctgg actctaaagt gggtggcaac tacaactacc tgtaccgcct gttccgtaag     420

tcaaacctga agccattcga gagggacatc agcactgaaa tctaccaggc cggatctacc     480
```

```
ccttgcaacg gtgtcgaggg cttcaactgc tacttccccc tgcagtccta cggtttccag    540
ccaactaacg gtgtgggcta ccagccttac agagtggtcg tgctgagctt cgaactgctc    600
cacgctcctg ctactgtgtg cggtccaaag aagtctacca acctggtcaa gaacaagtgc    660
gtgaacttca acttcaacgg cctgaccgga actggtgtcc tgaccgagag caacaagaag    720
ttcctgccct tccagcagtt cggaagggac atcgctgaca ccactgacgc tgtgcgcgac    780
cctcagaccc tggaaatcct ggacatcact ccatgctcat tcggaggtgt ctccgtgatc    840
acccctggca ccaacacttc taaccaggtc gctgtgctgt accaggacgt caactgcacc    900
gaggtccctg tggccatcca cgctgaccag ctgacccccca cttggcgcgt gtactccacc    960
ggcagcaacg tgttccagac tcgtgctggt tgcctgatcg gcgccgagca cgtgaacaac   1020
agctacgaat gcgacatccc catcggcgct ggaatctgcg cctcttacca gacccagact   1080
aacagcccac gcagggctcg ctctgtggcc tctcagtcaa tcatcgctta caccatgtca   1140
ctgggcgctg aaaactccgt ggcctactct aacaactcaa tcgccatccc caccaacttc   1200
actatcagcg tgaccactga gatcctgcca gtcagcatga ccaagacttc tgtggactgc   1260
actatgtaca tctgcggaga cagcaccgaa tgctctaacc tgctgctgca gtacggctct   1320
ttctgcaccc agctgaaccg tgctctgact ggaatcgccg tggagcagga caagaacact   1380
caggaagtct tcgctcaggt gaagcaaatc tacaagaccc cacctatcaa ggacttcggc   1440
ggattcaact tctcccagat cctgcctgac ccctccaagc caagcaagcg ctctttcatc   1500
gaggacctgc tgttcaacaa ggtcactctg gccgacgctg gattcatcaa gcagtacgga   1560
gactgcctgg gtgacatcgc cgctcgtgac ctgatctgcg ctcagaagtt caacggtctg   1620
accgtgctgc cccactgct gactgacgaa atgatcgccc agtacactag cgccctgctg    1680
gctggaacca tcacttctgg ttggaccttc ggtgctggcg ccgctctgca gatccctttc   1740
gctatgcaga tggcctaccg tttcaacgga atcggtgtca cccagaacgt gctgtacgag   1800
aaccagaagc tgatcgctaa ccagttcaac tcagccatcg gaaagatcca ggacagcctg   1860
agctctactg cctctgctct gggcaagctg caggacgtcg tgaaccagaa cgcccaggct   1920
ctgaacaccc tggtcaagca gctgtcatcc aacttcggtg ctatcagctc tgtgctgaac   1980
gacatcctgt cccgcctgga caaggtcgag gccgaagtgc agatcgaccg cctgatcact   2040
ggccgtctgc agtcactgca gacctacgtg actcagcagc tgatcagggc cgctgaaatc   2100
agagcctccg ctaacctggc cgctaccaag atgagcgagt gcgtcctggg tcaatctaag   2160
cgtgtggact tctgcggcaa gggataccac ctgatgtcat tccctcagtc tgctccccac   2220
ggtgtggtgt tcctgcacgt cacctacgtg ccagcccagg agaagaactt caccactgcc   2280
cctgctatct gccacgacgg caaggctcac ttccccaggg aaggtgtctt cgtgagcaac   2340
ggcacccact ggttcgtcac tcagagaaac ttctacgagc cacagatcat caccactgac   2400
aacactttcg tgtctggaaa ctgcgacgtg gtcatcggta tcgtcaacaa caccgtgtac   2460
gacccccctgc agccagagct ggactcattc aaggaggaac tggacaagta cttcaagaac   2520
cacacctccc ctgacgtcga cctgggcgac atctcaggaa tcaacgcttc cgtcgtgaac   2580
atccagaagg agatcgaccg cctgaacgaa gtggccaaga acctgaacga aagcctgatc   2640
gacctgcagg agctgggcaa gtacgaacag tacatcaagt ggcctcacca ccaccaccac   2700
caccac                                                              2706
```

<210> SEQ ID NO 54

<211> LENGTH: 888
<212> TYPE: PRT
<213> ORGANISM: Artificial Sequence
<220> FEATURE:
<223> OTHER INFORMATION: RECOMBINANT SPIKE PROTEIN

<400> SEQUENCE: 54

```
Ile Thr Asn Leu Cys Pro Phe Gly Glu Val Phe Asn Ala Thr Arg Phe
1               5                   10                  15

Ala Ser Val Tyr Ala Trp Asn Arg Lys Arg Ile Ser Asn Cys Val Ala
            20                  25                  30

Asp Tyr Ser Val Leu Tyr Asn Ser Ala Ser Phe Ser Thr Phe Lys Cys
        35                  40                  45

Tyr Gly Val Ser Pro Thr Lys Leu Asn Asp Leu Cys Phe Thr Asn Val
    50                  55                  60

Tyr Ala Asp Ser Phe Val Ile Arg Gly Asp Glu Val Arg Gln Ile Ala
65                  70                  75                  80

Pro Gly Gln Thr Gly Lys Ile Ala Asp Tyr Asn Tyr Lys Leu Pro Asp
                85                  90                  95

Asp Phe Thr Gly Cys Val Ile Ala Trp Asn Ser Asn Asn Leu Asp Ser
            100                 105                 110

Lys Val Gly Gly Asn Tyr Asn Tyr Leu Tyr Arg Leu Phe Arg Lys Ser
        115                 120                 125

Asn Leu Lys Pro Phe Glu Arg Asp Ile Ser Thr Glu Ile Tyr Gln Ala
    130                 135                 140

Gly Ser Thr Pro Cys Asn Gly Val Glu Gly Phe Asn Cys Tyr Phe Pro
145                 150                 155                 160

Leu Gln Ser Tyr Gly Phe Gln Pro Thr Asn Gly Val Gly Tyr Gln Pro
                165                 170                 175

Tyr Arg Val Val Val Leu Ser Phe Glu Leu Leu His Ala Pro Ala Thr
            180                 185                 190

Val Cys Gly Pro Lys Lys Ser Thr Asn Leu Val Lys Asn Lys Cys Val
        195                 200                 205

Asn Phe Asn Phe Asn Gly Leu Thr Gly Thr Gly Val Leu Thr Glu Ser
    210                 215                 220

Asn Lys Lys Phe Leu Pro Phe Gln Gln Phe Gly Arg Asp Ile Ala Asp
225                 230                 235                 240

Thr Thr Asp Ala Val Arg Asp Pro Gln Thr Leu Glu Ile Leu Asp Ile
                245                 250                 255

Thr Pro Cys Ser Phe Gly Gly Val Ser Val Ile Thr Pro Gly Thr Asn
            260                 265                 270

Thr Ser Asn Gln Val Ala Val Leu Tyr Gln Asp Val Asn Cys Thr Glu
        275                 280                 285

Val Pro Val Ala Ile His Ala Asp Gln Leu Thr Pro Thr Trp Arg Val
    290                 295                 300

Tyr Ser Thr Gly Ser Asn Val Phe Gln Thr Arg Ala Gly Cys Leu Ile
305                 310                 315                 320

Gly Ala Glu His Val Asn Asn Ser Tyr Glu Cys Asp Ile Pro Ile Gly
                325                 330                 335

Ala Gly Ile Cys Ala Ser Tyr Gln Thr Gln Thr Asn Ser Pro Arg Arg
            340                 345                 350

Ala Arg Ser Val Ala Ser Gln Ser Ile Ile Ala Tyr Thr Met Ser Leu
        355                 360                 365

Gly Ala Glu Asn Ser Val Ala Tyr Ser Asn Asn Ser Ile Ala Ile Pro
    370                 375                 380
```

-continued

```
Thr Asn Phe Thr Ile Ser Val Thr Thr Glu Ile Leu Pro Val Ser Met
385                 390                 395                 400

Thr Lys Thr Ser Val Asp Cys Thr Met Tyr Ile Cys Gly Asp Ser Thr
                405                 410                 415

Glu Cys Ser Asn Leu Leu Leu Gln Tyr Gly Ser Phe Cys Thr Gln Leu
            420                 425                 430

Asn Arg Ala Leu Thr Gly Ile Ala Val Glu Gln Asp Lys Asn Thr Gln
        435                 440                 445

Glu Val Phe Ala Gln Val Lys Gln Ile Tyr Lys Thr Pro Pro Ile Lys
    450                 455                 460

Asp Phe Gly Gly Phe Asn Phe Ser Gln Ile Leu Pro Asp Pro Ser Lys
465                 470                 475                 480

Pro Ser Lys Arg Ser Phe Ile Glu Asp Leu Leu Phe Asn Lys Val Thr
                485                 490                 495

Leu Ala Asp Ala Gly Phe Ile Lys Gln Tyr Gly Asp Cys Leu Gly Asp
            500                 505                 510

Ile Ala Ala Arg Asp Leu Ile Cys Ala Gln Lys Phe Asn Gly Leu Thr
        515                 520                 525

Val Leu Pro Pro Leu Leu Thr Asp Glu Met Ile Ala Gln Tyr Thr Ser
    530                 535                 540

Ala Leu Leu Ala Gly Thr Ile Thr Ser Gly Trp Thr Phe Gly Ala Gly
545                 550                 555                 560

Ala Ala Leu Gln Ile Pro Phe Ala Met Gln Met Ala Tyr Arg Phe Asn
                565                 570                 575

Gly Ile Gly Val Thr Gln Asn Val Leu Tyr Glu Asn Gln Lys Leu Ile
            580                 585                 590

Ala Asn Gln Phe Asn Ser Ala Ile Gly Lys Ile Gln Asp Ser Leu Ser
        595                 600                 605

Ser Thr Ala Ser Ala Leu Gly Lys Leu Gln Asp Val Val Asn Gln Asn
    610                 615                 620

Ala Gln Ala Leu Asn Thr Leu Val Lys Gln Leu Ser Ser Asn Phe Gly
625                 630                 635                 640

Ala Ile Ser Ser Val Leu Asn Asp Ile Leu Ser Arg Leu Asp Lys Val
                645                 650                 655

Glu Ala Glu Val Gln Ile Asp Arg Leu Ile Thr Gly Arg Leu Gln Ser
            660                 665                 670

Leu Gln Thr Tyr Val Thr Gln Gln Leu Ile Arg Ala Ala Glu Ile Arg
        675                 680                 685

Ala Ser Ala Asn Leu Ala Ala Thr Lys Met Ser Glu Cys Val Leu Gly
    690                 695                 700

Gln Ser Lys Arg Val Asp Phe Cys Gly Lys Gly Tyr His Leu Met Ser
705                 710                 715                 720

Phe Pro Gln Ser Ala Pro His Gly Val Val Phe Leu His Val Thr Tyr
                725                 730                 735

Val Pro Ala Gln Glu Lys Asn Phe Thr Thr Ala Pro Ala Ile Cys His
            740                 745                 750

Asp Gly Lys Ala His Phe Pro Arg Glu Gly Val Phe Val Ser Asn Gly
        755                 760                 765

Thr His Trp Phe Val Thr Gln Arg Asn Phe Tyr Glu Pro Gln Ile Ile
    770                 775                 780

Thr Thr Asp Asn Thr Phe Val Ser Gly Asn Cys Asp Val Val Ile Gly
785                 790                 795                 800
```

-continued

```
Ile Val Asn Asn Thr Val Tyr Asp Pro Leu Gln Pro Glu Leu Asp Ser
                805                 810                 815

Phe Lys Glu Glu Leu Asp Lys Tyr Phe Lys Asn His Thr Ser Pro Asp
            820                 825                 830

Val Asp Leu Gly Asp Ile Ser Gly Ile Asn Ala Ser Val Val Asn Ile
        835                 840                 845

Gln Lys Glu Ile Asp Arg Leu Asn Glu Val Ala Lys Asn Leu Asn Glu
    850                 855                 860

Ser Leu Ile Asp Leu Gln Glu Leu Gly Lys Tyr Glu Gln Tyr Ile Lys
865                 870                 875                 880

Trp Pro His His His His His His
                885
```

```
<210> SEQ ID NO 55
<211> LENGTH: 3819
<212> TYPE: DNA
<213> ORGANISM: Artificial Sequence
<220> FEATURE:
<223> OTHER INFORMATION: RECOMBINANT SPIKE PROTEIN

<400> SEQUENCE: 55

atgttcgtct tcctggtgct gctgcccctg gtgtccagcc agtgcgtgaa cctgaccact     60

aggactcagc tgcctcccgc ttacaccaac tcattcactc gcggtgtgta ctaccctgac    120

aaggtcttcc gttcttcagt gctgcactca actcaggacc tgttcctgcc cttcttctcc    180

aacgtcacct ggttccacgc catccacgtg tccggcacca acggcactaa gcgcttcgac    240

aacccagtgc tgcctttcaa cgacggtgtc tacttcgctt caaccgagaa gtccaacatc    300

atccgtggat ggatcttcgg caccactctg gacagcaaga ctcagtctct gctgatcgtc    360

aacaacgcca ccaacgtggt catcaaggtc tgcgaattcc agttctgcaa cgacccattc    420

ctgggcgtct actaccacaa gaacaacaag tcatggatgg agtccgaatt ccgcgtctac    480

tccagcgcta acaactgcac tttcgagtac gtgtcccagc ctttcctgat ggacctggaa    540

ggaaagcagg gtaacttcaa gaacctgagg gagttcgtgt tcaagaacat cgacggatac    600

ttcaagattt acagcaagca caccccaatc aacctggtgc gcgacctgcc tcagggtttc    660

tctgctctgg agccactggt ggacctgcct atcggcatca acatcacccg cttccagact    720

ctgctggctc tgcaccgttc ctacctgact ccaggcgact catcttctgg atggactgct    780

ggagctgctg cttactacgt gggctacctg cagcctcgca ccttcctgct gaagtacaac    840

gaaaacggaa ccatcactga cgccgtcgac tgcgctctgg accctctgtc agaaaccaag    900

tgcactctga agtccttcac cgtggagaag ggcatctacc agacttcaaa cttcagggtg    960

cagcccaccg aatccatcgt cagattccct aacatcacta acctgtgccc cttcggagag   1020

gtcttcaacg ccacccgctt cgcttccgtg tacgcctgga acaggaagag aatctcaaac   1080

tgcgtcgctg actactccgt gctgtacaac tcagcctcct tcagcacctt caagtgctac   1140

ggcgtgtcac caactaagct gaacgacctg tgcttcacca acgtctacgc cgactccttc   1200

gtgatcaggg gagacgaggt cagacagatc gctcctggcc agactggaaa gatcgccgac   1260

tacaactaca agctgcccga cgacttcacc ggttgcgtca tcgcttggaa cagcaacaac   1320

ctggactcta aagtgggtgg caactacaac tacctgtacc gcctgttccg taagtcaaac   1380

ctgaagccat tcgagaggga catcagcact gaaatctacc aggccggatc taccccttgc   1440

aacggtgtcg agggcttcaa ctgctacttc cccctgcagt cctacggttt ccagccaact   1500

aacggtgtgg gctaccagcc ttacagagtg gtcgtgctga gcttcgaact gctccacgct   1560
```

```
cctgctactg tgtgcggtcc aaagaagtct accaacctgg tcaagaacaa gtgcgtgaac   1620
ttcaacttca acggcctgac cggaactggt gtcctgaccg agagcaacaa gaagttcctg   1680
cccttccagc agttcggaag ggacatcgct gacaccactg acgctgtgcg cgaccctcag   1740
accctggaaa tcctggacat cactccatgc tcattcggag gtgtctccgt gatcacccct   1800
ggcaccaaca cttctaacca ggtcgctgtg ctgtaccagg acgtcaactg caccgaggtc   1860
cctgtggcca tccacgctga ccagctgacc cccacttggc gcgtgtactc caccggcagc   1920
aacgtgttcc agactcgtgc tggttgcctg atcggcgccg agcacgtgaa caacagctac   1980
gaatgcgaca tccccatcgg cgctggaatc tgcgcctctt accagaccca gactaacagc   2040
ccacagcagg ctcagtctgt ggcctctcag tcaatcatcg cttacaccat gtcactgggc   2100
gctgaaaact ccgtggccta ctctaacaac tcaatcgcca tccccaccaa cttcactatc   2160
agcgtgacca ctgagatcct gccagtcagc atgaccaaga cttctgtgga ctgcactatg   2220
tacatctgcg gagacagcac cgaatgctct aacctgctgc tgcagtacgg ctctttctgc   2280
acccagctga accgtgctct gactggaatc gccgtggagc aggacaagaa cactcaggaa   2340
gtcttcgctc aggtgaagca aatctacaag accccaccta tcaaggactt cggcggattc   2400
aacttctccc agatcctgcc tgacccctcc aagccaagca agcgctcttt catcgaggac   2460
ctgctgttca acaaggtcac tctggccgac gctggattca tcaagcagta cggagactgc   2520
ctgggtgaca tcgccgctcg tgacctgatc tgcgctcaga agttcaacgg tctgaccgtg   2580
ctgcccccac tgctgactga cgaaatgatc gcccagtaca ctagcgccct gctggctgga   2640
accatcactt ctggttggac cttcggtgct ggcgccgctc tgcagatccc tttcgctatg   2700
cagatggcct accgtttcaa cggaatcggt gtcacccaga acgtgctgta cgagaaccag   2760
aagctgatcg ctaaccagtt caactcagcc atcggaaaga tccaggacag cctgagctct   2820
actgcctctg ctctgggcaa gctgcaggac gtcgtgaacc agaacgccca ggctctgaac   2880
accctggtca agcagctgtc atccaacttc ggtgctatca gctctgtgct gaacgacatc   2940
ctgtcccgcc tggacaaggt cgaggccgaa gtgcagatcg accgcctgat cactggccgt   3000
ctgcagtcac tgcagaccta cgtgactcag cagctgatca gggccgctga aatcagagcc   3060
tccgctaacc tggccgctac caagatgagc gagtgcgtcc tgggtcaatc taagcgtgtg   3120
gacttctgcg gcaagggata ccacctgatg tcattccctc agtctgctcc ccacggtgtg   3180
gtgttcctgc acgtcaccta cgtgccagcc caggagaaga acttcaccac tgcccctgct   3240
atctgccacg acggcaaggc tcacttcccc agggaaggtg tcttcgtgag caacggcacc   3300
cactggttcg tcactcagag aaacttctac gagccacaga tcatcaccac tgacaacact   3360
ttcgtgtctg gaaactgcga cgtggtcatc ggtatcgtca acaacaccgt gtacgacccc   3420
ctgcagccag agctggactc attcaaggag gaactggaca agtacttcaa gaaccacacc   3480
tcccctgacg tcgacctggg cgacatctca ggaatcaacg cttccgtcgt gaacatccag   3540
aaggagatcg accgcctgaa cgaagtggcc aagaacctga acgaaagcct gatcgacctg   3600
caggagctgg gcaagtacga acagtacatc aagtggcctt ggtacatctg gctgggtttc   3660
atcgctggcc tcatcgctat cgtgatggtg accatcatgc tgtgctgcat gacttcatgc   3720
tgctcctgcc tgaagggctg ctgcagctgc ggatcttgct gcaagttcga cgaggacgac   3780
tctgaacccg tcctgaaggg cgtgaagctg cactacacc                          3819
```

<210> SEQ ID NO 56

<211> LENGTH: 1279
<212> TYPE: PRT
<213> ORGANISM: Artificial Sequence
<220> FEATURE:
<223> OTHER INFORMATION: RECOMBINANT SPIKE PROTEIN

<400> SEQUENCE: 56

```
Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380
```

-continued

```
Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Gln Gln Ala Gln Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800
```

-continued

```
Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
            980                 985                 990

Ile Asp Arg Leu Ile Thr Gly Arg  Leu Gln Ser Leu Gln  Thr Tyr Val
        995                 1000                 1005

Thr Gln  Gln Leu Ile Arg Ala  Ala Glu Ile Arg Ala  Ser Ala Asn
    1010                 1015                 1020

Leu Ala  Ala Thr Lys Met Ser  Glu Cys Val Leu Gly  Gln Ser Lys
    1025                 1030                 1035

Arg Val  Asp Phe Cys Gly Lys  Gly Tyr His Leu Met  Ser Phe Pro
    1040                 1045                 1050

Gln Ser  Ala Pro His Gly Val  Val Phe Leu His Val  Thr Tyr Val
    1055                 1060                 1065

Pro Ala  Gln Glu Lys Asn Phe  Thr Thr Ala Pro Ala  Ile Cys His
    1070                 1075                 1080

Asp Gly  Lys Ala His Phe Pro  Arg Glu Gly Val Phe  Val Ser Asn
    1085                 1090                 1095

Gly Thr  His Trp Phe Val Thr  Gln Arg Asn Phe Tyr  Glu Pro Gln
    1100                 1105                 1110

Ile Ile  Thr Thr Asp Asn Thr  Phe Val Ser Gly Asn  Cys Asp Val
    1115                 1120                 1125

Val Ile  Gly Ile Val Asn Asn  Thr Val Tyr Asp Pro  Leu Gln Pro
    1130                 1135                 1140

Glu Leu  Asp Ser Phe Lys Glu  Glu Leu Asp Lys Tyr  Phe Lys Asn
    1145                 1150                 1155

His Thr  Ser Pro Asp Val Asp  Leu Gly Asp Ile Ser  Gly Ile Asn
    1160                 1165                 1170

Ala Ser  Val Val Asn Ile Gln  Lys Glu Ile Asp Arg  Leu Asn Glu
    1175                 1180                 1185

Val Ala  Lys Asn Leu Asn Glu  Ser Leu Ile Asp Leu  Gln Glu Leu
    1190                 1195                 1200

Gly Lys  Tyr Glu Gln Tyr Ile  Lys Trp Pro Trp Tyr  Ile Trp Leu
```

```
    1205                1210                1215

Gly Phe  Ile Ala Gly Leu Ile  Ala Ile Val Met Val  Thr Ile Met
    1220                1225                1230

Leu Cys  Cys Met Thr Ser Cys  Cys Ser Cys Leu Lys  Gly Cys Cys
    1235                1240                1245

Ser Cys  Gly Ser Cys Cys Lys  Phe Asp Glu Asp Asp  Ser Glu Pro
    1250                1255                1260

Val Leu  Lys Gly Val Lys Leu  His Tyr Thr His His  His His His
    1265                1270                1275

His


<210> SEQ ID NO 57
<211> LENGTH: 3837
<212> TYPE: DNA
<213> ORGANISM: Artificial Sequence
<220> FEATURE:
<223> OTHER INFORMATION: RECOMBINANT SPIKE PROTEIN

<400> SEQUENCE: 57

atgttcgtct tcctggtgct gctgcccctg gtgtccagcc agtgcgtgaa cctgaccact     60

aggactcagc tgcctcccgc ttacaccaac tcattcactc gcggtgtgta ctaccctgac    120

aaggtcttcc gttcttcagt gctgcactca actcaggacc tgttcctgcc cttcttctcc    180

aacgtcacct ggttccacgc catccacgtg tccggcacca acggcactaa gcgcttcgac    240

aacccagtgc tgcctttcaa cgacggtgtc tacttcgctt caaccgagaa gtccaacatc    300

atccgtggat ggatcttcgg caccactctg gacagcaaga ctcagtctct gctgatcgtc    360

aacaacgcca ccaacgtggt catcaaggtc tgcgaattcc agttctgcaa cgacccattc    420

ctgggcgtct actaccacaa gaacaacaag tcatggatgg agtccgaatt ccgcgtctac    480

tccagcgcta acaactgcac tttcgagtac gtgtcccagc ctttcctgat ggacctggaa    540

ggaaagcagg gtaacttcaa gaacctgagg gagttcgtgt tcaagaacat cgacggatac    600

ttcaagattt acagcaagca caccccaatc aacctggtgc gcgacctgcc tcagggtttc    660

tctgctctgg agccactggt ggacctgcct atcggcatca acatcacccg cttccagact    720

ctgctggctc tgcaccgttc ctacctgact ccaggcgact catcttctgg atggactgct    780

ggagctgctg cttactacgt gggctacctg cagcctcgca ccttcctgct gaagtacaac    840

gaaaacggaa ccatcactga cgccgtcgac tgcgctctgg accctctgtc agaaaccaag    900

tgcactctga agtccttcac cgtggagaag ggcatctacc agacttcaaa cttcagggtg    960

cagcccaccg aatccatcgt cagattccct aacatcacta acctgtgccc cttcggagag   1020

gtcttcaacg ccacccgctt cgcttccgtg tacgcctgga acaggaagag aatctcaaac   1080

tgcgtcgctg actactccgt gctgtacaac tcagcctcct tcagcacctt caagtgctac   1140

ggcgtgtcac caactaagct gaacgacctg tgcttcacca acgtctacgc cgactccttc   1200

gtgatcaggg gagacgaggt cagacagatc gctcctggcc agactggaaa gatcgccgac   1260

tacaactaca agctgcccga cgacttcacc ggttgcgtca tcgcttggaa cagcaacaac   1320

ctggactcta aagtgggtgg caactacaac tacctgtacc gcctgttccg taagtcaaac   1380

ctgaagccat tcgagaggga catcagcact gaaatctacc aggccggatc taccccttgc   1440

aacggtgtcg agggcttcaa ctgctacttc cccctgcagt cctacggttt ccagccaact   1500

aacggtgtgg gctaccagcc ttacagagtg gtcgtgctga gcttcgaact gctccacgct   1560

cctgctactg tgtgcggtcc aaagaagtct accaacctgg tcaagaacaa gtgcgtgaac   1620
```

```
ttcaacttca acggcctgac cggaactggt gtcctgaccg agagcaacaa gaagttcctg   1680
cccttccagc agttcggaag ggacatcgct gacaccactg acgctgtgcg cgaccctcag   1740
accctggaaa tcctggacat cactccatgc tcattcggag gtgtctccgt gatcacccct   1800
ggcaccaaca cttctaacca ggtcgctgtg ctgtaccagg acgtcaactg caccgaggtc   1860
cctgtggcca tccacgctga ccagctgacc cccacttggc gcgtgtactc caccggcagc   1920
aacgtgttcc agactcgtgc tggttgcctg atcggcgccg agcacgtgaa caacagctac   1980
gaatgcgaca tccccatcgg cgctggaatc tgcgcctctt accagaccca gactaacagc   2040
ccacagcagg ctcagtctgt ggcctctcag tcaatcatcg cttacaccat gtcactgggc   2100
gctgaaaact ccgtggccta ctctaacaac tcaatcgcca tccccaccaa cttcactatc   2160
agcgtgacca ctgagatcct gccagtcagc atgaccaaga cttctgtgga ctgcactatg   2220
tacatctgcg gagacagcac cgaatgctct aacctgctgc tgcagtacgg ctctttctgc   2280
acccagctga accgtgctct gactggaatc gccgtggagc aggacaagaa cactcaggaa   2340
gtcttcgctc aggtgaagca aatctacaag accccaccta tcaaggactt cggcggattc   2400
aacttctccc agatcctgcc tgacccctcc aagccaagca agcgctcttt catcgaggac   2460
ctgctgttca acaaggtcac tctggccgac gctggattca tcaagcagta cggagactgc   2520
ctgggtgaca tcgccgctcg tgacctgatc tgcgctcaga agttcaacgg tctgaccgtg   2580
ctgcccccac tgctgactga cgaaatgatc gcccagtaca ctagcgccct gctggctgga   2640
accatcactt ctggttggac cttcggtgct ggcgccgctc tgcagatccc tttcgctatg   2700
cagatggcct accgtttcaa cggaatcggt gtcacccaga acgtgctgta cgagaaccag   2760
aagctgatcg ctaaccagtt caactcagcc atcggaaaga tccaggacag cctgagctct   2820
actgcctctg ctctgggcaa gctgcaggac gtcgtgaacc agaacgccca ggctctgaac   2880
accctggtca agcagctgtc atccaacttc ggtgctatca gctctgtgct gaacgacatc   2940
ctgtcccgcc tggacaaggt cgaggccgaa gtgcagatcg accgcctgat cactggccgt   3000
ctgcagtcac tgcagaccta cgtgactcag cagctgatca gggccgctga aatcagagcc   3060
tccgctaacc tggccgctac caagatgagc gagtgcgtcc tgggtcaatc taagcgtgtg   3120
gacttctgcg gcaagggata ccacctgatg tcattccctc agtctgctcc ccacggtgtg   3180
gtgttcctgc acgtcaccta cgtgccagcc caggagaaga acttcaccac tgcccctgct   3240
atctgccacg acggcaaggc tcacttcccc agggaaggtg tcttcgtgag caacggcacc   3300
cactggttcg tcactcagag aaacttctac gagccacaga tcatcaccac tgacaacact   3360
ttcgtgtctg gaaactgcga cgtggtcatc ggtatcgtca acaacaccgt gtacgacccc   3420
ctgcagccag agctggactc attcaaggag gaactggaca agtacttcaa gaaccacacc   3480
tcccctgacg tcgacctggg cgacatctca ggaatcaacg cttccgtcgt gaacatccag   3540
aaggagatcg accgcctgaa cgaagtggcc aagaacctga acgaaagcct gatcgacctg   3600
caggagctgg gcaagtacga acagtacatc aagtggcctt ggtacatctg gctgggtttc   3660
atcgctggcc tcatcgctat cgtgatggtg accatcatgc tgtgctgcat gacttcatgc   3720
tgctcctgcc tgaagggctg ctgcagctgc ggatcttgct gcaagttcga cgaggacgac   3780
tctgaacccg tcctgaaggg cgtgaagctg cactacaccc accaccacca ccaccac      3837
```

<210> SEQ ID NO 58
<211> LENGTH: 1266
<212> TYPE: PRT

```
<213> ORGANISM: Artificial Sequence
<220> FEATURE:
<223> OTHER INFORMATION: RECOMBINANT SPIKE PROTEIN

<400> SEQUENCE: 58

Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
            20                  25                  30

Ser Val Leu His Ser Thr Gln Asp Leu Phe Leu Pro Phe Phe Ser Asn
        35                  40                  45

Val Thr Trp Phe His Ala Ile His Val Ser Gly Thr Asn Gly Thr Lys
    50                  55                  60

Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                85                  90                  95

Leu Asp Ser Lys Thr Gln Ser Leu Leu Ile Val Asn Asn Ala Thr Asn
            100                 105                 110

Val Val Ile Lys Val Cys Glu Phe Gln Phe Cys Asn Asp Pro Phe Leu
        115                 120                 125

Gly Val Tyr Tyr His Lys Asn Asn Lys Ser Trp Met Glu Ser Glu Phe
    130                 135                 140

Arg Val Tyr Ser Ser Ala Asn Asn Cys Thr Phe Glu Tyr Val Ser Gln
145                 150                 155                 160

Pro Phe Leu Met Asp Leu Glu Gly Lys Gln Gly Asn Phe Lys Asn Leu
                165                 170                 175

Arg Glu Phe Val Phe Lys Asn Ile Asp Gly Tyr Phe Lys Ile Tyr Ser
            180                 185                 190

Lys His Thr Pro Ile Asn Leu Val Arg Asp Leu Pro Gln Gly Phe Ser
        195                 200                 205

Ala Leu Glu Pro Leu Val Asp Leu Pro Ile Gly Ile Asn Ile Thr Arg
    210                 215                 220

Phe Gln Thr Leu Leu Ala Leu His Arg Ser Tyr Leu Thr Pro Gly Asp
225                 230                 235                 240

Ser Ser Ser Gly Trp Thr Ala Gly Ala Ala Ala Tyr Tyr Val Gly Tyr
                245                 250                 255

Leu Gln Pro Arg Thr Phe Leu Leu Lys Tyr Asn Glu Asn Gly Thr Ile
            260                 265                 270

Thr Asp Ala Val Asp Cys Ala Leu Asp Pro Leu Ser Glu Thr Lys Cys
        275                 280                 285

Thr Leu Lys Ser Phe Thr Val Glu Lys Gly Ile Tyr Gln Thr Ser Asn
    290                 295                 300

Phe Arg Val Gln Pro Thr Glu Ser Ile Val Arg Phe Pro Asn Ile Thr
305                 310                 315                 320

Asn Leu Cys Pro Phe Gly Glu Val Phe Asn Ala Thr Arg Phe Ala Ser
                325                 330                 335

Val Tyr Ala Trp Asn Arg Lys Arg Ile Ser Asn Cys Val Ala Asp Tyr
            340                 345                 350

Ser Val Leu Tyr Asn Ser Ala Ser Phe Ser Thr Phe Lys Cys Tyr Gly
        355                 360                 365

Val Ser Pro Thr Lys Leu Asn Asp Leu Cys Phe Thr Asn Val Tyr Ala
    370                 375                 380

Asp Ser Phe Val Ile Arg Gly Asp Glu Val Arg Gln Ile Ala Pro Gly
```

-continued

```
385                 390                 395                 400

Gln Thr Gly Lys Ile Ala Asp Tyr Asn Tyr Lys Leu Pro Asp Asp Phe
                405                 410                 415

Thr Gly Cys Val Ile Ala Trp Asn Ser Asn Asn Leu Asp Ser Lys Val
            420                 425                 430

Gly Gly Asn Tyr Asn Tyr Leu Tyr Arg Leu Phe Arg Lys Ser Asn Leu
        435                 440                 445

Lys Pro Phe Glu Arg Asp Ile Ser Thr Glu Ile Tyr Gln Ala Gly Ser
    450                 455                 460

Thr Pro Cys Asn Gly Val Glu Gly Phe Asn Cys Tyr Phe Pro Leu Gln
465                 470                 475                 480

Ser Tyr Gly Phe Gln Pro Thr Asn Gly Val Gly Tyr Gln Pro Tyr Arg
                485                 490                 495

Val Val Val Leu Ser Phe Glu Leu Leu His Ala Pro Ala Thr Val Cys
            500                 505                 510

Gly Pro Lys Lys Ser Thr Asn Leu Val Lys Asn Lys Cys Val Asn Phe
        515                 520                 525

Asn Phe Asn Gly Leu Thr Gly Thr Gly Val Leu Thr Glu Ser Asn Lys
    530                 535                 540

Lys Phe Leu Pro Phe Gln Gln Phe Gly Arg Asp Ile Ala Asp Thr Thr
545                 550                 555                 560

Asp Ala Val Arg Asp Pro Gln Thr Leu Glu Ile Leu Asp Ile Thr Pro
                565                 570                 575

Cys Ser Phe Gly Gly Val Ser Val Ile Thr Pro Gly Thr Asn Thr Ser
            580                 585                 590

Asn Gln Val Ala Val Leu Tyr Gln Asp Val Asn Cys Thr Glu Val Pro
        595                 600                 605

Val Ala Ile His Ala Asp Gln Leu Thr Pro Thr Trp Arg Val Tyr Ser
    610                 615                 620

Thr Gly Ser Asn Val Phe Gln Thr Arg Ala Gly Cys Leu Ile Gly Ala
625                 630                 635                 640

Glu His Val Asn Asn Ser Tyr Glu Cys Asp Ile Pro Ile Gly Ala Gly
                645                 650                 655

Ile Cys Ala Ser Tyr Gln Thr Gln Thr Asn Ser Pro Gln Gln Ala Gln
            660                 665                 670

Ser Val Ala Ser Gln Ser Ile Ile Ala Tyr Thr Met Ser Leu Gly Ala
        675                 680                 685

Glu Asn Ser Val Ala Tyr Ser Asn Asn Ser Ile Ala Ile Pro Thr Asn
    690                 695                 700

Phe Thr Ile Ser Val Thr Thr Glu Ile Leu Pro Val Ser Met Thr Lys
705                 710                 715                 720

Thr Ser Val Asp Cys Thr Met Tyr Ile Cys Gly Asp Ser Thr Glu Cys
                725                 730                 735

Ser Asn Leu Leu Leu Gln Tyr Gly Ser Phe Cys Thr Gln Leu Asn Arg
            740                 745                 750

Ala Leu Thr Gly Ile Ala Val Glu Gln Asp Lys Asn Thr Gln Glu Val
        755                 760                 765

Phe Ala Gln Val Lys Gln Ile Tyr Lys Thr Pro Pro Ile Lys Asp Phe
    770                 775                 780

Gly Gly Phe Asn Phe Ser Gln Ile Leu Pro Asp Pro Ser Lys Pro Ser
785                 790                 795                 800

Lys Arg Ser Phe Ile Glu Asp Leu Leu Phe Asn Lys Val Thr Leu Ala
                805                 810                 815
```

-continued

```
Asp Ala Gly Phe Ile Lys Gln Tyr Gly Asp Cys Leu Gly Asp Ile Ala
            820                 825                 830

Ala Arg Asp Leu Ile Cys Ala Gln Lys Phe Asn Gly Leu Thr Val Leu
        835                 840                 845

Pro Pro Leu Leu Thr Asp Glu Met Ile Ala Gln Tyr Thr Ser Ala Leu
    850                 855                 860

Leu Ala Gly Thr Ile Thr Ser Gly Trp Thr Phe Gly Ala Gly Ala Ala
865                 870                 875                 880

Leu Gln Ile Pro Phe Ala Met Gln Met Ala Tyr Arg Phe Asn Gly Ile
                885                 890                 895

Gly Val Thr Gln Asn Val Leu Tyr Glu Asn Gln Lys Leu Ile Ala Asn
            900                 905                 910

Gln Phe Asn Ser Ala Ile Gly Lys Ile Gln Asp Ser Leu Ser Ser Thr
        915                 920                 925

Ala Ser Ala Leu Gly Lys Leu Gln Asp Val Val Asn Gln Asn Ala Gln
    930                 935                 940

Ala Leu Asn Thr Leu Val Lys Gln Leu Ser Ser Asn Phe Gly Ala Ile
945                 950                 955                 960

Ser Ser Val Leu Asn Asp Ile Leu Ser Arg Leu Asp Lys Val Glu Ala
                965                 970                 975

Glu Val Gln Ile Asp Arg Leu Ile Thr Gly Arg Leu Gln Ser Leu Gln
            980                 985                 990

Thr Tyr Val Thr Gln Gln Leu Ile  Arg Ala Ala Glu Ile  Arg Ala Ser
        995                 1000                1005

Ala Asn  Leu Ala Ala Thr Lys  Met Ser Glu Cys Val  Leu Gly Gln
    1010                1015                1020

Ser Lys  Arg Val Asp Phe Cys  Gly Lys Gly Tyr His  Leu Met Ser
    1025                1030                1035

Phe Pro  Gln Ser Ala Pro His  Gly Val Val Phe Leu  His Val Thr
    1040                1045                1050

Tyr Val  Pro Ala Gln Glu Lys  Asn Phe Thr Thr Ala  Pro Ala Ile
    1055                1060                1065

Cys His  Asp Gly Lys Ala His  Phe Pro Arg Glu Gly  Val Phe Val
    1070                1075                1080

Ser Asn  Gly Thr His Trp Phe  Val Thr Gln Arg Asn  Phe Tyr Glu
    1085                1090                1095

Pro Gln  Ile Ile Thr Thr Asp  Asn Thr Phe Val Ser  Gly Asn Cys
    1100                1105                1110

Asp Val  Val Ile Gly Ile Val  Asn Asn Thr Val Tyr  Asp Pro Leu
    1115                1120                1125

Gln Pro  Glu Leu Asp Ser Phe  Lys Glu Glu Leu Asp  Lys Tyr Phe
    1130                1135                1140

Lys Asn  His Thr Ser Pro Asp  Val Asp Leu Gly Asp  Ile Ser Gly
    1145                1150                1155

Ile Asn  Ala Ser Val Val Asn  Ile Gln Lys Glu Ile  Asp Arg Leu
    1160                1165                1170

Asn Glu  Val Ala Lys Asn Leu  Asn Glu Ser Leu Ile  Asp Leu Gln
    1175                1180                1185

Glu Leu  Gly Lys Tyr Glu Gln  Tyr Ile Lys Trp Pro  Trp Tyr Ile
    1190                1195                1200

Trp Leu  Gly Phe Ile Ala Gly  Leu Ile Ala Ile Val  Met Val Thr
    1205                1210                1215
```

-continued

```
Ile Met  Leu Cys Cys Met Thr  Ser Cys Cys Ser Cys  Leu Lys Gly
    1220                 1225                 1230

Cys Cys  Ser Cys Gly Ser Cys  Cys Lys Phe Asp Glu  Asp Asp Ser
    1235                 1240                 1245

Glu Pro  Val Leu Lys Gly Val  Lys Leu His Tyr Thr  His His His
    1250                 1255                 1260

His His  His
    1265


<210> SEQ ID NO 59
<211> LENGTH: 1219
<212> TYPE: PRT
<213> ORGANISM: Artificial Sequence
<220> FEATURE:
<223> OTHER INFORMATION: RECOMBINANT SPIKE PROTEIN

<400> SEQUENCE: 59

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300
```

-continued

```
Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Gln Gln Ala Gln Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
```

```
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
            980                 985                 990

Ile Asp Arg Leu Ile Thr Gly Arg  Leu Gln Ser Leu Gln  Thr Tyr Val
        995                 1000                1005

Thr Gln  Gln Leu Ile Arg Ala  Ala Glu Ile Arg Ala  Ser Ala Asn
    1010                1015                1020

Leu Ala  Ala Thr Lys Met Ser  Glu Cys Val Leu Gly  Gln Ser Lys
    1025                1030                1035

Arg Val  Asp Phe Cys Gly Lys  Gly Tyr His Leu Met  Ser Phe Pro
    1040                1045                1050

Gln Ser  Ala Pro His Gly Val  Val Phe Leu His Val  Thr Tyr Val
    1055                1060                1065

Pro Ala  Gln Glu Lys Asn Phe  Thr Thr Ala Pro Ala  Ile Cys His
    1070                1075                1080

Asp Gly  Lys Ala His Phe Pro  Arg Glu Gly Val Phe  Val Ser Asn
    1085                1090                1095

Gly Thr  His Trp Phe Val Thr  Gln Arg Asn Phe Tyr  Glu Pro Gln
    1100                1105                1110

Ile Ile  Thr Thr Asp Asn Thr  Phe Val Ser Gly Asn  Cys Asp Val
    1115                1120                1125

Val Ile  Gly Ile Val Asn Asn  Thr Val Tyr Asp Pro  Leu Gln Pro
    1130                1135                1140
```

```
Glu Leu  Asp Ser Phe Lys Glu  Glu Leu Asp Lys Tyr  Phe Lys Asn
    1145                 1150                 1155

His Thr  Ser Pro Asp Val Asp  Leu Gly Asp Ile Ser  Gly Ile Asn
    1160                 1165                 1170

Ala Ser  Val Val Asn Ile Gln  Lys Glu Ile Asp Arg  Leu Asn Glu
    1175                 1180                 1185

Val Ala  Lys Asn Leu Asn Glu  Ser Leu Ile Asp Leu  Gln Glu Leu
    1190                 1195                 1200

Gly Lys  Tyr Glu Gln Tyr Ile  Lys Trp Pro His His  His His His
    1205                 1210                 1215

His
```

```
<210> SEQ ID NO 60
<211> LENGTH: 3657
<212> TYPE: DNA
<213> ORGANISM: Artificial Sequence
<220> FEATURE:
<223> OTHER INFORMATION: RECOMBINANT SPIKE PROTEIN

<400> SEQUENCE: 60

atgttcgtct tcctggtgct gctgcccctg gtgtccagcc agtgcgtgaa cctgaccact     60

aggactcagc tgcctcccgc ttacaccaac tcattcactc gcggtgtgta ctaccctgac    120

aaggtcttcc gttcttcagt gctgcactca actcaggacc tgttcctgcc cttcttctcc    180

aacgtcacct ggttccacgc catccacgtg tccggcacca acggcactaa gcgcttcgac    240

aacccagtgc tgcctttcaa cgacggtgtc tacttcgctt caaccgagaa gtccaacatc    300

atccgtggat ggatcttcgg caccactctg gacagcaaga ctcagtctct gctgatcgtc    360

aacaacgcca ccaacgtggt catcaaggtc tgcgaattcc agttctgcaa cgacccattc    420

ctgggcgtct actaccacaa gaacaacaag tcatggatgg agtccgaatt ccgcgtctac    480

tccagcgcta acaactgcac tttcgagtac gtgtcccagc ctttcctgat ggacctggaa    540

ggaaagcagg gtaacttcaa gaacctgagg gagttcgtgt tcaagaacat cgacggatac    600

ttcaagattt acagcaagca caccccaatc aacctggtgc gcgacctgcc tcagggtttc    660

tctgctctgg agccactggt ggacctgcct atcggcatca acatcacccg cttccagact    720

ctgctggctc tgcaccgttc ctacctgact ccaggcgact catcttctgg atggactgct    780

ggagctgctg cttactacgt gggctacctg cagcctcgca ccttcctgct gaagtacaac    840

gaaaacggaa ccatcactga cgccgtcgac tgcgctctgg accctctgtc agaaaccaag    900

tgcactctga agtccttcac cgtggagaag ggcatctacc agacttcaaa cttcagggtg    960

cagcccaccg aatccatcgt cagattccct aacatcacta acctgtgccc cttcggagag   1020

gtcttcaacg ccacccgctt cgcttccgtg tacgcctgga acaggaagag aatctcaaac   1080

tgcgtcgctg actactccgt gctgtacaac tcagcctcct tcagcacctt caagtgctac   1140

ggcgtgtcac caactaagct gaacgacctg tgcttcacca acgtctacgc cgactccttc   1200

gtgatcaggg gagacgaggt cagacagatc gctcctggcc agactggaaa gatcgccgac   1260

tacaactaca agctgcccga cgacttcacc ggttgcgtca tcgcttggaa cagcaacaac   1320

ctggactcta aagtgggtgg caactacaac tacctgtacc gcctgttccg taagtcaaac   1380

ctgaagccat tcgagaggga catcagcact gaaatctacc aggccggatc taccccttgc   1440

aacggtgtcg agggcttcaa ctgctacttc cccctgcagt cctacggttt ccagccaact   1500

aacggtgtgg gctaccagcc ttacagagtg gtcgtgctga gcttcgaact gctccacgct   1560
```

```
cctgctactg tgtgcggtcc aaagaagtct accaacctgg tcaagaacaa gtgcgtgaac   1620
ttcaacttca acggcctgac cggaactggt gtcctgaccg agagcaacaa gaagttcctg   1680
cccttccagc agttcggaag ggacatcgct gacaccactg acgctgtgcg cgaccctcag   1740
accctggaaa tcctggacat cactccatgc tcattcggag gtgtctccgt gatcacccct   1800
ggcaccaaca cttctaacca ggtcgctgtg ctgtaccagg acgtcaactg caccgaggtc   1860
cctgtggcca tccacgctga ccagctgacc cccacttggc gcgtgtactc caccggcagc   1920
aacgtgttcc agactcgtgc tggttgcctg atcggcgccg agcacgtgaa caacagctac   1980
gaatgcgaca tccccatcgg cgctggaatc tgcgcctctt accagaccca gactaacagc   2040
ccacagcagg ctcagtctgt ggcctctcag tcaatcatcg cttacaccat gtcactgggc   2100
gctgaaaact ccgtggccta ctctaacaac tcaatcgcca tccccaccaa cttcactatc   2160
agcgtgacca ctgagatcct gccagtcagc atgaccaaga cttctgtgga ctgcactatg   2220
tacatctgcg gagacagcac cgaatgctct aacctgctgc tgcagtacgg ctctttctgc   2280
acccagctga accgtgctct gactggaatc gccgtggagc aggacaagaa cactcaggaa   2340
gtcttcgctc aggtgaagca aatctacaag accccaccta tcaaggactt cggcggattc   2400
aacttctccc agatcctgcc tgacccctcc aagccaagca agcgctcttt catcgaggac   2460
ctgctgttca acaaggtcac tctggccgac gctggattca tcaagcagta cggagactgc   2520
ctgggtgaca tcgccgctcg tgacctgatc tgcgctcaga agttcaacgg tctgaccgtg   2580
ctgcccccac tgctgactga cgaaatgatc gcccagtaca ctagcgccct gctggctgga   2640
accatcactt ctggttggac cttcggtgct ggcgccgctc tgcagatccc tttcgctatg   2700
cagatggcct accgtttcaa cggaatcggt gtcacccaga acgtgctgta cgagaaccag   2760
aagctgatcg ctaaccagtt caactcagcc atcggaaaga tccaggacag cctgagctct   2820
actgcctctg ctctgggcaa gctgcaggac gtcgtgaacc agaacgccca ggctctgaac   2880
accctggtca agcagctgtc atccaacttc ggtgctatca gctctgtgct gaacgacatc   2940
ctgtcccgcc tggacaaggt cgaggccgaa gtgcagatcg accgcctgat cactggccgt   3000
ctgcagtcac tgcagaccta cgtgactcag cagctgatca gggccgctga aatcagagcc   3060
tccgctaacc tggccgctac caagatgagc gagtgcgtcc tgggtcaatc taagcgtgtg   3120
gacttctgcg gcaagggata ccacctgatg tcattccctc agtctgctcc ccacggtgtg   3180
gtgttcctgc acgtcaccta cgtgccagcc caggagaaga acttcaccac tgcccctgct   3240
atctgccacg acggcaaggc tcacttcccc agggaaggtg tcttcgtgag caacggcacc   3300
cactggttcg tcactcagag aaacttctac gagccacaga tcatcaccac tgacaacact   3360
ttcgtgtctg gaaactgcga cgtggtcatc ggtatcgtca acaacaccgt gtacgacccc   3420
ctgcagccag agctggactc attcaaggag gaactggaca agtacttcaa gaaccacacc   3480
tcccctgacg tcgacctggg cgacatctca ggaatcaacg cttccgtcgt gaacatccag   3540
aaggagatcg accgcctgaa cgaagtggcc aagaacctga acgaaagcct gatcgacctg   3600
caggagctgg gcaagtacga acagtacatc aagtggcctc accaccacca ccaccac      3657
```

<210> SEQ ID NO 61
<211> LENGTH: 1205
<212> TYPE: PRT
<213> ORGANISM: Artificial Sequence
<220> FEATURE:
<223> OTHER INFORMATION: RECOMBINANT SPIKE PROTEIN

<400> SEQUENCE: 61

```
Cys Val Asn Leu Thr Thr Arg Thr Gln Leu Pro Pro Ala Tyr Thr Asn
1               5                   10                  15

Ser Phe Thr Arg Gly Val Tyr Tyr Pro Asp Lys Val Phe Arg Ser Ser
            20                  25                  30

Val Leu His Ser Thr Gln Asp Leu Phe Leu Pro Phe Phe Ser Asn Val
        35                  40                  45

Thr Trp Phe His Ala Ile His Val Ser Gly Thr Asn Gly Thr Lys Arg
    50                  55                  60

Phe Asp Asn Pro Val Leu Pro Phe Asn Asp Gly Val Tyr Phe Ala Ser
65                  70                  75                  80

Thr Glu Lys Ser Asn Ile Ile Arg Gly Trp Ile Phe Gly Thr Thr Leu
                85                  90                  95

Asp Ser Lys Thr Gln Ser Leu Leu Ile Val Asn Asn Ala Thr Asn Val
            100                 105                 110

Val Ile Lys Val Cys Glu Phe Gln Phe Cys Asn Asp Pro Phe Leu Gly
        115                 120                 125

Val Tyr Tyr His Lys Asn Asn Lys Ser Trp Met Glu Ser Glu Phe Arg
    130                 135                 140

Val Tyr Ser Ser Ala Asn Asn Cys Thr Phe Glu Tyr Val Ser Gln Pro
145                 150                 155                 160

Phe Leu Met Asp Leu Glu Gly Lys Gln Gly Asn Phe Lys Asn Leu Arg
                165                 170                 175

Glu Phe Val Phe Lys Asn Ile Asp Gly Tyr Phe Lys Ile Tyr Ser Lys
            180                 185                 190

His Thr Pro Ile Asn Leu Val Arg Asp Leu Pro Gln Gly Phe Ser Ala
        195                 200                 205

Leu Glu Pro Leu Val Asp Leu Pro Ile Gly Ile Asn Ile Thr Arg Phe
    210                 215                 220

Gln Thr Leu Leu Ala Leu His Arg Ser Tyr Leu Thr Pro Gly Asp Ser
225                 230                 235                 240

Ser Ser Gly Trp Thr Ala Gly Ala Ala Ala Tyr Tyr Val Gly Tyr Leu
                245                 250                 255

Gln Pro Arg Thr Phe Leu Leu Lys Tyr Asn Glu Asn Gly Thr Ile Thr
            260                 265                 270

Asp Ala Val Asp Cys Ala Leu Asp Pro Leu Ser Glu Thr Lys Cys Thr
        275                 280                 285

Leu Lys Ser Phe Thr Val Glu Lys Gly Ile Tyr Gln Thr Ser Asn Phe
    290                 295                 300

Arg Val Gln Pro Thr Glu Ser Ile Val Arg Phe Pro Asn Ile Thr Asn
305                 310                 315                 320

Leu Cys Pro Phe Gly Glu Val Phe Asn Ala Thr Arg Phe Ala Ser Val
                325                 330                 335

Tyr Ala Trp Asn Arg Lys Arg Ile Ser Asn Cys Val Ala Asp Tyr Ser
            340                 345                 350

Val Leu Tyr Asn Ser Ala Ser Phe Ser Thr Phe Lys Cys Tyr Gly Val
        355                 360                 365

Ser Pro Thr Lys Leu Asn Asp Leu Cys Phe Thr Asn Val Tyr Ala Asp
    370                 375                 380

Ser Phe Val Ile Arg Gly Asp Glu Val Arg Gln Ile Ala Pro Gly Gln
385                 390                 395                 400

Thr Gly Lys Ile Ala Asp Tyr Asn Tyr Lys Leu Pro Asp Asp Phe Thr
                405                 410                 415
```

```
Gly Cys Val Ile Ala Trp Asn Ser Asn Asn Leu Asp Ser Lys Val Gly
            420                 425                 430

Gly Asn Tyr Asn Tyr Leu Tyr Arg Leu Phe Arg Lys Ser Asn Leu Lys
        435                 440                 445

Pro Phe Glu Arg Asp Ile Ser Thr Glu Ile Tyr Gln Ala Gly Ser Thr
    450                 455                 460

Pro Cys Asn Gly Val Glu Gly Phe Asn Cys Tyr Phe Pro Leu Gln Ser
465                 470                 475                 480

Tyr Gly Phe Gln Pro Thr Asn Gly Val Gly Tyr Gln Pro Tyr Arg Val
                485                 490                 495

Val Val Leu Ser Phe Glu Leu Leu His Ala Pro Ala Thr Val Cys Gly
            500                 505                 510

Pro Lys Lys Ser Thr Asn Leu Val Lys Asn Lys Cys Val Asn Phe Asn
        515                 520                 525

Phe Asn Gly Leu Thr Gly Thr Gly Val Leu Thr Glu Ser Asn Lys Lys
    530                 535                 540

Phe Leu Pro Phe Gln Gln Phe Gly Arg Asp Ile Ala Asp Thr Thr Asp
545                 550                 555                 560

Ala Val Arg Asp Pro Gln Thr Leu Glu Ile Leu Asp Ile Thr Pro Cys
                565                 570                 575

Ser Phe Gly Gly Val Ser Val Ile Thr Pro Gly Thr Asn Thr Ser Asn
            580                 585                 590

Gln Val Ala Val Leu Tyr Gln Asp Val Asn Cys Thr Glu Val Pro Val
        595                 600                 605

Ala Ile His Ala Asp Gln Leu Thr Pro Thr Trp Arg Val Tyr Ser Thr
    610                 615                 620

Gly Ser Asn Val Phe Gln Thr Arg Ala Gly Cys Leu Ile Gly Ala Glu
625                 630                 635                 640

His Val Asn Asn Ser Tyr Glu Cys Asp Ile Pro Ile Gly Ala Gly Ile
                645                 650                 655

Cys Ala Ser Tyr Gln Thr Gln Thr Asn Ser Pro Gln Gln Ala Gln Ser
            660                 665                 670

Val Ala Ser Gln Ser Ile Ile Ala Tyr Thr Met Ser Leu Gly Ala Glu
        675                 680                 685

Asn Ser Val Ala Tyr Ser Asn Asn Ser Ile Ala Ile Pro Thr Asn Phe
    690                 695                 700

Thr Ile Ser Val Thr Thr Glu Ile Leu Pro Val Ser Met Thr Lys Thr
705                 710                 715                 720

Ser Val Asp Cys Thr Met Tyr Ile Cys Gly Asp Ser Thr Glu Cys Ser
                725                 730                 735

Asn Leu Leu Leu Gln Tyr Gly Ser Phe Cys Thr Gln Leu Asn Arg Ala
            740                 745                 750

Leu Thr Gly Ile Ala Val Glu Gln Asp Lys Asn Thr Gln Glu Val Phe
        755                 760                 765

Ala Gln Val Lys Gln Ile Tyr Lys Thr Pro Pro Ile Lys Asp Phe Gly
    770                 775                 780

Gly Phe Asn Phe Ser Gln Ile Leu Pro Asp Pro Ser Lys Pro Ser Lys
785                 790                 795                 800

Arg Ser Phe Ile Glu Asp Leu Leu Phe Asn Lys Val Thr Leu Ala Asp
                805                 810                 815

Ala Gly Phe Ile Lys Gln Tyr Gly Asp Cys Leu Gly Asp Ile Ala Ala
            820                 825                 830
```

```
Arg Asp Leu Ile Cys Ala Gln Lys Phe Asn Gly Leu Thr Val Leu Pro
        835                 840                 845

Pro Leu Leu Thr Asp Glu Met Ile Ala Gln Tyr Thr Ser Ala Leu Leu
    850                 855                 860

Ala Gly Thr Ile Thr Ser Gly Trp Thr Phe Gly Ala Gly Ala Ala Leu
865                 870                 875                 880

Gln Ile Pro Phe Ala Met Gln Met Ala Tyr Arg Phe Asn Gly Ile Gly
                885                 890                 895

Val Thr Gln Asn Val Leu Tyr Glu Asn Gln Lys Leu Ile Ala Asn Gln
            900                 905                 910

Phe Asn Ser Ala Ile Gly Lys Ile Gln Asp Ser Leu Ser Ser Thr Ala
        915                 920                 925

Ser Ala Leu Gly Lys Leu Gln Asp Val Val Asn Gln Asn Ala Gln Ala
    930                 935                 940

Leu Asn Thr Leu Val Lys Gln Leu Ser Ser Asn Phe Gly Ala Ile Ser
945                 950                 955                 960

Ser Val Leu Asn Asp Ile Leu Ser Arg Leu Asp Lys Val Glu Ala Glu
                965                 970                 975

Val Gln Ile Asp Arg Leu Ile Thr Gly Arg Leu Gln Ser Leu Gln Thr
            980                 985                 990

Tyr Val Thr Gln Gln Leu Ile Arg  Ala Ala Glu Ile Arg  Ala Ser Ala
        995                 1000                 1005

Asn Leu  Ala Ala Thr Lys Met  Ser Glu Cys Val Leu  Gly Gln Ser
    1010                 1015                 1020

Lys Arg  Val Asp Phe Cys Gly  Lys Gly Tyr His Leu  Met Ser Phe
    1025                 1030                 1035

Pro Gln  Ser Ala Pro His Gly  Val Val Phe Leu His  Val Thr Tyr
    1040                 1045                 1050

Val Pro  Ala Gln Glu Lys Asn  Phe Thr Thr Ala Pro  Ala Ile Cys
    1055                 1060                 1065

His Asp  Gly Lys Ala His Phe  Pro Arg Glu Gly Val  Phe Val Ser
    1070                 1075                 1080

Asn Gly  Thr His Trp Phe Val  Thr Gln Arg Asn Phe  Tyr Glu Pro
    1085                 1090                 1095

Gln Ile  Ile Thr Thr Asp Asn  Thr Phe Val Ser Gly  Asn Cys Asp
    1100                 1105                 1110

Val Val  Ile Gly Ile Val Asn  Asn Thr Val Tyr Asp  Pro Leu Gln
    1115                 1120                 1125

Pro Glu  Leu Asp Ser Phe Lys  Glu Glu Leu Asp Lys  Tyr Phe Lys
    1130                 1135                 1140

Asn His  Thr Ser Pro Asp Val  Asp Leu Gly Asp Ile  Ser Gly Ile
    1145                 1150                 1155

Asn Ala  Ser Val Val Asn Ile  Gln Lys Glu Ile Asp  Arg Leu Asn
    1160                 1165                 1170

Glu Val  Ala Lys Asn Leu Asn  Glu Ser Leu Ile Asp  Leu Gln Glu
    1175                 1180                 1185

Leu Gly  Lys Tyr Glu Gln Tyr  Ile Lys Trp Pro His  His His His
    1190                 1195                 1200

His His
    1205
```

<210> SEQ ID NO 62
<211> LENGTH: 1263
<212> TYPE: PRT

<213> ORGANISM: Artificial Sequence
<220> FEATURE:
<223> OTHER INFORMATION: RECOMBINANT SPIKE PROTEIN

<400> SEQUENCE: 62

```
Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
```

-continued

```
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Gln Gln Ala Gln Ser Val Ala
        675                 680                 685

Leu Gly Ala Glu Asn Ser Val Ala Tyr Ser Asn Asn Ser Ile Ala Ile
    690                 695                 700

Pro Thr Asn Phe Thr Ile Ser Val Thr Thr Glu Ile Leu Pro Val Ser
705                 710                 715                 720

Met Thr Lys Thr Ser Val Asp Cys Thr Met Tyr Ile Cys Gly Asp Ser
                725                 730                 735

Thr Glu Cys Ser Asn Leu Leu Leu Gln Tyr Gly Ser Phe Cys Thr Gln
            740                 745                 750

Leu Asn Arg Ala Leu Thr Gly Ile Ala Val Glu Gln Asp Lys Asn Thr
        755                 760                 765

Gln Glu Val Phe Ala Gln Val Lys Gln Ile Tyr Lys Thr Pro Pro Ile
    770                 775                 780

Lys Asp Phe Gly Gly Phe Asn Phe Ser Gln Ile Leu Pro Asp Pro Ser
785                 790                 795                 800

Lys Pro Ser Lys Arg Ser Phe Ile Glu Asp Leu Leu Phe Asn Lys Val
                805                 810                 815
```

-continued

```
Thr Leu Ala Asp Ala Gly Phe Ile Lys Gln Tyr Gly Asp Cys Leu Gly
            820                 825                 830

Asp Ile Ala Ala Arg Asp Leu Ile Cys Ala Gln Lys Phe Asn Gly Leu
        835                 840                 845

Thr Val Leu Pro Pro Leu Leu Thr Asp Glu Met Ile Ala Gln Tyr Thr
    850                 855                 860

Ser Ala Leu Leu Ala Gly Thr Ile Thr Ser Gly Trp Thr Phe Gly Ala
865                 870                 875                 880

Gly Ala Ala Leu Gln Ile Pro Phe Ala Met Gln Met Ala Tyr Arg Phe
                885                 890                 895

Asn Gly Ile Gly Val Thr Gln Asn Val Leu Tyr Glu Asn Gln Lys Leu
            900                 905                 910

Ile Ala Asn Gln Phe Asn Ser Ala Ile Gly Lys Ile Gln Asp Ser Leu
        915                 920                 925

Ser Ser Thr Ala Ser Ala Leu Gly Lys Leu Gln Asp Val Val Asn Gln
    930                 935                 940

Asn Ala Gln Ala Leu Asn Thr Leu Val Lys Gln Leu Ser Ser Asn Phe
945                 950                 955                 960

Gly Ala Ile Ser Ser Val Leu Asn Asp Ile Leu Ser Arg Leu Asp Lys
                965                 970                 975

Val Glu Ala Glu Val Gln Ile Asp Arg Leu Ile Thr Gly Arg Leu Gln
            980                 985                 990

Ser Leu Gln Thr Tyr Val Thr Gln  Gln Leu Ile Arg Ala  Ala Glu Ile
        995                 1000                 1005

Arg Ala  Ser Ala Asn Leu Ala  Ala Thr Lys Met Ser  Glu Cys Val
    1010                 1015                 1020

Leu Gly  Gln Ser Lys Arg Val  Asp Phe Cys Gly Lys  Gly Tyr His
    1025                 1030                 1035

Leu Met  Ser Phe Pro Gln Ser  Ala Pro His Gly Val  Val Phe Leu
    1040                 1045                 1050

His Val  Thr Tyr Val Pro Ala  Gln Glu Lys Asn Phe  Thr Thr Ala
    1055                 1060                 1065

Pro Ala  Ile Cys His Asp Gly  Lys Ala His Phe Pro  Arg Glu Gly
    1070                 1075                 1080

Val Phe  Val Ser Asn Gly Thr  His Trp Phe Val Thr  Gln Arg Asn
    1085                 1090                 1095

Phe Tyr  Glu Pro Gln Ile Ile  Thr Thr Asp Asn Thr  Phe Val Ser
    1100                 1105                 1110

Gly Asn  Cys Asp Val Val Ile  Gly Ile Val Asn Asn  Thr Val Tyr
    1115                 1120                 1125

Asp Pro  Leu Gln Pro Glu Leu  Asp Ser Phe Lys Glu  Glu Leu Asp
    1130                 1135                 1140

Lys Tyr  Phe Lys Asn His Thr  Ser Pro Asp Val Asp  Leu Gly Asp
    1145                 1150                 1155

Ile Ser  Gly Ile Asn Ala Ser  Val Val Asn Ile Gln  Lys Glu Ile
    1160                 1165                 1170

Asp Arg  Leu Asn Glu Val Ala  Lys Asn Leu Asn Glu  Ser Leu Ile
    1175                 1180                 1185

Asp Leu  Gln Glu Leu Gly Lys  Tyr Glu Gln Tyr Ile  Lys Trp Pro
    1190                 1195                 1200

Trp Tyr  Ile Trp Leu Gly Phe  Ile Ala Gly Leu Ile  Ala Ile Val
    1205                 1210                 1215
```

-continued

```
Met Val  Thr Ile Met Leu Cys  Cys Met Thr Ser Cys  Cys Ser Cys
    1220                 1225                 1230

Leu Lys  Gly Cys Cys Ser Cys  Gly Ser Cys Cys Lys  Phe Asp Glu
    1235                 1240                 1245

Asp Asp  Ser Glu Pro Val Leu  Lys Gly Val Lys Leu  His Tyr Thr
    1250                 1255                 1260


<210> SEQ ID NO 63
<211> LENGTH: 1250
<212> TYPE: PRT
<213> ORGANISM: Artificial Sequence
<220> FEATURE:
<223> OTHER INFORMATION: RECOMBINANT SPIKE PROTEIN

<400> SEQUENCE: 63

Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
            20                  25                  30

Ser Val Leu His Ser Thr Gln Asp Leu Phe Leu Pro Phe Phe Ser Asn
        35                  40                  45

Val Thr Trp Phe His Ala Ile His Val Ser Gly Thr Asn Gly Thr Lys
    50                  55                  60

Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                85                  90                  95

Leu Asp Ser Lys Thr Gln Ser Leu Leu Ile Val Asn Asn Ala Thr Asn
            100                 105                 110

Val Val Ile Lys Val Cys Glu Phe Gln Phe Cys Asn Asp Pro Phe Leu
        115                 120                 125

Gly Val Tyr Tyr His Lys Asn Asn Lys Ser Trp Met Glu Ser Glu Phe
    130                 135                 140

Arg Val Tyr Ser Ser Ala Asn Asn Cys Thr Phe Glu Tyr Val Ser Gln
145                 150                 155                 160

Pro Phe Leu Met Asp Leu Glu Gly Lys Gln Gly Asn Phe Lys Asn Leu
                165                 170                 175

Arg Glu Phe Val Phe Lys Asn Ile Asp Gly Tyr Phe Lys Ile Tyr Ser
            180                 185                 190

Lys His Thr Pro Ile Asn Leu Val Arg Asp Leu Pro Gln Gly Phe Ser
        195                 200                 205

Ala Leu Glu Pro Leu Val Asp Leu Pro Ile Gly Ile Asn Ile Thr Arg
    210                 215                 220

Phe Gln Thr Leu Leu Ala Leu His Arg Ser Tyr Leu Thr Pro Gly Asp
225                 230                 235                 240

Ser Ser Ser Gly Trp Thr Ala Gly Ala Ala Ala Tyr Tyr Val Gly Tyr
                245                 250                 255

Leu Gln Pro Arg Thr Phe Leu Leu Lys Tyr Asn Glu Asn Gly Thr Ile
            260                 265                 270

Thr Asp Ala Val Asp Cys Ala Leu Asp Pro Leu Ser Glu Thr Lys Cys
        275                 280                 285

Thr Leu Lys Ser Phe Thr Val Glu Lys Gly Ile Tyr Gln Thr Ser Asn
    290                 295                 300

Phe Arg Val Gln Pro Thr Glu Ser Ile Val Arg Phe Pro Asn Ile Thr
305                 310                 315                 320
```

```
Asn Leu Cys Pro Phe Gly Glu Val Phe Asn Ala Thr Arg Phe Ala Ser
                325                 330                 335

Val Tyr Ala Trp Asn Arg Lys Arg Ile Ser Asn Cys Val Ala Asp Tyr
            340                 345                 350

Ser Val Leu Tyr Asn Ser Ala Ser Phe Ser Thr Phe Lys Cys Tyr Gly
        355                 360                 365

Val Ser Pro Thr Lys Leu Asn Asp Leu Cys Phe Thr Asn Val Tyr Ala
    370                 375                 380

Asp Ser Phe Val Ile Arg Gly Asp Glu Val Arg Gln Ile Ala Pro Gly
385                 390                 395                 400

Gln Thr Gly Lys Ile Ala Asp Tyr Asn Tyr Lys Leu Pro Asp Asp Phe
                405                 410                 415

Thr Gly Cys Val Ile Ala Trp Asn Ser Asn Asn Leu Asp Ser Lys Val
            420                 425                 430

Gly Gly Asn Tyr Asn Tyr Leu Tyr Arg Leu Phe Arg Lys Ser Asn Leu
        435                 440                 445

Lys Pro Phe Glu Arg Asp Ile Ser Thr Glu Ile Tyr Gln Ala Gly Ser
    450                 455                 460

Thr Pro Cys Asn Gly Val Glu Gly Phe Asn Cys Tyr Phe Pro Leu Gln
465                 470                 475                 480

Ser Tyr Gly Phe Gln Pro Thr Asn Gly Val Gly Tyr Gln Pro Tyr Arg
                485                 490                 495

Val Val Val Leu Ser Phe Glu Leu Leu His Ala Pro Ala Thr Val Cys
            500                 505                 510

Gly Pro Lys Lys Ser Thr Asn Leu Val Lys Asn Lys Cys Val Asn Phe
        515                 520                 525

Asn Phe Asn Gly Leu Thr Gly Thr Gly Val Leu Thr Glu Ser Asn Lys
    530                 535                 540

Lys Phe Leu Pro Phe Gln Gln Phe Gly Arg Asp Ile Ala Asp Thr Thr
545                 550                 555                 560

Asp Ala Val Arg Asp Pro Gln Thr Leu Glu Ile Leu Asp Ile Thr Pro
                565                 570                 575

Cys Ser Phe Gly Gly Val Ser Val Ile Thr Pro Gly Thr Asn Thr Ser
            580                 585                 590

Asn Gln Val Ala Val Leu Tyr Gln Asp Val Asn Cys Thr Glu Val Pro
        595                 600                 605

Val Ala Ile His Ala Asp Gln Leu Thr Pro Thr Trp Arg Val Tyr Ser
    610                 615                 620

Thr Gly Ser Asn Val Phe Gln Thr Arg Ala Gly Cys Leu Ile Gly Ala
625                 630                 635                 640

Glu His Val Asn Asn Ser Tyr Glu Cys Asp Ile Pro Ile Gly Ala Gly
                645                 650                 655

Ile Cys Ala Ser Tyr Gln Thr Gln Thr Asn Ser Pro Gln Gln Ala Gln
            660                 665                 670

Ser Val Ala Leu Gly Ala Glu Asn Ser Val Ala Tyr Ser Asn Asn Ser
        675                 680                 685

Ile Ala Ile Pro Thr Asn Phe Thr Ile Ser Val Thr Thr Glu Ile Leu
    690                 695                 700

Pro Val Ser Met Thr Lys Thr Ser Val Asp Cys Thr Met Tyr Ile Cys
705                 710                 715                 720

Gly Asp Ser Thr Glu Cys Ser Asn Leu Leu Leu Gln Tyr Gly Ser Phe
                725                 730                 735

Cys Thr Gln Leu Asn Arg Ala Leu Thr Gly Ile Ala Val Glu Gln Asp
```

```
            740                 745                 750

Lys Asn Thr Gln Glu Val Phe Ala Gln Val Lys Gln Ile Tyr Lys Thr
        755                 760                 765

Pro Pro Ile Lys Asp Phe Gly Gly Phe Asn Phe Ser Gln Ile Leu Pro
    770                 775                 780

Asp Pro Ser Lys Pro Ser Lys Arg Ser Phe Ile Glu Asp Leu Leu Phe
785                 790                 795                 800

Asn Lys Val Thr Leu Ala Asp Ala Gly Phe Ile Lys Gln Tyr Gly Asp
                805                 810                 815

Cys Leu Gly Asp Ile Ala Ala Arg Asp Leu Ile Cys Ala Gln Lys Phe
            820                 825                 830

Asn Gly Leu Thr Val Leu Pro Pro Leu Leu Thr Asp Glu Met Ile Ala
        835                 840                 845

Gln Tyr Thr Ser Ala Leu Leu Ala Gly Thr Ile Thr Ser Gly Trp Thr
    850                 855                 860

Phe Gly Ala Gly Ala Ala Leu Gln Ile Pro Phe Ala Met Gln Met Ala
865                 870                 875                 880

Tyr Arg Phe Asn Gly Ile Gly Val Thr Gln Asn Val Leu Tyr Glu Asn
                885                 890                 895

Gln Lys Leu Ile Ala Asn Gln Phe Asn Ser Ala Ile Gly Lys Ile Gln
            900                 905                 910

Asp Ser Leu Ser Ser Thr Ala Ser Ala Leu Gly Lys Leu Gln Asp Val
        915                 920                 925

Val Asn Gln Asn Ala Gln Ala Leu Asn Thr Leu Val Lys Gln Leu Ser
    930                 935                 940

Ser Asn Phe Gly Ala Ile Ser Ser Val Leu Asn Asp Ile Leu Ser Arg
945                 950                 955                 960

Leu Asp Lys Val Glu Ala Glu Val Gln Ile Asp Arg Leu Ile Thr Gly
                965                 970                 975

Arg Leu Gln Ser Leu Gln Thr Tyr Val Thr Gln Gln Leu Ile Arg Ala
            980                 985                 990

Ala Glu Ile Arg Ala Ser Ala Asn  Leu Ala Ala Thr Lys  Met Ser Glu
        995                 1000                1005

Cys Val  Leu Gly Gln Ser Lys  Arg Val Asp Phe Cys  Gly Lys Gly
    1010                1015                1020

Tyr His  Leu Met Ser Phe Pro  Gln Ser Ala Pro His  Gly Val Val
    1025                1030                1035

Phe Leu  His Val Thr Tyr Val  Pro Ala Gln Glu Lys  Asn Phe Thr
    1040                1045                1050

Thr Ala  Pro Ala Ile Cys His  Asp Gly Lys Ala His  Phe Pro Arg
    1055                1060                1065

Glu Gly  Val Phe Val Ser Asn  Gly Thr His Trp Phe  Val Thr Gln
    1070                1075                1080

Arg Asn  Phe Tyr Glu Pro Gln  Ile Ile Thr Thr Asp  Asn Thr Phe
    1085                1090                1095

Val Ser  Gly Asn Cys Asp Val  Val Ile Gly Ile Val  Asn Asn Thr
    1100                1105                1110

Val Tyr  Asp Pro Leu Gln Pro  Glu Leu Asp Ser Phe  Lys Glu Glu
    1115                1120                1125

Leu Asp  Lys Tyr Phe Lys Asn  His Thr Ser Pro Asp  Val Asp Leu
    1130                1135                1140

Gly Asp  Ile Ser Gly Ile Asn  Ala Ser Val Val Asn  Ile Gln Lys
    1145                1150                1155
```

Glu Ile Asp Arg Leu Asn Glu Val Ala Lys Asn Leu Asn Glu Ser
1160 1165 1170

Leu Ile Asp Leu Gln Glu Leu Gly Lys Tyr Glu Gln Tyr Ile Lys
1175 1180 1185

Trp Pro Trp Tyr Ile Trp Leu Gly Phe Ile Ala Gly Leu Ile Ala
1190 1195 1200

Ile Val Met Val Thr Ile Met Leu Cys Cys Met Thr Ser Cys Cys
1205 1210 1215

Ser Cys Leu Lys Gly Cys Cys Ser Cys Gly Ser Cys Cys Lys Phe
1220 1225 1230

Asp Glu Asp Asp Ser Glu Pro Val Leu Lys Gly Val Lys Leu His
1235 1240 1245

Tyr Thr
1250

<210> SEQ ID NO 64
<211> LENGTH: 1263
<212> TYPE: PRT
<213> ORGANISM: Artificial Sequence
<220> FEATURE:
<223> OTHER INFORMATION: RECOMBINANT SPIKE PROTEIN

<400> SEQUENCE: 64

Met Phe Val Phe Leu Val Leu Leu Pro Leu Val Ser Ser Gln Cys Val
1 5 10 15

Asn Leu Thr Thr Arg Thr Gln Leu Pro Pro Ala Tyr Thr Asn Ser Phe
20 25 30

Thr Arg Gly Val Tyr Tyr Pro Asp Lys Val Phe Arg Ser Ser Val Leu
35 40 45

His Ser Thr Gln Asp Leu Phe Leu Pro Phe Phe Ser Asn Val Thr Trp
50 55 60

Phe His Ala Ile His Val Ser Gly Thr Asn Gly Thr Lys Arg Phe Asp
65 70 75 80

Asn Pro Val Leu Pro Phe Asn Asp Gly Val Tyr Phe Ala Ser Thr Glu
85 90 95

Lys Ser Asn Ile Ile Arg Gly Trp Ile Phe Gly Thr Thr Leu Asp Ser
100 105 110

Lys Thr Gln Ser Leu Leu Ile Val Asn Asn Ala Thr Asn Val Val Ile
115 120 125

Lys Val Cys Glu Phe Gln Phe Cys Asn Asp Pro Phe Leu Gly Val Tyr
130 135 140

Tyr His Lys Asn Asn Lys Ser Trp Met Glu Ser Glu Phe Arg Val Tyr
145 150 155 160

Ser Ser Ala Asn Asn Cys Thr Phe Glu Tyr Val Ser Gln Pro Phe Leu
165 170 175

Met Asp Leu Glu Gly Lys Gln Gly Asn Phe Lys Asn Leu Arg Glu Phe
180 185 190

Val Phe Lys Asn Ile Asp Gly Tyr Phe Lys Ile Tyr Ser Lys His Thr
195 200 205

Pro Ile Asn Leu Val Arg Asp Leu Pro Gln Gly Phe Ser Ala Leu Glu
210 215 220

Pro Leu Val Asp Leu Pro Ile Gly Ile Asn Ile Thr Arg Phe Gln Thr
225 230 235 240

Leu Leu Ala Leu His Arg Ser Tyr Leu Thr Pro Gly Asp Ser Ser Ser
245 250 255

-continued

```
Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670
```

-continued

```
Ser Tyr Gln Thr Gln Thr Asn Ser Pro Gln Gln Ala Gln Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Glu Ile Leu Pro Val Ser
705                 710                 715                 720

Met Thr Lys Thr Ser Val Asp Cys Thr Met Tyr Ile Cys Gly Asp Ser
                725                 730                 735

Thr Glu Cys Ser Asn Leu Leu Leu Gln Tyr Gly Ser Phe Cys Thr Gln
            740                 745                 750

Leu Asn Arg Ala Leu Thr Gly Ile Ala Val Glu Gln Asp Lys Asn Thr
        755                 760                 765

Gln Glu Val Phe Ala Gln Val Lys Gln Ile Tyr Lys Thr Pro Pro Ile
    770                 775                 780

Lys Asp Phe Gly Gly Phe Asn Phe Ser Gln Ile Leu Pro Asp Pro Ser
785                 790                 795                 800

Lys Pro Ser Lys Arg Ser Phe Ile Glu Asp Leu Leu Phe Asn Lys Val
                805                 810                 815

Thr Leu Ala Asp Ala Gly Phe Ile Lys Gln Tyr Gly Asp Cys Leu Gly
            820                 825                 830

Asp Ile Ala Ala Arg Asp Leu Ile Cys Ala Gln Lys Phe Asn Gly Leu
        835                 840                 845

Thr Val Leu Pro Pro Leu Leu Thr Asp Glu Met Ile Ala Gln Tyr Thr
    850                 855                 860

Ser Ala Leu Leu Ala Gly Thr Ile Thr Ser Gly Trp Thr Phe Gly Ala
865                 870                 875                 880

Gly Ala Ala Leu Gln Ile Pro Phe Ala Met Gln Met Ala Tyr Arg Phe
                885                 890                 895

Asn Gly Ile Gly Val Thr Gln Asn Val Leu Tyr Glu Asn Gln Lys Leu
            900                 905                 910

Ile Ala Asn Gln Phe Asn Ser Ala Ile Gly Lys Ile Gln Asp Ser Leu
        915                 920                 925

Ser Ser Thr Ala Ser Ala Leu Gly Lys Leu Gln Asp Val Val Asn Gln
    930                 935                 940

Asn Ala Gln Ala Leu Asn Thr Leu Val Lys Gln Leu Ser Ser Asn Phe
945                 950                 955                 960

Gly Ala Ile Ser Ser Val Leu Asn Asp Ile Leu Ser Arg Leu Asp Lys
                965                 970                 975

Val Glu Ala Glu Val Gln Ile Asp Arg Leu Ile Thr Gly Arg Leu Gln
            980                 985                 990

Ser Leu Gln Thr Tyr Val Thr Gln  Gln Leu Ile Arg Ala  Ala Glu Ile
        995                 1000                1005

Arg Ala  Ser Ala Asn Leu Ala  Ala Thr Lys Met Ser  Glu Cys Val
    1010                1015                1020

Leu Gly  Gln Ser Lys Arg Val  Asp Phe Cys Gly Lys  Gly Tyr His
    1025                1030                1035

Leu Met  Ser Phe Pro Gln Ser  Ala Pro His Gly Val  Val Phe Leu
    1040                1045                1050

His Val  Thr Tyr Val Pro Ala  Gln Glu Lys Asn Phe  Thr Thr Ala
    1055                1060                1065

Pro Ala  Ile Cys His Asp Gly  Lys Ala His Phe Pro  Arg Glu Gly
    1070                1075                1080

Val Phe  Val Ser Asn Gly Thr  His Trp Phe Val Thr  Gln Arg Asn
```

1085 1090 1095

Phe Tyr Glu Pro Gln Ile Ile Thr Thr Asp Asn Thr Phe Val Ser
1100 1105 1110

Gly Asn Cys Asp Val Val Ile Gly Ile Val Asn Asn Thr Val Tyr
1115 1120 1125

Asp Pro Leu Gln Pro Glu Leu Asp Ser Phe Lys Glu Glu Leu Asp
1130 1135 1140

Lys Tyr Phe Lys Asn His Thr Ser Pro Asp Val Asp Leu Gly Asp
1145 1150 1155

Ile Ser Gly Ile Asn Ala Ser Val Val Asn Ile Gln Lys Glu Ile
1160 1165 1170

Asp Arg Leu Asn Glu Val Ala Lys Asn Leu Asn Glu Ser Leu Ile
1175 1180 1185

Asp Leu Gln Glu Leu Gly Lys Tyr Glu Gln Tyr Ile Lys Trp Pro
1190 1195 1200

Trp Tyr Ile Trp Leu Gly Phe Ile Ala Gly Leu Ile Ala Ile Val
1205 1210 1215

Met Val Thr Ile Met Leu Cys Cys Met Thr Ser Cys Cys Ser Cys
1220 1225 1230

Leu Lys Gly Cys Cys Ser Cys Gly Ser Cys Cys Lys Phe Asp Glu
1235 1240 1245

Asp Asp Ser Glu Pro Val Leu Lys Gly Val Lys Leu His Tyr Thr
1250 1255 1260

<210> SEQ ID NO 65
<211> LENGTH: 1250
<212> TYPE: PRT
<213> ORGANISM: Artificial Sequence
<220> FEATURE:
<223> OTHER INFORMATION: RECOMBINANT SPIKE PROTEIN

<400> SEQUENCE: 65

Gln Cys Val Asn Leu Thr Thr Arg Thr Gln Leu Pro Pro Ala Tyr Thr
1 5 10 15

Asn Ser Phe Thr Arg Gly Val Tyr Tyr Pro Asp Lys Val Phe Arg Ser
20 25 30

Ser Val Leu His Ser Thr Gln Asp Leu Phe Leu Pro Phe Phe Ser Asn
35 40 45

Val Thr Trp Phe His Ala Ile His Val Ser Gly Thr Asn Gly Thr Lys
50 55 60

Arg Phe Asp Asn Pro Val Leu Pro Phe Asn Asp Gly Val Tyr Phe Ala
65 70 75 80

Ser Thr Glu Lys Ser Asn Ile Ile Arg Gly Trp Ile Phe Gly Thr Thr
85 90 95

Leu Asp Ser Lys Thr Gln Ser Leu Leu Ile Val Asn Asn Ala Thr Asn
100 105 110

Val Val Ile Lys Val Cys Glu Phe Gln Phe Cys Asn Asp Pro Phe Leu
115 120 125

Gly Val Tyr Tyr His Lys Asn Asn Lys Ser Trp Met Glu Ser Glu Phe
130 135 140

Arg Val Tyr Ser Ser Ala Asn Asn Cys Thr Phe Glu Tyr Val Ser Gln
145 150 155 160

Pro Phe Leu Met Asp Leu Glu Gly Lys Gln Gly Asn Phe Lys Asn Leu
165 170 175

Arg Glu Phe Val Phe Lys Asn Ile Asp Gly Tyr Phe Lys Ile Tyr Ser

-continued

```
            180                 185                 190

Lys His Thr Pro Ile Asn Leu Val Arg Asp Leu Pro Gln Gly Phe Ser
        195                 200                 205

Ala Leu Glu Pro Leu Val Asp Leu Pro Ile Gly Ile Asn Ile Thr Arg
    210                 215                 220

Phe Gln Thr Leu Leu Ala Leu His Arg Ser Tyr Leu Thr Pro Gly Asp
225                 230                 235                 240

Ser Ser Ser Gly Trp Thr Ala Gly Ala Ala Ala Tyr Tyr Val Gly Tyr
                245                 250                 255

Leu Gln Pro Arg Thr Phe Leu Leu Lys Tyr Asn Glu Asn Gly Thr Ile
            260                 265                 270

Thr Asp Ala Val Asp Cys Ala Leu Asp Pro Leu Ser Glu Thr Lys Cys
        275                 280                 285

Thr Leu Lys Ser Phe Thr Val Glu Lys Gly Ile Tyr Gln Thr Ser Asn
    290                 295                 300

Phe Arg Val Gln Pro Thr Glu Ser Ile Val Arg Phe Pro Asn Ile Thr
305                 310                 315                 320

Asn Leu Cys Pro Phe Gly Glu Val Phe Asn Ala Thr Arg Phe Ala Ser
                325                 330                 335

Val Tyr Ala Trp Asn Arg Lys Arg Ile Ser Asn Cys Val Ala Asp Tyr
            340                 345                 350

Ser Val Leu Tyr Asn Ser Ala Ser Phe Ser Thr Phe Lys Cys Tyr Gly
        355                 360                 365

Val Ser Pro Thr Lys Leu Asn Asp Leu Cys Phe Thr Asn Val Tyr Ala
    370                 375                 380

Asp Ser Phe Val Ile Arg Gly Asp Glu Val Arg Gln Ile Ala Pro Gly
385                 390                 395                 400

Gln Thr Gly Lys Ile Ala Asp Tyr Asn Tyr Lys Leu Pro Asp Asp Phe
                405                 410                 415

Thr Gly Cys Val Ile Ala Trp Asn Ser Asn Asn Leu Asp Ser Lys Val
            420                 425                 430

Gly Gly Asn Tyr Asn Tyr Leu Tyr Arg Leu Phe Arg Lys Ser Asn Leu
        435                 440                 445

Lys Pro Phe Glu Arg Asp Ile Ser Thr Glu Ile Tyr Gln Ala Gly Ser
    450                 455                 460

Thr Pro Cys Asn Gly Val Glu Gly Phe Asn Cys Tyr Phe Pro Leu Gln
465                 470                 475                 480

Ser Tyr Gly Phe Gln Pro Thr Asn Gly Val Gly Tyr Gln Pro Tyr Arg
                485                 490                 495

Val Val Val Leu Ser Phe Glu Leu Leu His Ala Pro Ala Thr Val Cys
            500                 505                 510

Gly Pro Lys Lys Ser Thr Asn Leu Val Lys Asn Lys Cys Val Asn Phe
        515                 520                 525

Asn Phe Asn Gly Leu Thr Gly Thr Gly Val Leu Thr Glu Ser Asn Lys
    530                 535                 540

Lys Phe Leu Pro Phe Gln Gln Phe Gly Arg Asp Ile Ala Asp Thr Thr
545                 550                 555                 560

Asp Ala Val Arg Asp Pro Gln Thr Leu Glu Ile Leu Asp Ile Thr Pro
                565                 570                 575

Cys Ser Phe Gly Gly Val Ser Val Ile Thr Pro Gly Thr Asn Thr Ser
            580                 585                 590

Asn Gln Val Ala Val Leu Tyr Gln Asp Val Asn Cys Thr Glu Val Pro
        595                 600                 605
```

```
Val Ala Ile His Ala Asp Gln Leu Thr Pro Thr Trp Arg Val Tyr Ser
    610                 615                 620

Thr Gly Ser Asn Val Phe Gln Thr Arg Ala Gly Cys Leu Ile Gly Ala
625                 630                 635                 640

Glu His Val Asn Asn Ser Tyr Glu Cys Asp Ile Pro Ile Gly Ala Gly
                645                 650                 655

Ile Cys Ala Ser Tyr Gln Thr Gln Thr Asn Ser Pro Gln Gln Ala Gln
            660                 665                 670

Ser Val Ala Ser Gln Ser Ile Ile Ala Tyr Thr Met Ser Leu Gly Ala
        675                 680                 685

Glu Asn Ser Val Ala Tyr Ser Asn Asn Ser Ile Ala Ile Glu Ile Leu
    690                 695                 700

Pro Val Ser Met Thr Lys Thr Ser Val Asp Cys Thr Met Tyr Ile Cys
705                 710                 715                 720

Gly Asp Ser Thr Glu Cys Ser Asn Leu Leu Leu Gln Tyr Gly Ser Phe
                725                 730                 735

Cys Thr Gln Leu Asn Arg Ala Leu Thr Gly Ile Ala Val Glu Gln Asp
            740                 745                 750

Lys Asn Thr Gln Glu Val Phe Ala Gln Val Lys Gln Ile Tyr Lys Thr
        755                 760                 765

Pro Pro Ile Lys Asp Phe Gly Gly Phe Asn Phe Ser Gln Ile Leu Pro
    770                 775                 780

Asp Pro Ser Lys Pro Ser Lys Arg Ser Phe Ile Glu Asp Leu Leu Phe
785                 790                 795                 800

Asn Lys Val Thr Leu Ala Asp Ala Gly Phe Ile Lys Gln Tyr Gly Asp
                805                 810                 815

Cys Leu Gly Asp Ile Ala Ala Arg Asp Leu Ile Cys Ala Gln Lys Phe
            820                 825                 830

Asn Gly Leu Thr Val Leu Pro Pro Leu Leu Thr Asp Glu Met Ile Ala
        835                 840                 845

Gln Tyr Thr Ser Ala Leu Leu Ala Gly Thr Ile Thr Ser Gly Trp Thr
    850                 855                 860

Phe Gly Ala Gly Ala Ala Leu Gln Ile Pro Phe Ala Met Gln Met Ala
865                 870                 875                 880

Tyr Arg Phe Asn Gly Ile Gly Val Thr Gln Asn Val Leu Tyr Glu Asn
                885                 890                 895

Gln Lys Leu Ile Ala Asn Gln Phe Asn Ser Ala Ile Gly Lys Ile Gln
            900                 905                 910

Asp Ser Leu Ser Ser Thr Ala Ser Ala Leu Gly Lys Leu Gln Asp Val
        915                 920                 925

Val Asn Gln Asn Ala Gln Ala Leu Asn Thr Leu Val Lys Gln Leu Ser
    930                 935                 940

Ser Asn Phe Gly Ala Ile Ser Ser Val Leu Asn Asp Ile Leu Ser Arg
945                 950                 955                 960

Leu Asp Lys Val Glu Ala Glu Val Gln Ile Asp Arg Leu Ile Thr Gly
                965                 970                 975

Arg Leu Gln Ser Leu Gln Thr Tyr Val Thr Gln Gln Leu Ile Arg Ala
            980                 985                 990

Ala Glu Ile Arg Ala Ser Ala Asn  Leu Ala Ala Thr Lys  Met Ser Glu
        995                 1000                 1005

Cys Val  Leu Gly Gln Ser Lys  Arg Val Asp Phe Cys  Gly Lys Gly
    1010                 1015                 1020
```

-continued

```
Tyr His  Leu Met Ser Phe Pro  Gln Ser Ala Pro His  Gly Val Val
    1025                 1030                 1035

Phe Leu  His Val Thr Tyr Val  Pro Ala Gln Glu Lys  Asn Phe Thr
    1040                 1045                 1050

Thr Ala  Pro Ala Ile Cys His  Asp Gly Lys Ala His  Phe Pro Arg
    1055                 1060                 1065

Glu Gly  Val Phe Val Ser Asn  Gly Thr His Trp Phe  Val Thr Gln
    1070                 1075                 1080

Arg Asn  Phe Tyr Glu Pro Gln  Ile Ile Thr Thr Asp  Asn Thr Phe
    1085                 1090                 1095

Val Ser  Gly Asn Cys Asp Val  Val Ile Gly Ile Val  Asn Asn Thr
    1100                 1105                 1110

Val Tyr  Asp Pro Leu Gln Pro  Glu Leu Asp Ser Phe  Lys Glu Glu
    1115                 1120                 1125

Leu Asp  Lys Tyr Phe Lys Asn  His Thr Ser Pro Asp  Val Asp Leu
    1130                 1135                 1140

Gly Asp  Ile Ser Gly Ile Asn  Ala Ser Val Val Asn  Ile Gln Lys
    1145                 1150                 1155

Glu Ile  Asp Arg Leu Asn Glu  Val Ala Lys Asn Leu  Asn Glu Ser
    1160                 1165                 1170

Leu Ile  Asp Leu Gln Glu Leu  Gly Lys Tyr Glu Gln  Tyr Ile Lys
    1175                 1180                 1185

Trp Pro  Trp Tyr Ile Trp Leu  Gly Phe Ile Ala Gly  Leu Ile Ala
    1190                 1195                 1200

Ile Val  Met Val Thr Ile Met  Leu Cys Cys Met Thr  Ser Cys Cys
    1205                 1210                 1215

Ser Cys  Leu Lys Gly Cys Cys  Ser Cys Gly Ser Cys  Cys Lys Phe
    1220                 1225                 1230

Asp Glu  Asp Asp Ser Glu Pro  Val Leu Lys Gly Val  Lys Leu His
    1235                 1240                 1245

Tyr Thr
    1250


<210> SEQ ID NO 66
<211> LENGTH: 1263
<212> TYPE: PRT
<213> ORGANISM: Artificial Sequence
<220> FEATURE:
<223> OTHER INFORMATION: RECOMBINANT SPIKE PROTEIN

<400> SEQUENCE: 66

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110
```

```
Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
```

-continued

```
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Gln Gln Ala Gln Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Ala Asp Ala Gly Phe Ile Lys Gln Tyr Gly Asp Cys Leu Gly
            820                 825                 830

Asp Ile Ala Ala Arg Asp Leu Ile Cys Ala Gln Lys Phe Asn Gly Leu
        835                 840                 845

Thr Val Leu Pro Pro Leu Leu Thr Asp Glu Met Ile Ala Gln Tyr Thr
    850                 855                 860

Ser Ala Leu Leu Ala Gly Thr Ile Thr Ser Gly Trp Thr Phe Gly Ala
865                 870                 875                 880

Gly Ala Ala Leu Gln Ile Pro Phe Ala Met Gln Met Ala Tyr Arg Phe
                885                 890                 895

Asn Gly Ile Gly Val Thr Gln Asn Val Leu Tyr Glu Asn Gln Lys Leu
            900                 905                 910

Ile Ala Asn Gln Phe Asn Ser Ala Ile Gly Lys Ile Gln Asp Ser Leu
        915                 920                 925

Ser Ser Thr Ala Ser Ala Leu Gly Lys Leu Gln Asp Val Val Asn Gln
    930                 935                 940

Asn Ala Gln Ala Leu Asn Thr Leu Val Lys Gln Leu Ser Ser Asn Phe
945                 950                 955                 960
```

-continued

```
Gly Ala Ile Ser Ser Val Leu Asn Asp Ile Leu Ser Arg Leu Asp Lys
                965                 970                 975

Val Glu Ala Glu Val Gln Ile Asp Arg Leu Ile Thr Gly Arg Leu Gln
            980                 985                 990

Ser Leu Gln Thr Tyr Val Thr Gln  Gln Leu Ile Arg Ala  Ala Glu Ile
        995                 1000                1005

Arg Ala  Ser Ala Asn Leu Ala  Ala Thr Lys Met Ser  Glu Cys Val
    1010                1015                1020

Leu Gly  Gln Ser Lys Arg Val  Asp Phe Cys Gly Lys  Gly Tyr His
    1025                1030                1035

Leu Met  Ser Phe Pro Gln Ser  Ala Pro His Gly Val  Val Phe Leu
    1040                1045                1050

His Val  Thr Tyr Val Pro Ala  Gln Glu Lys Asn Phe  Thr Thr Ala
    1055                1060                1065

Pro Ala  Ile Cys His Asp Gly  Lys Ala His Phe Pro  Arg Glu Gly
    1070                1075                1080

Val Phe  Val Ser Asn Gly Thr  His Trp Phe Val Thr  Gln Arg Asn
    1085                1090                1095

Phe Tyr  Glu Pro Gln Ile Ile  Thr Thr Asp Asn Thr  Phe Val Ser
    1100                1105                1110

Gly Asn  Cys Asp Val Val Ile  Gly Ile Val Asn Asn  Thr Val Tyr
    1115                1120                1125

Asp Pro  Leu Gln Pro Glu Leu  Asp Ser Phe Lys Glu  Glu Leu Asp
    1130                1135                1140

Lys Tyr  Phe Lys Asn His Thr  Ser Pro Asp Val Asp  Leu Gly Asp
    1145                1150                1155

Ile Ser  Gly Ile Asn Ala Ser  Val Val Asn Ile Gln  Lys Glu Ile
    1160                1165                1170

Asp Arg  Leu Asn Glu Val Ala  Lys Asn Leu Asn Glu  Ser Leu Ile
    1175                1180                1185

Asp Leu  Gln Glu Leu Gly Lys  Tyr Glu Gln Tyr Ile  Lys Trp Pro
    1190                1195                1200

Trp Tyr  Ile Trp Leu Gly Phe  Ile Ala Gly Leu Ile  Ala Ile Val
    1205                1210                1215

Met Val  Thr Ile Met Leu Cys  Cys Met Thr Ser Cys  Cys Ser Cys
    1220                1225                1230

Leu Lys  Gly Cys Cys Ser Cys  Gly Ser Cys Cys Lys  Phe Asp Glu
    1235                1240                1245

Asp Asp  Ser Glu Pro Val Leu  Lys Gly Val Lys Leu  His Tyr Thr
    1250                1255                1260


<210> SEQ ID NO 67
<211> LENGTH: 1250
<212> TYPE: PRT
<213> ORGANISM: Artificial Sequence
<220> FEATURE:
<223> OTHER INFORMATION: RECOMBINANT SPIKE PROTEIN

<400> SEQUENCE: 67

Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
            20                  25                  30

Ser Val Leu His Ser Thr Gln Asp Leu Phe Leu Pro Phe Phe Ser Asn
        35                  40                  45
```

```
Val Thr Trp Phe His Ala Ile His Val Ser Gly Thr Asn Gly Thr Lys
    50                  55                  60

Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                85                  90                  95

Leu Asp Ser Lys Thr Gln Ser Leu Leu Ile Val Asn Asn Ala Thr Asn
            100                 105                 110

Val Val Ile Lys Val Cys Glu Phe Gln Phe Cys Asn Asp Pro Phe Leu
        115                 120                 125

Gly Val Tyr Tyr His Lys Asn Asn Lys Ser Trp Met Glu Ser Glu Phe
    130                 135                 140

Arg Val Tyr Ser Ser Ala Asn Asn Cys Thr Phe Glu Tyr Val Ser Gln
145                 150                 155                 160

Pro Phe Leu Met Asp Leu Glu Gly Lys Gln Gly Asn Phe Lys Asn Leu
                165                 170                 175

Arg Glu Phe Val Phe Lys Asn Ile Asp Gly Tyr Phe Lys Ile Tyr Ser
            180                 185                 190

Lys His Thr Pro Ile Asn Leu Val Arg Asp Leu Pro Gln Gly Phe Ser
        195                 200                 205

Ala Leu Glu Pro Leu Val Asp Leu Pro Ile Gly Ile Asn Ile Thr Arg
    210                 215                 220

Phe Gln Thr Leu Leu Ala Leu His Arg Ser Tyr Leu Thr Pro Gly Asp
225                 230                 235                 240

Ser Ser Ser Gly Trp Thr Ala Gly Ala Ala Ala Tyr Tyr Val Gly Tyr
                245                 250                 255

Leu Gln Pro Arg Thr Phe Leu Leu Lys Tyr Asn Glu Asn Gly Thr Ile
            260                 265                 270

Thr Asp Ala Val Asp Cys Ala Leu Asp Pro Leu Ser Glu Thr Lys Cys
        275                 280                 285

Thr Leu Lys Ser Phe Thr Val Glu Lys Gly Ile Tyr Gln Thr Ser Asn
    290                 295                 300

Phe Arg Val Gln Pro Thr Glu Ser Ile Val Arg Phe Pro Asn Ile Thr
305                 310                 315                 320

Asn Leu Cys Pro Phe Gly Glu Val Phe Asn Ala Thr Arg Phe Ala Ser
                325                 330                 335

Val Tyr Ala Trp Asn Arg Lys Arg Ile Ser Asn Cys Val Ala Asp Tyr
            340                 345                 350

Ser Val Leu Tyr Asn Ser Ala Ser Phe Ser Thr Phe Lys Cys Tyr Gly
        355                 360                 365

Val Ser Pro Thr Lys Leu Asn Asp Leu Cys Phe Thr Asn Val Tyr Ala
    370                 375                 380

Asp Ser Phe Val Ile Arg Gly Asp Glu Val Arg Gln Ile Ala Pro Gly
385                 390                 395                 400

Gln Thr Gly Lys Ile Ala Asp Tyr Asn Tyr Lys Leu Pro Asp Asp Phe
                405                 410                 415

Thr Gly Cys Val Ile Ala Trp Asn Ser Asn Asn Leu Asp Ser Lys Val
            420                 425                 430

Gly Gly Asn Tyr Asn Tyr Leu Tyr Arg Leu Phe Arg Lys Ser Asn Leu
        435                 440                 445

Lys Pro Phe Glu Arg Asp Ile Ser Thr Glu Ile Tyr Gln Ala Gly Ser
    450                 455                 460
```

-continued

```
Thr Pro Cys Asn Gly Val Glu Gly Phe Asn Cys Tyr Phe Pro Leu Gln
465                 470                 475                 480

Ser Tyr Gly Phe Gln Pro Thr Asn Gly Val Gly Tyr Gln Pro Tyr Arg
                485                 490                 495

Val Val Val Leu Ser Phe Glu Leu Leu His Ala Pro Ala Thr Val Cys
            500                 505                 510

Gly Pro Lys Lys Ser Thr Asn Leu Val Lys Asn Lys Cys Val Asn Phe
        515                 520                 525

Asn Phe Asn Gly Leu Thr Gly Thr Gly Val Leu Thr Glu Ser Asn Lys
    530                 535                 540

Lys Phe Leu Pro Phe Gln Gln Phe Gly Arg Asp Ile Ala Asp Thr Thr
545                 550                 555                 560

Asp Ala Val Arg Asp Pro Gln Thr Leu Glu Ile Leu Asp Ile Thr Pro
                565                 570                 575

Cys Ser Phe Gly Gly Val Ser Val Ile Thr Pro Gly Thr Asn Thr Ser
            580                 585                 590

Asn Gln Val Ala Val Leu Tyr Gln Asp Val Asn Cys Thr Glu Val Pro
        595                 600                 605

Val Ala Ile His Ala Asp Gln Leu Thr Pro Thr Trp Arg Val Tyr Ser
    610                 615                 620

Thr Gly Ser Asn Val Phe Gln Thr Arg Ala Gly Cys Leu Ile Gly Ala
625                 630                 635                 640

Glu His Val Asn Asn Ser Tyr Glu Cys Asp Ile Pro Ile Gly Ala Gly
                645                 650                 655

Ile Cys Ala Ser Tyr Gln Thr Gln Thr Asn Ser Pro Gln Gln Ala Gln
            660                 665                 670

Ser Val Ala Ser Gln Ser Ile Ile Ala Tyr Thr Met Ser Leu Gly Ala
        675                 680                 685

Glu Asn Ser Val Ala Tyr Ser Asn Asn Ser Ile Ala Ile Pro Thr Asn
    690                 695                 700

Phe Thr Ile Ser Val Thr Thr Glu Ile Leu Pro Val Ser Met Thr Lys
705                 710                 715                 720

Thr Ser Val Asp Cys Thr Met Tyr Ile Cys Gly Asp Ser Thr Glu Cys
                725                 730                 735

Ser Asn Leu Leu Leu Gln Tyr Gly Ser Phe Cys Thr Gln Leu Asn Arg
            740                 745                 750

Ala Leu Thr Gly Ile Ala Val Glu Gln Asp Lys Asn Thr Gln Glu Val
        755                 760                 765

Phe Ala Gln Val Lys Gln Ile Tyr Lys Thr Pro Pro Ile Lys Asp Phe
    770                 775                 780

Gly Gly Phe Asn Phe Ser Gln Ile Leu Pro Asp Pro Ser Lys Pro Ser
785                 790                 795                 800

Lys Arg Ser Phe Ile Ala Asp Ala Gly Phe Ile Lys Gln Tyr Gly Asp
                805                 810                 815

Cys Leu Gly Asp Ile Ala Ala Arg Asp Leu Ile Cys Ala Gln Lys Phe
            820                 825                 830

Asn Gly Leu Thr Val Leu Pro Pro Leu Leu Thr Asp Glu Met Ile Ala
        835                 840                 845

Gln Tyr Thr Ser Ala Leu Leu Ala Gly Thr Ile Thr Ser Gly Trp Thr
    850                 855                 860

Phe Gly Ala Gly Ala Ala Leu Gln Ile Pro Phe Ala Met Gln Met Ala
865                 870                 875                 880

Tyr Arg Phe Asn Gly Ile Gly Val Thr Gln Asn Val Leu Tyr Glu Asn
```

-continued

```
                885                 890                 895

Gln Lys Leu Ile Ala Asn Gln Phe Asn Ser Ala Ile Gly Lys Ile Gln
            900                 905                 910

Asp Ser Leu Ser Ser Thr Ala Ser Ala Leu Gly Lys Leu Gln Asp Val
        915                 920                 925

Val Asn Gln Asn Ala Gln Ala Leu Asn Thr Leu Val Lys Gln Leu Ser
    930                 935                 940

Ser Asn Phe Gly Ala Ile Ser Ser Val Leu Asn Asp Ile Leu Ser Arg
945                 950                 955                 960

Leu Asp Lys Val Glu Ala Glu Val Gln Ile Asp Arg Leu Ile Thr Gly
                965                 970                 975

Arg Leu Gln Ser Leu Gln Thr Tyr Val Thr Gln Gln Leu Ile Arg Ala
            980                 985                 990

Ala Glu Ile Arg Ala Ser Ala Asn  Leu Ala Ala Thr Lys  Met Ser Glu
        995                 1000                1005

Cys Val  Leu Gly Gln Ser Lys  Arg Val Asp Phe Cys  Gly Lys Gly
    1010                 1015                 1020

Tyr His  Leu Met Ser Phe Pro  Gln Ser Ala Pro His  Gly Val Val
    1025                 1030                 1035

Phe Leu  His Val Thr Tyr Val  Pro Ala Gln Glu Lys  Asn Phe Thr
    1040                 1045                 1050

Thr Ala  Pro Ala Ile Cys His  Asp Gly Lys Ala His  Phe Pro Arg
    1055                 1060                 1065

Glu Gly  Val Phe Val Ser Asn  Gly Thr His Trp Phe  Val Thr Gln
    1070                 1075                 1080

Arg Asn  Phe Tyr Glu Pro Gln  Ile Ile Thr Thr Asp  Asn Thr Phe
    1085                 1090                 1095

Val Ser  Gly Asn Cys Asp Val  Val Ile Gly Ile Val  Asn Asn Thr
    1100                 1105                 1110

Val Tyr  Asp Pro Leu Gln Pro  Glu Leu Asp Ser Phe  Lys Glu Glu
    1115                 1120                 1125

Leu Asp  Lys Tyr Phe Lys Asn  His Thr Ser Pro Asp  Val Asp Leu
    1130                 1135                 1140

Gly Asp  Ile Ser Gly Ile Asn  Ala Ser Val Val Asn  Ile Gln Lys
    1145                 1150                 1155

Glu Ile  Asp Arg Leu Asn Glu  Val Ala Lys Asn Leu  Asn Glu Ser
    1160                 1165                 1170

Leu Ile  Asp Leu Gln Glu Leu  Gly Lys Tyr Glu Gln  Tyr Ile Lys
    1175                 1180                 1185

Trp Pro  Trp Tyr Ile Trp Leu  Gly Phe Ile Ala Gly  Leu Ile Ala
    1190                 1195                 1200

Ile Val  Met Val Thr Ile Met  Leu Cys Cys Met Thr  Ser Cys Cys
    1205                 1210                 1215

Ser Cys  Leu Lys Gly Cys Cys  Ser Cys Gly Ser Cys  Cys Lys Phe
    1220                 1225                 1230

Asp Glu  Asp Asp Ser Glu Pro  Val Leu Lys Gly Val  Lys Leu His
    1235                 1240                 1245

Tyr Thr
    1250
```

<210> SEQ ID NO 68
<211> LENGTH: 31
<212> TYPE: PRT
<213> ORGANISM: Artificial Sequence -continued
<220> FEATURE:
<223> OTHER INFORMATION: Foldon

<400> SEQUENCE: 68

```
Ser Ala Ile Gly Gly Tyr Ile Pro Glu Ala Pro Arg Asp Gly Gln Ala
1               5                   10                  15

Tyr Val Arg Lys Asp Gly Glu Trp Val Leu Leu Ser Thr Phe Leu
            20                  25                  30
```

<210> SEQ ID NO 69
<211> LENGTH: 202
<212> TYPE: PRT
<213> ORGANISM: Betacoronavirus severe acute respiratory syndrome coronavirus 2

<400> SEQUENCE: 69

```
Arg Phe Pro Asn Ile Thr Asn Leu Cys Pro Phe Gly Glu Val Phe Asn
1               5                   10                  15

Ala Thr Arg Phe Ala Ser Val Tyr Ala Trp Asn Arg Lys Arg Ile Ser
            20                  25                  30

Asn Cys Val Ala Asp Tyr Ser Val Leu Tyr Asn Ser Ala Ser Phe Ser
        35                  40                  45

Thr Phe Lys Cys Tyr Gly Val Ser Pro Thr Lys Leu Asn Asp Leu Cys
    50                  55                  60

Phe Thr Asn Val Tyr Ala Asp Ser Phe Val Ile Arg Gly Asp Glu Val
65                  70                  75                  80

Arg Gln Ile Ala Pro Gly Gln Thr Gly Lys Ile Ala Asp Tyr Asn Tyr
                85                  90                  95

Lys Leu Pro Asp Asp Phe Thr Gly Cys Val Ile Ala Trp Asn Ser Asn
            100                 105                 110

Asn Leu Asp Ser Lys Val Gly Gly Asn Tyr Asn Tyr Leu Tyr Arg Leu
        115                 120                 125

Phe Arg Lys Ser Asn Leu Lys Pro Phe Glu Arg Asp Ile Ser Thr Glu
    130                 135                 140

Ile Tyr Gln Ala Gly Ser Thr Pro Cys Asn Gly Val Glu Gly Phe Asn
145                 150                 155                 160

Cys Tyr Phe Pro Leu Gln Ser Tyr Gly Phe Gln Pro Thr Asn Gly Val
                165                 170                 175

Gly Tyr Gln Pro Tyr Arg Val Val Val Leu Ser Phe Glu Leu Leu His
            180                 185                 190

Ala Pro Ala Thr Val Cys Gly Pro Lys Lys
        195                 200
```

<210> SEQ ID NO 70
<211> LENGTH: 201
<212> TYPE: PRT
<213> ORGANISM: Betacoronavirus Severe acute respiratory syndrome-related coronavirus

<400> SEQUENCE: 70

```
Arg Phe Pro Asn Ile Thr Asn Leu Cys Pro Phe Gly Glu Val Phe Asn
1               5                   10                  15

Ala Thr Lys Phe Pro Ser Val Tyr Ala Trp Glu Arg Lys Lys Ile Ser
            20                  25                  30

Asn Cys Val Ala Asp Tyr Ser Val Leu Tyr Asn Ser Thr Phe Phe Ser
        35                  40                  45

Thr Phe Lys Cys Tyr Gly Val Ser Ala Thr Lys Leu Asn Asp Leu Cys
    50                  55                  60
```

```
Phe Ser Asn Val Tyr Ala Asp Ser Phe Val Val Lys Gly Asp Asp Val
65                  70                  75                  80

Arg Gln Ile Ala Pro Gly Gln Thr Gly Val Ile Ala Asp Tyr Asn Tyr
                85                  90                  95

Lys Leu Pro Asp Asp Phe Met Gly Cys Val Leu Ala Trp Asn Thr Arg
            100                 105                 110

Asn Ile Asp Ala Thr Ser Thr Gly Asn Tyr Asn Tyr Lys Tyr Arg Tyr
        115                 120                 125

Leu Arg His Gly Lys Leu Arg Pro Phe Glu Arg Asp Ile Ser Asn Val
    130                 135                 140

Pro Phe Ser Pro Asp Gly Lys Pro Cys Thr Pro Pro Ala Leu Asn Cys
145                 150                 155                 160

Tyr Trp Pro Leu Asn Asp Tyr Gly Phe Tyr Thr Thr Thr Gly Ile Gly
                165                 170                 175

Tyr Gln Pro Tyr Arg Val Val Val Leu Ser Phe Glu Leu Leu Asn Ala
            180                 185                 190

Pro Ala Thr Val Cys Gly Pro Lys Leu
        195                 200


<210> SEQ ID NO 71
<211> LENGTH: 239
<212> TYPE: PRT
<213> ORGANISM: Betacoronavirus Middle East respiratory syndrome-related
      coronavirus

<400> SEQUENCE: 71

Phe Glu Ala Lys Pro Ser Gly Ser Val Val Ala Glu Gly Val Glu Cys
1               5                   10                  15

Asp Phe Ser Pro Leu Leu Ser Gly Thr Pro Pro Gln Val Tyr Asn Phe
            20                  25                  30

Lys Arg Leu Val Phe Thr Asn Cys Asn Tyr Asn Leu Thr Lys Leu Leu
        35                  40                  45

Ser Leu Phe Ser Val Asn Asp Phe Thr Cys Ser Gln Ile Ser Pro Ala
    50                  55                  60

Ala Ile Ala Ser Asn Cys Tyr Ser Ser Leu Ile Leu Asp Tyr Phe Ser
65                  70                  75                  80

Tyr Pro Leu Ser Met Lys Ser Asp Leu Ser Val Ser Ser Ala Gly Pro
                85                  90                  95

Ile Ser Gln Phe Asn Tyr Lys Gln Ser Phe Ser Asn Pro Thr Cys Leu
            100                 105                 110

Ile Leu Ala Thr Val Pro His Asn Leu Thr Thr Ile Thr Lys Pro Leu
        115                 120                 125

Lys Tyr Ser Tyr Ile Asn Lys Cys Ser Arg Leu Leu Ser Asp Asp Arg
    130                 135                 140

Thr Glu Val Pro Gln Leu Val Asn Ala Asn Gln Tyr Ser Pro Cys Val
145                 150                 155                 160

Ser Ile Val Pro Ser Thr Val Trp Glu Asp Gly Asp Tyr Tyr Arg Lys
                165                 170                 175

Gln Leu Ser Pro Leu Glu Gly Gly Gly Trp Leu Val Ala Ser Gly Ser
            180                 185                 190

Thr Val Ala Met Thr Glu Gln Leu Gln Met Gly Phe Gly Ile Thr Val
        195                 200                 205

Gln Tyr Gly Thr Asp Thr Asn Ser Val Cys Pro Lys Leu Glu Phe Ala
    210                 215                 220
```

Asn Asp Thr Lys Ile Ala Ser Gln Leu Gly Asn Cys Val Glu Tyr
225 230 235

<210> SEQ ID NO 72
<211> LENGTH: 544
<212> TYPE: PRT
<213> ORGANISM: Artificial Sequence
<220> FEATURE:
<223> OTHER INFORMATION: RECOMBINANT SPIKE PROTEIN

<400> SEQUENCE: 72

Met Phe Val Phe Leu Val Leu Leu Pro Leu Val Ser Ser Arg Phe Pro
1 5 10 15

Asn Ile Thr Asn Leu Cys Pro Phe Gly Glu Val Phe Asn Ala Thr Arg
20 25 30

Phe Ala Ser Val Tyr Ala Trp Asn Arg Lys Arg Ile Ser Asn Cys Val
35 40 45

Ala Asp Tyr Ser Val Leu Tyr Asn Ser Ala Ser Phe Ser Thr Phe Lys
50 55 60

Cys Tyr Gly Val Ser Pro Thr Lys Leu Asn Asp Leu Cys Phe Thr Asn
65 70 75 80

Val Tyr Ala Asp Ser Phe Val Ile Arg Gly Asp Glu Val Arg Gln Ile
85 90 95

Ala Pro Gly Gln Thr Gly Lys Ile Ala Asp Tyr Asn Tyr Lys Leu Pro
100 105 110

Asp Asp Phe Thr Gly Cys Val Ile Ala Trp Asn Ser Asn Asn Leu Asp
115 120 125

Ser Lys Val Gly Gly Asn Tyr Asn Tyr Leu Tyr Arg Leu Phe Arg Lys
130 135 140

Ser Asn Leu Lys Pro Phe Glu Arg Asp Ile Ser Thr Glu Ile Tyr Gln
145 150 155 160

Ala Gly Ser Thr Pro Cys Asn Gly Val Glu Gly Phe Asn Cys Tyr Phe
165 170 175

Pro Leu Gln Ser Tyr Gly Phe Gln Pro Thr Asn Gly Val Gly Tyr Gln
180 185 190

Pro Tyr Arg Val Val Val Leu Ser Phe Glu Leu Leu His Ala Pro Ala
195 200 205

Thr Val Cys Gly Pro Lys Lys Ser Thr Asn Leu Val Lys Asn Lys Cys
210 215 220

Val Asn Phe Asn Phe Asn Gly Leu Thr Gly Thr Gly Val Leu Thr Glu
225 230 235 240

Ser Asn Lys Lys Phe Leu Pro Phe Gln Gln Phe Gly Arg Asp Ile Ala
245 250 255

Asp Thr Thr Asp Ala Val Arg Asp Pro Gln Thr Leu Glu Ile Leu Asp
260 265 270

Ile Thr Pro Cys Ser Phe Gly Gly Val Ser Val Ile Thr Pro Gly Thr
275 280 285

Asn Thr Ser Asn Gln Val Ala Val Leu Tyr Gln Asp Val Asn Cys Thr
290 295 300

Glu Arg Phe Pro Asn Ile Thr Asn Leu Cys Pro Phe Gly Glu Val Phe
305 310 315 320

Asn Ala Thr Arg Phe Ala Ser Val Tyr Ala Trp Asn Arg Lys Arg Ile
325 330 335

Ser Asn Cys Val Ala Asp Tyr Ser Val Leu Tyr Asn Ser Ala Ser Phe
340 345 350

```
Ser Thr Phe Lys Cys Tyr Gly Val Ser Pro Thr Lys Leu Asn Asp Leu
        355                 360                 365

Cys Phe Thr Asn Val Tyr Ala Asp Ser Phe Val Ile Arg Gly Asp Glu
    370                 375                 380

Val Arg Gln Ile Ala Pro Gly Gln Thr Gly Lys Ile Ala Asp Tyr Asn
385                 390                 395                 400

Tyr Lys Leu Pro Asp Asp Phe Thr Gly Cys Val Ile Ala Trp Asn Ser
                405                 410                 415

Asn Asn Leu Asp Ser Lys Val Gly Gly Asn Tyr Asn Tyr Leu Tyr Arg
            420                 425                 430

Leu Phe Arg Lys Ser Asn Leu Lys Pro Phe Glu Arg Asp Ile Ser Thr
        435                 440                 445

Glu Ile Tyr Gln Ala Gly Ser Thr Pro Cys Asn Gly Val Glu Gly Phe
    450                 455                 460

Asn Cys Tyr Phe Pro Leu Gln Ser Tyr Gly Phe Gln Pro Thr Asn Gly
465                 470                 475                 480

Val Gly Tyr Gln Pro Tyr Arg Val Val Val Leu Ser Phe Glu Leu Leu
                485                 490                 495

His Ala Pro Ala Thr Val Cys Gly Pro Lys Lys Ser Ala Ile Gly Gly
            500                 505                 510

Tyr Ile Pro Glu Ala Pro Arg Asp Gly Gln Ala Tyr Val Arg Lys Asp
        515                 520                 525

Gly Glu Trp Val Leu Leu Ser Thr Phe Leu His His His His His His
    530                 535                 540


<210> SEQ ID NO 73
<211> LENGTH: 531
<212> TYPE: PRT
<213> ORGANISM: Artificial Sequence
<220> FEATURE:
<223> OTHER INFORMATION: RECOMBINANT SPIKE PROTEIN

<400> SEQUENCE: 73

Arg Phe Pro Asn Ile Thr Asn Leu Cys Pro Phe Gly Glu Val Phe Asn
1               5                   10                  15

Ala Thr Arg Phe Ala Ser Val Tyr Ala Trp Asn Arg Lys Arg Ile Ser
            20                  25                  30

Asn Cys Val Ala Asp Tyr Ser Val Leu Tyr Asn Ser Ala Ser Phe Ser
        35                  40                  45

Thr Phe Lys Cys Tyr Gly Val Ser Pro Thr Lys Leu Asn Asp Leu Cys
    50                  55                  60

Phe Thr Asn Val Tyr Ala Asp Ser Phe Val Ile Arg Gly Asp Glu Val
65                  70                  75                  80

Arg Gln Ile Ala Pro Gly Gln Thr Gly Lys Ile Ala Asp Tyr Asn Tyr
                85                  90                  95

Lys Leu Pro Asp Asp Phe Thr Gly Cys Val Ile Ala Trp Asn Ser Asn
            100                 105                 110

Asn Leu Asp Ser Lys Val Gly Gly Asn Tyr Asn Tyr Leu Tyr Arg Leu
        115                 120                 125

Phe Arg Lys Ser Asn Leu Lys Pro Phe Glu Arg Asp Ile Ser Thr Glu
    130                 135                 140

Ile Tyr Gln Ala Gly Ser Thr Pro Cys Asn Gly Val Glu Gly Phe Asn
145                 150                 155                 160

Cys Tyr Phe Pro Leu Gln Ser Tyr Gly Phe Gln Pro Thr Asn Gly Val
                165                 170                 175
```

Gly Tyr Gln Pro Tyr Arg Val Val Val Leu Ser Phe Glu Leu Leu His
180 185 190

Ala Pro Ala Thr Val Cys Gly Pro Lys Lys Ser Thr Asn Leu Val Lys
195 200 205

Asn Lys Cys Val Asn Phe Asn Phe Asn Gly Leu Thr Gly Thr Gly Val
210 215 220

Leu Thr Glu Ser Asn Lys Lys Phe Leu Pro Phe Gln Gln Phe Gly Arg
225 230 235 240

Asp Ile Ala Asp Thr Thr Asp Ala Val Arg Asp Pro Gln Thr Leu Glu
245 250 255

Ile Leu Asp Ile Thr Pro Cys Ser Phe Gly Gly Val Ser Val Ile Thr
260 265 270

Pro Gly Thr Asn Thr Ser Asn Gln Val Ala Val Leu Tyr Gln Asp Val
275 280 285

Asn Cys Thr Glu Arg Phe Pro Asn Ile Thr Asn Leu Cys Pro Phe Gly
290 295 300

Glu Val Phe Asn Ala Thr Arg Phe Ala Ser Val Tyr Ala Trp Asn Arg
305 310 315 320

Lys Arg Ile Ser Asn Cys Val Ala Asp Tyr Ser Val Leu Tyr Asn Ser
325 330 335

Ala Ser Phe Ser Thr Phe Lys Cys Tyr Gly Val Ser Pro Thr Lys Leu
340 345 350

Asn Asp Leu Cys Phe Thr Asn Val Tyr Ala Asp Ser Phe Val Ile Arg
355 360 365

Gly Asp Glu Val Arg Gln Ile Ala Pro Gly Gln Thr Gly Lys Ile Ala
370 375 380

Asp Tyr Asn Tyr Lys Leu Pro Asp Asp Phe Thr Gly Cys Val Ile Ala
385 390 395 400

Trp Asn Ser Asn Asn Leu Asp Ser Lys Val Gly Gly Asn Tyr Asn Tyr
405 410 415

Leu Tyr Arg Leu Phe Arg Lys Ser Asn Leu Lys Pro Phe Glu Arg Asp
420 425 430

Ile Ser Thr Glu Ile Tyr Gln Ala Gly Ser Thr Pro Cys Asn Gly Val
435 440 445

Glu Gly Phe Asn Cys Tyr Phe Pro Leu Gln Ser Tyr Gly Phe Gln Pro
450 455 460

Thr Asn Gly Val Gly Tyr Gln Pro Tyr Arg Val Val Val Leu Ser Phe
465 470 475 480

Glu Leu Leu His Ala Pro Ala Thr Val Cys Gly Pro Lys Lys Ser Ala
485 490 495

Ile Gly Gly Tyr Ile Pro Glu Ala Pro Arg Asp Gly Gln Ala Tyr Val
500 505 510

Arg Lys Asp Gly Glu Trp Val Leu Leu Ser Thr Phe Leu His His His
515 520 525

His His His
530

<210> SEQ ID NO 74
<211> LENGTH: 544
<212> TYPE: PRT
<213> ORGANISM: Artificial Sequence
<220> FEATURE:
<223> OTHER INFORMATION: RECOMBINANT SPIKE PROTEIN

<400> SEQUENCE: 74

-continued

```
Met Phe Val Phe Leu Val Leu Leu Pro Leu Val Ser Ser Arg Phe Pro
1               5                   10                  15

Asn Ile Thr Asn Leu Cys Pro Phe Gly Glu Val Phe Asn Ala Thr Arg
            20                  25                  30

Phe Ala Ser Val Tyr Ala Trp Asn Arg Lys Arg Ile Ser Asn Cys Val
        35                  40                  45

Ala Asp Tyr Ser Val Leu Tyr Asn Ser Ala Ser Phe Ser Thr Phe Lys
    50                  55                  60

Cys Tyr Gly Val Ser Pro Thr Lys Leu Asn Asp Leu Cys Phe Thr Asn
65                  70                  75                  80

Val Tyr Ala Asp Ser Phe Val Ile Arg Gly Asp Glu Val Arg Gln Ile
                85                  90                  95

Ala Pro Gly Gln Thr Gly Lys Ile Ala Asp Tyr Asn Tyr Lys Leu Pro
            100                 105                 110

Asp Asp Phe Thr Gly Cys Val Ile Ala Trp Asn Ser Asn Asn Leu Asp
        115                 120                 125

Ser Lys Val Gly Gly Asn Tyr Asn Tyr Leu Tyr Arg Leu Phe Arg Lys
    130                 135                 140

Ser Asn Leu Lys Pro Phe Glu Arg Asp Ile Ser Thr Glu Ile Tyr Gln
145                 150                 155                 160

Ala Gly Ser Thr Pro Cys Asn Gly Val Glu Gly Phe Asn Cys Tyr Phe
                165                 170                 175

Pro Leu Gln Ser Tyr Gly Phe Gln Pro Thr Asn Gly Val Gly Tyr Gln
            180                 185                 190

Pro Tyr Arg Val Val Val Leu Ser Phe Glu Leu Leu His Ala Pro Ala
        195                 200                 205

Thr Val Cys Gly Pro Lys Lys Ser Thr Asn Leu Val Lys Asn Lys Cys
    210                 215                 220

Val Asn Phe Asn Phe Asn Gly Leu Thr Gly Thr Gly Val Leu Thr Glu
225                 230                 235                 240

Ser Asn Lys Lys Phe Leu Pro Phe Gln Gln Phe Gly Arg Asp Ile Ala
                245                 250                 255

Asp Thr Thr Asp Ala Val Arg Asp Pro Gln Thr Leu Glu Ile Leu Asp
            260                 265                 270

Ile Thr Pro Cys Ser Phe Gly Gly Val Ser Val Ile Thr Pro Gly Thr
        275                 280                 285

Asn Thr Ser Asn Gln Val Ala Val Leu Tyr Gln Asp Val Asn Cys Thr
    290                 295                 300

Glu Arg Phe Pro Asn Ile Thr Asn Leu Cys Pro Phe Gly Glu Val Phe
305                 310                 315                 320

Asn Ala Thr Arg Phe Ala Ser Val Tyr Ala Trp Asn Arg Lys Arg Ile
                325                 330                 335

Ser Asn Cys Val Ala Asp Tyr Ser Val Leu Tyr Asn Ser Ala Ser Phe
            340                 345                 350

Ser Thr Phe Lys Cys Tyr Gly Val Ser Pro Thr Lys Leu Asn Asp Leu
        355                 360                 365

Cys Phe Thr Asn Val Tyr Ala Asp Ser Phe Val Ile Arg Gly Asp Glu
    370                 375                 380

Val Arg Gln Ile Ala Pro Gly Gln Thr Gly Lys Ile Ala Asp Tyr Asn
385                 390                 395                 400

Tyr Lys Leu Pro Asp Asp Phe Thr Gly Cys Val Ile Ala Trp Asn Ser
                405                 410                 415

Asn Asn Leu Asp Ser Lys Val Gly Gly Asn Tyr Asn Tyr Leu Tyr Arg
```

```
            420                 425                 430

Leu Phe Arg Lys Ser Asn Leu Lys Pro Phe Glu Arg Asp Ile Ser Thr
        435                 440                 445

Glu Ile Tyr Gln Ala Gly Ser Thr Pro Cys Asn Gly Val Glu Gly Phe
    450                 455                 460

Asn Cys Tyr Phe Pro Leu Gln Ser Tyr Gly Phe Gln Pro Thr Asn Gly
465                 470                 475                 480

Val Gly Tyr Gln Pro Tyr Arg Val Val Val Leu Ser Phe Glu Leu Leu
                485                 490                 495

His Ala Pro Ala Thr Val Cys Gly Pro Lys Lys Ser Ala Ile Gly Gly
            500                 505                 510

Tyr Ile Pro Glu Ala Pro Arg Asp Gly Gln Ala Tyr Val Arg Lys Asp
        515                 520                 525

Gly Glu Trp Val Leu Leu Ser Thr Phe Leu His His His His His His
    530                 535                 540


<210> SEQ ID NO 75
<211> LENGTH: 531
<212> TYPE: PRT
<213> ORGANISM: Artificial Sequence
<220> FEATURE:
<223> OTHER INFORMATION: RECOMBINANT SPIKE PROTEIN

<400> SEQUENCE: 75

Arg Phe Pro Asn Ile Thr Asn Leu Cys Pro Phe Gly Glu Val Phe Asn
1               5                   10                  15

Ala Thr Arg Phe Ala Ser Val Tyr Ala Trp Asn Arg Lys Arg Ile Ser
            20                  25                  30

Asn Cys Val Ala Asp Tyr Ser Val Leu Tyr Asn Ser Ala Ser Phe Ser
        35                  40                  45

Thr Phe Lys Cys Tyr Gly Val Ser Pro Thr Lys Leu Asn Asp Leu Cys
    50                  55                  60

Phe Thr Asn Val Tyr Ala Asp Ser Phe Val Ile Arg Gly Asp Glu Val
65                  70                  75                  80

Arg Gln Ile Ala Pro Gly Gln Thr Gly Lys Ile Ala Asp Tyr Asn Tyr
                85                  90                  95

Lys Leu Pro Asp Asp Phe Thr Gly Cys Val Ile Ala Trp Asn Ser Asn
            100                 105                 110

Asn Leu Asp Ser Lys Val Gly Gly Asn Tyr Asn Tyr Leu Tyr Arg Leu
        115                 120                 125

Phe Arg Lys Ser Asn Leu Lys Pro Phe Glu Arg Asp Ile Ser Thr Glu
    130                 135                 140

Ile Tyr Gln Ala Gly Ser Thr Pro Cys Asn Gly Val Glu Gly Phe Asn
145                 150                 155                 160

Cys Tyr Phe Pro Leu Gln Ser Tyr Gly Phe Gln Pro Thr Asn Gly Val
                165                 170                 175

Gly Tyr Gln Pro Tyr Arg Val Val Val Leu Ser Phe Glu Leu Leu His
            180                 185                 190

Ala Pro Ala Thr Val Cys Gly Pro Lys Lys Ser Thr Asn Leu Val Lys
        195                 200                 205

Asn Lys Cys Val Asn Phe Asn Phe Asn Gly Leu Thr Gly Thr Gly Val
    210                 215                 220

Leu Thr Glu Ser Asn Lys Lys Phe Leu Pro Phe Gln Gln Phe Gly Arg
225                 230                 235                 240

Asp Ile Ala Asp Thr Thr Asp Ala Val Arg Asp Pro Gln Thr Leu Glu
```

```
                245                 250                 255

Ile Leu Asp Ile Thr Pro Cys Ser Phe Gly Gly Val Ser Val Ile Thr
            260                 265                 270

Pro Gly Thr Asn Thr Ser Asn Gln Val Ala Val Leu Tyr Gln Asp Val
        275                 280                 285

Asn Cys Thr Glu Arg Phe Pro Asn Ile Thr Asn Leu Cys Pro Phe Gly
    290                 295                 300

Glu Val Phe Asn Ala Thr Arg Phe Ala Ser Val Tyr Ala Trp Asn Arg
305                 310                 315                 320

Lys Arg Ile Ser Asn Cys Val Ala Asp Tyr Ser Val Leu Tyr Asn Ser
                325                 330                 335

Ala Ser Phe Ser Thr Phe Lys Cys Tyr Gly Val Ser Pro Thr Lys Leu
            340                 345                 350

Asn Asp Leu Cys Phe Thr Asn Val Tyr Ala Asp Ser Phe Val Ile Arg
        355                 360                 365

Gly Asp Glu Val Arg Gln Ile Ala Pro Gly Gln Thr Gly Lys Ile Ala
    370                 375                 380

Asp Tyr Asn Tyr Lys Leu Pro Asp Asp Phe Thr Gly Cys Val Ile Ala
385                 390                 395                 400

Trp Asn Ser Asn Asn Leu Asp Ser Lys Val Gly Gly Asn Tyr Asn Tyr
                405                 410                 415

Leu Tyr Arg Leu Phe Arg Lys Ser Asn Leu Lys Pro Phe Glu Arg Asp
            420                 425                 430

Ile Ser Thr Glu Ile Tyr Gln Ala Gly Ser Thr Pro Cys Asn Gly Val
        435                 440                 445

Glu Gly Phe Asn Cys Tyr Phe Pro Leu Gln Ser Tyr Gly Phe Gln Pro
    450                 455                 460

Thr Asn Gly Val Gly Tyr Gln Pro Tyr Arg Val Val Val Leu Ser Phe
465                 470                 475                 480

Glu Leu Leu His Ala Pro Ala Thr Val Cys Gly Pro Lys Lys Ser Ala
                485                 490                 495

Ile Gly Gly Tyr Ile Pro Glu Ala Pro Arg Asp Gly Gln Ala Tyr Val
            500                 505                 510

Arg Lys Asp Gly Glu Trp Val Leu Leu Ser Thr Phe Leu His His His
        515                 520                 525

His His His
    530


<210> SEQ ID NO 76
<211> LENGTH: 470
<212> TYPE: PRT
<213> ORGANISM: Artificial Sequence
<220> FEATURE:
<223> OTHER INFORMATION: RECOMBINANT SPIKE PROTEIN

<400> SEQUENCE: 76

Met Phe Val Phe Leu Val Leu Leu Pro Leu Val Ser Ser Arg Phe Pro
1               5                   10                  15

Asn Ile Thr Asn Leu Cys Pro Phe Gly Glu Val Phe Asn Ala Thr Arg
            20                  25                  30

Phe Ala Ser Val Tyr Ala Trp Asn Arg Lys Arg Ile Ser Asn Cys Val
        35                  40                  45

Ala Asp Tyr Ser Val Leu Tyr Asn Ser Ala Ser Phe Ser Thr Phe Lys
    50                  55                  60

Cys Tyr Gly Val Ser Pro Thr Lys Leu Asn Asp Leu Cys Phe Thr Asn
```

```
65                  70                  75                  80

Val Tyr Ala Asp Ser Phe Val Ile Arg Gly Asp Glu Val Arg Gln Ile
                85                  90                  95

Ala Pro Gly Gln Thr Gly Lys Ile Ala Asp Tyr Asn Tyr Lys Leu Pro
            100                 105                 110

Asp Asp Phe Thr Gly Cys Val Ile Ala Trp Asn Ser Asn Asn Leu Asp
        115                 120                 125

Ser Lys Val Gly Gly Asn Tyr Asn Tyr Leu Tyr Arg Leu Phe Arg Lys
    130                 135                 140

Ser Asn Leu Lys Pro Phe Glu Arg Asp Ile Ser Thr Glu Ile Tyr Gln
145                 150                 155                 160

Ala Gly Ser Thr Pro Cys Asn Gly Val Glu Gly Phe Asn Cys Tyr Phe
                165                 170                 175

Pro Leu Gln Ser Tyr Gly Phe Gln Pro Thr Asn Gly Val Gly Tyr Gln
            180                 185                 190

Pro Tyr Arg Val Val Val Leu Ser Phe Glu Leu Leu His Ala Pro Ala
        195                 200                 205

Thr Val Cys Gly Pro Lys Lys Ser Gly Gly Gly Ser Gly Gly Gly Ser
    210                 215                 220

Gly Gly Gly Ser Gly Gly Gly Ser Arg Phe Pro Asn Ile Thr Asn Leu
225                 230                 235                 240

Cys Pro Phe Gly Glu Val Phe Asn Ala Thr Lys Phe Pro Ser Val Tyr
                245                 250                 255

Ala Trp Glu Arg Lys Lys Ile Ser Asn Cys Val Ala Asp Tyr Ser Val
            260                 265                 270

Leu Tyr Asn Ser Thr Phe Phe Ser Thr Phe Lys Cys Tyr Gly Val Ser
        275                 280                 285

Ala Thr Lys Leu Asn Asp Leu Cys Phe Ser Asn Val Tyr Ala Asp Ser
    290                 295                 300

Phe Val Val Lys Gly Asp Asp Val Arg Gln Ile Ala Pro Gly Gln Thr
305                 310                 315                 320

Gly Val Ile Ala Asp Tyr Asn Tyr Lys Leu Pro Asp Asp Phe Met Gly
                325                 330                 335

Cys Val Leu Ala Trp Asn Thr Arg Asn Ile Asp Ala Thr Ser Thr Gly
            340                 345                 350

Asn Tyr Asn Tyr Lys Tyr Arg Tyr Leu Arg His Gly Lys Leu Arg Pro
        355                 360                 365

Phe Glu Arg Asp Ile Ser Asn Val Pro Phe Ser Pro Asp Gly Lys Pro
    370                 375                 380

Cys Thr Pro Pro Ala Leu Asn Cys Tyr Trp Pro Leu Asn Asp Tyr Gly
385                 390                 395                 400

Phe Tyr Thr Thr Thr Gly Ile Gly Tyr Gln Pro Tyr Arg Val Val Val
                405                 410                 415

Leu Ser Phe Glu Leu Leu Asn Ala Pro Ala Thr Val Cys Gly Pro Lys
            420                 425                 430

Leu Ser Ala Ile Gly Gly Tyr Ile Pro Glu Ala Pro Arg Asp Gly Gln
        435                 440                 445

Ala Tyr Val Arg Lys Asp Gly Glu Trp Val Leu Leu Ser Thr Phe Leu
    450                 455                 460

His His His His His His
465                 470

<210> SEQ ID NO 77
```

<211> LENGTH: 464
<212> TYPE: PRT
<213> ORGANISM: Artificial Sequence
<220> FEATURE:
<223> OTHER INFORMATION: RECOMBINANT SPIKE PROTEIN

<400> SEQUENCE: 77

Met Phe Val Phe Leu Val Leu Leu Pro Leu Val Ser Ser Arg Phe Pro
1 5 10 15

Asn Ile Thr Asn Leu Cys Pro Phe Gly Glu Val Phe Asn Ala Thr Arg
20 25 30

Phe Ala Ser Val Tyr Ala Trp Asn Arg Lys Arg Ile Ser Asn Cys Val
35 40 45

Ala Asp Tyr Ser Val Leu Tyr Asn Ser Ala Ser Phe Ser Thr Phe Lys
50 55 60

Cys Tyr Gly Val Ser Pro Thr Lys Leu Asn Asp Leu Cys Phe Thr Asn
65 70 75 80

Val Tyr Ala Asp Ser Phe Val Ile Arg Gly Asp Glu Val Arg Gln Ile
85 90 95

Ala Pro Gly Gln Thr Gly Lys Ile Ala Asp Tyr Asn Tyr Lys Leu Pro
100 105 110

Asp Asp Phe Thr Gly Cys Val Ile Ala Trp Asn Ser Asn Asn Leu Asp
115 120 125

Ser Lys Val Gly Gly Asn Tyr Asn Tyr Leu Tyr Arg Leu Phe Arg Lys
130 135 140

Ser Asn Leu Lys Pro Phe Glu Arg Asp Ile Ser Thr Glu Ile Tyr Gln
145 150 155 160

Ala Gly Ser Thr Pro Cys Asn Gly Val Glu Gly Phe Asn Cys Tyr Phe
165 170 175

Pro Leu Gln Ser Tyr Gly Phe Gln Pro Thr Asn Gly Val Gly Tyr Gln
180 185 190

Pro Tyr Arg Val Val Val Leu Ser Phe Glu Leu Leu His Ala Pro Ala
195 200 205

Thr Val Cys Gly Pro Lys Lys Ser Gly Gly Gly Ser Gly Gly Gly Ser
210 215 220

Gly Gly Gly Ser Gly Gly Gly Ser Arg Phe Pro Asn Ile Thr Asn Leu
225 230 235 240

Cys Pro Phe Gly Glu Val Phe Asn Ala Thr Lys Phe Pro Ser Val Tyr
245 250 255

Ala Trp Glu Arg Lys Lys Ile Ser Asn Cys Val Ala Asp Tyr Ser Val
260 265 270

Leu Tyr Asn Ser Thr Phe Phe Ser Thr Phe Lys Cys Tyr Gly Val Ser
275 280 285

Ala Thr Lys Leu Asn Asp Leu Cys Phe Ser Asn Val Tyr Ala Asp Ser
290 295 300

Phe Val Val Lys Gly Asp Asp Val Arg Gln Ile Ala Pro Gly Gln Thr
305 310 315 320

Gly Val Ile Ala Asp Tyr Asn Tyr Lys Leu Pro Asp Asp Phe Met Gly
325 330 335

Cys Val Leu Ala Trp Asn Thr Arg Asn Ile Asp Ala Thr Ser Thr Gly
340 345 350

Asn Tyr Asn Tyr Lys Tyr Arg Tyr Leu Arg His Gly Lys Leu Arg Pro
355 360 365

Phe Glu Arg Asp Ile Ser Asn Val Pro Phe Ser Pro Asp Gly Lys Pro
370 375 380

-continued

```
Cys Thr Pro Pro Ala Leu Asn Cys Tyr Trp Pro Leu Asn Asp Tyr Gly
385                 390                 395                 400

Phe Tyr Thr Thr Thr Gly Ile Gly Tyr Gln Pro Tyr Arg Val Val Val
                405                 410                 415

Leu Ser Phe Glu Leu Leu Asn Ala Pro Ala Thr Val Cys Gly Pro Lys
            420                 425                 430

Leu Ser Ala Ile Gly Gly Tyr Ile Pro Glu Ala Pro Arg Asp Gly Gln
        435                 440                 445

Ala Tyr Val Arg Lys Asp Gly Glu Trp Val Leu Leu Ser Thr Phe Leu
    450                 455                 460


<210> SEQ ID NO 78
<211> LENGTH: 457
<212> TYPE: PRT
<213> ORGANISM: Artificial Sequence
<220> FEATURE:
<223> OTHER INFORMATION: RECOMBINANT SPIKE PROTEIN

<400> SEQUENCE: 78

Arg Phe Pro Asn Ile Thr Asn Leu Cys Pro Phe Gly Glu Val Phe Asn
1               5                   10                  15

Ala Thr Arg Phe Ala Ser Val Tyr Ala Trp Asn Arg Lys Arg Ile Ser
            20                  25                  30

Asn Cys Val Ala Asp Tyr Ser Val Leu Tyr Asn Ser Ala Ser Phe Ser
        35                  40                  45

Thr Phe Lys Cys Tyr Gly Val Ser Pro Thr Lys Leu Asn Asp Leu Cys
    50                  55                  60

Phe Thr Asn Val Tyr Ala Asp Ser Phe Val Ile Arg Gly Asp Glu Val
65                  70                  75                  80

Arg Gln Ile Ala Pro Gly Gln Thr Gly Lys Ile Ala Asp Tyr Asn Tyr
                85                  90                  95

Lys Leu Pro Asp Asp Phe Thr Gly Cys Val Ile Ala Trp Asn Ser Asn
            100                 105                 110

Asn Leu Asp Ser Lys Val Gly Gly Asn Tyr Asn Tyr Leu Tyr Arg Leu
        115                 120                 125

Phe Arg Lys Ser Asn Leu Lys Pro Phe Glu Arg Asp Ile Ser Thr Glu
    130                 135                 140

Ile Tyr Gln Ala Gly Ser Thr Pro Cys Asn Gly Val Glu Gly Phe Asn
145                 150                 155                 160

Cys Tyr Phe Pro Leu Gln Ser Tyr Gly Phe Gln Pro Thr Asn Gly Val
                165                 170                 175

Gly Tyr Gln Pro Tyr Arg Val Val Val Leu Ser Phe Glu Leu Leu His
            180                 185                 190

Ala Pro Ala Thr Val Cys Gly Pro Lys Lys Ser Gly Gly Gly Ser Gly
        195                 200                 205

Gly Gly Ser Gly Gly Gly Ser Gly Gly Gly Ser Arg Phe Pro Asn Ile
    210                 215                 220

Thr Asn Leu Cys Pro Phe Gly Glu Val Phe Asn Ala Thr Lys Phe Pro
225                 230                 235                 240

Ser Val Tyr Ala Trp Glu Arg Lys Lys Ile Ser Asn Cys Val Ala Asp
                245                 250                 255

Tyr Ser Val Leu Tyr Asn Ser Thr Phe Phe Ser Thr Phe Lys Cys Tyr
            260                 265                 270

Gly Val Ser Ala Thr Lys Leu Asn Asp Leu Cys Phe Ser Asn Val Tyr
        275                 280                 285
```

```
Ala Asp Ser Phe Val Val Lys Gly Asp Asp Val Arg Gln Ile Ala Pro
    290                 295                 300

Gly Gln Thr Gly Val Ile Ala Asp Tyr Asn Tyr Lys Leu Pro Asp Asp
305                 310                 315                 320

Phe Met Gly Cys Val Leu Ala Trp Asn Thr Arg Asn Ile Asp Ala Thr
                325                 330                 335

Ser Thr Gly Asn Tyr Asn Tyr Lys Tyr Arg Tyr Leu Arg His Gly Lys
            340                 345                 350

Leu Arg Pro Phe Glu Arg Asp Ile Ser Asn Val Pro Phe Ser Pro Asp
        355                 360                 365

Gly Lys Pro Cys Thr Pro Pro Ala Leu Asn Cys Tyr Trp Pro Leu Asn
    370                 375                 380

Asp Tyr Gly Phe Tyr Thr Thr Thr Gly Ile Gly Tyr Gln Pro Tyr Arg
385                 390                 395                 400

Val Val Val Leu Ser Phe Glu Leu Leu Asn Ala Pro Ala Thr Val Cys
                405                 410                 415

Gly Pro Lys Leu Ser Ala Ile Gly Gly Tyr Ile Pro Glu Ala Pro Arg
            420                 425                 430

Asp Gly Gln Ala Tyr Val Arg Lys Asp Gly Glu Trp Val Leu Leu Ser
        435                 440                 445

Thr Phe Leu His His His His His His
    450                 455
```

```
<210> SEQ ID NO 79
<211> LENGTH: 451
<212> TYPE: PRT
<213> ORGANISM: Artificial Sequence
<220> FEATURE:
<223> OTHER INFORMATION: RECOMBINANT SPIKE PROTEIN

<400> SEQUENCE: 79

Arg Phe Pro Asn Ile Thr Asn Leu Cys Pro Phe Gly Glu Val Phe Asn
1               5                   10                  15

Ala Thr Arg Phe Ala Ser Val Tyr Ala Trp Asn Arg Lys Arg Ile Ser
            20                  25                  30

Asn Cys Val Ala Asp Tyr Ser Val Leu Tyr Asn Ser Ala Ser Phe Ser
        35                  40                  45

Thr Phe Lys Cys Tyr Gly Val Ser Pro Thr Lys Leu Asn Asp Leu Cys
    50                  55                  60

Phe Thr Asn Val Tyr Ala Asp Ser Phe Val Ile Arg Gly Asp Glu Val
65                  70                  75                  80

Arg Gln Ile Ala Pro Gly Gln Thr Gly Lys Ile Ala Asp Tyr Asn Tyr
                85                  90                  95

Lys Leu Pro Asp Asp Phe Thr Gly Cys Val Ile Ala Trp Asn Ser Asn
            100                 105                 110

Asn Leu Asp Ser Lys Val Gly Gly Asn Tyr Asn Tyr Leu Tyr Arg Leu
        115                 120                 125

Phe Arg Lys Ser Asn Leu Lys Pro Phe Glu Arg Asp Ile Ser Thr Glu
    130                 135                 140

Ile Tyr Gln Ala Gly Ser Thr Pro Cys Asn Gly Val Glu Gly Phe Asn
145                 150                 155                 160

Cys Tyr Phe Pro Leu Gln Ser Tyr Gly Phe Gln Pro Thr Asn Gly Val
                165                 170                 175

Gly Tyr Gln Pro Tyr Arg Val Val Val Leu Ser Phe Glu Leu Leu His
            180                 185                 190
```

```
Ala Pro Ala Thr Val Cys Gly Pro Lys Lys Ser Gly Gly Gly Ser Gly
        195                 200                 205

Gly Gly Ser Gly Gly Gly Ser Gly Gly Gly Ser Arg Phe Pro Asn Ile
    210                 215                 220

Thr Asn Leu Cys Pro Phe Gly Glu Val Phe Asn Ala Thr Lys Phe Pro
225                 230                 235                 240

Ser Val Tyr Ala Trp Glu Arg Lys Lys Ile Ser Asn Cys Val Ala Asp
                245                 250                 255

Tyr Ser Val Leu Tyr Asn Ser Thr Phe Phe Ser Thr Phe Lys Cys Tyr
            260                 265                 270

Gly Val Ser Ala Thr Lys Leu Asn Asp Leu Cys Phe Ser Asn Val Tyr
        275                 280                 285

Ala Asp Ser Phe Val Val Lys Gly Asp Asp Val Arg Gln Ile Ala Pro
    290                 295                 300

Gly Gln Thr Gly Val Ile Ala Asp Tyr Asn Tyr Lys Leu Pro Asp Asp
305                 310                 315                 320

Phe Met Gly Cys Val Leu Ala Trp Asn Thr Arg Asn Ile Asp Ala Thr
                325                 330                 335

Ser Thr Gly Asn Tyr Asn Tyr Lys Tyr Arg Tyr Leu Arg His Gly Lys
            340                 345                 350

Leu Arg Pro Phe Glu Arg Asp Ile Ser Asn Val Pro Phe Ser Pro Asp
        355                 360                 365

Gly Lys Pro Cys Thr Pro Pro Ala Leu Asn Cys Tyr Trp Pro Leu Asn
    370                 375                 380

Asp Tyr Gly Phe Tyr Thr Thr Thr Gly Ile Gly Tyr Gln Pro Tyr Arg
385                 390                 395                 400

Val Val Val Leu Ser Phe Glu Leu Leu Asn Ala Pro Ala Thr Val Cys
                405                 410                 415

Gly Pro Lys Leu Ser Ala Ile Gly Gly Tyr Ile Pro Glu Ala Pro Arg
            420                 425                 430

Asp Gly Gln Ala Tyr Val Arg Lys Asp Gly Glu Trp Val Leu Leu Ser
        435                 440                 445

Thr Phe Leu
    450


<210> SEQ ID NO 80
<211> LENGTH: 726
<212> TYPE: PRT
<213> ORGANISM: Artificial Sequence
<220> FEATURE:
<223> OTHER INFORMATION: RECOMBINANT SPIKE PROTEIN

<400> SEQUENCE: 80

Met Phe Val Phe Leu Val Leu Leu Pro Leu Val Ser Ser Arg Phe Pro
1               5                   10                  15

Asn Ile Thr Asn Leu Cys Pro Phe Gly Glu Val Phe Asn Ala Thr Arg
            20                  25                  30

Phe Ala Ser Val Tyr Ala Trp Asn Arg Lys Arg Ile Ser Asn Cys Val
        35                  40                  45

Ala Asp Tyr Ser Val Leu Tyr Asn Ser Ala Ser Phe Ser Thr Phe Lys
    50                  55                  60

Cys Tyr Gly Val Ser Pro Thr Lys Leu Asn Asp Leu Cys Phe Thr Asn
65                  70                  75                  80

Val Tyr Ala Asp Ser Phe Val Ile Arg Gly Asp Glu Val Arg Gln Ile
                85                  90                  95
```

-continued

```
Ala Pro Gly Gln Thr Gly Lys Ile Ala Asp Tyr Asn Tyr Lys Leu Pro
            100                 105                 110

Asp Asp Phe Thr Gly Cys Val Ile Ala Trp Asn Ser Asn Asn Leu Asp
        115                 120                 125

Ser Lys Val Gly Gly Asn Tyr Asn Tyr Leu Tyr Arg Leu Phe Arg Lys
    130                 135                 140

Ser Asn Leu Lys Pro Phe Glu Arg Asp Ile Ser Thr Glu Ile Tyr Gln
145                 150                 155                 160

Ala Gly Ser Thr Pro Cys Asn Gly Val Glu Gly Phe Asn Cys Tyr Phe
                165                 170                 175

Pro Leu Gln Ser Tyr Gly Phe Gln Pro Thr Asn Gly Val Gly Tyr Gln
            180                 185                 190

Pro Tyr Arg Val Val Val Leu Ser Phe Glu Leu Leu His Ala Pro Ala
        195                 200                 205

Thr Val Cys Gly Pro Lys Lys Ser Gly Gly Gly Ser Gly Gly Gly Ser
    210                 215                 220

Gly Gly Gly Ser Gly Gly Gly Ser Phe Glu Ala Lys Pro Ser Gly Ser
225                 230                 235                 240

Val Val Ala Glu Gly Val Glu Cys Asp Phe Ser Pro Leu Leu Ser Gly
                245                 250                 255

Thr Pro Pro Gln Val Tyr Asn Phe Lys Arg Leu Val Phe Thr Asn Cys
            260                 265                 270

Asn Tyr Asn Leu Thr Lys Leu Leu Ser Leu Phe Ser Val Asn Asp Phe
        275                 280                 285

Thr Cys Ser Gln Ile Ser Pro Ala Ala Ile Ala Ser Asn Cys Tyr Ser
    290                 295                 300

Ser Leu Ile Leu Asp Tyr Phe Ser Tyr Pro Leu Ser Met Lys Ser Asp
305                 310                 315                 320

Leu Ser Val Ser Ser Ala Gly Pro Ile Ser Gln Phe Asn Tyr Lys Gln
                325                 330                 335

Ser Phe Ser Asn Pro Thr Cys Leu Ile Leu Ala Thr Val Pro His Asn
            340                 345                 350

Leu Thr Thr Ile Thr Lys Pro Leu Lys Tyr Ser Tyr Ile Asn Lys Cys
        355                 360                 365

Ser Arg Leu Leu Ser Asp Asp Arg Thr Glu Val Pro Gln Leu Val Asn
    370                 375                 380

Ala Asn Gln Tyr Ser Pro Cys Val Ser Ile Val Pro Ser Thr Val Trp
385                 390                 395                 400

Glu Asp Gly Asp Tyr Tyr Arg Lys Gln Leu Ser Pro Leu Glu Gly Gly
                405                 410                 415

Gly Trp Leu Val Ala Ser Gly Ser Thr Val Ala Met Thr Glu Gln Leu
            420                 425                 430

Gln Met Gly Phe Gly Ile Thr Val Gln Tyr Gly Thr Asp Thr Asn Ser
        435                 440                 445

Val Cys Pro Lys Leu Glu Phe Ala Asn Asp Thr Lys Ile Ala Ser Gln
    450                 455                 460

Leu Gly Asn Cys Val Glu Tyr Ser Gly Gly Gly Ser Gly Gly Gly Ser
465                 470                 475                 480

Gly Gly Gly Ser Gly Gly Gly Ser Arg Phe Pro Asn Ile Thr Asn Leu
                485                 490                 495

Cys Pro Phe Gly Glu Val Phe Asn Ala Thr Lys Phe Pro Ser Val Tyr
            500                 505                 510
```

```
Ala Trp Glu Arg Lys Lys Ile Ser Asn Cys Val Ala Asp Tyr Ser Val
        515                 520                 525

Leu Tyr Asn Ser Thr Phe Phe Ser Thr Phe Lys Cys Tyr Gly Val Ser
    530                 535                 540

Ala Thr Lys Leu Asn Asp Leu Cys Phe Ser Asn Val Tyr Ala Asp Ser
545                 550                 555                 560

Phe Val Val Lys Gly Asp Asp Val Arg Gln Ile Ala Pro Gly Gln Thr
                565                 570                 575

Gly Val Ile Ala Asp Tyr Asn Tyr Lys Leu Pro Asp Asp Phe Met Gly
            580                 585                 590

Cys Val Leu Ala Trp Asn Thr Arg Asn Ile Asp Ala Thr Ser Thr Gly
        595                 600                 605

Asn Tyr Asn Tyr Lys Tyr Arg Tyr Leu Arg His Gly Lys Leu Arg Pro
    610                 615                 620

Phe Glu Arg Asp Ile Ser Asn Val Pro Phe Ser Pro Asp Gly Lys Pro
625                 630                 635                 640

Cys Thr Pro Pro Ala Leu Asn Cys Tyr Trp Pro Leu Asn Asp Tyr Gly
                645                 650                 655

Phe Tyr Thr Thr Thr Gly Ile Gly Tyr Gln Pro Tyr Arg Val Val Val
            660                 665                 670

Leu Ser Phe Glu Leu Leu Asn Ala Pro Ala Thr Val Cys Gly Pro Lys
        675                 680                 685

Leu Ser Ala Ile Gly Gly Tyr Ile Pro Glu Ala Pro Arg Asp Gly Gln
    690                 695                 700

Ala Tyr Val Arg Lys Asp Gly Glu Trp Val Leu Leu Ser Thr Phe Leu
705                 710                 715                 720

His His His His His His
                725


<210> SEQ ID NO 81
<211> LENGTH: 720
<212> TYPE: PRT
<213> ORGANISM: Artificial Sequence
<220> FEATURE:
<223> OTHER INFORMATION: RECOMBINANT SPIKE PROTEIN

<400> SEQUENCE: 81

Met Phe Val Phe Leu Val Leu Leu Pro Leu Val Ser Ser Arg Phe Pro
1               5                   10                  15

Asn Ile Thr Asn Leu Cys Pro Phe Gly Glu Val Phe Asn Ala Thr Arg
            20                  25                  30

Phe Ala Ser Val Tyr Ala Trp Asn Arg Lys Arg Ile Ser Asn Cys Val
        35                  40                  45

Ala Asp Tyr Ser Val Leu Tyr Asn Ser Ala Ser Phe Ser Thr Phe Lys
    50                  55                  60

Cys Tyr Gly Val Ser Pro Thr Lys Leu Asn Asp Leu Cys Phe Thr Asn
65                  70                  75                  80

Val Tyr Ala Asp Ser Phe Val Ile Arg Gly Asp Glu Val Arg Gln Ile
                85                  90                  95

Ala Pro Gly Gln Thr Gly Lys Ile Ala Asp Tyr Asn Tyr Lys Leu Pro
            100                 105                 110

Asp Asp Phe Thr Gly Cys Val Ile Ala Trp Asn Ser Asn Asn Leu Asp
        115                 120                 125

Ser Lys Val Gly Gly Asn Tyr Asn Tyr Leu Tyr Arg Leu Phe Arg Lys
    130                 135                 140
```

```
Ser Asn Leu Lys Pro Phe Glu Arg Asp Ile Ser Thr Glu Ile Tyr Gln
145                 150                 155                 160

Ala Gly Ser Thr Pro Cys Asn Gly Val Glu Gly Phe Asn Cys Tyr Phe
                165                 170                 175

Pro Leu Gln Ser Tyr Gly Phe Gln Pro Thr Asn Gly Val Gly Tyr Gln
            180                 185                 190

Pro Tyr Arg Val Val Val Leu Ser Phe Glu Leu Leu His Ala Pro Ala
        195                 200                 205

Thr Val Cys Gly Pro Lys Lys Ser Gly Gly Gly Ser Gly Gly Gly Ser
    210                 215                 220

Gly Gly Gly Ser Gly Gly Gly Ser Phe Glu Ala Lys Pro Ser Gly Ser
225                 230                 235                 240

Val Val Ala Glu Gly Val Glu Cys Asp Phe Ser Pro Leu Leu Ser Gly
                245                 250                 255

Thr Pro Pro Gln Val Tyr Asn Phe Lys Arg Leu Val Phe Thr Asn Cys
            260                 265                 270

Asn Tyr Asn Leu Thr Lys Leu Leu Ser Leu Phe Ser Val Asn Asp Phe
        275                 280                 285

Thr Cys Ser Gln Ile Ser Pro Ala Ala Ile Ala Ser Asn Cys Tyr Ser
    290                 295                 300

Ser Leu Ile Leu Asp Tyr Phe Ser Tyr Pro Leu Ser Met Lys Ser Asp
305                 310                 315                 320

Leu Ser Val Ser Ser Ala Gly Pro Ile Ser Gln Phe Asn Tyr Lys Gln
                325                 330                 335

Ser Phe Ser Asn Pro Thr Cys Leu Ile Leu Ala Thr Val Pro His Asn
            340                 345                 350

Leu Thr Thr Ile Thr Lys Pro Leu Lys Tyr Ser Tyr Ile Asn Lys Cys
        355                 360                 365

Ser Arg Leu Leu Ser Asp Asp Arg Thr Glu Val Pro Gln Leu Val Asn
    370                 375                 380

Ala Asn Gln Tyr Ser Pro Cys Val Ser Ile Val Pro Ser Thr Val Trp
385                 390                 395                 400

Glu Asp Gly Asp Tyr Tyr Arg Lys Gln Leu Ser Pro Leu Glu Gly Gly
                405                 410                 415

Gly Trp Leu Val Ala Ser Gly Ser Thr Val Ala Met Thr Glu Gln Leu
            420                 425                 430

Gln Met Gly Phe Gly Ile Thr Val Gln Tyr Gly Thr Asp Thr Asn Ser
        435                 440                 445

Val Cys Pro Lys Leu Glu Phe Ala Asn Asp Thr Lys Ile Ala Ser Gln
    450                 455                 460

Leu Gly Asn Cys Val Glu Tyr Ser Gly Gly Gly Ser Gly Gly Gly Ser
465                 470                 475                 480

Gly Gly Gly Ser Gly Gly Gly Ser Arg Phe Pro Asn Ile Thr Asn Leu
                485                 490                 495

Cys Pro Phe Gly Glu Val Phe Asn Ala Thr Lys Phe Pro Ser Val Tyr
            500                 505                 510

Ala Trp Glu Arg Lys Lys Ile Ser Asn Cys Val Ala Asp Tyr Ser Val
        515                 520                 525

Leu Tyr Asn Ser Thr Phe Phe Ser Thr Phe Lys Cys Tyr Gly Val Ser
    530                 535                 540

Ala Thr Lys Leu Asn Asp Leu Cys Phe Ser Asn Val Tyr Ala Asp Ser
545                 550                 555                 560

Phe Val Val Lys Gly Asp Asp Val Arg Gln Ile Ala Pro Gly Gln Thr
```

565 570 575

Gly Val Ile Ala Asp Tyr Asn Tyr Lys Leu Pro Asp Asp Phe Met Gly
580 585 590

Cys Val Leu Ala Trp Asn Thr Arg Asn Ile Asp Ala Thr Ser Thr Gly
595 600 605

Asn Tyr Asn Tyr Lys Tyr Arg Tyr Leu Arg His Gly Lys Leu Arg Pro
610 615 620

Phe Glu Arg Asp Ile Ser Asn Val Pro Phe Ser Pro Asp Gly Lys Pro
625 630 635 640

Cys Thr Pro Pro Ala Leu Asn Cys Tyr Trp Pro Leu Asn Asp Tyr Gly
645 650 655

Phe Tyr Thr Thr Thr Gly Ile Gly Tyr Gln Pro Tyr Arg Val Val Val
660 665 670

Leu Ser Phe Glu Leu Leu Asn Ala Pro Ala Thr Val Cys Gly Pro Lys
675 680 685

Leu Ser Ala Ile Gly Gly Tyr Ile Pro Glu Ala Pro Arg Asp Gly Gln
690 695 700

Ala Tyr Val Arg Lys Asp Gly Glu Trp Val Leu Leu Ser Thr Phe Leu
705 710 715 720

<210> SEQ ID NO 82
<211> LENGTH: 713
<212> TYPE: PRT
<213> ORGANISM: Artificial Sequence
<220> FEATURE:
<223> OTHER INFORMATION: RECOMBINANT SPIKE PROTEIN

<400> SEQUENCE: 82

Arg Phe Pro Asn Ile Thr Asn Leu Cys Pro Phe Gly Glu Val Phe Asn
1 5 10 15

Ala Thr Arg Phe Ala Ser Val Tyr Ala Trp Asn Arg Lys Arg Ile Ser
20 25 30

Asn Cys Val Ala Asp Tyr Ser Val Leu Tyr Asn Ser Ala Ser Phe Ser
35 40 45

Thr Phe Lys Cys Tyr Gly Val Ser Pro Thr Lys Leu Asn Asp Leu Cys
50 55 60

Phe Thr Asn Val Tyr Ala Asp Ser Phe Val Ile Arg Gly Asp Glu Val
65 70 75 80

Arg Gln Ile Ala Pro Gly Gln Thr Gly Lys Ile Ala Asp Tyr Asn Tyr
85 90 95

Lys Leu Pro Asp Asp Phe Thr Gly Cys Val Ile Ala Trp Asn Ser Asn
100 105 110

Asn Leu Asp Ser Lys Val Gly Gly Asn Tyr Asn Tyr Leu Tyr Arg Leu
115 120 125

Phe Arg Lys Ser Asn Leu Lys Pro Phe Glu Arg Asp Ile Ser Thr Glu
130 135 140

Ile Tyr Gln Ala Gly Ser Thr Pro Cys Asn Gly Val Glu Gly Phe Asn
145 150 155 160

Cys Tyr Phe Pro Leu Gln Ser Tyr Gly Phe Gln Pro Thr Asn Gly Val
165 170 175

Gly Tyr Gln Pro Tyr Arg Val Val Val Leu Ser Phe Glu Leu Leu His
180 185 190

Ala Pro Ala Thr Val Cys Gly Pro Lys Lys Ser Gly Gly Gly Ser Gly
195 200 205

Gly Gly Ser Gly Gly Gly Ser Gly Gly Gly Ser Phe Glu Ala Lys Pro

```
    210                 215                 220

Ser Gly Ser Val Val Ala Glu Gly Val Glu Cys Asp Phe Ser Pro Leu
225                 230                 235                 240

Leu Ser Gly Thr Pro Pro Gln Val Tyr Asn Phe Lys Arg Leu Val Phe
                245                 250                 255

Thr Asn Cys Asn Tyr Asn Leu Thr Lys Leu Leu Ser Leu Phe Ser Val
            260                 265                 270

Asn Asp Phe Thr Cys Ser Gln Ile Ser Pro Ala Ala Ile Ala Ser Asn
        275                 280                 285

Cys Tyr Ser Ser Leu Ile Leu Asp Tyr Phe Ser Tyr Pro Leu Ser Met
    290                 295                 300

Lys Ser Asp Leu Ser Val Ser Ser Ala Gly Pro Ile Ser Gln Phe Asn
305                 310                 315                 320

Tyr Lys Gln Ser Phe Ser Asn Pro Thr Cys Leu Ile Leu Ala Thr Val
                325                 330                 335

Pro His Asn Leu Thr Thr Ile Thr Lys Pro Leu Lys Tyr Ser Tyr Ile
            340                 345                 350

Asn Lys Cys Ser Arg Leu Leu Ser Asp Asp Arg Thr Glu Val Pro Gln
        355                 360                 365

Leu Val Asn Ala Asn Gln Tyr Ser Pro Cys Val Ser Ile Val Pro Ser
    370                 375                 380

Thr Val Trp Glu Asp Gly Asp Tyr Tyr Arg Lys Gln Leu Ser Pro Leu
385                 390                 395                 400

Glu Gly Gly Gly Trp Leu Val Ala Ser Gly Ser Thr Val Ala Met Thr
                405                 410                 415

Glu Gln Leu Gln Met Gly Phe Gly Ile Thr Val Gln Tyr Gly Thr Asp
            420                 425                 430

Thr Asn Ser Val Cys Pro Lys Leu Glu Phe Ala Asn Asp Thr Lys Ile
        435                 440                 445

Ala Ser Gln Leu Gly Asn Cys Val Glu Tyr Ser Gly Gly Gly Ser Gly
    450                 455                 460

Gly Gly Ser Gly Gly Gly Ser Gly Gly Gly Ser Arg Phe Pro Asn Ile
465                 470                 475                 480

Thr Asn Leu Cys Pro Phe Gly Glu Val Phe Asn Ala Thr Lys Phe Pro
                485                 490                 495

Ser Val Tyr Ala Trp Glu Arg Lys Lys Ile Ser Asn Cys Val Ala Asp
            500                 505                 510

Tyr Ser Val Leu Tyr Asn Ser Thr Phe Phe Ser Thr Phe Lys Cys Tyr
        515                 520                 525

Gly Val Ser Ala Thr Lys Leu Asn Asp Leu Cys Phe Ser Asn Val Tyr
    530                 535                 540

Ala Asp Ser Phe Val Val Lys Gly Asp Asp Val Arg Gln Ile Ala Pro
545                 550                 555                 560

Gly Gln Thr Gly Val Ile Ala Asp Tyr Asn Tyr Lys Leu Pro Asp Asp
                565                 570                 575

Phe Met Gly Cys Val Leu Ala Trp Asn Thr Arg Asn Ile Asp Ala Thr
            580                 585                 590

Ser Thr Gly Asn Tyr Asn Tyr Lys Tyr Arg Tyr Leu Arg His Gly Lys
        595                 600                 605

Leu Arg Pro Phe Glu Arg Asp Ile Ser Asn Val Pro Phe Ser Pro Asp
    610                 615                 620

Gly Lys Pro Cys Thr Pro Pro Ala Leu Asn Cys Tyr Trp Pro Leu Asn
625                 630                 635                 640
```

```
Asp Tyr Gly Phe Tyr Thr Thr Thr Gly Ile Gly Tyr Gln Pro Tyr Arg
                645                 650                 655

Val Val Val Leu Ser Phe Glu Leu Leu Asn Ala Pro Ala Thr Val Cys
            660                 665                 670

Gly Pro Lys Leu Ser Ala Ile Gly Gly Tyr Ile Pro Glu Ala Pro Arg
        675                 680                 685

Asp Gly Gln Ala Tyr Val Arg Lys Asp Gly Glu Trp Val Leu Leu Ser
    690                 695                 700

Thr Phe Leu His His His His His His
705                 710


<210> SEQ ID NO 83
<211> LENGTH: 707
<212> TYPE: PRT
<213> ORGANISM: Artificial Sequence
<220> FEATURE:
<223> OTHER INFORMATION: RECOMBINANT SPIKE PROTEIN

<400> SEQUENCE: 83

Arg Phe Pro Asn Ile Thr Asn Leu Cys Pro Phe Gly Glu Val Phe Asn
1               5                   10                  15

Ala Thr Arg Phe Ala Ser Val Tyr Ala Trp Asn Arg Lys Arg Ile Ser
            20                  25                  30

Asn Cys Val Ala Asp Tyr Ser Val Leu Tyr Asn Ser Ala Ser Phe Ser
        35                  40                  45

Thr Phe Lys Cys Tyr Gly Val Ser Pro Thr Lys Leu Asn Asp Leu Cys
    50                  55                  60

Phe Thr Asn Val Tyr Ala Asp Ser Phe Val Ile Arg Gly Asp Glu Val
65                  70                  75                  80

Arg Gln Ile Ala Pro Gly Gln Thr Gly Lys Ile Ala Asp Tyr Asn Tyr
                85                  90                  95

Lys Leu Pro Asp Asp Phe Thr Gly Cys Val Ile Ala Trp Asn Ser Asn
            100                 105                 110

Asn Leu Asp Ser Lys Val Gly Gly Asn Tyr Asn Tyr Leu Tyr Arg Leu
        115                 120                 125

Phe Arg Lys Ser Asn Leu Lys Pro Phe Glu Arg Asp Ile Ser Thr Glu
    130                 135                 140

Ile Tyr Gln Ala Gly Ser Thr Pro Cys Asn Gly Val Glu Gly Phe Asn
145                 150                 155                 160

Cys Tyr Phe Pro Leu Gln Ser Tyr Gly Phe Gln Pro Thr Asn Gly Val
                165                 170                 175

Gly Tyr Gln Pro Tyr Arg Val Val Val Leu Ser Phe Glu Leu Leu His
            180                 185                 190

Ala Pro Ala Thr Val Cys Gly Pro Lys Lys Ser Gly Gly Gly Ser Gly
        195                 200                 205

Gly Gly Ser Gly Gly Gly Ser Gly Gly Gly Ser Phe Glu Ala Lys Pro
    210                 215                 220

Ser Gly Ser Val Val Ala Glu Gly Val Glu Cys Asp Phe Ser Pro Leu
225                 230                 235                 240

Leu Ser Gly Thr Pro Pro Gln Val Tyr Asn Phe Lys Arg Leu Val Phe
                245                 250                 255

Thr Asn Cys Asn Tyr Asn Leu Thr Lys Leu Leu Ser Leu Phe Ser Val
            260                 265                 270

Asn Asp Phe Thr Cys Ser Gln Ile Ser Pro Ala Ala Ile Ala Ser Asn
        275                 280                 285
```

```
Cys Tyr Ser Ser Leu Ile Leu Asp Tyr Phe Ser Tyr Pro Leu Ser Met
    290                 295                 300

Lys Ser Asp Leu Ser Val Ser Ser Ala Gly Pro Ile Ser Gln Phe Asn
305                 310                 315                 320

Tyr Lys Gln Ser Phe Ser Asn Pro Thr Cys Leu Ile Leu Ala Thr Val
                325                 330                 335

Pro His Asn Leu Thr Thr Ile Thr Lys Pro Leu Lys Tyr Ser Tyr Ile
            340                 345                 350

Asn Lys Cys Ser Arg Leu Leu Ser Asp Asp Arg Thr Glu Val Pro Gln
        355                 360                 365

Leu Val Asn Ala Asn Gln Tyr Ser Pro Cys Val Ser Ile Val Pro Ser
    370                 375                 380

Thr Val Trp Glu Asp Gly Asp Tyr Tyr Arg Lys Gln Leu Ser Pro Leu
385                 390                 395                 400

Glu Gly Gly Gly Trp Leu Val Ala Ser Gly Ser Thr Val Ala Met Thr
                405                 410                 415

Glu Gln Leu Gln Met Gly Phe Gly Ile Thr Val Gln Tyr Gly Thr Asp
            420                 425                 430

Thr Asn Ser Val Cys Pro Lys Leu Glu Phe Ala Asn Asp Thr Lys Ile
        435                 440                 445

Ala Ser Gln Leu Gly Asn Cys Val Glu Tyr Ser Gly Gly Gly Ser Gly
    450                 455                 460

Gly Gly Ser Gly Gly Gly Ser Gly Gly Gly Ser Arg Phe Pro Asn Ile
465                 470                 475                 480

Thr Asn Leu Cys Pro Phe Gly Glu Val Phe Asn Ala Thr Lys Phe Pro
                485                 490                 495

Ser Val Tyr Ala Trp Glu Arg Lys Lys Ile Ser Asn Cys Val Ala Asp
            500                 505                 510

Tyr Ser Val Leu Tyr Asn Ser Thr Phe Phe Ser Thr Phe Lys Cys Tyr
        515                 520                 525

Gly Val Ser Ala Thr Lys Leu Asn Asp Leu Cys Phe Ser Asn Val Tyr
    530                 535                 540

Ala Asp Ser Phe Val Val Lys Gly Asp Asp Val Arg Gln Ile Ala Pro
545                 550                 555                 560

Gly Gln Thr Gly Val Ile Ala Asp Tyr Asn Tyr Lys Leu Pro Asp Asp
                565                 570                 575

Phe Met Gly Cys Val Leu Ala Trp Asn Thr Arg Asn Ile Asp Ala Thr
            580                 585                 590

Ser Thr Gly Asn Tyr Asn Tyr Lys Tyr Arg Tyr Leu Arg His Gly Lys
        595                 600                 605

Leu Arg Pro Phe Glu Arg Asp Ile Ser Asn Val Pro Phe Ser Pro Asp
    610                 615                 620

Gly Lys Pro Cys Thr Pro Pro Ala Leu Asn Cys Tyr Trp Pro Leu Asn
625                 630                 635                 640

Asp Tyr Gly Phe Tyr Thr Thr Thr Gly Ile Gly Tyr Gln Pro Tyr Arg
                645                 650                 655

Val Val Val Leu Ser Phe Glu Leu Leu Asn Ala Pro Ala Thr Val Cys
            660                 665                 670

Gly Pro Lys Leu Ser Ala Ile Gly Gly Tyr Ile Pro Glu Ala Pro Arg
        675                 680                 685

Asp Gly Gln Ala Tyr Val Arg Lys Asp Gly Glu Trp Val Leu Leu Ser
    690                 695                 700
```

Thr Phe Leu
705

<210> SEQ ID NO 84
<211> LENGTH: 1273
<212> TYPE: PRT
<213> ORGANISM: Artificial Sequence
<220> FEATURE:
<223> OTHER INFORMATION: RECOMBINANT SPIKE PROTEIN

<400> SEQUENCE: 84

Met Phe Val Phe Leu Val Leu Leu Pro Leu Val Ser Ser Gln Cys Val
1 5 10 15

Asn Leu Thr Thr Arg Thr Gln Leu Pro Pro Ala Tyr Thr Asn Ser Phe
20 25 30

Thr Arg Gly Val Tyr Tyr Pro Asp Lys Val Phe Arg Ser Ser Val Leu
35 40 45

His Ser Thr Gln Asp Leu Phe Leu Pro Phe Phe Ser Asn Val Thr Trp
50 55 60

Phe His Ala Ile His Val Ser Gly Thr Asn Gly Thr Lys Arg Phe Asp
65 70 75 80

Asn Pro Val Leu Pro Phe Asn Asp Gly Val Tyr Phe Ala Ser Thr Glu
85 90 95

Lys Ser Asn Ile Ile Arg Gly Trp Ile Phe Gly Thr Thr Leu Asp Ser
100 105 110

Lys Thr Gln Ser Leu Leu Ile Val Asn Asn Ala Thr Asn Val Val Ile
115 120 125

Lys Val Cys Glu Phe Gln Phe Cys Asn Asp Pro Phe Leu Gly Val Tyr
130 135 140

Tyr His Lys Asn Asn Lys Ser Trp Met Glu Ser Glu Phe Arg Val Tyr
145 150 155 160

Ser Ser Ala Asn Asn Cys Thr Phe Glu Tyr Val Ser Gln Pro Phe Leu
165 170 175

Met Asp Leu Glu Gly Lys Gln Gly Asn Phe Lys Asn Leu Arg Glu Phe
180 185 190

Val Phe Lys Asn Ile Asp Gly Tyr Phe Lys Ile Tyr Ser Lys His Thr
195 200 205

Pro Ile Asn Leu Val Arg Asp Leu Pro Gln Gly Phe Ser Ala Leu Glu
210 215 220

Pro Leu Val Asp Leu Pro Ile Gly Ile Asn Ile Thr Arg Phe Gln Thr
225 230 235 240

Leu Leu Ala Leu His Arg Ser Tyr Leu Thr Pro Gly Asp Ser Ser Ser
245 250 255

Gly Trp Thr Ala Gly Ala Ala Ala Tyr Tyr Val Gly Tyr Leu Gln Pro
260 265 270

Arg Thr Phe Leu Leu Lys Tyr Asn Glu Asn Gly Thr Ile Thr Asp Ala
275 280 285

Val Asp Cys Ala Leu Asp Pro Leu Ser Glu Thr Lys Cys Thr Leu Lys
290 295 300

Ser Phe Thr Val Glu Lys Gly Ile Tyr Gln Thr Ser Asn Phe Arg Val
305 310 315 320

Gln Pro Thr Glu Ser Ile Val Arg Phe Pro Asn Ile Thr Asn Leu Cys
325 330 335

Pro Phe Gly Glu Val Phe Asn Ala Thr Arg Phe Ala Ser Val Tyr Ala
340 345 350

-continued

```
Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
```

```
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Pro Pro Glu Ala Glu Val Gln
            980                 985                 990

Ile Asp Arg Leu Ile Thr Gly Arg  Leu Gln Ser Leu Gln  Thr Tyr Val
        995                 1000                1005

Thr Gln  Gln Leu Ile Arg Ala  Ala Glu Ile Arg Ala  Ser Ala Asn
    1010                 1015                 1020

Leu Ala  Ala Thr Lys Met Ser  Glu Cys Val Leu Gly  Gln Ser Lys
    1025                 1030                 1035

Arg Val  Asp Phe Cys Gly Lys  Gly Tyr His Leu Met  Ser Phe Pro
    1040                 1045                 1050

Gln Ser  Ala Pro His Gly Val  Val Phe Leu His Val  Thr Tyr Val
    1055                 1060                 1065

Pro Ala  Gln Glu Lys Asn Phe  Thr Thr Ala Pro Ala  Ile Cys His
    1070                 1075                 1080

Asp Gly  Lys Ala His Phe Pro  Arg Glu Gly Val Phe  Val Ser Asn
    1085                 1090                 1095

Gly Thr  His Trp Phe Val Thr  Gln Arg Asn Phe Tyr  Glu Pro Gln
    1100                 1105                 1110

Ile Ile  Thr Thr Asp Asn Thr  Phe Val Ser Gly Asn  Cys Asp Val
    1115                 1120                 1125

Val Ile  Gly Ile Val Asn Asn  Thr Val Tyr Asp Pro  Leu Gln Pro
    1130                 1135                 1140

Glu Leu  Asp Ser Phe Lys Glu  Glu Leu Asp Lys Tyr  Phe Lys Asn
    1145                 1150                 1155

His Thr  Ser Pro Asp Val Asp  Leu Gly Asp Ile Ser  Gly Ile Asn
    1160                 1165                 1170

Ala Ser  Val Val Asn Ile Gln  Lys Glu Ile Asp Arg  Leu Asn Glu
    1175                 1180                 1185
```

```
Val Ala  Lys Asn Leu Asn Glu  Ser Leu Ile Asp Leu  Gln Glu Leu
    1190                 1195                 1200

Gly Lys  Tyr Glu Gln Tyr Ile  Lys Trp Pro Trp Tyr  Ile Trp Leu
    1205                 1210                 1215

Gly Phe  Ile Ala Gly Leu Ile  Ala Ile Val Met Val  Thr Ile Met
    1220                 1225                 1230

Leu Cys  Cys Met Thr Ser Cys  Cys Ser Cys Leu Lys  Gly Cys Cys
    1235                 1240                 1245

Ser Cys  Gly Ser Cys Cys Lys  Phe Asp Glu Asp Asp  Ser Glu Pro
    1250                 1255                 1260

Val Leu  Lys Gly Val Lys Leu  His Tyr Thr
    1265                 1270


<210> SEQ ID NO 85
<211> LENGTH: 1260
<212> TYPE: PRT
<213> ORGANISM: Artificial Sequence
<220> FEATURE:
<223> OTHER INFORMATION: RECOMBINANT SPIKE PROTEIN

<400> SEQUENCE: 85

Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
            20                  25                  30

Ser Val Leu His Ser Thr Gln Asp Leu Phe Leu Pro Phe Phe Ser Asn
        35                  40                  45

Val Thr Trp Phe His Ala Ile His Val Ser Gly Thr Asn Gly Thr Lys
    50                  55                  60

Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                85                  90                  95

Leu Asp Ser Lys Thr Gln Ser Leu Leu Ile Val Asn Asn Ala Thr Asn
            100                 105                 110

Val Val Ile Lys Val Cys Glu Phe Gln Phe Cys Asn Asp Pro Phe Leu
        115                 120                 125

Gly Val Tyr Tyr His Lys Asn Asn Lys Ser Trp Met Glu Ser Glu Phe
    130                 135                 140

Arg Val Tyr Ser Ser Ala Asn Asn Cys Thr Phe Glu Tyr Val Ser Gln
145                 150                 155                 160

Pro Phe Leu Met Asp Leu Glu Gly Lys Gln Gly Asn Phe Lys Asn Leu
                165                 170                 175

Arg Glu Phe Val Phe Lys Asn Ile Asp Gly Tyr Phe Lys Ile Tyr Ser
            180                 185                 190

Lys His Thr Pro Ile Asn Leu Val Arg Asp Leu Pro Gln Gly Phe Ser
        195                 200                 205

Ala Leu Glu Pro Leu Val Asp Leu Pro Ile Gly Ile Asn Ile Thr Arg
    210                 215                 220

Phe Gln Thr Leu Leu Ala Leu His Arg Ser Tyr Leu Thr Pro Gly Asp
225                 230                 235                 240

Ser Ser Ser Gly Trp Thr Ala Gly Ala Ala Ala Tyr Tyr Val Gly Tyr
                245                 250                 255

Leu Gln Pro Arg Thr Phe Leu Leu Lys Tyr Asn Glu Asn Gly Thr Ile
            260                 265                 270
```

-continued

```
Thr Asp Ala Val Asp Cys Ala Leu Asp Pro Leu Ser Glu Thr Lys Cys
        275                 280                 285

Thr Leu Lys Ser Phe Thr Val Glu Lys Gly Ile Tyr Gln Thr Ser Asn
    290                 295                 300

Phe Arg Val Gln Pro Thr Glu Ser Ile Val Arg Phe Pro Asn Ile Thr
305                 310                 315                 320

Asn Leu Cys Pro Phe Gly Glu Val Phe Asn Ala Thr Arg Phe Ala Ser
                325                 330                 335

Val Tyr Ala Trp Asn Arg Lys Arg Ile Ser Asn Cys Val Ala Asp Tyr
            340                 345                 350

Ser Val Leu Tyr Asn Ser Ala Ser Phe Ser Thr Phe Lys Cys Tyr Gly
        355                 360                 365

Val Ser Pro Thr Lys Leu Asn Asp Leu Cys Phe Thr Asn Val Tyr Ala
    370                 375                 380

Asp Ser Phe Val Ile Arg Gly Asp Glu Val Arg Gln Ile Ala Pro Gly
385                 390                 395                 400

Gln Thr Gly Lys Ile Ala Asp Tyr Asn Tyr Lys Leu Pro Asp Asp Phe
                405                 410                 415

Thr Gly Cys Val Ile Ala Trp Asn Ser Asn Asn Leu Asp Ser Lys Val
            420                 425                 430

Gly Gly Asn Tyr Asn Tyr Leu Tyr Arg Leu Phe Arg Lys Ser Asn Leu
        435                 440                 445

Lys Pro Phe Glu Arg Asp Ile Ser Thr Glu Ile Tyr Gln Ala Gly Ser
    450                 455                 460

Thr Pro Cys Asn Gly Val Glu Gly Phe Asn Cys Tyr Phe Pro Leu Gln
465                 470                 475                 480

Ser Tyr Gly Phe Gln Pro Thr Asn Gly Val Gly Tyr Gln Pro Tyr Arg
                485                 490                 495

Val Val Val Leu Ser Phe Glu Leu Leu His Ala Pro Ala Thr Val Cys
            500                 505                 510

Gly Pro Lys Lys Ser Thr Asn Leu Val Lys Asn Lys Cys Val Asn Phe
        515                 520                 525

Asn Phe Asn Gly Leu Thr Gly Thr Gly Val Leu Thr Glu Ser Asn Lys
    530                 535                 540

Lys Phe Leu Pro Phe Gln Gln Phe Gly Arg Asp Ile Ala Asp Thr Thr
545                 550                 555                 560

Asp Ala Val Arg Asp Pro Gln Thr Leu Glu Ile Leu Asp Ile Thr Pro
                565                 570                 575

Cys Ser Phe Gly Gly Val Ser Val Ile Thr Pro Gly Thr Asn Thr Ser
            580                 585                 590

Asn Gln Val Ala Val Leu Tyr Gln Asp Val Asn Cys Thr Glu Val Pro
        595                 600                 605

Val Ala Ile His Ala Asp Gln Leu Thr Pro Thr Trp Arg Val Tyr Ser
    610                 615                 620

Thr Gly Ser Asn Val Phe Gln Thr Arg Ala Gly Cys Leu Ile Gly Ala
625                 630                 635                 640

Glu His Val Asn Asn Ser Tyr Glu Cys Asp Ile Pro Ile Gly Ala Gly
                645                 650                 655

Ile Cys Ala Ser Tyr Gln Thr Gln Thr Asn Ser Pro Arg Arg Ala Arg
            660                 665                 670

Ser Val Ala Ser Gln Ser Ile Ile Ala Tyr Thr Met Ser Leu Gly Ala
        675                 680                 685
```

```
Glu Asn Ser Val Ala Tyr Ser Asn Asn Ser Ile Ala Ile Pro Thr Asn
    690                 695                 700

Phe Thr Ile Ser Val Thr Thr Glu Ile Leu Pro Val Ser Met Thr Lys
705                 710                 715                 720

Thr Ser Val Asp Cys Thr Met Tyr Ile Cys Gly Asp Ser Thr Glu Cys
                725                 730                 735

Ser Asn Leu Leu Leu Gln Tyr Gly Ser Phe Cys Thr Gln Leu Asn Arg
            740                 745                 750

Ala Leu Thr Gly Ile Ala Val Glu Gln Asp Lys Asn Thr Gln Glu Val
        755                 760                 765

Phe Ala Gln Val Lys Gln Ile Tyr Lys Thr Pro Pro Ile Lys Asp Phe
    770                 775                 780

Gly Gly Phe Asn Phe Ser Gln Ile Leu Pro Asp Pro Ser Lys Pro Ser
785                 790                 795                 800

Lys Arg Ser Phe Ile Glu Asp Leu Leu Phe Asn Lys Val Thr Leu Ala
                805                 810                 815

Asp Ala Gly Phe Ile Lys Gln Tyr Gly Asp Cys Leu Gly Asp Ile Ala
            820                 825                 830

Ala Arg Asp Leu Ile Cys Ala Gln Lys Phe Asn Gly Leu Thr Val Leu
        835                 840                 845

Pro Pro Leu Leu Thr Asp Glu Met Ile Ala Gln Tyr Thr Ser Ala Leu
    850                 855                 860

Leu Ala Gly Thr Ile Thr Ser Gly Trp Thr Phe Gly Ala Gly Ala Ala
865                 870                 875                 880

Leu Gln Ile Pro Phe Ala Met Gln Met Ala Tyr Arg Phe Asn Gly Ile
                885                 890                 895

Gly Val Thr Gln Asn Val Leu Tyr Glu Asn Gln Lys Leu Ile Ala Asn
            900                 905                 910

Gln Phe Asn Ser Ala Ile Gly Lys Ile Gln Asp Ser Leu Ser Ser Thr
        915                 920                 925

Ala Ser Ala Leu Gly Lys Leu Gln Asp Val Val Asn Gln Asn Ala Gln
    930                 935                 940

Ala Leu Asn Thr Leu Val Lys Gln Leu Ser Ser Asn Phe Gly Ala Ile
945                 950                 955                 960

Ser Ser Val Leu Asn Asp Ile Leu Ser Arg Leu Asp Pro Pro Glu Ala
                965                 970                 975

Glu Val Gln Ile Asp Arg Leu Ile Thr Gly Arg Leu Gln Ser Leu Gln
            980                 985                 990

Thr Tyr Val Thr Gln Gln Leu Ile  Arg Ala Ala Glu Ile  Arg Ala Ser
        995                 1000                1005

Ala Asn  Leu Ala Ala Thr Lys  Met Ser Glu Cys Val  Leu Gly Gln
    1010                1015                1020

Ser Lys  Arg Val Asp Phe Cys  Gly Lys Gly Tyr His  Leu Met Ser
    1025                1030                1035

Phe Pro  Gln Ser Ala Pro His  Gly Val Val Phe Leu  His Val Thr
    1040                1045                1050

Tyr Val  Pro Ala Gln Glu Lys  Asn Phe Thr Thr Ala  Pro Ala Ile
    1055                1060                1065

Cys His  Asp Gly Lys Ala His  Phe Pro Arg Glu Gly  Val Phe Val
    1070                1075                1080

Ser Asn  Gly Thr His Trp Phe  Val Thr Gln Arg Asn  Phe Tyr Glu
    1085                1090                1095

Pro Gln  Ile Ile Thr Thr Asp  Asn Thr Phe Val Ser  Gly Asn Cys
```

```
    1100                1105                1110

Asp Val  Val Ile Gly Ile Val  Asn Asn Thr Val Tyr  Asp Pro Leu
    1115                1120                1125

Gln Pro  Glu Leu Asp Ser Phe  Lys Glu Glu Leu Asp  Lys Tyr Phe
    1130                1135                1140

Lys Asn  His Thr Ser Pro Asp  Val Asp Leu Gly Asp  Ile Ser Gly
    1145                1150                1155

Ile Asn  Ala Ser Val Val Asn  Ile Gln Lys Glu Ile  Asp Arg Leu
    1160                1165                1170

Asn Glu  Val Ala Lys Asn Leu  Asn Glu Ser Leu Ile  Asp Leu Gln
    1175                1180                1185

Glu Leu  Gly Lys Tyr Glu Gln  Tyr Ile Lys Trp Pro  Trp Tyr Ile
    1190                1195                1200

Trp Leu  Gly Phe Ile Ala Gly  Leu Ile Ala Ile Val  Met Val Thr
    1205                1210                1215

Ile Met  Leu Cys Cys Met Thr  Ser Cys Cys Ser Cys  Leu Lys Gly
    1220                1225                1230

Cys Cys  Ser Cys Gly Ser Cys  Cys Lys Phe Asp Glu  Asp Asp Ser
    1235                1240                1245

Glu Pro  Val Leu Lys Gly Val  Lys Leu His Tyr Thr
    1250                1255                1260


<210> SEQ ID NO 86
<211> LENGTH: 1273
<212> TYPE: PRT
<213> ORGANISM: Artificial Sequence
<220> FEATURE:
<223> OTHER INFORMATION: RECOMBINANT SPIKE PROTEIN

<400> SEQUENCE: 86

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
```

```
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620
```

```
His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Gln Gln Ala Gln Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Pro Pro Glu Ala Glu Val Gln
            980                 985                 990

Ile Asp Arg Leu Ile Thr Gly Arg  Leu Gln Ser Leu Gln  Thr Tyr Val
        995                 1000                1005

Thr Gln  Gln Leu Ile Arg Ala  Ala Glu Ile Arg Ala  Ser Ala Asn
    1010                1015                1020

Leu Ala  Ala Thr Lys Met Ser  Glu Cys Val Leu Gly  Gln Ser Lys
    1025                1030                1035
```

```
Arg Val  Asp Phe Cys Gly Lys  Gly Tyr His Leu Met  Ser Phe Pro
    1040                 1045                 1050

Gln Ser  Ala Pro His Gly Val  Val Phe Leu His Val  Thr Tyr Val
    1055                 1060                 1065

Pro Ala  Gln Glu Lys Asn Phe  Thr Thr Ala Pro Ala  Ile Cys His
    1070                 1075                 1080

Asp Gly  Lys Ala His Phe Pro  Arg Glu Gly Val Phe  Val Ser Asn
    1085                 1090                 1095

Gly Thr  His Trp Phe Val Thr  Gln Arg Asn Phe Tyr  Glu Pro Gln
    1100                 1105                 1110

Ile Ile  Thr Thr Asp Asn Thr  Phe Val Ser Gly Asn  Cys Asp Val
    1115                 1120                 1125

Val Ile  Gly Ile Val Asn Asn  Thr Val Tyr Asp Pro  Leu Gln Pro
    1130                 1135                 1140

Glu Leu  Asp Ser Phe Lys Glu  Glu Leu Asp Lys Tyr  Phe Lys Asn
    1145                 1150                 1155

His Thr  Ser Pro Asp Val Asp  Leu Gly Asp Ile Ser  Gly Ile Asn
    1160                 1165                 1170

Ala Ser  Val Val Asn Ile Gln  Lys Glu Ile Asp Arg  Leu Asn Glu
    1175                 1180                 1185

Val Ala  Lys Asn Leu Asn Glu  Ser Leu Ile Asp Leu  Gln Glu Leu
    1190                 1195                 1200

Gly Lys  Tyr Glu Gln Tyr Ile  Lys Trp Pro Trp Tyr  Ile Trp Leu
    1205                 1210                 1215

Gly Phe  Ile Ala Gly Leu Ile  Ala Ile Val Met Val  Thr Ile Met
    1220                 1225                 1230

Leu Cys  Cys Met Thr Ser Cys  Cys Ser Cys Leu Lys  Gly Cys Cys
    1235                 1240                 1245

Ser Cys  Gly Ser Cys Cys Lys  Phe Asp Glu Asp Asp  Ser Glu Pro
    1250                 1255                 1260

Val Leu  Lys Gly Val Lys Leu  His Tyr Thr
    1265                 1270
```

<210> SEQ ID NO 87
<211> LENGTH: 1260
<212> TYPE: PRT
<213> ORGANISM: Artificial Sequence
<220> FEATURE:
<223> OTHER INFORMATION: RECOMBINANT SPIKE PROTEIN

<400> SEQUENCE: 87

```
Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
            20                  25                  30

Ser Val Leu His Ser Thr Gln Asp Leu Phe Leu Pro Phe Phe Ser Asn
        35                  40                  45

Val Thr Trp Phe His Ala Ile His Val Ser Gly Thr Asn Gly Thr Lys
    50                  55                  60

Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                85                  90                  95

Leu Asp Ser Lys Thr Gln Ser Leu Leu Ile Val Asn Asn Ala Thr Asn
            100                 105                 110
```

-continued

```
Val Val Ile Lys Val Cys Glu Phe Gln Phe Cys Asn Asp Pro Phe Leu
        115                 120                 125

Gly Val Tyr Tyr His Lys Asn Asn Lys Ser Trp Met Glu Ser Glu Phe
    130                 135                 140

Arg Val Tyr Ser Ser Ala Asn Asn Cys Thr Phe Glu Tyr Val Ser Gln
145                 150                 155                 160

Pro Phe Leu Met Asp Leu Glu Gly Lys Gln Gly Asn Phe Lys Asn Leu
                165                 170                 175

Arg Glu Phe Val Phe Lys Asn Ile Asp Gly Tyr Phe Lys Ile Tyr Ser
            180                 185                 190

Lys His Thr Pro Ile Asn Leu Val Arg Asp Leu Pro Gln Gly Phe Ser
        195                 200                 205

Ala Leu Glu Pro Leu Val Asp Leu Pro Ile Gly Ile Asn Ile Thr Arg
    210                 215                 220

Phe Gln Thr Leu Leu Ala Leu His Arg Ser Tyr Leu Thr Pro Gly Asp
225                 230                 235                 240

Ser Ser Ser Gly Trp Thr Ala Gly Ala Ala Ala Tyr Tyr Val Gly Tyr
                245                 250                 255

Leu Gln Pro Arg Thr Phe Leu Leu Lys Tyr Asn Glu Asn Gly Thr Ile
            260                 265                 270

Thr Asp Ala Val Asp Cys Ala Leu Asp Pro Leu Ser Glu Thr Lys Cys
        275                 280                 285

Thr Leu Lys Ser Phe Thr Val Glu Lys Gly Ile Tyr Gln Thr Ser Asn
    290                 295                 300

Phe Arg Val Gln Pro Thr Glu Ser Ile Val Arg Phe Pro Asn Ile Thr
305                 310                 315                 320

Asn Leu Cys Pro Phe Gly Glu Val Phe Asn Ala Thr Arg Phe Ala Ser
                325                 330                 335

Val Tyr Ala Trp Asn Arg Lys Arg Ile Ser Asn Cys Val Ala Asp Tyr
            340                 345                 350

Ser Val Leu Tyr Asn Ser Ala Ser Phe Ser Thr Phe Lys Cys Tyr Gly
        355                 360                 365

Val Ser Pro Thr Lys Leu Asn Asp Leu Cys Phe Thr Asn Val Tyr Ala
    370                 375                 380

Asp Ser Phe Val Ile Arg Gly Asp Glu Val Arg Gln Ile Ala Pro Gly
385                 390                 395                 400

Gln Thr Gly Lys Ile Ala Asp Tyr Asn Tyr Lys Leu Pro Asp Asp Phe
                405                 410                 415

Thr Gly Cys Val Ile Ala Trp Asn Ser Asn Asn Leu Asp Ser Lys Val
            420                 425                 430

Gly Gly Asn Tyr Asn Tyr Leu Tyr Arg Leu Phe Arg Lys Ser Asn Leu
        435                 440                 445

Lys Pro Phe Glu Arg Asp Ile Ser Thr Glu Ile Tyr Gln Ala Gly Ser
    450                 455                 460

Thr Pro Cys Asn Gly Val Glu Gly Phe Asn Cys Tyr Phe Pro Leu Gln
465                 470                 475                 480

Ser Tyr Gly Phe Gln Pro Thr Asn Gly Val Gly Tyr Gln Pro Tyr Arg
                485                 490                 495

Val Val Val Leu Ser Phe Glu Leu Leu His Ala Pro Ala Thr Val Cys
            500                 505                 510

Gly Pro Lys Lys Ser Thr Asn Leu Val Lys Asn Lys Cys Val Asn Phe
        515                 520                 525

Asn Phe Asn Gly Leu Thr Gly Thr Gly Val Leu Thr Glu Ser Asn Lys
```

530 535 540

Lys Phe Leu Pro Phe Gln Gln Phe Gly Arg Asp Ile Ala Asp Thr Thr
545 550 555 560

Asp Ala Val Arg Asp Pro Gln Thr Leu Glu Ile Leu Asp Ile Thr Pro
565 570 575

Cys Ser Phe Gly Gly Val Ser Val Ile Thr Pro Gly Thr Asn Thr Ser
580 585 590

Asn Gln Val Ala Val Leu Tyr Gln Asp Val Asn Cys Thr Glu Val Pro
595 600 605

Val Ala Ile His Ala Asp Gln Leu Thr Pro Thr Trp Arg Val Tyr Ser
610 615 620

Thr Gly Ser Asn Val Phe Gln Thr Arg Ala Gly Cys Leu Ile Gly Ala
625 630 635 640

Glu His Val Asn Asn Ser Tyr Glu Cys Asp Ile Pro Ile Gly Ala Gly
645 650 655

Ile Cys Ala Ser Tyr Gln Thr Gln Thr Asn Ser Pro Gln Gln Ala Gln
660 665 670

Ser Val Ala Ser Gln Ser Ile Ile Ala Tyr Thr Met Ser Leu Gly Ala
675 680 685

Glu Asn Ser Val Ala Tyr Ser Asn Asn Ser Ile Ala Ile Pro Thr Asn
690 695 700

Phe Thr Ile Ser Val Thr Thr Glu Ile Leu Pro Val Ser Met Thr Lys
705 710 715 720

Thr Ser Val Asp Cys Thr Met Tyr Ile Cys Gly Asp Ser Thr Glu Cys
725 730 735

Ser Asn Leu Leu Leu Gln Tyr Gly Ser Phe Cys Thr Gln Leu Asn Arg
740 745 750

Ala Leu Thr Gly Ile Ala Val Glu Gln Asp Lys Asn Thr Gln Glu Val
755 760 765

Phe Ala Gln Val Lys Gln Ile Tyr Lys Thr Pro Pro Ile Lys Asp Phe
770 775 780

Gly Gly Phe Asn Phe Ser Gln Ile Leu Pro Asp Pro Ser Lys Pro Ser
785 790 795 800

Lys Arg Ser Phe Ile Glu Asp Leu Leu Phe Asn Lys Val Thr Leu Ala
805 810 815

Asp Ala Gly Phe Ile Lys Gln Tyr Gly Asp Cys Leu Gly Asp Ile Ala
820 825 830

Ala Arg Asp Leu Ile Cys Ala Gln Lys Phe Asn Gly Leu Thr Val Leu
835 840 845

Pro Pro Leu Leu Thr Asp Glu Met Ile Ala Gln Tyr Thr Ser Ala Leu
850 855 860

Leu Ala Gly Thr Ile Thr Ser Gly Trp Thr Phe Gly Ala Gly Ala Ala
865 870 875 880

Leu Gln Ile Pro Phe Ala Met Gln Met Ala Tyr Arg Phe Asn Gly Ile
885 890 895

Gly Val Thr Gln Asn Val Leu Tyr Glu Asn Gln Lys Leu Ile Ala Asn
900 905 910

Gln Phe Asn Ser Ala Ile Gly Lys Ile Gln Asp Ser Leu Ser Ser Thr
915 920 925

Ala Ser Ala Leu Gly Lys Leu Gln Asp Val Val Asn Gln Asn Ala Gln
930 935 940

Ala Leu Asn Thr Leu Val Lys Gln Leu Ser Ser Asn Phe Gly Ala Ile
945 950 955 960

```
Ser Ser Val Leu Asn Asp Ile Leu Ser Arg Leu Asp Pro Pro Glu Ala
                965                 970                 975

Glu Val Gln Ile Asp Arg Leu Ile Thr Gly Arg Leu Gln Ser Leu Gln
            980                 985                 990

Thr Tyr Val Thr Gln Gln Leu Ile  Arg Ala Ala Glu Ile  Arg Ala Ser
        995                 1000                1005

Ala Asn  Leu Ala Ala Thr Lys  Met Ser Glu Cys Val  Leu Gly Gln
    1010                 1015                 1020

Ser Lys  Arg Val Asp Phe Cys  Gly Lys Gly Tyr His  Leu Met Ser
    1025                 1030                 1035

Phe Pro  Gln Ser Ala Pro His  Gly Val Val Phe Leu  His Val Thr
    1040                 1045                 1050

Tyr Val  Pro Ala Gln Glu Lys  Asn Phe Thr Thr Ala  Pro Ala Ile
    1055                 1060                 1065

Cys His  Asp Gly Lys Ala His  Phe Pro Arg Glu Gly  Val Phe Val
    1070                 1075                 1080

Ser Asn  Gly Thr His Trp Phe  Val Thr Gln Arg Asn  Phe Tyr Glu
    1085                 1090                 1095

Pro Gln  Ile Ile Thr Thr Asp  Asn Thr Phe Val Ser  Gly Asn Cys
    1100                 1105                 1110

Asp Val  Val Ile Gly Ile Val  Asn Asn Thr Val Tyr  Asp Pro Leu
    1115                 1120                 1125

Gln Pro  Glu Leu Asp Ser Phe  Lys Glu Glu Leu Asp  Lys Tyr Phe
    1130                 1135                 1140

Lys Asn  His Thr Ser Pro Asp  Val Asp Leu Gly Asp  Ile Ser Gly
    1145                 1150                 1155

Ile Asn  Ala Ser Val Val Asn  Ile Gln Lys Glu Ile  Asp Arg Leu
    1160                 1165                 1170

Asn Glu  Val Ala Lys Asn Leu  Asn Glu Ser Leu Ile  Asp Leu Gln
    1175                 1180                 1185

Glu Leu  Gly Lys Tyr Glu Gln  Tyr Ile Lys Trp Pro  Trp Tyr Ile
    1190                 1195                 1200

Trp Leu  Gly Phe Ile Ala Gly  Leu Ile Ala Ile Val  Met Val Thr
    1205                 1210                 1215

Ile Met  Leu Cys Cys Met Thr  Ser Cys Cys Ser Cys  Leu Lys Gly
    1220                 1225                 1230

Cys Cys  Ser Cys Gly Ser Cys  Cys Lys Phe Asp Glu  Asp Asp Ser
    1235                 1240                 1245

Glu Pro  Val Leu Lys Gly Val  Lys Leu His Tyr Thr
    1250                 1255                 1260


<210> SEQ ID NO 88
<211> LENGTH: 1219
<212> TYPE: PRT
<213> ORGANISM: Artificial Sequence
<220> FEATURE:
<223> OTHER INFORMATION: RECOMBINANT SPIKE PROTEIN

<400> SEQUENCE: 88

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45
```

-continued

```
His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460
```

```
Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Gln Gln Ala Gln Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
```

```
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Pro Pro Glu Ala Glu Val Gln
            980                 985                 990

Ile Asp Arg Leu Ile Thr Gly Arg  Leu Gln Ser Leu Gln  Thr Tyr Val
        995                 1000                1005

Thr Gln  Gln Leu Ile Arg Ala  Ala Glu Ile Arg Ala  Ser Ala Asn
    1010                 1015                 1020

Leu Ala  Ala Thr Lys Met Ser  Glu Cys Val Leu Gly  Gln Ser Lys
    1025                 1030                 1035

Arg Val  Asp Phe Cys Gly Lys  Gly Tyr His Leu Met  Ser Phe Pro
    1040                 1045                 1050

Gln Ser  Ala Pro His Gly Val  Val Phe Leu His Val  Thr Tyr Val
    1055                 1060                 1065

Pro Ala  Gln Glu Lys Asn Phe  Thr Thr Ala Pro Ala  Ile Cys His
    1070                 1075                 1080

Asp Gly  Lys Ala His Phe Pro  Arg Glu Gly Val Phe  Val Ser Asn
    1085                 1090                 1095

Gly Thr  His Trp Phe Val Thr  Gln Arg Asn Phe Tyr  Glu Pro Gln
    1100                 1105                 1110

Ile Ile  Thr Thr Asp Asn Thr  Phe Val Ser Gly Asn  Cys Asp Val
    1115                 1120                 1125

Val Ile  Gly Ile Val Asn Asn  Thr Val Tyr Asp Pro  Leu Gln Pro
    1130                 1135                 1140

Glu Leu  Asp Ser Phe Lys Glu  Glu Leu Asp Lys Tyr  Phe Lys Asn
    1145                 1150                 1155

His Thr  Ser Pro Asp Val Asp  Leu Gly Asp Ile Ser  Gly Ile Asn
    1160                 1165                 1170

Ala Ser  Val Val Asn Ile Gln  Lys Glu Ile Asp Arg  Leu Asn Glu
    1175                 1180                 1185

Val Ala  Lys Asn Leu Asn Glu  Ser Leu Ile Asp Leu  Gln Glu Leu
    1190                 1195                 1200

Gly Lys  Tyr Glu Gln Tyr Ile  Lys Trp Pro His His  His His His
    1205                 1210                 1215

His
```

<210> SEQ ID NO 89
<211> LENGTH: 1206
<212> TYPE: PRT
<213> ORGANISM: Artificial Sequence
<220> FEATURE:
<223> OTHER INFORMATION: RECOMBINANT SPIKE PROTEIN

<400> SEQUENCE: 89

```
Gln Cys Val Asn Leu Thr Thr Arg Thr Gln Leu Pro Pro Ala Tyr Thr
1               5                   10                  15
```

```
Asn Ser Phe Thr Arg Gly Val Tyr Tyr Pro Asp Lys Val Phe Arg Ser
            20                  25                  30

Ser Val Leu His Ser Thr Gln Asp Leu Phe Leu Pro Phe Phe Ser Asn
        35                  40                  45

Val Thr Trp Phe His Ala Ile His Val Ser Gly Thr Asn Gly Thr Lys
    50                  55                  60

Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                85                  90                  95

Leu Asp Ser Lys Thr Gln Ser Leu Leu Ile Val Asn Asn Ala Thr Asn
            100                 105                 110

Val Val Ile Lys Val Cys Glu Phe Gln Phe Cys Asn Asp Pro Phe Leu
        115                 120                 125

Gly Val Tyr Tyr His Lys Asn Asn Lys Ser Trp Met Glu Ser Glu Phe
    130                 135                 140

Arg Val Tyr Ser Ser Ala Asn Asn Cys Thr Phe Glu Tyr Val Ser Gln
145                 150                 155                 160

Pro Phe Leu Met Asp Leu Glu Gly Lys Gln Gly Asn Phe Lys Asn Leu
                165                 170                 175

Arg Glu Phe Val Phe Lys Asn Ile Asp Gly Tyr Phe Lys Ile Tyr Ser
            180                 185                 190

Lys His Thr Pro Ile Asn Leu Val Arg Asp Leu Pro Gln Gly Phe Ser
        195                 200                 205

Ala Leu Glu Pro Leu Val Asp Leu Pro Ile Gly Ile Asn Ile Thr Arg
    210                 215                 220

Phe Gln Thr Leu Leu Ala Leu His Arg Ser Tyr Leu Thr Pro Gly Asp
225                 230                 235                 240

Ser Ser Ser Gly Trp Thr Ala Gly Ala Ala Ala Tyr Tyr Val Gly Tyr
                245                 250                 255

Leu Gln Pro Arg Thr Phe Leu Leu Lys Tyr Asn Glu Asn Gly Thr Ile
            260                 265                 270

Thr Asp Ala Val Asp Cys Ala Leu Asp Pro Leu Ser Glu Thr Lys Cys
        275                 280                 285

Thr Leu Lys Ser Phe Thr Val Glu Lys Gly Ile Tyr Gln Thr Ser Asn
    290                 295                 300

Phe Arg Val Gln Pro Thr Glu Ser Ile Val Arg Phe Pro Asn Ile Thr
305                 310                 315                 320

Asn Leu Cys Pro Phe Gly Glu Val Phe Asn Ala Thr Arg Phe Ala Ser
                325                 330                 335

Val Tyr Ala Trp Asn Arg Lys Arg Ile Ser Asn Cys Val Ala Asp Tyr
            340                 345                 350

Ser Val Leu Tyr Asn Ser Ala Ser Phe Ser Thr Phe Lys Cys Tyr Gly
        355                 360                 365

Val Ser Pro Thr Lys Leu Asn Asp Leu Cys Phe Thr Asn Val Tyr Ala
    370                 375                 380

Asp Ser Phe Val Ile Arg Gly Asp Glu Val Arg Gln Ile Ala Pro Gly
385                 390                 395                 400

Gln Thr Gly Lys Ile Ala Asp Tyr Asn Tyr Lys Leu Pro Asp Asp Phe
                405                 410                 415

Thr Gly Cys Val Ile Ala Trp Asn Ser Asn Asn Leu Asp Ser Lys Val
            420                 425                 430
```

```
Gly Gly Asn Tyr Asn Tyr Leu Tyr Arg Leu Phe Arg Lys Ser Asn Leu
        435                 440                 445

Lys Pro Phe Glu Arg Asp Ile Ser Thr Glu Ile Tyr Gln Ala Gly Ser
    450                 455                 460

Thr Pro Cys Asn Gly Val Glu Gly Phe Asn Cys Tyr Phe Pro Leu Gln
465                 470                 475                 480

Ser Tyr Gly Phe Gln Pro Thr Asn Gly Val Gly Tyr Gln Pro Tyr Arg
                485                 490                 495

Val Val Val Leu Ser Phe Glu Leu Leu His Ala Pro Ala Thr Val Cys
            500                 505                 510

Gly Pro Lys Lys Ser Thr Asn Leu Val Lys Asn Lys Cys Val Asn Phe
        515                 520                 525

Asn Phe Asn Gly Leu Thr Gly Thr Gly Val Leu Thr Glu Ser Asn Lys
    530                 535                 540

Lys Phe Leu Pro Phe Gln Gln Phe Gly Arg Asp Ile Ala Asp Thr Thr
545                 550                 555                 560

Asp Ala Val Arg Asp Pro Gln Thr Leu Glu Ile Leu Asp Ile Thr Pro
                565                 570                 575

Cys Ser Phe Gly Gly Val Ser Val Ile Thr Pro Gly Thr Asn Thr Ser
            580                 585                 590

Asn Gln Val Ala Val Leu Tyr Gln Asp Val Asn Cys Thr Glu Val Pro
        595                 600                 605

Val Ala Ile His Ala Asp Gln Leu Thr Pro Thr Trp Arg Val Tyr Ser
    610                 615                 620

Thr Gly Ser Asn Val Phe Gln Thr Arg Ala Gly Cys Leu Ile Gly Ala
625                 630                 635                 640

Glu His Val Asn Asn Ser Tyr Glu Cys Asp Ile Pro Ile Gly Ala Gly
                645                 650                 655

Ile Cys Ala Ser Tyr Gln Thr Gln Thr Asn Ser Pro Gln Gln Ala Gln
            660                 665                 670

Ser Val Ala Ser Gln Ser Ile Ile Ala Tyr Thr Met Ser Leu Gly Ala
        675                 680                 685

Glu Asn Ser Val Ala Tyr Ser Asn Asn Ser Ile Ala Ile Pro Thr Asn
    690                 695                 700

Phe Thr Ile Ser Val Thr Thr Glu Ile Leu Pro Val Ser Met Thr Lys
705                 710                 715                 720

Thr Ser Val Asp Cys Thr Met Tyr Ile Cys Gly Asp Ser Thr Glu Cys
                725                 730                 735

Ser Asn Leu Leu Leu Gln Tyr Gly Ser Phe Cys Thr Gln Leu Asn Arg
            740                 745                 750

Ala Leu Thr Gly Ile Ala Val Glu Gln Asp Lys Asn Thr Gln Glu Val
        755                 760                 765

Phe Ala Gln Val Lys Gln Ile Tyr Lys Thr Pro Pro Ile Lys Asp Phe
    770                 775                 780

Gly Gly Phe Asn Phe Ser Gln Ile Leu Pro Asp Pro Ser Lys Pro Ser
785                 790                 795                 800

Lys Arg Ser Phe Ile Glu Asp Leu Leu Phe Asn Lys Val Thr Leu Ala
                805                 810                 815

Asp Ala Gly Phe Ile Lys Gln Tyr Gly Asp Cys Leu Gly Asp Ile Ala
            820                 825                 830

Ala Arg Asp Leu Ile Cys Ala Gln Lys Phe Asn Gly Leu Thr Val Leu
        835                 840                 845

Pro Pro Leu Leu Thr Asp Glu Met Ile Ala Gln Tyr Thr Ser Ala Leu
```

```
    850                 855                 860

Leu Ala Gly Thr Ile Thr Ser Gly Trp Thr Phe Gly Ala Gly Ala Ala
865                 870                 875                 880

Leu Gln Ile Pro Phe Ala Met Gln Met Ala Tyr Arg Phe Asn Gly Ile
                885                 890                 895

Gly Val Thr Gln Asn Val Leu Tyr Glu Asn Gln Lys Leu Ile Ala Asn
            900                 905                 910

Gln Phe Asn Ser Ala Ile Gly Lys Ile Gln Asp Ser Leu Ser Ser Thr
        915                 920                 925

Ala Ser Ala Leu Gly Lys Leu Gln Asp Val Val Asn Gln Asn Ala Gln
    930                 935                 940

Ala Leu Asn Thr Leu Val Lys Gln Leu Ser Ser Asn Phe Gly Ala Ile
945                 950                 955                 960

Ser Ser Val Leu Asn Asp Ile Leu Ser Arg Leu Asp Pro Pro Glu Ala
                965                 970                 975

Glu Val Gln Ile Asp Arg Leu Ile Thr Gly Arg Leu Gln Ser Leu Gln
            980                 985                 990

Thr Tyr Val Thr Gln Gln Leu Ile  Arg Ala Ala Glu Ile  Arg Ala Ser
        995                 1000                1005

Ala Asn  Leu Ala Ala Thr Lys  Met Ser Glu Cys Val  Leu Gly Gln
    1010                 1015                 1020

Ser Lys  Arg Val Asp Phe Cys  Gly Lys Gly Tyr His  Leu Met Ser
    1025                 1030                 1035

Phe Pro  Gln Ser Ala Pro His  Gly Val Val Phe Leu  His Val Thr
    1040                 1045                 1050

Tyr Val  Pro Ala Gln Glu Lys  Asn Phe Thr Thr Ala  Pro Ala Ile
    1055                 1060                 1065

Cys His  Asp Gly Lys Ala His  Phe Pro Arg Glu Gly  Val Phe Val
    1070                 1075                 1080

Ser Asn  Gly Thr His Trp Phe  Val Thr Gln Arg Asn  Phe Tyr Glu
    1085                 1090                 1095

Pro Gln  Ile Ile Thr Thr Asp  Asn Thr Phe Val Ser  Gly Asn Cys
    1100                 1105                 1110

Asp Val  Val Ile Gly Ile Val  Asn Asn Thr Val Tyr  Asp Pro Leu
    1115                 1120                 1125

Gln Pro  Glu Leu Asp Ser Phe  Lys Glu Glu Leu Asp  Lys Tyr Phe
    1130                 1135                 1140

Lys Asn  His Thr Ser Pro Asp  Val Asp Leu Gly Asp  Ile Ser Gly
    1145                 1150                 1155

Ile Asn  Ala Ser Val Val Asn  Ile Gln Lys Glu Ile  Asp Arg Leu
    1160                 1165                 1170

Asn Glu  Val Ala Lys Asn Leu  Asn Glu Ser Leu Ile  Asp Leu Gln
    1175                 1180                 1185

Glu Leu  Gly Lys Tyr Glu Gln  Tyr Ile Lys Trp Pro  His His His
    1190                 1195                 1200

His His  His
    1205


<210> SEQ ID NO 90
<211> LENGTH: 17
<212> TYPE: PRT
<213> ORGANISM: Artificial Sequence
<220> FEATURE:
<223> OTHER INFORMATION: Linker
```

<400> SEQUENCE: 90

Ser Gly Gly Gly Ser Gly Gly Gly Ser Gly Gly Gly Ser Gly Gly Gly
1 5 10 15

Ser

<210> SEQ ID NO 91
<211> LENGTH: 4
<212> TYPE: PRT
<213> ORGANISM: Artificial Sequence
<220> FEATURE:
<223> OTHER INFORMATION: Linker

<400> SEQUENCE: 91

Ser Gly Gly Gly
1

<210> SEQ ID NO 92
<211> LENGTH: 4
<212> TYPE: PRT
<213> ORGANISM: Artificial Sequence
<220> FEATURE:
<223> OTHER INFORMATION: Linker

<400> SEQUENCE: 92

Gly Gly Gly Ser
1

<210> SEQ ID NO 93
<211> LENGTH: 5
<212> TYPE: PRT
<213> ORGANISM: Artificial Sequence
<220> FEATURE:
<223> OTHER INFORMATION: Linker

<400> SEQUENCE: 93

Gly Gly Gly Gly Ser
1 5

<210> SEQ ID NO 94
<211> LENGTH: 90
<212> TYPE: PRT
<213> ORGANISM: Artificial Sequence
<220> FEATURE:
<223> OTHER INFORMATION: RECOMBINANT SPIKE PROTEIN

<400> SEQUENCE: 94

Ser Thr Asn Leu Val Lys Asn Lys Cys Val Asn Phe Asn Phe Asn Gly
1 5 10 15

Leu Thr Gly Thr Gly Val Leu Thr Glu Ser Asn Lys Lys Phe Leu Pro
20 25 30

Phe Gln Gln Phe Gly Arg Asp Ile Ala Asp Thr Thr Asp Ala Val Arg
35 40 45

Asp Pro Gln Thr Leu Glu Ile Leu Asp Ile Thr Pro Cys Ser Phe Gly
50 55 60

Gly Val Ser Val Ile Thr Pro Gly Thr Asn Thr Ser Asn Gln Val Ala
65 70 75 80

Val Leu Tyr Gln Asp Val Asn Cys Thr Glu
85 90

<210> SEQ ID NO 95
<211> LENGTH: 3639
<212> TYPE: DNA
<213> ORGANISM: Artificial Sequence

<220> FEATURE:
<223> OTHER INFORMATION: RECOMBINANT SPIKE PROTEIN

<400> SEQUENCE: 95

```
atgttcgtct tcctggtgct gctgcccctg gtgtccagcc agtgcgtgaa cctgaccact     60
aggactcagc tgcctcccgc ttacaccaac tcattcactc gcggtgtgta ctaccctgac    120
aaggtcttcc gttcttcagt gctgcactca actcaggacc tgttcctgcc cttcttctcc    180
aacgtcacct ggttccacgc catccacgtg tccggcacca acggcactaa gcgcttcgac    240
aacccagtgc tgcctttcaa cgacggtgtc tacttcgctt caaccgagaa gtccaacatc    300
atccgtggat ggatcttcgg caccactctg gacagcaaga ctcagtctct gctgatcgtc    360
aacaacgcca ccaacgtggt catcaaggtc tgcgaattcc agttctgcaa cgacccattc    420
ctgggcgtct actaccacaa gaacaacaag tcatggatgg agtccgaatt ccgcgtctac    480
tccagcgcta acaactgcac tttcgagtac gtgtcccagc ctttcctgat ggacctggaa    540
ggaaagcagg gtaacttcaa gaacctgagg gagttcgtgt tcaagaacat cgacggatac    600
ttcaagattt acagcaagca caccccaatc aacctggtgc gcgacctgcc tcagggtttc    660
tctgctctgg agccactggt ggacctgcct atcggcatca acatcacccg cttccagact    720
ctgctggctc tgcaccgttc ctacctgact ccaggcgact catcttctgg atggactgct    780
ggagctgctg cttactacgt gggctacctg cagcctcgca ccttcctgct gaagtacaac    840
gaaaacggaa ccatcactga cgccgtcgac tgcgctctgg accctctgtc agaaaccaag    900
tgcactctga agtccttcac cgtggagaag ggcatctacc agacttcaaa cttcagggtg    960
cagcccaccg aatccatcgt cagattccct aacatcacta acctgtgccc cttcggagag   1020
gtcttcaacg ccacccgctt cgcttccgtg tacgcctgga acaggaagag aatctcaaac   1080
tgcgtcgctg actactccgt gctgtacaac tcagcctcct tcagcacctt caagtgctac   1140
ggcgtgtcac caactaagct gaacgacctg tgcttcacca acgtctacgc cgactccttc   1200
gtgatcaggg gagacgaggt cagacagatc gctcctggcc agactggaaa gatcgccgac   1260
tacaactaca agctgcccga cgacttcacc ggttgcgtca tcgcttggaa cagcaacaac   1320
ctggactcta aagtgggtgg caactacaac tacctgtacc gcctgttccg taagtcaaac   1380
ctgaagccat tcgagaggga catcagcact gaaatctacc aggccggatc taccccttgc   1440
aacggtgtcg agggcttcaa ctgctacttc cccctgcagt cctacggttt ccagccaact   1500
aacggtgtgg gctaccagcc ttacagagtg gtcgtgctga gcttcgaact gctccacgct   1560
cctgctactg tgtgcggtcc aaagaagtct accaacctgg tcaagaacaa gtgcgtgaac   1620
ttcaacttca acggcctgac cggaactggt gtcctgaccg agagcaacaa gaagttcctg   1680
cccttccagc agttcggaag ggacatcgct gacaccactg acgctgtgcg cgaccctcag   1740
accctggaaa tcctggacat cactccatgc tcattcggag gtgtctccgt gatcacccct   1800
ggcaccaaca cttctaacca ggtcgctgtg ctgtaccagg acgtcaactg caccgaggtc   1860
cctgtggcca tccacgctga ccagctgacc cccacttggc gcgtgtactc caccggcagc   1920
aacgtgttcc agactcgtgc tggttgcctg atcggcgccg agcacgtgaa caacagctac   1980
gaatgcgaca tccccatcgg cgctggaatc tgcgcctctt accagaccca gactaacagc   2040
ccacgcaggg ctcgctctgt ggcctctcag tcaatcatcg cttacaccat gtcactgggc   2100
gctgaaaact ccgtggccta ctctaacaac tcaatcgcca tccccaccaa cttcactatc   2160
agcgtgacca ctgagatcct gccagtcagc atgaccaaga cttctgtgga ctgcactatg   2220
```

```
tacatctgcg gagacagcac cgaatgctct aacctgctgc tgcagtacgg ctctttctgc   2280

acccagctga accgtgctct gactggaatc gccgtggagc aggacaagaa cactcaggaa   2340

gtcttcgctc aggtgaagca aatctacaag accccaccta tcaaggactt cggcggattc   2400

aacttctccc agatcctgcc tgacccctcc aagccaagca agcgctcttt catcgaggac   2460

ctgctgttca acaaggtcac tctggccgac gctggattca tcaagcagta cggagactgc   2520

ctgggtgaca tcgccgctcg tgacctgatc tgcgctcaga agttcaacgg tctgaccgtg   2580

ctgcccccac tgctgactga cgaaatgatc gcccagtaca ctagcgccct gctggctgga   2640

accatcactt ctggttggac cttcggtgct ggcgccgctc tgcagatccc tttcgctatg   2700

cagatggcct accgtttcaa cggaatcggt gtcacccaga acgtgctgta cgagaaccag   2760

aagctgatcg ctaaccagtt caactcagcc atcggaaaga tccaggacag cctgagctct   2820

actgcctctg ctctgggcaa gctgcaggac gtcgtgaacc agaacgccca ggctctgaac   2880

accctggtca agcagctgtc atccaacttc ggtgctatca gctctgtgct gaacgacatc   2940

ctgtcccgcc tggacaaggt cgaggccgaa gtgcagatcg accgcctgat cactggccgt   3000

ctgcagtcac tgcagaccta cgtgactcag cagctgatca gggccgctga aatcagagcc   3060

tccgctaacc tggccgctac caagatgagc gagtgcgtcc tgggtcaatc taagcgtgtg   3120

gacttctgcg gcaagggata ccacctgatg tcattccctc agtctgctcc ccacggtgtg   3180

gtgttcctgc acgtcaccta cgtgccagcc caggagaaga acttcaccac tgcccctgct   3240

atctgccacg acggcaaggc tcacttcccc agggaaggtg tcttcgtgag caacggcacc   3300

cactggttcg tcactcagag aaacttctac gagccacaga tcatcaccac tgacaacact   3360

ttcgtgtctg gaaactgcga cgtggtcatc ggtatcgtca acaacaccgt gtacgacccc   3420

ctgcagccag agctggactc attcaaggag gaactggaca agtacttcaa gaaccacacc   3480

tcccctgacg tcgacctggg cgacatctca ggaatcaacg cttccgtcgt gaacatccag   3540

aaggagatcg accgcctgaa cgaagtggcc aagaacctga acgaaagcct gatcgacctg   3600

caggagctgg gcaagtacga acagtacatc aagtggcct                          3639
```

```
<210> SEQ ID NO 96
<211> LENGTH: 3822
<212> TYPE: DNA
<213> ORGANISM: Artificial Sequence
<220> FEATURE:
<223> OTHER INFORMATION: RECOMBINANT SPIKE PROTEIN

<400> SEQUENCE: 96
```

```
atgttcgtct tcctggtgct gctgcccctg gtgtccagcc agtgcgtgaa cctgaccact     60

aggactcagc tgcctcccgc ttacaccaac tcattcactc gcggtgtgta ctaccctgac    120

aaggtcttcc gttcttcagt gctgcactca actcaggacc tgttcctgcc cttcttctcc    180

aacgtcacct ggttccacgc catccacgtg tccggcacca acggcactaa gcgcttcgac    240

aacccagtgc tgcctttcaa cgacggtgtc tacttcgctt caaccgagaa gtccaacatc    300

atccgtggat ggatcttcgg caccactctg gacagcaaga ctcagtctct gctgatcgtc    360

aacaacgcca ccaacgtggt catcaaggtc tgcgaattcc agttctgcaa cgacccattc    420

ctgggcgtct actaccacaa gaacaacaag tcatggatgg agtccgaatt ccgcgtctac    480

tccagcgcta acaactgcac tttcgagtac gtgtcccagc ctttcctgat ggacctggaa    540

ggaaagcagg gtaacttcaa gaacctgagg gagttcgtgt tcaagaacat cgacggatac    600

ttcaagattt acagcaagca caccccaatc aacctggtgc gcgacctgcc tcagggtttc    660
```

-continued

```
tctgctctgg agccactggt ggacctgcct atcggcatca acatcacccg cttccagact    720
ctgctggctc tgcaccgttc ctacctgact ccaggcgact catcttctgg atggactgct    780
ggagctgctg cttactacgt gggctacctg cagcctcgca ccttcctgct gaagtacaac    840
gaaaacggaa ccatcactga cgccgtcgac tgcgctctgg accctctgtc agaaaccaag    900
tgcactctga agtccttcac cgtggagaag ggcatctacc agacttcaaa cttcagggtg    960
cagcccaccg aatccatcgt cagattccct aacatcacta acctgtgccc cttcggagag   1020
gtcttcaacg ccacccgctt cgcttccgtg tacgcctgga acaggaagag aatctcaaac   1080
tgcgtcgctg actactccgt gctgtacaac tcagcctcct tcagcacctt caagtgctac   1140
ggcgtgtcac caactaagct gaacgacctg tgcttcacca acgtctacgc cgactccttc   1200
gtgatcaggg gagacgaggt cagacagatc gctcctggcc agactggaaa gatcgccgac   1260
tacaactaca agctgcccga cgacttcacc ggttgcgtca tcgcttggaa cagcaacaac   1320
ctggactcta aagtgggtgg caactacaac tacctgtacc gcctgttccg taagtcaaac   1380
ctgaagccat tcgagaggga catcagcact gaaatctacc aggccggatc taccccttgc   1440
aacggtgtcg agggcttcaa ctgctacttc cccctgcagt cctacggttt ccagccaact   1500
aacggtgtgg gctaccagcc ttacagagtg gtcgtgctga gcttcgaact gctccacgct   1560
cctgctactg tgtgcggtcc aaagaagtct accaacctgg tcaagaacaa gtgcgtgaac   1620
ttcaacttca acggcctgac cggaactggt gtcctgaccg agagcaacaa gaagttcctg   1680
cccttccagc agttcggaag ggacatcgct gacaccactg acgctgtgcg cgaccctcag   1740
accctggaaa tcctggacat cactccatgc tcattcggag gtgtctccgt gatcacccct   1800
ggcaccaaca cttctaacca ggtcgctgtg ctgtaccagg acgtcaactg caccgaggtc   1860
cctgtggcca tccacgctga ccagctgacc cccacttggc gcgtgtactc caccggcagc   1920
aacgtgttcc agactcgtgc tggttgcctg atcggcgccg agcacgtgaa caacagctac   1980
gaatgcgaca tccccatcgg cgctggaatc tgcgcctctt accagaccca gactaacagc   2040
ccacagcagg ctcagtctgt ggcctctcag tcaatcatcg cttacaccat gtcactgggc   2100
gctgaaaact ccgtggccta ctctaacaac tcaatcgcca tccccaccaa cttcactatc   2160
agcgtgacca ctgagatcct gccagtcagc atgaccaaga cttctgtgga ctgcactatg   2220
tacatctgcg gagacagcac cgaatgctct aacctgctgc tgcagtacgg ctctttctgc   2280
acccagctga accgtgctct gactggaatc gccgtggagc aggacaagaa cactcaggaa   2340
gtcttcgctc aggtgaagca aatctacaag accccaccta tcaaggactt cggcggattc   2400
aacttctccc agatcctgcc tgacccctcc aagccaagca agcgctcttt catcgaggac   2460
ctgctgttca acaaggtcac tctggccgac gctggattca tcaagcagta cggagactgc   2520
ctgggtgaca tcgccgctcg tgacctgatc tgcgctcaga agttcaacgg tctgaccgtg   2580
ctgcccccac tgctgactga cgaaatgatc gcccagtaca ctagcgccct gctggctgga   2640
accatcactt ctggttggac cttcggtgct ggcgccgctc tgcagatccc tttcgctatg   2700
cagatggcct accgtttcaa cggaatcggt gtcacccaga acgtgctgta cgagaaccag   2760
aagctgatcg ctaaccagtt caactcagcc atcggaaaga tccaggacag cctgagctct   2820
actgcctctg ctctgggcaa gctgcaggac gtcgtgaacc agaacgccca ggctctgaac   2880
accctggtca agcagctgtc atccaacttc ggtgctatca gctctgtgct gaacgacatc   2940
ctgtcccgcc tggaccctcc cgaggccgaa gtgcagatcg accgcctgat cactggccgt   3000
```

```
ctgcagtcac tgcagaccta cgtgactcag cagctgatca gggccgctga aatcagagcc   3060

tccgctaacc tggccgctac caagatgagc gagtgcgtcc tgggtcaatc taagcgtgtg   3120

gacttctgcg gcaagggata ccacctgatg tcattccctc agtctgctcc ccacggtgtg   3180

gtgttcctgc acgtcaccta cgtgccagcc caggagaaga acttcaccac tgcccctgct   3240

atctgccacg acggcaaggc tcacttcccc agggaaggtg tcttcgtgag caacggcacc   3300

cactggttcg tcactcagag aaacttctac gagccacaga tcatcaccac tgacaacact   3360

ttcgtgtctg gaaactgcga cgtggtcatc ggtatcgtca acaacaccgt gtacgacccc   3420

ctgcagccag agctggactc attcaaggag gaactggaca agtacttcaa gaaccacacc   3480

tcccctgacg tcgacctggg cgacatctca ggaatcaacg cttccgtcgt gaacatccag   3540

aaggagatcg accgcctgaa cgaagtggcc aagaacctga acgaaagcct gatcgacctg   3600

caggagctgg gcaagtacga acagtacatc aagtggcctt ggtacatctg gctgggtttc   3660

atcgctggcc tcatcgctat cgtgatggtg accatcatgc tgtgctgcat gacttcatgc   3720

tgctcctgcc tgaagggctg ctgcagctgc ggatcttgct gcaagttcga cgaggacgac   3780

tctgaacccg tcctgaaggg cgtgaagctg cactacacct aa                      3822
```

<210> SEQ ID NO 97
<211> LENGTH: 4
<212> TYPE: PRT
<213> ORGANISM: Artificial Sequence
<220> FEATURE:
<223> OTHER INFORMATION: Recombinant Furin Cleavage Site

<400> SEQUENCE: 97

Gly Ser Ala Ser
1

<210> SEQ ID NO 98
<211> LENGTH: 8
<212> TYPE: PRT
<213> ORGANISM: Artificial Sequence
<220> FEATURE:
<223> OTHER INFORMATION: HRV3C Cleavage Site

<400> SEQUENCE: 98

Leu Glu Val Leu Phe Gln Gly Pro
1               5

<210> SEQ ID NO 99
<211> LENGTH: 8
<212> TYPE: PRT
<213> ORGANISM: Artificial Sequence
<220> FEATURE:
<223> OTHER INFORMATION: Strep-tag

<400> SEQUENCE: 99

Trp Ser His Pro Gln Phe Glu Lys
1               5

<210> SEQ ID NO 100
<211> LENGTH: 6
<212> TYPE: PRT
<213> ORGANISM: Artificial Sequence
<220> FEATURE:
<223> OTHER INFORMATION: 6X-His Tag

<400> SEQUENCE: 100

His His His His His His
1               5

<210> SEQ ID NO 101
<211> LENGTH: 10
<212> TYPE: PRT
<213> ORGANISM: Artificial Sequence
<220> FEATURE:
<223> OTHER INFORMATION: His-Tag
<220> FEATURE:
<221> NAME/KEY: MISC_FEATURE
<222> LOCATION: (6)..(6)
<223> OTHER INFORMATION: May be present or absent
<220> FEATURE:
<221> NAME/KEY: MISC_FEATURE
<222> LOCATION: (7)..(7)
<223> OTHER INFORMATION: May be present or absent
<220> FEATURE:
<221> NAME/KEY: MISC_FEATURE
<222> LOCATION: (8)..(8)
<223> OTHER INFORMATION: May be present or absent
<220> FEATURE:
<221> NAME/KEY: MISC_FEATURE
<222> LOCATION: (9)..(9)
<223> OTHER INFORMATION: May be present or absent
<220> FEATURE:
<221> NAME/KEY: MISC_FEATURE
<222> LOCATION: (10)..(10)
<223> OTHER INFORMATION: May be present or absent

<400> SEQUENCE: 101

```
His His His His His His His His His His
1               5                   10
```

<210> SEQ ID NO 102
<211> LENGTH: 8
<212> TYPE: PRT
<213> ORGANISM: Artificial Sequence
<220> FEATURE:
<223> OTHER INFORMATION: 8X-His Tag

<400> SEQUENCE: 102

```
His His His His His His His His
1               5
```

<210> SEQ ID NO 103
<211> LENGTH: 30
<212> TYPE: PRT
<213> ORGANISM: Artificial Sequence
<220> FEATURE:
<223> OTHER INFORMATION: FOLDON

<400> SEQUENCE: 103

```
Gly Tyr Ile Pro Glu Ala Pro Arg Asp Gly Gln Ala Tyr Val Arg Lys
1               5                   10                  15

Asp Gly Glu Trp Val Leu Leu Ser Thr Phe Leu Ser Pro Ala
            20                  25                  30
```

<210> SEQ ID NO 104
<211> LENGTH: 10
<212> TYPE: PRT
<213> ORGANISM: Artificial Sequence
<220> FEATURE:
<223> OTHER INFORMATION: RECOMBINANT SPIKE PROTEIN

<400> SEQUENCE: 104

```
Glu Asp Leu Leu Phe Asn Lys Val Thr Leu
1               5                   10
```

<210> SEQ ID NO 105
<211> LENGTH: 1263

```
<212> TYPE: PRT
<213> ORGANISM: Artificial Sequence
<220> FEATURE:
<223> OTHER INFORMATION: RECOMBINANT SPIKE PROTEIN

<400> SEQUENCE: 105

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380
```

```
Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Gln Gln Ala Gln Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
```

-continued

```
                805                 810                 815

Phe Ile Ala Asp Ala Gly Phe Ile Lys Gln Tyr Gly Asp Cys Leu Gly
            820                 825                 830

Asp Ile Ala Ala Arg Asp Leu Ile Cys Ala Gln Lys Phe Asn Gly Leu
        835                 840                 845

Thr Val Leu Pro Pro Leu Leu Thr Asp Glu Met Ile Ala Gln Tyr Thr
    850                 855                 860

Ser Ala Leu Leu Ala Gly Thr Ile Thr Ser Gly Trp Thr Phe Gly Ala
865                 870                 875                 880

Gly Ala Ala Leu Gln Ile Pro Phe Ala Met Gln Met Ala Tyr Arg Phe
                885                 890                 895

Asn Gly Ile Gly Val Thr Gln Asn Val Leu Tyr Glu Asn Gln Lys Leu
            900                 905                 910

Ile Ala Asn Gln Phe Asn Ser Ala Ile Gly Lys Ile Gln Asp Ser Leu
        915                 920                 925

Ser Ser Thr Ala Ser Ala Leu Gly Lys Leu Gln Asp Val Val Asn Gln
    930                 935                 940

Asn Ala Gln Ala Leu Asn Thr Leu Val Lys Gln Leu Ser Ser Asn Phe
945                 950                 955                 960

Gly Ala Ile Ser Ser Val Leu Asn Asp Ile Leu Ser Arg Leu Asp Pro
                965                 970                 975

Pro Glu Ala Glu Val Gln Ile Asp Arg Leu Ile Thr Gly Arg Leu Gln
            980                 985                 990

Ser Leu Gln Thr Tyr Val Thr Gln  Gln Leu Ile Arg Ala  Ala Glu Ile
        995                 1000                1005

Arg Ala  Ser Ala Asn Leu Ala  Ala Thr Lys Met Ser  Glu Cys Val
    1010                1015                1020

Leu Gly  Gln Ser Lys Arg Val  Asp Phe Cys Gly Lys  Gly Tyr His
    1025                1030                1035

Leu Met  Ser Phe Pro Gln Ser  Ala Pro His Gly Val  Val Phe Leu
    1040                1045                1050

His Val  Thr Tyr Val Pro Ala  Gln Glu Lys Asn Phe  Thr Thr Ala
    1055                1060                1065

Pro Ala  Ile Cys His Asp Gly  Lys Ala His Phe Pro  Arg Glu Gly
    1070                1075                1080

Val Phe  Val Ser Asn Gly Thr  His Trp Phe Val Thr  Gln Arg Asn
    1085                1090                1095

Phe Tyr  Glu Pro Gln Ile Ile  Thr Thr Asp Asn Thr  Phe Val Ser
    1100                1105                1110

Gly Asn  Cys Asp Val Val Ile  Gly Ile Val Asn Asn  Thr Val Tyr
    1115                1120                1125

Asp Pro  Leu Gln Pro Glu Leu  Asp Ser Phe Lys Glu  Glu Leu Asp
    1130                1135                1140

Lys Tyr  Phe Lys Asn His Thr  Ser Pro Asp Val Asp  Leu Gly Asp
    1145                1150                1155

Ile Ser  Gly Ile Asn Ala Ser  Val Val Asn Ile Gln  Lys Glu Ile
    1160                1165                1170

Asp Arg  Leu Asn Glu Val Ala  Lys Asn Leu Asn Glu  Ser Leu Ile
    1175                1180                1185

Asp Leu  Gln Glu Leu Gly Lys  Tyr Glu Gln Tyr Ile  Lys Trp Pro
    1190                1195                1200

Trp Tyr  Ile Trp Leu Gly Phe  Ile Ala Gly Leu Ile  Ala Ile Val
    1205                1210                1215
```

```
Met Val  Thr Ile Met Leu Cys  Cys Met Thr Ser Cys  Cys Ser Cys
    1220                 1225                 1230

Leu Lys  Gly Cys Cys Ser Cys  Gly Ser Cys Cys Lys  Phe Asp Glu
    1235                 1240                 1245

Asp Asp  Ser Glu Pro Val Leu  Lys Gly Val Lys Leu  His Tyr Thr
    1250                 1255                 1260


<210> SEQ ID NO 106
<211> LENGTH: 1250
<212> TYPE: PRT
<213> ORGANISM: Artificial Sequence
<220> FEATURE:
<223> OTHER INFORMATION: RECOMBINANT SPIKE PROTEIN

<400> SEQUENCE: 106

Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
            20                  25                  30

Ser Val Leu His Ser Thr Gln Asp Leu Phe Leu Pro Phe Phe Ser Asn
        35                  40                  45

Val Thr Trp Phe His Ala Ile His Val Ser Gly Thr Asn Gly Thr Lys
    50                  55                  60

Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                85                  90                  95

Leu Asp Ser Lys Thr Gln Ser Leu Leu Ile Val Asn Asn Ala Thr Asn
            100                 105                 110

Val Val Ile Lys Val Cys Glu Phe Gln Phe Cys Asn Asp Pro Phe Leu
        115                 120                 125

Gly Val Tyr Tyr His Lys Asn Asn Lys Ser Trp Met Glu Ser Glu Phe
    130                 135                 140

Arg Val Tyr Ser Ser Ala Asn Asn Cys Thr Phe Glu Tyr Val Ser Gln
145                 150                 155                 160

Pro Phe Leu Met Asp Leu Glu Gly Lys Gln Gly Asn Phe Lys Asn Leu
                165                 170                 175

Arg Glu Phe Val Phe Lys Asn Ile Asp Gly Tyr Phe Lys Ile Tyr Ser
            180                 185                 190

Lys His Thr Pro Ile Asn Leu Val Arg Asp Leu Pro Gln Gly Phe Ser
        195                 200                 205

Ala Leu Glu Pro Leu Val Asp Leu Pro Ile Gly Ile Asn Ile Thr Arg
    210                 215                 220

Phe Gln Thr Leu Leu Ala Leu His Arg Ser Tyr Leu Thr Pro Gly Asp
225                 230                 235                 240

Ser Ser Ser Gly Trp Thr Ala Gly Ala Ala Ala Tyr Tyr Val Gly Tyr
                245                 250                 255

Leu Gln Pro Arg Thr Phe Leu Leu Lys Tyr Asn Glu Asn Gly Thr Ile
            260                 265                 270

Thr Asp Ala Val Asp Cys Ala Leu Asp Pro Leu Ser Glu Thr Lys Cys
        275                 280                 285

Thr Leu Lys Ser Phe Thr Val Glu Lys Gly Ile Tyr Gln Thr Ser Asn
    290                 295                 300

Phe Arg Val Gln Pro Thr Glu Ser Ile Val Arg Phe Pro Asn Ile Thr
305                 310                 315                 320
```

Asn Leu Cys Pro Phe Gly Glu Val Phe Asn Ala Thr Arg Phe Ala Ser
325 330 335

Val Tyr Ala Trp Asn Arg Lys Arg Ile Ser Asn Cys Val Ala Asp Tyr
340 345 350

Ser Val Leu Tyr Asn Ser Ala Ser Phe Ser Thr Phe Lys Cys Tyr Gly
355 360 365

Val Ser Pro Thr Lys Leu Asn Asp Leu Cys Phe Thr Asn Val Tyr Ala
370 375 380

Asp Ser Phe Val Ile Arg Gly Asp Glu Val Arg Gln Ile Ala Pro Gly
385 390 395 400

Gln Thr Gly Lys Ile Ala Asp Tyr Asn Tyr Lys Leu Pro Asp Asp Phe
405 410 415

Thr Gly Cys Val Ile Ala Trp Asn Ser Asn Asn Leu Asp Ser Lys Val
420 425 430

Gly Gly Asn Tyr Asn Tyr Leu Tyr Arg Leu Phe Arg Lys Ser Asn Leu
435 440 445

Lys Pro Phe Glu Arg Asp Ile Ser Thr Glu Ile Tyr Gln Ala Gly Ser
450 455 460

Thr Pro Cys Asn Gly Val Glu Gly Phe Asn Cys Tyr Phe Pro Leu Gln
465 470 475 480

Ser Tyr Gly Phe Gln Pro Thr Asn Gly Val Gly Tyr Gln Pro Tyr Arg
485 490 495

Val Val Val Leu Ser Phe Glu Leu Leu His Ala Pro Ala Thr Val Cys
500 505 510

Gly Pro Lys Lys Ser Thr Asn Leu Val Lys Asn Lys Cys Val Asn Phe
515 520 525

Asn Phe Asn Gly Leu Thr Gly Thr Gly Val Leu Thr Glu Ser Asn Lys
530 535 540

Lys Phe Leu Pro Phe Gln Gln Phe Gly Arg Asp Ile Ala Asp Thr Thr
545 550 555 560

Asp Ala Val Arg Asp Pro Gln Thr Leu Glu Ile Leu Asp Ile Thr Pro
565 570 575

Cys Ser Phe Gly Gly Val Ser Val Ile Thr Pro Gly Thr Asn Thr Ser
580 585 590

Asn Gln Val Ala Val Leu Tyr Gln Asp Val Asn Cys Thr Glu Val Pro
595 600 605

Val Ala Ile His Ala Asp Gln Leu Thr Pro Thr Trp Arg Val Tyr Ser
610 615 620

Thr Gly Ser Asn Val Phe Gln Thr Arg Ala Gly Cys Leu Ile Gly Ala
625 630 635 640

Glu His Val Asn Asn Ser Tyr Glu Cys Asp Ile Pro Ile Gly Ala Gly
645 650 655

Ile Cys Ala Ser Tyr Gln Thr Gln Thr Asn Ser Pro Gln Gln Ala Gln
660 665 670

Ser Val Ala Ser Gln Ser Ile Ile Ala Tyr Thr Met Ser Leu Gly Ala
675 680 685

Glu Asn Ser Val Ala Tyr Ser Asn Asn Ser Ile Ala Ile Pro Thr Asn
690 695 700

Phe Thr Ile Ser Val Thr Thr Glu Ile Leu Pro Val Ser Met Thr Lys
705 710 715 720

Thr Ser Val Asp Cys Thr Met Tyr Ile Cys Gly Asp Ser Thr Glu Cys
725 730 735

-continued

```
Ser Asn Leu Leu Leu Gln Tyr Gly Ser Phe Cys Thr Gln Leu Asn Arg
            740                 745                 750

Ala Leu Thr Gly Ile Ala Val Glu Gln Asp Lys Asn Thr Gln Glu Val
        755                 760                 765

Phe Ala Gln Val Lys Gln Ile Tyr Lys Thr Pro Pro Ile Lys Asp Phe
    770                 775                 780

Gly Gly Phe Asn Phe Ser Gln Ile Leu Pro Asp Pro Ser Lys Pro Ser
785                 790                 795                 800

Lys Arg Ser Phe Ile Ala Asp Ala Gly Phe Ile Lys Gln Tyr Gly Asp
                805                 810                 815

Cys Leu Gly Asp Ile Ala Ala Arg Asp Leu Ile Cys Ala Gln Lys Phe
            820                 825                 830

Asn Gly Leu Thr Val Leu Pro Pro Leu Leu Thr Asp Glu Met Ile Ala
        835                 840                 845

Gln Tyr Thr Ser Ala Leu Leu Ala Gly Thr Ile Thr Ser Gly Trp Thr
    850                 855                 860

Phe Gly Ala Gly Ala Ala Leu Gln Ile Pro Phe Ala Met Gln Met Ala
865                 870                 875                 880

Tyr Arg Phe Asn Gly Ile Gly Val Thr Gln Asn Val Leu Tyr Glu Asn
                885                 890                 895

Gln Lys Leu Ile Ala Asn Gln Phe Asn Ser Ala Ile Gly Lys Ile Gln
            900                 905                 910

Asp Ser Leu Ser Ser Thr Ala Ser Ala Leu Gly Lys Leu Gln Asp Val
        915                 920                 925

Val Asn Gln Asn Ala Gln Ala Leu Asn Thr Leu Val Lys Gln Leu Ser
    930                 935                 940

Ser Asn Phe Gly Ala Ile Ser Ser Val Leu Asn Asp Ile Leu Ser Arg
945                 950                 955                 960

Leu Asp Pro Pro Glu Ala Glu Val Gln Ile Asp Arg Leu Ile Thr Gly
                965                 970                 975

Arg Leu Gln Ser Leu Gln Thr Tyr Val Thr Gln Gln Leu Ile Arg Ala
            980                 985                 990

Ala Glu Ile Arg Ala Ser Ala Asn  Leu Ala Ala Thr Lys  Met Ser Glu
        995                 1000                1005

Cys Val  Leu Gly Gln Ser Lys  Arg Val Asp Phe Cys  Gly Lys Gly
    1010                1015                1020

Tyr His  Leu Met Ser Phe Pro  Gln Ser Ala Pro His  Gly Val Val
    1025                1030                1035

Phe Leu  His Val Thr Tyr Val  Pro Ala Gln Glu Lys  Asn Phe Thr
    1040                1045                1050

Thr Ala  Pro Ala Ile Cys His  Asp Gly Lys Ala His  Phe Pro Arg
    1055                1060                1065

Glu Gly  Val Phe Val Ser Asn  Gly Thr His Trp Phe  Val Thr Gln
    1070                1075                1080

Arg Asn  Phe Tyr Glu Pro Gln  Ile Ile Thr Thr Asp  Asn Thr Phe
    1085                1090                1095

Val Ser  Gly Asn Cys Asp Val  Val Ile Gly Ile Val  Asn Asn Thr
    1100                1105                1110

Val Tyr  Asp Pro Leu Gln Pro  Glu Leu Asp Ser Phe  Lys Glu Glu
    1115                1120                1125

Leu Asp  Lys Tyr Phe Lys Asn  His Thr Ser Pro Asp  Val Asp Leu
    1130                1135                1140

Gly Asp  Ile Ser Gly Ile Asn  Ala Ser Val Val Asn  Ile Gln Lys
```

```
    1145                1150                1155

Glu Ile  Asp Arg Leu Asn Glu  Val Ala Lys Asn Leu  Asn Glu Ser
    1160                1165                1170

Leu Ile  Asp Leu Gln Glu Leu  Gly Lys Tyr Glu Gln  Tyr Ile Lys
    1175                1180                1185

Trp Pro  Trp Tyr Ile Trp Leu  Gly Phe Ile Ala Gly  Leu Ile Ala
    1190                1195                1200

Ile Val  Met Val Thr Ile Met  Leu Cys Cys Met Thr  Ser Cys Cys
    1205                1210                1215

Ser Cys  Leu Lys Gly Cys Cys  Ser Cys Gly Ser Cys  Cys Lys Phe
    1220                1225                1230

Asp Glu  Asp Asp Ser Glu Pro  Val Leu Lys Gly Val  Lys Leu His
    1235                1240                1245

Tyr Thr
    1250


<210> SEQ ID NO 107
<211> LENGTH: 1263
<212> TYPE: PRT
<213> ORGANISM: Artificial Sequence
<220> FEATURE:
<223> OTHER INFORMATION: RECOMBINANT SPIKE PROTEIN

<400> SEQUENCE: 107

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
```

```
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670
```

```
Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Ala Asp Ala Gly Phe Ile Lys Gln Tyr Gly Asp Cys Leu Gly
            820                 825                 830

Asp Ile Ala Ala Arg Asp Leu Ile Cys Ala Gln Lys Phe Asn Gly Leu
        835                 840                 845

Thr Val Leu Pro Pro Leu Leu Thr Asp Glu Met Ile Ala Gln Tyr Thr
    850                 855                 860

Ser Ala Leu Leu Ala Gly Thr Ile Thr Ser Gly Trp Thr Phe Gly Ala
865                 870                 875                 880

Gly Ala Ala Leu Gln Ile Pro Phe Ala Met Gln Met Ala Tyr Arg Phe
                885                 890                 895

Asn Gly Ile Gly Val Thr Gln Asn Val Leu Tyr Glu Asn Gln Lys Leu
            900                 905                 910

Ile Ala Asn Gln Phe Asn Ser Ala Ile Gly Lys Ile Gln Asp Ser Leu
        915                 920                 925

Ser Ser Thr Ala Ser Ala Leu Gly Lys Leu Gln Asp Val Val Asn Gln
    930                 935                 940

Asn Ala Gln Ala Leu Asn Thr Leu Val Lys Gln Leu Ser Ser Asn Phe
945                 950                 955                 960

Gly Ala Ile Ser Ser Val Leu Asn Asp Ile Leu Ser Arg Leu Asp Lys
                965                 970                 975

Val Glu Ala Glu Val Gln Ile Asp Arg Leu Ile Thr Gly Arg Leu Gln
            980                 985                 990

Ser Leu Gln Thr Tyr Val Thr Gln  Gln Leu Ile Arg Ala  Ala Glu Ile
        995                 1000                 1005

Arg Ala  Ser Ala Asn Leu Ala  Ala Thr Lys Met Ser  Glu Cys Val
    1010                 1015                 1020

Leu Gly  Gln Ser Lys Arg Val  Asp Phe Cys Gly Lys  Gly Tyr His
    1025                 1030                 1035

Leu Met  Ser Phe Pro Gln Ser  Ala Pro His Gly Val  Val Phe Leu
    1040                 1045                 1050

His Val  Thr Tyr Val Pro Ala  Gln Glu Lys Asn Phe  Thr Thr Ala
    1055                 1060                 1065

Pro Ala  Ile Cys His Asp Gly  Lys Ala His Phe Pro  Arg Glu Gly
    1070                 1075                 1080
```

-continued

```
Val Phe  Val Ser Asn Gly Thr  His Trp Phe Val Thr  Gln Arg Asn
    1085                 1090                 1095

Phe Tyr  Glu Pro Gln Ile Ile  Thr Thr Asp Asn Thr  Phe Val Ser
    1100                 1105                 1110

Gly Asn  Cys Asp Val Val Ile  Gly Ile Val Asn Asn  Thr Val Tyr
    1115                 1120                 1125

Asp Pro  Leu Gln Pro Glu Leu  Asp Ser Phe Lys Glu  Glu Leu Asp
    1130                 1135                 1140

Lys Tyr  Phe Lys Asn His Thr  Ser Pro Asp Val Asp  Leu Gly Asp
    1145                 1150                 1155

Ile Ser  Gly Ile Asn Ala Ser  Val Val Asn Ile Gln  Lys Glu Ile
    1160                 1165                 1170

Asp Arg  Leu Asn Glu Val Ala  Lys Asn Leu Asn Glu  Ser Leu Ile
    1175                 1180                 1185

Asp Leu  Gln Glu Leu Gly Lys  Tyr Glu Gln Tyr Ile  Lys Trp Pro
    1190                 1195                 1200

Trp Tyr  Ile Trp Leu Gly Phe  Ile Ala Gly Leu Ile  Ala Ile Val
    1205                 1210                 1215

Met Val  Thr Ile Met Leu Cys  Cys Met Thr Ser Cys  Cys Ser Cys
    1220                 1225                 1230

Leu Lys  Gly Cys Cys Ser Cys  Gly Ser Cys Cys Lys  Phe Asp Glu
    1235                 1240                 1245

Asp Asp  Ser Glu Pro Val Leu  Lys Gly Val Lys Leu  His Tyr Thr
    1250                 1255                 1260


<210> SEQ ID NO 108
<211> LENGTH: 1250
<212> TYPE: PRT
<213> ORGANISM: Artificial Sequence
<220> FEATURE:
<223> OTHER INFORMATION: RECOMBINANT SPIKE PROTEIN

<400> SEQUENCE: 108

Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
            20                  25                  30

Ser Val Leu His Ser Thr Gln Asp Leu Phe Leu Pro Phe Phe Ser Asn
        35                  40                  45

Val Thr Trp Phe His Ala Ile His Val Ser Gly Thr Asn Gly Thr Lys
    50                  55                  60

Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                85                  90                  95

Leu Asp Ser Lys Thr Gln Ser Leu Leu Ile Val Asn Asn Ala Thr Asn
            100                 105                 110

Val Val Ile Lys Val Cys Glu Phe Gln Phe Cys Asn Asp Pro Phe Leu
        115                 120                 125

Gly Val Tyr Tyr His Lys Asn Asn Lys Ser Trp Met Glu Ser Glu Phe
    130                 135                 140

Arg Val Tyr Ser Ser Ala Asn Asn Cys Thr Phe Glu Tyr Val Ser Gln
145                 150                 155                 160

Pro Phe Leu Met Asp Leu Glu Gly Lys Gln Gly Asn Phe Lys Asn Leu
                165                 170                 175
```

```
Arg Glu Phe Val Phe Lys Asn Ile Asp Gly Tyr Phe Lys Ile Tyr Ser
            180                 185                 190

Lys His Thr Pro Ile Asn Leu Val Arg Asp Leu Pro Gln Gly Phe Ser
        195                 200                 205

Ala Leu Glu Pro Leu Val Asp Leu Pro Ile Gly Ile Asn Ile Thr Arg
    210                 215                 220

Phe Gln Thr Leu Leu Ala Leu His Arg Ser Tyr Leu Thr Pro Gly Asp
225                 230                 235                 240

Ser Ser Ser Gly Trp Thr Ala Gly Ala Ala Ala Tyr Tyr Val Gly Tyr
                245                 250                 255

Leu Gln Pro Arg Thr Phe Leu Leu Lys Tyr Asn Glu Asn Gly Thr Ile
            260                 265                 270

Thr Asp Ala Val Asp Cys Ala Leu Asp Pro Leu Ser Glu Thr Lys Cys
        275                 280                 285

Thr Leu Lys Ser Phe Thr Val Glu Lys Gly Ile Tyr Gln Thr Ser Asn
    290                 295                 300

Phe Arg Val Gln Pro Thr Glu Ser Ile Val Arg Phe Pro Asn Ile Thr
305                 310                 315                 320

Asn Leu Cys Pro Phe Gly Glu Val Phe Asn Ala Thr Arg Phe Ala Ser
                325                 330                 335

Val Tyr Ala Trp Asn Arg Lys Arg Ile Ser Asn Cys Val Ala Asp Tyr
            340                 345                 350

Ser Val Leu Tyr Asn Ser Ala Ser Phe Ser Thr Phe Lys Cys Tyr Gly
        355                 360                 365

Val Ser Pro Thr Lys Leu Asn Asp Leu Cys Phe Thr Asn Val Tyr Ala
    370                 375                 380

Asp Ser Phe Val Ile Arg Gly Asp Glu Val Arg Gln Ile Ala Pro Gly
385                 390                 395                 400

Gln Thr Gly Lys Ile Ala Asp Tyr Asn Tyr Lys Leu Pro Asp Asp Phe
                405                 410                 415

Thr Gly Cys Val Ile Ala Trp Asn Ser Asn Asn Leu Asp Ser Lys Val
            420                 425                 430

Gly Gly Asn Tyr Asn Tyr Leu Tyr Arg Leu Phe Arg Lys Ser Asn Leu
        435                 440                 445

Lys Pro Phe Glu Arg Asp Ile Ser Thr Glu Ile Tyr Gln Ala Gly Ser
    450                 455                 460

Thr Pro Cys Asn Gly Val Glu Gly Phe Asn Cys Tyr Phe Pro Leu Gln
465                 470                 475                 480

Ser Tyr Gly Phe Gln Pro Thr Asn Gly Val Gly Tyr Gln Pro Tyr Arg
                485                 490                 495

Val Val Val Leu Ser Phe Glu Leu Leu His Ala Pro Ala Thr Val Cys
            500                 505                 510

Gly Pro Lys Lys Ser Thr Asn Leu Val Lys Asn Lys Cys Val Asn Phe
        515                 520                 525

Asn Phe Asn Gly Leu Thr Gly Thr Gly Val Leu Thr Glu Ser Asn Lys
    530                 535                 540

Lys Phe Leu Pro Phe Gln Gln Phe Gly Arg Asp Ile Ala Asp Thr Thr
545                 550                 555                 560

Asp Ala Val Arg Asp Pro Gln Thr Leu Glu Ile Leu Asp Ile Thr Pro
                565                 570                 575

Cys Ser Phe Gly Gly Val Ser Val Ile Thr Pro Gly Thr Asn Thr Ser
            580                 585                 590

Asn Gln Val Ala Val Leu Tyr Gln Asp Val Asn Cys Thr Glu Val Pro
```

-continued

```
        595                 600                 605

Val Ala Ile His Ala Asp Gln Leu Thr Pro Thr Trp Arg Val Tyr Ser
    610                 615                 620

Thr Gly Ser Asn Val Phe Gln Thr Arg Ala Gly Cys Leu Ile Gly Ala
625                 630                 635                 640

Glu His Val Asn Asn Ser Tyr Glu Cys Asp Ile Pro Ile Gly Ala Gly
                645                 650                 655

Ile Cys Ala Ser Tyr Gln Thr Gln Thr Asn Ser Pro Arg Arg Ala Arg
            660                 665                 670

Ser Val Ala Ser Gln Ser Ile Ile Ala Tyr Thr Met Ser Leu Gly Ala
        675                 680                 685

Glu Asn Ser Val Ala Tyr Ser Asn Asn Ser Ile Ala Ile Pro Thr Asn
    690                 695                 700

Phe Thr Ile Ser Val Thr Thr Glu Ile Leu Pro Val Ser Met Thr Lys
705                 710                 715                 720

Thr Ser Val Asp Cys Thr Met Tyr Ile Cys Gly Asp Ser Thr Glu Cys
                725                 730                 735

Ser Asn Leu Leu Leu Gln Tyr Gly Ser Phe Cys Thr Gln Leu Asn Arg
            740                 745                 750

Ala Leu Thr Gly Ile Ala Val Glu Gln Asp Lys Asn Thr Gln Glu Val
        755                 760                 765

Phe Ala Gln Val Lys Gln Ile Tyr Lys Thr Pro Pro Ile Lys Asp Phe
    770                 775                 780

Gly Gly Phe Asn Phe Ser Gln Ile Leu Pro Asp Pro Ser Lys Pro Ser
785                 790                 795                 800

Lys Arg Ser Phe Ile Ala Asp Ala Gly Phe Ile Lys Gln Tyr Gly Asp
                805                 810                 815

Cys Leu Gly Asp Ile Ala Ala Arg Asp Leu Ile Cys Ala Gln Lys Phe
            820                 825                 830

Asn Gly Leu Thr Val Leu Pro Pro Leu Leu Thr Asp Glu Met Ile Ala
        835                 840                 845

Gln Tyr Thr Ser Ala Leu Leu Ala Gly Thr Ile Thr Ser Gly Trp Thr
    850                 855                 860

Phe Gly Ala Gly Ala Ala Leu Gln Ile Pro Phe Ala Met Gln Met Ala
865                 870                 875                 880

Tyr Arg Phe Asn Gly Ile Gly Val Thr Gln Asn Val Leu Tyr Glu Asn
                885                 890                 895

Gln Lys Leu Ile Ala Asn Gln Phe Asn Ser Ala Ile Gly Lys Ile Gln
            900                 905                 910

Asp Ser Leu Ser Ser Thr Ala Ser Ala Leu Gly Lys Leu Gln Asp Val
        915                 920                 925

Val Asn Gln Asn Ala Gln Ala Leu Asn Thr Leu Val Lys Gln Leu Ser
    930                 935                 940

Ser Asn Phe Gly Ala Ile Ser Ser Val Leu Asn Asp Ile Leu Ser Arg
945                 950                 955                 960

Leu Asp Lys Val Glu Ala Glu Val Gln Ile Asp Arg Leu Ile Thr Gly
                965                 970                 975

Arg Leu Gln Ser Leu Gln Thr Tyr Val Thr Gln Gln Leu Ile Arg Ala
            980                 985                 990

Ala Glu Ile Arg Ala Ser Ala Asn  Leu Ala Ala Thr Lys  Met Ser Glu
        995                 1000                 1005

Cys Val  Leu Gly Gln Ser Lys  Arg Val Asp Phe Cys  Gly Lys Gly
    1010                 1015                 1020
```

Tyr His Leu Met Ser Phe Pro Gln Ser Ala Pro His Gly Val Val
1025 1030 1035

Phe Leu His Val Thr Tyr Val Pro Ala Gln Glu Lys Asn Phe Thr
1040 1045 1050

Thr Ala Pro Ala Ile Cys His Asp Gly Lys Ala His Phe Pro Arg
1055 1060 1065

Glu Gly Val Phe Val Ser Asn Gly Thr His Trp Phe Val Thr Gln
1070 1075 1080

Arg Asn Phe Tyr Glu Pro Gln Ile Ile Thr Thr Asp Asn Thr Phe
1085 1090 1095

Val Ser Gly Asn Cys Asp Val Val Ile Gly Ile Val Asn Asn Thr
1100 1105 1110

Val Tyr Asp Pro Leu Gln Pro Glu Leu Asp Ser Phe Lys Glu Glu
1115 1120 1125

Leu Asp Lys Tyr Phe Lys Asn His Thr Ser Pro Asp Val Asp Leu
1130 1135 1140

Gly Asp Ile Ser Gly Ile Asn Ala Ser Val Val Asn Ile Gln Lys
1145 1150 1155

Glu Ile Asp Arg Leu Asn Glu Val Ala Lys Asn Leu Asn Glu Ser
1160 1165 1170

Leu Ile Asp Leu Gln Glu Leu Gly Lys Tyr Glu Gln Tyr Ile Lys
1175 1180 1185

Trp Pro Trp Tyr Ile Trp Leu Gly Phe Ile Ala Gly Leu Ile Ala
1190 1195 1200

Ile Val Met Val Thr Ile Met Leu Cys Cys Met Thr Ser Cys Cys
1205 1210 1215

Ser Cys Leu Lys Gly Cys Cys Ser Cys Gly Ser Cys Cys Lys Phe
1220 1225 1230

Asp Glu Asp Asp Ser Glu Pro Val Leu Lys Gly Val Lys Leu His
1235 1240 1245

Tyr Thr
1250

<210> SEQ ID NO 109
<211> LENGTH: 1273
<212> TYPE: PRT
<213> ORGANISM: Artificial Sequence
<220> FEATURE:
<223> OTHER INFORMATION: Recombinant CoV S polypeptide

<400> SEQUENCE: 109

Met Phe Val Phe Leu Val Leu Leu Pro Leu Val Ser Ser Gln Cys Val
1 5 10 15

Asn Leu Thr Thr Arg Thr Gln Leu Pro Pro Ala Tyr Thr Asn Ser Phe
20 25 30

Thr Arg Gly Val Tyr Tyr Pro Asp Lys Val Phe Arg Ser Ser Val Leu
35 40 45

His Ser Thr Gln Asp Leu Phe Leu Pro Phe Phe Ser Asn Val Thr Trp
50 55 60

Phe His Ala Ile His Val Ser Gly Thr Asn Gly Thr Lys Arg Phe Asp
65 70 75 80

Asn Pro Val Leu Pro Phe Asn Asp Gly Val Tyr Phe Ala Ser Thr Glu
85 90 95

Lys Ser Asn Ile Ile Arg Gly Trp Ile Phe Gly Thr Thr Leu Asp Ser
100 105 110

```
Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525
```

-continued

```
Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Gly Ser Ala Ser Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
```

945 950 955 960

Thr Leu Val Lys Gln Leu Ser Ser Asn Phe Gly Ala Ile Ser Ser Val
965 970 975

Leu Asn Asp Ile Leu Ser Arg Leu Asp Pro Pro Glu Ala Glu Val Gln
980 985 990

Ile Asp Arg Leu Ile Thr Gly Arg Leu Gln Ser Leu Gln Thr Tyr Val
995 1000 1005

Thr Gln Gln Leu Ile Arg Ala Ala Glu Ile Arg Ala Ser Ala Asn
1010 1015 1020

Leu Ala Ala Thr Lys Met Ser Glu Cys Val Leu Gly Gln Ser Lys
1025 1030 1035

Arg Val Asp Phe Cys Gly Lys Gly Tyr His Leu Met Ser Phe Pro
1040 1045 1050

Gln Ser Ala Pro His Gly Val Val Phe Leu His Val Thr Tyr Val
1055 1060 1065

Pro Ala Gln Glu Lys Asn Phe Thr Thr Ala Pro Ala Ile Cys His
1070 1075 1080

Asp Gly Lys Ala His Phe Pro Arg Glu Gly Val Phe Val Ser Asn
1085 1090 1095

Gly Thr His Trp Phe Val Thr Gln Arg Asn Phe Tyr Glu Pro Gln
1100 1105 1110

Ile Ile Thr Thr Asp Asn Thr Phe Val Ser Gly Asn Cys Asp Val
1115 1120 1125

Val Ile Gly Ile Val Asn Asn Thr Val Tyr Asp Pro Leu Gln Pro
1130 1135 1140

Glu Leu Asp Ser Phe Lys Glu Glu Leu Asp Lys Tyr Phe Lys Asn
1145 1150 1155

His Thr Ser Pro Asp Val Asp Leu Gly Asp Ile Ser Gly Ile Asn
1160 1165 1170

Ala Ser Val Val Asn Ile Gln Lys Glu Ile Asp Arg Leu Asn Glu
1175 1180 1185

Val Ala Lys Asn Leu Asn Glu Ser Leu Ile Asp Leu Gln Glu Leu
1190 1195 1200

Gly Lys Tyr Glu Gln Tyr Ile Lys Trp Pro Trp Tyr Ile Trp Leu
1205 1210 1215

Gly Phe Ile Ala Gly Leu Ile Ala Ile Val Met Val Thr Ile Met
1220 1225 1230

Leu Cys Cys Met Thr Ser Cys Cys Ser Cys Leu Lys Gly Cys Cys
1235 1240 1245

Ser Cys Gly Ser Cys Cys Lys Phe Asp Glu Asp Asp Ser Glu Pro
1250 1255 1260

Val Leu Lys Gly Val Lys Leu His Tyr Thr
1265 1270

<210> SEQ ID NO 110
<211> LENGTH: 1260
<212> TYPE: PRT
<213> ORGANISM: Artificial Sequence
<220> FEATURE:
<223> OTHER INFORMATION: Recombinant CoV S polypeptide

<400> SEQUENCE: 110

Gln Cys Val Asn Leu Thr Thr Arg Thr Gln Leu Pro Pro Ala Tyr Thr
1 5 10 15

Asn Ser Phe Thr Arg Gly Val Tyr Tyr Pro Asp Lys Val Phe Arg Ser

```
            20                  25                  30

Ser Val Leu His Ser Thr Gln Asp Leu Phe Leu Pro Phe Phe Ser Asn
        35                  40                  45

Val Thr Trp Phe His Ala Ile His Val Ser Gly Thr Asn Gly Thr Lys
    50                  55                  60

Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                85                  90                  95

Leu Asp Ser Lys Thr Gln Ser Leu Leu Ile Val Asn Asn Ala Thr Asn
            100                 105                 110

Val Val Ile Lys Val Cys Glu Phe Gln Phe Cys Asn Asp Pro Phe Leu
        115                 120                 125

Gly Val Tyr Tyr His Lys Asn Asn Lys Ser Trp Met Glu Ser Glu Phe
    130                 135                 140

Arg Val Tyr Ser Ser Ala Asn Asn Cys Thr Phe Glu Tyr Val Ser Gln
145                 150                 155                 160

Pro Phe Leu Met Asp Leu Glu Gly Lys Gln Gly Asn Phe Lys Asn Leu
                165                 170                 175

Arg Glu Phe Val Phe Lys Asn Ile Asp Gly Tyr Phe Lys Ile Tyr Ser
            180                 185                 190

Lys His Thr Pro Ile Asn Leu Val Arg Asp Leu Pro Gln Gly Phe Ser
        195                 200                 205

Ala Leu Glu Pro Leu Val Asp Leu Pro Ile Gly Ile Asn Ile Thr Arg
    210                 215                 220

Phe Gln Thr Leu Leu Ala Leu His Arg Ser Tyr Leu Thr Pro Gly Asp
225                 230                 235                 240

Ser Ser Ser Gly Trp Thr Ala Gly Ala Ala Ala Tyr Tyr Val Gly Tyr
                245                 250                 255

Leu Gln Pro Arg Thr Phe Leu Leu Lys Tyr Asn Glu Asn Gly Thr Ile
            260                 265                 270

Thr Asp Ala Val Asp Cys Ala Leu Asp Pro Leu Ser Glu Thr Lys Cys
        275                 280                 285

Thr Leu Lys Ser Phe Thr Val Glu Lys Gly Ile Tyr Gln Thr Ser Asn
    290                 295                 300

Phe Arg Val Gln Pro Thr Glu Ser Ile Val Arg Phe Pro Asn Ile Thr
305                 310                 315                 320

Asn Leu Cys Pro Phe Gly Glu Val Phe Asn Ala Thr Arg Phe Ala Ser
                325                 330                 335

Val Tyr Ala Trp Asn Arg Lys Arg Ile Ser Asn Cys Val Ala Asp Tyr
            340                 345                 350

Ser Val Leu Tyr Asn Ser Ala Ser Phe Ser Thr Phe Lys Cys Tyr Gly
        355                 360                 365

Val Ser Pro Thr Lys Leu Asn Asp Leu Cys Phe Thr Asn Val Tyr Ala
    370                 375                 380

Asp Ser Phe Val Ile Arg Gly Asp Glu Val Arg Gln Ile Ala Pro Gly
385                 390                 395                 400

Gln Thr Gly Lys Ile Ala Asp Tyr Asn Tyr Lys Leu Pro Asp Asp Phe
                405                 410                 415

Thr Gly Cys Val Ile Ala Trp Asn Ser Asn Asn Leu Asp Ser Lys Val
            420                 425                 430

Gly Gly Asn Tyr Asn Tyr Leu Tyr Arg Leu Phe Arg Lys Ser Asn Leu
        435                 440                 445
```

-continued

```
Lys Pro Phe Glu Arg Asp Ile Ser Thr Glu Ile Tyr Gln Ala Gly Ser
    450                 455                 460

Thr Pro Cys Asn Gly Val Glu Gly Phe Asn Cys Tyr Phe Pro Leu Gln
465                 470                 475                 480

Ser Tyr Gly Phe Gln Pro Thr Asn Gly Val Gly Tyr Gln Pro Tyr Arg
                485                 490                 495

Val Val Val Leu Ser Phe Glu Leu Leu His Ala Pro Ala Thr Val Cys
            500                 505                 510

Gly Pro Lys Lys Ser Thr Asn Leu Val Lys Asn Lys Cys Val Asn Phe
        515                 520                 525

Asn Phe Asn Gly Leu Thr Gly Thr Gly Val Leu Thr Glu Ser Asn Lys
    530                 535                 540

Lys Phe Leu Pro Phe Gln Gln Phe Gly Arg Asp Ile Ala Asp Thr Thr
545                 550                 555                 560

Asp Ala Val Arg Asp Pro Gln Thr Leu Glu Ile Leu Asp Ile Thr Pro
                565                 570                 575

Cys Ser Phe Gly Gly Val Ser Val Ile Thr Pro Gly Thr Asn Thr Ser
            580                 585                 590

Asn Gln Val Ala Val Leu Tyr Gln Asp Val Asn Cys Thr Glu Val Pro
        595                 600                 605

Val Ala Ile His Ala Asp Gln Leu Thr Pro Thr Trp Arg Val Tyr Ser
    610                 615                 620

Thr Gly Ser Asn Val Phe Gln Thr Arg Ala Gly Cys Leu Ile Gly Ala
625                 630                 635                 640

Glu His Val Asn Asn Ser Tyr Glu Cys Asp Ile Pro Ile Gly Ala Gly
                645                 650                 655

Ile Cys Ala Ser Tyr Gln Thr Gln Thr Asn Ser Pro Gly Ser Ala Ser
            660                 665                 670

Ser Val Ala Ser Gln Ser Ile Ile Ala Tyr Thr Met Ser Leu Gly Ala
        675                 680                 685

Glu Asn Ser Val Ala Tyr Ser Asn Asn Ser Ile Ala Ile Pro Thr Asn
    690                 695                 700

Phe Thr Ile Ser Val Thr Thr Glu Ile Leu Pro Val Ser Met Thr Lys
705                 710                 715                 720

Thr Ser Val Asp Cys Thr Met Tyr Ile Cys Gly Asp Ser Thr Glu Cys
                725                 730                 735

Ser Asn Leu Leu Leu Gln Tyr Gly Ser Phe Cys Thr Gln Leu Asn Arg
            740                 745                 750

Ala Leu Thr Gly Ile Ala Val Glu Gln Asp Lys Asn Thr Gln Glu Val
        755                 760                 765

Phe Ala Gln Val Lys Gln Ile Tyr Lys Thr Pro Pro Ile Lys Asp Phe
    770                 775                 780

Gly Gly Phe Asn Phe Ser Gln Ile Leu Pro Asp Pro Ser Lys Pro Ser
785                 790                 795                 800

Lys Arg Ser Phe Ile Glu Asp Leu Leu Phe Asn Lys Val Thr Leu Ala
                805                 810                 815

Asp Ala Gly Phe Ile Lys Gln Tyr Gly Asp Cys Leu Gly Asp Ile Ala
            820                 825                 830

Ala Arg Asp Leu Ile Cys Ala Gln Lys Phe Asn Gly Leu Thr Val Leu
        835                 840                 845

Pro Pro Leu Leu Thr Asp Glu Met Ile Ala Gln Tyr Thr Ser Ala Leu
    850                 855                 860
```

```
Leu Ala Gly Thr Ile Thr Ser Gly Trp Thr Phe Gly Ala Gly Ala Ala
865                 870                 875                 880

Leu Gln Ile Pro Phe Ala Met Gln Met Ala Tyr Arg Phe Asn Gly Ile
                885                 890                 895

Gly Val Thr Gln Asn Val Leu Tyr Glu Asn Gln Lys Leu Ile Ala Asn
            900                 905                 910

Gln Phe Asn Ser Ala Ile Gly Lys Ile Gln Asp Ser Leu Ser Ser Thr
        915                 920                 925

Ala Ser Ala Leu Gly Lys Leu Gln Asp Val Val Asn Gln Asn Ala Gln
    930                 935                 940

Ala Leu Asn Thr Leu Val Lys Gln Leu Ser Ser Asn Phe Gly Ala Ile
945                 950                 955                 960

Ser Ser Val Leu Asn Asp Ile Leu Ser Arg Leu Asp Pro Pro Glu Ala
                965                 970                 975

Glu Val Gln Ile Asp Arg Leu Ile Thr Gly Arg Leu Gln Ser Leu Gln
            980                 985                 990

Thr Tyr Val Thr Gln Gln Leu Ile  Arg Ala Ala Glu Ile  Arg Ala Ser
        995                 1000                1005

Ala Asn  Leu Ala Ala Thr Lys  Met Ser Glu Cys Val  Leu Gly Gln
    1010                1015                1020

Ser Lys  Arg Val Asp Phe Cys  Gly Lys Gly Tyr His  Leu Met Ser
    1025                1030                1035

Phe Pro  Gln Ser Ala Pro His  Gly Val Val Phe Leu  His Val Thr
    1040                1045                1050

Tyr Val  Pro Ala Gln Glu Lys  Asn Phe Thr Thr Ala  Pro Ala Ile
    1055                1060                1065

Cys His  Asp Gly Lys Ala His  Phe Pro Arg Glu Gly  Val Phe Val
    1070                1075                1080

Ser Asn  Gly Thr His Trp Phe  Val Thr Gln Arg Asn  Phe Tyr Glu
    1085                1090                1095

Pro Gln  Ile Ile Thr Thr Asp  Asn Thr Phe Val Ser  Gly Asn Cys
    1100                1105                1110

Asp Val  Val Ile Gly Ile Val  Asn Asn Thr Val Tyr  Asp Pro Leu
    1115                1120                1125

Gln Pro  Glu Leu Asp Ser Phe  Lys Glu Glu Leu Asp  Lys Tyr Phe
    1130                1135                1140

Lys Asn  His Thr Ser Pro Asp  Val Asp Leu Gly Asp  Ile Ser Gly
    1145                1150                1155

Ile Asn  Ala Ser Val Val Asn  Ile Gln Lys Glu Ile  Asp Arg Leu
    1160                1165                1170

Asn Glu  Val Ala Lys Asn Leu  Asn Glu Ser Leu Ile  Asp Leu Gln
    1175                1180                1185

Glu Leu  Gly Lys Tyr Glu Gln  Tyr Ile Lys Trp Pro  Trp Tyr Ile
    1190                1195                1200

Trp Leu  Gly Phe Ile Ala Gly  Leu Ile Ala Ile Val  Met Val Thr
    1205                1210                1215

Ile Met  Leu Cys Cys Met Thr  Ser Cys Cys Ser Cys  Leu Lys Gly
    1220                1225                1230

Cys Cys  Ser Cys Gly Ser Cys  Cys Lys Phe Asp Glu  Asp Asp Ser
    1235                1240                1245

Glu Pro  Val Leu Lys Gly Val  Lys Leu His Tyr Thr
    1250                1255                1260
```

-continued

```
<210> SEQ ID NO 111
<211> LENGTH: 4
<212> TYPE: PRT
<213> ORGANISM: Artificial Sequence
<220> FEATURE:
<223> OTHER INFORMATION: Recombinant Furin Cleavage Site

<400> SEQUENCE: 111

Gly Ser Gly Ala
1
```